United States Patent
Zhang

(10) Patent No.: US 12,297,436 B2
(45) Date of Patent: May 13, 2025

(54) SYSTEMS, METHODS, AND COMPOSITIONS FOR TARGETED NUCLEIC ACID EDITING

(71) Applicants: The Broad Institute, Inc., Cambridge, MA (US); Massachusetts Institute of Technology, Cambridge, MA (US)

(72) Inventor: Feng Zhang, Cambridge, MA (US)

(73) Assignees: The Broad Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 724 days.

(21) Appl. No.: 16/614,424

(22) PCT Filed: May 18, 2018

(86) PCT No.: PCT/US2018/033427
§ 371 (c)(1),
(2) Date: Nov. 18, 2019

(87) PCT Pub. No.: WO2018/231726
PCT Pub. Date: Nov. 22, 2018

(65) Prior Publication Data
US 2020/0181623 A1 Jun. 11, 2020

Related U.S. Application Data

(60) Provisional application No. 62/508,300, filed on May 18, 2017.

(51) Int. Cl.
| | |
|---|---|
| *C12N 15/62* | (2006.01) |
| *C12N 9/22* | (2006.01) |
| *C12N 9/78* | (2006.01) |
| *C12N 15/10* | (2006.01) |
| *C12N 15/11* | (2006.01) |

(52) U.S. Cl.
CPC .............. *C12N 15/62* (2013.01); *C12N 9/22* (2013.01); *C12N 9/78* (2013.01); *C12N 15/102* (2013.01); *C12N 15/111* (2013.01); *C12Y 305/04005* (2013.01)

(58) Field of Classification Search
CPC . C12N 15/62; C12N 9/22; C12N 9/78; C12N 15/102; C12N 15/111; C12Y 305/04005
See application file for complete search history.

(56) References Cited

U.S. PATENT DOCUMENTS

| | | |
|---|---|---|
| 4,186,183 A | 1/1980 | Steck et al. |
| 4,217,344 A | 8/1980 | Vanlerberghe et al. |
| 4,235,871 A | 11/1980 | Papahadjopoulos et al. |
| 4,261,975 A | 4/1981 | Fullerton et al. |
| 4,485,054 A | 11/1984 | Mezei et al. |
| 4,501,728 A | 2/1985 | Geho et al. |
| 4,751,180 A | 6/1988 | Cousens et al. |
| 4,769,061 A | 9/1988 | Comai |
| 4,774,085 A | 9/1988 | Fidler |
| 4,797,368 A | 1/1989 | Carter et al. |
| 4,810,648 A | 3/1989 | Stalker |
| 4,837,028 A | 6/1989 | Allen |
| 4,873,316 A | 10/1989 | Meade et al. |
| 4,897,355 A | 1/1990 | Eppstein et al. |
| 4,935,233 A | 6/1990 | Bell et al. |
| 4,940,835 A | 7/1990 | Shah et al. |
| 4,946,787 A | 8/1990 | Eppstein et al. |
| 4,975,374 A | 12/1990 | Goodman et al. |
| 5,049,386 A | 9/1991 | Eppstein et al. |
| 5,173,414 A | 12/1992 | Lebkowski et al. |
| 5,266,317 A | 11/1993 | Tomalski et al. |
| 5,273,894 A | 12/1993 | Strauch et al. |
| 5,276,268 A | 1/1994 | Strauch et al. |
| 5,494,813 A | 2/1996 | Hepher et al. |
| 5,543,158 A | 8/1996 | Gref et al. |
| 5,561,236 A | 10/1996 | Leemans et al. |
| 5,563,055 A | 10/1996 | Townsend et al. |
| 5,580,859 A | 12/1996 | Felgner et al. |
| 5,589,466 A | 12/1996 | Felgner et al. |
| 5,593,972 A | 1/1997 | Weiner et al. |
| 5,637,489 A | 6/1997 | Strauch et al. |
| 5,646,024 A | 7/1997 | Leemans et al. |
| 5,648,477 A | 7/1997 | Leemans et al. |
| 5,686,281 A | 11/1997 | Roberts |
| 5,712,107 A | 1/1998 | Nichols |
| 5,739,082 A | 4/1998 | Donn |
| 5,789,156 A | 8/1998 | Bujard et al. |
| 5,814,618 A | 9/1998 | Bujard et al. |
| 5,824,790 A | 10/1998 | Keeling et al. |
| 5,843,728 A | 12/1998 | Seed et al. |
| 5,846,946 A | 12/1998 | Huebner et al. |
| 5,851,828 A | 12/1998 | Seed et al. |
| 5,855,913 A | 1/1999 | Hanes et al. |
| 5,858,358 A | 1/1999 | June et al. |
| 5,869,326 A | 2/1999 | Hofmann |
| 5,883,223 A | 3/1999 | Gray |
| 5,906,936 A | 5/1999 | Eshhar et al. |
| 5,908,810 A | 6/1999 | Donn |
| 5,908,975 A | 6/1999 | Caimi et al. |
| 5,912,170 A | 6/1999 | Seed et al. |
| 5,912,172 A | 6/1999 | Eshhar et al. |

(Continued)

FOREIGN PATENT DOCUMENTS

| | | |
|---|---|---|
| CN | 104004782 A | 8/2014 |
| EP | 0 242 246 A1 | 10/1987 |

(Continued)

OTHER PUBLICATIONS

Fu B et al. Target-dependent Nickase Activities of CRISPR-Cas nucleases Cpf1 and Cas9. 2019. Nature Microbiology. 4(5):888-897. (Year: 2019).*

(Continued)

*Primary Examiner* — Paul J Holland
(74) *Attorney, Agent, or Firm* — F. Brent Nix, Esq.; Johnson, Marcou, Isaacs & Nix, LLC; Drew P. Harding

(57) ABSTRACT

The invention provides for systems, methods, and compositions for targeting and editing nucleic acids. In particular, the invention provides non-naturally occurring or engineered DNA-targeting systems comprising a DNA-targeting Cpf1 protein, at least one guide molecule, and at least one cytidine deaminase protein or catalytic domain thereof.

25 Claims, No Drawings

Specification includes a Sequence Listing.

(56) References Cited

U.S. PATENT DOCUMENTS

| | | | |
|---|---|---|---|
| 5,985,309 A | 11/1999 | Edwards et al. |
| 6,004,811 A | 12/1999 | Seed et al. |
| 6,007,845 A | 12/1999 | Domb et al. |
| 6,013,861 A | 1/2000 | Bird et al. |
| 6,248,876 B1 | 6/2001 | Barry et al. |
| 6,284,240 B1 | 9/2001 | Seed et al. |
| 6,284,479 B1 | 9/2001 | Nichols |
| 6,352,694 B1 | 3/2002 | June et al. |
| 6,392,013 B1 | 5/2002 | Seed et al. |
| 6,410,014 B1 | 6/2002 | Seed et al. |
| 6,489,458 B2 | 12/2002 | Hackett et al. |
| 6,534,055 B1 | 3/2003 | June et al. |
| 6,603,061 B1 | 8/2003 | Armstrong et al. |
| 6,734,341 B2 | 5/2004 | Singletary et al. |
| 6,750,059 B1 | 6/2004 | Blakesley et al. |
| 6,753,162 B1 | 6/2004 | Seed et al. |
| 6,768,044 B1 | 7/2004 | Boudec et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,112,665 B1 | 9/2006 | Leemans et al. |
| 7,144,575 B2 | 12/2006 | June et al. |
| 7,148,203 B2 | 12/2006 | Hackett et al. |
| 7,160,682 B2 | 1/2007 | Hackett et al. |
| 7,175,843 B2 | 2/2007 | June et al. |
| 7,232,566 B2 | 6/2007 | June et al. |
| 7,259,015 B2 | 8/2007 | Kingsman et al. |
| 7,303,910 B2 | 12/2007 | Bebbington et al. |
| 7,351,585 B2 | 4/2008 | Mitrophanous et al. |
| 7,572,631 B2 | 8/2009 | Berenson et al. |
| 7,741,465 B1 | 6/2010 | Eshhar et al. |
| 7,745,651 B2 | 6/2010 | Heyes et al. |
| 7,776,321 B2 | 8/2010 | Cascalho et al. |
| 7,799,565 B2 | 9/2010 | MacLachlan et al. |
| 7,803,397 B2 | 9/2010 | Heyes et al. |
| 7,838,658 B2 | 11/2010 | MacLachlan et al. |
| 7,868,149 B2 | 1/2011 | Boukharov et al. |
| 7,901,708 B2 | 3/2011 | MacLachlan et al. |
| 7,915,399 B2 | 3/2011 | MacLachlan et al. |
| 7,982,027 B2 | 7/2011 | MacLachlan et al. |
| 7,985,739 B2 | 7/2011 | Kay et al. |
| 8,044,019 B2 | 10/2011 | Uno et al. |
| 8,058,069 B2 | 11/2011 | Yaworski et al. |
| 8,088,379 B2 | 1/2012 | Robbins et al. |
| 8,101,741 B2 | 1/2012 | MacLachlan et al. |
| 8,188,263 B2 | 5/2012 | MacLachlan et al. |
| 8,211,422 B2 | 7/2012 | Eshhar et al. |
| 8,227,432 B2 | 7/2012 | Hackett et al. |
| 8,236,943 B2 | 8/2012 | Lee et al. |
| 8,283,333 B2 | 10/2012 | Yaworski et al. |
| 8,372,951 B2 | 2/2013 | Chang et al. |
| 8,399,645 B2 | 3/2013 | Campana et al. |
| 8,404,658 B2 | 3/2013 | Hajjar et al. |
| 8,454,972 B2 | 6/2013 | Nabel et al. |
| 8,575,305 B2 | 11/2013 | Gait et al. |
| 8,614,194 B1 | 12/2013 | Chen et al. |
| 8,697,359 B1 | 4/2014 | Zhang |
| 8,697,854 B2 | 4/2014 | Schendel et al. |
| 8,709,843 B2 | 4/2014 | Shakuda |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,906,682 B2 | 12/2014 | June et al. |
| 8,911,993 B2 | 12/2014 | June et al. |
| 8,916,381 B1 | 12/2014 | June et al. |
| 8,932,814 B2 | 1/2015 | Cong et al. |
| 8,945,839 B2 | 2/2015 | Zhang |
| 8,975,071 B1 | 3/2015 | June et al. |
| 8,993,233 B2 | 3/2015 | Zhang et al. |
| 8,999,641 B2 | 4/2015 | Zhang et al. |
| 9,101,584 B2 | 8/2015 | June et al. |
| 9,102,760 B2 | 8/2015 | June et al. |
| 9,102,761 B2 | 8/2015 | June et al. |
| 9,301,923 B2 | 4/2016 | Baryza et al. |
| 2002/0031826 A1 | 3/2002 | Nichols |
| 2003/0087817 A1 | 5/2003 | Cox et al. |
| 2004/0013648 A1 | 1/2004 | Kingsman et al. |
| 2004/0142476 A1 | 7/2004 | Evans et al. |
| 2004/0171156 A1 | 9/2004 | Hartley et al. |
| 2004/0242517 A1 | 12/2004 | Cascalho et al. |
| 2005/0019923 A1 | 1/2005 | Uchegbu et al. |
| 2006/0281180 A1 | 12/2006 | Radcliffe et al. |
| 2007/0025970 A1 | 2/2007 | Kingsman et al. |
| 2007/0054961 A1 | 3/2007 | Maden et al. |
| 2007/0266453 A1 | 11/2007 | Anderson et al. |
| 2008/0267903 A1 | 10/2008 | Uchegbu et al. |
| 2009/0007284 A1 | 1/2009 | Radcliffe et al. |
| 2009/0017543 A1 | 1/2009 | Wilkes et al. |
| 2009/0018016 A1 | 1/2009 | Duck et al. |
| 2009/0100536 A1 | 4/2009 | Adams et al. |
| 2009/0111106 A1 | 4/2009 | Mitrophanous et al. |
| 2009/0144850 A1 | 6/2009 | Van Winkle et al. |
| 2010/0317109 A1 | 12/2010 | Maden et al. |
| 2011/0027239 A1 | 2/2011 | Paek |
| 2011/0117189 A1 | 5/2011 | Mazzone et al. |
| 2011/0293571 A1 | 12/2011 | Widdowson et al. |
| 2011/0293703 A1 | 12/2011 | Mahon et al. |
| 2012/0003201 A1 | 1/2012 | Nicholas et al. |
| 2012/0164118 A1 | 6/2012 | Trobridge et al. |
| 2012/0251560 A1 | 10/2012 | Dahlman et al. |
| 2012/0251618 A1 | 10/2012 | Schrum et al. |
| 2012/0295960 A1 | 11/2012 | Palfi et al. |
| 2013/0071414 A1 | 3/2013 | Dotti et al. |
| 2013/0185823 A1 | 7/2013 | Kuang et al. |
| 2013/0244279 A1 | 9/2013 | De Fougerolles et al. |
| 2013/0245107 A1 | 9/2013 | De Fougerolles et al. |
| 2013/0252281 A1 | 9/2013 | De Fougerolles et al. |
| 2013/0302401 A1 | 11/2013 | Ma et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |
| 2015/0184139 A1 | 7/2015 | Zhang et al. |
| 2016/0208243 A1 | 7/2016 | Zhang et al. |
| 2017/0306335 A1 | 10/2017 | Zhang et al. |
| 2017/0349894 A1 | 12/2017 | Dahlman et al. |
| 2018/0010134 A1 | 1/2018 | Sharp et al. |
| 2018/0044662 A1 | 2/2018 | Platt et al. |
| 2019/0071717 A1 | 3/2019 | Zhang et al. |
| 2019/0256900 A1 | 8/2019 | Zhang et al. |

FOREIGN PATENT DOCUMENTS

| | | |
|---|---|---|
| EP | 0 264 166 A1 | 4/1988 |
| EP | 0 333 033 A1 | 9/1989 |
| EP | 0 571 427 A1 | 12/1993 |
| EP | 0 663 956 A1 | 7/1995 |
| EP | 0 719 338 A1 | 7/1996 |
| EP | 0 728 213 A1 | 8/1996 |
| EP | 1 519 714 A1 | 4/2005 |
| EP | 1 664 316 A1 | 6/2006 |

(56) References Cited

FOREIGN PATENT DOCUMENTS

| | | |
|---|---|---|
| EP | 1 766 035 A1 | 3/2007 |
| EP | 1 781 593 A2 | 5/2007 |
| EP | 1 887 079 A1 | 2/2008 |
| EP | 1 999 263 A1 | 12/2008 |
| EP | 2 764 A2 | 8/2014 |
| EP | 2 784 162 A1 | 10/2014 |
| EP | 771 468 B1 | 2/2015 |
| EP | 3 009 511 A2 | 4/2016 |
| JP | 2006-304779 A | 11/2006 |
| WO | 91/16024 A1 | 10/1991 |
| WO | 91/17424 A1 | 11/1991 |
| WO | 92/15322 A1 | 9/1992 |
| WO | 93/01294 A1 | 1/1993 |
| WO | 93/02197 A1 | 2/1993 |
| WO | 93/06487 A1 | 4/1993 |
| WO | 93/19181 A1 | 9/1993 |
| WO | 93/24641 A2 | 12/1993 |
| WO | 94/04693 A2 | 3/1994 |
| WO | 94/09144 A1 | 4/1994 |
| WO | 94/11520 A2 | 5/1994 |
| WO | 94/26877 A1 | 11/1994 |
| WO | 95/04826 A1 | 2/1995 |
| WO | 95/26407 A1 | 10/1995 |
| WO | 95/31553 A1 | 11/1995 |
| WO | 95/35026 A1 | 12/1995 |
| WO | 96/01904 A1 | 1/1996 |
| WO | 96/15248 A1 | 5/1996 |
| WO | 96/19581 A1 | 6/1996 |
| WO | 96/21023 A1 | 7/1996 |
| WO | 96/27674 A1 | 9/1996 |
| WO | 96/30517 A1 | 10/1996 |
| WO | 96/34968 A2 | 11/1996 |
| WO | 96/38567 A2 | 12/1996 |
| WO | 97/11188 A1 | 3/1997 |
| WO | 97/20936 A1 | 6/1997 |
| WO | 97/26362 A1 | 7/1997 |
| WO | 97/32985 A1 | 9/1997 |
| WO | 97/42328 A1 | 11/1997 |
| WO | 97/44472 A1 | 11/1997 |
| WO | 97/45545 A1 | 12/1997 |
| WO | 97/47806 A1 | 12/1997 |
| WO | 97/47807 A1 | 12/1997 |
| WO | 97/47808 A1 | 12/1997 |
| WO | 97/49450 A1 | 12/1997 |
| WO | 98/20145 A2 | 5/1998 |
| WO | 98/22604 A1 | 5/1998 |
| WO | 98/27212 A1 | 6/1998 |
| WO | 98/32326 A2 | 7/1998 |
| WO | 98/39460 A1 | 9/1998 |
| WO | 98/40503 A1 | 9/1998 |
| WO | 98/52609 A1 | 11/1998 |
| WO | 99/12950 A2 | 3/1999 |
| WO | 99/24585 A1 | 5/1999 |
| WO | 99/24586 A1 | 5/1999 |
| WO | 99/24593 A1 | 5/1999 |
| WO | 99/53072 A1 | 10/1999 |
| WO | 99/58654 A2 | 11/1999 |
| WO | 99/58688 A2 | 11/1999 |
| WO | 99/58690 A2 | 11/1999 |
| WO | 99/66050 A1 | 12/1999 |
| WO | 00/04173 A1 | 1/2000 |
| WO | 00/08175 A2 | 2/2000 |
| WO | 00/08184 A1 | 2/2000 |
| WO | 00/08185 A1 | 2/2000 |
| WO | 00/11192 A2 | 3/2000 |
| WO | 00/14249 A1 | 3/2000 |
| WO | 00/22140 A1 | 4/2000 |
| WO | 00/28052 A2 | 5/2000 |
| WO | 00/47727 A2 | 8/2000 |
| WO | 00/73422 A1 | 12/2000 |
| WO | 00/77229 A2 | 12/2000 |
| WO | 01/12782 A2 | 2/2001 |
| WO | 01/12826 A2 | 2/2001 |
| WO | 01/19975 A2 | 3/2001 |
| WO | 011/4569 A2 | 3/2001 |
| WO | 01/98509 A2 | 12/2001 |
| WO | 02/08391 A2 | 1/2002 |
| WO | 02/34923 A2 | 5/2002 |
| WO | 02/46387 A2 | 6/2002 |
| WO | 02/079410 A2 | 10/2002 |
| WO | 02/083911 A1 | 10/2002 |
| WO | 02/101059 A2 | 12/2002 |
| WO | 03/020763 A2 | 3/2003 |
| WO | 03/033540 A2 | 4/2003 |
| WO | 03/071860 A2 | 9/2003 |
| WO | 2004/033685 A1 | 4/2004 |
| WO | 2004/044004 A2 | 5/2004 |
| WO | 2004/056999 A1 | 7/2004 |
| WO | 2004/074322 A1 | 9/2004 |
| WO | 2004/078983 A2 | 9/2004 |
| WO | 2004/090140 A2 | 10/2004 |
| WO | 2005/002359 A2 | 1/2005 |
| WO | 2005/012515 A2 | 2/2005 |
| WO | 2005/012529 A1 | 2/2005 |
| WO | 2005/030941 A1 | 4/2005 |
| WO | 2005/030942 A1 | 4/2005 |
| WO | 2005/095617 A2 | 10/2005 |
| WO | 2005/095618 A2 | 10/2005 |
| WO | 2005/095619 A1 | 10/2005 |
| WO | 2005/095632 A2 | 10/2005 |
| WO | 2005/105152 A2 | 11/2005 |
| WO | 2005/107437 A2 | 11/2005 |
| WO | 2005/113595 A2 | 12/2005 |
| WO | 2005/114215 A2 | 12/2005 |
| WO | 2005/123927 A1 | 12/2005 |
| WO | 2006/000830 A2 | 1/2006 |
| WO | 2006/018319 A1 | 2/2006 |
| WO | 2006/032538 A1 | 3/2006 |
| WO | 2006/045633 A1 | 5/2006 |
| WO | 2006/063862 A1 | 6/2006 |
| WO | 2006/069782 A2 | 7/2006 |
| WO | 2006/072603 A2 | 7/2006 |
| WO | 2006/103107 A1 | 10/2006 |
| WO | 2006/108702 A1 | 10/2006 |
| WO | 2006/125962 A2 | 11/2006 |
| WO | 2006/133827 A2 | 12/2006 |
| WO | 2007/009823 A1 | 1/2007 |
| WO | 2007/039314 A2 | 4/2007 |
| WO | 2007/039315 A1 | 4/2007 |
| WO | 2007/039316 A1 | 4/2007 |
| WO | 2007/107326 A1 | 9/2007 |
| WO | 2007/121947 A1 | 11/2007 |
| WO | 2008/038002 A2 | 4/2008 |
| WO | 2008/039818 A2 | 4/2008 |
| WO | 2008/042156 A1 | 4/2008 |
| WO | 2008/064289 A2 | 5/2008 |
| WO | 2009/144079 A1 | 12/2009 |
| WO | 2010/061186 A2 | 6/2010 |
| WO | 2010/096488 A1 | 8/2010 |
| WO | 2011/028929 A3 | 10/2011 |
| WO | 2011/146862 A1 | 11/2011 |
| WO | 2012/079000 A2 | 6/2012 |
| WO | 2012/135025 A2 | 10/2012 |
| WO | 2013/039889 A1 | 3/2013 |
| WO | 2013/040371 A2 | 3/2013 |
| WO | 2013/046247 A1 | 4/2013 |
| WO | 2013/122472 A1 | 8/2013 |
| WO | 2013/158141 A1 | 10/2013 |
| WO | 2013/166321 A1 | 11/2013 |
| WO | 2013/176915 A1 | 11/2013 |
| WO | 2014/011987 A1 | 1/2014 |
| WO | 2014/018423 A2 | 1/2014 |
| WO | 2014/018863 A1 | 1/2014 |
| WO | 2014/059173 A2 | 4/2014 |
| WO | 2014/083173 A1 | 6/2014 |
| WO | 2014/093595 A1 | 6/2014 |
| WO | 2014/093622 A1 | 6/2014 |
| WO | 2014/093635 A1 | 6/2014 |
| WO | 2014/093655 A2 | 6/2014 |
| WO | 2014/093661 A2 | 6/2014 |
| WO | 2014/093694 A1 | 6/2014 |
| WO | 2014/093701 A1 | 6/2014 |
| WO | 2014/093709 A1 | 6/2014 |
| WO | 2014/093712 A1 | 6/2014 |

(56) References Cited

FOREIGN PATENT DOCUMENTS

| | | |
|---|---|---|
| WO | 2014/093718 A1 | 6/2014 |
| WO | 2014/118272 A1 | 8/2014 |
| WO | 2014/134165 A1 | 9/2014 |
| WO | 2014/172606 A1 | 10/2014 |
| WO | 2014/184744 A1 | 11/2014 |
| WO | 2014/191128 A1 | 12/2014 |
| WO | 2014/204723 A1 | 12/2014 |
| WO | 2014/204724 A1 | 12/2014 |
| WO | 2014/204725 A1 | 12/2014 |
| WO | 2014/204726 A1 | 12/2014 |
| WO | 2014/204727 A1 | 12/2014 |
| WO | 2014/204728 A1 | 12/2014 |
| WO | 2014/204729 A1 | 12/2014 |
| WO | 2015/058052 A1 | 4/2015 |
| WO | 2015/070083 A1 | 5/2015 |
| WO | 2015/082080 A1 | 6/2015 |
| WO | 2015/089351 A1 | 6/2015 |
| WO | 2015/089354 A1 | 6/2015 |
| WO | 2015/089364 A1 | 6/2015 |
| WO | 2015/089406 A1 | 6/2015 |
| WO | 2015/089419 A2 | 6/2015 |
| WO | 2015/089427 A1 | 6/2015 |
| WO | 2015/089462 A1 | 6/2015 |
| WO | 2015/089465 A1 | 6/2015 |
| WO | 2015/089473 A1 | 6/2015 |
| WO | 2015/089486 A2 | 6/2015 |
| WO | 2015/109752 A1 | 7/2015 |
| WO | 2015/138855 A1 | 9/2015 |
| WO | 2016/028682 A1 | 2/2016 |
| WO | 2016/049024 A2 | 3/2016 |
| WO | 2016/049258 A2 | 3/2016 |
| WO | 2016/094867 A1 | 6/2016 |
| WO | 2016/094874 A1 | 6/2016 |
| WO | 2016/094880 A1 | 6/2016 |
| WO | 2016/106244 A1 | 6/2016 |
| WO | 2016/094872 A9 | 8/2016 |
| WO | 2016/161516 A1 | 10/2016 |
| WO | 2016/205711 A1 | 12/2016 |
| WO | 2017/070605 A1 | 4/2017 |
| WO | 2017/070632 A2 | 4/2017 |

OTHER PUBLICATIONS

Singh RK et al. Protein Engineering Approaches in the Post-Genomic Era. 2017. Current Protein and Peptide Science. 18, p. 1-11. (Year: 2017).*
Zhang M et al. Propagated Perturbations from a Peripheral Mutation Show Interactions Supporting WW Domain Thermostability. 2018. Structure. 26, 1474-1485. (Year: 2018).*
The Broad Institute, Inc., "Notification Concerning Transmittal of International Preliminary Report on Patentability for PCT/US2018/033427", Nov. 28, 2019, 8 pages.
Canver, et al., "BCL11A Enhancer Dissection by Cas9- mediated in Situ Saturating Mutagenesis", Nature, vol. 527, No. 7577, Nov. 12, 2015, 192-197.
Chen, et al., "Genome-Wide CRISPR Screen in a Mouse Model of Tumor Growth and Metastasis", Cell, vol. 160, No. 6, Mar. 12, 2015, 1246-1260.
Cong, et al., "Multiplex Genome Engineering Using CRISPR/Cas Systems", Science, vol. 339, No. 6121, Feb. 15, 2013, 819-823.
Doench, et al., "Rational Design of Highly Active SgRNAs for CRISPR-Cas9-Mediated Gene Inactivation", Nature Biotechnology, vol. 32, No. 12, Dec. 2014, 1262-1267.
Gao, et al., "Engineered Cpf1 Enzymes with Altered PAM Specificities", Nature Biotechnology, vol. 35, No. 8, Dec. 4, 2016, 1-17.
Harris, et al., "RNA Editing Enzyme APOBEC1 and Some of Its Homologs Can Act as DNA Mutators", Molecular Cell, vol. 10, Issue 5, Nov. 2002, 1247-1253.
Hsu, et al., "Development and Applications of CRISPR-Cas9 for Genome Engineering", Cell, vol. 157, No. 6, Jun. 5, 2014, 1262-1278.

Hsu, et al., "DNA Targeting Specificity of RNA-Guided Cas9 Nucleases", Nature Biotechnology, vol. 31, No. 9, Sep. 2013, 827-832.
Hur, et al., "Targeted Mutagenesis in Mice by Electroporation of Cpf1 Ribonucleoproteins", Nat Biotechnol, vol. 34, No. 8, Aug. 2016, 807-808.
Jiang, et al., "RNA-Guided Editing of Bacterial Genomes Using CRISPR-Cas Systems", Nature Biotechnology, vol. 31, No. 3, Mar. 2013, 233-239.
Kim, et al., "Genome-Wide Analysis Reveals Specificities of Cpf1 Endonucleases in Human Cells", Nature Biotechnology, vol. 34, No. 8, Aug. 2016, 863-888.
Konermann, et al., "Genome-Scale Transcriptional Activation by an Engineered CRISPR-Cas9 Complex", Nature, vol. 517, No. 7536, Jan. 29, 2015, 583-588.
Konermann, et al., "Optical Control of Mammalian Endogenous Transcription and Epigenetic States", Nature, vol. 500, No. 7463, Aug. 22, 2013, 472-476.
Nishimasu, et al., "Crystal Structure of Cas9 in Complex with Guide RNA and Target DNA", Cell, vol. 156, No. 5, Feb. 27, 2014, 935-949.
Nishimasu, et al., "Crystal Structure of *Staphylococcus aureus* Cas9", Cell, vol. 162, No. 5, Aug. 27, 2015, 1113-1126.
Parnas, et al., "A Genome-Wide CRISPR Screen in Primary Immune Cells to Dissect Regulatory Networks", Cell, vol. 162, No. 3, Jul. 30, 2015, 675-686.
Platt, et al., "CRISPR-Cas9 Knockin Mice for Genome Editing and Cancer Modeling", Cell, vol. 159, No. 2, Oct. 9, 2014, 440-455.
Port, et al., "Expansion of the CRISPR Toolbox in an Animal with tRNA-Flanked Cas9 and Cpf1 gRNAs", Biorxiv, 2016, 10 pages.
Ramanan, et al., "CRISPR/Cas9 Cleavage of Viral DNA Efficiently Suppresses Hepatitis B Virus", Scientific Reports, vol. 5, No. 10833, Jun. 2, 2015, 9 pages.
Ran, et al., "Double Nicking by RNA-Guided CRISPR Cas9 for Enhanced Genome Editing Specificity", Cell, vol. 154, No. 6, Sep. 12, 2013, 1380-1389.
Ran, et al., "Genome Engineering Using the CRISPR-Cas9 System", Nature Protocols, vol. 8, No. 11, Nov. 2013, 2281-2308.
Ran, et al., "In Vivo Genome Editing using *Staphylococcus aureaus* Cas9", Nature, vol. 520, No. 7546, Apr. 9, 2015, 186-191.
Shalem, et al., "Genome-Scale CRISPR-Cas9 Knockout Screening in Human Cells", Science, vol. 343, No. 6166, Jan. 3, 2014, 84-87.
Shalem, et al., "High-Throughput Functional Genomics Using CRISPR-Cas9", Nature Reviews Genetics, vol. 16, No. 5, May 2015, 299-311.
Shmakov, et al., "Discovery and Functional Characterization of Diverse Class 2 CRISPR-Cas Systems", Molecular Cell, vol. 60, No. 3, Nov. 5, 2015, 385-397.
Slaymaker, et al., "Rationally Engineered Cas9 Nucleases with Improved Specificity", Science, vol. 351, No. 6268, Jan. 1, 2016, 84-88.
Swiech, et al., "In Vivo Interrogation of Gene Function in the Mammalian Brain Using CRISPR-Cas9", Nature Biotechnology, vol. 33, No. 1, Jan. 2015, 102-106.
Tsai, et al., "Dimeric CRISPR RNA-Guided FokI Nucleases for Highly Specific Genome Editing", Nature Biotechnology, vol. 32, No. 6, Jun. 2014, 569-577.
Wang, et al., "Genetic Screens in Human Cells Using the CRISPR/Cas9 System", Science, vol. 343, No. 6166, Jan. 3, 2014, 80-84.
Wang, et al., "One-Step Generation of Mice Carrying Mutations in Multiple Genes by CRISPR/Cas-Mediated Genome Engineering", Cell, vol. 153, No. 4, May 9, 2013, 910-918.
Wu, et al., "Genome-Wide Binding of the CRISPR Endonuclease Cas9 in Mammalian Cells", Nature Biotechnology, vol. 32, No. 7, Jul. 2014, 670-676.
Xu, et al., "Sequence Determinants of Improved CRISPR SgRNA Design", Genome Research, vol. 25, No. 8, Aug. 2015, 1147-1157.
Yamano, et al., "Crystal Structure of Cpf1 in Complex with Guide RNA and Target DNA", Cell, vol. 165, No. 4, May 5, 2016, 949-962.
Zetsche, et al., "A Split-Cas9 Architecture for Inducible Genome Editing and Transcription Modulation", Nature Biotechnology, vol. 33, No. 2, Feb. 2015, 139-142.

(56) References Cited

OTHER PUBLICATIONS

Malzahn, et al., "Plant Genome Editing with TALEN and CRISPR", Cell & Bioscience, vol. 7, 2017, pp. 1-18.

Kim, et al., "Increasing the Genome-Targeting Scope and Precision of Base Editing with Engineered Cas9-Cytidine Deaminase Fusions", Nature Biotechnology, vol. 35, No. 4, 2017, 371-376.

Komor, et al., "Programmable Editing of a Target Base in Genomic DNA without Double-Stranded DNA Cleavage", Nature, vol. 533, No. 7603, May 19, 2016, 420-424.

The Broad Institute, Inc., et al., "Notification of Transmittal of the International Search Report and the Written Opinion of the International Searching Authority, or the Declaration", 13 pages.

Zetsche, et al., "Cpf1 is a Single RNA-Guided Endonuclease of a Class 2 CRISPR-Cas System", Cell, vol. 163, No. 3, Oct. 22, 2015, 759-771.

\* cited by examiner

```
                        SEQUENCE LISTING

<160> NUMBER OF SEQ ID NOS: 80

<210> SEQ ID NO 1
    <211> LENGTH: 15
    <212> TYPE: PRT
    <213> ORGANISM: Artificial Sequence
    <220> FEATURE:
    <223> OTHER INFORMATION: Synthetic

<400> SEQUENCE: 1

Gly Gly Gly Gly Ser Gly Gly Gly Gly Ser Gly Gly Gly Gly Ser
    1               5                   10                  15

<210> SEQ ID NO 2
    <211> LENGTH: 20
    <212> TYPE: PRT
    <213> ORGANISM: Artificial Sequence
    <220> FEATURE:
    <223> OTHER INFORMATION: Synthetic

<400> SEQUENCE: 2

Gly Gly Gly Gly Ser Gly Gly Gly Gly Ser Gly Gly Gly Gly Ser Gly
    1               5                   10                  15

Gly Gly Gly Ser
                20

<210> SEQ ID NO 3
    <211> LENGTH: 25
    <212> TYPE: PRT
    <213> ORGANISM: Artificial Sequence
    <220> FEATURE:
    <223> OTHER INFORMATION: Synthetic

<400> SEQUENCE: 3

Gly Gly Gly Gly Ser Gly Gly Gly Gly Ser Gly Gly Gly Gly Ser Gly
    1               5                   10                  15

Gly Gly Gly Ser Gly Gly Gly Gly Ser
                20                  25

<210> SEQ ID NO 4
```

<210> SEQ ID NO 4
<211> LENGTH: 30
<212> TYPE: PRT
<213> ORGANISM: Artificial Sequence
<220> FEATURE:
<223> OTHER INFORMATION: Synthetic

<400> SEQUENCE: 4

```
Gly Gly Gly Gly Ser Gly Gly Gly Gly Ser Gly Gly Gly Gly Ser Gly
1               5                   10                  15
Gly Gly Gly Ser Gly Gly Gly Gly Ser Gly Gly Gly Gly Ser
            20                  25                  30
```

<210> SEQ ID NO 5
<211> LENGTH: 35
<212> TYPE: PRT
<213> ORGANISM: Artificial Sequence
<220> FEATURE:
<223> OTHER INFORMATION: Synthetic

<400> SEQUENCE: 5

```
Gly Gly Gly Gly Ser Gly Gly Gly Gly Ser Gly Gly Gly Gly Ser Gly
1               5                   10                  15
Gly Gly Gly Ser Gly Gly Gly Gly Ser Gly Gly Gly Gly Ser Gly Gly
            20                  25                  30
Gly Gly Ser
        35
```

<210> SEQ ID NO 6
<211> LENGTH: 40
<212> TYPE: PRT
<213> ORGANISM: Artificial Sequence
<220> FEATURE:
<223> OTHER INFORMATION: Synthetic

<400> SEQUENCE: 6

```
Gly Gly Gly Gly Ser Gly Gly Gly Gly Ser Gly Gly Gly Gly Ser Gly
1               5                   10                  15
Gly Gly Gly Ser Gly Gly Gly Gly Ser Gly Gly Gly Gly Ser Gly Gly
            20                  25                  30
Gly Gly Ser Gly Gly Gly Gly Ser
        35                  40
```

<210> SEQ ID NO 7
<211> LENGTH: 45
<212> TYPE: PRT
<213> ORGANISM: Artificial Sequence
<220> FEATURE:
<223> OTHER INFORMATION: Synthetic

<400> SEQUENCE: 7

```
Gly Gly Gly Gly Ser Gly Gly Gly Gly Ser Gly Gly Gly Gly Ser Gly
1               5                   10                  15
Gly Gly Gly Ser Gly Gly Gly Gly Ser Gly Gly Gly Gly Ser Gly Gly
            20                  25                  30
Gly Gly Ser Gly Gly Gly Gly Ser Gly Gly Gly Gly Ser
        35                  40                  45
```

<210> SEQ ID NO 8
<211> LENGTH: 50
<212> TYPE: PRT
<213> ORGANISM: Artificial Sequence
<220> FEATURE:
<223> OTHER INFORMATION: Synthetic

<400> SEQUENCE: 8

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30

Gly Gly Ser Gly Gly Gly Gly Ser Gly Gly Gly Gly Ser Gly Gly Gly
            35                  40                  45

Gly Ser
    50

<210> SEQ ID NO 9
<211> LENGTH: 55
<212> TYPE: PRT
<213> ORGANISM: Artificial Sequence
<220> FEATURE:
<223> OTHER INFORMATION: Synthetic

<400> SEQUENCE: 9

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30

Gly Gly Ser Gly Gly Gly Gly Ser Gly Gly Gly Gly Ser Gly Gly Gly
            35                  40                  45

Gly Ser Gly Gly Gly Gly Ser
    50                  55

<210> SEQ ID NO 10
<211> LENGTH: 15
<212> TYPE: PRT
<213> ORGANISM: Artificial Sequence
<220> FEATURE:
<223> OTHER INFORMATION: Synthetic

<400> SEQUENCE: 10

Gly Ser Gly Gly Ser Gly Gly Ser Gly Gly Ser Gly Gly Ser Gly
1               5                   10                  15

<210> SEQ ID NO 11
<211> LENGTH: 32
<212> TYPE: PRT
<213> ORGANISM: Artificial Sequence
<220> FEATURE:
<223> OTHER INFORMATION: Synthetic

<400> SEQUENCE: 11

Leu Glu Pro Gly Glu Lys Pro Tyr Lys Cys Pro Glu Cys Gly Lys Ser
1               5                   10                  15

Phe Ser Gln Ser Gly Ala Leu Thr Arg His Gln Arg Thr His Thr Arg
                20                  25                  30

<210> SEQ ID NO 12
<211> LENGTH: 9
<212> TYPE: PRT
<213> ORGANISM: Artificial Sequence
<220> FEATURE:
<223> OTHER INFORMATION: Synthetic

<400> SEQUENCE: 12

Gly Gly Ser Gly Gly Ser Gly Gly Ser
1               5

```
<210> SEQ ID NO 13
<211> LENGTH: 15
<212> TYPE: PRT
<213> ORGANISM: Artificial Sequence
<220> FEATURE:
<223> OTHER INFORMATION: Synthetic

<400> SEQUENCE: 13

Gly Gly Gly Gly Ser Gly Gly Gly Gly Ser Gly Gly Gly Gly Ser
1               5                   10                  15

<210> SEQ ID NO 14
<211> LENGTH: 30
<212> TYPE: PRT
<213> ORGANISM: Artificial Sequence
<220> FEATURE:
<223> OTHER INFORMATION: Synthetic

<400> SEQUENCE: 14

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 15
<211> LENGTH: 45
<212> TYPE: PRT
<213> ORGANISM: Artificial Sequence
<220> FEATURE:
<223> OTHER INFORMATION: Synthetic

<400> SEQUENCE: 15

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser
        35                  40                  45

<210> SEQ ID NO 16
<211> LENGTH: 60
<212> TYPE: PRT
<213> ORGANISM: Artificial Sequence
<220> FEATURE:
<223> OTHER INFORMATION: Synthetic

<400> SEQUENCE: 16

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser
    50                  55                  60

<210> SEQ ID NO 17
<211> LENGTH: 5
<212> TYPE: PRT
<213> ORGANISM: Artificial Sequence
<220> FEATURE:
<223> OTHER INFORMATION: Synthetic

<400> SEQUENCE: 17
```

```
Gly Gly Gly Gly Ser
1               5

<210> SEQ ID NO 18
<211> LENGTH: 10
<212> TYPE: PRT
<213> ORGANISM: Artificial Sequence
<220> FEATURE:
<223> OTHER INFORMATION: Synthetic

<400> SEQUENCE: 18

Gly Gly Gly Gly Ser Gly Gly Gly Gly Ser
1               5                   10

<210> SEQ ID NO 19
<211> LENGTH: 20
<212> TYPE: PRT
<213> ORGANISM: Artificial Sequence
<220> FEATURE:
<223> OTHER INFORMATION: Synthetic

<400> SEQUENCE: 19

Gly Gly Gly Gly Ser Gly Gly Gly Gly Ser Gly Gly Gly Gly Ser Gly
1               5                   10                  15

Gly Gly Gly Ser
            20

<210> SEQ ID NO 20
<211> LENGTH: 25
<212> TYPE: PRT
<213> ORGANISM: Artificial Sequence
<220> FEATURE:
<223> OTHER INFORMATION: Synthetic

<400> SEQUENCE: 20

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 21
<211> LENGTH: 35
<212> TYPE: PRT
<213> ORGANISM: Artificial Sequence
<220> FEATURE:
<223> OTHER INFORMATION: Synthetic

<400> SEQUENCE: 21

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 22
<211> LENGTH: 40
<212> TYPE: PRT
<213> ORGANISM: Artificial Sequence
<220> FEATURE:
<223> OTHER INFORMATION: Synthetic

<400> SEQUENCE: 22

Gly Gly Gly Gly Ser Gly Gly Gly Gly Ser Gly Gly Gly Gly Ser Gly
1               5                   10                  15
```

Gly Gly Gly Ser Gly Gly Gly Ser Gly Gly Gly Ser Gly Gly
            20                  25                  30

Gly Gly Ser Gly Gly Gly Gly Ser
        35                  40

<210> SEQ ID NO 23
<211> LENGTH: 50
<212> TYPE: PRT
<213> ORGANISM: Artificial Sequence
<220> FEATURE:
<223> OTHER INFORMATION: Synthetic

<400> SEQUENCE: 23

Gly Gly Gly Gly Ser Gly Gly Gly Ser Gly Gly Gly Ser Gly
1               5                   10                  15

Gly Gly Gly Ser Gly Gly Gly Gly Ser Gly Gly Gly Ser Gly Gly
            20                  25                  30

Gly Gly Ser Gly Gly Gly Gly Ser Gly Gly Gly Ser Gly Gly
        35                  40                  45

Gly Ser
    50

<210> SEQ ID NO 24
<211> LENGTH: 55
<212> TYPE: PRT
<213> ORGANISM: Artificial Sequence
<220> FEATURE:
<223> OTHER INFORMATION: Synthetic

<400> SEQUENCE: 24

Gly Gly Gly Gly Ser Gly Gly Gly Gly Ser Gly Gly Gly Ser Gly
1               5                   10                  15

Gly Gly Gly Ser Gly Gly Gly Ser Gly Gly Gly Gly Ser Gly Gly
            20                  25                  30

Gly Gly Ser Gly Gly Gly Gly Ser Gly Gly Gly Ser Gly Gly Gly
        35                  40                  45

Gly Ser Gly Gly Gly Gly Ser
    50                  55

<210> SEQ ID NO 25
<211> LENGTH: 32
<212> TYPE: PRT
<213> ORGANISM: Artificial Sequence
<220> FEATURE:
<223> OTHER INFORMATION: Synthetic

<400> SEQUENCE: 25

Leu Glu Pro Gly Glu Lys Pro Tyr Lys Cys Pro Glu Cys Gly Lys Ser
1               5                   10                  15

Phe Ser Gln Ser Gly Ala Leu Thr Arg His Gln Arg Thr His Thr Arg
            20                  25                  30

<210> SEQ ID NO 26
<211> LENGTH: 32
<212> TYPE: PRT
<213> ORGANISM: Artificial Sequence
<220> FEATURE:
<223> OTHER INFORMATION: Synthetic

<400> SEQUENCE: 26

Leu Glu Pro Gly Glu Lys Pro Tyr Lys Cys Pro Glu Cys Gly Lys Ser
1               5                   10                  15

Phe Ser Gln Ser Gly Ala Leu Thr Arg His Gln Arg Thr His Thr Arg
                20                  25                  30

<210> SEQ ID NO 27
<211> LENGTH: 32
<212> TYPE: PRT
<213> ORGANISM: Artificial Sequence
<220> FEATURE:
<223> OTHER INFORMATION: Synthetic

<400> SEQUENCE: 27

Leu Glu Pro Gly Glu Lys Pro Tyr Lys Cys Pro Glu Cys Gly Lys Ser
1               5                   10                  15

Phe Ser Gln Ser Gly Ala Leu Thr Arg His Gln Arg Thr His Thr Arg
                20                  25                  30

<210> SEQ ID NO 28
<211> LENGTH: 20
<212> TYPE: PRT
<213> ORGANISM: Artificial Sequence
<220> FEATURE:
<223> OTHER INFORMATION: Synthetic

<400> SEQUENCE: 28

Pro Lys Lys Lys Arg Lys Val Glu Ala Ser Pro Lys Lys Arg Lys
1               5                   10                  15

Val Glu Ala Ser
            20

<210> SEQ ID NO 29
<211> LENGTH: 229
<212> TYPE: PRT
<213> ORGANISM: Rattus sp.

<400> SEQUENCE: 29

Met Ser Ser Glu Thr Gly Pro Val Ala Val Asp Pro Thr Leu Arg Arg
1               5                   10                  15

Arg Ile Glu Pro His Glu Phe Glu Val Phe Phe Asp Pro Arg Glu Leu
                20                  25                  30

Arg Lys Glu Thr Cys Leu Leu Tyr Glu Ile Asn Trp Gly Gly Arg His
            35                  40                  45

Ser Ile Trp Arg His Thr Ser Gln Asn Thr Asn Lys His Val Glu Val
        50                  55                  60

Asn Phe Ile Glu Lys Phe Thr Thr Glu Arg Tyr Phe Cys Pro Asn Thr
65                  70                  75                  80

Arg Cys Ser Ile Thr Trp Phe Leu Ser Trp Ser Pro Cys Gly Glu Cys
                85                  90                  95

Ser Arg Ala Ile Thr Glu Phe Leu Ser Arg Tyr Pro His Val Thr Leu
                100                 105                 110

Phe Ile Tyr Ile Ala Arg Leu Tyr His His Ala Asp Pro Arg Asn Arg
            115                 120                 125

Gln Gly Leu Arg Asp Leu Ile Ser Ser Gly Val Thr Ile Gln Ile Met
        130                 135                 140

Thr Glu Gln Glu Ser Gly Tyr Cys Trp Arg Asn Phe Val Asn Tyr Ser
145                 150                 155                 160

Pro Ser Asn Glu Ala His Trp Pro Arg Tyr Pro His Leu Trp Val Arg
                165                 170                 175

Leu Tyr Val Leu Glu Leu Tyr Cys Ile Ile Leu Gly Leu Pro Pro Cys
            180                 185                 190

Leu Asn Ile Leu Arg Arg Lys Gln Pro Gln Leu Thr Phe Phe Thr Ile
        195                 200                 205

Ala Leu Gln Ser Cys His Tyr Gln Arg Leu Pro His Ile Leu Trp
    210                 215                 220

Ala Thr Gly Leu Lys
225

<210> SEQ ID NO 30
<211> LENGTH: 236
<212> TYPE: PRT
<213> ORGANISM: Homo sapien

<400> SEQUENCE: 30

Met Thr Ser Glu Lys Gly Pro Ser Gly Asp Pro Thr Leu Arg Arg
1               5                   10                  15

Arg Ile Glu Pro Trp Glu Phe Asp Val Phe Tyr Asp Pro Arg Glu Leu
                20                  25                  30

Arg Lys Glu Ala Cys Leu Leu Tyr Glu Ile Lys Trp Gly Met Ser Arg
            35                  40                  45

Lys Ile Trp Arg Ser Ser Gly Lys Asn Thr Thr Asn His Val Glu Val
50                  55                  60

Asn Phe Ile Lys Lys Phe Thr Ser Glu Arg Asp Phe His Pro Ser Met
65                  70                  75                  80

Ser Cys Ser Ile Thr Trp Phe Leu Ser Trp Ser Pro Cys Trp Glu Cys
                85                  90                  95

Ser Gln Ala Ile Arg Glu Phe Leu Ser Arg His Pro Gly Val Thr Leu
            100                 105                 110

Val Ile Tyr Val Ala Arg Leu Phe Trp His Met Asp Gln Gln Asn Arg
        115                 120                 125

Gln Gly Leu Arg Asp Leu Val Asn Ser Gly Val Thr Ile Gln Ile Met
    130                 135                 140

Arg Ala Ser Glu Tyr Tyr His Cys Trp Arg Asn Phe Val Asn Tyr Pro
145                 150                 155                 160

Pro Gly Asp Glu Ala His Trp Pro Gln Tyr Pro Pro Leu Trp Met Met
                165                 170                 175

Leu Tyr Ala Leu Glu Leu His Cys Ile Ile Leu Ser Leu Pro Pro Cys
            180                 185                 190

Leu Lys Ile Ser Arg Arg Trp Gln Asn His Leu Thr Phe Phe Arg Leu
        195                 200                 205

His Leu Gln Asn Cys His Tyr Gln Thr Ile Pro His Ile Leu Leu
    210                 215                 220

Ala Thr Gly Leu Ile His Pro Ser Val Ala Trp Arg
225                 230                 235

<210> SEQ ID NO 31
<211> LENGTH: 325
<212> TYPE: PRT
<213> ORGANISM: Homo sapien

<400> SEQUENCE: 31

Met Glu Leu Lys Tyr His Pro Glu Met Arg Phe Phe His Trp Phe Ser
1               5                   10                  15

Lys Trp Arg Lys Leu His Arg Asp Gln Glu Tyr Glu Val Thr Trp Tyr
                20                  25                  30

Ile Ser Trp Ser Pro Cys Thr Lys Cys Thr Arg Asp Met Ala Thr Phe
            35                  40                  45

```
Leu Ala Glu Asp Pro Lys Val Thr Leu Thr Ile Phe Val Ala Arg Leu
            50                  55                  60

Tyr Tyr Phe Trp Asp Pro Asp Tyr Gln Glu Ala Leu Arg Ser Leu Cys
 65                  70                  75                  80

Gln Lys Arg Asp Gly Pro Arg Ala Thr Met Lys Ile Met Asn Tyr Asp
                    85                  90                  95

Glu Phe Gln His Cys Trp Ser Lys Phe Val Tyr Ser Gln Arg Glu Leu
                100                 105                 110

Phe Glu Pro Trp Asn Asn Leu Pro Lys Tyr Tyr Ile Leu Leu His Ile
            115                 120                 125

Met Leu Gly Glu Ile Leu Arg His Ser Met Asp Pro Thr Phe Thr
130                 135                 140

Phe Asn Phe Asn Asn Glu Pro Trp Val Arg Gly Arg His Glu Thr Tyr
145                 150                 155                 160

Leu Cys Tyr Glu Val Glu Arg Met His Asn Asp Thr Trp Val Leu Leu
                165                 170                 175

Asn Gln Arg Arg Gly Phe Leu Cys Asn Gln Ala Pro His Lys His Gly
                180                 185                 190

Phe Leu Glu Gly Arg His Ala Glu Leu Cys Phe Leu Asp Val Ile Pro
            195                 200                 205

Phe Trp Lys Leu Asp Leu Asp Gln Asp Tyr Arg Val Thr Cys Phe Thr
210                 215                 220

Ser Trp Ser Pro Cys Phe Ser Cys Ala Gln Glu Met Ala Lys Phe Ile
225                 230                 235                 240

Ser Lys Asn Lys His Val Ser Leu Cys Ile Phe Thr Ala Arg Ile Tyr
                245                 250                 255

Asp Asp Gln Gly Arg Cys Gln Glu Gly Leu Arg Thr Leu Ala Glu Ala
                260                 265                 270

Gly Ala Lys Ile Ser Ile Met Thr Tyr Ser Glu Phe Lys His Cys Trp
            275                 280                 285

Asp Thr Phe Val Asp His Gln Gly Cys Pro Phe Gln Pro Trp Asp Gly
            290                 295                 300

Leu Asp Glu His Ser Gln Asp Leu Ser Gly Arg Leu Arg Ala Ile Leu
305                 310                 315                 320

Gln Asn Gln Glu Asn
                325

<210> SEQ ID NO 32
<211> LENGTH: 208
<212> TYPE: PRT
<213> ORGANISM: Petromyzon marinus

<400> SEQUENCE: 32

Met Thr Asp Ala Glu Tyr Val Arg Ile His Glu Lys Leu Asp Ile Tyr
 1               5                  10                  15

Thr Phe Lys Lys Gln Phe Phe Asn Asn Lys Lys Ser Val Ser His Arg
                20                  25                  30

Cys Tyr Val Leu Phe Glu Leu Lys Arg Arg Gly Glu Arg Arg Ala Cys
                35                  40                  45

Phe Trp Gly Tyr Ala Val Asn Lys Pro Gln Ser Gly Thr Glu Arg Gly
            50                  55                  60

Ile His Ala Glu Ile Phe Ser Ile Arg Lys Val Glu Glu Tyr Leu Arg
 65                 70                  75                  80

Asp Asn Pro Gly Gln Phe Thr Ile Asn Trp Tyr Ser Ser Trp Ser Pro
```

85                  90                  95
Cys Ala Asp Cys Ala Glu Lys Ile Leu Glu Trp Tyr Asn Gln Glu Leu
                100                 105                 110

Arg Gly Asn Gly His Thr Leu Lys Ile Trp Ala Cys Lys Leu Tyr Tyr
                115                 120                 125

Glu Lys Asn Ala Arg Asn Gln Ile Gly Leu Trp Asn Leu Arg Asp Asn
                130                 135                 140

Gly Val Gly Leu Asn Val Met Val Ser Glu His Tyr Gln Cys Cys Arg
145                 150                 155                 160

Lys Ile Phe Ile Gln Ser Ser His Asn Gln Leu Asn Glu Asn Arg Trp
                165                 170                 175

Leu Glu Lys Thr Leu Lys Arg Ala Glu Lys Arg Arg Ser Glu Leu Ser
                180                 185                 190

Ile Met Ile Gln Val Lys Ile Leu His Thr Thr Lys Ser Pro Ala Val
                195                 200                 205

<210> SEQ ID NO 33
<211> LENGTH: 200
<212> TYPE: PRT
<213> ORGANISM: Homo sapiens

<400> SEQUENCE: 33

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
                20                  25                  30

Val Lys Arg Arg Asp Ser Ala Thr Ser Phe Ser Leu Asp Phe Gly Tyr
                35                  40                  45

Leu Arg Asn Lys Asn Gly Cys His Val Glu Leu Leu Phe Leu Arg Tyr
            50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Tyr Leu Ser Leu Arg Ile Phe Thr Ala Arg
                100                 105                 110

Leu Tyr Phe Cys Glu Asp Arg Lys Ala Glu Pro Glu Gly Leu Arg Arg
                115                 120                 125

Leu His Arg Ala Gly Val Gln Ile Ala Ile Met Thr Phe Lys Asp Tyr
                130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
                180                 185                 190

Phe Arg Thr Leu Gly Leu Leu Asp
                195                 200

<210> SEQ ID NO 34
<211> LENGTH: 181
<212> TYPE: PRT
<213> ORGANISM: Homo sapiens

<400> SEQUENCE: 34

Met Asp Ser Leu Leu Met Asn Arg Arg Lys Phe Leu Tyr Gln Phe Lys

```
                1               5                      10                      15
            Asn Val Arg Trp Ala Lys Gly Arg Arg Glu Thr Tyr Leu Cys Tyr Val
                                20                      25                      30
            Val Lys Arg Arg Asp Ser Ala Thr Ser Phe Ser Leu Asp Phe Gly Tyr
                                35                      40                      45
            Leu Arg Asn Lys Asn Gly Cys His Val Glu Leu Phe Leu Arg Tyr
                                50                      55                      60
            Ile Ser Asp Trp Asp Leu Asp Pro Gly Arg Cys Tyr Arg Val Thr Trp
             65                     70                      75                      80
            Phe Thr Ser Trp Ser Pro Cys Tyr Asp Cys Ala Arg His Val Ala Asp
                                85                      90                      95
            Phe Leu Arg Gly Asn Pro Asn Leu Ser Leu Arg Ile Phe Thr Ala Arg
                                100                     105                     110
            Leu Tyr Phe Cys Glu Asp Arg Lys Ala Glu Pro Glu Gly Leu Arg Arg
                                115                     120                     125
            Leu His Arg Ala Gly Val Gln Ile Ala Ile Met Thr Phe Lys Asp Tyr
                                130                     135                     140
            Phe Tyr Cys Trp Asn Thr Phe Val Glu Asn His Glu Arg Thr Phe Lys
            145                     150                     155                     160
            Ala Trp Glu Gly Leu His Glu Asn Ser Val Arg Leu Ser Arg Gln Leu
                                165                     170                     175
            Arg Arg Ile Leu Leu
                                180
```

<210> SEQ ID NO 35
<211> LENGTH: 84
<212> TYPE: PRT
<213> ORGANISM: Artificial Sequence
<220> FEATURE:
<223> OTHER INFORMATION: Synthetic

<400> SEQUENCE: 35

```
            Met Thr Asn Leu Ser Asp Ile Ile Glu Lys Glu Thr Gly Lys Gln Leu
             1               5                      10                      15
            Val Ile Gln Glu Ser Ile Leu Met Leu Pro Glu Glu Val Glu Glu Val
                                20                      25                      30
            Ile Gly Asn Lys Pro Glu Ser Asp Ile Leu Val His Thr Ala Tyr Asp
                                35                      40                      45
            Glu Ser Thr Asp Glu Asn Val Met Leu Leu Thr Ser Asp Ala Pro Glu
                                50                      55                      60
            Tyr Lys Pro Trp Ala Leu Val Ile Gln Asp Ser Asn Gly Glu Asn Lys
             65                     70                      75                      80
            Ile Lys Met Leu
```

<210> SEQ ID NO 36

<400> SEQUENCE: 36

000

<210> SEQ ID NO 37
<211> LENGTH: 7
<212> TYPE: PRT
<213> ORGANISM: Simian Virus 40

<400> SEQUENCE: 37

```
            Pro Lys Lys Lys Arg Lys Val
             1               5
```

<210> SEQ ID NO 38
<211> LENGTH: 10
<212> TYPE: PRT
<213> ORGANISM: Simian Virus 40

<400> SEQUENCE: 38

Pro Lys Lys Lys Arg Lys Val Glu Ala Ser
1               5                   10

<210> SEQ ID NO 39
<211> LENGTH: 16
<212> TYPE: PRT
<213> ORGANISM: Artificial Sequence
<220> FEATURE:
<223> OTHER INFORMATION: Synthetic

<400> SEQUENCE: 39

Lys Arg Pro Ala Ala Thr Lys Lys Ala Gly Gln Ala Lys Lys Lys Lys
1               5                   10                  15

<210> SEQ ID NO 40
<211> LENGTH: 9
<212> TYPE: PRT
<213> ORGANISM: Artificial Sequence
<220> FEATURE:
<223> OTHER INFORMATION: Synthetic

<400> SEQUENCE: 40

Pro Ala Ala Lys Arg Val Lys Leu Asp
1               5

<210> SEQ ID NO 41
<211> LENGTH: 10
<212> TYPE: PRT
<213> ORGANISM: Artificial Sequence
<220> FEATURE:
<223> OTHER INFORMATION: Synthetic

<400> SEQUENCE: 41

Arg Gln Arg Arg Asn Glu Leu Lys Arg Ser
1               5                   10

<210> SEQ ID NO 42
<211> LENGTH: 38
<212> TYPE: PRT
<213> ORGANISM: Artificial Sequence
<220> FEATURE:
<223> OTHER INFORMATION: Synthetic

<400> SEQUENCE: 42

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 43
<211> LENGTH: 42
<212> TYPE: PRT
<213> ORGANISM: Artificial Sequence
<220> FEATURE:
<223> OTHER INFORMATION: Synthetic

<400> SEQUENCE: 43

```
Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
                20                  25                  30

Asp Glu Gln Ile Leu Lys Arg Arg Asn Val
            35                  40

<210> SEQ ID NO 44
<211> LENGTH: 8
<212> TYPE: PRT
<213> ORGANISM: Artificial Sequence
<220> FEATURE:
<223> OTHER INFORMATION: Synthetic

<400> SEQUENCE: 44

Val Ser Arg Lys Arg Pro Arg Pro
1               5

<210> SEQ ID NO 45
<211> LENGTH: 8
<212> TYPE: PRT
<213> ORGANISM: Artificial Sequence
<220> FEATURE:
<223> OTHER INFORMATION: Synthetic

<400> SEQUENCE: 45

Pro Pro Lys Lys Ala Arg Glu Asp
1               5

<210> SEQ ID NO 46
<211> LENGTH: 8
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid

<400> SEQUENCE: 46

Pro Xaa Pro Lys Lys Lys Pro Leu
1               5

<210> SEQ ID NO 47
<211> LENGTH: 12
<212> TYPE: PRT
<213> ORGANISM: Mus sp.

<400> SEQUENCE: 47

Ser Ala Leu Ile Lys Lys Lys Lys Lys Met Ala Pro
1               5                   10

<210> SEQ ID NO 48
<211> LENGTH: 5
<212> TYPE: PRT
<213> ORGANISM: Influenza virus NS1

<400> SEQUENCE: 48

Asp Arg Leu Arg Arg
1               5

<210> SEQ ID NO 49
<211> LENGTH: 7
<212> TYPE: PRT
<213> ORGANISM: Influenza virus NS1
```

<400> SEQUENCE: 49

Pro Lys Gln Lys Lys Arg Lys
1               5

<210> SEQ ID NO 50
<211> LENGTH: 10
<212> TYPE: PRT
<213> ORGANISM: Hepatitis virus

<400> SEQUENCE: 50

Arg Lys Leu Lys Lys Lys Ile Lys Lys Leu
1               5                   10

<210> SEQ ID NO 51
<211> LENGTH: 10
<212> TYPE: PRT
<213> ORGANISM: Mus sp.

<400> SEQUENCE: 51

Arg Glu Lys Lys Lys Phe Leu Lys Arg Arg
1               5                   10

<210> SEQ ID NO 52
<211> LENGTH: 17
<212> TYPE: PRT
<213> ORGANISM: Homo sapiens

<400> SEQUENCE: 52

Arg Lys Cys Leu Gln Ala Gly Met Asn Leu Glu Ala Arg Lys Thr Lys
1               5                   10                  15

Lys

<210> SEQ ID NO 53
<211> LENGTH: 17
<212> TYPE: PRT
<213> ORGANISM: Homo sapiens

<400> SEQUENCE: 53

Arg Lys Cys Leu Gln Ala Gly Met Asn Leu Glu Ala Arg Lys Thr Lys
1               5                   10                  15

Lys

<210> SEQ ID NO 54
<211> LENGTH: 1345
<212> TYPE: PRT
<213> ORGANISM: Franscisella tularensis

<400> SEQUENCE: 54

Met Ser Ile Tyr Gln Glu Phe Val Asn Lys Tyr Ser Leu Ser Lys Thr
1               5 10 15

Leu Arg Phe Glu Leu Ile Pro Gln Gly Lys Thr Leu Glu Asn Ile Lys
20 25 30

Ala Arg Gly Leu Ile Leu Asp Asp Glu Lys Arg Ala Lys Asp Tyr Lys
35 40 45

Lys Ala Lys Gln Ile Ile Asp Lys Tyr His Gln Phe Phe Ile Glu Glu
50 55 60

Ile Leu Ser Ser Val Cys Ile Ser Glu Asp Leu Leu Gln Asn Tyr Ser
65 70 75 80

Asp Val Tyr Phe Lys Leu Lys Lys Ser Asp Asp Asp Asn Leu Gln Lys
85 90 95

```
Asp Phe Lys Ser Ala Lys Asp Thr Ile Lys Lys Gln Ile Ser Glu Tyr
                100                 105                 110
Ile Lys Asp Ser Glu Lys Phe Lys Asn Leu Phe Asn Gln Asn Leu Ile
            115                 120                 125
Asp Ala Lys Lys Gly Gln Glu Ser Asp Leu Ile Leu Trp Leu Lys Gln
        130                 135                 140
Ser Lys Asp Asn Gly Ile Glu Leu Phe Lys Ala Asn Ser Asp Ile Thr
145                 150                 155                 160
Asp Ile Asp Glu Ala Leu Glu Ile Ile Lys Ser Phe Lys Gly Trp Thr
                165                 170                 175
Thr Tyr Phe Lys Gly Phe His Glu Asn Arg Lys Asn Val Tyr Ser Ser
            180                 185                 190
Asn Asp Ile Pro Thr Ser Ile Ile Tyr Arg Ile Val Asp Asp Asn Leu
        195                 200                 205
Pro Lys Phe Leu Glu Asn Lys Ala Lys Tyr Glu Ser Leu Lys Asp Lys
210                 215                 220
Ala Pro Glu Ala Ile Asn Tyr Glu Gln Ile Lys Lys Asp Leu Ala Glu
225                 230                 235                 240
Glu Leu Thr Phe Asp Ile Asp Tyr Lys Thr Ser Glu Val Asn Gln Arg
                245                 250                 255
Val Phe Ser Leu Asp Glu Val Phe Glu Ile Ala Asn Phe Asn Asn Tyr
            260                 265                 270
Leu Asn Gln Ser Gly Ile Thr Lys Phe Asn Thr Ile Ile Gly Gly Lys
        275                 280                 285
Phe Val Asn Gly Glu Asn Thr Lys Arg Lys Gly Ile Asn Glu Tyr Ile
290                 295                 300
Asn Leu Tyr Ser Gln Gln Ile Asn Asp Lys Thr Leu Lys Lys Tyr Lys
305                 310                 315                 320
Met Ser Val Leu Phe Lys Gln Ile Leu Ser Asp Thr Glu Ser Lys Ser
                325                 330                 335
Phe Val Ile Asp Lys Leu Glu Asp Ser Asp Val Val Thr Thr Met
            340                 345                 350
Gln Ser Phe Tyr Glu Gln Ile Ala Ala Phe Lys Thr Val Glu Glu Lys
        355                 360                 365
Ser Ile Lys Glu Thr Leu Ser Leu Leu Phe Asp Asp Leu Lys Ala Gln
370                 375                 380
Lys Leu Asp Leu Ser Lys Ile Tyr Phe Lys Asn Asp Lys Ser Leu Thr
385                 390                 395                 400
Asp Leu Ser Gln Gln Val Phe Asp Asp Tyr Ser Val Ile Gly Thr Ala
                405                 410                 415
Val Leu Glu Tyr Ile Thr Gln Gln Ile Ala Pro Lys Asn Leu Asp Asn
            420                 425                 430
Pro Ser Lys Lys Glu Gln Glu Leu Ile Ala Lys Lys Thr Glu Lys Ala
        435                 440                 445
Lys Tyr Leu Ser Leu Glu Thr Ile Lys Leu Ala Leu Glu Glu Phe Asn
450                 455                 460
Lys His Arg Asp Ile Asp Lys Gln Cys Arg Phe Glu Glu Ile Leu Ala
465                 470                 475                 480
Asn Phe Ala Ala Ile Pro Met Ile Phe Asp Glu Ile Ala Gln Asn Lys
                485                 490                 495
Asp Asn Leu Ala Gln Ile Ser Ile Lys Tyr Gln Asn Gln Gly Lys Lys
            500                 505                 510
Asp Leu Leu Gln Ala Ser Ala Glu Asp Asp Val Lys Ala Ile Lys Asp
```

```
                515                 520                 525
Leu Leu Asp Gln Thr Asn Asn Leu Leu His Lys Leu Lys Ile Phe His
    530                 535                 540
Ile Ser Gln Ser Glu Asp Lys Ala Asn Ile Leu Asp Lys Asp Glu His
545                 550                 555                 560
Phe Tyr Leu Val Phe Glu Glu Cys Tyr Phe Glu Leu Ala Asn Ile Val
                565                 570                 575
Pro Leu Tyr Asn Lys Ile Arg Asn Tyr Ile Thr Gln Lys Pro Tyr Ser
            580                 585                 590
Asp Glu Lys Phe Lys Leu Asn Phe Glu Asn Ser Thr Leu Ala Asn Gly
        595                 600                 605
Trp Asp Lys Asn Lys Glu Pro Asp Asn Thr Ala Ile Leu Phe Ile Lys
    610                 615                 620
Asp Asp Lys Tyr Tyr Leu Gly Val Met Asn Lys Lys Asn Asn Lys Ile
625                 630                 635                 640
Phe Asp Asp Lys Ala Ile Lys Glu Asn Lys Gly Glu Gly Tyr Lys Lys
                645                 650                 655
Ile Val Tyr Lys Leu Leu Pro Gly Ala Asn Lys Met Leu Pro Lys Val
            660                 665                 670
Phe Phe Ser Ala Lys Ser Ile Lys Phe Tyr Asn Pro Ser Glu Asp Ile
        675                 680                 685
Leu Arg Ile Arg Asn His Ser Thr His Thr Lys Asn Gly Ser Pro Gln
    690                 695                 700
Lys Gly Tyr Glu Lys Phe Glu Phe Asn Ile Glu Asp Cys Arg Lys Phe
705                 710                 715                 720
Ile Asp Phe Tyr Lys Gln Ser Ile Ser Lys His Pro Glu Trp Lys Asp
                725                 730                 735
Phe Gly Phe Arg Phe Ser Asp Thr Gln Arg Tyr Asn Ser Ile Asp Glu
            740                 745                 750
Phe Tyr Arg Glu Val Glu Asn Gln Gly Tyr Lys Leu Thr Phe Glu Asn
        755                 760                 765
Ile Ser Glu Ser Tyr Ile Asp Ser Val Val Asn Gln Gly Lys Leu Tyr
    770                 775                 780
Leu Phe Gln Ile Tyr Asn Lys Asp Phe Ser Ala Tyr Ser Lys Gly Arg
785                 790                 795                 800
Pro Asn Leu His Thr Leu Tyr Trp Lys Ala Leu Phe Asp Glu Arg Asn
                805                 810                 815
Leu Gln Asp Val Val Tyr Lys Leu Asn Gly Glu Ala Glu Leu Phe Tyr
            820                 825                 830
Arg Lys Gln Ser Ile Pro Lys Lys Ile Thr His Pro Ala Lys Glu Ala
        835                 840                 845
Ile Ala Asn Lys Asn Lys Asp Asn Pro Lys Lys Glu Ser Val Phe Glu
    850                 855                 860
Tyr Asp Leu Ile Lys Asp Lys Arg Phe Thr Glu Asp Lys Phe Phe Phe
865                 870                 875                 880
His Cys Pro Ile Thr Ile Asn Phe Lys Ser Ser Gly Ala Asn Lys Phe
                885                 890                 895
Asn Asp Glu Ile Asn Leu Leu Lys Glu Lys Ala Asn Asp Val His
            900                 905                 910
Ile Leu Ser Ile Asp Arg Gly Glu Arg His Leu Ala Tyr Tyr Thr Leu
        915                 920                 925
Val Asp Gly Lys Gly Asn Ile Ile Lys Gln Asp Thr Phe Asn Ile Ile
    930                 935                 940
```

```
Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu Tyr Asn Ala Ile Val Val Phe Glu Asp Leu
        995                1000                1005

Asn Phe Gly Phe Lys Arg Gly Arg Phe Lys Val Glu Lys Gln Val
    1010                1015                1020

Tyr Gln Lys Leu Glu Lys Met Leu Ile Glu Lys Leu Asn Tyr Leu
    1025                1030                1035

Val Phe Lys Asp Asn Glu Phe Asp Lys Thr Gly Gly Val Leu Arg
    1040                1045                1050

Ala Tyr Gln Leu Thr Ala Pro Phe Glu Thr Phe Lys Lys Met Gly
    1055                1060                1065

Lys Gln Thr Gly Ile Ile Tyr Tyr Val Pro Ala Gly Phe Thr Ser
    1070                1075                1080

Lys Ile Cys Pro Val Thr Gly Phe Val Asn Gln Leu Tyr Pro Lys
    1085                1090                1095

Tyr Glu Ser Val Ser Lys Ser Gln Glu Phe Phe Ser Lys Phe Asp
    1100                1105                1110

Lys Ile Cys Tyr Asn Leu Asp Lys Gly Tyr Phe Glu Phe Ser Phe
    1115                1120                1125

Asp Tyr Lys Asn Phe Gly Asp Lys Ala Ala Lys Gly Lys Trp Thr
    1130                1135                1140

Ile Ala Ser Phe Gly Ser Arg Leu Ile Asn Phe Arg Asn Ser Asp
    1145                1150                1155

Lys Asn His Asn Trp Asp Thr Arg Glu Val Tyr Pro Thr Lys Glu
    1160                1165                1170

Leu Glu Lys Leu Leu Lys Asp Tyr Ser Ile Glu Tyr Gly His Gly
    1175                1180                1185

Glu Cys Ile Lys Ala Ala Ile Cys Gly Glu Ser Asp Lys Lys Phe
    1190                1195                1200

Phe Ala Lys Leu Thr Ser Val Leu Asn Thr Ile Leu Gln Met Arg
    1205                1210                1215

Asn Ser Lys Thr Gly Thr Glu Leu Asp Tyr Leu Ile Ser Pro Val
    1220                1225                1230

Ala Asp Val Asn Gly Asn Phe Phe Asp Ser Arg Gln Ala Pro Lys
    1235                1240                1245

Asn Met Pro Gln Asp Ala Asp Ala Asn Gly Ala Tyr His Ile Gly
    1250                1255                1260

Leu Lys Gly Leu Met Leu Leu Gly Arg Ile Lys Asn Asn Gln Glu
    1265                1270                1275

Gly Lys Lys Leu Asn Leu Val Ile Lys Asn Glu Glu Tyr Phe Glu
    1280                1285                1290

Phe Val Gln Asn Arg Asn Asn Lys Arg Pro Ala Ala Thr Lys Lys
    1295                1300                1305

Ala Gly Gln Ala Lys Lys Lys Lys Gly Ser Tyr Pro Tyr Asp Val
    1310                1315                1320

Pro Asp Tyr Ala Tyr Pro Tyr Asp Val Pro Asp Tyr Ala Tyr Pro
    1325                1330                1335
```

```
Tyr Asp Val Pro Asp Tyr Ala
    1340            1345

<210> SEQ ID NO 55
<211> LENGTH: 1278
<212> TYPE: PRT
<213> ORGANISM: Lachnospiraceae bacterium

<400> SEQUENCE: 55

Met Asp Tyr Gly Asn Gly Gln Phe Glu Arg Arg Ala Pro Leu Thr Lys
1               5                   10                  15

Thr Ile Thr Leu Arg Leu Lys Pro Ile Gly Glu Thr Arg Glu Thr Ile
            20                  25                  30

Arg Glu Gln Lys Leu Leu Glu Gln Asp Ala Ala Phe Arg Lys Leu Val
        35                  40                  45

Glu Thr Val Thr Pro Ile Val Asp Asp Cys Ile Arg Lys Ile Ala Asp
    50                  55                  60

Asn Ala Leu Cys His Phe Gly Thr Glu Tyr Asp Phe Ser Cys Leu Gly
65                  70                  75                  80

Asn Ala Ile Ser Lys Asn Asp Ser Lys Ala Ile Lys Lys Glu Thr Glu
                85                  90                  95

Lys Val Glu Lys Leu Leu Ala Lys Val Leu Thr Glu Asn Leu Pro Asp
            100                 105                 110

Gly Leu Arg Lys Val Asn Asp Ile Asn Ser Ala Ala Phe Ile Gln Asp
        115                 120                 125

Thr Leu Thr Ser Phe Val Gln Asp Asp Ala Asp Lys Arg Val Leu Ile
    130                 135                 140

Gln Glu Leu Lys Gly Lys Thr Val Leu Met Gln Arg Phe Leu Thr Thr
145                 150                 155                 160

Arg Ile Thr Ala Leu Thr Val Trp Leu Pro Asp Arg Val Phe Glu Asn
                165                 170                 175

Phe Asn Ile Phe Ile Glu Asn Ala Glu Lys Met Arg Ile Leu Leu Asp
            180                 185                 190

Ser Pro Leu Asn Glu Lys Ile Met Lys Phe Asp Pro Asp Ala Glu Gln
        195                 200                 205

Tyr Ala Ser Leu Glu Phe Tyr Gly Gln Cys Leu Ser Gln Lys Asp Ile
    210                 215                 220

Asp Ser Tyr Asn Leu Ile Ile Ser Gly Ile Tyr Ala Asp Asp Glu Val
225                 230                 235                 240

Lys Asn Pro Gly Ile Asn Glu Ile Val Lys Glu Tyr Asn Gln Gln Ile
                245                 250                 255

Arg Gly Asp Lys Asp Glu Ser Pro Leu Pro Lys Leu Lys Lys Leu His
            260                 265                 270

Lys Gln Ile Leu Met Pro Val Glu Lys Ala Phe Phe Val Arg Val Leu
        275                 280                 285

Ser Asn Asp Ser Asp Ala Arg Ser Ile Leu Glu Lys Ile Leu Lys Asp
    290                 295                 300

Thr Glu Met Leu Pro Ser Lys Ile Ile Glu Ala Met Lys Glu Ala Asp
305                 310                 315                 320

Ala Gly Asp Ile Ala Val Tyr Gly Ser Arg Leu His Glu Leu Ser His
                325                 330                 335

Val Ile Tyr Gly Asp His Gly Lys Leu Ser Gln Ile Ile Tyr Asp Lys
            340                 345                 350

Glu Ser Lys Arg Ile Ser Glu Leu Met Glu Thr Leu Ser Pro Lys Glu
        355                 360                 365
```

```
Arg Lys Glu Ser Lys Lys Arg Leu Glu Gly Leu Glu Glu His Ile Arg
    370                 375                 380
Lys Ser Thr Tyr Thr Phe Asp Glu Leu Asn Arg Tyr Ala Glu Lys Asn
385                 390                 395                 400
Val Met Ala Ala Tyr Ile Ala Ala Val Glu Glu Ser Cys Ala Glu Ile
                405                 410                 415
Met Arg Lys Glu Lys Asp Leu Arg Thr Leu Leu Ser Lys Glu Asp Val
            420                 425                 430
Lys Ile Arg Gly Asn Arg His Asn Thr Leu Ile Val Lys Asn Tyr Phe
        435                 440                 445
Asn Ala Trp Thr Val Phe Arg Asn Leu Ile Arg Ile Leu Arg Arg Lys
    450                 455                 460
Ser Glu Ala Glu Ile Asp Ser Asp Phe Tyr Asp Val Leu Asp Asp Ser
465                 470                 475                 480
Val Glu Val Leu Ser Leu Thr Tyr Lys Gly Glu Asn Leu Cys Arg Ser
                485                 490                 495
Tyr Ile Thr Lys Lys Ile Gly Ser Asp Leu Lys Pro Glu Ile Ala Thr
            500                 505                 510
Tyr Gly Ser Ala Leu Arg Pro Asn Ser Arg Trp Trp Ser Pro Gly Glu
        515                 520                 525
Lys Phe Asn Val Lys Phe His Thr Ile Val Arg Arg Asp Gly Arg Leu
    530                 535                 540
Tyr Tyr Phe Ile Leu Pro Lys Gly Ala Lys Pro Val Glu Leu Glu Asp
545                 550                 555                 560
Met Asp Gly Asp Ile Glu Cys Leu Gln Met Arg Lys Ile Pro Asn Pro
                565                 570                 575
Thr Ile Phe Leu Pro Lys Leu Val Phe Lys Asp Pro Glu Ala Phe Phe
            580                 585                 590
Arg Asp Asn Pro Glu Ala Asp Glu Phe Val Phe Leu Ser Gly Met Lys
        595                 600                 605
Ala Pro Val Thr Ile Thr Arg Glu Thr Tyr Glu Ala Tyr Arg Tyr Lys
    610                 615                 620
Leu Tyr Thr Val Gly Lys Leu Arg Asp Gly Glu Val Ser Glu Glu Glu
625                 630                 635                 640
Tyr Lys Arg Ala Leu Leu Gln Val Leu Thr Ala Tyr Lys Glu Phe Leu
                645                 650                 655
Glu Asn Arg Met Ile Tyr Ala Asp Leu Asn Phe Gly Phe Lys Asp Leu
            660                 665                 670
Glu Glu Tyr Lys Asp Ser Ser Glu Phe Ile Lys Gln Val Glu Thr His
        675                 680                 685
Asn Thr Phe Met Cys Trp Ala Lys Val Ser Ser Gln Leu Asp Asp
    690                 695                 700
Leu Val Lys Ser Gly Asn Gly Leu Leu Phe Glu Ile Trp Ser Glu Arg
705                 710                 715                 720
Leu Glu Ser Tyr Tyr Lys Tyr Gly Asn Glu Lys Val Leu Arg Gly Tyr
                725                 730                 735
Glu Gly Val Leu Leu Ser Ile Leu Lys Asp Glu Asn Leu Val Ser Met
            740                 745                 750
Arg Thr Leu Leu Asn Ser Arg Pro Met Leu Val Tyr Arg Pro Lys Glu
        755                 760                 765
Ser Ser Lys Pro Met Val Val His Arg Asp Gly Ser Arg Val Val Asp
    770                 775                 780
```

```
Arg Phe Asp Lys Asp Gly Lys Tyr Ile Pro Glu Val His Asp Glu
785                 790                 795                 800

Leu Tyr Arg Phe Phe Asn Asn Leu Leu Ile Lys Glu Lys Leu Gly Glu
            805                 810                 815

Lys Ala Arg Lys Ile Leu Asp Asn Lys Lys Val Lys Val Lys Val Leu
        820                 825                 830

Glu Ser Glu Arg Val Lys Trp Ser Lys Phe Tyr Asp Glu Gln Phe Ala
        835                 840                 845

Val Thr Phe Ser Val Lys Lys Asn Ala Asp Cys Leu Asp Thr Thr Lys
    850                 855                 860

Asp Leu Asn Ala Glu Val Met Glu Gln Tyr Ser Glu Ser Asn Arg Leu
865                 870                 875                 880

Ile Leu Ile Arg Asn Thr Thr Asp Ile Leu Tyr Tyr Leu Val Leu Asp
            885                 890                 895

Lys Asn Gly Lys Val Leu Lys Gln Arg Ser Leu Asn Ile Ile Asn Asp
        900                 905                 910

Gly Ala Arg Asp Val Asp Trp Lys Glu Arg Phe Arg Gln Val Thr Lys
        915                 920                 925

Asp Arg Asn Glu Gly Tyr Asn Glu Trp Asp Tyr Ser Arg Thr Ser Asn
930                 935                 940

Asp Leu Lys Glu Val Tyr Leu Asn Tyr Ala Leu Lys Glu Ile Ala Glu
945                 950                 955                 960

Ala Val Ile Glu Tyr Asn Ala Ile Leu Ile Ile Glu Lys Met Ser Asn
            965                 970                 975

Ala Phe Lys Asp Lys Tyr Ser Phe Leu Asp Asp Val Thr Phe Lys Gly
        980                 985                 990

Phe Glu Thr Lys Leu Leu Ala Lys Leu Ser Asp Leu His Phe Arg Gly
        995                 1000                1005

Ile Lys Asp Gly Glu Pro Cys Ser Phe Thr Asn Pro Leu Gln Leu
    1010                1015                1020

Cys Gln Asn Asp Ser Asn Lys Ile Leu Gln Asp Gly Val Ile Phe
    1025                1030                1035

Met Val Pro Asn Ser Met Thr Arg Ser Leu Asp Pro Asp Thr Gly
    1040                1045                1050

Phe Ile Phe Ala Ile Asn Asp His Asn Ile Arg Thr Lys Lys Ala
    1055                1060                1065

Lys Leu Asn Phe Leu Ser Lys Phe Asp Gln Leu Lys Val Ser Ser
    1070                1075                1080

Glu Gly Cys Leu Ile Met Lys Tyr Ser Gly Asp Ser Leu Pro Thr
    1085                1090                1095

His Asn Thr Asp Asn Arg Val Trp Asn Cys Cys Cys Asn His Pro
    1100                1105                1110

Ile Thr Asn Tyr Asp Arg Glu Thr Lys Lys Val Glu Phe Ile Glu
    1115                1120                1125

Glu Pro Val Glu Glu Leu Ser Arg Val Leu Glu Glu Asn Gly Ile
    1130                1135                1140

Glu Thr Asp Thr Glu Leu Asn Lys Leu Asn Glu Arg Glu Asn Val
    1145                1150                1155

Pro Gly Lys Val Val Asp Ala Ile Tyr Ser Leu Val Leu Asn Tyr
    1160                1165                1170

Leu Arg Gly Thr Val Ser Gly Val Ala Gly Gln Arg Ala Val Tyr
    1175                1180                1185

Tyr Ser Pro Val Thr Gly Lys Lys Tyr Asp Ile Ser Phe Ile Gln
```

```
                    1190                1195                1200
Ala Met Asn Leu Asn Arg Lys Cys Asp Tyr Tyr Arg Ile Gly Ser
            1205                1210                1215
Lys Glu Arg Gly Glu Trp Thr Asp Phe Val Ala Gln Leu Ile Asn
            1220                1225                1230
Lys Arg Pro Ala Ala Thr Lys Lys Ala Gly Gln Ala Lys Lys Lys
            1235                1240                1245
Lys Gly Ser Tyr Pro Tyr Asp Val Pro Asp Tyr Ala Tyr Pro Tyr
            1250                1255                1260
Asp Val Pro Asp Tyr Ala Tyr Pro Tyr Asp Val Pro Asp Tyr Ala
            1265                1270                1275

<210> SEQ ID NO 56
<211> LENGTH: 1286
<212> TYPE: PRT
<213> ORGANISM: Butyrivibrio proteoclasticus

<400> SEQUENCE: 56

Met Leu Leu Tyr Glu Asn Tyr Thr Lys Arg Asn Gln Ile Thr Lys Ser
1               5                   10                  15
Leu Arg Leu Glu Leu Arg Pro Gln Gly Lys Thr Leu Arg Asn Ile Lys
            20                  25                  30
Glu Leu Asn Leu Leu Glu Gln Asp Lys Ala Ile Tyr Ala Leu Leu Glu
        35                  40                  45
Arg Leu Lys Pro Val Ile Asp Glu Gly Ile Lys Asp Ile Ala Arg Asp
    50                  55                  60
Thr Leu Lys Asn Cys Glu Leu Ser Phe Glu Lys Leu Tyr Glu His Phe
65                  70                  75                  80
Leu Ser Gly Asp Lys Lys Ala Tyr Ala Lys Glu Ser Glu Arg Leu Lys
                85                  90                  95
Lys Glu Ile Val Lys Thr Leu Ile Lys Asn Leu Pro Glu Gly Ile Gly
            100                 105                 110
Lys Ile Ser Glu Ile Asn Ser Ala Lys Tyr Leu Asn Gly Val Leu Tyr
        115                 120                 125
Asp Phe Ile Asp Lys Thr His Lys Asp Ser Glu Lys Gln Asn Ile
    130                 135                 140
Leu Ser Asp Ile Leu Glu Thr Lys Gly Tyr Leu Ala Leu Phe Ser Lys
145                 150                 155                 160
Phe Leu Thr Ser Arg Ile Thr Thr Leu Glu Gln Ser Met Pro Lys Arg
                165                 170                 175
Val Ile Glu Asn Phe Glu Ile Tyr Ala Ala Asn Ile Pro Lys Met Gln
            180                 185                 190
Asp Ala Leu Glu Arg Gly Ala Val Ser Phe Ala Ile Glu Tyr Glu Ser
        195                 200                 205
Ile Cys Ser Val Asp Tyr Tyr Asn Gln Ile Leu Ser Gln Glu Asp Ile
    210                 215                 220
Asp Ser Tyr Asn Arg Leu Ile Ser Gly Ile Met Asp Glu Asp Gly Ala
225                 230                 235                 240
Lys Glu Lys Gly Ile Asn Gln Thr Ile Ser Glu Lys Asn Ile Lys Ile
                245                 250                 255
Lys Ser Glu His Leu Glu Glu Lys Pro Phe Arg Ile Leu Lys Gln Leu
            260                 265                 270
His Lys Gln Ile Leu Glu Glu Arg Glu Lys Ala Phe Thr Ile Asp His
        275                 280                 285
```

-continued

```
Ile Asp Ser Asp Glu Glu Val Val Gln Val Thr Lys Glu Ala Phe Glu
290                 295                 300
Gln Thr Lys Glu Gln Trp Glu Asn Ile Lys Lys Ile Asn Gly Phe Tyr
305                 310                 315                 320
Ala Lys Asp Pro Gly Asp Ile Thr Leu Phe Ile Val Val Gly Pro Asn
            325                 330                 335
Gln Thr His Val Leu Ser Gln Leu Ile Tyr Gly His Asp Arg Ile
            340                 345                 350
Arg Leu Leu Leu Glu Glu Tyr Glu Lys Asn Thr Leu Glu Val Leu Pro
            355                 360                 365
Arg Arg Thr Lys Ser Glu Lys Ala Arg Tyr Asp Lys Phe Val Asn Ala
370                 375                 380
Val Pro Lys Lys Val Ala Lys Glu Ser His Thr Phe Asp Gly Leu Gln
385                 390                 395                 400
Lys Met Thr Gly Asp Asp Arg Leu Phe Ile Leu Tyr Arg Asp Glu Leu
            405                 410                 415
Ala Arg Asn Tyr Met Arg Ile Lys Glu Ala Tyr Gly Thr Phe Glu Arg
            420                 425                 430
Asp Ile Leu Lys Ser Arg Arg Gly Ile Lys Gly Asn Arg Asp Val Gln
            435                 440                 445
Glu Ser Leu Val Ser Phe Tyr Asp Glu Leu Thr Lys Phe Arg Ser Ala
450                 455                 460
Leu Arg Ile Ile Asn Ser Gly Asn Asp Glu Lys Ala Asp Pro Ile Phe
465                 470                 475                 480
Tyr Asn Thr Phe Asp Gly Ile Phe Glu Lys Ala Asn Arg Thr Tyr Lys
            485                 490                 495
Ala Glu Asn Leu Cys Arg Asn Tyr Val Thr Lys Ser Pro Ala Asp Asp
            500                 505                 510
Ala Arg Ile Met Ala Ser Cys Leu Gly Thr Pro Ala Arg Leu Arg Thr
            515                 520                 525
His Trp Trp Asn Gly Glu Glu Asn Phe Ala Ile Asn Asp Val Ala Met
530                 535                 540
Ile Arg Arg Gly Asp Glu Tyr Tyr Tyr Phe Val Leu Thr Pro Asp Val
545                 550                 555                 560
Lys Pro Val Asp Leu Lys Thr Lys Asp Glu Thr Asp Ala Gln Ile Phe
            565                 570                 575
Val Gln Arg Lys Gly Ala Lys Ser Phe Leu Gly Leu Pro Lys Ala Leu
            580                 585                 590
Phe Lys Cys Ile Leu Glu Pro Tyr Phe Glu Ser Pro Glu His Lys Asn
            595                 600                 605
Asp Lys Asn Cys Val Ile Glu Glu Tyr Val Ser Lys Pro Leu Thr Ile
610                 615                 620
Asp Arg Arg Ala Tyr Asp Ile Phe Lys Asn Gly Thr Phe Lys Lys Thr
625                 630                 635                 640
Asn Ile Gly Ile Asp Gly Leu Thr Glu Glu Lys Phe Lys Asp Asp Cys
            645                 650                 655
Arg Tyr Leu Ile Asp Val Tyr Lys Glu Phe Ile Ala Val Tyr Thr Arg
            660                 665                 670
Tyr Ser Cys Phe Asn Met Ser Gly Leu Lys Arg Ala Asp Glu Tyr Asn
            675                 680                 685
Asp Ile Gly Glu Phe Phe Ser Asp Val Asp Thr Arg Leu Cys Thr Met
690                 695                 700
Glu Trp Ile Pro Val Ser Phe Glu Arg Ile Asn Asp Met Val Asp Lys
```

-continued

```
            705                 710                 715                 720
Lys Glu Gly Leu Leu Phe Leu Val Arg Ser Met Phe Leu Tyr Asn Arg
                    725                 730                 735
Pro Arg Lys Pro Tyr Glu Arg Thr Phe Ile Gln Leu Phe Ser Asp Ser
                    740                 745                 750
Asn Met Glu His Thr Ser Met Leu Leu Asn Ser Arg Ala Met Ile Gln
                    755                 760                 765
Tyr Arg Ala Ala Ser Leu Pro Arg Arg Val Thr His Lys Lys Gly Ser
                    770                 775                 780
Ile Leu Val Ala Leu Arg Asp Ser Asn Gly Glu His Ile Pro Met His
785                 790                 795                 800
Ile Arg Glu Ala Ile Tyr Lys Met Lys Asn Asn Phe Asp Ile Ser Ser
                    805                 810                 815
Glu Asp Phe Ile Met Ala Lys Ala Tyr Leu Ala Glu His Asp Val Ala
                    820                 825                 830
Ile Lys Lys Ala Asn Glu Asp Ile Ile Arg Asn Arg Arg Tyr Thr Glu
                    835                 840                 845
Asp Lys Phe Phe Leu Ser Leu Ser Tyr Thr Lys Asn Ala Asp Ile Ser
850                 855                 860
Ala Arg Thr Leu Asp Tyr Ile Asn Asp Lys Val Glu Glu Asp Thr Gln
865                 870                 875                 880
Asp Ser Arg Met Ala Val Ile Val Thr Arg Asn Leu Lys Asp Leu Thr
                    885                 890                 895
Tyr Val Ala Val Val Asp Glu Lys Asn Asn Val Leu Glu Glu Lys Ser
                    900                 905                 910
Leu Asn Glu Ile Asp Gly Val Asn Tyr Arg Glu Leu Leu Lys Glu Arg
                    915                 920                 925
Thr Lys Ile Lys Tyr His Asp Lys Thr Arg Leu Trp Gln Tyr Asp Val
                    930                 935                 940
Ser Ser Lys Gly Leu Lys Glu Ala Tyr Val Glu Leu Ala Val Thr Gln
945                 950                 955                 960
Ile Ser Lys Leu Ala Thr Lys Tyr Asn Ala Val Val Val Glu Ser
                    965                 970                 975
Met Ser Ser Thr Phe Lys Asp Lys Phe Ser Phe Leu Asp Glu Gln Ile
                    980                 985                 990
Phe Lys Ala Phe Glu Ala Arg Leu Cys Ala Arg Met Ser Asp Leu Ser
                    995                 1000                1005
Phe Asn Thr Ile Lys Glu Gly Glu Ala Gly Ser Ile Ser Asn Pro
                    1010                1015                1020
Ile Gln Val Ser Asn Asn Asn Gly Asn Ser Tyr Gln Asp Gly Val
                    1025                1030                1035
Ile Tyr Phe Leu Asn Asn Ala Tyr Thr Arg Thr Leu Cys Pro Asp
                    1040                1045                1050
Thr Gly Phe Val Asp Val Phe Asp Lys Thr Arg Leu Ile Thr Met
                    1055                1060                1065
Gln Ser Lys Arg Gln Phe Ala Lys Met Lys Asp Ile Arg Ile
                    1070                1075                1080
Asp Asp Gly Glu Met Leu Phe Thr Phe Asn Leu Glu Glu Tyr Pro
                    1085                1090                1095
Thr Lys Arg Leu Leu Asp Arg Lys Glu Trp Thr Val Lys Ile Ala
                    1100                1105                1110
Gly Asp Gly Ser Tyr Phe Asp Lys Asp Lys Gly Glu Tyr Val Tyr
                    1115                1120                1125
```

```
Val Asn Asp Ile Val Arg Glu Gln Ile Ile Pro Ala Leu Leu Glu
    1130            1135            1140

Asp Lys Ala Val Phe Asp Gly Asn Met Ala Glu Lys Phe Leu Asp
    1145            1150            1155

Lys Thr Ala Ile Ser Gly Lys Ser Val Glu Leu Ile Tyr Lys Trp
    1160            1165            1170

Phe Ala Asn Ala Leu Tyr Gly Ile Ile Thr Lys Lys Asp Gly Glu
    1175            1180            1185

Lys Ile Tyr Arg Ser Pro Ile Thr Gly Thr Glu Ile Asp Val Ser
    1190            1195            1200

Lys Asn Thr Thr Tyr Asn Phe Gly Lys Lys Phe Met Phe Lys Gln
    1205            1210            1215

Glu Tyr Arg Gly Asp Gly Asp Phe Leu Asp Ala Phe Leu Asn Tyr
    1220            1225            1230

Met Gln Ala Gln Asp Ile Ala Val Lys Arg Pro Ala Ala Thr Lys
    1235            1240            1245

Lys Ala Gly Gln Ala Lys Lys Lys Lys Gly Ser Tyr Pro Tyr Asp
    1250            1255            1260

Val Pro Asp Tyr Ala Tyr Pro Tyr Asp Val Pro Asp Tyr Ala Tyr
    1265            1270            1275

Pro Tyr Asp Val Pro Asp Tyr Ala
    1280            1285

<210> SEQ ID NO 57
<211> LENGTH: 1522
<212> TYPE: PRT
<213> ORGANISM: Peregrinibacteria bacterium

<400> SEQUENCE: 57

Met Ser Asn Phe Phe Lys Asn Phe Thr Asn Leu Tyr Glu Leu Ser Lys
1               5                   10                  15

Thr Leu Arg Phe Glu Leu Lys Pro Val Gly Asp Thr Leu Thr Asn Met
                20                  25                  30

Lys Asp His Leu Glu Tyr Asp Glu Lys Leu Gln Thr Phe Leu Lys Asp
        35                  40                  45

Gln Asn Ile Asp Asp Ala Tyr Gln Ala Leu Lys Pro Gln Phe Asp Glu
    50                  55                  60

Ile His Glu Glu Phe Ile Thr Asp Ser Leu Glu Ser Lys Lys Ala Lys
65                  70                  75                  80

Glu Ile Asp Phe Ser Glu Tyr Leu Asp Leu Phe Gln Glu Lys Lys Glu
                85                  90                  95

Leu Asn Asp Ser Glu Lys Lys Leu Arg Asn Lys Ile Gly Glu Thr Phe
            100                 105                 110

Asn Lys Ala Gly Glu Lys Trp Lys Lys Glu Lys Tyr Pro Gln Tyr Glu
        115                 120                 125

Trp Lys Lys Gly Ser Lys Ile Ala Asn Gly Ala Asp Ile Leu Ser Cys
    130                 135                 140

Gln Asp Met Leu Gln Phe Ile Lys Tyr Lys Asn Pro Glu Asp Glu Lys
145                 150                 155                 160

Ile Lys Asn Tyr Ile Asp Asp Thr Leu Lys Gly Phe Phe Thr Tyr Phe
                165                 170                 175

Gly Gly Phe Asn Gln Asn Arg Ala Asn Tyr Tyr Glu Thr Lys Lys Glu
            180                 185                 190

Ala Ser Thr Ala Val Ala Thr Arg Ile Val His Glu Asn Leu Pro Lys
```

```
            195                 200                 205
Phe Cys Asp Asn Val Ile Gln Phe Lys His Ile Ile Lys Arg Lys Lys
210                 215                 220
Asp Gly Thr Val Glu Lys Thr Glu Arg Lys Thr Glu Tyr Leu Asn Ala
225                 230                 235                 240
Tyr Gln Tyr Leu Lys Asn Asn Lys Ile Thr Gln Ile Lys Asp Ala
            245                 250                 255
Glu Thr Glu Lys Met Ile Glu Ser Thr Pro Ile Ala Glu Lys Ile Phe
            260                 265                 270
Asp Val Tyr Tyr Phe Ser Ser Cys Leu Ser Gln Lys Gln Ile Glu Glu
            275                 280                 285
Tyr Asn Arg Ile Ile Gly His Tyr Asn Leu Leu Ile Asn Leu Tyr Asn
            290                 295                 300
Gln Ala Lys Arg Ser Glu Gly Lys His Leu Ser Ala Asn Glu Lys Lys
305                 310                 315                 320
Tyr Lys Asp Leu Pro Lys Phe Lys Thr Leu Tyr Lys Gln Ile Gly Cys
                325                 330                 335
Gly Lys Lys Lys Asp Leu Phe Tyr Thr Ile Lys Cys Asp Thr Glu Glu
            340                 345                 350
Glu Ala Asn Lys Ser Arg Asn Glu Gly Lys Glu Ser His Ser Val Glu
            355                 360                 365
Glu Ile Ile Asn Lys Ala Gln Glu Ala Ile Asn Lys Tyr Phe Lys Ser
            370                 375                 380
Asn Asn Asp Cys Glu Asn Ile Asn Thr Val Pro Asp Phe Ile Asn Tyr
385                 390                 395                 400
Ile Leu Thr Lys Glu Asn Tyr Glu Gly Val Tyr Trp Ser Lys Ala Ala
                405                 410                 415
Met Asn Thr Ile Ser Asp Lys Tyr Phe Ala Asn Tyr His Asp Leu Gln
            420                 425                 430
Asp Arg Leu Lys Glu Ala Lys Val Phe Gln Lys Ala Asp Lys Lys Ser
            435                 440                 445
Glu Asp Asp Ile Lys Ile Pro Glu Ala Ile Glu Leu Ser Gly Leu Phe
450                 455                 460
Gly Val Leu Asp Ser Leu Ala Asp Trp Gln Thr Thr Leu Phe Lys Ser
465                 470                 475                 480
Ser Ile Leu Ser Asn Glu Asp Lys Leu Lys Ile Ile Thr Asp Ser Gln
                485                 490                 495
Thr Pro Ser Glu Ala Leu Leu Lys Met Ile Phe Asn Asp Ile Glu Lys
                500                 505                 510
Asn Met Glu Ser Phe Leu Lys Glu Thr Asn Asp Ile Ile Thr Leu Lys
            515                 520                 525
Lys Tyr Lys Gly Asn Lys Glu Gly Thr Glu Lys Ile Lys Gln Trp Phe
            530                 535                 540
Asp Tyr Thr Leu Ala Ile Asn Arg Met Leu Lys Tyr Phe Leu Val Lys
545                 550                 555                 560
Glu Asn Lys Ile Lys Gly Asn Ser Leu Asp Thr Asn Ile Ser Glu Ala
                565                 570                 575
Leu Lys Thr Leu Ile Tyr Ser Asp Asp Ala Glu Trp Phe Lys Trp Tyr
            580                 585                 590
Asp Ala Leu Arg Asn Tyr Leu Thr Gln Lys Pro Gln Asp Glu Ala Lys
            595                 600                 605
Glu Asn Lys Leu Lys Leu Asn Phe Asp Asn Pro Ser Leu Ala Gly Gly
            610                 615                 620
```

-continued

Trp Asp Val Asn Lys Glu Cys Ser Asn Phe Cys Val Ile Leu Lys Asp
625                 630                 635                 640

Lys Asn Glu Lys Lys Tyr Leu Ala Ile Met Lys Lys Gly Glu Asn Thr
            645                 650                 655

Leu Phe Gln Lys Glu Trp Thr Glu Gly Arg Gly Lys Asn Leu Thr Lys
        660                 665                 670

Lys Ser Asn Pro Leu Phe Glu Ile Asn Cys Glu Ile Leu Ser Lys
            675                 680                 685

Met Glu Tyr Asp Phe Trp Ala Asp Val Ser Lys Met Ile Pro Lys Cys
        690                 695                 700

Ser Thr Gln Leu Lys Ala Val Val Asn His Phe Lys Gln Ser Asp Asn
705                 710                 715                 720

Glu Phe Ile Phe Pro Ile Gly Tyr Lys Val Thr Ser Gly Glu Lys Phe
                725                 730                 735

Arg Glu Glu Cys Lys Ile Ser Lys Gln Asp Phe Glu Leu Asn Asn Lys
            740                 745                 750

Val Phe Asn Lys Asn Glu Leu Ser Val Thr Ala Met Arg Tyr Asp Leu
        755                 760                 765

Ser Ser Thr Gln Glu Lys Gln Tyr Ile Lys Ala Phe Gln Lys Glu Tyr
770                 775                 780

Trp Glu Leu Leu Phe Lys Gln Glu Lys Arg Asp Thr Lys Leu Thr Asn
785                 790                 795                 800

Asn Glu Ile Phe Asn Glu Trp Ile Asn Phe Cys Asn Lys Lys Tyr Ser
                805                 810                 815

Glu Leu Leu Ser Trp Glu Arg Lys Tyr Lys Asp Ala Leu Thr Asn Trp
            820                 825                 830

Ile Asn Phe Cys Lys Tyr Phe Leu Ser Lys Tyr Pro Lys Thr Thr Leu
        835                 840                 845

Phe Asn Tyr Ser Phe Lys Glu Ser Glu Asn Tyr Asn Ser Leu Asp Glu
850                 855                 860

Phe Tyr Arg Asp Val Asp Ile Cys Ser Tyr Lys Leu Asn Ile Asn Thr
865                 870                 875                 880

Thr Ile Asn Lys Ser Ile Leu Asp Arg Leu Val Glu Glu Gly Lys Leu
                885                 890                 895

Tyr Leu Phe Glu Ile Lys Asn Gln Asp Ser Asn Asp Gly Lys Ser Ile
            900                 905                 910

Gly His Lys Asn Asn Leu His Thr Ile Tyr Trp Asn Ala Ile Phe Glu
        915                 920                 925

Asn Phe Asp Asn Arg Pro Lys Leu Asn Gly Glu Ala Glu Ile Phe Tyr
        930                 935                 940

Arg Lys Ala Ile Ser Lys Asp Lys Leu Gly Ile Val Lys Gly Lys Lys
945                 950                 955                 960

Thr Lys Asn Gly Thr Glu Ile Ile Lys Asn Tyr Arg Phe Ser Lys Glu
                965                 970                 975

Lys Phe Ile Leu His Val Pro Ile Thr Leu Asn Phe Cys Ser Asn Asn
            980                 985                 990

Glu Tyr Val Asn Asp Ile Val Asn Thr Lys Phe Tyr Asn Phe Ser Asn
            995                 1000                1005

Leu His Phe Leu Gly Ile Asp Arg Gly Glu Lys His Leu Ala Tyr
        1010                1015                1020

Tyr Ser Leu Val Asn Lys Asn Gly Glu Ile Val Asp Gln Gly Thr
        1025                1030                1035

-continued

```
Leu Asn Leu Pro Phe Thr Asp Lys Asp Gly Asn Gln Arg Ser Ile
    1040                1045                1050

Lys Lys Glu Lys Tyr Phe Tyr Asn Lys Gln Glu Asp Lys Trp Glu
    1055                1060                1065

Ala Lys Glu Val Asp Cys Trp Asn Tyr Asn Asp Leu Leu Asp Ala
    1070                1075                1080

Met Ala Ser Asn Arg Asp Met Ala Arg Lys Asn Trp Gln Arg Ile
    1085                1090                1095

Gly Thr Ile Lys Glu Ala Lys Asn Gly Tyr Val Ser Leu Val Ile
    1100                1105                1110

Arg Lys Ile Ala Asp Leu Ala Val Asn Asn Glu Arg Pro Ala Phe
    1115                1120                1125

Ile Val Leu Glu Asp Leu Asn Thr Gly Phe Lys Arg Ser Arg Gln
    1130                1135                1140

Lys Ile Asp Lys Ser Val Tyr Gln Lys Phe Glu Leu Ala Leu Ala
    1145                1150                1155

Lys Lys Leu Asn Phe Leu Val Asp Lys Asn Ala Lys Arg Asp Glu
    1160                1165                1170

Ile Gly Ser Pro Thr Lys Ala Leu Gln Leu Thr Pro Pro Val Asn
    1175                1180                1185

Asn Tyr Gly Asp Ile Glu Asn Lys Lys Gln Ala Gly Ile Met Leu
    1190                1195                1200

Tyr Thr Arg Ala Asn Tyr Thr Ser Gln Thr Asp Pro Ala Thr Gly
    1205                1210                1215

Trp Arg Lys Thr Ile Tyr Leu Lys Ala Gly Pro Glu Glu Thr Thr
    1220                1225                1230

Tyr Lys Lys Asp Gly Lys Ile Lys Asn Lys Ser Val Lys Asp Gln
    1235                1240                1245

Ile Ile Glu Thr Phe Thr Asp Ile Gly Phe Asp Gly Lys Asp Tyr
    1250                1255                1260

Tyr Phe Glu Tyr Asp Lys Gly Glu Phe Val Asp Glu Lys Thr Gly
    1265                1270                1275

Glu Ile Lys Pro Lys Lys Trp Arg Leu Tyr Ser Gly Glu Asn Gly
    1280                1285                1290

Lys Ser Leu Asp Arg Phe Arg Gly Glu Arg Glu Lys Asp Lys Tyr
    1295                1300                1305

Glu Trp Lys Ile Asp Lys Ile Asp Ile Val Lys Ile Leu Asp Asp
    1310                1315                1320

Leu Phe Val Asn Phe Asp Lys Asn Ile Ser Leu Leu Lys Gln Leu
    1325                1330                1335

Lys Glu Gly Val Glu Leu Thr Arg Asn Asn Glu His Gly Thr Gly
    1340                1345                1350

Glu Ser Leu Arg Phe Ala Ile Asn Leu Ile Gln Gln Ile Arg Asn
    1355                1360                1365

Thr Gly Asn Asn Glu Arg Asp Asn Asp Phe Ile Leu Ser Pro Val
    1370                1375                1380

Arg Asp Glu Asn Gly Lys His Phe Asp Ser Arg Glu Tyr Trp Asp
    1385                1390                1395

Lys Glu Thr Lys Gly Glu Lys Ile Ser Met Pro Ser Ser Gly Asp
    1400                1405                1410

Ala Asn Gly Ala Phe Asn Ile Ala Arg Lys Gly Ile Ile Met Asn
    1415                1420                1425

Ala His Ile Leu Ala Asn Ser Asp Ser Lys Asp Leu Ser Leu Phe
```

```
                   1430                  1435                  1440

Val Ser Asp Glu Trp Asp Leu His Leu Asn Asn Lys Thr Glu
    1445                  1450                  1455

Trp Lys Lys Gln Leu Asn Ile Phe Ser Ser Arg Lys Ala Met Ala
1460                      1465                  1470

Lys Arg Lys Lys Lys Arg Pro Ala Ala Thr Lys Lys Ala Gly Gln
    1475                  1480                  1485

Ala Lys Lys Lys Gly Ser Tyr Pro Tyr Asp Val Pro Asp Tyr
    1490                  1495                  1500

Ala Tyr Pro Tyr Asp Val Pro Asp Tyr Ala Tyr Pro Tyr Asp Val
    1505                  1510                  1515

Pro Asp Tyr Ala
    1520

<210> SEQ ID NO 58
<211> LENGTH: 1397
<212> TYPE: PRT
<213> ORGANISM: Parcubacteria bacterium

<400> SEQUENCE: 58

Met Glu Asn Ile Phe Asp Gln Phe Ile Gly Lys Tyr Ser Leu Ser Lys
1               5                   10                  15

Thr Leu Arg Phe Glu Leu Lys Pro Val Gly Lys Thr Glu Asp Phe Leu
            20                  25                  30

Lys Ile Asn Lys Val Phe Glu Lys Asp Gln Thr Ile Asp Asp Ser Tyr
        35                  40                  45

Asn Gln Ala Lys Phe Tyr Phe Asp Ser Leu His Gln Lys Phe Ile Asp
    50                  55                  60

Ala Ala Leu Ala Ser Asp Lys Thr Ser Glu Leu Ser Phe Gln Asn Phe
65                  70                  75                  80

Ala Asp Val Leu Glu Lys Gln Asn Lys Ile Ile Leu Asp Lys Lys Arg
                85                  90                  95

Glu Met Gly Ala Leu Arg Lys Arg Asp Lys Asn Ala Val Gly Ile Asp
            100                 105                 110

Arg Leu Gln Lys Glu Ile Asn Asp Ala Glu Asp Ile Ile Gln Lys Glu
        115                 120                 125

Lys Glu Lys Ile Tyr Lys Asp Val Arg Thr Leu Phe Asp Asn Glu Ala
    130                 135                 140

Glu Ser Trp Lys Thr Tyr Tyr Gln Glu Arg Glu Val Asp Gly Lys Lys
145                 150                 155                 160

Ile Thr Phe Ser Lys Ala Asp Leu Lys Gln Lys Gly Ala Asp Phe Leu
                165                 170                 175

Thr Ala Ala Gly Ile Leu Lys Val Leu Lys Tyr Glu Phe Pro Glu Glu
            180                 185                 190

Lys Glu Lys Glu Phe Gln Ala Lys Asn Gln Pro Ser Leu Phe Val Glu
        195                 200                 205

Glu Lys Glu Asn Pro Gly Gln Lys Arg Tyr Ile Phe Asp Ser Phe Asp
    210                 215                 220

Lys Phe Ala Gly Tyr Leu Thr Lys Phe Gln Gln Thr Lys Lys Asn Leu
225                 230                 235                 240

Tyr Ala Ala Asp Gly Thr Ser Thr Ala Val Ala Thr Arg Ile Ala Asp
                245                 250                 255

Asn Phe Ile Ile Phe His Gln Asn Thr Lys Val Phe Arg Asp Lys Tyr
            260                 265                 270
```

```
Lys Asn Asn His Thr Asp Leu Gly Phe Asp Glu Glu Asn Ile Phe Glu
            275                 280                 285

Ile Glu Arg Tyr Lys Asn Cys Leu Leu Gln Arg Glu Ile Glu His Ile
        290                 295                 300

Lys Asn Glu Asn Ser Tyr Asn Lys Ile Ile Gly Arg Ile Asn Lys Lys
305                 310                 315                 320

Ile Lys Glu Tyr Arg Asp Gln Lys Ala Lys Asp Thr Lys Leu Thr Lys
                325                 330                 335

Ser Asp Phe Pro Phe Phe Lys Asn Leu Asp Lys Gln Ile Leu Gly Glu
            340                 345                 350

Val Glu Lys Glu Lys Gln Leu Ile Glu Lys Thr Arg Glu Lys Thr Glu
        355                 360                 365

Glu Asp Val Leu Ile Glu Arg Phe Lys Glu Phe Ile Glu Asn Asn Glu
370                 375                 380

Glu Arg Phe Thr Ala Ala Lys Lys Leu Met Asn Ala Phe Cys Asn Gly
385                 390                 395                 400

Glu Phe Glu Ser Glu Tyr Glu Gly Ile Tyr Leu Lys Asn Lys Ala Ile
                405                 410                 415

Asn Thr Ile Ser Arg Arg Trp Phe Val Ser Asp Arg Asp Phe Glu Leu
            420                 425                 430

Lys Leu Pro Gln Gln Lys Ser Lys Asn Lys Ser Glu Lys Asn Glu Pro
        435                 440                 445

Lys Val Lys Lys Phe Ile Ser Ile Ala Glu Ile Lys Asn Ala Val Glu
        450                 455                 460

Glu Leu Asp Gly Asp Ile Phe Lys Ala Val Phe Tyr Asp Lys Lys Ile
465                 470                 475                 480

Ile Ala Gln Gly Gly Ser Lys Leu Glu Gln Phe Leu Val Ile Trp Lys
                485                 490                 495

Tyr Glu Phe Glu Tyr Leu Phe Arg Asp Ile Glu Arg Glu Asn Gly Glu
            500                 505                 510

Lys Leu Leu Gly Tyr Asp Ser Cys Leu Lys Ile Ala Lys Gln Leu Gly
        515                 520                 525

Ile Phe Pro Gln Glu Lys Glu Ala Arg Glu Lys Ala Thr Ala Val Ile
        530                 535                 540

Lys Asn Tyr Ala Asp Ala Gly Leu Gly Ile Phe Gln Met Met Lys Tyr
545                 550                 555                 560

Phe Ser Leu Asp Asp Lys Asp Arg Lys Asn Thr Pro Gly Gln Leu Ser
                565                 570                 575

Thr Asn Phe Tyr Ala Glu Tyr Asp Gly Tyr Tyr Lys Asp Phe Glu Phe
            580                 585                 590

Ile Lys Tyr Tyr Asn Glu Phe Arg Asn Phe Ile Thr Lys Lys Pro Phe
        595                 600                 605

Asp Glu Asp Lys Ile Lys Leu Asn Phe Glu Asn Gly Ala Leu Leu Lys
    610                 615                 620

Gly Trp Asp Glu Asn Lys Glu Tyr Asp Phe Met Gly Val Ile Leu Lys
625                 630                 635                 640

Lys Glu Gly Arg Leu Tyr Leu Gly Ile Met His Lys Asn His Arg Lys
                645                 650                 655

Leu Phe Gln Ser Met Gly Asn Ala Lys Gly Asp Asn Ala Asn Arg Tyr
            660                 665                 670

Gln Lys Met Ile Tyr Lys Gln Ile Ala Asp Ala Ser Lys Asp Val Pro
        675                 680                 685

Arg Leu Leu Leu Thr Ser Lys Lys Ala Met Glu Lys Phe Lys Pro Ser
```

-continued

```
            690                 695                 700
Gln Glu Ile Leu Arg Ile Lys Lys Glu Lys Thr Phe Lys Arg Glu Ser
705                 710                 715                 720

Lys Asn Phe Ser Leu Arg Asp Leu His Ala Leu Ile Glu Tyr Tyr Arg
                725                 730                 735

Asn Cys Ile Pro Gln Tyr Ser Asn Trp Ser Phe Tyr Asp Phe Gln Phe
                740                 745                 750

Gln Asp Thr Gly Lys Tyr Gln Asn Ile Lys Glu Phe Thr Asp Asp Val
                755                 760                 765

Gln Lys Tyr Gly Tyr Lys Ile Ser Phe Arg Asp Ile Asp Asp Glu Tyr
                770                 775                 780

Ile Asn Gln Ala Leu Asn Glu Gly Lys Met Tyr Leu Phe Glu Val Val
785                 790                 795                 800

Asn Lys Asp Ile Tyr Asn Thr Lys Asn Gly Ser Lys Asn Leu His Thr
                805                 810                 815

Leu Tyr Phe Glu His Ile Leu Ser Ala Glu Asn Leu Asn Asp Pro Val
                820                 825                 830

Phe Lys Leu Ser Gly Met Ala Glu Ile Phe Gln Arg Gln Pro Ser Val
                835                 840                 845

Asn Glu Arg Glu Lys Ile Thr Thr Gln Lys Asn Gln Cys Ile Leu Asp
                850                 855                 860

Lys Gly Asp Arg Ala Tyr Lys Tyr Arg Arg Tyr Thr Glu Lys Lys Ile
865                 870                 875                 880

Met Phe His Met Ser Leu Val Leu Asn Thr Gly Lys Gly Glu Ile Lys
                885                 890                 895

Gln Val Gln Phe Asn Lys Ile Ile Asn Gln Arg Ile Ser Ser Ser Asp
                900                 905                 910

Asn Glu Met Arg Val Asn Val Ile Gly Ile Asp Arg Gly Glu Lys Asn
                915                 920                 925

Leu Leu Tyr Tyr Ser Val Val Lys Gln Asn Gly Glu Ile Ile Glu Gln
                930                 935                 940

Ala Ser Leu Asn Glu Ile Asn Gly Val Asn Tyr Arg Asp Lys Leu Ile
945                 950                 955                 960

Glu Arg Glu Lys Glu Arg Leu Lys Asn Arg Gln Ser Trp Lys Pro Val
                965                 970                 975

Val Lys Ile Lys Asp Leu Lys Lys Gly Tyr Ile Ser His Val Ile His
                980                 985                 990

Lys Ile Cys Gln Leu Ile Glu Lys Tyr Ser Ala Ile Val Val Leu Glu
                995                 1000                1005

Asp Leu Asn Met Arg Phe Lys Gln Ile Arg Gly Gly Ile Glu Arg
        1010            1015                1020

Ser Val Tyr Gln Gln Phe Glu Lys Ala Leu Ile Asp Lys Leu Gly
        1025            1030                1035

Tyr Leu Val Phe Lys Asp Asn Arg Asp Leu Arg Ala Pro Gly Gly
        1040            1045                1050

Val Leu Asn Gly Tyr Gln Leu Ser Ala Pro Phe Val Ser Phe Glu
        1055            1060                1065

Lys Met Arg Lys Gln Thr Gly Ile Leu Phe Tyr Thr Gln Ala Glu
        1070            1075                1080

Tyr Thr Ser Lys Thr Asp Pro Ile Thr Gly Phe Arg Lys Asn Val
        1085            1090                1095

Tyr Ile Ser Asn Ser Ala Ser Leu Asp Lys Ile Lys Glu Ala Val
        1100            1105                1110
```

Lys Lys Phe Asp Ala Ile Gly Trp Asp Gly Lys Glu Gln Ser Tyr
1115                1120                1125

Phe Phe Lys Tyr Asn Pro Tyr Asn Leu Ala Asp Glu Lys Tyr Lys
1130                1135                1140

Asn Ser Thr Val Ser Lys Glu Trp Ala Ile Phe Ala Ser Ala Pro
1145                1150                1155

Arg Ile Arg Arg Gln Lys Gly Glu Asp Gly Tyr Trp Lys Tyr Asp
1160                1165                1170

Arg Val Lys Val Asn Glu Glu Phe Glu Lys Leu Leu Lys Val Trp
1175                1180                1185

Asn Phe Val Asn Pro Lys Ala Thr Asp Ile Lys Gln Glu Ile Ile
1190                1195                1200

Lys Lys Glu Lys Ala Gly Asp Leu Gln Gly Glu Lys Glu Leu Asp
1205                1210                1215

Gly Arg Leu Arg Asn Phe Trp His Ser Phe Ile Tyr Leu Phe Asn
1220                1225                1230

Leu Val Leu Glu Leu Arg Asn Ser Phe Ser Leu Gln Ile Lys Ile
1235                1240                1245

Lys Ala Gly Glu Val Ile Ala Val Asp Glu Gly Val Asp Phe Ile
1250                1255                1260

Ala Ser Pro Val Lys Pro Phe Phe Thr Thr Pro Asn Pro Tyr Ile
1265                1270                1275

Pro Ser Asn Leu Cys Trp Leu Ala Val Glu Asn Ala Asp Ala Asn
1280                1285                1290

Gly Ala Tyr Asn Ile Ala Arg Lys Gly Val Met Ile Leu Lys Lys
1295                1300                1305

Ile Arg Glu His Ala Lys Lys Asp Pro Glu Phe Lys Lys Leu Pro
1310                1315                1320

Asn Leu Phe Ile Ser Asn Ala Glu Trp Asp Glu Ala Ala Arg Asp
1325                1330                1335

Trp Gly Lys Tyr Ala Gly Thr Thr Ala Leu Asn Leu Asp His Lys
1340                1345                1350

Arg Pro Ala Ala Thr Lys Lys Ala Gly Gln Ala Lys Lys Lys Lys
1355                1360                1365

Gly Ser Tyr Pro Tyr Asp Val Pro Asp Tyr Ala Tyr Pro Tyr Asp
1370                1375                1380

Val Pro Asp Tyr Ala Tyr Pro Tyr Asp Val Pro Asp Tyr Ala
1385                1390                1395

<210> SEQ ID NO 59
<211> LENGTH: 1295
<212> TYPE: PRT
<213> ORGANISM: Smithella sp.

<400> SEQUENCE: 59

Met Gln Thr Leu Phe Glu Asn Phe Thr Asn Gln Tyr Pro Val Ser Lys
1               5                   10                  15

Thr Leu Arg Phe Glu Leu Ile Pro Gln Gly Lys Thr Lys Asp Phe Ile
                20                  25                  30

Glu Gln Lys Gly Leu Leu Lys Lys Asp Glu Asp Arg Ala Glu Lys Tyr
            35                  40                  45

Lys Lys Val Lys Asn Ile Ile Asp Glu Tyr His Lys Asp Phe Ile Glu
        50                  55                  60

Lys Ser Leu Asn Gly Leu Lys Leu Asp Gly Leu Glu Lys Tyr Lys Thr

```
                65                  70                  75                  80
Leu Tyr Leu Lys Gln Glu Lys Asp Asp Lys Asp Lys Lys Ala Phe Asp
                    85                  90                  95
Lys Glu Lys Glu Asn Leu Arg Lys Gln Ile Ala Asn Ala Phe Arg Asn
                    100                 105                 110
Asn Glu Lys Phe Lys Thr Leu Phe Ala Lys Glu Leu Ile Lys Asn Asp
                    115                 120                 125
Leu Met Ser Phe Ala Cys Glu Glu Asp Lys Lys Asn Val Lys Glu Phe
                    130                 135                 140
Glu Ala Phe Thr Thr Tyr Phe Thr Gly Phe His Gln Asn Arg Ala Asn
145                                 150                 155                 160
Met Tyr Val Ala Asp Glu Lys Arg Thr Ala Ile Ala Ser Arg Leu Ile
                    165                 170                 175
His Glu Asn Leu Pro Lys Phe Ile Asp Asn Ile Lys Ile Phe Glu Lys
                    180                 185                 190
Met Lys Lys Glu Ala Pro Glu Leu Leu Ser Pro Phe Asn Gln Thr Leu
                    195                 200                 205
Lys Asp Met Lys Asp Val Ile Lys Gly Thr Thr Leu Glu Glu Ile Phe
                    210                 215                 220
Ser Leu Asp Tyr Phe Asn Lys Thr Leu Thr Gln Ser Gly Ile Asp Ile
225                                 230                 235                 240
Tyr Asn Ser Val Ile Gly Gly Arg Thr Pro Glu Glu Gly Lys Thr Lys
                    245                 250                 255
Ile Lys Gly Leu Asn Glu Tyr Ile Asn Thr Asp Phe Asn Gln Lys Gln
                    260                 265                 270
Thr Asp Lys Lys Lys Arg Gln Pro Lys Phe Lys Gln Leu Tyr Lys Gln
                    275                 280                 285
Ile Leu Ser Asp Arg Gln Ser Leu Ser Phe Ile Ala Glu Ala Phe Lys
                    290                 295                 300
Asn Asp Thr Glu Ile Leu Glu Ala Ile Glu Lys Phe Tyr Val Asn Glu
305                                 310                 315                 320
Leu Leu His Phe Ser Asn Glu Gly Lys Ser Thr Asn Val Leu Asp Ala
                    325                 330                 335
Ile Lys Asn Ala Val Ser Asn Leu Glu Ser Phe Asn Leu Thr Lys Met
                    340                 345                 350
Tyr Phe Arg Ser Gly Ala Ser Leu Thr Asp Val Ser Arg Lys Val Phe
                    355                 360                 365
Gly Glu Trp Ser Ile Ile Asn Arg Ala Leu Asp Asn Tyr Tyr Ala Thr
                    370                 375                 380
Thr Tyr Pro Ile Lys Pro Arg Glu Lys Ser Glu Lys Tyr Glu Glu Arg
385                                 390                 395                 400
Lys Glu Lys Trp Leu Lys Gln Asp Phe Asn Val Ser Leu Ile Gln Thr
                    405                 410                 415
Ala Ile Asp Glu Tyr Asp Asn Glu Thr Val Lys Gly Lys Asn Ser Gly
                    420                 425                 430
Lys Val Ile Ala Asp Tyr Phe Ala Lys Phe Cys Asp Asp Lys Glu Thr
                    435                 440                 445
Asp Leu Ile Gln Lys Val Asn Glu Gly Tyr Ile Ala Val Lys Asp Leu
                    450                 455                 460
Leu Asn Thr Pro Cys Pro Glu Asn Glu Lys Leu Gly Ser Asn Lys Asp
465                                 470                 475                 480
Gln Val Lys Gln Ile Lys Ala Phe Met Asp Ser Ile Met Asp Ile Met
                    485                 490                 495
```

```
His Phe Val Arg Pro Leu Ser Leu Lys Asp Thr Asp Lys Glu Lys Asp
                500                 505                 510

Glu Thr Phe Tyr Ser Leu Phe Thr Pro Leu Tyr Asp His Leu Thr Gln
            515                 520                 525

Thr Ile Ala Leu Tyr Asn Lys Val Arg Asn Tyr Leu Thr Gln Lys Pro
        530                 535                 540

Tyr Ser Thr Glu Lys Ile Lys Leu Asn Phe Glu Asn Ser Thr Leu Leu
545                 550                 555                 560

Gly Gly Trp Asp Leu Asn Lys Glu Thr Asp Asn Thr Ala Ile Ile Leu
                565                 570                 575

Arg Lys Asp Asn Leu Tyr Tyr Leu Gly Ile Met Asp Lys Arg His Asn
            580                 585                 590

Arg Ile Phe Arg Asn Val Pro Lys Ala Asp Lys Lys Asp Phe Cys Tyr
        595                 600                 605

Glu Lys Met Val Tyr Lys Leu Leu Pro Gly Ala Asn Lys Met Leu Pro
        610                 615                 620

Lys Val Phe Phe Ser Gln Ser Arg Ile Gln Glu Phe Thr Pro Ser Ala
625                 630                 635                 640

Lys Leu Leu Glu Asn Tyr Ala Asn Glu Thr His Lys Lys Gly Asp Asn
                645                 650                 655

Phe Asn Leu Asn His Cys His Lys Leu Ile Asp Phe Phe Lys Asp Ser
            660                 665                 670

Ile Asn Lys His Glu Asp Trp Lys Asn Phe Asp Phe Arg Phe Ser Ala
        675                 680                 685

Thr Ser Thr Tyr Ala Asp Leu Ser Gly Phe Tyr His Glu Val Glu His
        690                 695                 700

Gln Gly Tyr Lys Ile Ser Phe Gln Ser Val Ala Asp Ser Phe Ile Asp
705                 710                 715                 720

Asp Leu Val Asn Glu Gly Lys Leu Tyr Leu Phe Gln Ile Tyr Asn Lys
                725                 730                 735

Asp Phe Ser Pro Phe Ser Lys Gly Lys Pro Asn Leu His Thr Leu Tyr
            740                 745                 750

Trp Lys Met Leu Phe Asp Glu Asn Asn Leu Lys Asp Val Val Tyr Lys
        755                 760                 765

Leu Asn Gly Glu Ala Glu Val Phe Tyr Arg Lys Lys Ser Ile Ala Glu
        770                 775                 780

Lys Asn Thr Thr Ile His Lys Ala Asn Glu Ser Ile Ile Asn Lys Asn
785                 790                 795                 800

Pro Asp Asn Pro Lys Ala Thr Ser Thr Phe Asn Tyr Asp Ile Val Lys
                805                 810                 815

Asp Lys Arg Tyr Thr Ile Asp Lys Phe Gln Phe His Ile Pro Ile Thr
            820                 825                 830

Met Asn Phe Lys Ala Glu Gly Ile Phe Asn Met Asn Gln Arg Val Asn
        835                 840                 845

Gln Phe Leu Lys Ala Asn Pro Asp Ile Asn Ile Gly Ile Asp Arg
        850                 855                 860

Gly Glu Arg His Leu Leu Tyr Tyr Ala Leu Ile Asn Gln Lys Gly Lys
865                 870                 875                 880

Ile Leu Lys Gln Asp Thr Leu Asn Val Ile Ala Asn Glu Lys Gln Lys
                885                 890                 895

Val Asp Tyr His Asn Leu Leu Asp Lys Lys Glu Gly Asp Arg Ala Thr
            900                 905                 910
```

```
Ala Arg Gln Glu Trp Gly Val Ile Glu Thr Ile Lys Glu Leu Lys Glu
        915                 920                 925

Gly Tyr Leu Ser Gln Val Ile His Lys Leu Thr Asp Leu Met Ile Glu
        930                 935                 940

Asn Asn Ala Ile Ile Val Met Glu Asp Leu Asn Phe Gly Phe Lys Arg
945                 950                 955                 960

Gly Arg Gln Lys Val Glu Lys Gln Val Tyr Gln Lys Phe Glu Lys Met
                965                 970                 975

Leu Ile Asp Lys Leu Asn Tyr Leu Val Asp Lys Asn Lys Ala Asn
        980                 985                 990

Glu Leu Gly Gly Leu Leu Asn Ala Phe Gln Leu Ala Asn Lys Phe Glu
        995                 1000                1005

Ser Phe Gln Lys Met Gly Lys Gln Asn Gly Phe Ile Phe Tyr Val
    1010                1015                1020

Pro Ala Trp Asn Thr Ser Lys Thr Asp Pro Ala Thr Gly Phe Ile
    1025                1030                1035

Asp Phe Leu Lys Pro Arg Tyr Glu Asn Leu Asn Gln Ala Lys Asp
    1040                1045                1050

Phe Phe Glu Lys Phe Asp Ser Ile Arg Leu Asn Ser Lys Ala Asp
    1055                1060                1065

Tyr Phe Glu Phe Ala Phe Asp Phe Lys Asn Phe Thr Glu Lys Ala
    1070                1075                1080

Asp Gly Gly Arg Thr Lys Trp Thr Val Cys Thr Thr Asn Glu Asp
    1085                1090                1095

Arg Tyr Ala Trp Asn Arg Ala Leu Asn Asn Arg Gly Ser Gln
    1100                1105                1110

Glu Lys Tyr Asp Ile Thr Ala Glu Leu Lys Ser Leu Phe Asp Gly
    1115                1120                1125

Lys Val Asp Tyr Lys Ser Gly Lys Asp Leu Lys Gln Gln Ile Ala
    1130                1135                1140

Ser Gln Glu Ser Ala Asp Phe Phe Lys Ala Leu Met Lys Asn Leu
    1145                1150                1155

Ser Ile Thr Leu Ser Leu Arg His Asn Asn Gly Glu Lys Gly Asp
    1160                1165                1170

Asn Glu Gln Asp Tyr Ile Leu Ser Pro Val Ala Asp Ser Lys Gly
    1175                1180                1185

Arg Phe Phe Asp Ser Arg Lys Ala Asp Asp Met Pro Lys Asn
    1190                1195                1200

Ala Asp Ala Asn Gly Ala Tyr His Ile Ala Leu Lys Gly Leu Trp
    1205                1210                1215

Cys Leu Glu Gln Ile Ser Lys Thr Asp Asp Leu Lys Lys Val Lys
    1220                1225                1230

Leu Ala Ile Ser Asn Lys Glu Trp Leu Glu Phe Val Gln Thr Leu
    1235                1240                1245

Lys Gly Lys Arg Pro Ala Ala Thr Lys Lys Ala Gly Gln Ala Lys
    1250                1255                1260

Lys Lys Lys Gly Ser Tyr Pro Tyr Asp Val Pro Asp Tyr Ala Tyr
    1265                1270                1275

Pro Tyr Asp Val Pro Asp Tyr Ala Tyr Pro Tyr Asp Val Pro Asp
    1280                1285                1290

Tyr Ala
    1295
```

```
<210> SEQ ID NO 60
<211> LENGTH: 1352
<212> TYPE: PRT
<213> ORGANISM: Acidaminococcus sp.

<400> SEQUENCE: 60
```

| | | | | | | | | | | | | | | |
|---|---|---|---|---|---|---|---|---|---|---|---|---|---|---|
| Met | Thr | Gln | Phe | Glu | Gly | Phe | Thr | Asn | Leu | Tyr | Gln | Val | Ser | Lys | Thr |
| 1 | | | | 5 | | | | | 10 | | | | | 15 | |

| Leu | Arg | Phe | Glu | Leu | Ile | Pro | Gln | Gly | Lys | Thr | Leu | Lys | His | Ile | Gln |
| | | | 20 | | | | | 25 | | | | | 30 | | |

| Glu | Gln | Gly | Phe | Ile | Glu | Glu | Asp | Lys | Ala | Arg | Asn | Asp | His | Tyr | Lys |
| | | 35 | | | | | 40 | | | | | 45 | | | |

| Glu | Leu | Lys | Pro | Ile | Ile | Asp | Arg | Ile | Tyr | Lys | Thr | Tyr | Ala | Asp | Gln |
| | 50 | | | | | 55 | | | | | 60 | | | | |

| Cys | Leu | Gln | Leu | Val | Gln | Leu | Asp | Trp | Glu | Asn | Leu | Ser | Ala | Ala | Ile |
| 65 | | | | | 70 | | | | | 75 | | | | | 80 |

| Asp | Ser | Tyr | Arg | Lys | Glu | Lys | Thr | Glu | Glu | Thr | Arg | Asn | Ala | Leu | Ile |
| | | | | 85 | | | | | 90 | | | | | 95 | |

| Glu | Glu | Gln | Ala | Thr | Tyr | Arg | Asn | Ala | Ile | His | Asp | Tyr | Phe | Ile | Gly |
| | | | 100 | | | | | 105 | | | | | 110 | | |

| Arg | Thr | Asp | Asn | Leu | Thr | Asp | Ala | Ile | Asn | Lys | Arg | His | Ala | Glu | Ile |
| | | | 115 | | | | | 120 | | | | | 125 | | |

| Tyr | Lys | Gly | Leu | Phe | Lys | Ala | Glu | Leu | Phe | Asn | Gly | Lys | Val | Leu | Lys |
| | 130 | | | | | 135 | | | | | 140 | | | | |

| Gln | Leu | Gly | Thr | Val | Thr | Thr | Thr | Glu | His | Glu | Asn | Ala | Leu | Leu | Arg |
| 145 | | | | | 150 | | | | | 155 | | | | | 160 |

| Ser | Phe | Asp | Lys | Phe | Thr | Thr | Tyr | Phe | Ser | Gly | Phe | Tyr | Glu | Asn | Arg |
| | | | | 165 | | | | | 170 | | | | | 175 | |

| Lys | Asn | Val | Phe | Ser | Ala | Glu | Asp | Ile | Ser | Thr | Ala | Ile | Pro | His | Arg |
| | | | 180 | | | | | 185 | | | | | 190 | | |

| Ile | Val | Gln | Asp | Asn | Phe | Pro | Lys | Phe | Lys | Glu | Asn | Cys | His | Ile | Phe |
| | | | 195 | | | | | 200 | | | | | 205 | | |

| Thr | Arg | Leu | Ile | Thr | Ala | Val | Pro | Ser | Leu | Arg | Glu | His | Phe | Glu | Asn |
| | 210 | | | | | 215 | | | | | 220 | | | | |

| Val | Lys | Lys | Ala | Ile | Gly | Ile | Phe | Val | Ser | Thr | Ser | Ile | Glu | Glu | Val |
| 225 | | | | | 230 | | | | | 235 | | | | | 240 |

| Phe | Ser | Phe | Pro | Phe | Tyr | Asn | Gln | Leu | Leu | Thr | Gln | Thr | Gln | Ile | Asp |
| | | | | 245 | | | | | 250 | | | | | 255 | |

| Leu | Tyr | Asn | Gln | Leu | Leu | Gly | Gly | Ile | Ser | Arg | Glu | Ala | Gly | Thr | Glu |
| | | | 260 | | | | | 265 | | | | | 270 | | |

| Lys | Ile | Lys | Gly | Leu | Asn | Glu | Val | Leu | Asn | Leu | Ala | Ile | Gln | Lys | Asn |
| | | | 275 | | | | | 280 | | | | | 285 | | |

| Asp | Glu | Thr | Ala | His | Ile | Ile | Ala | Ser | Leu | Pro | His | Arg | Phe | Ile | Pro |
| | 290 | | | | | 295 | | | | | 300 | | | | |

| Leu | Phe | Lys | Gln | Ile | Leu | Ser | Asp | Arg | Asn | Thr | Leu | Ser | Phe | Ile | Leu |
| 305 | | | | | 310 | | | | | 315 | | | | | 320 |

| Glu | Glu | Phe | Lys | Ser | Asp | Glu | Glu | Val | Ile | Gln | Ser | Phe | Cys | Lys | Tyr |
| | | | | 325 | | | | | 330 | | | | | 335 | |

| Lys | Thr | Leu | Leu | Arg | Asn | Glu | Asn | Val | Leu | Glu | Thr | Ala | Glu | Ala | Leu |
| | | | 340 | | | | | 345 | | | | | 350 | | |

| Phe | Asn | Glu | Leu | Asn | Ser | Ile | Asp | Leu | Thr | His | Ile | Phe | Ile | Ser | His |
| | | | 355 | | | | | 360 | | | | | 365 | | |

| Lys | Lys | Leu | Glu | Thr | Ile | Ser | Ser | Ala | Leu | Cys | Asp | His | Trp | Asp | Thr |
| | 370 | | | | | 375 | | | | | 380 | | | | |

```
Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ser Ala Ala Gly Lys Glu Leu Ser
            420                 425                 430

Glu Ala Phe Lys Gln Lys Thr Ser Glu Ile Leu Ser His Ala His Ala
            435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
            515                 520                 525

Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
            645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
            725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
```

-continued

```
                805                 810                 815
Pro Ile Pro Asp Thr Leu Tyr Gln Glu Leu Tyr Asp Tyr Val Asn His
            820                 825                 830
Arg Leu Ser His Asp Leu Ser Asp Glu Ala Arg Ala Leu Leu Pro Asn
            835                 840                 845
Val Ile Thr Lys Glu Val Ser His Glu Ile Ile Lys Asp Arg Arg Phe
            850                 855                 860
Thr Ser Asp Lys Phe Phe Phe His Val Pro Ile Thr Leu Asn Tyr Gln
865                 870                 875                 880
Ala Ala Asn Ser Pro Ser Lys Phe Asn Gln Arg Val Asn Ala Tyr Leu
                885                 890                 895
Lys Glu His Pro Glu Thr Pro Ile Ile Gly Ile Asp Arg Gly Glu Arg
            900                 905                 910
Asn Leu Ile Tyr Ile Thr Val Ile Asp Ser Thr Gly Lys Ile Leu Glu
            915                 920                 925
Gln Arg Ser Leu Asn Thr Ile Gln Gln Phe Asp Tyr Gln Lys Lys Leu
            930                 935                 940
Asp Asn Arg Glu Lys Glu Arg Val Ala Ala Arg Gln Ala Trp Ser Val
945                 950                 955                 960
Val Gly Thr Ile Lys Asp Leu Lys Gln Gly Tyr Leu Ser Gln Val Ile
                965                 970                 975
His Glu Ile Val Asp Leu Met Ile His Tyr Gln Ala Val Val Val Leu
            980                 985                 990
Glu Asn Leu Asn Phe Gly Phe Lys Ser Lys Arg Thr Gly Ile Ala Glu
            995                 1000                1005
Lys Ala Val Tyr Gln Gln Phe Glu Lys Met Leu Ile Asp Lys Leu
            1010                1015                1020
Asn Cys Leu Val Leu Lys Asp Tyr Pro Ala Glu Lys Val Gly Gly
            1025                1030                1035
Val Leu Asn Pro Tyr Gln Leu Thr Asp Gln Phe Thr Ser Phe Ala
            1040                1045                1050
Lys Met Gly Thr Gln Ser Gly Phe Leu Phe Tyr Val Pro Ala Pro
            1055                1060                1065
Tyr Thr Ser Lys Ile Asp Pro Leu Thr Gly Phe Val Asp Pro Phe
            1070                1075                1080
Val Trp Lys Thr Ile Lys Asn His Glu Ser Arg Lys His Phe Leu
            1085                1090                1095
Glu Gly Phe Asp Phe Leu His Tyr Asp Val Lys Thr Gly Asp Phe
            1100                1105                1110
Ile Leu His Phe Lys Met Asn Arg Asn Leu Ser Phe Gln Arg Gly
            1115                1120                1125
Leu Pro Gly Phe Met Pro Ala Trp Asp Ile Val Phe Glu Lys Asn
            1130                1135                1140
Glu Thr Gln Phe Asp Ala Lys Gly Thr Pro Phe Ile Ala Gly Lys
            1145                1150                1155
Arg Ile Val Pro Val Ile Glu Asn His Arg Phe Thr Gly Arg Tyr
            1160                1165                1170
Arg Asp Leu Tyr Pro Ala Asn Glu Leu Ile Ala Leu Leu Glu Glu
            1175                1180                1185
Lys Gly Ile Val Phe Arg Asp Gly Ser Asn Ile Leu Pro Lys Leu
            1190                1195                1200
Leu Glu Asn Asp Asp Ser His Ala Ile Asp Thr Met Val Ala Leu
            1205                1210                1215
```

```
Ile Arg Ser Val Leu Gln Met Arg Asn Ser Asn Ala Ala Thr Gly
    1220                1225                1230

Glu Asp Tyr Ile Asn Ser Pro Val Arg Asp Leu Asn Gly Val Cys
    1235                1240                1245

Phe Asp Ser Arg Phe Gln Asn Pro Glu Trp Pro Met Asp Ala Asp
    1250                1255                1260

Ala Asn Gly Ala Tyr His Ile Ala Leu Lys Gly Gln Leu Leu Leu
    1265                1270                1275

Asn His Leu Lys Glu Ser Lys Asp Leu Lys Leu Gln Asn Gly Ile
    1280                1285                1290

Ser Asn Gln Asp Trp Leu Ala Tyr Ile Gln Glu Leu Arg Asn Lys
    1295                1300                1305

Arg Pro Ala Ala Thr Lys Lys Ala Gly Gln Ala Lys Lys Lys Lys
    1310                1315                1320

Gly Ser Tyr Pro Tyr Asp Val Pro Asp Tyr Ala Tyr Pro Tyr Asp
    1325                1330                1335

Val Pro Asp Tyr Ala Tyr Pro Tyr Asp Val Pro Asp Tyr Ala
    1340                1345                1350

<210> SEQ ID NO 61
<211> LENGTH: 1251
<212> TYPE: PRT
<213> ORGANISM: Lachnospiraceae bacterium

<400> SEQUENCE: 61

Met Tyr Tyr Glu Ser Leu Thr Lys Gln Tyr Pro Val Ser Lys Thr Ile
1               5                   10                  15

Arg Asn Glu Leu Ile Pro Ile Gly Lys Thr Leu Asp Asn Ile Arg Gln
            20                  25                  30

Asn Asn Ile Leu Glu Ser Asp Val Lys Arg Lys Gln Asn Tyr Glu His
        35                  40                  45

Val Lys Gly Ile Leu Asp Glu Tyr His Lys Gln Leu Ile Asn Glu Ala
    50                  55                  60

Leu Asp Asn Cys Thr Leu Pro Ser Leu Lys Ile Ala Ala Glu Ile Tyr
65                  70                  75                  80

Leu Lys Asn Gln Lys Glu Val Ser Asp Arg Glu Asp Phe Asn Lys Thr
                85                  90                  95

Gln Asp Leu Leu Arg Lys Glu Val Val Glu Lys Leu Lys Ala His Glu
            100                 105                 110

Asn Phe Thr Lys Ile Gly Lys Lys Asp Ile Leu Asp Leu Leu Glu Lys
        115                 120                 125

Leu Pro Ser Ile Ser Glu Asp Asp Tyr Asn Ala Leu Glu Ser Phe Arg
    130                 135                 140

Asn Phe Tyr Thr Tyr Phe Thr Ser Tyr Asn Lys Val Arg Glu Asn Leu
145                 150                 155                 160

Tyr Ser Asp Lys Glu Lys Ser Ser Thr Val Ala Tyr Arg Leu Ile Asn
                165                 170                 175

Glu Asn Phe Pro Lys Phe Leu Asp Asn Val Lys Ser Tyr Arg Phe Val
            180                 185                 190

Lys Thr Ala Gly Ile Leu Ala Asp Gly Leu Gly Glu Glu Gln Asp
        195                 200                 205

Ser Leu Phe Ile Val Glu Thr Phe Asn Lys Thr Leu Thr Gln Asp Gly
    210                 215                 220

Ile Asp Thr Tyr Asn Ser Gln Val Gly Lys Ile Asn Ser Ser Ile Asn
```

```
        225                 230                 235                 240
Leu Tyr Asn Gln Lys Asn Gln Lys Ala Asn Gly Phe Arg Lys Ile Pro
                245                 250                 255
Lys Met Lys Met Leu Tyr Lys Gln Ile Leu Ser Asp Arg Glu Glu Ser
                260                 265                 270
Phe Ile Asp Glu Phe Gln Ser Asp Glu Val Leu Ile Asp Asn Val Glu
                275                 280                 285
Ser Tyr Gly Ser Val Leu Ile Glu Ser Leu Lys Ser Ser Lys Val Ser
            290                 295                 300
Ala Phe Phe Asp Ala Leu Arg Glu Ser Lys Gly Lys Asn Val Tyr Val
305                 310                 315                 320
Lys Asn Asp Leu Ala Lys Thr Ala Met Ser Asn Ile Val Phe Glu Asn
                325                 330                 335
Trp Arg Thr Phe Asp Asp Leu Leu Asn Gln Glu Tyr Asp Leu Ala Asn
                340                 345                 350
Glu Asn Lys Lys Lys Asp Asp Lys Tyr Phe Glu Lys Arg Gln Lys Glu
                355                 360                 365
Leu Lys Lys Asn Lys Ser Tyr Ser Leu Glu His Leu Cys Asn Leu Ser
            370                 375                 380
Glu Asp Ser Cys Asn Leu Ile Glu Asn Tyr Ile His Gln Ile Ser Asp
385                 390                 395                 400
Asp Ile Glu Asn Ile Ile Asn Asn Glu Thr Phe Leu Arg Ile Val
                405                 410                 415
Ile Asn Glu His Asp Arg Ser Arg Lys Leu Ala Lys Asn Arg Lys Ala
                420                 425                 430
Val Lys Ala Ile Lys Asp Phe Leu Asp Ser Ile Lys Val Leu Glu Arg
            435                 440                 445
Glu Leu Lys Leu Ile Asn Ser Ser Gly Gln Glu Leu Glu Lys Asp Leu
                450                 455                 460
Ile Val Tyr Ser Ala His Glu Glu Leu Leu Val Glu Leu Lys Gln Val
465                 470                 475                 480
Asp Ser Leu Tyr Asn Met Thr Arg Asn Tyr Leu Thr Lys Lys Pro Phe
                485                 490                 495
Ser Thr Glu Lys Val Lys Leu Asn Phe Asn Arg Ser Thr Leu Leu Asn
                500                 505                 510
Gly Trp Asp Arg Asn Lys Glu Thr Asp Asn Leu Gly Val Leu Leu Leu
                515                 520                 525
Lys Asp Gly Lys Tyr Tyr Leu Gly Ile Met Asn Thr Ser Ala Asn Lys
            530                 535                 540
Ala Phe Val Asn Pro Pro Val Ala Lys Thr Glu Lys Val Phe Lys Lys
545                 550                 555                 560
Val Asp Tyr Lys Leu Leu Pro Val Pro Asn Gln Met Leu Pro Lys Val
                565                 570                 575
Phe Phe Ala Lys Ser Asn Ile Asp Phe Tyr Asn Pro Ser Ser Glu Ile
                580                 585                 590
Tyr Ser Asn Tyr Lys Lys Gly Thr His Lys Lys Gly Asn Met Phe Ser
            595                 600                 605
Leu Glu Asp Cys His Asn Leu Ile Asp Phe Phe Lys Glu Ser Ile Ser
            610                 615                 620
Lys His Glu Asp Trp Ser Lys Phe Gly Phe Phe Ser Asp Thr Ala
625                 630                 635                 640
Ser Tyr Asn Asp Ile Ser Glu Phe Tyr Arg Glu Val Glu Lys Gln Gly
                645                 650                 655
```

```
Tyr Lys Leu Thr Tyr Thr Asp Ile Asp Glu Thr Tyr Ile Asn Asp Leu
            660                 665                 670

Ile Glu Arg Asn Glu Leu Tyr Leu Phe Gln Ile Tyr Asn Lys Asp Phe
            675                 680                 685

Ser Met Tyr Ser Lys Gly Lys Leu Asn Leu His Thr Leu Tyr Phe Met
            690                 695                 700

Met Leu Phe Asp Gln Arg Asn Ile Asp Asp Val Val Tyr Lys Leu Asn
705                 710                 715                 720

Gly Glu Ala Glu Val Phe Tyr Arg Pro Ala Ser Ile Ser Glu Asp Glu
                725                 730                 735

Leu Ile Ile His Lys Ala Gly Glu Glu Ile Lys Asn Lys Asn Pro Asn
            740                 745                 750

Arg Ala Arg Thr Lys Glu Thr Ser Thr Phe Ser Tyr Asp Ile Val Lys
            755                 760                 765

Asp Lys Arg Tyr Ser Lys Asp Lys Phe Thr Leu His Ile Pro Ile Thr
            770                 775                 780

Met Asn Phe Gly Val Asp Glu Val Lys Arg Phe Asn Asp Ala Val Asn
785                 790                 795                 800

Ser Ala Ile Arg Ile Asp Glu Asn Val Asn Val Ile Gly Ile Asp Arg
            805                 810                 815

Gly Glu Arg Asn Leu Leu Tyr Val Val Val Ile Asp Ser Lys Gly Asn
            820                 825                 830

Ile Leu Glu Gln Ile Ser Leu Asn Ser Ile Ile Asn Lys Glu Tyr Asp
            835                 840                 845

Ile Glu Thr Asp Tyr His Ala Leu Leu Asp Glu Arg Glu Gly Gly Arg
            850                 855                 860

Asp Lys Ala Arg Lys Asp Trp Asn Thr Val Glu Asn Ile Arg Asp Leu
865                 870                 875                 880

Lys Ala Gly Tyr Leu Ser Gln Val Val Asn Val Val Ala Lys Leu Val
            885                 890                 895

Leu Lys Tyr Asn Ala Ile Ile Cys Leu Glu Asp Leu Asn Phe Gly Phe
            900                 905                 910

Lys Arg Gly Arg Gln Lys Val Glu Lys Gln Val Tyr Gln Lys Phe Glu
            915                 920                 925

Lys Met Leu Ile Asp Lys Leu Asn Tyr Leu Val Ile Asp Lys Ser Arg
930                 935                 940

Glu Gln Thr Ser Pro Lys Glu Leu Gly Gly Ala Leu Asn Ala Leu Gln
945                 950                 955                 960

Leu Thr Ser Lys Phe Lys Ser Phe Lys Glu Leu Gly Lys Gln Ser Gly
            965                 970                 975

Val Ile Tyr Tyr Val Pro Ala Tyr Leu Thr Ser Lys Ile Asp Pro Thr
            980                 985                 990

Thr Gly Phe Ala Asn Leu Phe Tyr Met Lys Cys Glu Asn Val Glu Lys
            995                 1000                1005

Ser Lys Arg Phe Phe Asp Gly Phe Asp Phe Ile Arg Phe Asn Ala
            1010                1015                1020

Leu Glu Asn Val Phe Glu Phe Gly Phe Asp Tyr Arg Ser Phe Thr
            1025                1030                1035

Gln Arg Ala Cys Gly Ile Asn Ser Lys Trp Thr Val Cys Thr Asn
            1040                1045                1050

Gly Glu Arg Ile Ile Lys Tyr Arg Asn Pro Asp Lys Asn Asn Met
            1055                1060                1065
```

Phe Asp Glu Lys Val Val Val Thr Asp Glu Met Lys Asn Leu
1070              1075              1080

Phe Glu Gln Tyr Lys Ile Pro Tyr Glu Asp Gly Arg Asn Val Lys
1085              1090              1095

Asp Met Ile Ile Ser Asn Glu Glu Ala Glu Phe Tyr Arg Arg Leu
1100              1105              1110

Tyr Arg Leu Leu Gln Gln Thr Leu Gln Met Arg Asn Ser Thr Ser
1115              1120              1125

Asp Gly Thr Arg Asp Tyr Ile Ile Ser Pro Val Lys Asn Lys Arg
1130              1135              1140

Glu Ala Tyr Phe Asn Ser Glu Leu Ser Asp Gly Ser Val Pro Lys
1145              1150              1155

Asp Ala Asp Ala Asn Gly Ala Tyr Asn Ile Ala Arg Lys Gly Leu
1160              1165              1170

Trp Val Leu Glu Gln Ile Arg Gln Lys Ser Glu Gly Glu Lys Ile
1175              1180              1185

Asn Leu Ala Met Thr Asn Ala Glu Trp Leu Glu Tyr Ala Gln Thr
1190              1195              1200

His Leu Leu Lys Arg Pro Ala Ala Thr Lys Lys Ala Gly Gln Ala
1205              1210              1215

Lys Lys Lys Lys Gly Ser Tyr Pro Tyr Asp Val Pro Asp Tyr Ala
1220              1225              1230

Tyr Pro Tyr Asp Val Pro Asp Tyr Ala Tyr Pro Tyr Asp Val Pro
1235              1240              1245

Asp Tyr Ala
1250

<210> SEQ ID NO 62
<211> LENGTH: 1283
<212> TYPE: PRT
<213> ORGANISM: Candidatus Methanoplasma termitum

<400> SEQUENCE: 62

Met Asn Asn Tyr Asp Glu Phe Thr Lys Leu Tyr Pro Ile Gln Lys Thr
1               5                   10                  15

Ile Arg Phe Glu Leu Lys Pro Gln Gly Arg Thr Met Glu His Leu Glu
            20                  25                  30

Thr Phe Asn Phe Phe Glu Glu Asp Arg Asp Arg Ala Glu Lys Tyr Lys
        35                  40                  45

Ile Leu Lys Glu Ala Ile Asp Glu Tyr His Lys Lys Phe Ile Asp Glu
    50                  55                  60

His Leu Thr Asn Met Ser Leu Asp Trp Asn Ser Leu Lys Gln Ile Ser
65                  70                  75                  80

Glu Lys Tyr Tyr Lys Ser Arg Glu Glu Lys Asp Lys Lys Val Phe Leu
                85                  90                  95

Ser Glu Gln Lys Arg Met Arg Gln Glu Ile Val Ser Glu Phe Lys Lys
            100                 105                 110

Asp Asp Arg Phe Lys Asp Leu Phe Ser Lys Lys Leu Phe Ser Glu Leu
        115                 120                 125

Leu Lys Glu Glu Ile Tyr Lys Lys Gly Asn His Gln Glu Ile Asp Ala
    130                 135                 140

Leu Lys Ser Phe Asp Lys Phe Ser Gly Tyr Phe Ile Gly Leu His Glu
145                 150                 155                 160

Asn Arg Lys Asn Met Tyr Ser Asp Gly Asp Glu Ile Thr Ala Ile Ser
                165                 170                 175

-continued

```
Asn Arg Ile Val Asn Glu Asn Phe Pro Lys Phe Leu Asp Asn Leu Gln
            180                 185                 190
Lys Tyr Gln Glu Ala Arg Lys Lys Tyr Pro Glu Trp Ile Ile Lys Ala
        195                 200                 205
Glu Ser Ala Leu Val Ala His Asn Ile Lys Met Asp Glu Val Phe Ser
    210                 215                 220
Leu Glu Tyr Phe Asn Lys Val Leu Asn Gln Glu Gly Ile Gln Arg Tyr
225                 230                 235                 240
Asn Leu Ala Leu Gly Gly Tyr Val Thr Lys Ser Gly Glu Lys Met Met
                245                 250                 255
Gly Leu Asn Asp Ala Leu Asn Leu Ala His Gln Ser Glu Lys Ser Ser
            260                 265                 270
Lys Gly Arg Ile His Met Thr Pro Leu Phe Lys Gln Ile Leu Ser Glu
        275                 280                 285
Lys Glu Ser Phe Ser Tyr Ile Pro Asp Val Phe Thr Glu Asp Ser Gln
    290                 295                 300
Leu Leu Pro Ser Ile Gly Gly Phe Phe Ala Gln Ile Glu Asn Asp Lys
305                 310                 315                 320
Asp Gly Asn Ile Phe Asp Arg Ala Leu Glu Leu Ile Ser Ser Tyr Ala
                325                 330                 335
Glu Tyr Asp Thr Glu Arg Ile Tyr Ile Arg Gln Ala Asp Ile Asn Arg
            340                 345                 350
Val Ser Asn Val Ile Phe Gly Glu Trp Gly Thr Leu Gly Gly Leu Met
        355                 360                 365
Arg Glu Tyr Lys Ala Asp Ser Ile Asn Asp Ile Asn Leu Glu Arg Thr
    370                 375                 380
Cys Lys Lys Val Asp Lys Trp Leu Asp Ser Lys Glu Phe Ala Leu Ser
385                 390                 395                 400
Asp Val Leu Glu Ala Ile Lys Arg Thr Gly Asn Asn Asp Ala Phe Asn
                405                 410                 415
Glu Tyr Ile Ser Lys Met Arg Thr Ala Arg Glu Lys Ile Asp Ala Ala
            420                 425                 430
Arg Lys Glu Met Lys Phe Ile Ser Glu Lys Ile Ser Gly Asp Glu Glu
        435                 440                 445
Ser Ile His Ile Ile Lys Thr Leu Leu Asp Ser Val Gln Gln Phe Leu
    450                 455                 460
His Phe Phe Asn Leu Phe Lys Ala Arg Gln Asp Ile Pro Leu Asp Gly
465                 470                 475                 480
Ala Phe Tyr Ala Glu Phe Asp Glu Val His Ser Lys Leu Phe Ala Ile
                485                 490                 495
Val Pro Leu Tyr Asn Lys Val Arg Asn Tyr Leu Thr Lys Asn Asn Leu
            500                 505                 510
Asn Thr Lys Lys Ile Lys Leu Asn Phe Lys Asn Pro Thr Leu Ala Asn
        515                 520                 525
Gly Trp Asp Gln Asn Lys Val Tyr Asp Tyr Ala Ser Leu Ile Phe Leu
    530                 535                 540
Arg Asp Gly Asn Tyr Tyr Leu Gly Ile Ile Asn Pro Lys Arg Lys Lys
545                 550                 555                 560
Asn Ile Lys Phe Glu Gln Gly Ser Gly Asn Gly Pro Phe Tyr Arg Lys
                565                 570                 575
Met Val Tyr Lys Gln Ile Pro Gly Pro Asn Lys Asn Leu Pro Arg Val
            580                 585                 590
```

```
Phe Leu Thr Ser Thr Lys Gly Lys Glu Tyr Lys Pro Ser Lys Glu
            595                 600                 605

Ile Ile Glu Gly Tyr Glu Ala Asp Lys His Ile Arg Gly Asp Lys Phe
        610                 615                 620

Asp Leu Asp Phe Cys His Lys Leu Ile Asp Phe Phe Lys Glu Ser Ile
625                 630                 635                 640

Glu Lys His Lys Asp Trp Ser Lys Phe Asn Phe Tyr Phe Ser Pro Thr
                645                 650                 655

Glu Ser Tyr Gly Asp Ile Ser Glu Phe Tyr Leu Asp Val Glu Lys Gln
                660                 665                 670

Gly Tyr Arg Met His Phe Glu Asn Ile Ser Ala Glu Thr Ile Asp Glu
            675                 680                 685

Tyr Val Glu Lys Gly Asp Leu Phe Leu Phe Gln Ile Tyr Asn Lys Asp
        690                 695                 700

Phe Val Lys Ala Ala Thr Gly Lys Lys Asp Met His Thr Ile Tyr Trp
705                 710                 715                 720

Asn Ala Ala Phe Ser Pro Glu Asn Leu Gln Asp Val Val Lys Leu
                725                 730                 735

Asn Gly Glu Ala Glu Leu Phe Tyr Arg Asp Lys Ser Asp Ile Lys Glu
            740                 745                 750

Ile Val His Arg Glu Gly Glu Ile Leu Val Asn Arg Thr Tyr Asn Gly
        755                 760                 765

Arg Thr Pro Val Pro Asp Lys Ile His Lys Lys Leu Thr Asp Tyr His
770                 775                 780

Asn Gly Arg Thr Lys Asp Leu Gly Glu Ala Lys Glu Tyr Leu Asp Lys
785                 790                 795                 800

Val Arg Tyr Phe Lys Ala His Tyr Asp Ile Thr Lys Asp Arg Arg Tyr
                805                 810                 815

Leu Asn Asp Lys Ile Tyr Phe His Val Pro Leu Thr Leu Asn Phe Lys
            820                 825                 830

Ala Asn Gly Lys Lys Asn Leu Asn Lys Met Val Ile Glu Lys Phe Leu
        835                 840                 845

Ser Asp Glu Lys Ala His Ile Ile Gly Ile Asp Arg Gly Glu Arg Asn
850                 855                 860

Leu Leu Tyr Tyr Ser Ile Ile Asp Arg Ser Gly Lys Ile Ile Asp Gln
865                 870                 875                 880

Gln Ser Leu Asn Val Ile Asp Gly Phe Asp Tyr Arg Glu Lys Leu Asn
                885                 890                 895

Gln Arg Glu Ile Glu Met Lys Asp Ala Arg Gln Ser Trp Asn Ala Ile
            900                 905                 910

Gly Lys Ile Lys Asp Leu Lys Glu Gly Tyr Leu Ser Lys Ala Val His
        915                 920                 925

Glu Ile Thr Lys Met Ala Ile Gln Tyr Asn Ala Ile Val Val Met Glu
930                 935                 940

Glu Leu Asn Tyr Gly Phe Lys Arg Gly Arg Phe Lys Val Glu Lys Gln
945                 950                 955                 960

Ile Tyr Gln Lys Phe Glu Asn Met Leu Ile Asp Lys Met Asn Tyr Leu
                965                 970                 975

Val Phe Lys Asp Ala Pro Asp Glu Ser Pro Gly Gly Val Leu Asn Ala
            980                 985                 990

Tyr Gln Leu Thr Asn Pro Leu Glu  Ser Phe Ala Lys Leu  Gly Lys Gln
        995                 1000                1005

Thr Gly  Ile Leu Phe Tyr Val  Pro Ala Ala Tyr Thr  Ser Lys Ile
```

-continued

```
            1010                1015                1020
Asp Pro Thr Thr Gly Phe Val Asn Leu Phe Asn Thr Ser Ser Lys
        1025                1030                1035

Thr Asn Ala Gln Glu Arg Lys Glu Phe Leu Gln Lys Phe Glu Ser
    1040                1045                1050

Ile Ser Tyr Ser Ala Lys Asp Gly Gly Ile Phe Ala Phe Ala Phe
    1055                1060                1065

Asp Tyr Arg Lys Phe Gly Thr Ser Lys Thr Asp His Lys Asn Val
    1070                1075                1080

Trp Thr Ala Tyr Thr Asn Gly Glu Arg Met Arg Tyr Ile Lys Glu
    1085                1090                1095

Lys Lys Arg Asn Glu Leu Phe Asp Pro Ser Lys Glu Ile Lys Glu
    1100                1105                1110

Ala Leu Thr Ser Ser Gly Ile Lys Tyr Asp Gly Gly Gln Asn Ile
    1115                1120                1125

Leu Pro Asp Ile Leu Arg Ser Asn Asn Asn Gly Leu Ile Tyr Thr
    1130                1135                1140

Met Tyr Ser Ser Phe Ile Ala Ala Ile Gln Met Arg Val Tyr Asp
    1145                1150                1155

Gly Lys Glu Asp Tyr Ile Ile Ser Pro Ile Lys Asn Ser Lys Gly
    1160                1165                1170

Glu Phe Phe Arg Thr Asp Pro Lys Arg Arg Glu Leu Pro Ile Asp
    1175                1180                1185

Ala Asp Ala Asn Gly Ala Tyr Asn Ile Ala Leu Arg Gly Glu Leu
    1190                1195                1200

Thr Met Arg Ala Ile Ala Glu Lys Phe Asp Pro Asp Ser Glu Lys
    1205                1210                1215

Met Ala Lys Leu Glu Leu Lys His Lys Asp Trp Phe Glu Phe Met
    1220                1225                1230

Gln Thr Arg Gly Asp Lys Arg Pro Ala Ala Thr Lys Lys Ala Gly
    1235                1240                1245

Gln Ala Lys Lys Lys Lys Gly Ser Tyr Pro Tyr Asp Val Pro Asp
    1250                1255                1260

Tyr Ala Tyr Pro Tyr Asp Val Pro Asp Tyr Ala Tyr Pro Tyr Asp
    1265                1270                1275

Val Pro Asp Tyr Ala
    1280

<210> SEQ ID NO 63
<211> LENGTH: 1327
<212> TYPE: PRT
<213> ORGANISM: Eubacterium eligens

<400> SEQUENCE: 63

Met Asn Gly Asn Arg Ser Ile Val Tyr Arg Glu Phe Val Gly Val Ile
1               5                   10                  15

Pro Val Ala Lys Thr Leu Arg Asn Glu Leu Arg Pro Val Gly His Thr
            20                  25                  30

Gln Glu His Ile Ile Gln Asn Gly Leu Ile Gln Glu Asp Glu Leu Arg
        35                  40                  45

Gln Glu Lys Ser Thr Glu Leu Lys Asn Ile Met Asp Asp Tyr Tyr Arg
    50                  55                  60

Glu Tyr Ile Asp Lys Ser Leu Ser Gly Val Thr Asp Leu Asp Phe Thr
65                  70                  75                  80
```

```
Leu Leu Phe Glu Leu Met Asn Leu Val Gln Ser Ser Pro Ser Lys Asp
                    85                  90                  95

Asn Lys Lys Ala Leu Glu Lys Glu Gln Ser Lys Met Arg Glu Gln Ile
            100                 105                 110

Cys Thr His Leu Gln Ser Asp Ser Asn Tyr Lys Asn Ile Phe Asn Ala
            115                 120                 125

Lys Leu Leu Lys Glu Ile Leu Pro Asp Phe Ile Lys Asn Tyr Asn Gln
            130                 135                 140

Tyr Asp Val Lys Asp Lys Ala Gly Lys Leu Glu Thr Leu Ala Leu Phe
145                 150                 155                 160

Asn Gly Phe Ser Thr Tyr Phe Thr Asp Phe Phe Glu Lys Arg Lys Asn
                    165                 170                 175

Val Phe Thr Lys Glu Ala Val Ser Thr Ser Ile Ala Tyr Arg Ile Val
            180                 185                 190

His Glu Asn Ser Leu Ile Phe Leu Ala Asn Met Thr Ser Tyr Lys Lys
            195                 200                 205

Ile Ser Glu Lys Ala Leu Asp Glu Ile Glu Val Ile Glu Lys Asn Asn
            210                 215                 220

Gln Asp Lys Met Gly Asp Trp Glu Leu Asn Gln Ile Phe Asn Pro Asp
225                 230                 235                 240

Phe Tyr Asn Met Val Leu Ile Gln Ser Gly Ile Asp Phe Tyr Asn Glu
                    245                 250                 255

Ile Cys Gly Val Val Asn Ala His Met Asn Leu Tyr Cys Gln Gln Thr
            260                 265                 270

Lys Asn Asn Tyr Asn Leu Phe Lys Met Arg Lys Leu His Lys Gln Ile
            275                 280                 285

Leu Ala Tyr Thr Ser Thr Ser Phe Glu Val Pro Lys Met Phe Glu Asp
            290                 295                 300

Asp Met Ser Val Tyr Asn Ala Val Asn Ala Phe Ile Asp Glu Thr Glu
305                 310                 315                 320

Lys Gly Asn Ile Ile Gly Lys Leu Lys Asp Ile Val Asn Lys Tyr Asp
                    325                 330                 335

Glu Leu Asp Glu Lys Arg Ile Tyr Ile Ser Lys Asp Phe Tyr Glu Thr
            340                 345                 350

Leu Ser Cys Phe Met Ser Gly Asn Trp Asn Leu Ile Thr Gly Cys Val
            355                 360                 365

Glu Asn Phe Tyr Asp Glu Asn Ile His Ala Lys Gly Lys Ser Lys Glu
            370                 375                 380

Glu Lys Val Lys Lys Ala Val Lys Glu Asp Lys Tyr Lys Ser Ile Asn
385                 390                 395                 400

Asp Val Asn Asp Leu Val Glu Lys Tyr Ile Asp Glu Lys Glu Arg Asn
                    405                 410                 415

Glu Phe Lys Asn Ser Asn Ala Lys Gln Tyr Ile Arg Glu Ile Ser Asn
            420                 425                 430

Ile Ile Thr Asp Thr Glu Thr Ala His Leu Glu Tyr Asp Asp His Ile
            435                 440                 445

Ser Leu Ile Glu Ser Glu Glu Lys Ala Asp Glu Met Lys Lys Arg Leu
            450                 455                 460

Asp Met Tyr Met Asn Met Tyr His Trp Ala Lys Ala Phe Ile Val Asp
465                 470                 475                 480

Glu Val Leu Asp Arg Asp Glu Met Phe Tyr Ser Asp Ile Asp Asp Ile
                    485                 490                 495

Tyr Asn Ile Leu Glu Asn Ile Val Pro Leu Tyr Asn Arg Val Arg Asn
```

```
                500             505             510
Tyr Val Thr Gln Lys Pro Tyr Asn Ser Lys Lys Ile Lys Leu Asn Phe
            515             520             525

Gln Ser Pro Thr Leu Ala Asn Gly Trp Ser Gln Ser Lys Glu Phe Asp
            530             535             540

Asn Asn Ala Ile Ile Leu Ile Arg Asp Asn Lys Tyr Tyr Leu Ala Ile
545             550             555             560

Phe Asn Ala Lys Asn Lys Pro Asp Lys Lys Ile Ile Gln Gly Asn Ser
                565             570             575

Asp Lys Lys Asn Asp Asn Asp Tyr Lys Lys Met Val Tyr Asn Leu Leu
                580             585             590

Pro Gly Ala Asn Lys Met Leu Pro Lys Val Phe Leu Ser Lys Lys Gly
            595             600             605

Ile Glu Thr Phe Lys Pro Ser Asp Tyr Ile Ile Ser Gly Tyr Asn Ala
            610             615             620

His Lys His Ile Lys Thr Ser Glu Asn Phe Asp Ile Ser Phe Cys Arg
625             630             635             640

Asp Leu Ile Asp Tyr Phe Lys Asn Ser Ile Glu Lys His Ala Glu Trp
                645             650             655

Arg Lys Tyr Glu Phe Lys Phe Ser Ala Thr Asp Ser Tyr Ser Asp Ile
                660             665             670

Ser Glu Phe Tyr Arg Glu Val Glu Met Gln Gly Tyr Arg Ile Asp Trp
            675             680             685

Thr Tyr Ile Ser Glu Ala Asp Ile Asn Lys Leu Asp Glu Glu Gly Lys
            690             695             700

Ile Tyr Leu Phe Gln Ile Tyr Asn Lys Asp Phe Ala Glu Asn Ser Thr
705             710             715             720

Gly Lys Glu Asn Leu His Thr Met Tyr Phe Lys Asn Ile Phe Ser Glu
                725             730             735

Glu Asn Leu Lys Asp Ile Ile Ile Lys Leu Asn Gly Gln Ala Glu Leu
            740             745             750

Phe Tyr Arg Arg Ala Ser Val Lys Asn Pro Val Lys His Lys Lys Asp
            755             760             765

Ser Val Leu Val Asn Lys Thr Tyr Lys Asn Gln Leu Asp Asn Gly Asp
            770             775             780

Val Val Arg Ile Pro Ile Pro Asp Asp Ile Tyr Asn Glu Ile Tyr Lys
785             790             795             800

Met Tyr Asn Gly Tyr Ile Lys Glu Ser Asp Leu Ser Glu Ala Ala Lys
                805             810             815

Glu Tyr Leu Asp Lys Val Glu Val Arg Thr Ala Gln Lys Asp Ile Val
            820             825             830

Lys Asp Tyr Arg Tyr Thr Val Asp Lys Tyr Phe Ile His Thr Pro Ile
            835             840             845

Thr Ile Asn Tyr Lys Val Thr Ala Arg Asn Asn Val Asn Asp Met Val
850             855             860

Val Lys Tyr Ile Ala Gln Asn Asp Asp Ile His Val Ile Gly Ile Asp
865             870             875             880

Arg Gly Glu Arg Asn Leu Ile Tyr Ile Ser Val Ile Asp Ser His Gly
                885             890             895

Asn Ile Val Lys Gln Lys Ser Tyr Asn Ile Leu Asn Asn Tyr Asp Tyr
                900             905             910

Lys Lys Lys Leu Val Glu Lys Glu Lys Thr Arg Glu Tyr Ala Arg Lys
            915             920             925
```

```
Asn Trp Lys Ser Ile Gly Asn Ile Lys Glu Leu Lys Glu Gly Tyr Ile
    930                 935                 940

Ser Gly Val Val His Glu Ile Ala Met Leu Ile Val Glu Tyr Asn Ala
945                 950                 955                 960

Ile Ile Ala Met Glu Asp Leu Asn Tyr Gly Phe Lys Arg Gly Arg Phe
                965                 970                 975

Lys Val Glu Arg Gln Val Tyr Gln Lys Phe Glu Ser Met Leu Ile Asn
                980                 985                 990

Lys Leu Asn Tyr Phe Ala Ser Lys Glu Lys Ser Val Asp Glu Pro Gly
        995                 1000                1005

Gly Leu Leu Lys Gly Tyr Gln Leu Thr Tyr Val Pro Asp Asn Ile
    1010                1015                1020

Lys Asn Leu Gly Lys Gln Cys Gly Val Ile Phe Tyr Val Pro Ala
    1025                1030                1035

Ala Phe Thr Ser Lys Ile Asp Pro Ser Thr Gly Phe Ile Ser Ala
    1040                1045                1050

Phe Asn Phe Lys Ser Ile Ser Thr Asn Ala Ser Arg Lys Gln Phe
    1055                1060                1065

Phe Met Gln Phe Asp Glu Ile Arg Tyr Cys Ala Glu Lys Asp Met
    1070                1075                1080

Phe Ser Phe Gly Phe Asp Tyr Asn Asn Phe Asp Thr Tyr Asn Ile
    1085                1090                1095

Thr Met Gly Lys Thr Gln Trp Thr Val Tyr Thr Asn Gly Glu Arg
    1100                1105                1110

Leu Gln Ser Glu Phe Asn Asn Ala Arg Arg Thr Gly Lys Thr Lys
    1115                1120                1125

Ser Ile Asn Leu Thr Glu Thr Ile Lys Leu Leu Leu Glu Asp Asn
    1130                1135                1140

Glu Ile Asn Tyr Ala Asp Gly His Asp Ile Arg Ile Asp Met Glu
    1145                1150                1155

Lys Met Asp Glu Asp Lys Lys Ser Glu Phe Phe Ala Gln Leu Leu
    1160                1165                1170

Ser Leu Tyr Lys Leu Thr Val Gln Met Arg Asn Ser Tyr Thr Glu
    1175                1180                1185

Ala Glu Glu Gln Glu Asn Gly Ile Ser Tyr Asp Lys Ile Ile Ser
    1190                1195                1200

Pro Val Ile Asn Asp Glu Gly Glu Phe Phe Asp Ser Asp Asn Tyr
    1205                1210                1215

Lys Glu Ser Asp Asp Lys Glu Cys Lys Met Pro Lys Asp Ala Asp
    1220                1225                1230

Ala Asn Gly Ala Tyr Cys Ile Ala Leu Lys Gly Leu Tyr Glu Val
    1235                1240                1245

Leu Lys Ile Lys Ser Glu Trp Thr Glu Asp Gly Phe Asp Arg Asn
    1250                1255                1260

Cys Leu Lys Leu Pro His Ala Glu Trp Leu Asp Phe Ile Gln Asn
    1265                1270                1275

Lys Arg Tyr Glu Lys Arg Pro Ala Ala Thr Lys Lys Ala Gly Gln
    1280                1285                1290

Ala Lys Lys Lys Lys Gly Ser Tyr Pro Tyr Asp Val Pro Asp Tyr
    1295                1300                1305

Ala Tyr Pro Tyr Asp Val Pro Asp Tyr Ala Tyr Pro Tyr Asp Val
    1310                1315                1320
```

```
Pro Asp Tyr Ala
    1325

<210> SEQ ID NO 64
<211> LENGTH: 1418
<212> TYPE: PRT
<213> ORGANISM: Moraxella bovoculi

<400> SEQUENCE: 64

Met Leu Phe Gln Asp Phe Thr His Leu Tyr Pro Leu Ser Lys Thr Val
1               5                   10                  15

Arg Phe Glu Leu Lys Pro Ile Asp Arg Thr Leu Glu His Ile His Ala
            20                  25                  30

Lys Asn Phe Leu Ser Gln Asp Glu Thr Met Ala Asp Met His Gln Lys
        35                  40                  45

Val Lys Val Ile Leu Asp Asp Tyr His Arg Asp Phe Ile Ala Asp Met
50                  55                  60

Met Gly Glu Val Lys Leu Thr Lys Leu Ala Glu Phe Tyr Asp Val Tyr
65                  70                  75                  80

Leu Lys Phe Arg Lys Asn Pro Lys Asp Asp Glu Leu Gln Lys Gln Leu
            85                  90                  95

Lys Asp Leu Gln Ala Val Leu Arg Lys Glu Ile Val Lys Pro Ile Gly
        100                 105                 110

Asn Gly Gly Lys Tyr Lys Ala Gly Tyr Asp Arg Leu Phe Gly Ala Lys
    115                 120                 125

Leu Phe Lys Asp Gly Lys Glu Leu Gly Asp Leu Ala Lys Phe Val Ile
130                 135                 140

Ala Gln Glu Gly Glu Ser Ser Pro Lys Leu Ala His Leu Ala His Phe
145                 150                 155                 160

Glu Lys Phe Ser Thr Tyr Phe Thr Gly Phe His Asp Asn Arg Lys Asn
            165                 170                 175

Met Tyr Ser Asp Glu Asp Lys His Thr Ala Ile Ala Tyr Arg Leu Ile
        180                 185                 190

His Glu Asn Leu Pro Arg Phe Ile Asp Asn Leu Gln Ile Leu Thr Thr
    195                 200                 205

Ile Lys Gln Lys His Ser Ala Leu Tyr Asp Gln Ile Ile Asn Glu Leu
210                 215                 220

Thr Ala Ser Gly Leu Asp Val Ser Leu Ala Ser His Leu Asp Gly Tyr
225                 230                 235                 240

His Lys Leu Leu Thr Gln Glu Gly Ile Thr Ala Tyr Asn Thr Leu Leu
            245                 250                 255

Gly Gly Ile Ser Gly Glu Ala Gly Ser Pro Lys Ile Gln Gly Ile Asn
        260                 265                 270

Glu Leu Ile Asn Ser His His Asn Gln His Cys His Lys Ser Glu Arg
    275                 280                 285

Ile Ala Lys Leu Arg Pro Leu His Lys Gln Ile Leu Ser Asp Gly Met
290                 295                 300

Ser Val Ser Phe Leu Pro Ser Lys Phe Ala Asp Asp Ser Glu Met Cys
305                 310                 315                 320

Gln Ala Val Asn Glu Phe Tyr Arg His Tyr Ala Asp Val Phe Ala Lys
            325                 330                 335

Val Gln Ser Leu Phe Asp Gly Phe Asp Asp His Gln Lys Asp Gly Ile
        340                 345                 350

Tyr Val Glu His Lys Asn Leu Asn Glu Leu Ser Lys Gln Ala Phe Gly
    355                 360                 365
```

```
Asp Phe Ala Leu Leu Gly Arg Val Leu Asp Gly Tyr Tyr Val Asp Val
    370                 375                 380

Val Asn Pro Glu Phe Asn Glu Arg Phe Ala Lys Ala Lys Thr Asp Asn
385                 390                 395                 400

Ala Lys Ala Lys Leu Thr Lys Glu Lys Asp Lys Phe Ile Lys Gly Val
                405                 410                 415

His Ser Leu Ala Ser Leu Glu Gln Ala Ile Glu His Tyr Thr Ala Arg
                420                 425                 430

His Asp Asp Glu Ser Val Gln Ala Gly Lys Leu Gly Gln Tyr Phe Lys
            435                 440                 445

His Gly Leu Ala Gly Val Asp Asn Pro Ile Gln Lys Ile His Asn Asn
    450                 455                 460

His Ser Thr Ile Lys Gly Phe Leu Glu Arg Glu Arg Pro Ala Gly Glu
465                 470                 475                 480

Arg Ala Leu Pro Lys Ile Lys Ser Gly Lys Asn Pro Glu Met Thr Gln
                485                 490                 495

Leu Arg Gln Leu Lys Glu Leu Leu Asp Asn Ala Leu Asn Val Ala His
                500                 505                 510

Phe Ala Lys Leu Leu Thr Thr Lys Thr Thr Leu Asp Asn Gln Asp Gly
            515                 520                 525

Asn Phe Tyr Gly Glu Phe Gly Val Leu Tyr Asp Glu Leu Ala Lys Ile
    530                 535                 540

Pro Thr Leu Tyr Asn Lys Val Arg Asp Tyr Leu Ser Gln Lys Pro Phe
545                 550                 555                 560

Ser Thr Glu Lys Tyr Lys Leu Asn Phe Gly Asn Pro Thr Leu Leu Asn
                565                 570                 575

Gly Trp Asp Leu Asn Lys Glu Lys Asp Asn Phe Gly Val Ile Leu Gln
            580                 585                 590

Lys Asp Gly Cys Tyr Tyr Leu Ala Leu Leu Asp Lys Ala His Lys Lys
            595                 600                 605

Val Phe Asp Asn Ala Pro Asn Thr Gly Lys Ser Ile Tyr Gln Lys Met
    610                 615                 620

Ile Tyr Lys Tyr Leu Glu Val Arg Lys Gln Phe Pro Lys Val Phe Phe
625                 630                 635                 640

Ser Lys Glu Ala Ile Ala Ile Asn Tyr His Pro Ser Lys Glu Leu Val
                645                 650                 655

Glu Ile Lys Asp Lys Gly Arg Gln Arg Ser Asp Asp Glu Arg Leu Lys
                660                 665                 670

Leu Tyr Arg Phe Ile Leu Glu Cys Leu Lys Ile His Pro Lys Tyr Asp
            675                 680                 685

Lys Lys Phe Glu Gly Ala Ile Gly Asp Ile Gln Leu Phe Lys Lys Asp
    690                 695                 700

Lys Lys Gly Arg Glu Val Pro Ile Ser Glu Lys Asp Leu Phe Asp Lys
705                 710                 715                 720

Ile Asn Gly Ile Phe Ser Ser Lys Pro Lys Leu Glu Met Glu Asp Phe
                725                 730                 735

Phe Ile Gly Glu Phe Lys Arg Tyr Asn Pro Ser Gln Asp Leu Val Asp
            740                 745                 750

Gln Tyr Asn Ile Tyr Lys Lys Ile Asp Ser Asn Asp Asn Arg Lys Lys
    755                 760                 765

Glu Asn Phe Tyr Asn Asn His Pro Lys Phe Lys Lys Asp Leu Val Arg
770                 775                 780
```

-continued

```
Tyr Tyr Tyr Glu Ser Met Cys Lys His Glu Glu Trp Glu Ser Phe
785                 790                 795                 800

Glu Phe Ser Lys Lys Leu Gln Asp Ile Gly Cys Tyr Val Asp Val Asn
                805                 810                 815

Glu Leu Phe Thr Glu Ile Glu Thr Arg Arg Leu Asn Tyr Lys Ile Ser
            820                 825                 830

Phe Cys Asn Ile Asn Ala Asp Tyr Ile Asp Glu Leu Val Glu Gln Gly
        835                 840                 845

Gln Leu Tyr Leu Phe Gln Ile Tyr Asn Lys Asp Phe Ser Pro Lys Ala
    850                 855                 860

His Gly Lys Pro Asn Leu His Thr Leu Tyr Phe Lys Ala Leu Phe Ser
865                 870                 875                 880

Glu Asp Asn Leu Ala Asp Pro Ile Tyr Lys Leu Asn Gly Glu Ala Gln
                885                 890                 895

Ile Phe Tyr Arg Lys Ala Ser Leu Asp Met Asn Glu Thr Thr Ile His
            900                 905                 910

Arg Ala Gly Glu Val Leu Glu Asn Lys Asn Pro Asp Asn Pro Lys Lys
        915                 920                 925

Arg Gln Phe Val Tyr Asp Ile Ile Lys Asp Lys Arg Tyr Thr Gln Asp
    930                 935                 940

Lys Phe Met Leu His Val Pro Ile Thr Met Asn Phe Gly Val Gln Gly
945                 950                 955                 960

Met Thr Ile Lys Glu Phe Asn Lys Lys Val Asn Gln Ser Ile Gln Gln
                965                 970                 975

Tyr Asp Glu Val Asn Val Ile Gly Ile Asp Arg Gly Glu Arg His Leu
            980                 985                 990

Leu Tyr Leu Thr Val Ile Asn Ser Lys Gly Glu Ile Leu Glu Gln Cys
    995                 1000                1005

Ser Leu Asn Asp Ile Thr Thr Ala Ser Ala Asn Gly Thr Gln Met
    1010                1015                1020

Thr Thr Pro Tyr His Lys Ile Leu Asp Lys Arg Glu Ile Glu Arg
    1025                1030                1035

Leu Asn Ala Arg Val Gly Trp Gly Glu Ile Glu Thr Ile Lys Glu
    1040                1045                1050

Leu Lys Ser Gly Tyr Leu Ser His Val Val His Gln Ile Ser Gln
    1055                1060                1065

Leu Met Leu Lys Tyr Asn Ala Ile Val Val Leu Glu Asp Leu Asn
    1070                1075                1080

Phe Gly Phe Lys Arg Gly Arg Phe Lys Val Glu Lys Gln Ile Tyr
    1085                1090                1095

Gln Asn Phe Glu Asn Ala Leu Ile Lys Lys Leu Asn His Leu Val
    1100                1105                1110

Leu Lys Asp Lys Ala Asp Asp Glu Ile Gly Ser Tyr Lys Asn Ala
    1115                1120                1125

Leu Gln Leu Thr Asn Asn Phe Thr Asp Leu Lys Ser Ile Gly Lys
    1130                1135                1140

Gln Thr Gly Phe Leu Phe Tyr Val Pro Ala Trp Asn Thr Ser Lys
    1145                1150                1155

Ile Asp Pro Glu Thr Gly Phe Val Asp Leu Leu Lys Pro Arg Tyr
    1160                1165                1170

Glu Asn Ile Ala Gln Ser Gln Ala Phe Phe Gly Lys Phe Asp Lys
    1175                1180                1185

Ile Cys Tyr Asn Ala Asp Lys Asp Tyr Phe Glu Phe His Ile Asp
```

-continued

```
                1190                1195                1200

Tyr Ala Lys Phe Thr Asp Lys Ala Lys Asn Ser Arg Gln Ile Trp
        1205                1210                1215

Thr Ile Cys Ser His Gly Asp Lys Arg Tyr Val Tyr Asp Lys Thr
        1220                1225                1230

Ala Asn Gln Asn Lys Gly Ala Ala Lys Gly Ile Asn Val Asn Asp
        1235                1240                1245

Glu Leu Lys Ser Leu Phe Ala Arg His His Ile Asn Glu Lys Gln
        1250                1255                1260

Pro Asn Leu Val Met Asp Ile Cys Gln Asn Asn Asp Lys Glu Phe
        1265                1270                1275

His Lys Ser Leu Met Tyr Leu Leu Lys Thr Leu Leu Ala Leu Arg
        1280                1285                1290

Tyr Ser Asn Ala Ser Ser Asp Glu Asp Phe Ile Leu Ser Pro Val
        1295                1300                1305

Ala Asn Asp Glu Gly Val Phe Phe Asn Ser Ala Leu Ala Asp Asp
        1310                1315                1320

Thr Gln Pro Gln Asn Ala Asp Ala Asn Gly Ala Tyr His Ile Ala
        1325                1330                1335

Leu Lys Gly Leu Trp Leu Leu Asn Glu Leu Lys Asn Ser Asp Asp
        1340                1345                1350

Leu Asn Lys Val Lys Leu Ala Ile Asp Asn Gln Thr Trp Leu Asn
        1355                1360                1365

Phe Ala Gln Asn Arg Lys Arg Pro Ala Ala Thr Lys Lys Ala Gly
        1370                1375                1380

Gln Ala Lys Lys Lys Gly Ser Tyr Pro Tyr Asp Val Pro Asp
        1385                1390                1395

Tyr Ala Tyr Pro Tyr Asp Val Pro Asp Tyr Ala Tyr Pro Tyr Asp
        1400                1405                1410

Val Pro Asp Tyr Ala
        1415

<210> SEQ ID NO 65
<211> LENGTH: 1308
<212> TYPE: PRT
<213> ORGANISM: Leptospira inadai

<400> SEQUENCE: 65

Met Glu Asp Tyr Ser Gly Phe Val Asn Ile Tyr Ser Ile Gln Lys Thr
1               5                   10                  15

Leu Arg Phe Glu Leu Lys Pro Val Gly Lys Thr Leu Glu His Ile Glu
            20                  25                  30

Lys Lys Gly Phe Leu Lys Asp Lys Ile Arg Ala Glu Asp Tyr Lys
        35                  40                  45

Ala Val Lys Lys Ile Ile Asp Lys Tyr His Arg Ala Tyr Ile Glu Glu
    50                  55                  60

Val Phe Asp Ser Val Leu His Gln Lys Lys Lys Asp Lys Thr Arg
65                  70                  75                  80

Phe Ser Thr Gln Phe Ile Lys Glu Ile Lys Glu Phe Ser Glu Leu Tyr
                85                  90                  95

Tyr Lys Thr Glu Lys Asn Ile Pro Asp Lys Glu Arg Leu Glu Ala Leu
            100                 105                 110

Ser Glu Lys Leu Arg Lys Met Leu Val Gly Ala Phe Lys Gly Glu Phe
        115                 120                 125
```

```
Ser Glu Glu Val Ala Glu Lys Tyr Lys Asn Leu Phe Ser Lys Glu Leu
    130                 135                 140

Ile Arg Asn Glu Ile Glu Lys Phe Cys Glu Thr Asp Glu Glu Arg Lys
145                 150                 155                 160

Gln Val Ser Asn Phe Lys Ser Phe Thr Thr Tyr Phe Thr Gly Phe His
                165                 170                 175

Ser Asn Arg Gln Asn Ile Tyr Ser Asp Glu Lys Lys Ser Thr Ala Ile
            180                 185                 190

Gly Tyr Arg Ile Ile His Gln Asn Leu Pro Lys Phe Leu Asp Asn Leu
        195                 200                 205

Lys Ile Ile Glu Ser Ile Gln Arg Arg Phe Lys Asp Phe Pro Trp Ser
210                 215                 220

Asp Leu Lys Lys Asn Leu Lys Lys Ile Asp Lys Asn Ile Lys Leu Thr
225                 230                 235                 240

Glu Tyr Phe Ser Ile Asp Gly Phe Val Asn Val Leu Asn Gln Lys Gly
                245                 250                 255

Ile Asp Ala Tyr Asn Thr Ile Leu Gly Gly Lys Ser Glu Glu Ser Gly
            260                 265                 270

Glu Lys Ile Gln Gly Leu Asn Glu Tyr Ile Asn Leu Tyr Arg Gln Lys
        275                 280                 285

Asn Asn Ile Asp Arg Lys Asn Leu Pro Asn Val Lys Ile Leu Phe Lys
290                 295                 300

Gln Ile Leu Gly Asp Arg Glu Thr Lys Ser Phe Ile Pro Glu Ala Phe
305                 310                 315                 320

Pro Asp Asp Gln Ser Val Leu Asn Ser Ile Thr Glu Phe Ala Lys Tyr
                325                 330                 335

Leu Lys Leu Asp Lys Lys Lys Ser Ile Ile Ala Glu Leu Lys Lys
            340                 345                 350

Phe Leu Ser Ser Phe Asn Arg Tyr Glu Leu Asp Gly Ile Tyr Leu Ala
        355                 360                 365

Asn Asp Asn Ser Leu Ala Ser Ile Ser Thr Phe Leu Phe Asp Asp Trp
370                 375                 380

Ser Phe Ile Lys Lys Ser Val Ser Phe Lys Tyr Asp Glu Ser Val Gly
385                 390                 395                 400

Asp Pro Lys Lys Ile Lys Ser Pro Leu Lys Tyr Glu Lys Glu Lys
                405                 410                 415

Glu Lys Trp Leu Lys Gln Lys Tyr Tyr Thr Ile Ser Phe Leu Asn Asp
            420                 425                 430

Ala Ile Glu Ser Tyr Ser Lys Ser Gln Asp Glu Lys Arg Val Lys Ile
        435                 440                 445

Arg Leu Glu Ala Tyr Phe Ala Glu Phe Lys Ser Lys Asp Asp Ala Lys
450                 455                 460

Lys Gln Phe Asp Leu Leu Glu Arg Ile Glu Glu Ala Tyr Ala Ile Val
465                 470                 475                 480

Glu Pro Leu Leu Gly Ala Glu Tyr Pro Arg Asp Arg Asn Leu Lys Ala
                485                 490                 495

Asp Lys Lys Glu Val Gly Lys Ile Lys Asp Phe Leu Asp Ser Ile Lys
            500                 505                 510

Ser Leu Gln Phe Phe Leu Lys Pro Leu Leu Ser Ala Glu Ile Phe Asp
        515                 520                 525

Glu Lys Asp Leu Gly Phe Tyr Asn Gln Leu Glu Gly Tyr Tyr Glu Glu
530                 535                 540

Ile Asp Ser Ile Gly His Leu Tyr Asn Lys Val Arg Asn Tyr Leu Thr
```

```
              545                 550                 555                 560
Gly Lys Ile Tyr Ser Lys Glu Lys Phe Lys Leu Asn Phe Glu Asn Ser
                565                 570                 575

Thr Leu Leu Lys Gly Trp Asp Glu Asn Arg Glu Val Ala Asn Leu Cys
                580                 585                 590

Val Ile Phe Arg Glu Asp Gln Lys Tyr Tyr Leu Gly Val Met Asp Lys
                595                 600                 605

Glu Asn Asn Thr Ile Leu Ser Asp Ile Pro Lys Val Lys Pro Asn Glu
                610                 615                 620

Leu Phe Tyr Glu Lys Met Val Tyr Lys Leu Ile Pro Thr Pro His Met
625                 630                 635                 640

Gln Leu Pro Arg Ile Ile Phe Ser Ser Asp Asn Leu Ser Ile Tyr Asn
                645                 650                 655

Pro Ser Lys Ser Ile Leu Lys Ile Arg Glu Ala Lys Ser Phe Lys Glu
                660                 665                 670

Gly Lys Asn Phe Lys Leu Lys Asp Cys His Lys Phe Ile Asp Phe Tyr
                675                 680                 685

Lys Glu Ser Ile Ser Lys Asn Glu Asp Trp Ser Arg Phe Asp Phe Lys
                690                 695                 700

Phe Ser Lys Thr Ser Ser Tyr Glu Asn Ile Ser Glu Phe Tyr Arg Glu
705                 710                 715                 720

Val Glu Arg Gln Gly Tyr Asn Leu Asp Phe Lys Lys Val Ser Lys Phe
                725                 730                 735

Tyr Ile Asp Ser Leu Val Glu Asp Gly Lys Leu Tyr Leu Phe Gln Ile
                740                 745                 750

Tyr Asn Lys Asp Phe Ser Ile Phe Ser Lys Gly Lys Pro Asn Leu His
                755                 760                 765

Thr Ile Tyr Phe Arg Ser Leu Phe Ser Lys Glu Asn Leu Lys Asp Val
                770                 775                 780

Cys Leu Lys Leu Asn Gly Glu Ala Glu Met Phe Phe Arg Lys Lys Ser
785                 790                 795                 800

Ile Asn Tyr Asp Glu Lys Lys Arg Glu Gly His His Pro Glu Leu
                805                 810                 815

Phe Glu Lys Leu Lys Tyr Pro Ile Leu Lys Asp Lys Arg Tyr Ser Glu
                820                 825                 830

Asp Lys Phe Gln Phe His Leu Pro Ile Ser Leu Asn Phe Lys Ser Lys
                835                 840                 845

Glu Arg Leu Asn Phe Asn Leu Lys Val Asn Glu Phe Leu Lys Arg Asn
850                 855                 860

Lys Asp Ile Asn Ile Ile Gly Ile Asp Arg Gly Glu Arg Asn Leu Leu
865                 870                 875                 880

Tyr Leu Val Met Ile Asn Gln Lys Gly Glu Ile Leu Lys Gln Thr Leu
                885                 890                 895

Leu Asp Ser Met Gln Ser Gly Lys Gly Arg Pro Glu Ile Asn Tyr Lys
                900                 905                 910

Glu Lys Leu Gln Glu Lys Glu Ile Glu Arg Asp Lys Ala Arg Lys Ser
                915                 920                 925

Trp Gly Thr Val Glu Asn Ile Lys Glu Leu Lys Glu Gly Tyr Leu Ser
                930                 935                 940

Ile Val Ile His Gln Ile Ser Lys Leu Met Val Glu Asn Asn Ala Ile
945                 950                 955                 960

Val Val Leu Glu Asp Leu Asn Ile Gly Phe Lys Arg Gly Arg Gln Lys
                965                 970                 975
```

Val Glu Arg Gln Val Tyr Gln Lys Phe Glu Lys Met Leu Ile Asp Lys
                980                 985                 990

Leu Asn Phe Leu Val Phe Lys Glu Asn Lys Pro Thr Glu Pro Gly Gly
            995                1000                1005

Val Leu Lys Ala Tyr Gln Leu Thr Asp Glu Phe Gln Ser Phe Glu
    1010                1015                1020

Lys Leu Ser Lys Gln Thr Gly Phe Leu Phe Tyr Val Pro Ser Trp
    1025                1030                1035

Asn Thr Ser Lys Ile Asp Pro Arg Thr Gly Phe Ile Asp Phe Leu
    1040                1045                1050

His Pro Ala Tyr Glu Asn Ile Glu Lys Ala Lys Gln Trp Ile Asn
    1055                1060                1065

Lys Phe Asp Ser Ile Arg Phe Asn Ser Lys Met Asp Trp Phe Glu
    1070                1075                1080

Phe Thr Ala Asp Thr Arg Lys Phe Ser Glu Asn Leu Met Leu Gly
    1085                1090                1095

Lys Asn Arg Val Trp Val Ile Cys Thr Thr Asn Val Glu Arg Tyr
    1100                1105                1110

Phe Thr Ser Lys Thr Ala Asn Ser Ser Ile Gln Tyr Asn Ser Ile
    1115                1120                1125

Gln Ile Thr Glu Lys Leu Lys Glu Leu Phe Val Asp Ile Pro Phe
    1130                1135                1140

Ser Asn Gly Gln Asp Leu Lys Pro Glu Ile Leu Arg Lys Asn Asp
    1145                1150                1155

Ala Val Phe Phe Lys Ser Leu Leu Phe Tyr Ile Lys Thr Thr Leu
    1160                1165                1170

Ser Leu Arg Gln Asn Asn Gly Lys Lys Gly Glu Glu Lys Asp
    1175                1180                1185

Phe Ile Leu Ser Pro Val Val Asp Ser Lys Gly Arg Phe Phe Asn
    1190                1195                1200

Ser Leu Glu Ala Ser Asp Asp Glu Pro Lys Asp Ala Asp Ala Asn
    1205                1210                1215

Gly Ala Tyr His Ile Ala Leu Lys Gly Leu Met Asn Leu Leu Val
    1220                1225                1230

Leu Asn Glu Thr Lys Glu Glu Asn Leu Ser Arg Pro Lys Trp Lys
    1235                1240                1245

Ile Lys Asn Lys Asp Trp Leu Glu Phe Val Trp Glu Arg Asn Arg
    1250                1255                1260

Lys Arg Pro Ala Ala Thr Lys Lys Ala Gly Gln Ala Lys Lys Lys
    1265                1270                1275

Lys Gly Ser Tyr Pro Tyr Asp Val Pro Asp Tyr Ala Tyr Pro Tyr
    1280                1285                1290

Asp Val Pro Asp Tyr Ala Tyr Pro Tyr Asp Val Pro Asp Tyr Ala
    1295                1300                1305

<210> SEQ ID NO 66
<211> LENGTH: 1273
<212> TYPE: PRT
<213> ORGANISM: Lachnospiraceae bacterium

<400> SEQUENCE: 66

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp

```
                 20                  25                  30
Asn Lys Arg Leu Leu Val Glu Asp Glu Lys Ala Glu Asp Tyr Lys
             35                  40                  45
Gly Val Lys Lys Leu Leu Asp Arg Tyr Tyr Leu Ser Phe Ile Asn Asp
         50                  55                  60
Val Leu His Ser Ile Lys Leu Lys Asn Leu Asn Asn Tyr Ile Ser Leu
 65                  70                  75                  80
Phe Arg Lys Lys Thr Arg Thr Glu Lys Glu Asn Lys Glu Leu Glu Asn
                 85                  90                  95
Leu Glu Ile Asn Leu Arg Lys Glu Ile Ala Lys Ala Phe Lys Gly Asn
             100                 105                 110
Glu Gly Tyr Lys Ser Leu Phe Lys Lys Asp Ile Ile Glu Thr Ile Leu
             115                 120                 125
Pro Glu Phe Leu Asp Asp Lys Asp Glu Ile Ala Leu Val Asn Ser Phe
             130                 135                 140
Asn Gly Phe Thr Thr Ala Phe Thr Gly Phe Phe Asp Asn Arg Glu Asn
145                 150                 155                 160
Met Phe Ser Glu Glu Ala Lys Ser Thr Ser Ile Ala Phe Arg Cys Ile
                 165                 170                 175
Asn Glu Asn Leu Thr Arg Tyr Ile Ser Asn Met Asp Ile Phe Glu Lys
             180                 185                 190
Val Asp Ala Ile Phe Asp Lys His Glu Val Gln Glu Ile Lys Glu Lys
             195                 200                 205
Ile Leu Asn Ser Asp Tyr Asp Val Glu Asp Phe Phe Glu Gly Glu Phe
             210                 215                 220
Phe Asn Phe Val Leu Thr Gln Glu Gly Ile Asp Val Tyr Asn Ala Ile
225                 230                 235                 240
Ile Gly Gly Phe Val Thr Glu Ser Gly Glu Lys Ile Lys Gly Leu Asn
                 245                 250                 255
Glu Tyr Ile Asn Leu Tyr Asn Gln Lys Thr Lys Gln Lys Leu Pro Lys
             260                 265                 270
Phe Lys Pro Leu Tyr Lys Gln Val Leu Ser Asp Arg Glu Ser Leu Ser
             275                 280                 285
Phe Tyr Gly Glu Gly Tyr Thr Ser Asp Glu Glu Val Leu Glu Val Phe
             290                 295                 300
Arg Asn Thr Leu Asn Lys Asn Ser Glu Ile Phe Ser Ser Ile Lys Lys
305                 310                 315                 320
Leu Glu Lys Leu Phe Lys Asn Phe Asp Glu Tyr Ser Ser Ala Gly Ile
             325                 330                 335
Phe Val Lys Asn Gly Pro Ala Ile Ser Thr Ile Ser Lys Asp Ile Phe
             340                 345                 350
Gly Glu Trp Asn Val Ile Arg Asp Lys Trp Asn Ala Glu Tyr Asp Asp
             355                 360                 365
Ile His Leu Lys Lys Lys Ala Val Val Thr Glu Lys Tyr Glu Asp Asp
             370                 375                 380
Arg Arg Lys Ser Phe Lys Lys Ile Gly Ser Phe Ser Leu Glu Gln Leu
385                 390                 395                 400
Gln Glu Tyr Ala Asp Ala Asp Leu Ser Val Val Glu Lys Leu Lys Glu
             405                 410                 415
Ile Ile Ile Gln Lys Val Asp Glu Ile Tyr Lys Val Tyr Gly Ser Ser
             420                 425                 430
Glu Lys Leu Phe Asp Ala Asp Phe Val Leu Glu Lys Ser Leu Lys Lys
             435                 440                 445
```

-continued

```
Asn Asp Ala Val Val Ala Ile Met Lys Asp Leu Leu Asp Ser Val Lys
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
                500                 505                 510

Gln Lys Pro Tyr Ser Lys Asp Lys Phe Lys Leu Tyr Phe Gln Asn Pro
            515                 520                 525

Gln Phe Met Gly Gly Trp Asp Lys Asp Lys Glu Thr Asp Tyr Arg Ala
        530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Val Asn Gly
                565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
        595                 600                 605

Ser Glu Asp Ile Gln Lys Ile Tyr Lys Asn Gly Thr Phe Lys Lys Gly
    610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
        675                 680                 685

Glu Val Asp Lys Leu Val Glu Glu Gly Lys Leu Tyr Met Phe Gln Ile
    690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
        755                 760                 765

Asn Pro Asp Asn Pro Lys Lys Thr Thr Thr Leu Ser Tyr Asp Val Tyr
    770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
            820                 825                 830

Arg Gly Glu Arg Asn Leu Leu Tyr Ile Val Val Asp Gly Lys Gly
        835                 840                 845

Asn Ile Val Glu Gln Tyr Ser Leu Asn Glu Ile Asn Asn Phe Asn
    850                 855                 860
```

-continued

```
Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
            885                 890                 895

Lys Glu Leu Lys Ala Gly Tyr Ile Ser Gln Val Val His Lys Ile Cys
        900                 905                 910

Glu Leu Val Glu Lys Tyr Asp Ala Val Ile Ala Leu Glu Asp Leu Asn
            915                 920                 925

Ser Gly Phe Lys Asn Ser Arg Val Lys Val Lys Gln Val Tyr Gln
        930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
            980                 985                 990

Ile Phe Tyr Ile Pro Ala Trp Leu Thr Ser Lys Ile Asp Pro Ser Thr
        995                 1000                1005

Gly Phe Val Asn Leu Leu Lys Thr Lys Tyr Thr Ser Ile Ala Asp
    1010                1015                1020

Ser Lys Lys Phe Ile Ser Ser Phe Asp Arg Ile Met Tyr Val Pro
    1025                1030                1035

Glu Glu Asp Leu Phe Glu Phe Ala Leu Asp Tyr Lys Asn Phe Ser
    1040                1045                1050

Arg Thr Asp Ala Asp Tyr Ile Lys Lys Trp Lys Leu Tyr Ser Tyr
    1055                1060                1065

Gly Asn Arg Ile Arg Ile Phe Arg Asn Pro Lys Lys Asn Asn Val
    1070                1075                1080

Phe Asp Trp Glu Glu Val Cys Leu Thr Ser Ala Tyr Lys Glu Leu
    1085                1090                1095

Phe Asn Lys Tyr Gly Ile Asn Tyr Gln Gln Gly Asp Ile Arg Ala
    1100                1105                1110

Leu Leu Cys Glu Gln Ser Asp Lys Ala Phe Tyr Ser Ser Phe Met
    1115                1120                1125

Ala Leu Met Ser Leu Met Leu Gln Met Arg Asn Ser Ile Thr Gly
    1130                1135                1140

Arg Thr Asp Val Asp Phe Leu Ile Ser Pro Val Lys Asn Ser Asp
    1145                1150                1155

Gly Ile Phe Tyr Asp Ser Arg Asn Tyr Glu Ala Gln Glu Asn Ala
    1160                1165                1170

Ile Leu Pro Lys Asn Ala Asp Ala Asn Gly Ala Tyr Asn Ile Ala
    1175                1180                1185

Arg Lys Val Leu Trp Ala Ile Gly Gln Phe Lys Lys Ala Glu Asp
    1190                1195                1200

Glu Lys Leu Asp Lys Val Lys Ile Ala Ile Ser Asn Lys Glu Trp
    1205                1210                1215

Leu Glu Tyr Ala Gln Thr Ser Val Lys His Lys Arg Pro Ala Ala
    1220                1225                1230

Thr Lys Lys Ala Gly Gln Ala Lys Lys Lys Lys Gly Ser Tyr Pro
    1235                1240                1245

Tyr Asp Val Pro Asp Tyr Ala Tyr Pro Tyr Asp Val Pro Asp Tyr
    1250                1255                1260

Ala Tyr Pro Tyr Asp Val Pro Asp Tyr Ala
```

<210> SEQ ID NO 67
<211> LENGTH: 1305
<212> TYPE: PRT
<213> ORGANISM: Porphyromonas crevioricanis

<400> SEQUENCE: 67

```
Met Asp Ser Leu Lys Asp Phe Thr Asn Leu Tyr Pro Val Ser Lys Thr
1               5                   10                  15
Leu Arg Phe Glu Leu Lys Pro Val Gly Lys Thr Leu Glu Asn Ile Glu
            20                  25                  30
Lys Ala Gly Ile Leu Lys Glu Asp Glu His Arg Ala Glu Ser Tyr Arg
        35                  40                  45
Arg Val Lys Lys Ile Ile Asp Thr Tyr His Lys Val Phe Ile Asp Ser
    50                  55                  60
Ser Leu Glu Asn Met Ala Lys Met Gly Ile Glu Asn Glu Ile Lys Ala
65                  70                  75                  80
Met Leu Gln Ser Phe Cys Glu Leu Tyr Lys Lys Asp His Arg Thr Glu
                85                  90                  95
Gly Glu Asp Lys Ala Leu Asp Lys Ile Arg Ala Val Leu Arg Gly Leu
            100                 105                 110
Ile Val Gly Ala Phe Thr Gly Val Cys Gly Arg Arg Glu Asn Thr Val
        115                 120                 125
Gln Asn Glu Lys Tyr Glu Ser Leu Phe Lys Glu Lys Leu Ile Lys Glu
    130                 135                 140
Ile Leu Pro Asp Phe Val Leu Ser Thr Glu Ala Glu Ser Leu Pro Phe
145                 150                 155                 160
Ser Val Glu Glu Ala Thr Arg Ser Leu Lys Glu Phe Asp Ser Phe Thr
                165                 170                 175
Ser Tyr Phe Ala Gly Phe Tyr Glu Asn Arg Lys Asn Ile Tyr Ser Thr
            180                 185                 190
Lys Pro Gln Ser Thr Ala Ile Ala Tyr Arg Leu Ile His Glu Asn Leu
        195                 200                 205
Pro Lys Phe Ile Asp Asn Ile Leu Val Phe Gln Lys Ile Lys Glu Pro
    210                 215                 220
Ile Ala Lys Glu Leu Glu His Ile Arg Ala Asp Phe Ser Ala Gly Gly
225                 230                 235                 240
Tyr Ile Lys Lys Asp Glu Arg Leu Glu Asp Ile Phe Ser Leu Asn Tyr
                245                 250                 255
Tyr Ile His Val Leu Ser Gln Ala Gly Ile Glu Lys Tyr Asn Ala Leu
            260                 265                 270
Ile Gly Lys Ile Val Thr Glu Gly Asp Gly Glu Met Lys Gly Leu Asn
        275                 280                 285
Glu His Ile Asn Leu Tyr Asn Gln Gln Arg Gly Arg Glu Asp Arg Leu
    290                 295                 300
Pro Leu Phe Arg Pro Leu Tyr Lys Gln Ile Leu Ser Asp Arg Glu Gln
305                 310                 315                 320
Leu Ser Tyr Leu Pro Glu Ser Phe Glu Lys Asp Glu Glu Leu Leu Arg
                325                 330                 335
Ala Leu Lys Glu Phe Tyr Asp His Ile Ala Glu Asp Ile Leu Gly Arg
            340                 345                 350
Thr Gln Gln Leu Met Thr Ser Ile Ser Glu Tyr Asp Leu Ser Arg Ile
        355                 360                 365
```

```
Tyr Val Arg Asn Asp Ser Gln Leu Thr Asp Ile Ser Lys Lys Met Leu
    370                 375                 380

Gly Asp Trp Asn Ala Ile Tyr Met Ala Arg Glu Arg Ala Tyr Asp His
385                 390                 395                 400

Glu Gln Ala Pro Lys Arg Ile Thr Ala Lys Tyr Glu Arg Asp Arg Ile
                405                 410                 415

Lys Ala Leu Lys Gly Glu Ser Ile Ser Leu Ala Asn Leu Asn Ser
                420                 425                 430

Cys Ile Ala Phe Leu Asp Asn Val Arg Asp Cys Arg Val Asp Thr Tyr
                435                 440                 445

Leu Ser Thr Leu Gly Gln Lys Glu Gly Pro His Gly Leu Ser Asn Leu
    450                 455                 460

Val Glu Asn Val Phe Ala Ser Tyr His Glu Ala Glu Gln Leu Leu Ser
465                 470                 475                 480

Phe Pro Tyr Pro Glu Glu Asn Asn Leu Ile Gln Asp Lys Asp Asn Val
                485                 490                 495

Val Leu Ile Lys Asn Leu Leu Asp Asn Ile Ser Asp Leu Gln Arg Phe
                500                 505                 510

Leu Lys Pro Leu Trp Gly Met Gly Asp Glu Pro Asp Lys Asp Glu Arg
                515                 520                 525

Phe Tyr Gly Glu Tyr Asn Tyr Ile Arg Gly Ala Leu Asp Gln Val Ile
                530                 535                 540

Pro Leu Tyr Asn Lys Val Arg Asn Tyr Leu Thr Arg Lys Pro Tyr Ser
545                 550                 555                 560

Thr Arg Lys Val Lys Leu Asn Phe Gly Asn Ser Gln Leu Leu Ser Gly
                565                 570                 575

Trp Asp Arg Asn Lys Glu Lys Asp Asn Ser Cys Val Ile Leu Arg Lys
                580                 585                 590

Gly Gln Asn Phe Tyr Leu Ala Ile Met Asn Asn Arg His Lys Arg Ser
                595                 600                 605

Phe Glu Asn Lys Met Leu Pro Glu Tyr Lys Glu Gly Glu Pro Tyr Phe
    610                 615                 620

Glu Lys Met Asp Tyr Lys Phe Leu Pro Asp Pro Asn Lys Met Leu Pro
625                 630                 635                 640

Lys Val Phe Leu Ser Lys Lys Gly Ile Glu Ile Tyr Lys Pro Ser Pro
                645                 650                 655

Lys Leu Leu Glu Gln Tyr Gly His Gly Thr His Lys Lys Gly Asp Thr
                660                 665                 670

Phe Ser Met Asp Asp Leu His Glu Leu Ile Asp Phe Phe Lys His Ser
                675                 680                 685

Ile Glu Ala His Glu Asp Trp Lys Gln Phe Gly Phe Lys Phe Ser Asp
    690                 695                 700

Thr Ala Thr Tyr Glu Asn Val Ser Ser Phe Tyr Arg Glu Val Glu Asp
705                 710                 715                 720

Gln Gly Tyr Lys Leu Ser Phe Arg Lys Val Ser Glu Ser Tyr Val Tyr
                725                 730                 735

Ser Leu Ile Asp Gln Gly Lys Leu Tyr Leu Phe Gln Ile Tyr Asn Lys
                740                 745                 750

Asp Phe Ser Pro Cys Ser Lys Gly Thr Pro Asn Leu His Thr Leu Tyr
                755                 760                 765

Trp Arg Met Leu Phe Asp Glu Arg Asn Leu Ala Asp Val Ile Tyr Lys
    770                 775                 780

Leu Asp Gly Lys Ala Glu Ile Phe Phe Arg Glu Lys Ser Leu Lys Asn
```

-continued

```
                785                 790                 795                 800
Asp His Pro Thr His Pro Ala Gly Lys Pro Ile Lys Lys Ser Arg
                    805                 810                 815

Gln Lys Lys Gly Glu Glu Ser Leu Phe Glu Tyr Asp Leu Val Lys Asp
                    820                 825                 830

Arg Arg Tyr Thr Met Asp Lys Phe Gln Phe His Val Pro Ile Thr Met
                    835                 840                 845

Asn Phe Lys Cys Ser Ala Gly Ser Lys Val Asn Asp Met Val Asn Ala
                    850                 855                 860

His Ile Arg Glu Ala Lys Asp Met His Val Ile Gly Ile Asp Arg Gly
865                 870                 875                 880

Glu Arg Asn Leu Leu Tyr Ile Cys Val Ile Asp Ser Arg Gly Thr Ile
                    885                 890                 895

Leu Asp Gln Ile Ser Leu Asn Thr Ile Asn Asp Ile Asp Tyr His Asp
                    900                 905                 910

Leu Leu Glu Ser Arg Asp Lys Asp Arg Gln Gln Glu His Arg Asn Trp
                    915                 920                 925

Gln Thr Ile Glu Gly Ile Lys Glu Leu Lys Gln Gly Tyr Leu Ser Gln
                    930                 935                 940

Ala Val His Arg Ile Ala Glu Leu Met Val Ala Tyr Lys Ala Val Val
945                 950                 955                 960

Ala Leu Glu Asp Leu Asn Met Gly Phe Lys Arg Gly Arg Gln Lys Val
                    965                 970                 975

Glu Ser Ser Val Tyr Gln Gln Phe Glu Lys Gln Leu Ile Asp Lys Leu
                    980                 985                 990

Asn Tyr Leu Val Asp Lys Lys Lys Arg Pro Glu Asp Ile Gly Gly Leu
                    995                 1000                1005

Leu Arg Ala Tyr Gln Phe Thr Ala Pro Phe Lys Ser Phe Lys Glu
            1010                1015                1020

Met Gly Lys Gln Asn Gly Phe Leu Phe Tyr Ile Pro Ala Trp Asn
            1025                1030                1035

Thr Ser Asn Ile Asp Pro Thr Thr Gly Phe Val Asn Leu Phe His
            1040                1045                1050

Val Gln Tyr Glu Asn Val Asp Lys Ala Lys Ser Phe Phe Gln Lys
            1055                1060                1065

Phe Asp Ser Ile Ser Tyr Asn Pro Lys Lys Asp Trp Phe Glu Phe
            1070                1075                1080

Ala Phe Asp Tyr Lys Asn Phe Thr Lys Lys Ala Glu Gly Ser Arg
            1085                1090                1095

Ser Met Trp Ile Leu Cys Thr His Gly Ser Arg Ile Lys Asn Phe
            1100                1105                1110

Arg Asn Ser Gln Lys Asn Gly Gln Trp Asp Ser Glu Glu Phe Ala
            1115                1120                1125

Leu Thr Glu Ala Phe Lys Ser Leu Phe Val Arg Tyr Glu Ile Asp
            1130                1135                1140

Tyr Thr Ala Asp Leu Lys Thr Ala Ile Val Asp Glu Lys Gln Lys
            1145                1150                1155

Asp Phe Phe Val Asp Leu Leu Lys Leu Phe Lys Leu Thr Val Gln
            1160                1165                1170

Met Arg Asn Ser Trp Lys Glu Lys Asp Leu Asp Tyr Leu Ile Ser
            1175                1180                1185

Pro Val Ala Gly Ala Asp Gly Arg Phe Phe Asp Thr Arg Glu Gly
            1190                1195                1200
```

Asn Lys Ser Leu Pro Lys Asp Ala Asp Ala Asn Gly Ala Tyr Asn
1205                1210                1215

Ile Ala Leu Lys Gly Leu Trp Ala Leu Arg Gln Ile Arg Gln Thr
1220                1225                1230

Ser Glu Gly Gly Lys Leu Lys Leu Ala Ile Ser Asn Lys Glu Trp
1235                1240                1245

Leu Gln Phe Val Gln Glu Arg Ser Tyr Glu Lys Asp Lys Arg Pro
1250                1255                1260

Ala Ala Thr Lys Lys Ala Gly Gln Ala Lys Lys Lys Gly Ser
1265                1270                1275

Tyr Pro Tyr Asp Val Pro Asp Tyr Ala Tyr Pro Tyr Asp Val Pro
1280                1285                1290

Asp Tyr Ala Tyr Pro Tyr Asp Val Pro Asp Tyr Ala
1295                1300                1305

<210> SEQ ID NO 68
<211> LENGTH: 1368
<212> TYPE: PRT
<213> ORGANISM: Prevotella disiens

<400> SEQUENCE: 68

Met Glu Asn Tyr Gln Glu Phe Thr Asn Leu Phe Gln Leu Asn Lys Thr
1               5                   10                  15

Leu Arg Phe Glu Leu Lys Pro Ile Gly Lys Thr Cys Glu Leu Leu Glu
                20                  25                  30

Glu Gly Lys Ile Phe Ala Ser Gly Ser Phe Leu Glu Lys Asp Lys Val
            35                  40                  45

Arg Ala Asp Asn Val Ser Tyr Val Lys Lys Glu Ile Asp Lys Lys His
        50                  55                  60

Lys Ile Phe Ile Glu Glu Thr Leu Ser Ser Phe Ser Ile Ser Asn Asp
65                  70                  75                  80

Leu Leu Lys Gln Tyr Phe Asp Cys Tyr Asn Gly Leu Lys Ala Phe Lys
                85                  90                  95

Lys Asp Cys Lys Ser Asp Glu Glu Val Lys Lys Thr Ala Leu Arg
            100                 105                 110

Asn Lys Cys Thr Ser Ile Gln Arg Ala Met Arg Glu Ala Ile Ser Gln
        115                 120                 125

Ala Phe Leu Lys Ser Pro Gln Lys Lys Leu Leu Ala Ile Lys Asn Leu
    130                 135                 140

Ile Glu Asn Val Phe Lys Ala Asp Glu Asn Val Gln His Phe Ser Glu
145                 150                 155                 160

Phe Thr Ser Tyr Phe Ser Gly Phe Glu Thr Asn Arg Glu Asn Phe Tyr
                165                 170                 175

Ser Asp Glu Glu Lys Ser Thr Ser Ile Ala Tyr Arg Leu Val His Asp
            180                 185                 190

Asn Leu Pro Ile Phe Ile Lys Asn Ile Tyr Ile Phe Glu Lys Leu Lys
        195                 200                 205

Glu Gln Phe Asp Ala Lys Thr Leu Ser Glu Ile Phe Glu Asn Tyr Lys
    210                 215                 220

Leu Tyr Val Ala Gly Ser Ser Leu Asp Glu Val Phe Ser Leu Glu Tyr
225                 230                 235                 240

Phe Asn Asn Thr Leu Thr Gln Lys Gly Ile Asp Asn Tyr Asn Ala Val
                245                 250                 255

Ile Gly Lys Ile Val Lys Glu Asp Lys Gln Glu Ile Gln Gly Leu Asn

```
            260                 265                 270
Glu His Ile Asn Leu Tyr Asn Gln Lys His Lys Asp Arg Arg Leu Pro
            275                 280             285
Phe Phe Ile Ser Leu Lys Lys Gln Ile Leu Ser Asp Arg Glu Ala Leu
            290                 295             300
Ser Trp Leu Pro Asp Met Phe Lys Asn Asp Ser Glu Val Ile Lys Ala
305                     310                 315                 320
Leu Lys Gly Phe Tyr Ile Glu Asp Gly Phe Glu Asn Asn Val Leu Thr
                    325                 330                 335
Pro Leu Ala Thr Leu Leu Ser Ser Leu Asp Lys Tyr Asn Leu Asn Gly
                340                 345                 350
Ile Phe Ile Arg Asn Asn Glu Ala Leu Ser Ser Leu Ser Gln Asn Val
            355                 360                 365
Tyr Arg Asn Phe Ser Ile Asp Glu Ala Ile Asp Ala Asn Ala Glu Leu
        370                 375                 380
Gln Thr Phe Asn Asn Tyr Glu Leu Ile Ala Asn Ala Leu Arg Ala Lys
385                     390                 395                 400
Ile Lys Lys Glu Thr Lys Gln Gly Arg Lys Ser Phe Glu Lys Tyr Glu
                    405                 410                 415
Glu Tyr Ile Asp Lys Lys Val Lys Ala Ile Asp Ser Leu Ser Ile Gln
                420                 425                 430
Glu Ile Asn Glu Leu Val Glu Asn Tyr Val Ser Glu Phe Asn Ser Asn
            435                 440                 445
Ser Gly Asn Met Pro Arg Lys Val Glu Asp Tyr Phe Ser Leu Met Arg
        450                 455                 460
Lys Gly Asp Phe Gly Ser Asn Asp Leu Ile Glu Asn Ile Lys Thr Lys
465                     470                 475                 480
Leu Ser Ala Ala Glu Lys Leu Leu Gly Thr Lys Tyr Gln Glu Thr Ala
                    485                 490                 495
Lys Asp Ile Phe Lys Lys Asp Glu Asn Ser Lys Leu Ile Lys Glu Leu
                500                 505                 510
Leu Asp Ala Thr Lys Gln Phe Gln His Phe Ile Lys Pro Leu Leu Gly
            515                 520                 525
Thr Gly Glu Glu Ala Asp Arg Asp Leu Val Phe Tyr Gly Asp Phe Leu
        530                 535                 540
Pro Leu Tyr Glu Lys Phe Glu Glu Leu Thr Leu Leu Tyr Asn Lys Val
545                     550                 555                 560
Arg Asn Arg Leu Thr Gln Lys Pro Tyr Ser Lys Asp Lys Ile Arg Leu
                    565                 570                 575
Cys Phe Asn Lys Pro Lys Leu Met Thr Gly Trp Val Asp Ser Lys Thr
                580                 585                 590
Glu Lys Ser Asp Asn Gly Thr Gln Tyr Gly Gly Tyr Leu Phe Arg Lys
            595                 600                 605
Lys Asn Glu Ile Gly Glu Tyr Asp Tyr Phe Leu Gly Ile Ser Ser Lys
        610                 615                 620
Ala Gln Leu Phe Arg Lys Asn Glu Ala Val Ile Gly Asp Tyr Glu Arg
625                     630                 635                 640
Leu Asp Tyr Tyr Gln Pro Lys Ala Asn Thr Ile Tyr Gly Ser Ala Tyr
                    645                 650                 655
Glu Gly Glu Asn Ser Tyr Lys Glu Asp Lys Lys Arg Leu Asn Lys Val
                660                 665                 670
Ile Ile Ala Tyr Ile Glu Gln Ile Lys Gln Thr Asn Ile Lys Lys Ser
            675                 680                 685
```

```
Ile Ile Glu Ser Ile Ser Lys Tyr Pro Asn Ile Ser Asp Asp Lys
690                 695                 700

Val Thr Pro Ser Ser Leu Leu Glu Lys Ile Lys Lys Val Ser Ile Asp
705                 710                 715                 720

Ser Tyr Asn Gly Ile Leu Ser Phe Lys Ser Phe Gln Ser Val Asn Lys
                725                 730                 735

Glu Val Ile Asp Asn Leu Leu Lys Thr Ile Ser Pro Leu Lys Asn Lys
            740                 745                 750

Ala Glu Phe Leu Asp Leu Ile Asn Lys Asp Tyr Gln Ile Phe Thr Glu
        755                 760                 765

Val Gln Ala Val Ile Asp Glu Ile Cys Lys Gln Lys Thr Phe Ile Tyr
770                 775                 780

Phe Pro Ile Ser Asn Val Glu Leu Glu Lys Glu Met Gly Asp Lys Asp
785                 790                 795                 800

Lys Pro Leu Cys Leu Phe Gln Ile Ser Asn Lys Asp Leu Ser Phe Ala
                805                 810                 815

Lys Thr Phe Ser Ala Asn Leu Arg Lys Lys Arg Gly Ala Glu Asn Leu
            820                 825                 830

His Thr Met Leu Phe Lys Ala Leu Met Glu Gly Asn Gln Asp Asn Leu
        835                 840                 845

Asp Leu Gly Ser Gly Ala Ile Phe Tyr Arg Ala Lys Ser Leu Asp Gly
    850                 855                 860

Asn Lys Pro Thr His Pro Ala Asn Glu Ala Ile Lys Cys Arg Asn Val
865                 870                 875                 880

Ala Asn Lys Asp Lys Val Ser Leu Phe Thr Tyr Asp Ile Tyr Lys Asn
                885                 890                 895

Arg Arg Tyr Met Glu Asn Lys Phe Leu Phe His Leu Ser Ile Val Gln
            900                 905                 910

Asn Tyr Lys Ala Ala Asn Asp Ser Ala Gln Leu Asn Ser Ser Ala Thr
        915                 920                 925

Glu Tyr Ile Arg Lys Ala Asp Asp Leu His Ile Ile Gly Ile Asp Arg
    930                 935                 940

Gly Glu Arg Asn Leu Leu Tyr Tyr Ser Val Ile Asp Met Lys Gly Asn
945                 950                 955                 960

Ile Val Glu Gln Asp Ser Leu Asn Ile Ile Arg Asn Asn Asp Leu Glu
                965                 970                 975

Thr Asp Tyr His Asp Leu Leu Asp Lys Arg Glu Lys Glu Arg Lys Ala
            980                 985                 990

Asn Arg Gln Asn Trp Glu Ala Val Glu Gly Ile Lys Asp Leu Lys Lys
        995                 1000                1005

Gly Tyr Leu Ser Gln Ala Val His Gln Ile Ala Gln Leu Met Leu
    1010                1015                1020

Lys Tyr Asn Ala Ile Ile Ala Leu Glu Asp Leu Gly Gln Met Phe
    1025                1030                1035

Val Thr Arg Gly Gln Lys Ile Glu Lys Ala Val Tyr Gln Gln Phe
    1040                1045                1050

Glu Lys Ser Leu Val Asp Lys Leu Ser Tyr Leu Val Asp Lys Lys
    1055                1060                1065

Arg Pro Tyr Asn Glu Leu Gly Gly Ile Leu Lys Ala Tyr Gln Leu
    1070                1075                1080

Ala Ser Ser Ile Thr Lys Asn Asn Ser Asp Lys Gln Asn Gly Phe
    1085                1090                1095
```

-continued

```
Leu Phe Tyr Val Pro Ala Trp Asn Thr Ser Lys Ile Asp Pro Val
    1100                1105                1110

Thr Gly Phe Thr Asp Leu Leu Arg Pro Lys Ala Met Thr Ile Lys
    1115                1120                1125

Glu Ala Gln Asp Phe Phe Gly Ala Phe Asp Asn Ile Ser Tyr Asn
    1130                1135                1140

Asp Lys Gly Tyr Phe Glu Phe Glu Thr Asn Tyr Asp Lys Phe Lys
    1145                1150                1155

Ile Arg Met Lys Ser Ala Gln Thr Arg Trp Thr Ile Cys Thr Phe
    1160                1165                1170

Gly Asn Arg Ile Lys Arg Lys Lys Asp Lys Asn Tyr Trp Asn Tyr
    1175                1180                1185

Glu Glu Val Glu Leu Thr Glu Glu Phe Lys Lys Leu Phe Lys Asp
    1190                1195                1200

Ser Asn Ile Asp Tyr Glu Asn Cys Asn Leu Lys Glu Glu Ile Gln
    1205                1210                1215

Asn Lys Asp Asn Arg Lys Phe Phe Asp Asp Leu Ile Lys Leu Leu
    1220                1225                1230

Gln Leu Thr Leu Gln Met Arg Asn Ser Asp Asp Lys Gly Asn Asp
    1235                1240                1245

Tyr Ile Ile Ser Pro Val Ala Asn Ala Glu Gly Gln Phe Phe Asp
    1250                1255                1260

Ser Arg Asn Gly Asp Lys Lys Leu Pro Leu Asp Ala Asp Ala Asn
    1265                1270                1275

Gly Ala Tyr Asn Ile Ala Arg Lys Gly Leu Trp Asn Ile Arg Gln
    1280                1285                1290

Ile Lys Gln Thr Lys Asn Asp Lys Lys Leu Asn Leu Ser Ile Ser
    1295                1300                1305

Ser Thr Glu Trp Leu Asp Phe Val Arg Glu Lys Pro Tyr Leu Lys
    1310                1315                1320

Lys Arg Pro Ala Ala Thr Lys Lys Ala Gly Gln Ala Lys Lys Lys
    1325                1330                1335

Lys Gly Ser Tyr Pro Tyr Asp Val Pro Asp Tyr Ala Tyr Pro Tyr
    1340                1345                1350

Asp Val Pro Asp Tyr Ala Tyr Pro Tyr Asp Val Pro Asp Tyr Ala
    1355                1360                1365

<210> SEQ ID NO 69
<211> LENGTH: 1291
<212> TYPE: PRT
<213> ORGANISM: Porphyromonas macacae

<400> SEQUENCE: 69

Met Lys Thr Gln His Phe Phe Glu Asp Phe Thr Ser Leu Tyr Ser Leu
1               5                   10                  15

Ser Lys Thr Ile Arg Phe Glu Leu Lys Pro Ile Gly Lys Thr Leu Glu
            20                  25                  30

Asn Ile Lys Lys Asn Gly Leu Ile Arg Arg Asp Glu Gln Arg Leu Asp
        35                  40                  45

Asp Tyr Glu Lys Leu Lys Lys Val Ile Asp Glu Tyr His Glu Asp Phe
    50                  55                  60

Ile Ala Asn Ile Leu Ser Ser Phe Ser Phe Ser Glu Glu Ile Leu Gln
65                  70                  75                  80

Ser Tyr Ile Gln Asn Leu Ser Glu Ser Glu Ala Arg Ala Lys Ile Glu
                85                  90                  95
```

```
Lys Thr Met Arg Asp Thr Leu Ala Lys Ala Phe Ser Glu Asp Glu Arg
            100                 105                 110

Tyr Lys Ser Ile Phe Lys Lys Glu Leu Val Lys Lys Asp Ile Pro Val
            115                 120                 125

Trp Cys Pro Ala Tyr Lys Ser Leu Cys Lys Lys Phe Asp Asn Phe Thr
            130                 135                 140

Thr Ser Leu Val Pro Phe His Glu Asn Arg Lys Asn Leu Tyr Thr Ser
145                 150                 155                 160

Asn Glu Ile Thr Ala Ser Ile Pro Tyr Arg Ile Val His Val Asn Leu
                165                 170                 175

Pro Lys Phe Ile Gln Asn Ile Glu Ala Leu Cys Glu Leu Gln Lys Lys
            180                 185                 190

Met Gly Ala Asp Leu Tyr Leu Glu Met Met Glu Asn Leu Arg Asn Val
            195                 200                 205

Trp Pro Ser Phe Val Lys Thr Pro Asp Asp Leu Cys Asn Leu Lys Thr
            210                 215                 220

Tyr Asn His Leu Met Val Gln Ser Ser Ile Ser Glu Tyr Asn Arg Phe
225                 230                 235                 240

Val Gly Gly Tyr Ser Thr Glu Asp Gly Thr Lys His Gln Gly Ile Asn
                245                 250                 255

Glu Trp Ile Asn Ile Tyr Arg Gln Arg Asn Lys Glu Met Arg Leu Pro
            260                 265                 270

Gly Leu Val Phe Leu His Lys Gln Ile Leu Ala Lys Val Asp Ser Ser
            275                 280                 285

Ser Phe Ile Ser Asp Thr Leu Glu Asn Asp Asp Gln Val Phe Cys Val
            290                 295                 300

Leu Arg Gln Phe Arg Lys Leu Phe Trp Asn Thr Val Ser Ser Lys Glu
305                 310                 315                 320

Asp Asp Ala Ala Ser Leu Lys Asp Leu Phe Cys Gly Leu Ser Gly Tyr
                325                 330                 335

Asp Pro Glu Ala Ile Tyr Val Ser Asp Ala His Leu Ala Thr Ile Ser
            340                 345                 350

Lys Asn Ile Phe Asp Arg Trp Asn Tyr Ile Ser Asp Ala Ile Arg Arg
            355                 360                 365

Lys Thr Glu Val Leu Met Pro Arg Lys Lys Glu Ser Val Glu Arg Tyr
370                 375                 380

Ala Glu Lys Ile Ser Lys Gln Ile Lys Arg Gln Ser Tyr Ser Leu
385                 390                 395                 400

Ala Glu Leu Asp Asp Leu Leu Ala His Tyr Ser Glu Glu Ser Leu Pro
                405                 410                 415

Ala Gly Phe Ser Leu Leu Ser Tyr Phe Thr Ser Leu Gly Gly Gln Lys
            420                 425                 430

Tyr Leu Val Ser Asp Gly Glu Val Ile Leu Tyr Glu Glu Gly Ser Asn
            435                 440                 445

Ile Trp Asp Glu Val Leu Ile Ala Phe Arg Asp Leu Gln Val Ile Leu
            450                 455                 460

Asp Lys Asp Phe Thr Glu Lys Lys Leu Gly Lys Asp Glu Glu Ala Val
465                 470                 475                 480

Ser Val Ile Lys Lys Ala Leu Asp Ser Ala Leu Arg Leu Arg Lys Phe
                485                 490                 495

Phe Asp Leu Leu Ser Gly Thr Gly Ala Glu Ile Arg Arg Asp Ser Ser
            500                 505                 510
```

```
Phe Tyr Ala Leu Tyr Thr Asp Arg Met Asp Lys Leu Lys Gly Leu Leu
            515                 520                 525

Lys Met Tyr Asp Lys Val Arg Asn Tyr Leu Thr Lys Lys Pro Tyr Ser
        530                 535                 540

Ile Glu Lys Phe Lys Leu His Phe Asp Asn Pro Ser Leu Leu Ser Gly
545                 550                 555                 560

Trp Asp Lys Asn Lys Glu Leu Asn Asn Leu Ser Val Ile Phe Arg Gln
                565                 570                 575

Asn Gly Tyr Tyr Tyr Leu Gly Ile Met Thr Pro Lys Gly Lys Asn Leu
            580                 585                 590

Phe Lys Thr Leu Pro Lys Leu Gly Ala Glu Glu Met Phe Tyr Glu Lys
        595                 600                 605

Met Glu Tyr Lys Gln Ile Ala Glu Pro Met Leu Met Leu Pro Lys Val
        610                 615                 620

Phe Phe Pro Lys Lys Thr Lys Pro Ala Phe Ala Pro Asp Gln Ser Val
625                 630                 635                 640

Val Asp Ile Tyr Asn Lys Lys Thr Phe Lys Thr Gly Gln Lys Gly Phe
                645                 650                 655

Asn Lys Lys Asp Leu Tyr Arg Leu Ile Asp Phe Tyr Lys Glu Ala Leu
            660                 665                 670

Thr Val His Glu Trp Lys Leu Phe Asn Phe Ser Phe Ser Pro Thr Glu
        675                 680                 685

Gln Tyr Arg Asn Ile Gly Glu Phe Phe Asp Glu Val Arg Glu Gln Ala
        690                 695                 700

Tyr Lys Val Ser Met Val Asn Val Pro Ala Ser Tyr Ile Asp Glu Ala
705                 710                 715                 720

Val Glu Asn Gly Lys Leu Tyr Leu Phe Gln Ile Tyr Asn Lys Asp Phe
                725                 730                 735

Ser Pro Tyr Ser Lys Gly Ile Pro Asn Leu His Thr Leu Tyr Trp Lys
            740                 745                 750

Ala Leu Phe Ser Glu Gln Asn Gln Ser Arg Val Tyr Lys Leu Cys Gly
        755                 760                 765

Gly Gly Glu Leu Phe Tyr Arg Lys Ala Ser Leu His Met Gln Asp Thr
770                 775                 780

Thr Val His Pro Lys Gly Ile Ser Ile His Lys Lys Asn Leu Asn Lys
785                 790                 795                 800

Lys Gly Glu Thr Ser Leu Phe Asn Tyr Asp Leu Val Lys Asp Lys Arg
                805                 810                 815

Phe Thr Glu Asp Lys Phe Phe Phe His Val Pro Ile Ser Ile Asn Tyr
            820                 825                 830

Lys Asn Lys Lys Ile Thr Asn Val Asn Gln Met Val Arg Asp Tyr Ile
        835                 840                 845

Ala Gln Asn Asp Asp Leu Gln Ile Ile Gly Ile Asp Arg Gly Glu Arg
        850                 855                 860

Asn Leu Leu Tyr Ile Ser Arg Ile Asp Thr Arg Gly Asn Leu Leu Glu
865                 870                 875                 880

Gln Phe Ser Leu Asn Val Ile Glu Ser Asp Lys Gly Asp Leu Arg Thr
                885                 890                 895

Asp Tyr Gln Lys Ile Leu Gly Asp Arg Glu Gln Glu Arg Leu Arg Arg
            900                 905                 910

Arg Gln Glu Trp Lys Ser Ile Glu Ser Ile Lys Asp Leu Lys Asp Gly
        915                 920                 925

Tyr Met Ser Gln Val Val His Lys Ile Cys Asn Met Val Val Glu His
```

```
                930             935             940
Lys Ala Ile Val Val Leu Glu Asn Leu Asn Leu Ser Phe Met Lys Gly
945             950             955             960

Arg Lys Lys Val Glu Lys Ser Val Tyr Glu Lys Phe Glu Arg Met Leu
                965             970             975

Val Asp Lys Leu Asn Tyr Leu Val Val Asp Lys Lys Asn Leu Ser Asn
            980             985             990

Glu Pro Gly Gly Leu Tyr Ala Ala Tyr Gln Leu Thr Asn Pro Leu Phe
        995             1000            1005

Ser Phe Glu Glu Leu His Arg Tyr Pro Gln Ser Gly Ile Leu Phe
    1010            1015            1020

Phe Val Asp Pro Trp Asn Thr Ser Leu Thr Asp Pro Ser Thr Gly
    1025            1030            1035

Phe Val Asn Leu Leu Gly Arg Ile Asn Tyr Thr Asn Val Gly Asp
    1040            1045            1050

Ala Arg Lys Phe Phe Asp Arg Phe Asn Ala Ile Arg Tyr Asp Gly
    1055            1060            1065

Lys Gly Asn Ile Leu Phe Asp Leu Asp Leu Ser Arg Phe Asp Val
    1070            1075            1080

Arg Val Glu Thr Gln Arg Lys Leu Trp Thr Leu Thr Thr Phe Gly
    1085            1090            1095

Ser Arg Ile Ala Lys Ser Lys Ser Gly Lys Trp Met Val Glu
    1100            1105            1110

Arg Ile Glu Asn Leu Ser Leu Cys Phe Leu Glu Leu Phe Glu Gln
    1115            1120            1125

Phe Asn Ile Gly Tyr Arg Val Glu Lys Asp Leu Lys Lys Ala Ile
    1130            1135            1140

Leu Ser Gln Asp Arg Lys Glu Phe Tyr Val Arg Leu Ile Tyr Leu
    1145            1150            1155

Phe Asn Leu Met Met Gln Ile Arg Asn Ser Asp Gly Glu Glu Asp
    1160            1165            1170

Tyr Ile Leu Ser Pro Ala Leu Asn Glu Lys Asn Leu Gln Phe Asp
    1175            1180            1185

Ser Arg Leu Ile Glu Ala Lys Asp Leu Pro Val Asp Ala Asp Ala
    1190            1195            1200

Asn Gly Ala Tyr Asn Val Ala Arg Lys Gly Leu Met Val Val Gln
    1205            1210            1215

Arg Ile Lys Arg Gly Asp His Glu Ser Ile His Arg Ile Gly Arg
    1220            1225            1230

Ala Gln Trp Leu Arg Tyr Val Gln Glu Gly Ile Val Glu Lys Arg
    1235            1240            1245

Pro Ala Ala Thr Lys Lys Ala Gly Gln Ala Lys Lys Lys Lys Gly
    1250            1255            1260

Ser Tyr Pro Tyr Asp Val Pro Asp Tyr Ala Tyr Pro Tyr Asp Val
    1265            1270            1275

Pro Asp Tyr Ala Tyr Pro Tyr Asp Val Pro Asp Tyr Ala
    1280            1285            1290
```

<210> SEQ ID NO 70
<211> LENGTH: 1343
<212> TYPE: PRT
<213> ORGANISM: Thiomicrospira sp.

<400> SEQUENCE: 70

```
Met Thr Lys Thr Phe Asp Ser Glu Phe Phe Asn Leu Tyr Ser Leu Gln
1               5                   10                  15
Lys Thr Val Arg Phe Glu Leu Lys Pro Val Gly Glu Thr Ala Ser Phe
            20                  25                  30
Val Glu Asp Phe Lys Asn Glu Gly Leu Lys Arg Val Val Ser Glu Asp
            35                  40                  45
Glu Arg Arg Ala Val Asp Tyr Gln Lys Val Lys Glu Ile Ile Asp Asp
50                  55                  60
Tyr His Arg Asp Phe Ile Glu Glu Ser Leu Asn Tyr Phe Pro Glu Gln
65                  70                  75                  80
Val Ser Lys Asp Ala Leu Glu Gln Ala Phe His Leu Tyr Gln Lys Leu
                85                  90                  95
Lys Ala Ala Lys Val Glu Glu Arg Glu Lys Ala Leu Lys Glu Trp Glu
            100                 105                 110
Ala Leu Gln Lys Lys Leu Arg Glu Lys Val Val Lys Cys Phe Ser Asp
            115                 120                 125
Ser Asn Lys Ala Arg Phe Ser Arg Ile Asp Lys Lys Glu Leu Ile Lys
            130                 135                 140
Glu Asp Leu Ile Asn Trp Leu Val Ala Gln Asn Arg Glu Asp Asp Ile
145                 150                 155                 160
Pro Thr Val Glu Thr Phe Asn Asn Phe Thr Thr Tyr Phe Thr Gly Phe
                165                 170                 175
His Glu Asn Arg Lys Asn Ile Tyr Ser Lys Asp His Ala Thr Ala
                180                 185                 190
Ile Ser Phe Arg Leu Ile His Glu Asn Leu Pro Lys Phe Phe Asp Asn
            195                 200                 205
Val Ile Ser Phe Asn Lys Leu Lys Glu Gly Phe Pro Glu Leu Lys Phe
210                 215                 220
Asp Lys Val Lys Glu Asp Leu Glu Val Asp Tyr Asp Leu Lys His Ala
225                 230                 235                 240
Phe Glu Ile Glu Tyr Phe Val Asn Phe Val Thr Gln Ala Gly Ile Asp
                245                 250                 255
Gln Tyr Asn Tyr Leu Leu Gly Gly Lys Thr Leu Glu Asp Gly Thr Lys
            260                 265                 270
Lys Gln Gly Met Asn Glu Gln Ile Asn Leu Phe Lys Gln Gln Gln Thr
            275                 280                 285
Arg Asp Lys Ala Arg Gln Ile Pro Lys Leu Ile Pro Leu Phe Lys Gln
            290                 295                 300
Ile Leu Ser Glu Arg Thr Glu Ser Gln Ser Phe Ile Pro Lys Gln Phe
305                 310                 315                 320
Glu Ser Asp Gln Glu Leu Phe Asp Ser Leu Gln Lys Leu His Asn Asn
                325                 330                 335
Cys Gln Asp Lys Phe Thr Val Leu Gln Gln Ala Ile Leu Gly Leu Ala
            340                 345                 350
Glu Ala Asp Leu Lys Lys Val Phe Ile Lys Thr Ser Asp Leu Asn Ala
            355                 360                 365
Leu Ser Asn Thr Ile Phe Gly Asn Tyr Ser Val Phe Ser Asp Ala Leu
370                 375                 380
Asn Leu Tyr Lys Glu Ser Leu Lys Thr Lys Ala Gln Glu Ala Phe
385                 390                 395                 400
Glu Lys Leu Pro Ala His Ser Ile His Asp Leu Ile Gln Tyr Leu Glu
                405                 410                 415
Gln Phe Asn Ser Ser Leu Asp Ala Glu Lys Gln Gln Ser Thr Asp Thr
```

```
                420             425             430
Val Leu Asn Tyr Phe Ile Lys Thr Asp Glu Leu Tyr Ser Arg Phe Ile
            435                 440             445

Lys Ser Thr Ser Glu Ala Phe Thr Gln Val Gln Pro Leu Phe Glu Leu
450                     455                 460

Glu Ala Leu Ser Ser Lys Arg Arg Pro Pro Glu Ser Glu Asp Glu Gly
465                 470                  475                 480

Ala Lys Gly Gln Glu Gly Phe Glu Gln Ile Lys Arg Ile Lys Ala Tyr
                485                 490             495

Leu Asp Thr Leu Met Glu Ala Val His Phe Ala Lys Pro Leu Tyr Leu
            500                 505             510

Val Lys Gly Arg Lys Met Ile Glu Gly Leu Asp Lys Asp Gln Ser Phe
        515                 520             525

Tyr Glu Ala Phe Glu Met Ala Tyr Gln Glu Leu Glu Ser Leu Ile Ile
    530                 535             540

Pro Ile Tyr Asn Lys Ala Arg Ser Tyr Leu Ser Arg Lys Pro Phe Lys
545                 550             555                 560

Ala Asp Lys Phe Lys Ile Asn Phe Asp Asn Asn Thr Leu Leu Ser Gly
            565                 570             575

Trp Asp Ala Asn Lys Glu Thr Ala Asn Ala Ser Ile Leu Phe Lys Lys
            580                 585             590

Asp Gly Leu Tyr Tyr Leu Gly Ile Met Pro Lys Gly Lys Thr Phe Leu
        595                 600             605

Phe Asp Tyr Phe Val Ser Ser Glu Asp Ser Glu Lys Leu Lys Gln Arg
    610                 615             620

Arg Gln Lys Thr Ala Glu Glu Ala Leu Ala Gln Asp Gly Glu Ser Tyr
625                 630             635                 640

Phe Glu Lys Ile Arg Tyr Lys Leu Leu Pro Gly Ala Ser Lys Met Leu
            645                 650             655

Pro Lys Val Phe Phe Ser Asn Lys Asn Ile Gly Phe Tyr Asn Pro Ser
            660                 665             670

Asp Asp Ile Leu Arg Ile Arg Asn Thr Ala Ser His Thr Lys Asn Gly
        675                 680             685

Thr Pro Gln Lys Gly His Ser Lys Val Glu Phe Asn Leu Asn Asp Cys
    690                 695             700

His Lys Met Ile Asp Phe Phe Lys Ser Ser Ile Gln Lys His Pro Glu
705                 710             715                 720

Trp Gly Ser Phe Gly Phe Thr Phe Ser Asp Thr Ser Asp Phe Glu Asp
            725                 730             735

Met Ser Ala Phe Tyr Arg Glu Val Glu Asn Gln Gly Tyr Val Ile Ser
            740                 745             750

Phe Asp Lys Ile Lys Glu Thr Tyr Ile Gln Ser Gln Val Glu Gln Gly
        755                 760             765

Asn Leu Tyr Leu Phe Gln Ile Tyr Asn Lys Asp Phe Ser Pro Tyr Ser
    770                 775             780

Lys Gly Lys Pro Asn Leu His Thr Leu Tyr Trp Lys Ala Leu Phe Glu
785                 790             795                 800

Glu Ala Asn Leu Asn Asn Val Val Ala Lys Leu Asn Gly Glu Ala Glu
            805                 810             815

Ile Phe Phe Arg Arg His Ser Ile Lys Ala Ser Asp Lys Val Val His
            820                 825             830

Pro Ala Asn Gln Ala Ile Asp Asn Lys Asn Pro His Thr Glu Lys Thr
        835                 840             845
```

```
Gln Ser Thr Phe Glu Tyr Asp Leu Val Lys Asp Lys Arg Tyr Thr Gln
    850                 855                 860

Asp Lys Phe Phe Phe His Val Pro Ile Ser Leu Asn Phe Lys Ala Gln
865                 870                 875                 880

Gly Val Ser Lys Phe Asn Asp Lys Val Asn Gly Phe Leu Lys Gly Asn
                885                 890                 895

Pro Asp Val Asn Ile Ile Gly Ile Asp Arg Gly Glu Arg His Leu Leu
            900                 905                 910

Tyr Phe Thr Val Val Asn Gln Lys Gly Glu Ile Leu Val Gln Glu Ser
        915                 920                 925

Leu Asn Thr Leu Met Ser Asp Lys Gly His Val Asn Asp Tyr Gln Gln
    930                 935                 940

Lys Leu Asp Lys Lys Glu Gln Glu Arg Asp Ala Ala Arg Lys Ser Trp
945                 950                 955                 960

Thr Thr Val Glu Asn Ile Lys Glu Leu Lys Glu Gly Tyr Leu Ser His
                965                 970                 975

Val Val His Lys Leu Ala His Leu Ile Ile Lys Tyr Asn Ala Ile Val
            980                 985                 990

Cys Leu Glu Asp Leu Asn Phe Gly Phe Lys Arg Gly Arg Phe Lys Val
        995                 1000                1005

Glu Lys Gln Val Tyr Gln Lys Phe Glu Lys Ala Leu Ile Asp Lys
    1010                1015                1020

Leu Asn Tyr Leu Val Phe Lys Glu Lys Glu Leu Gly Glu Val Gly
    1025                1030                1035

His Tyr Leu Thr Ala Tyr Gln Leu Thr Ala Pro Phe Glu Ser Phe
    1040                1045                1050

Lys Lys Leu Gly Lys Gln Ser Gly Ile Leu Phe Tyr Val Pro Ala
    1055                1060                1065

Asp Tyr Thr Ser Lys Ile Asp Pro Thr Thr Gly Phe Val Asn Phe
    1070                1075                1080

Leu Asp Leu Arg Tyr Gln Ser Val Glu Lys Ala Lys Gln Leu Leu
    1085                1090                1095

Ser Asp Phe Asn Ala Ile Arg Phe Asn Ser Val Gln Asn Tyr Phe
    1100                1105                1110

Glu Phe Glu Ile Asp Tyr Lys Lys Leu Thr Pro Lys Arg Lys Val
    1115                1120                1125

Gly Thr Gln Ser Lys Trp Val Ile Cys Thr Tyr Gly Asp Val Arg
    1130                1135                1140

Tyr Gln Asn Arg Arg Asn Gln Lys Gly His Trp Glu Thr Glu Glu
    1145                1150                1155

Val Asn Val Thr Glu Lys Leu Lys Ala Leu Phe Ala Ser Asp Ser
    1160                1165                1170

Lys Thr Thr Thr Val Ile Asp Tyr Ala Asn Asp Asp Asn Leu Ile
    1175                1180                1185

Asp Val Ile Leu Glu Gln Asp Lys Ala Ser Phe Phe Lys Glu Leu
    1190                1195                1200

Leu Trp Leu Leu Lys Leu Thr Met Thr Leu Arg His Ser Lys Ile
    1205                1210                1215

Lys Ser Glu Asp Asp Phe Ile Leu Ser Pro Val Lys Asn Glu Gln
    1220                1225                1230

Gly Glu Phe Tyr Asp Ser Arg Lys Ala Gly Glu Val Trp Pro Lys
    1235                1240                1245
```

```
Asp Ala Asp Ala Asn Gly Ala Tyr His Ile Ala Leu Lys Gly Leu
    1250                1255                1260

Trp Asn Leu Gln Gln Ile Asn Gln Trp Glu Lys Gly Lys Thr Leu
1265                1270                1275

Asn Leu Ala Ile Lys Asn Gln Asp Trp Phe Ser Phe Ile Gln Glu
    1280                1285                1290

Lys Pro Tyr Gln Glu Lys Arg Pro Ala Ala Thr Lys Lys Ala Gly
1295                1300                1305

Gln Ala Lys Lys Lys Gly Ser Tyr Pro Tyr Asp Val Pro Asp
    1310                1315                1320

Tyr Ala Tyr Pro Tyr Asp Val Pro Asp Tyr Ala Tyr Pro Tyr Asp
    1325                1330                1335

Val Pro Asp Tyr Ala
    1340

<210> SEQ ID NO 71
<211> LENGTH: 1296
<212> TYPE: PRT
<213> ORGANISM: Moraxella bovoculi

<400> SEQUENCE: 71

Met Leu Phe Gln Asp Phe Thr His Leu Tyr Pro Leu Ser Lys Thr Val
1               5                   10                  15

Arg Phe Glu Leu Lys Pro Ile Gly Arg Thr Leu Glu His Ile His Ala
            20                  25                  30

Lys Asn Phe Leu Ser Gln Asp Glu Thr Met Ala Asp Met Tyr Gln Lys
        35                  40                  45

Val Lys Val Ile Leu Asp Asp Tyr His Arg Asp Phe Ile Ala Asp Met
50                  55                  60

Met Gly Glu Val Lys Leu Thr Lys Leu Ala Glu Phe Tyr Asp Val Tyr
65                  70                  75                  80

Leu Lys Phe Arg Lys Asn Pro Lys Asp Asp Gly Leu Gln Lys Gln Leu
                85                  90                  95

Lys Asp Leu Gln Ala Val Leu Arg Lys Glu Ser Val Lys Pro Ile Gly
            100                 105                 110

Ser Gly Gly Lys Tyr Lys Thr Gly Tyr Asp Arg Leu Phe Gly Ala Lys
        115                 120                 125

Leu Phe Lys Asp Gly Lys Glu Leu Gly Asp Leu Ala Lys Phe Val Ile
    130                 135                 140

Ala Gln Glu Gly Glu Ser Ser Pro Lys Leu Ala His Leu Ala His Phe
145                 150                 155                 160

Glu Lys Phe Ser Thr Tyr Phe Thr Gly Phe His Asp Asn Arg Lys Asn
                165                 170                 175

Met Tyr Ser Asp Glu Asp Lys His Thr Ala Ile Ala Tyr Arg Leu Ile
            180                 185                 190

His Glu Asn Leu Pro Arg Phe Ile Asp Asn Leu Gln Ile Leu Thr Thr
        195                 200                 205

Ile Lys Gln Lys His Ser Ala Leu Tyr Asp Gln Ile Ile Asn Glu Leu
    210                 215                 220

Thr Ala Ser Gly Leu Asp Val Ser Leu Ala Ser His Leu Asp Gly Tyr
225                 230                 235                 240

His Lys Leu Leu Thr Gln Glu Gly Ile Thr Ala Tyr Asn Arg Ile Ile
                245                 250                 255

Gly Glu Val Asn Gly Tyr Thr Asn Lys His Asn Gln Ile Cys His Lys
            260                 265                 270
```

```
Ser Glu Arg Ile Ala Lys Leu Arg Pro Leu His Lys Gln Ile Leu Ser
    275                 280                 285

Asp Gly Met Gly Val Ser Phe Leu Pro Ser Lys Phe Ala Asp Asp Ser
290                 295                 300

Glu Met Cys Gln Ala Val Asn Glu Phe Tyr Arg His Tyr Thr Asp Val
305                 310                 315                 320

Phe Ala Lys Val Gln Ser Leu Phe Asp Gly Phe Asp Asp His Gln Lys
                325                 330                 335

Asp Gly Ile Tyr Val Glu His Lys Asn Leu Asn Glu Leu Ser Lys Gln
                340                 345                 350

Ala Phe Gly Asp Phe Ala Leu Leu Gly Arg Val Leu Asp Gly Tyr Tyr
            355                 360                 365

Val Asp Val Val Asn Pro Glu Phe Asn Glu Arg Phe Ala Lys Ala Lys
370                 375                 380

Thr Asp Asn Ala Lys Ala Lys Leu Thr Lys Glu Lys Asp Lys Phe Ile
385                 390                 395                 400

Lys Gly Val His Ser Leu Ala Ser Leu Glu Gln Ala Ile Glu His His
                405                 410                 415

Thr Ala Arg His Asp Asp Glu Ser Val Gln Ala Gly Lys Leu Gly Gln
            420                 425                 430

Tyr Phe Lys His Gly Leu Ala Gly Val Asp Asn Pro Ile Gln Lys Ile
            435                 440                 445

His Asn Asn His Ser Thr Ile Lys Gly Phe Leu Glu Arg Glu Arg Pro
450                 455                 460

Ala Gly Glu Arg Ala Leu Pro Lys Ile Lys Ser Gly Lys Asn Pro Glu
465                 470                 475                 480

Met Thr Gln Leu Arg Gln Leu Lys Glu Leu Leu Asp Asn Ala Leu Asn
                485                 490                 495

Val Ala His Phe Ala Lys Leu Leu Thr Thr Lys Thr Thr Leu Asp Asn
            500                 505                 510

Gln Asp Gly Asn Phe Tyr Gly Glu Phe Gly Val Leu Tyr Asp Glu Leu
    515                 520                 525

Ala Lys Ile Pro Thr Leu Tyr Asn Lys Val Arg Asp Tyr Leu Ser Gln
        530                 535                 540

Lys Pro Phe Ser Thr Glu Lys Tyr Lys Leu Asn Phe Gly Asn Pro Thr
545                 550                 555                 560

Leu Leu Asn Gly Trp Asp Leu Asn Lys Glu Lys Asp Asn Phe Gly Val
            565                 570                 575

Ile Leu Gln Lys Asp Gly Cys Tyr Tyr Leu Ala Leu Leu Asp Lys Ala
            580                 585                 590

His Lys Lys Val Phe Asp Asn Ala Pro Asn Thr Gly Lys Asn Val Tyr
    595                 600                 605

Gln Lys Met Val Tyr Lys Leu Leu Pro Gly Pro Asn Lys Met Leu Pro
610                 615                 620

Lys Val Phe Phe Ala Lys Ser Asn Leu Asp Tyr Tyr Asn Pro Ser Ala
625                 630                 635                 640

Glu Leu Leu Asp Lys Tyr Ala Lys Gly Thr His Lys Lys Gly Asp Asn
                645                 650                 655

Phe Asn Leu Lys Asp Cys His Ala Leu Ile Asp Phe Lys Ala Gly
            660                 665                 670

Ile Asn Lys His Pro Glu Trp Gln His Phe Gly Phe Lys Phe Ser Pro
            675                 680                 685
```

```
Thr Ser Ser Tyr Arg Asp Leu Ser Asp Phe Tyr Arg Glu Val Glu Pro
    690             695             700

Gln Gly Tyr Gln Val Lys Phe Val Asp Ile Asn Ala Asp Tyr Ile Asp
705             710             715             720

Glu Leu Val Glu Gln Gly Lys Leu Tyr Leu Phe Gln Ile Tyr Asn Lys
                725             730             735

Asp Phe Ser Pro Lys Ala His Gly Lys Pro Asn Leu His Thr Leu Tyr
            740             745             750

Phe Lys Ala Leu Phe Ser Glu Asp Asn Leu Ala Asp Pro Ile Tyr Lys
        755             760             765

Leu Asn Gly Glu Ala Gln Ile Phe Tyr Arg Lys Ala Ser Leu Asp Met
770             775             780

Asn Glu Thr Thr Ile His Arg Ala Gly Glu Val Leu Glu Asn Lys Asn
785             790             795             800

Pro Asp Asn Pro Lys Lys Arg Gln Phe Val Tyr Asp Ile Ile Lys Asp
            805             810             815

Lys Arg Tyr Thr Gln Asp Lys Phe Met Leu His Val Pro Ile Thr Met
            820             825             830

Asn Phe Gly Val Gln Gly Met Thr Ile Lys Glu Phe Asn Lys Lys Val
        835             840             845

Asn Gln Ser Ile Gln Gln Tyr Asp Glu Val Asn Val Ile Gly Ile Asp
850             855             860

Arg Gly Glu Arg His Leu Leu Tyr Leu Thr Val Ile Asn Ser Lys Gly
865             870             875             880

Glu Ile Leu Glu Gln Arg Ser Leu Asn Asp Ile Thr Thr Ala Ser Ala
            885             890             895

Asn Gly Thr Gln Val Thr Thr Pro Tyr His Lys Ile Leu Asp Lys Arg
        900             905             910

Glu Ile Glu Arg Leu Asn Ala Arg Val Gly Trp Gly Glu Ile Glu Thr
    915             920             925

Ile Lys Glu Leu Lys Ser Gly Tyr Leu Ser His Val Val His Gln Ile
    930             935             940

Asn Gln Leu Met Leu Lys Tyr Asn Ala Ile Val Val Leu Glu Asp Leu
945             950             955             960

Asn Phe Gly Phe Lys Arg Gly Arg Phe Lys Val Glu Lys Gln Ile Tyr
            965             970             975

Gln Asn Phe Glu Asn Ala Leu Ile Lys Lys Leu Asn His Leu Val Leu
            980             985             990

Lys Asp Lys Ala Asp Asp Glu Ile Gly Ser Tyr Lys Asn Ala Leu Gln
        995             1000            1005

Leu Thr Asn Asn Phe Thr Asp Leu Lys Ser Ile Gly Lys Gln Thr
    1010            1015            1020

Gly Phe Leu Phe Tyr Val Pro Ala Trp Asn Thr Ser Lys Ile Asp
    1025            1030            1035

Pro Glu Thr Gly Phe Val Asp Leu Leu Lys Pro Arg Tyr Glu Asn
    1040            1045            1050

Ile Ala Gln Ser Gln Ala Phe Phe Gly Lys Phe Asp Lys Ile Cys
    1055            1060            1065

Tyr Asn Thr Asp Lys Gly Tyr Phe Glu Phe His Ile Asp Tyr Ala
    1070            1075            1080

Lys Phe Thr Asp Lys Ala Lys Asn Ser Arg Gln Lys Trp Ala Ile
    1085            1090            1095

Cys Ser His Gly Asp Lys Arg Tyr Val Tyr Asp Lys Thr Ala Asn
```

```
              1100               1105                1110
Gln Asn Lys Gly Ala Ala Lys Gly Ile Asn Val Asn Asp Glu Leu
        1115                1120                1125
Lys Ser Leu Phe Ala Arg Tyr His Ile Asn Asp Lys Gln Pro Asn
    1130                1135                1140
Leu Val Met Asp Ile Cys Gln Asn Asn Asp Lys Glu Phe His Lys
    1145                1150                1155
Ser Leu Met Cys Leu Leu Lys Thr Leu Leu Ala Leu Arg Tyr Ser
    1160                1165                1170
Asn Ala Ser Ser Asp Glu Asp Phe Ile Leu Ser Pro Val Ala Asn
    1175                1180                1185
Asp Glu Gly Val Phe Phe Asn Ser Ala Leu Ala Asp Asp Thr Gln
    1190                1195                1200
Pro Gln Asn Ala Asp Ala Asn Gly Ala Tyr His Ile Ala Leu Lys
    1205                1210                1215
Gly Leu Trp Leu Leu Asn Glu Leu Lys Asn Ser Asp Asp Leu Asn
    1220                1225                1230
Lys Val Lys Leu Ala Ile Asp Asn Gln Thr Trp Leu Asn Phe Ala
    1235                1240                1245
Gln Asn Arg Lys Arg Pro Ala Ala Thr Lys Lys Ala Gly Gln Ala
    1250                1255                1260
Lys Lys Lys Lys Gly Ser Tyr Pro Tyr Asp Val Pro Asp Tyr Ala
    1265                1270                1275
Tyr Pro Tyr Asp Val Pro Asp Tyr Ala Tyr Pro Tyr Asp Val Pro
    1280                1285                1290
Asp Tyr Ala
    1295

<210> SEQ ID NO 72
<211> LENGTH: 1306
<212> TYPE: PRT
<213> ORGANISM: Moraxella bovoculi

<400> SEQUENCE: 72

Met Leu Phe Gln Asp Phe Thr His Leu Tyr Pro Leu Ser Lys Thr Val
1               5                  10                  15

Arg Phe Glu Leu Lys Pro Ile Gly Lys Thr Leu Glu His Ile His Ala
            20                  25                  30

Lys Asn Phe Leu Asn Gln Asp Glu Thr Met Ala Asp Met Tyr Gln Lys
        35                  40                  45

Val Lys Ala Ile Leu Asp Asp Tyr His Arg Asp Phe Ile Ala Asp Met
    50                  55                  60

Met Gly Glu Val Lys Leu Thr Lys Leu Ala Glu Phe Tyr Asp Val Tyr
65                  70                  75                  80

Leu Lys Phe Arg Lys Asn Pro Lys Asp Gly Leu Gln Lys Gln Leu
            85                  90                  95

Lys Asp Leu Gln Ala Val Leu Arg Lys Glu Ile Val Lys Pro Ile Gly
            100                 105                 110

Asn Gly Gly Lys Tyr Lys Ala Gly Tyr Asp Arg Leu Phe Gly Ala Lys
        115                 120                 125

Leu Phe Lys Asp Gly Lys Glu Leu Gly Asp Leu Ala Lys Phe Val Ile
    130                 135                 140

Ala Gln Glu Gly Glu Ser Ser Pro Lys Leu Ala His Leu Ala His Phe
145                 150                 155                 160
```

```
Glu Lys Phe Ser Thr Tyr Phe Thr Gly Phe His Asp Asn Arg Lys Asn
                165                 170                 175

Met Tyr Ser Asp Glu Asp Lys His Thr Ala Ile Ala Tyr Arg Leu Ile
            180                 185                 190

His Glu Asn Leu Pro Arg Phe Ile Asp Asn Leu Gln Ile Leu Ala Thr
        195                 200                 205

Ile Lys Gln Lys His Ser Ala Leu Tyr Asp Gln Ile Ile Asn Glu Leu
    210                 215                 220

Thr Ala Ser Gly Leu Asp Val Ser Leu Ala Ser His Leu Asp Gly Tyr
225                 230                 235                 240

His Lys Leu Leu Thr Gln Glu Gly Ile Thr Ala Tyr Asn Thr Leu Leu
                245                 250                 255

Gly Gly Ile Ser Gly Glu Ala Gly Ser Arg Lys Ile Gln Gly Ile Asn
            260                 265                 270

Glu Leu Ile Asn Ser His His Asn Gln His Cys His Lys Ser Glu Arg
        275                 280                 285

Ile Ala Lys Leu Arg Pro Leu His Lys Gln Ile Leu Ser Asp Gly Met
    290                 295                 300

Gly Val Ser Phe Leu Pro Ser Lys Phe Ala Asp Asp Ser Glu Val Cys
305                 310                 315                 320

Gln Ala Val Asn Glu Phe Tyr Arg His Tyr Ala Asp Val Phe Ala Lys
                325                 330                 335

Val Gln Ser Leu Phe Asp Gly Phe Asp Asp Tyr Gln Lys Asp Gly Ile
            340                 345                 350

Tyr Val Glu Tyr Lys Asn Leu Asn Glu Leu Ser Lys Gln Ala Phe Gly
        355                 360                 365

Asp Phe Ala Leu Leu Gly Arg Val Leu Asp Gly Tyr Tyr Val Asp Val
    370                 375                 380

Val Asn Pro Glu Phe Asn Glu Arg Phe Ala Lys Ala Lys Thr Asp Asn
385                 390                 395                 400

Ala Lys Ala Lys Leu Thr Lys Glu Lys Asp Lys Phe Ile Lys Gly Val
                405                 410                 415

His Ser Leu Ala Ser Leu Glu Gln Ala Ile Glu His Tyr Thr Ala Arg
            420                 425                 430

His Asp Asp Glu Ser Val Gln Ala Gly Lys Leu Gly Gln Tyr Phe Lys
        435                 440                 445

His Gly Leu Ala Gly Val Asp Asn Pro Ile Gln Lys Ile His Asn Asn
    450                 455                 460

His Ser Thr Ile Lys Gly Phe Leu Glu Arg Glu Arg Pro Ala Gly Glu
465                 470                 475                 480

Arg Ala Leu Pro Lys Ile Lys Ser Asp Lys Ser Pro Glu Ile Arg Gln
                485                 490                 495

Leu Lys Glu Leu Leu Asp Asn Ala Leu Asn Val Ala His Phe Ala Lys
            500                 505                 510

Leu Leu Thr Thr Lys Thr Thr Leu His Asn Gln Asp Gly Asn Phe Tyr
        515                 520                 525

Gly Glu Phe Gly Ala Leu Tyr Asp Glu Leu Ala Lys Ile Ala Thr Leu
    530                 535                 540

Tyr Asn Lys Val Arg Asp Tyr Leu Ser Gln Lys Pro Phe Ser Thr Glu
545                 550                 555                 560

Lys Tyr Lys Leu Asn Phe Gly Asn Pro Thr Leu Leu Asn Gly Trp Asp
                565                 570                 575

Leu Asn Lys Glu Lys Asp Asn Phe Gly Val Ile Leu Gln Lys Asp Gly
```

-continued

```
                580                 585                 590
    Cys Tyr Tyr Leu Ala Leu Leu Asp Lys Ala His Lys Lys Val Phe Asp
                595                 600                 605

Asn Ala Pro Asn Thr Gly Lys Ser Val Tyr Gln Lys Met Ile Tyr Lys
                610                 615                 620

Leu Leu Pro Gly Pro Asn Lys Met Leu Pro Lys Val Phe Phe Ala Lys
    625                 630                 635                 640

Ser Asn Leu Asp Tyr Tyr Asn Pro Ser Ala Glu Leu Leu Asp Lys Tyr
                        645                 650                 655

Ala Gln Gly Thr His Lys Lys Gly Asp Asn Phe Asn Leu Lys Asp Cys
                        660                 665                 670

His Ala Leu Ile Asp Phe Phe Lys Ala Gly Ile Asn Lys His Pro Glu
                        675                 680                 685

Trp Gln His Phe Gly Phe Lys Phe Ser Pro Thr Ser Ser Tyr Gln Asp
                        690                 695                 700

Leu Ser Asp Phe Tyr Arg Glu Val Glu Pro Gln Gly Tyr Gln Val Lys
    705                 710                 715                 720

Phe Val Asp Ile Asn Ala Asp Tyr Ile Asn Glu Leu Val Glu Gln Gly
                        725                 730                 735

Gln Leu Tyr Leu Phe Gln Ile Tyr Asn Lys Asp Phe Ser Pro Lys Ala
                        740                 745                 750

His Gly Lys Pro Asn Leu His Thr Leu Tyr Phe Lys Ala Leu Phe Ser
                        755                 760                 765

Glu Asp Asn Leu Val Asn Pro Ile Tyr Lys Leu Asn Gly Glu Ala Glu
                        770                 775                 780

Ile Phe Tyr Arg Lys Ala Ser Leu Asp Met Asn Glu Thr Thr Ile His
    785                 790                 795                 800

Arg Ala Gly Glu Val Leu Glu Asn Lys Asn Pro Asp Asn Pro Lys Lys
                        805                 810                 815

Arg Gln Phe Val Tyr Asp Ile Ile Lys Asp Lys Arg Tyr Thr Gln Asp
                        820                 825                 830

Lys Phe Met Leu His Val Pro Ile Thr Met Asn Phe Gly Val Gln Gly
                        835                 840                 845

Met Thr Ile Lys Glu Phe Asn Lys Lys Val Asn Gln Ser Ile Gln Gln
                        850                 855                 860

Tyr Asp Glu Val Asn Val Ile Gly Ile Asp Arg Gly Glu Arg His Leu
    865                 870                 875                 880

Leu Tyr Leu Thr Val Ile Asn Ser Lys Gly Glu Ile Leu Glu Gln Arg
                        885                 890                 895

Ser Leu Asn Asp Ile Thr Thr Ala Ser Ala Asn Gly Thr Gln Met Thr
                        900                 905                 910

Thr Pro Tyr His Lys Ile Leu Asp Lys Arg Glu Ile Glu Arg Leu Asn
                        915                 920                 925

Ala Arg Val Gly Trp Gly Glu Ile Glu Thr Ile Lys Glu Leu Lys Ser
                        930                 935                 940

Gly Tyr Leu Ser His Val Val His Gln Ile Ser Gln Leu Met Leu Lys
    945                 950                 955                 960

Tyr Asn Ala Ile Val Val Leu Glu Asp Leu Asn Phe Gly Phe Lys Arg
                        965                 970                 975

Gly Arg Phe Lys Val Glu Lys Gln Ile Tyr Gln Asn Phe Glu Asn Ala
                        980                 985                 990

Leu Ile Lys Lys Leu Asn His Leu Val Leu Lys Asp Lys Ala Asp Asp
                        995                1000                1005
```

```
Glu Ile Gly Ser Tyr Lys Asn Ala Leu Gln Leu Thr Asn Asn Phe
    1010                1015                1020

Thr Asp Leu Lys Ser Ile Gly Lys Gln Thr Gly Phe Leu Phe Tyr
    1025                1030                1035

Val Pro Ala Trp Asn Thr Ser Lys Ile Asp Pro Glu Thr Gly Phe
    1040                1045                1050

Val Asp Leu Leu Lys Pro Arg Tyr Glu Asn Ile Ala Gln Ser Gln
    1055                1060                1065

Ala Phe Phe Gly Lys Phe Asp Lys Ile Cys Tyr Asn Ala Asp Arg
    1070                1075                1080

Gly Tyr Phe Glu Phe His Ile Asp Tyr Ala Lys Phe Asn Asp Lys
    1085                1090                1095

Ala Lys Asn Ser Arg Gln Ile Trp Lys Ile Cys Ser His Gly Asp
    1100                1105                1110

Lys Arg Tyr Val Tyr Asp Lys Thr Ala Asn Gln Asn Lys Gly Ala
    1115                1120                1125

Thr Ile Gly Val Asn Val Asn Asp Glu Leu Lys Ser Leu Phe Thr
    1130                1135                1140

Arg Tyr His Ile Asn Asp Lys Gln Pro Asn Leu Val Met Asp Ile
    1145                1150                1155

Cys Gln Asn Asn Asp Lys Glu Phe His Lys Ser Leu Met Tyr Leu
    1160                1165                1170

Leu Lys Thr Leu Leu Ala Leu Arg Tyr Ser Asn Ala Ser Ser Asp
    1175                1180                1185

Glu Asp Phe Ile Leu Ser Pro Val Ala Asn Asp Glu Gly Val Phe
    1190                1195                1200

Phe Asn Ser Ala Leu Ala Asp Asp Thr Gln Pro Gln Asn Ala Asp
    1205                1210                1215

Ala Asn Gly Ala Tyr His Ile Ala Leu Lys Gly Leu Trp Leu Leu
    1220                1225                1230

Asn Glu Leu Lys Asn Ser Asp Asp Leu Asn Lys Val Lys Leu Ala
    1235                1240                1245

Ile Asp Asn Gln Thr Trp Leu Asn Phe Ala Gln Asn Arg Lys Arg
    1250                1255                1260

Pro Ala Ala Thr Lys Lys Ala Gly Gln Ala Lys Lys Lys Lys Gly
    1265                1270                1275

Ser Tyr Pro Tyr Asp Val Pro Asp Tyr Ala Tyr Pro Tyr Asp Val
    1280                1285                1290

Pro Asp Tyr Ala Tyr Pro Tyr Asp Val Pro Asp Tyr Ala
    1295                1300                1305

<210> SEQ ID NO 73
<211> LENGTH: 1251
<212> TYPE: PRT
<213> ORGANISM: Butyrivibrio sp.

<400> SEQUENCE: 73

Met Tyr Tyr Gln Asn Leu Thr Lys Lys Tyr Pro Val Ser Lys Thr Ile
1               5                   10                  15

Arg Asn Glu Leu Ile Pro Ile Gly Lys Thr Leu Glu Asn Ile Arg Lys
                20                  25                  30

Asn Asn Ile Leu Glu Ser Asp Val Lys Arg Lys Gln Asp Tyr Glu His
            35                  40                  45

Val Lys Gly Ile Met Asp Glu Tyr His Lys Gln Leu Ile Asn Glu Ala
```

```
                50             55             60
Leu Asp Asn Tyr Met Leu Pro Ser Leu Asn Gln Ala Glu Ile Tyr
65              70              75              80

Leu Lys Lys His Val Asp Val Glu Asp Arg Glu Glu Phe Lys Thr
                85              90              95

Gln Asp Leu Leu Arg Arg Glu Val Thr Gly Arg Leu Lys Glu His Glu
            100             105             110

Asn Tyr Thr Lys Ile Gly Lys Lys Asp Ile Leu Asp Leu Leu Glu Lys
            115             120             125

Leu Pro Ser Ile Ser Glu Glu Asp Tyr Asn Ala Leu Glu Ser Phe Arg
130             135             140

Asn Phe Tyr Thr Tyr Phe Thr Ser Tyr Asn Lys Val Arg Glu Asn Leu
145             150             155             160

Tyr Ser Asp Glu Glu Lys Ser Ser Thr Val Ala Tyr Arg Leu Ile Asn
            165             170             175

Glu Asn Leu Pro Lys Phe Leu Asp Asn Ile Lys Ser Tyr Ala Phe Val
            180             185             190

Lys Ala Ala Gly Val Leu Ala Asp Cys Ile Glu Glu Glu Gln Asp
            195             200             205

Ala Leu Phe Met Val Glu Thr Phe Asn Met Thr Leu Thr Gln Glu Gly
            210             215             220

Ile Asp Met Tyr Asn Tyr Gln Ile Gly Lys Val Asn Ser Ala Ile Asn
225             230             235             240

Leu Tyr Asn Gln Lys Asn His Lys Val Glu Glu Phe Lys Lys Ile Pro
            245             250             255

Lys Met Lys Val Leu Tyr Lys Gln Ile Leu Ser Asp Arg Glu Glu Val
            260             265             270

Phe Ile Gly Glu Phe Lys Asp Asp Glu Thr Leu Leu Ser Ser Ile Gly
            275             280             285

Ala Tyr Gly Asn Val Leu Met Thr Tyr Leu Lys Ser Glu Lys Ile Asn
            290             295             300

Ile Phe Phe Asp Ala Leu Arg Glu Ser Glu Gly Lys Asn Val Tyr Val
305             310             315             320

Lys Asn Asp Leu Ser Lys Thr Thr Met Ser Asn Ile Val Phe Gly Ser
            325             330             335

Trp Ser Ala Phe Asp Glu Leu Leu Asn Gln Glu Tyr Asp Leu Ala Asn
            340             345             350

Glu Asn Lys Lys Lys Asp Asp Lys Tyr Phe Glu Lys Arg Gln Lys Glu
            355             360             365

Leu Lys Lys Asn Lys Ser Tyr Thr Leu Glu Gln Met Ser Asn Leu Ser
            370             375             380

Lys Glu Asp Ile Ser Pro Ile Glu Asn Tyr Ile Glu Arg Ile Ser Glu
385             390             395             400

Asp Ile Glu Lys Ile Cys Ile Tyr Asn Gly Glu Phe Glu Lys Ile Val
            405             410             415

Val Asn Glu His Asp Ser Ser Arg Lys Leu Ser Lys Asn Ile Lys Ala
            420             425             430

Val Lys Val Ile Lys Asp Tyr Leu Asp Ser Ile Lys Glu Leu Glu His
            435             440             445

Asp Ile Lys Leu Ile Asn Gly Ser Gly Gln Glu Leu Glu Lys Asn Leu
450             455             460

Val Val Tyr Val Gly Gln Glu Glu Ala Leu Glu Gln Leu Arg Pro Val
465             470             475             480
```

-continued

Asp Ser Leu Tyr Asn Leu Thr Arg Asn Tyr Leu Thr Lys Lys Pro Phe
            485                 490                 495
Ser Thr Glu Lys Val Lys Leu Asn Phe Asn Lys Ser Thr Leu Leu Asn
            500                 505                 510
Gly Trp Asp Lys Asn Lys Glu Thr Asp Asn Leu Gly Ile Leu Phe Phe
            515                 520                 525
Lys Asp Gly Lys Tyr Tyr Leu Gly Ile Met Asn Thr Thr Ala Asn Lys
        530                 535                 540
Ala Phe Val Asn Pro Pro Ala Ala Lys Thr Glu Asn Val Phe Lys Lys
545                 550                 555                 560
Val Asp Tyr Lys Leu Leu Pro Gly Ser Asn Lys Met Leu Pro Lys Val
                565                 570                 575
Phe Phe Ala Lys Ser Asn Ile Gly Tyr Tyr Asn Pro Ser Thr Glu Leu
            580                 585                 590
Tyr Ser Asn Tyr Lys Lys Gly Thr His Lys Lys Gly Pro Ser Phe Ser
        595                 600                 605
Ile Asp Asp Cys His Asn Leu Ile Asp Phe Phe Lys Glu Ser Ile Lys
        610                 615                 620
Lys His Glu Asp Trp Ser Lys Phe Gly Phe Glu Phe Ser Asp Thr Ala
625                 630                 635                 640
Asp Tyr Arg Asp Ile Ser Glu Phe Tyr Arg Glu Val Glu Lys Gln Gly
                645                 650                 655
Tyr Lys Leu Thr Phe Thr Asp Ile Asp Glu Ser Tyr Ile Asn Asp Leu
                660                 665                 670
Ile Glu Lys Asn Glu Leu Tyr Leu Phe Gln Ile Tyr Asn Lys Asp Phe
        675                 680                 685
Ser Glu Tyr Ser Lys Gly Lys Leu Asn Leu His Thr Leu Tyr Phe Met
        690                 695                 700
Met Leu Phe Asp Gln Arg Asn Leu Asp Asn Val Val Tyr Lys Leu Asn
705                 710                 715                 720
Gly Glu Ala Glu Val Phe Tyr Arg Pro Ala Ser Ile Ala Glu Asn Glu
                725                 730                 735
Leu Val Ile His Lys Ala Gly Glu Gly Ile Lys Asn Lys Asn Pro Asn
                740                 745                 750
Arg Ala Lys Val Lys Glu Thr Ser Thr Phe Ser Tyr Asp Ile Val Lys
        755                 760                 765
Asp Lys Arg Tyr Ser Lys Tyr Lys Phe Thr Leu His Ile Pro Ile Thr
        770                 775                 780
Met Asn Phe Gly Val Asp Glu Val Arg Arg Phe Asn Asp Val Ile Asn
785                 790                 795                 800
Asn Ala Leu Arg Thr Asp Asp Asn Val Asn Val Ile Gly Ile Asp Arg
                805                 810                 815
Gly Glu Arg Asn Leu Leu Tyr Val Val Val Ile Asn Ser Glu Gly Lys
                820                 825                 830
Ile Leu Glu Gln Ile Ser Leu Asn Ser Ile Ile Asn Lys Glu Tyr Asp
        835                 840                 845
Ile Glu Thr Asn Tyr His Ala Leu Leu Asp Glu Arg Glu Asp Asp Arg
        850                 855                 860
Asn Lys Ala Arg Lys Asp Trp Asn Thr Ile Glu Asn Ile Lys Glu Leu
865                 870                 875                 880
Lys Thr Gly Tyr Leu Ser Gln Val Val Asn Val Val Ala Lys Leu Val
                885                 890                 895

Leu Lys Tyr Asn Ala Ile Ile Cys Leu Glu Asp Leu Asn Phe Gly Phe
            900                 905                 910

Lys Arg Gly Arg Gln Lys Val Glu Lys Gln Val Tyr Gln Lys Phe Glu
        915                 920                 925

Lys Met Leu Ile Glu Lys Leu Asn Tyr Leu Val Ile Asp Lys Ser Arg
    930                 935                 940

Glu Gln Val Ser Pro Glu Lys Met Gly Gly Ala Leu Asn Ala Leu Gln
945                 950                 955                 960

Leu Thr Ser Lys Phe Lys Ser Phe Ala Glu Leu Gly Lys Gln Ser Gly
                965                 970                 975

Ile Ile Tyr Tyr Val Pro Ala Tyr Leu Thr Ser Lys Ile Asp Pro Thr
            980                 985                 990

Thr Gly Phe Val Asn Leu Phe Tyr Ile Lys Tyr Glu Asn Ile Glu Lys
        995                 1000                1005

Ala Lys Gln Phe Phe Asp Gly Phe Asp Phe Ile Arg Phe Asn Lys
    1010                1015                1020

Lys Asp Asp Met Phe Glu Phe Ser Phe Asp Tyr Lys Ser Phe Thr
    1025                1030                1035

Gln Lys Ala Cys Gly Ile Arg Ser Lys Trp Ile Val Tyr Thr Asn
    1040                1045                1050

Gly Glu Arg Ile Ile Lys Tyr Pro Asn Pro Glu Lys Asn Asn Leu
    1055                1060                1065

Phe Asp Glu Lys Val Ile Asn Val Thr Asp Glu Ile Lys Gly Leu
    1070                1075                1080

Phe Lys Gln Tyr Arg Ile Pro Tyr Glu Asn Gly Glu Asp Ile Lys
    1085                1090                1095

Glu Ile Ile Ile Ser Lys Ala Glu Ala Asp Phe Tyr Lys Arg Leu
    1100                1105                1110

Phe Arg Leu Leu His Gln Thr Leu Gln Met Arg Asn Ser Thr Ser
    1115                1120                1125

Asp Gly Thr Arg Asp Tyr Ile Ile Ser Pro Val Lys Asn Asp Arg
    1130                1135                1140

Gly Glu Phe Phe Cys Ser Glu Phe Ser Glu Gly Thr Met Pro Lys
    1145                1150                1155

Asp Ala Asp Ala Asn Gly Ala Tyr Asn Ile Ala Arg Lys Gly Leu
    1160                1165                1170

Trp Val Leu Glu Gln Ile Arg Gln Lys Asp Glu Gly Glu Lys Val
    1175                1180                1185

Asn Leu Ser Met Thr Asn Ala Glu Trp Leu Lys Tyr Ala Gln Leu
    1190                1195                1200

His Leu Leu Lys Arg Pro Ala Ala Thr Lys Lys Ala Gly Gln Ala
    1205                1210                1215

Lys Lys Lys Lys Gly Ser Tyr Pro Tyr Asp Val Pro Asp Tyr Ala
    1220                1225                1230

Tyr Pro Tyr Asp Val Pro Asp Tyr Ala Tyr Pro Tyr Asp Val Pro
    1235                1240                1245

Asp Tyr Ala
1250

<210> SEQ ID NO 74
<211> LENGTH: 1262
<212> TYPE: PRT
<213> ORGANISM: Eubacterium rectale

<400> SEQUENCE: 74

-continued

```
Met Asn Asn Gly Thr Asn Asn Phe Gln Asn Phe Ile Gly Ile Ser Ser
1               5                   10                  15
Leu Gln Lys Thr Leu Arg Asn Ala Leu Ile Pro Thr Glu Thr Thr Gln
            20                  25                  30
Gln Phe Ile Val Lys Asn Gly Ile Ile Lys Glu Asp Glu Leu Arg Gly
        35                  40                  45
Glu Asn Arg Gln Ile Leu Lys Asp Ile Met Asp Tyr Tyr Arg Gly
50                  55                  60
Phe Ile Ser Glu Thr Leu Ser Ser Ile Asp Asp Ile Asp Trp Thr Ser
65                  70                  75                  80
Leu Phe Glu Lys Met Glu Ile Gln Leu Lys Asn Gly Asp Asn Lys Asp
                85                  90                  95
Thr Leu Ile Lys Glu Gln Thr Glu Tyr Arg Lys Ala Ile His Lys Lys
                100                 105                 110
Phe Ala Asn Asp Asp Arg Phe Lys Asn Met Phe Ser Ala Lys Leu Ile
        115                 120                 125
Ser Asp Ile Leu Pro Glu Phe Val Ile His Asn Asn Asn Tyr Ser Ala
    130                 135                 140
Ser Glu Lys Glu Lys Thr Gln Val Ile Lys Leu Phe Ser Arg Phe
145                 150                 155                 160
Ala Thr Ser Phe Lys Asp Tyr Phe Lys Asn Arg Ala Asn Cys Phe Ser
            165                 170                 175
Ala Asp Asp Ile Ser Ser Ser Cys His Arg Ile Val Asn Asp Asn
            180                 185                 190
Ala Glu Ile Phe Phe Ser Asn Ala Leu Val Tyr Arg Arg Ile Val Lys
        195                 200                 205
Ser Leu Ser Asn Asp Asp Ile Asn Lys Ile Ser Gly Asp Met Lys Asp
210                 215                 220
Ser Leu Lys Glu Met Ser Leu Glu Glu Ile Tyr Ser Tyr Glu Lys Tyr
225                 230                 235                 240
Gly Glu Phe Ile Thr Gln Glu Gly Ile Ser Phe Tyr Asn Asp Ile Cys
            245                 250                 255
Gly Lys Val Asn Ser Phe Met Asn Leu Tyr Cys Gln Lys Asn Lys Glu
            260                 265                 270
Asn Lys Asn Leu Tyr Lys Leu Gln Lys Leu His Lys Gln Ile Leu Cys
        275                 280                 285
Ile Ala Asp Thr Ser Tyr Glu Val Pro Tyr Lys Phe Glu Ser Asp Glu
    290                 295                 300
Glu Val Tyr Gln Ser Val Asn Gly Phe Leu Asp Asn Ile Ser Ser Lys
305                 310                 315                 320
His Ile Val Glu Arg Leu Arg Lys Ile Gly Asp Asn Tyr Asn Gly Tyr
            325                 330                 335
Asn Leu Asp Lys Ile Tyr Ile Val Ser Lys Phe Tyr Glu Ser Val Ser
            340                 345                 350
Gln Lys Thr Tyr Arg Asp Trp Glu Thr Ile Asn Thr Ala Leu Glu Ile
        355                 360                 365
His Tyr Asn Asn Ile Leu Pro Gly Asn Gly Lys Ser Lys Ala Asp Lys
    370                 375                 380
Val Lys Lys Ala Val Lys Asn Asp Leu Gln Lys Ser Ile Thr Glu Ile
385                 390                 395                 400
Asn Glu Leu Val Ser Asn Tyr Lys Leu Cys Ser Asp Asp Asn Ile Lys
            405                 410                 415
```

```
Ala Glu Thr Tyr Ile His Glu Ile Ser His Ile Leu Asn Asn Phe Glu
            420                 425                 430
Ala Gln Glu Leu Lys Tyr Asn Pro Glu Ile His Leu Val Glu Ser Glu
            435                 440                 445
Leu Lys Ala Ser Glu Leu Lys Asn Val Leu Asp Val Ile Met Asn Ala
        450                 455                 460
Phe His Trp Cys Ser Val Phe Met Thr Glu Leu Val Asp Lys Asp
465                 470                 475                 480
Asn Asn Phe Tyr Ala Glu Leu Glu Glu Ile Tyr Asp Glu Ile Tyr Pro
                485                 490                 495
Val Ile Ser Leu Tyr Asn Leu Val Arg Asn Tyr Val Thr Gln Lys Pro
            500                 505                 510
Tyr Ser Thr Lys Lys Ile Lys Leu Asn Phe Gly Ile Pro Thr Leu Ala
            515                 520                 525
Asp Gly Trp Ser Lys Ser Lys Glu Tyr Ser Asn Asn Ala Ile Ile Leu
        530                 535                 540
Met Arg Asp Asn Leu Tyr Tyr Leu Gly Ile Phe Asn Ala Lys Asn Lys
545                 550                 555                 560
Pro Asp Lys Lys Ile Ile Glu Gly Asn Thr Ser Glu Asn Lys Gly Asp
                565                 570                 575
Tyr Lys Lys Met Ile Tyr Asn Leu Leu Pro Gly Pro Asn Lys Met Ile
            580                 585                 590
Pro Lys Val Phe Leu Ser Ser Lys Thr Gly Val Glu Thr Tyr Lys Pro
            595                 600                 605
Ser Ala Tyr Ile Leu Glu Gly Tyr Lys Gln Asn Lys His Ile Lys Ser
        610                 615                 620
Ser Lys Asp Phe Asp Ile Thr Phe Cys His Asp Leu Ile Asp Tyr Phe
625                 630                 635                 640
Lys Asn Cys Ile Ala Ile His Pro Glu Trp Lys Asn Phe Gly Phe Asp
                645                 650                 655
Phe Ser Asp Thr Ser Thr Tyr Glu Asp Ile Ser Gly Phe Tyr Arg Glu
            660                 665                 670
Val Glu Leu Gln Gly Tyr Lys Ile Asp Trp Thr Tyr Ile Ser Glu Lys
            675                 680                 685
Asp Ile Asp Leu Leu Gln Glu Lys Gly Gln Leu Tyr Leu Phe Gln Ile
        690                 695                 700
Tyr Asn Lys Asp Phe Ser Lys Lys Ser Thr Gly Asn Asp Asn Leu His
705                 710                 715                 720
Thr Met Tyr Leu Lys Asn Leu Phe Ser Glu Glu Asn Leu Lys Asp Ile
                725                 730                 735
Val Leu Lys Leu Asn Gly Glu Ala Glu Ile Phe Phe Arg Lys Ser Ser
            740                 745                 750
Ile Lys Asn Pro Ile Ile His Lys Lys Gly Ser Ile Leu Val Asn Arg
            755                 760                 765
Thr Tyr Glu Ala Glu Glu Lys Asp Gln Phe Gly Asn Gln Ile Val Arg
        770                 775                 780
Lys Asn Ile Pro Glu Asn Ile Tyr Gln Glu Leu Tyr Lys Tyr Phe Asn
785                 790                 795                 800
Asp Lys Ser Asp Lys Glu Leu Ser Asp Glu Ala Ala Lys Leu Lys Asn
                805                 810                 815
Val Val Gly His His Glu Ala Ala Thr Asn Ile Val Lys Asp Tyr Arg
            820                 825                 830
Tyr Thr Tyr Asp Lys Tyr Phe Leu His Met Pro Ile Thr Ile Asn Phe
```

```
                835                 840                 845
Lys Ala Asn Lys Thr Gly Phe Ile Asn Asp Arg Ile Leu Gln Tyr Ile
    850                 855                 860
Ala Lys Glu Lys Asp Leu His Val Ile Gly Ile Asp Arg Gly Glu Arg
865                 870                 875                 880
Asn Leu Ile Tyr Val Ser Val Ile Asp Thr Cys Gly Asn Ile Val Glu
                885                 890                 895
Gln Lys Ser Phe Asn Ile Val Asn Gly Tyr Asp Tyr Gln Ile Lys Leu
            900                 905                 910
Lys Gln Gln Glu Gly Ala Arg Gln Ile Ala Arg Lys Glu Trp Lys Glu
            915                 920                 925
Ile Gly Lys Ile Lys Glu Ile Lys Glu Gly Tyr Leu Ser Leu Val Ile
            930                 935                 940
His Glu Ile Ser Lys Met Val Ile Lys Tyr Asn Ala Ile Ile Ala Met
945                 950                 955                 960
Glu Asp Leu Ser Tyr Gly Phe Lys Lys Gly Arg Phe Lys Val Glu Arg
                965                 970                 975
Gln Val Tyr Gln Lys Phe Glu Thr Met Leu Ile Asn Lys Leu Asn Tyr
            980                 985                 990
Leu Val Phe Lys Asp Ile Ser Ile Thr Glu Asn Gly Gly Leu Leu Lys
            995                 1000                1005
Gly Tyr Gln Leu Thr Tyr Ile Pro Asp Lys Leu Lys Asn Val Gly
    1010                1015                1020
His Gln Cys Gly Cys Ile Phe Tyr Val Pro Ala Ala Tyr Thr Ser
    1025                1030                1035
Lys Ile Asp Pro Thr Thr Gly Phe Val Asn Ile Phe Lys Phe Lys
    1040                1045                1050
Asp Leu Thr Val Asp Ala Lys Arg Glu Phe Ile Lys Lys Phe Asp
    1055                1060                1065
Ser Ile Arg Tyr Asp Ser Glu Lys Asn Leu Phe Cys Phe Thr Phe
    1070                1075                1080
Asp Tyr Asn Asn Phe Ile Thr Gln Asn Thr Val Met Ser Lys Ser
    1085                1090                1095
Ser Trp Ser Val Tyr Thr Tyr Gly Val Arg Ile Lys Arg Arg Phe
    1100                1105                1110
Val Asn Gly Arg Phe Ser Asn Glu Ser Asp Thr Ile Asp Ile Thr
    1115                1120                1125
Lys Asp Met Glu Lys Thr Leu Glu Met Thr Asp Ile Asn Trp Arg
    1130                1135                1140
Asp Gly His Asp Leu Arg Gln Asp Ile Ile Asp Tyr Glu Ile Val
    1145                1150                1155
Gln His Ile Phe Glu Ile Phe Arg Leu Thr Val Gln Met Arg Asn
    1160                1165                1170
Ser Leu Ser Glu Leu Glu Asp Arg Asp Tyr Asp Arg Leu Ile Ser
    1175                1180                1185
Pro Val Leu Asn Glu Asn Asn Ile Phe Tyr Asp Ser Ala Lys Ala
    1190                1195                1200
Gly Asp Ala Leu Pro Lys Asp Ala Asp Ala Asn Gly Ala Tyr Cys
    1205                1210                1215
Ile Ala Leu Lys Gly Leu Tyr Glu Ile Lys Gln Ile Thr Glu Asn
    1220                1225                1230
Trp Lys Glu Asp Gly Lys Phe Ser Arg Asp Lys Leu Lys Ile Ser
    1235                1240                1245
```

```
Asn Lys Asp Trp Phe Asp Phe Ile Gln Asn Lys Arg Tyr Leu
    1250            1255            1260

<210> SEQ ID NO 75
<211> LENGTH: 1263
<212> TYPE: PRT
<213> ORGANISM: Eubacterium rectale

<400> SEQUENCE: 75

Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
            20                  25                  30

Gln Phe Ile Val Lys Asn Gly Ile Ile Lys Glu Asp Glu Leu Arg Gly
        35                  40                  45

Glu Asn Arg Gln Ile Leu Lys Asp Ile Met Asp Asp Tyr Tyr Arg Gly
    50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Ala Glu Lys Arg Lys Ala Ile Tyr Lys Lys
            100                 105                 110

Phe Ala Asp Asp Asp Arg Phe Lys Asn Met Phe Ser Ala Lys Leu Ile
        115                 120                 125

Ser Asp Ile Leu Pro Glu Phe Val Ile His Asn Asn Tyr Ser Ala
130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
        180                 185                 190

Ala Glu Ile Phe Phe Ser Asn Ala Leu Val Tyr Arg Arg Ile Val Lys
    195                 200                 205

Asn Leu Ser Asn Asp Asp Ile Asn Lys Ile Ser Gly Asp Met Lys Asp
210                 215                 220

Ser Leu Lys Glu Met Ser Leu Asp Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
            260                 265                 270

Asn Lys Asn Leu Tyr Lys Leu Arg Lys Leu His Lys Gln Ile Leu Cys
        275                 280                 285

Ile Ala Asp Thr Ser Tyr Glu Val Pro Tyr Lys Phe Glu Ser Asp Glu
    290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
                325                 330                 335

Asn Leu Asp Lys Ile Tyr Ile Val Ser Arg Phe Tyr Glu Ser Val Ser
            340                 345                 350

Gln Lys Thr Tyr Arg Asp Trp Glu Thr Ile Asn Thr Ala Leu Glu Ile
```

```
              355                 360                 365
His Tyr Asn Asn Ile Leu Pro Gly Asn Gly Lys Ser Lys Ala Asp Lys
    370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Pro Asp Asp Asn Ile Lys
                405                 410                 415

Ala Glu Thr Tyr Ile His Glu Ile Ser His Ile Leu Asn Asn Phe Glu
            420                 425                 430

Ala Gln Glu Leu Lys Tyr Asn Pro Glu Ile His Leu Val Glu Ser Glu
        435                 440                 445

Leu Lys Ala Ser Glu Leu Lys Asn Val Leu Asp Val Ile Met Asn Ala
    450                 455                 460

Phe His Trp Cys Ser Val Phe Met Thr Glu Leu Val Asp Lys Asp
465                 470                 475                 480

Asn Asn Phe Tyr Ala Glu Leu Glu Ile Tyr Asp Glu Ile Tyr Pro
                485                 490                 495

Val Ile Ser Leu Tyr Asn Leu Val Arg Asn Tyr Val Thr Gln Lys Pro
            500                 505                 510

Tyr Ser Thr Lys Lys Ile Lys Leu Asn Phe Gly Ile Pro Thr Leu Ala
        515                 520                 525

Asp Gly Trp Ser Lys Ser Lys Glu Tyr Ser Asn Asn Ala Ile Ile Leu
    530                 535                 540

Met Arg Asp Asn Leu Tyr Tyr Leu Gly Ile Phe Asn Ala Lys Asn Lys
545                 550                 555                 560

Pro Asp Lys Lys Ile Ile Glu Gly Asn Thr Ser Glu Asn Lys Gly Asp
                565                 570                 575

Tyr Lys Lys Met Ile Tyr Asn Leu Leu Pro Gly Pro Asn Lys Met Ile
            580                 585                 590

Pro Lys Val Phe Leu Ser Ser Lys Thr Gly Val Glu Thr Tyr Lys Pro
        595                 600                 605

Ser Ala Tyr Ile Leu Glu Gly Tyr Lys Gln Asn Lys His Leu Lys Ser
    610                 615                 620

Ser Lys Asp Phe Asp Ile Thr Phe Cys Arg Asp Leu Ile Asp Tyr Phe
625                 630                 635                 640

Lys Asn Cys Ile Ala Ile His Pro Glu Trp Lys Asn Phe Gly Phe Asp
                645                 650                 655

Phe Ser Asp Thr Ser Thr Tyr Glu Asp Ile Ser Gly Phe Tyr Arg Glu
            660                 665                 670

Val Glu Leu Gln Gly Tyr Lys Ile Asp Trp Thr Tyr Ile Ser Glu Lys
        675                 680                 685

Asp Ile Asp Leu Leu Gln Lys Gly Gln Leu Tyr Leu Phe Gln Ile
    690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Ile
                725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
        755                 760                 765

Thr Tyr Glu Ala Glu Glu Lys Asp Gln Phe Gly Asn Ile Gln Ile Val
    770                 775                 780
```

```
Arg Lys Thr Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                805                 810                 815

Asn Val Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
        835                 840                 845

Phe Lys Ala Asn Lys Thr Ser Phe Ile Asn Asp Arg Ile Leu Gln Tyr
850                 855                 860

Ile Ala Lys Glu Asn Asp Leu His Val Ile Gly Ile Asp Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Arg Lys Glu Trp Lys
        915                 920                 925

Glu Ile Gly Lys Ile Lys Glu Ile Lys Glu Gly Tyr Leu Ser Leu Val
    930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975

Arg Gln Val Tyr Gln Lys Phe Glu Thr Met Leu Ile Asn Lys Leu Asn
            980                 985                 990

Tyr Leu Val Phe Lys Asp Ile Ser Ile Thr Glu Asn Gly Gly Leu Leu
        995                 1000                1005

Lys Gly Tyr Gln Leu Thr Tyr Ile Pro Glu Lys Leu Lys Asn Val
    1010                1015                1020

Gly His Gln Cys Gly Cys Ile Phe Tyr Val Pro Ala Ala Tyr Thr
    1025                1030                1035

Ser Lys Ile Asp Pro Thr Thr Gly Phe Ala Asn Ile Phe Lys Phe
    1040                1045                1050

Lys Asp Leu Thr Val Asp Ala Lys Arg Glu Phe Ile Lys Lys Phe
    1055                1060                1065

Asp Ser Ile Arg Tyr Asp Ser Glu Lys Asn Leu Phe Cys Phe Thr
    1070                1075                1080

Phe Asp Tyr Asn Asn Phe Ile Thr Gln Asn Thr Val Met Ser Lys
    1085                1090                1095

Ser Ser Trp Ser Val Tyr Thr Tyr Gly Val Arg Ile Lys Arg Arg
    1100                1105                1110

Phe Val Asn Gly Arg Phe Ser Asn Glu Ser Asp Thr Ile Asp Ile
    1115                1120                1125

Thr Lys Asp Met Glu Lys Thr Leu Glu Met Thr Asp Ile Asn Trp
    1130                1135                1140

Arg Asp Gly His Asp Leu Arg Gln Asp Ile Ile Asp Tyr Glu Ile
    1145                1150                1155

Val Gln His Ile Phe Glu Ile Phe Lys Leu Thr Val Gln Met Arg
    1160                1165                1170

Asn Ser Leu Ser Glu Leu Glu Asp Arg Asp Tyr Asp Arg Leu Ile
    1175                1180                1185
```

```
Ser Pro Val Leu Asn Glu Asn Asn Ile Phe Tyr Asp Ser Ala Lys
    1190                1195                1200

Ala Gly Asp Ala Leu Pro Lys Asp Ala Asp Ala Asn Gly Ala Tyr
    1205                1210                1215

Cys Ile Ala Leu Lys Gly Leu Tyr Glu Ile Lys Gln Ile Thr Glu
    1220                1225                1230

Asn Trp Lys Glu Asp Gly Lys Phe Ser Arg Asp Lys Leu Lys Ile
    1235                1240                1245

Ser Asn Lys Asp Trp Phe Asp Phe Ile Gln Asn Lys Arg Tyr Leu
    1250                1255                1260

<210> SEQ ID NO 76
<211> LENGTH: 1263
<212> TYPE: PRT
<213> ORGANISM: Eubacterium rectale

<400> SEQUENCE: 76

Met Asn Gly Thr Asn Phe Gln Asn Phe Ile Gly Ile Ser Ser
1               5                   10                  15

Leu Gln Lys Thr Leu Arg Asn Ala Leu Thr Pro Thr Glu Thr Thr Gln
                20                  25                  30

Gln Phe Ile Val Lys Asn Gly Ile Ile Lys Glu Asp Glu Leu Arg Gly
            35                  40                  45

Glu Asn Arg Gln Ile Leu Lys Asp Ile Met Asp Tyr Tyr Arg Gly
    50                  55                  60

Phe Ile Ser Glu Thr Leu Ser Ser Ile Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Ala Glu Lys Arg Lys Ala Ile Tyr Lys Lys
                100                 105                 110

Phe Ala Asp Asp Asp Arg Phe Lys Asn Met Phe Ser Ala Lys Leu Ile
            115                 120                 125

Ser Asp Ile Leu Pro Glu Phe Val Ile His Asn Asn Asn Tyr Ser Ala
130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
            180                 185                 190

Ala Glu Ile Phe Phe Ser Asn Ala Leu Val Tyr Arg Arg Ile Val Lys
        195                 200                 205

Asn Leu Ser Asn Asp Asp Ile Asn Lys Ile Ser Gly Asp Met Lys Asp
    210                 215                 220

Ser Leu Lys Lys Met Ser Leu Glu Lys Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
            260                 265                 270

Asn Lys Asn Leu Tyr Lys Leu Arg Lys Leu His Lys Gln Ile Leu Cys
        275                 280                 285

Ile Ala Asp Thr Ser Tyr Glu Val Pro Tyr Lys Phe Glu Ser Asp Glu
    290                 295                 300
```

```
Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
                325                 330                 335

Asn Leu Asp Lys Ile Tyr Ile Val Ser Lys Phe Tyr Glu Ser Val Ser
            340                 345                 350

Gln Lys Thr Tyr Arg Asp Trp Glu Thr Ile Asn Thr Ala Leu Glu Ile
        355                 360                 365

His Tyr Asn Asn Ile Leu Pro Gly Asn Gly Lys Ser Lys Ala Asp Lys
    370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Pro Asp Asp Asn Ile Lys
                405                 410                 415

Ala Glu Thr Tyr Ile His Glu Ile Ser His Ile Leu Asn Asn Phe Glu
            420                 425                 430

Ala Gln Glu Leu Lys Tyr Asn Pro Glu Ile His Leu Val Glu Ser Glu
        435                 440                 445

Leu Lys Ala Ser Glu Leu Lys Asn Val Leu Asp Val Ile Met Asn Ala
    450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
                485                 490                 495

Val Ile Ser Leu Tyr Asn Leu Val Arg Asn Tyr Val Thr Gln Lys Pro
            500                 505                 510

Tyr Ser Thr Lys Lys Ile Lys Leu Asn Phe Gly Ile Pro Thr Leu Ala
        515                 520                 525

Asp Gly Trp Ser Lys Ser Lys Glu Tyr Ser Asn Asn Ala Ile Ile Leu
    530                 535                 540

Met Arg Asp Asn Leu Tyr Tyr Leu Gly Ile Phe Asn Ala Lys Asn Lys
545                 550                 555                 560

Pro Glu Lys Lys Ile Ile Glu Gly Asn Thr Ser Glu Asn Lys Gly Asp
                565                 570                 575

Tyr Lys Lys Met Ile Tyr Asn Leu Leu Pro Gly Pro Asn Lys Met Ile
            580                 585                 590

Pro Lys Val Phe Leu Ser Ser Lys Thr Gly Val Glu Thr Tyr Lys Pro
        595                 600                 605

Ser Ala Tyr Ile Leu Glu Gly Tyr Lys Gln Asn Lys His Leu Lys Ser
    610                 615                 620

Ser Lys Asp Phe Asp Ile Thr Phe Cys Arg Asp Leu Ile Asp Tyr Phe
625                 630                 635                 640

Lys Asn Cys Ile Ala Ile His Pro Glu Trp Lys Asn Phe Gly Phe Asp
                645                 650                 655

Phe Ser Asp Thr Ser Thr Tyr Glu Asp Ile Ser Gly Phe Tyr Arg Glu
            660                 665                 670

Val Glu Leu Gln Gly Tyr Lys Ile Asp Trp Thr Tyr Ile Ser Glu Lys
        675                 680                 685

Asp Ile Asp Leu Leu Gln Glu Lys Gly Gln Leu Tyr Leu Phe Gln Ile
    690                 695                 700

Tyr Asn Lys Asp Phe Ser Lys Lys Ser Thr Gly Asn Asp Asn Leu His
705                 710                 715                 720
```

-continued

```
Thr Met Tyr Leu Lys Asn Leu Phe Ser Glu Glu Asn Leu Lys Asp Val
            725                 730                 735
Val Leu Lys Leu Asn Gly Glu Ala Glu Ile Phe Phe Arg Lys Ser Ser
            740                 745                 750
Ile Lys Asn Pro Ile Ile His Lys Lys Gly Ser Ile Leu Val Asn Arg
            755                 760                 765
Thr Tyr Glu Ala Glu Glu Lys Asp Gln Phe Gly Asn Ile Gln Ile Val
            770                 775                 780
Arg Lys Thr Ile Pro Glu Asn Ile Tyr Gln Glu Leu Tyr Lys Tyr Phe
785                 790                 795                 800
Asn Asp Lys Ser Asp Lys Glu Leu Ser Asp Glu Ala Ala Lys Leu Lys
            805                 810                 815
Asn Ala Val Gly His His Glu Ala Ala Thr Asn Ile Val Lys Asp Tyr
            820                 825                 830
Arg Tyr Thr Tyr Asp Lys Tyr Phe Leu His Met Pro Ile Thr Ile Asn
            835                 840                 845
Phe Lys Ala Asn Lys Thr Ser Phe Ile Asn Asp Arg Ile Leu Gln Tyr
            850                 855                 860
Ile Ala Lys Glu Lys Asp Leu His Val Ile Gly Ile Asp Arg Gly Glu
865                 870                 875                 880
Arg Asn Leu Ile Tyr Val Ser Val Ile Asp Thr Cys Gly Asn Ile Val
            885                 890                 895
Glu Gln Lys Ser Phe Asn Ile Val Asn Gly Tyr Asp Tyr Gln Ile Lys
            900                 905                 910
Leu Lys Gln Gln Glu Gly Ala Arg Gln Ile Ala Arg Lys Glu Trp Lys
            915                 920                 925
Glu Ile Gly Lys Ile Lys Glu Ile Lys Glu Gly Tyr Leu Ser Leu Val
            930                 935                 940
Ile His Glu Ile Ser Lys Met Val Ile Lys Tyr Asn Ala Ile Ile Ala
945                 950                 955                 960
Met Glu Asp Leu Ser Tyr Gly Phe Lys Lys Gly Arg Phe Lys Val Glu
            965                 970                 975
Arg Gln Val Tyr Gln Lys Phe Glu Thr Met Leu Ile Asn Lys Leu Asn
            980                 985                 990
Tyr Leu Val Phe Lys Asp Ile Ser Ile Thr Glu Asn Gly Gly Leu Leu
            995                 1000                1005
Lys Gly Tyr Gln Leu Thr Tyr Ile Pro Glu Lys Leu Lys Asn Val
            1010                1015                1020
Gly His Gln Cys Gly Cys Ile Phe Tyr Val Pro Ala Ala Tyr Thr
            1025                1030                1035
Ser Lys Ile Asp Pro Thr Thr Gly Phe Val Asn Ile Phe Lys Phe
            1040                1045                1050
Lys Asp Leu Thr Val Asp Ala Lys Arg Glu Phe Ile Lys Lys Phe
            1055                1060                1065
Asp Ser Ile Arg Tyr Asp Ser Asp Lys Asn Leu Phe Cys Phe Thr
            1070                1075                1080
Phe Asp Tyr Asn Asn Phe Ile Thr Gln Asn Thr Val Met Ser Lys
            1085                1090                1095
Ser Ser Trp Ser Val Tyr Thr Tyr Gly Val Arg Ile Lys Arg Arg
            1100                1105                1110
Phe Val Asn Gly Arg Phe Ser Asn Glu Ser Asp Thr Ile Asp Ile
            1115                1120                1125
Thr Lys Asp Met Glu Lys Thr Leu Glu Met Thr Asp Ile Asn Trp
```

```
                    1130                1135                1140
Arg  Asp  Gly  His  Asp  Leu  Arg  Gln  Asp  Ile  Ile  Asp  Tyr  Glu  Ile
          1145                1150                1155

Val  Gln  His  Ile  Phe  Glu  Ile  Phe  Lys  Leu  Thr  Val  Gln  Met  Arg
     1160                1165                1170

Asn  Ser  Leu  Ser  Glu  Leu  Glu  Asp  Arg  Asn  Tyr  Asp  Arg  Leu  Ile
1175                1180                1185

Ser  Pro  Val  Leu  Asn  Glu  Asn  Asn  Ile  Phe  Tyr  Asp  Ser  Ala  Lys
     1190                1195                1200

Ala  Gly  Asp  Ala  Leu  Pro  Lys  Asp  Ala  Asp  Ala  Asn  Gly  Ala  Tyr
1205                1210                1215

Cys  Ile  Ala  Leu  Lys  Gly  Leu  Tyr  Glu  Ile  Lys  Gln  Ile  Thr  Glu
     1220                1225                1230

Asn  Trp  Lys  Glu  Asp  Gly  Lys  Phe  Ser  Arg  Asp  Lys  Leu  Lys  Ile
1235                1240                1245

Ser  Asn  Lys  Asp  Trp  Phe  Asp  Phe  Ile  Gln  Asn  Lys  Arg  Tyr  Leu
     1250                1255                1260
```

<210> SEQ ID NO 77
<211> LENGTH: 1263
<212> TYPE: PRT
<213> ORGANISM: Eubacterium sp..

<400> SEQUENCE: 77

```
Met  Asn  Asn  Gly  Thr  Asn  Asn  Phe  Gln  Asn  Phe  Ile  Gly  Ile  Ser  Ser
1              5                   10                  15

Leu  Gln  Lys  Thr  Leu  Arg  Asn  Ala  Leu  Ile  Pro  Thr  Glu  Thr  Thr  Gln
          20                  25                  30

Gln  Phe  Ile  Val  Lys  Asn  Gly  Ile  Ile  Lys  Glu  Asp  Glu  Leu  Arg  Gly
     35                  40                  45

Lys  Asn  Arg  Gln  Ile  Leu  Lys  Asp  Ile  Met  Asp  Asp  Tyr  Tyr  Arg  Gly
50                  55                  60

Phe  Ile  Ser  Glu  Thr  Leu  Ser  Ser  Ile  Asp  Asp  Ile  Asp  Trp  Thr  Ser
65                  70                  75                  80

Leu  Phe  Glu  Lys  Met  Glu  Ile  Gln  Leu  Lys  Asn  Gly  Asp  Asn  Lys  Asp
               85                  90                  95

Thr  Leu  Ile  Lys  Glu  Gln  Ala  Glu  Lys  Arg  Lys  Ala  Ile  Tyr  Lys  Lys
          100                 105                 110

Phe  Ala  Asp  Asp  Asp  Arg  Phe  Lys  Asn  Met  Phe  Ser  Ala  Lys  Leu  Ile
          115                 120                 125

Ser  Asp  Ile  Leu  Pro  Glu  Phe  Val  Ile  His  Asn  Asn  Asn  Tyr  Ser  Ala
     130                 135                 140

Ser  Glu  Lys  Lys  Glu  Lys  Thr  Gln  Val  Ile  Lys  Leu  Phe  Ser  Arg  Phe
145                 150                 155                 160

Ala  Thr  Ser  Phe  Lys  Asp  Tyr  Phe  Lys  Asn  Arg  Ala  Asn  Cys  Phe  Ser
               165                 170                 175

Ala  Asp  Asp  Ile  Ser  Ser  Ser  Cys  His  Arg  Ile  Val  Asn  Asp  Asn
          180                 185                 190

Ala  Glu  Ile  Phe  Phe  Ser  Asn  Ala  Leu  Val  Tyr  Arg  Arg  Ile  Val  Lys
          195                 200                 205

Asn  Leu  Ser  Asn  Asp  Asp  Ile  Asn  Lys  Ile  Ser  Gly  Asp  Met  Lys  Asp
     210                 215                 220

Ser  Leu  Lys  Glu  Met  Ser  Leu  Glu  Glu  Ile  Tyr  Ser  Tyr  Glu  Lys  Tyr
225                 230                 235                 240
```

-continued

```
Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
            260                 265                 270

Asn Lys Asn Leu Tyr Lys Leu Arg Lys Leu His Lys Gln Ile Leu Cys
        275                 280                 285

Ile Ala Asp Thr Ser Tyr Glu Val Pro Tyr Lys Phe Glu Ser Asp Glu
290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Asp Tyr
                325                 330                 335

Asn Leu Asp Lys Ile Tyr Ile Val Ser Lys Phe Tyr Glu Ser Val Ser
            340                 345                 350

Gln Lys Thr Tyr Arg Asp Trp Glu Thr Ile Asn Thr Ala Leu Glu Ile
        355                 360                 365

His Tyr Asn Asn Ile Leu Pro Gly Asn Gly Lys Ser Lys Ala Asp Lys
370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asp Asn Ile Lys
                405                 410                 415

Ala Glu Thr Tyr Ile His Glu Ile Ser His Ile Leu Asn Asn Phe Glu
            420                 425                 430

Ala His Glu Leu Lys Tyr Asn Pro Glu Ile His Leu Val Glu Ser Glu
        435                 440                 445

Leu Lys Ala Ser Glu Leu Lys Asn Val Leu Asp Ile Ile Met Asn Ala
450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
                485                 490                 495

Val Ile Ser Leu Tyr Asn Leu Val Arg Asn Tyr Val Thr Gln Lys Pro
            500                 505                 510

Tyr Ser Thr Lys Lys Ile Lys Leu Asn Phe Gly Ile Pro Thr Leu Ala
        515                 520                 525

Asp Gly Trp Ser Lys Ser Lys Glu Tyr Ser Asn Asn Ala Ile Ile Leu
530                 535                 540

Met Arg Asp Asn Leu Tyr Tyr Leu Gly Ile Phe Asn Ala Lys Asn Lys
545                 550                 555                 560

Pro Asp Lys Lys Ile Ile Glu Gly Asn Thr Ser Glu Asn Lys Gly Asp
                565                 570                 575

Tyr Lys Lys Met Ile Tyr Asn Leu Leu Pro Gly Pro Asn Lys Met Ile
            580                 585                 590

Pro Lys Val Phe Leu Ser Ser Lys Thr Gly Val Glu Thr Tyr Lys Pro
        595                 600                 605

Ser Ala Tyr Ile Leu Glu Gly Tyr Lys Gln Asn Lys His Leu Lys Ser
610                 615                 620

Ser Lys Asp Phe Asp Ile Thr Phe Cys His Asp Leu Ile Asp Tyr Phe
625                 630                 635                 640

Lys Asn Cys Ile Ala Ile His Pro Glu Trp Lys Asn Phe Gly Phe Asp
                645                 650                 655

Phe Ser Asp Thr Ser Ala Tyr Glu Asp Ile Ser Gly Phe Tyr Arg Glu
```

-continued

```
                660                 665                 670
Val Glu Leu Gln Gly Tyr Lys Ile Asp Trp Thr Tyr Ile Ser Glu Lys
            675                 680                 685

Asp Ile Asp Leu Leu Gln Glu Lys Gly Gln Leu Tyr Leu Phe Gln Ile
            690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Ile
                725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
            755                 760                 765

Thr Tyr Glu Ala Glu Glu Lys Asp Gln Phe Gly Asn Ile Gln Ile Val
            770                 775                 780

Arg Lys Thr Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                805                 810                 815

Asn Val Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
            835                 840                 845

Phe Lys Ala Asn Lys Thr Ser Phe Ile Asn Asp Arg Ile Leu Gln Tyr
            850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Arg Lys Glu Trp Lys
            915                 920                 925

Glu Ile Gly Lys Ile Lys Glu Ile Lys Glu Gly Tyr Leu Ser Leu Val
            930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975

Arg Gln Val Tyr Gln Lys Phe Glu Thr Met Leu Ile Asn Lys Leu Asn
            980                 985                 990

Tyr Leu Val Phe Lys Asp Ile Ser Ile Thr Glu Asn Gly Gly Leu Leu
            995                 1000                1005

Lys Gly Tyr Gln Leu Thr Tyr Ile Pro Asp Lys Leu Lys Asn Val
            1010                1015                1020

Gly His Gln Cys Gly Cys Ile Phe Tyr Val Pro Ala Ala Tyr Thr
            1025                1030                1035

Ser Lys Ile Asp Pro Thr Thr Gly Phe Val Asn Ile Phe Lys Phe
            1040                1045                1050

Lys Asp Leu Thr Val Asp Ala Lys Arg Glu Phe Ile Lys Lys Phe
            1055                1060                1065

Asp Ser Ile Arg Tyr Asp Ser Glu Lys Asn Leu Phe Cys Phe Thr
            1070                1075                1080
```

```
Phe Asp Tyr Asn Asn Phe Ile Thr Gln Asn Thr Val Met Ser Lys
    1085                1090                1095

Ser Ser Trp Ser Val Tyr Thr Tyr Gly Val Arg Ile Lys Arg Arg
    1100                1105                1110

Phe Val Asn Gly Arg Phe Ser Asn Glu Ser Asp Thr Ile Asp Ile
    1115                1120                1125

Thr Lys Asp Met Glu Lys Thr Leu Glu Met Thr Asp Ile Asn Trp
    1130                1135                1140

Arg Asp Gly His Asp Leu Arg Gln Asp Ile Ile Asp Tyr Glu Ile
    1145                1150                1155

Val Gln His Ile Phe Glu Ile Phe Lys Leu Thr Val Gln Met Arg
    1160                1165                1170

Asn Ser Leu Ser Glu Leu Glu Asp Arg Asp Tyr Asp Arg Leu Ile
    1175                1180                1185

Ser Pro Val Leu Asn Glu Asn Asn Ile Phe Tyr Asp Ser Ala Lys
    1190                1195                1200

Ala Gly Tyr Ala Leu Pro Lys Asp Ala Asp Ala Asn Gly Ala Tyr
    1205                1210                1215

Cys Ile Ala Leu Lys Gly Leu Tyr Glu Ile Lys Gln Ile Thr Glu
    1220                1225                1230

Asn Trp Lys Glu Asp Gly Lys Phe Ser Arg Asp Lys Leu Lys Ile
    1235                1240                1245

Ser Asn Lys Asp Trp Phe Asp Phe Ile Gln Asn Lys Arg Tyr Leu
    1250                1255                1260

<210> SEQ ID NO 78
<211> LENGTH: 181
<212> TYPE: PRT
<213> ORGANISM: Erwinia tasmaniensis

<400> SEQUENCE: 78

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Gln Thr Gly Glu
        35                  40                  45

Thr Lys Glu Lys Thr Glu Trp His Arg Val Val Leu Phe Gly Lys Leu
    50                  55                  60

Ala Glu Val Ala Gly Glu Tyr Leu Arg Lys Gly Ser Gln Val Tyr Ile
65                  70                  75                  80

Glu Gly Ala Leu Gln Thr Arg Lys Trp Thr Asp Gln Ala Gly Val Glu
                85                  90                  95

Lys Tyr Thr Thr Glu Val Val Val Asn Val Gly Gly Thr Met Gln Met
            100                 105                 110

Leu Gly Gly Arg Ser Gln Gly Gly Gly Ala Ser Ala Gly Gly Gln Asn
        115                 120                 125

Gly Gly Ser Asn Asn Gly Trp Gly Gln Pro Gln Gln Pro Gln Gly Gly
    130                 135                 140

Asn Gln Phe Ser Gly Gly Ala Gln Gln Ala Arg Pro Gln Gln Gln
145                 150                 155                 160

Pro Gln Gln Asn Asn Ala Pro Ala Asn Asn Glu Pro Pro Ile Asp Phe
                165                 170                 175

Asp Asp Asp Ile Pro
            180
```

<210> SEQ ID NO 79
<211> LENGTH: 209
<212> TYPE: PRT
<213> ORGANISM: Artificial Sequence
<220> FEATURE:
<223> OTHER INFORMATION: Synthetic

<400> SEQUENCE: 79

```
Met Ala Gly Ala Gln Asp Phe Val Pro His Thr Ala Asp Leu Ala Glu
1               5                   10                  15
Leu Ala Ala Ala Gly Glu Cys Arg Gly Cys Gly Leu Tyr Arg Asp
            20                  25                  30
Ala Thr Gln Ala Val Phe Gly Ala Gly Gly Arg Ser Ala Arg Ile Met
        35                  40                  45
Met Ile Gly Glu Gln Pro Gly Asp Lys Glu Asp Leu Ala Gly Leu Pro
    50                  55                  60
Phe Val Gly Pro Ala Gly Arg Leu Leu Asp Arg Ala Leu Glu Ala Ala
65                  70                  75                  80
Asp Ile Asp Arg Asp Ala Leu Tyr Val Thr Asn Ala Val Lys His Phe
                85                  90                  95
Lys Phe Thr Arg Ala Ala Gly Gly Lys Arg Arg Ile His Lys Thr Pro
            100                 105                 110
Ser Arg Thr Glu Val Val Ala Cys Arg Pro Trp Leu Ile Ala Glu Met
        115                 120                 125
Thr Ser Val Glu Pro Asp Val Val Leu Leu Gly Ala Thr Ala Ala
    130                 135                 140
Lys Ala Leu Leu Gly Asn Asp Phe Arg Val Thr Gln His Arg Gly Glu
145                 150                 155                 160
Val Leu His Val Asp Asp Val Pro Gly Asp Pro Ala Leu Val Ala Thr
                165                 170                 175
Val His Pro Ser Ser Leu Leu Arg Gly Pro Lys Glu Glu Arg Glu Ser
            180                 185                 190
Ala Phe Ala Gly Leu Val Asp Asp Leu Arg Val Ala Ala Asp Val Arg
        195                 200                 205
Pro
```

<210> SEQ ID NO 80
<211> LENGTH: 313
<212> TYPE: PRT
<213> ORGANISM: Artificial Sequence
<220> FEATURE:
<223> OTHER INFORMATION: Synthetic

<400> SEQUENCE: 80

```
Met Ile Gly Gln Lys Thr Leu Tyr Ser Phe Phe Ser Pro Ser Pro Ala
1               5                   10                  15
Arg Lys Arg His Ala Pro Ser Pro Glu Pro Ala Val Gln Gly Thr Gly
            20                  25                  30
Val Ala Gly Val Pro Glu Glu Ser Gly Asp Ala Ala Ile Pro Ala
        35                  40                  45
Lys Lys Ala Pro Ala Gly Gln Glu Glu Pro Gly Thr Pro Pro Ser Ser
    50                  55                  60
Pro Leu Ser Ala Glu Gln Leu Asp Arg Ile Gln Arg Asn Lys Ala Ala
65                  70                  75                  80
Ala Leu Leu Arg Leu Ala Ala Arg Asn Val Pro Val Gly Phe Gly Glu
```

```
                       85                  90                  95
Ser Trp Lys Lys His Leu Ser Gly Glu Phe Gly Lys Pro Tyr Phe Ile
            100                 105                 110

Lys Leu Met Gly Phe Val Ala Glu Glu Arg Lys His Tyr Thr Val Tyr
            115                 120                 125

Pro Pro Pro His Gln Val Phe Thr Trp Thr Gln Met Cys Asp Ile Lys
            130                 135                 140

Asp Val Lys Val Val Ile Leu Gly Gln Glu Pro Tyr His Gly Pro Asn
145                 150                 155                 160

Gln Ala His Gly Leu Cys Phe Ser Val Gln Arg Pro Val Pro Pro Pro
                165                 170                 175

Pro Ser Leu Glu Asn Ile Tyr Lys Glu Leu Ser Thr Asp Ile Glu Asp
                180                 185                 190

Phe Val His Pro Gly His Gly Asp Leu Ser Gly Trp Ala Lys Gln Gly
            195                 200                 205

Val Leu Leu Leu Asn Ala Val Leu Thr Val Arg Ala His Gln Ala Asn
            210                 215                 220

Ser His Lys Glu Arg Gly Trp Glu Gln Phe Thr Asp Ala Val Val Ser
225                 230                 235                 240

Trp Leu Asn Gln Asn Ser Asn Gly Leu Val Phe Leu Leu Trp Gly Ser
                245                 250                 255

Tyr Ala Gln Lys Lys Gly Ser Ala Ile Asp Arg Lys Arg His His Val
                260                 265                 270

Leu Gln Thr Ala His Pro Ser Pro Leu Ser Val Tyr Arg Gly Phe Phe
            275                 280                 285

Gly Cys Arg His Phe Ser Lys Thr Asn Glu Leu Leu Gln Lys Ser Gly
        290                 295                 300

Lys Lys Pro Ile Asp Trp Lys Glu Leu
305                 310
```

SYSTEMS, METHODS, AND COMPOSITIONS FOR TARGETED NUCLEIC ACID EDITING

RELATED APPLICATIONS AND INCORPORATION BY REFERENCE

This application is a U.S. National Stage of International Application No. PCT/US2018/033427, filed, May 18, 2018, which claims priority to U.S. Provisional Application No. 62/508,300 filed May 18, 2017, which is incorporated herein by reference in its entirety.

STATEMENT AS TO FEDERALLY SPONSORED RESEARCH

This invention was made with government support under grant numbers M100706 and MH110049 awarded by the National Institutes of Health. The government has certain rights in the invention.

REFERENCE TO AN ELECTRONIC SEQUENCE LISTING

The contents of the electronic sequence listing ("BROD_3760WP_ST25.txt", 307,181 bytes, created on Nov. 15, 2019) is herein incorporated by reference in its entirety.

FIELD OF THE INVENTION

The present invention generally relates to systems, methods, and compositions for targeting and editing nucleic acids, in particular for programmable deamination of cytosine at a target locus of interest.

BACKGROUND

Recent advances in genome sequencing techniques and analysis methods have significantly accelerated the ability to catalog and map genetic factors associated with a diverse range of biological functions and diseases. Precise genome targeting technologies are needed to enable systematic reverse engineering of causal genetic variations by allowing selective perturbation of individual genetic elements, as well as to advance synthetic biology, biotechnological, and medical applications. Although genome-editing techniques such as designer zinc fingers, transcription activator-like effectors (TALEs), or homing meganucleases are available for producing targeted genome perturbations, there remains a need for new genome engineering technologies that employ novel strategies and molecular mechanisms and are affordable, easy to set up, scalable, and amenable to targeting multiple positions within the eukaryotic genome. This would provide a major resource for new applications in genome engineering and biotechnology.

Point mutations A→G and T→C represent about 12% of known pathogenic SNPs. Programmable deamination of cytosine has been reported and may be used for correction of A→G and T→C point mutations. For example, Komor et al., Nature (2016) 533:420-424 reports targeted deamination of cytosine by APOBEC1 cytidine deaminase in a non-targeted DNA stranded displaced by the binding of a Cas9-guide RNA complex to a targeted DNA strand, which results in conversion of cytosine to uracil. See also Kim et al., Nature Biotechnology (2017) 35:371-376; Shimatani et al., Nature Biotechnology (2017) doi:10.1038/nbt.3833; Zong et al., Nature Biotechnology (2017) doi:10.1038/nbt.3811; Yang Nature Communication (2016) doi:10.1038/ncomms13330.

Novel systems and methods which allow specific correction of these point mutations and pathogenic SNPs are of interest.

SUMMARY OF THE INVENTION

At least a first aspect of the invention relates to a method of modifying an Cytosine in a target locus of interest, the method comprising delivering to the locus: (a) a Cpf1 nickase protein; (b) a guide molecule which comprises a guide sequence linked to a direct repeat sequence; and (c) a cytidine deaminase protein or catalytic domain thereof, wherein the cytidine deaminase protein or catalytic domain thereof is covalently or non-covalently linked to the Cpf1 nickase protein or the guide molecule or is adapted to link thereto after delivery; wherein guide molecule forms a complex with the Cpf1 nickase and directs the complex to bind a first DNA strand at the target locus of interest, wherein the guide sequence is capable of hybridizing with a target sequence comprising said Cytosine within said first DNA strand to form a heteroduplex that comprises a non-pairing Adenine or Uracil opposite to said Cytosine; wherein the Cpf1 nickase protein nicks a second DNA strand at the target locus of interest displaced by the formation of the heteroduplex; wherein the cytidine deaminase protein or catalytic domain thereof deaminates the Cytosine in the heteroduplex opposite to the non-pairing Adenine or Uracil.

In some embodiments, the cytidine deaminase protein or catalytic domain thereof is fused to N- or C-terminus of the Cpf1 nickase protein. In some embodiments, the cytidine protein or catalytic domain thereof is fused to the Cpf1 nickase protein by a linker. In some embodiments, the linker is (GGGGS)$_{3-11}$ (SEQ ID NOS: 1-9), GSG$_5$ (SEQ ID NO: 10) or LEPGEKPYKCPECGKSFSQSGALTRHQRTHTR (SEQ ID NO: 11).

In some embodiments, the cytidine deaminase protein or catalytic domain thereof is linked to an adaptor protein and the guide molecule or the Cpf1 nickase protein comprises an aptamer sequence capable of binding to the adaptor protein. In some embodiments, the adaptor sequence is selected from MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1.

In some embodiments, the cytidine deaminase protein or catalytic domain thereof is inserted into an internal loop of the Cpf1 nickase protein.

In some embodiments, said Cpf1 nickase comprises a mutation in the Nuc domain. In some embodiments, the Cpf1 nickase comprises a mutation corresponding to R1226A in AsCpf1.

In some embodiments, said Cpf1 nickase has part or all of the Nuc domain removed.

In some embodiments, the guide sequence of the guide molecule comprises at least one further mismatches or non-pairing nucleotide with the target sequence, adjacent to said non-pairing Adenine or Uracil. In some embodiments, the guide sequence comprises a stretch of three to five consecutive mismatches with the target sequence. In some embodiments the guide sequence comprises less than 6 consecutive mismatches with the target sequence.

In some embodiments, the guide molecule binds to Cpf1 and is capable of forming a heteroduplex of about 24 nt with the target sequence. In some embodiments, the guide molecule binds to Cpf1 and is capable of forming a heteroduplex of more than 24 nt with the target sequence.

In some embodiments, the guide sequence comprises at least one further non-pairing nucleotide with said target sequence, adjacent to said non-pairing Adenine or Uracil. In some embodiments, the guide sequence comprises a stretch of three to five consecutive non-pairing nucleotides with said target sequence.

In some embodiments, the cytidine deaminase is a human, rat or lamprey cytidine deaminase. In some embodiments, the cytidine deaminase is an apolipoprotein B mRNA-editing complex (APOBEC) family deaminase, an activation-induced deaminase (AID), or a cytidine deaminase 1 (CDA1).

In some embodiments, the cytidine deaminase is an APOBEC1 deaminase comprising one or more mutations corresponding to W90A, W90Y, R118A, H121R, H122R, R126A, R126E, or R132E in rat APOBEC1, or an APOBEC3G deaminase comprising one or more mutations corresponding to W285A, W285Y, R313A, D316R, D317R, R320A, R320E, or R326E in human APOBEC3G.

In some embodiments, the Cpf1 nickase protein is derived from a bacterial species selected from the group consisting of *Francisella tularensis, Prevotella albensis, Lachnospiraceae bacterium, Butyrivibrio proteoclasticus, Peregrinibacteria bacterium, Parcubacteria bacterium, Smithella* sp.*, Acidaminococcus* sp.*, Lachnospiraceae bacterium, Candidatus Methanoplasma termitum, Eubacterium eligens, Moraxella bovoculi, Leptospira inadai, Porphyromonas crevioricanis, Prevotella disiens* and *Porphyromonas macacae, Succinivibrio dextrinosolvens, Prevotella disiens, Flavobacterium branchiophilum, Helcococcus kunzii, Eubacterium* sp.*, Microgenomates (Roizmanbacteria) bacterium, Flavobacterium* sp.*, Prevotella brevis, Moraxella caprae, Bacteroidetes oral, Porphyromonas cansulci, Synergistes jonesii, Prevotella bryantii, Anaerovibrio* sp.*, Butyrivibrio fibrisolvens, Candidatus Methanomethylophilus, Butyrivibrio* sp.*, Oribacterium* sp.*, Pseudobutyrivibrio ruminis* and *Proteocatella sphenisci*.

In some embodiments, the natural PAM sequence is TTN, where N is A/C/G or T and the CRISPR-Cas protein is FnCpf1 or wherein the PAM sequence is TTTV, where V is A/C or G and the CRISPR-Cas protein is PaCpf1p, LbCpf1 or AsCpf1. In some embodiments the Cpf1 nickase protein has been modified to alter PAM-recognition.

In some embodiments, the target locus of interest is within a cell. In some embodiments, the cell is a eukaryotic cell. In some embodiments, the cell is a non-human animal cell. In some embodiments, the cell is a human cell. In some embodiments, the cell is a plant cell.

In some embodiments, the target locus of interest is within an animal. In some embodiments, the target locus of interest is within a plant. In some embodiments, the target locus of interest is comprised in a DNA molecule in vitro.

In some embodiments, the components (a), (b) and (c) are delivered to the cell as a ribonucleoprotein complex.

In some embodiments, the components (a), (b) and (c) are delivered to the cell as one or more polynucleotide molecules. In some embodiments, the one or more polynucleotide molecules comprise one or more mRNA molecules encoding components (a) and/or (c).

In some embodiments, the one or more polynucleotide molecules are comprised within one or more vectors. In some embodiments, the one or more polynucleotide molecules comprise one or more regulatory elements operably configured to express the Cpf1 nickase protein, the guide molecule, and the cytidine deaminase protein or catalytic domain thereof, optionally wherein the one or more regulatory elements comprise inducible promoters.

In some embodiments, the Cpf1 nickase protein and optionally the cytidine deaminase protein or catalytic domain thereof comprise one or more heterologous nuclear localization signal(s) (NLS(s)).

In some embodiments, the cytidine deaminase is delivered together with a uracil glycosylase inhibitor (UGI), where the UGI is covalently linked to said cytidine deaminase and/or said Cpf1 nickase.

In some embodiments, the one or more polynucleotide molecules or the ribonucleoprotein complex are delivered via particles, vesicles, or one or more viral vectors.

In some embodiments, the particles comprise a lipid, a sugar, a metal or a protein. In some embodiments, the particles comprise lipid nanoparticles.

In some embodiments, the vesicles comprise exosomes or liposomes. In some embodiments, the one or more viral vectors comprise one or more of adenovirus, one or more lentivirus or one or more adeno-associated virus.

In some embodiments, the method modifies a cell, a cell line or an organism by manipulation of one or more target sequences at genomic loci of interest.

At least a second aspect of the invention relates to a method for treating or preventing a disease using the method described herein, wherein the deamination of the Cytosine at the target locus of interest remedies a disease caused by a T→C or A→G point mutation or pathogenic SNP.

At least a third aspect of the invention relates to a method for knock-out or knock-down an undesirable activity of a gene or regulatory element thereof, wherein the deamination of the Cytosine at the target locus of interest inactivates a target gene or a target regulatory element at the target locus.

At least a fourth aspect of the invention relates to a modified cell obtained from the method described above, or progeny thereof, wherein the cell comprises an Uracil or a Thymine in replace of the Cytosine in the target locus of interest compared to a corresponding cell not subjected to the method.

In some embodiments, the modified cell is a eukaryotic cell. In some embodiments, the modified cell is an animal cell. In some embodiments, the modified cell is a human cell. In some embodiments, the modified cell is a plant cell.

In some embodiments, the modified cell is a therapeutic T cell. In some embodiments, the modified cell is an antibody-producing B cell.

At least a fifth aspect of the invention relates to a non-human animal or a plant comprising the modified cell described herein.

At least a sixth aspect of the invention relates to a method for cell therapy, comprising administering to a patient in need thereof the modified cell described herein, wherein the presence of the modified cell remedies a disease in the patient.

At least a seventh aspect of the invention relates to an engineered, non-naturally occurring system suitable for modifying an Cytosine in a target locus of interest, comprising: a guide molecule which comprises a guide sequence linked to a direct repeat, or a nucleotide sequence encoding the guide molecule; a Cpf1 nickase protein, or one or more nucleotide sequences encoding the Cpf1 nickase protein; a cytidine deaminase protein or catalytic domain thereof, or one or more nucleotide sequences encoding; wherein the cytidine deaminase protein or catalytic domain thereof is covalently or non-covalently linked to the Cpf1 nickase protein or the guide molecule or is adapted to link thereto after delivery; wherein the guide sequence is capable of hybridizing with a target sequence on a first DNA strand comprising a Cytosine on a first strand at the target locus, but comprises an Adenine or Uracil at the position corresponding to said Cytosine; and wherein the Cpf1 nickase protein is capable of nicking a non-target sequence in a second DNA strand, complementary to said first DNA strand. Accordingly, the application provides kits comprising or consisting of the components of the CD-functionalized CRISPR system described herein.

At least an eighth aspect of the invention relates to an engineered, non-naturally occurring vector system suitable for modifying an Cytosine in a target locus of interest, comprising one or more vectors comprising: a first regulatory element operably linked to one or more nucleotide sequences encoding a guide molecule which comprises a guide sequence linked to a direct repeat; a second regulatory element operably linked to a nucleotide sequence encoding a Cpf1 nickase protein; and optionally a nucleotide sequence encoding a cytidine deaminase protein or catalytic domain thereof which is under control of the first or second regulatory element or operably linked to a third regulatory element; wherein, if the nucleotide sequence encoding a cytidine deaminase protein or catalytic domain thereof is operably linked to a third regulatory element, the cytidine deaminase protein or catalytic domain thereof is adapted to link to the guide molecule or the Cpf1 nickase protein after expression; wherein said guide sequence is capable of hybridizing with a target sequence comprising a Cytosine within said target locus, but comprises an Adenine or Uracil at the position corresponding to said Cytosine; wherein components (a), (b) and (c) are located on the same or different vectors of the system; and wherein the Cpf1 nickase protein is capable of nicking a non-target sequence in a second DNA strand complementary to said first DNA strand. Accordingly, the application provides kits comprising or consisting of vectors encoding of the components of the CD-functionalized CRISPR system described herein.

At least an ninth aspect of the invention relates to in vitro, ex vivo or in vivo host cell or cell line or progeny thereof comprising the engineered, non-naturally occurring system or vector system described herein.

In some embodiments, the host cell is a eukaryotic cell. In some embodiments, the host cell is an animal cell. In some embodiments, the host cell is a human cell. In some embodiments, the host cell is a plant cell.

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

Methods for Targeted Deamination of Cytosine

In one aspect the present invention provides methods for targeted deamination of cytosine in a DNA, more particularly in a locus of interest. According to the methods of the invention, the cytidine deaminase (CD) protein is recruited specifically to the relevant Cytosine in the locus of interest by a CRISPR-Cas complex which can specifically bind to a target sequence. In order to achieve this, the cytidine deaminase protein can either be covalently linked to the CRISPR-Cas enzyme or be provided as a separate protein, but adapted so as to ensure recruitment thereof to the CRISPR-Cas complex.

In particular embodiments, of the methods of the present invention, recruitment of the cytidine deaminase to the target locus is ensured by fusing the cytidine deaminase or catalytic domain thereof to the CRISPR-Cas protein, which is a Cpf1 protein. Methods of generating a fusion protein from two separate proteins are known in the art and typically involve the use of spacers or linkers. The Cpf1 protein can be fused to the cytidine deaminase protein or catalytic domain thereof on either the N- or C-terminal end thereof. In particular embodiments, the CRISPR-Cas protein is a Cpf1 protein and is linked to the N-terminus of the deaminase protein or its catalytic domain.

The term "linker" as used in reference to a fusion protein refers to a molecule which joins the proteins to form a fusion protein. Generally, such molecules have no specific biological activity other than to join or to preserve some minimum distance or other spatial relationship between the proteins. However, in certain embodiments, the linker may be selected to influence some property of the linker and/or the fusion protein such as the folding, net charge, or hydrophobicity of the linker.

Suitable linkers for use in the methods of the present invention are well known to those of skill in the art and include, but are not limited to, straight or branched-chain carbon linkers, heterocyclic carbon linkers, or peptide linkers. However, as used herein the linker may also be a covalent bond (carbon-carbon bond or carbon-heteroatom bond). In particular embodiments, the linker is used to separate the CRISPR-Cas protein and the cytidine deaminase by a distance sufficient to ensure that each protein retains its required functional property. Preferred peptide linker sequences adopt a flexible extended conformation and do not exhibit a propensity for developing an ordered secondary structure. In certain embodiments, the linker can be a chemical moiety which can be monomeric, dimeric, multimeric or polymeric. Preferably, the linker comprises amino acids. Typical amino acids in flexible linkers include Gly, Asn and Ser. Accordingly, in particular embodiments, the linker comprises a combination of one or more of Gly, Asn and Ser amino acids. Other near neutral amino acids, such as Thr and Ala, also may be used in the linker sequence. Exemplary linkers are disclosed in Maratea et al. (1985), Gene 40: 39-46; Murphy et al. (1986) Proc. Nat'l. Acad. Sci. USA 83: 8258-62; U.S. Pat. Nos. 4,935,233; and 4,751,180. For example, GlySer linkers GGS, GGGS or GSG can be used. GGS, GSG, GGGS or GGGGS linkers can be used in repeats of 3 (such as (GGS)$_3$ (SEQ ID NO: 12), (GGGGS)3) or 5, 6, 7, 9 or even 12 or more, to provide suitable lengths. In particular embodiments, linkers such as (GGGGS)$_3$ (SEQ ID NO: 13) are preferably used herein. (GGGGS)$_6$ (SEQ ID NO: 14), (GGGGS)$_9$ (SEQ ID NO: 15) or (GGGGS)$_{12}$ (SEQ ID NO: 16) may preferably be used as alternatives. Other preferred alternatives are (GGGGS)$_1$ (SEQ ID NO: 17), (GGGGS)$_2$ (SEQ ID NO: 18), (GGGGS)$_4$ (SEQ ID NO: 19), (GGGGS)$_5$ (SEQ ID NO: 20), (GGGGS)$_7$ (SEQ ID NO: 21), (GGGGS)$_8$ (SEQ ID NO: 22), (GGGGS)$_{10}$ (SEQ ID NO: 23), or (GGGGS)$_{11}$ (SEQ ID NO: 24). In yet a further embodiment, LEPGEKPYKCPECGKSFSQSGAL-TRHQRTHTR (SEQ ID NO: 25) is used as a linker. In yet an additional embodiment, the linker is XTEN linker. In particular embodiments, the CRISPR-cas protein is a Cpf1 protein and is linked to the deaminase protein or its catalytic domain by means of an LEP-GEKPYKCPECGKSFSQSGALTRHQRTHTR (SEQ ID NO:26) linker. In further particular embodiments, the Cpf1 protein is linked C-terminally to the N-terminus of a deaminase protein or its catalytic domain by means of an LEP- GEKPYKCPECGKSFSQSGALTRHQRTHTR (SEQ ID NO:27) linker. In addition, N- and C-terminal NLSs can also function as linker (e.g., PKKKRKVEASSPKKRKVEAS (SEQ ID NO:28)).

In particular embodiments of the methods of the present invention, the cytidine deaminase protein or catalytic domain thereof is delivered to the cell or expressed within the cell as a separate protein, but is modified so as to be able to link to either the Cpf1 protein or the guide molecule. In particular embodiments, this is ensured by the use of orthogonal RNA-binding protein or adaptor protein/aptamer combinations that exist within the diversity of bacteriophage coat proteins. Examples of such coat proteins include but are not limited to: MS2, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1. Aptamers can be naturally occurring or synthetic oligonucleotides that have been engineered through repeated rounds of in vitro selection or SELEX (systematic evolution of ligands by exponential enrichment) to bind to a specific target.

In particular embodiments of the methods and systems of the present invention, the guide molecule is provided with one or more distinct RNA loop(s) or distinct sequence(s) that can recruit an adaptor protein. A guide molecule may be extended, without colliding with the Cpf1 protein by the insertion of distinct RNA loop(s) or distinct sequence(s) that may recruit adaptor proteins that can bind to the distinct RNA loop(s) or distinct sequence(s). Examples of modified guides and their use in recruiting effector domains to the CRISPR-Cas complex are provided in Konermann (Nature 2015, 517(7536): 583-588). In particular embodiments, the aptamer is a minimal hairpin aptamer which selectively binds dimerized MS2 bacteriophage coat proteins in mammalian cells and is introduced into the guide molecule, such as in the stemloop and/or in a tetraloop. In these embodiments, the cytidine deaminase protein is fused to MS2. The cytidine deaminase protein is then co-delivered together with the CRISPR-Cas protein and corresponding guide RNA.

The term "CD-functionalized CRISPR system" as used here refers to a nucleic acid targeting and editing system comprising (a) a CRISPR-Cas protein, more particularly a Cpf1 protein which is catalytically inactive or a nickase; (b) a guide molecule which comprises a guide sequence; and (c) a cytidine deaminase protein or catalytic domain thereof; wherein the cytidine deaminase protein or catalytic domain thereof is covalently or non-covalently linked to the CRISPR-Cas protein or the guide molecule or is adapted to link thereto after delivery; wherein the guide sequence is partially or substantially complementary to the target sequence but comprises a non-pairing Adenine or Uracil corresponding to the C being targeted for deamination, resulting in a C-A/U mismatch in a heteroduplex formed by the guide sequence and the target sequence. In particular embodiments, the guide sequence further comprises at least one additional mismatch or non-pairing nucleotide with the target sequence, adjacent to said non-pairing Adenine or Uracil. This results in a region of single strand DNA at the location of the Cytosine of interest in the target strand, allowing the cytidine deaminase to act specifically thereon. In some embodiments, the guide sequence of the guide molecule comprises at least one further mismatch or non-pairing nucleotide with the target sequence, adjacent to said non-pairing Adenine or Uracil. In some embodiments, the guide sequence comprises a stretch of three to five consecutive mismatches with the target sequence. In some embodiments the guide sequence comprises less than 8 consecutive mismatches with the target sequence. In some embodiments, the guide sequence comprises one or more mismatches 3' and one or more mismatches 5' of the non-pairing Adenine or Uracil. In particular embodiments, the guide sequence comprises one, two three or four mismatches with the target sequence on each side of the non-pairing Adenine of Uracil. Details on the aspect of the guide of the CD-functionalized CRISPR-Cas system are provided herein below.

In some embodiments, the components (a), (b) and (c) are delivered to the cell as a ribonucleoprotein complex. The ribonucleoprotein complex can be delivered via one or more lipid nanoparticles.

In some embodiments, the components (a), (b) and (c) are delivered to the cell as one or more RNA molecules, such as one or more guide RNAs and one or more mRNA molecules encoding the CRISPR-Cas protein, the cytidine deaminase protein, and optionally the adaptor protein. The RNA molecules can be delivered via one or more lipid nanoparticles.

In some embodiments, the components (a), (b) and (c) are delivered to the cell as one or more DNA molecules. In some embodiments, the one or more DNA molecules are comprised within one or more vectors such as viral vectors (e.g., AAV). In some embodiments, the one or more DNA molecules comprise one or more regulatory elements operably configured to express the CRISPR-Cas protein, the guide molecule, and the cytidine deaminase protein or catalytic domain thereof, optionally wherein the one or more regulatory elements comprise inducible promoters. For application in eukaryotic cells, the Cpf1 protein and/or the cytidine deaminase are preferably NLS-tagged.

In some embodiments, the CRISPR-Cas protein is a Cpf1 nickase. In some embodiments, the Cpf1 nickase is capable of nicking a non-targeted DNA strand at the target locus of interest displaced by the formation of the heteroduplex between the targeted DNA strand and the guide molecule. In some embodiments, the Cpf1 nickase comprises a mutation in the Nuc domain. Details on the aspect of the CRISPR-Cas protein in the CD-functionalized CRISPR-Cas system are provided herein elsewhere.

In some embodiments, the Cpf1 nickase comprises a mutation corresponding to R1226A in AsCpf1.

In some embodiments, the CRISPR-Cas protein is a dead Cpf1. In some embodiments, the dead Cpf1 comprises a mutation in the RuvC domain. In some embodiments, the dead Cpf1 comprises a mutation corresponding to D908A or E993A in AsCpf1.

In some embodiments of the guide molecule is capable of hybridizing with a target sequence comprising the C to be deaminated within a first DNA strand at the target locus to form a heteroduplex which comprises a non-pairing A or U opposite to said C, optionally within a stretch of up to 5, 6, 7 or 8 mismatching nucleotides. Upon heteroduplex formation, the guide molecule forms a complex with the Cpf1 protein and directs the complex to bind said first DNA strand at the target locus of interest, allowing the targeted C to be deaminased by the CD. Details on the aspect of the guide of the CD-functionalized CRISPR-Cas system are provided herein below.

In some embodiments, a Cpf1 guide RNA having a canonical length (e.g., about 24 nt for AsCpf1) is used to form a heteroduplex with the target DNA. In some embodiments, a Cpf1 guide molecule longer than the canonical length (e.g., >24 nt for AsCpf1) is used to form a heteroduplex with the target DNA including outside of the Cpf1-guide RNA-target DNA complex. In certain example embodiments, the guide sequence has a length of about 20-53 nt, or about 25-53 nt, or about 29-53 nt capable of forming a DNA-RNA duplex with said target sequence. In certain other example embodiments, the guide sequence has a length of about 40-50 nt capable of forming a DNA-RNA duplex with said target sequence. In certain example embodiments, the distance between said non-pairing C and the 5' end of said guide sequence is 20-30 nucleotides. In certain example embodiments, the distance between said non-pairing C and the 3' end of said guide sequence is 20-30 nucleotides. In particular embodiments, the guide sequence comprises more than one mismatch corresponding to different adenosine sites in the target DNA sequence or wherein two guide molecules are used, each comprising a mismatch corresponding to a different adenosine sites in the target RNA sequence.

In at least a first design, the CD-functionalized CRISPR system comprises (a) a cytidine deaminase fused or linked to a CRISPR-Cas protein, wherein the CRISPR-Cas protein is catalytically inactive or a nickase, and (b) a guide molecule comprising a guide sequence designed to introduce a C-A/U mismatch in a heteroduplex formed between the guide sequence and the target sequence. In some embodiments, the CRISPR-Cas protein and/or the cytidine deaminase are NLS-tagged, on either the N- or C-terminus or both.

In at least a second design, the CD-functionalized CRISPR system comprises (a) a CRISPR-Cas protein that is catalytically inactive or a nickase, (b) a guide molecule comprising a guide sequence designed to introduce a C-A/U mismatch in a heteroduplex formed between the guide sequence and the target sequence, and an aptamer sequence (e.g., MS2 RNA motif or PP7 RNA motif) capable of binding to an adaptor protein (e.g., MS2 coating protein or PP7 coat protein), and (c) a cytidine deaminase fused or linked to an adaptor protein, wherein the binding of the aptamer and the adaptor protein recruits the cytidine deaminase to the heteroduplex formed between the guide sequence and the target sequence for targeted deamination at the C of the C-A/U mismatch. In some embodiments, the adaptor protein and/or the cytidine deaminase are NLS-tagged, on either the N- or C-terminus or both. The CRISPR-Cas protein can also be NLS-tagged.

The use of different aptamers and corresponding adaptor proteins also allows orthogonal gene editing to be implemented. In one example in which cytidine deaminase are used in combination with adenosine deaminase for orthogonal gene editing/deamination, sgRNA targeting different loci are modified with distinct RNA loops in order to recruit MS2-adenosine deaminase and PP7-cytidine deaminase (or PP7-adenosine deaminase and MS2-cytidine deaminase), respectively, resulting in orthogonal deamination of A or C at the target loci of interested, respectively. PP7 is the RNA-binding coat protein of the bacteriophage *Pseudomonas*. Like MS2, it binds a specific RNA sequence and secondary structure. The PP7 RNA-recognition motif is distinct from that of MS2. Consequently, PP7 and MS2 can be multiplexed to mediate distinct effects at different genomic loci simultaneously. For example, an sgRNA targeting locus A can be modified with MS2 loops, recruiting MS2-cytidine deaminase, while another sgRNA targeting locus B can be modified with PP7 loops, recruiting PP7-adenosine deaminase. In the same cell, orthogonal, locus-specific modifications are thus realized. This principle can be extended to incorporate other orthogonal RNA-binding proteins.

In at least a third design, the CD-functionalized CRISPR system comprises (a) a cytidine deaminase inserted into an internal loop or unstructured region of a CRISPR-Cas protein, wherein the CRISPR-Cas protein is catalytically inactive or a nickase, and (b) a guide molecule comprising a guide sequence designed to introduce a C-A/U mismatch in a heteroduplex formed between the guide sequence and the target sequence.

CRISPR-Cas protein split sites that are suitable for insertion of cytidine deaminase can be identified with the help of a crystal structure. One can use the crystal structure of an ortholog if a relatively high degree of homology exists between the ortholog and the intended CRISPR-Cas protein.

The split position may be located within a region or loop. Preferably, the split position occurs where an interruption of the amino acid sequence does not result in the partial or full destruction of a structural feature (e.g. alpha-helixes or β-sheets). Unstructured regions (regions that did not show up in the crystal structure because these regions are not structured enough to be "frozen" in a crystal) are often preferred options. The positions within the unstructured regions or outside loops may not need to be exactly the numbers provided above, but may vary by, for example 1, 2, 3, 4, 5, 6, 7, 8, 9, or even 10 amino acids either side of the position given above, depending on the size of the loop, so long as the split position still falls within an unstructured region of outside loop.

For Cpf1, several small stretches of unstructured regions have been predicted within the Cpf1 primary structure (see WO2016205711, the content of which is hereby incorporated by reference). Unstructured regions, which are exposed to the solvent and not conserved within different Cpf1 orthologs, are preferred sides for splits.

The following table presents non-limiting potential split regions within AsCpf1 and LbCpf1. A split site within such a region may be opportune.

| Split region | AsCpf1 | LbCpf1 |
|---|---|---|
| 1 | 575-588 | 566-571 |
| 2 | 631-645 | 754-757 |
| 3 | 653-664 | — |
| 4 | 818-844 | — |

For Fn, As and Lb Cpf1 mutants, it should be readily apparent what the corresponding position for a potential split site is, for example, based on a sequence alignment. For non-Fn, As and Lb enzymes one can use the crystal structure of an ortholog if a relatively high degree of homology exists between the ortholog and the intended Cpf1, or one can use computational prediction.

The CD-functionalized CRISPR system described herein can be used to target a specific Cytosine within a DNA sequence for deamination. For example, the guide molecule can form a complex with the CRISPR-Cas protein and directs the complex to bind a target sequence at the target locus of interest. Because the guide sequence is designed to have a non-pairing A or U with the Cytosine of interest, which in particular embodiments is extended to a stretch of non-pairing nucleotides, the heteroduplex formed between the guide sequence and the target sequence comprises a region of single strand DNA, which directs the cytidine deaminase to contact and deaminate the C opposite to the non-pairing A or U, converting it to an Uracil (U). Since Uracil (U) base pairs with A and functions like T in cellular process, the targeted deamination of C described herein are useful for correction of undesirable T-C and A-G mutations, as well as for obtaining desirable G-A and C-T mutations. Alternatively, the guide sequence can be designed to be upstream or downstream of the Cytosine of interest, allowing the DNA-RNA duplex to form upstream or downstream of the Cytosine of interesting, such that the cytidine deaminase can contact and deaminate the C in a region of single strand DNA outside the DNA-RNA duplex.

The use of a Cpf1 nickase that nicks the non-targeted DNA strand is particularly advantageous. Subsequent to the deamination of the targeted C, the U:G mismatch obtained can be processed by mismatch repair mechanisms, which preferentially repair the nicked strand of a mismatch. The nick (single-strand DNA break) made by the Cpf1 nickase on the non-targeted DNA strand containing the mismatched G facilitates removal of the mismatched G via mismatch repair mechanisms, leading to conversion of the U:G mismatch to the desired U:A or T:A outcome (i.e., a G to A change on the non-targeted DNA strand).

In addition to facilitating the aforementioned G to A change on the non-targeted DNA strand, the Cpf1 nickase can also facilitate repair of unintended deamination of C on the non-targeted DNA strand. Without being bound by limitation, in some embodiments, the CD-functionalized CRISPR system described herein may cause unintended deamination of at least one C on the non-targeted DNA strand, when the non-targeted DNA strand is displaced by the binding of the Cpf1-guide complex with the targeted DNA strand, and it is believed that nicking of the non-targeted DNA strand by the Cpf1 nickase will facilitate repair of such unintended deamination by mismatch repair mechanisms, which preferentially repair the nicked strand of a mismatch.

In some embodiments, the CD-functionalized CRISPR system is used for targeted deamination in a DNA molecule in vitro. In some embodiments, the CD-functionalized CRISPR system is used for targeted deamination in a DNA molecule within a cell. The cell can be a eukaryotic cell, such as a animal cell, a mammalian cell, a human, or a plant cell.

The invention also relates to a method for treating or preventing a disease by the targeted deamination using the CD-functionalized CRISPR system, wherein the deamination of the C restores a healthy genotype at the target locus of interest, which remedies a disease caused by a T→C or A→G point mutation or a pathogenic SNP.

The invention also relates to a method for knocking-out or knocking-down an undesirable activity of a gene or regulatory element thereof, wherein the deamination of the Cytosine at the target locus of interest inactivates a target gene or a target regulatory element at the target locus. For example, in one embodiment, the targeted deamination by the CD-functionalized CRISPR system can cause a nonsense mutation resulting in a premature stop codon in an endogenous gene. This may alter the expression of the endogenous gene and can lead to a desirable trait in the edited cell. In another embodiment, the targeted deamination by the CD-functionalized CRISPR system can cause a nonconservative missense mutation resulting in a code for a different amino acid residue in an endogenous gene. This may alter the function of the endogenous gene expressed and can also lead to a desirable trait in the edited cell.

The invention also relates to a modified cell obtained by the targeted deamination using the CD-functionalized CRISPR system, or progeny thereof, wherein the modified cell comprises an U or T in replace of the C in the target locus of interest compared to a corresponding cell before the targeted deamination. The modified cell can be a eukaryotic cell, such as an animal cell, a plant cell, a mammalian cell, or a human cell.

In some embodiments, the modified cell is a therapeutic T cell, such as a T cell suitable for CAR-T therapies. The modification may result in one or more desirable traits in the therapeutic T cell, including but not limited to, reduced expression of an immune checkpoint receptor (e.g., PDA, CTLA4), reduced expression of HLA proteins (e.g., B2M, HLA-A), and reduced expression of an endogenous TCR.

In some embodiments, the modified cell is an antibody-producing B cell. The modification may results in one or more desirable traits in the B cell, including but not limited to, enhanced antibody production.

The invention also relates to a modified non-human animal or a modified plant. The modified non-human animal can be a farm animal. The modified plant can be an agricultural crop.

The invention further relates to a method for cell therapy, comprising administering to a patient in need thereof the modified cell described herein, wherein the presence of the modified cell remedies a disease in the patient. In one embodiment, the modified cell for cell therapy is a CAR-T cell capable of recognizing and/or attacking a tumor cell. In another embodiment, the modified cell for cell therapy is a stem cell, such as a neural stem cell, a mesenchymal stem cell, a hematopoietic stem cell, or an iPSC cell.

The invention additionally relates to an engineered, non-naturally occurring system suitable for modifying an Cytosine in a target locus of interest, comprising: a guide molecule which comprises a guide sequence, or a nucleotide sequence encoding the guide molecule; a CRISPR-Cas protein, or one or more nucleotide sequences encoding the CRISPR-Cas protein; a cytidine deaminase protein or catalytic domain thereof, or one or more nucleotide sequences encoding; wherein the cytidine deaminase protein or catalytic domain thereof is covalently or non-covalently linked to the CRISPR-Cas protein or the guide molecule or is adapted to link thereto after delivery; wherein the guide sequence is capable of hybridizing with a target sequence comprising an Cytosine within the target locus, but comprises a Adenine or Uracil at the position corresponding to the Cytosine.

The invention additionally relates to an engineered, non-naturally occurring vector system suitable for modifying an Cytosine in a target locus of interest, comprising one or more vectors comprising: a first regulatory element operably linked to one or more nucleotide sequences encoding a guide molecule which comprises a guide sequence; a second regulatory element operably linked to a nucleotide sequence encoding a CRISPR-Cas protein; and optionally a nucleotide sequence encoding a cytidine deaminase protein or catalytic domain thereof which is under control of the first or second regulatory element or operably linked to a third regulatory element; wherein, if the nucleotide sequence encoding a cytidine deaminase protein or catalytic domain thereof is operably linked to a third regulatory element, the cytidine deaminase protein or catalytic domain thereof is adapted to link to the guide molecule or the Crispr-Cas protein after expression; wherein the guide sequence is capable of hybridizing with a target sequence comprising an Cytosine within the target locus, but comprises an Adenine or a Uracil at the position corresponding to the Cytosine; wherein components (a), (b) and (c) are located on the same or different vectors of the system.

The invention additionally relates to in vitro, ex vivo or in vivo host cell or cell line or progeny thereof comprising the engineered, non-naturally occurring system or vector system described herein. The host cell can be a eukaryotic cell, such as an animal cell, a plant cell, a mammalian cell, or a human cell.

Cytidine Deaminase

The term "cytidine deaminase" or "cytidine deaminase protein" as used herein refers to a protein, a polypeptide, or one or more functional domain(s) of a protein or a polypeptide that is capable of catalyzing a hydrolytic deamination reaction that converts an cytosine (or an cytosine moiety of a molecule) to an uracil (or a uracil moiety of a molecule), as shown below. In some embodiments, the cytosine-containing molecule is an cytidine (C), and the uracil-containing molecule is an uridine (U). The cytosine-containing molecule can be deoxyribonucleic acid (DNA) or ribonucleic acid (RNA).

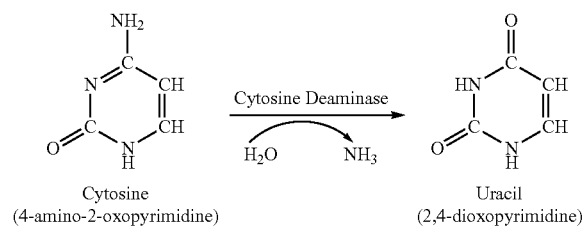

Cytosine
(4-amino-2-oxopyrimidine)

Uracil
(2,4-dioxopyrimidine)

According to the present disclosure, cytidine deaminases that can be used in connection with the present disclosure include, but are not limited to, members of the enzyme family known as apolipoprotein B mRNA-editing complex (APOBEC) family deaminase, an activation-induced deaminase (AID), or a cytidine deaminase 1 (CDA1). In particular embodiments, the deaminase in an APOBEC1 deaminase, an APOBEC2 deaminase, an APOBEC3A deaminase, an APOBEC3B deaminase, an APOBEC3C deaminase, and APOBEC3D deaminase, an APOBEC3E deaminase, an APOBEC3F deaminase an APOBEC3G deaminase, an APOBEC3H deaminase, or an APOBEC4 deaminase.

In the methods and systems of the present invention, the cytidine deaminase is capable of targeting Cytosine in a DNA single strand. In certain example embodiments the cytidine deaminase may edit on a single strand present outside of the binding component e.g. bound Cas13. In other example embodiments, the cytidine deaminase may edit at a localized bubble, such as a localized bubble formed by a mismatch at the target edit site but the guide sequence. In certain example embodiments the cytidine deaminase may contain mutations that help focus the area of activity such as those disclosed in Kim et al., Nature Biotechnology (2017) 35(4):371-377 (doi:10.1038/nbt.3803).

In some embodiments, the cytidine deaminase is derived from one or more metazoa species, including but not limited to, mammals, birds, frogs, squids, fish, flies and worms. In some embodiments, the cytidine deaminase is a human, primate, cow, dog rat or mouse cytidine deaminase.

In some embodiments, the cytidine deaminase is a human APOBEC, including hAPOBEC1 or hAPOBEC3. In some embodiments, the cytidine deaminase is a human AID.

In some embodiments, the cytidine deaminase protein recognizes and converts one or more target cytosine residue(s) in a single-stranded bubble of a DNA-RNA heteroduplex into uracil residues (s). In some embodiments, the cytidine deaminase protein recognizes a binding window on the single-stranded bubble of a DNA-RNA heteroduplex. In some embodiments, the binding window contains at least one target cytosine residue(s). In some embodiments, the binding window is in the range of about 3 bp to about 100 bp. In some embodiments, the binding window is in the range of about 5 bp to about 50 bp. In some embodiments, the binding window is in the range of about 10 bp to about 30 bp. In some embodiments, the binding window is about 1 bp, 2 bp, 3 bp, 5 bp, 7 bp, 10 bp, 15 bp, 20 bp, 25 bp, 30 bp, 40 bp, 45 bp, 50 bp, 55 bp, 60 bp, 65 bp, 70 bp, 75 bp, 80 bp, 85 bp, 90 bp, 95 bp, or 100 bp.

In some embodiments, the cytidine deaminase protein comprises one or more deaminase domains. Not intended to be bound by theory, it is contemplated that the deaminase domain functions to recognize and convert one or more target cytosine (C) residue(s) contained in a single-stranded bubble of a DNA-RNA heteroduplex into (an) uracil (U) residue (s). In some embodiments, the deaminase domain comprises an active center. In some embodiments, the active center comprises a zinc ion. In some embodiments, amino acid residues in or near the active center interact with one or more nucleotide(s) 5' to a target cytosine residue. In some embodiments, amino acid residues in or near the active center interact with one or more nucleotide(s) 3' to a target cytosine residue.

In some embodiments, the cytidine deaminase comprises human APOBEC1 full protein (hAPOBEC1) or the deaminase domain thereof (hAPOBEC1-D) or a C-terminally truncated version thereof (hAPOBEC-T). In some embodiments, the cytidine deaminase is an APOBEC family member that is homologous to hAPOBEC1, hAPOBEC-D or hAPOBEC-T. In some embodiments, the cytidine deaminase comprises human AID1 full protein (hAID) or the deaminase domain thereof (hAID-D) or a C-terminally truncated version thereof (hAID-T). In some embodiments, the cytidine deaminase is an AID family member that is homologous to hAID, hAID-D or hAID-T. In some embodiments, the hAID-T is a hAID which is C-terminally truncated by about 20 amino acids.

In some embodiments, the cytidine deaminase comprises the wild-type amino acid sequence of a cytosine deaminase. In some embodiments, the cytidine deaminase comprises one or more mutations in the cytosine deaminase sequence, such that the editing efficiency, and/or substrate editing preference of the cytosine deaminase is changed according to specific needs.

Certain mutations of APOBEC1 and APOBEC3 proteins have been described in Kim et al., Nature Biotechnology (2017) 35(4):371-377 (doi:10.1038/nbt.3803); and Harris et al. Mol. Cell (2002) 10:1247-1253, each of which is incorporated herein by reference in its entirety.

In some embodiments, the cytidine deaminase is an APOBEC1 deaminase comprising one or more mutations at amino acid positions corresponding to W90, R118, H121, H122, R126, or R132 in rat APOBEC1, or an APOBEC3G deaminase comprising one or more mutations at amino acid positions corresponding to W285, R313, D316, D317X, R320, or R326 in human APOBEC3G.

In some embodiments, the cytidine deaminase comprises a mutation at tryptophan$^{90}$ of the rat APOBEC1 amino acid sequence, or a corresponding position in a homologous APOBEC protein, such as tryptophan$^{285}$ of APOBEC3G. In some embodiments, the tryptophan residue at position 90 is replaced by an tyrosine or phenylalanine residue (W90Y or W90F).

In some embodiments, the cytidine deaminase comprises a mutation at Arginine$^{118}$ of the rat APOBEC1 amino acid sequence, or a corresponding position in a homologous APOBEC protein. In some embodiments, the arginine residue at position 118 is replaced by an alanine residue (R118A).

In some embodiments, the cytidine deaminase comprises a mutation at Histidine[121] of the rat APOBEC1 amino acid sequence, or a corresponding position in a homologous APOBEC protein. In some embodiments, the histidine residue at position 121 is replaced by an arginine residue (H121R).

In some embodiments, the cytidine deaminase comprises a mutation at Histidine[122] of the rat APOBEC1 amino acid sequence, or a corresponding position in a homologous APOBEC protein. In some embodiments, the histidine residue at position 122 is replaced by an arginine residue (H122R).

In some embodiments, the cytidine deaminase comprises a mutation at Arginine[126] of the rat APOBEC1 amino acid sequence, or a corresponding position in a homologous APOBEC protein, such as Arginine[320] of APOBEC3G. In some embodiments, the arginine residue at position 126 is replaced by an alanine residue (R126A) or by a glutamic acid (R126E).

In some embodiments, the cytidine deaminase comprises a mutation at arginine[132] of the APOBEC1 amino acid sequence, or a corresponding position in a homologous APOBEC protein. In some embodiments, the arginine residue at position 132 is replaced by a glutamic acid residue (R132E).

In some embodiments, to narrow the width of the editing window, the cytidine deaminase may comprise one or more of the mutations: W90Y, W90F, R126E and R132E, based on amino acid sequence positions of rat APOBEC1, and mutations in a homologous APOBEC protein corresponding to the above.

In some embodiments, to reduce editing efficiency, the cytidine deaminase may comprise one or more of the mutations: W90A, R118A, R132E, based on amino acid sequence positions of rat APOBEC1, and mutations in a homologous APOBEC protein corresponding to the above. In particular embodiments, it can be of interest to use a cytidine deaminase enzyme with reduced efficacy to reduce off-target effects.

In some embodiments, the cytidine deaminase is wild-type rat APOBEC1 (rAPOBEC1, SEQ ID NO:29) or a catalytic domain thereof. In some embodiments, the cytidine deaminase comprises one or more mutations in the rAPOBEC1 sequence, such that the editing efficiency, and/or substrate editing preference of rAPOBEC1 is changed according to specific needs.

rAPOBEC1:
(SEQ ID NO: 29)
MSSETGPVAVDPTLRRRIEPHEFEVFFDPRELRKETCLLYEINWGGRH

SIWRHTSQNTNKHVEVNFIEKFTTERYFCPNTRCSITWFLSWSPCGEC

SRAITEFLSRYPHVTLFIYIARLYHHADPRNRQGLRDLISSGVTIQIM

TEQESGYCWRNFVNYSPSNEAHWPRYPHLWVRLYVLELYCIILGLPPC

LNILRRKQPQLTFFTIALQSCHYQRLPPHILWATGLK

In some embodiments, the cytidine deaminase is wild-type human APOBEC1 (hAPOBEC1, SEQ ID NO:30) or a catalytic domain thereof. In some embodiments, the cytidine deaminase comprises one or more mutations in the hAPOBEC1 sequence, such that the editing efficiency, and/or substrate editing preference of hAPOBEC1 is changed according to specific needs.

hAPOBEC1:
(SEQ ID NO: 30)
MTSEKGPSTGDPTLRRRIEPWEFDVFYDPRELRKEACLLYEIKWGMSR

KIWRSSGKNTTNHVEVNFIKKFTSERDFHPSMSCSITWFLSWSPCWEC

SQAIREFLSRHPGVTLVIYVARLFWHMDQQNRQGLRDLVNSGVTIQIM

RASEYYHCWRNFVNYPPGDEAHWPQYPPLWMMLYALELHCIILSLPPC

LKISRRWQNHLTFFRLHLQNCHYQTIPPHILLATGLIHPSVAWR

In some embodiments, the cytidine deaminase is wild-type human APOBEC3G (hAPOBEC3G, SEQ ID NO:31) or a catalytic domain thereof. In some embodiments, the cytidine deaminase comprises one or more mutations in the hAPOBEC3G sequence, such that the editing efficiency, and/or substrate editing preference of hAPOBEC3G is changed according to specific needs.

hAPOBEC3G:

hAPOBEC3G:
(SEQ ID NO: 31)
MELKYHPEMRFFHWFSKWRKLHRDQEYEVTWYISWSPCTKCTRDMATF

LAEDPKVTLTIFVARLYYFWDPDYQEALRSLCQKRDGPRATMKIMNYD

EFQHCWSKFVYSQRELFEPWNNLPKYYILLHIMLGEILRHSMDPPTFT

FNFNNEPWVRGRHETYLCYEVERMHNDTWVLLNQRRGFLCNQAPHKHG

FLEGRHAELCFLDVIPFWKLDLDQDYRVTCFTSWSPCFSCAQEMAKFI

SKNKHVSLCIFTARIYDDQGRCQEGLRTLAEAGAKISIMTYSEFKHCW

DTFVDHQGCPFQPWDGLDEHSQDLSGRLRAILQNQEN

In some embodiments, the cytidine deaminase is wild-type *Petromyzon marinus* CDA1 (pmCDA1, SEQ ID NO:32) or a catalytic domain thereof. In some embodiments, the cytidine deaminase comprises one or more mutations in the pmCDA1 sequence, such that the editing efficiency, and/or substrate editing preference of pmCDA1 is changed according to specific needs.

pmCDA1:
(SEQ ID NO: 32)
MTDAEYVRIHEKLDIYTFKKQFFNNKKSVSHRCYVLFELKRRGERRAC

FWGYAVNKPQSGTERGIHAEIFSIRKVEEYLRDNPGQFTINWYSSWSP

CADCAEKILEWYNQELRGNGHTLKIWACKLYYEKNARNQIGLWNLRDN

GVGLNVMVSEHYQCCRKIFIQSSHNQLNENRWLEKTLKRAEKRRSELS

IMIQVKILHTTKSPAV

In some embodiments, the cytidine deaminase is wild-type human AID (hAID, SEQ ID NO:33) or a catalytic domain thereof. In some embodiments, the cytidine deaminase comprises one or more mutations in the pmCDA1 sequence, such that the editing efficiency, and/or substrate editing preference of pmCDA1 is changed according to specific needs.

hAID:

(SEQ ID NO: 33)
MDSLLMNRRKFLYQFKNVRWAKGRRETYLCYVVKRRDSATSFSLDFGY

LRNKNGCHVELLFLRYISDWDLDPGRCYRVTWFTSWSPCYDCARHVAD

FLRGNPYLSLRIFTARLYFCEDRKAEPEGLRRLHRAGVQIAIMTFKDY

FYCWNTFVENHERTFKAWEGLHENSVRLSRQLRRILLPLYEVDDLRDA

FRTLGLLD

In some embodiments, the cytidine deaminase is truncated version of hAID (hAID-DC, SEQ ID NO:34) or a catalytic domain thereof. In some embodiments, the cytidine deaminase comprises one or more mutations in the hAID-DC sequence, such that the editing efficiency, and/or substrate editing preference of hAID-DC is changed according to specific needs.

hAID-DC:

(SEQ ID NO: 34)
MDSLLMNRRKFLYQFKNVRWAKGRRETYLCYVVKRRDSATSFSLDFGY

LRNKNGCHVELLFLRYISDWDLDPGRCYRVTWFTSWSPCYDCARHVAD

FLRGNPNLSLRIFTARLYFCEDRKAEPEGLRRLHRAGVQIAIMTFKDY

FYCWNTFVENHERTFKAWEGLHENSVRLSRQLRRILL

Additional embodiments of the cytidine deaminase are disclosed in WO WO2017/070632, titled "Nucleobase Editor and Uses Thereof," which is incorporated herein by reference in its entirety.

In some embodiments, the cytidine deaminase has an efficient deamination window that encloses the nucleotides susceptible to deamination editing. Accordingly, in some embodiments, the "editing window width" refers to the number of nucleotide positions at a given target site for which editing efficiency of the cytidine deaminase exceeds the half-maximal value for that target site. In some embodiments, the cytidine deaminase has an editing window width in the range of about 1 to about 6 nucleotides. In some embodiments, the editing window width of the cytidine deaminase is 1, 2, 3, 4, 5, or 6 nucleotides.

Not intended to be bound by theory, it is contemplated that in some embodiments, the length of the linker sequence affects the editing window width. In some embodiments, the editing window width increases (e.g., from about 3 to about 6 nucleotides) as the linker length extends (e.g., from about 3 to about 21 amino acids). In a non-limiting example, a 16-residue linker offers an efficient deamination window of about 5 nucleotides. In some embodiments, the length of the guide RNA affects the editing window width. In some embodiments, shortening the guide RNA leads to a narrowed efficient deamination window of the cytidine deaminase.

In some embodiments, mutations to the cytidine deaminase affect the editing window width. In some embodiments, the cytidine deaminase component of the CD-functionalized CRISPR system comprises one or more mutations that reduce the catalytic efficiency of the cytidine deaminase, such that the deaminase is prevented from deamination of multiple cytidines per DNA binding event. In some embodiments, tryptophan at residue 90 (W90) of APOBEC1 or a corresponding tryptophan residue in a homologous sequence is mutated. In some embodiments, the Cpf1 nickase is fused to or linked to an APOBEC1 mutant that comprises a W90Y or W90F mutation. In some embodiments, tryptophan at residue 285 (W285) of APOBEC3G, or a corresponding tryptophan residue in a homologous sequence is mutated. In some embodiments, the Cpf1 nickase is fused to or linked to an APOBEC3G mutant that comprises a W285Y or W285F mutation.

In some embodiments, the cytidine deaminase component of CD-functionalized CRISPR system comprises one or more mutations that reduce tolerance for non-optimal presentation of a cytidine to the deaminase active site. In some embodiments, the cytidine deaminase comprises one or more mutations that alter substrate binding activity of the deaminase active site. In some embodiments, the cytidine deaminase comprises one or more mutations that alter the conformation of DNA to be recognized and bound by the deaminase active site. In some embodiments, the cytidine deaminase comprises one or more mutations that alter the substrate accessibility to the deaminase active site. In some embodiments, arginine at residue 126 (R126) of APOBEC1 or a corresponding arginine residue in a homologous sequence is mutated. In some embodiments, the Cpf1 nickase is fused to or linked to an APOBEC1 that comprises a R126A or R126E mutation. In some embodiments, tryptophan at residue 320 (R320) of APOBEC3G, or a corresponding arginine residue in a homologous sequence is mutated. In some embodiments, the Cpf1 nickase is fused to or linked to an APOBEC3G mutant that comprises a R320A or R320E mutation. In some embodiments, arginine at residue 132 (R132) of APOBEC1 or a corresponding arginine residue in a homologous sequence is mutated. In some embodiments, the Cpf1 nickase is fused to or linked to an APOBEC1 mutant that comprises a R132E mutation.

In some embodiments, the APOBEC1 domain of the CD-functionalized CRISPR system comprises one, two, or three mutations selected from W90Y, W90F, R126A, R126E, and R132E. In some embodiments, the APOBEC1 domain comprises double mutations of W90Y and R126E. In some embodiments, the APOBEC1 domain comprises double mutations of W90Y and R132E. In some embodiments, the APOBEC1 domain comprises double mutations of R126E and R132E. In some embodiments, the APOBEC1 domain comprises three mutations of W90Y, R126E and R132E.

In some embodiments, one or more mutations in the cytidine deaminase as disclosed herein reduce the editing window width to about 2 nucleotides. In some embodiments, one or more mutations in the cytidine deaminase as disclosed herein reduce the editing window width to about 1 nucleotide. In some embodiments, one or more mutations in the cytidine deaminase as disclosed herein reduce the editing window width while only minimally or modestly affecting the editing efficiency of the enzyme. In some embodiments, one or more mutations in the cytidine deaminase as disclosed herein reduce the editing window width without reducing the editing efficiency of the enzyme. In some embodiments, one or more mutations in the cytidine deaminase as disclosed herein enable discrimination of neighboring cytidine nucleotides, which would be otherwise edited with similar efficiency by the cytidine deaminase.

In some embodiments, the cytidine deaminase protein further comprises or is connected to one or more double-stranded RNA (dsRNA) binding motifs (dsRBMs) or domains (dsRBDs) for recognizing and binding to double-stranded nucleic acid substrates. In some embodiments, the interaction between the cytidine deaminase and the substrate is mediated by one or more additional protein factor(s), including a CRISPR/CAS protein factor. In some embodiments, the interaction between the cytidine deaminase and the substrate is further mediated by one or more nucleic acid component(s), including a guide RNA.

According to the present invention, the substrate of the cytidine deaminase is an DNA single strand bubble of a DNA-RNA heteroduplex comprising a Cytosine of interest, made accessible to the cytidine deaminase upon binding of the guide molecule to its DNA target which then forms the CRISPR-Cas complex with the CRISPR-Cas enzyme, whereby the cytosine deaminase is fused to or is capable of binding to one or more components of the CRISPR-Cas complex, i.e. the CRISPR-Cas enzyme and/or the guide molecule. The particular features of the guide molecule and CRISPR-Cas enzyme are detailed below.

CRISPR-Cas Protein and Guide

In the methods and systems of the present invention use is made of a CRISPR-Cas protein and corresponding guide molecule. More particularly, the CRISPR-Cas protein is a class 2 CRISPR-Cas protein. In certain embodiments, said CRISPR-Cas protein Cpf1. The CRISPR-Cas system does not require the generation of customized proteins to target specific sequences but rather a single Cas protein can be programmed by guide molecule to recognize a specific nucleic acid target, in other words the Cas enzyme protein can be recruited to a specific nucleic acid target locus of interest using said guide molecule.

Guide Molecule

The guide molecule or guide RNA of a Class 2 type V CRISPR-Cas protein comprises a tracr-mate sequence (encompassing a "direct repeat") and a guide sequence (also referred to as a "spacer" in the context of an endogenous CRISPR system). Indeed, in contrast to the type II CRISPR-Cas proteins, the CRISPR-Cas Cpf1 protein does not rely on the presence of a tracr sequence. In embodiments, the CRISPR-Cas system or complex as described herein does not comprise and/or does not rely on the presence of a tracr sequence (e.g. if the Cas protein is Cpf1). In certain embodiments, the guide molecule may comprise, consist essentially of, or consist of a direct repeat sequence fused or linked to a guide sequence or spacer sequence.

In general, a CRISPR system is characterized by elements that promote the formation of a CRISPR complex at the site of a target sequence. In the context of formation of a CRISPR complex, "target sequence" refers to a sequence to which a guide sequence is designed to have complementarity, where hybridization between a target DNA sequence and a guide sequence promotes the formation of a CRISPR complex.

The terms "guide molecule" and "guide RNA" are used interchangeably herein to refer to RNA-based molecules that are capable of forming a complex with a CRISPR-Cas protein and comprises a guide sequence having sufficient complementarity with a target nucleic acid sequence to hybridize with the target nucleic acid sequence and direct sequence-specific binding of the complex to the target nucleic acid sequence. The guide molecule or guide RNA specifically encompasses RNA-based molecules having one or more chemically modifications (e.g., by chemical linking two ribonucleotides or by replacement of one or more ribonucleotides with one or more deoxyribonucleotides), as described herein.

As used herein, the term "guide sequence" in the context of a CRISPR-Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. In the context of the present invention the target nucleic acid sequence or target sequence is the sequence comprising the target cytosine to be deaminated also referred to herein as the "target cytosine". In some embodiments, the degree of complementarity, when optimally aligned using a suitable alignment algorithm, is about or more than about 50%, 60%, 75%, 80%, 85%, 90%, 95%, 97.5%, 99%, or more. However, as detailed herein, preferably, given that the presence of at least one mismatch with the target sequence is provided. Indeed, in the context of the present invention the guide molecule comprises a guide sequence that is designed to have at least one mismatch with the target sequence, such that a heteroduplex formed between the guide sequence and the target sequence comprises a non-pairing A or U in the guide sequence opposite to the target C for deamination on the target sequence. Accordingly, the degree of complementarity is preferably less than 99%. For instance, where the guide sequence consists of 24 nucleotides, the degree of complementarity is more particularly about 96% or less. In particular embodiments, the guide sequence is designed to have a stretch of two or more adjacent mismatching nucleotides, such that the degree of complementarity over the entire guide sequence is further reduced. For instance, where the guide sequence consists of 24 nucleotides, the degree of complementarity is more particularly about 96% or less, more particularly, about 92% or less, more particularly about 88% or less, more particularly about 84% or less, more particularly about 80% or less, more particularly about 76% or less, more particularly about 72% or less, depending on whether the stretch of two or more mismatching nucleotides encompasses 2, 3, 4, 5, 6 or 7 nucleotides, etc. In some embodiments, aside from the stretch of one or more mismatching nucleotides, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence (or a sequence in the vicinity thereof) may be evaluated in a test tube by providing the target nucleic acid sequence, components of a nucleic acid-targeting complex, including the guide sequence to be tested and a control guide sequence different from the test guide sequence, and comparing binding or rate of cleavage at or in the vicinity of the target sequence between the test and control guide sequence reactions. Other assays are possible, and will occur to those skilled in the art. A guide sequence, and hence a nucleic acid-targeting guide RNA may be selected to target any target nucleic acid sequence.

In certain embodiments, the guide sequence or spacer length of the guide molecules is from 15 to 50 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer. In certain example embodiment, the guide sequence is 15, 16, 17, 18, 19, 20, 21, 22, 23, 24, 25, 26, 27, 28, 29, 30, 31, 32, 33, 34, 35, 36, 37, 38, 39 40, 41, 42, 43, 44, 45, 46, 47 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nt.

In some embodiments, the guide sequence is an RNA sequence of between 10 to 50 nt in length, but more particularly of about 20-30 nt advantageously about 20 nt, 23-25 nt or 24 nt. The guide sequence is selected so as to ensure that it hybridizes to the target sequence comprising the cytosine to be deaminated. This is described more in detail below. Selection can encompass further steps which increase efficacy and specificity of deamination.

In some embodiments, the C-U/A mismatch corresponding to the target site of interest is located close to the center of the target sequence and thus the center of the guide sequence, thereby restricting the cytidine deaminase to a narrow editing window (e.g., about 4 bp wide). In some embodiments, the target sequence may comprise more than one target cytosine to be deaminated. In further embodiments the target sequence may further comprise one or more cytosines to be deaminated 3' to the target cytosine site. In these embodiments, further C-U/A mismatches can be provided in the guide sequence. Depending on their location within the target sequence, these may be located within the same or a separate stretch of mismatching or non-pairing nucleotides in the guide sequence. In some embodiments, to avoid off-target editing, the target sequence does not have further mismatched cytosines within the target sequence.

In some embodiments, a Cpf1 guide sequence having a canonical length (e.g., about 24 nt for AsCpf1) is used to hybridize with the target DNA. In some embodiments, a Cpf1 guide molecule longer than the canonical length (e.g., >24 nt for AsCpf1) is used to hybridize with the target DNA, such that a region of the guide sequence hybridizes with a region of the DNA strand outside of the Cpf1-guide RNA-target DNA complex. This can be of interest where deamination of more than one cytosine within a given stretch of nucleotides is of interest. In alternative embodiments, it is of interest to maintain the limitation of the canonical guide sequence length. In some embodiments, the guide sequence is designed to introduce a C-U/A mismatch outside of the canonical length of Cpf1 guide, distant from the PAM sequence, which may decrease steric hindrance by Cpf1 and increase the frequency of contact between the cytidine deaminase and the C-U/A mismatch.

In some embodiments, the sequence of the guide molecule (direct repeat and/or spacer) is selected to reduce the degree secondary structure within the guide molecule. In some embodiments, about or less than about 75%, 50%, 40%, 30%, 25%, 20%, 15%, 10%, 5%, 1%, or fewer of the nucleotides of the nucleic acid-targeting guide RNA participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and PA Carr and GM Church, 2009, Nature Biotechnology 27(12): 1151-62).

In some embodiments, it is of interest to reduce the susceptibility of the guide molecule to RNA cleavage, such as to cleavage by Cpf1. Accordingly, in particular embodiments, the guide molecule is adjusted to avoid cleavage by Cpf1 or other RNA-cleaving enzymes.

In certain embodiments, the guide molecule comprises non-naturally occurring nucleic acids and/or non-naturally occurring nucleotides and/or nucleotide analogs, and/or chemically modifications. Preferably, these non-naturally occurring nucleic acids and non-naturally occurring nucleotides are located outside the guide sequence. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, or 2'-fluoro analogs. Further examples of modified bases include, but are not limited to, 2-aminopurine, 5-bromo-uridine, pseudouridine, inosine, 7-methylguanosine. Examples of guide RNA chemical modifications include, without limitation, incorporation of 2'-O-methyl (M), 2'-O-methyl 3'phosphorothioate (MS), S-constrained ethyl(cEt), or 2'-O-methyl 3'thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015 Ragdarm et al., 0215, *PNAS, E*7110-E7111; Allerson et al., *J. Med. Chem.* 2005, 48:901-904; Bramsen et al., *Front. Genet.*, 2012, 3:154; Deng et al., *PNAS*, 2015, 112:11870-11875; Sharma et al., *MedChemComm.*, 2014, 5:1454-1471; Hendel et al., *Nat. Biotechnol.* (2015) 33(9): 985-989; Li et al., *Nature Biomedical Engineering*, 2017, 1, 0066 DOI:10.1038/s41551-017-0066). In some embodiments, the 5' and/or 3' end of a guide RNA is modified by a variety of functional moieties including fluorescent dyes, polyethylene glycol, cholesterol, proteins, or detection tags. (See Kelly et al., 2016, *J. Biotech.* 233:74-83). In certain embodiments, a guide comprises ribonucleotides in a region that binds to a target DNA and one or more deoxyribonucleotides and/or nucleotide analogs in a region that binds to Cpf1. In an embodiment of the invention, deoxyribonucleotides and/or nucleotide analogs are incorporated in engineered guide structures, such as, without limitation, stem-loop regions, and the seed region. For Cpf1 guide, in certain embodiments, the modification is not in the 5'-handle of the stem-loop regions. Chemical modification in the 5'-handle of the stem-loop region of a guide may abolish its function (see Li, et al., *Nature Biomedical Engineering*, 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemicially modified with 2'-O-methyl (M), 2'-O-methyl 3' phosphorothioate (MS), S-constrained ethyl(cEt), or 2'-O-methyl 3' thioPACE (MSP). Such modification can enhance genome editing efficiency (see Hendel et al., *Nat. Biotechnol.* (2015) 33(9): 985-989). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemically modified with 2'-O-Me, 2'-F or S-constrained ethyl(cEt). Such chemically modified guide can mediate enhanced levels of gene disruption (see Ragdarm et al., 0215, *PNAS*, E7110-E7111). In an embodiment of the invention, a guide is modified to comprise a chemical moiety at its 3' and/or 5' end. Such moieties include, but are not limited to amine, azide, alkyne, thio, dibenzocyclooctyne (DBCO), or Rhodamine. In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., *eLife*, 2017, 6:e25312, DOI:10.7554).

In some embodiments, the guide comprises a modified Cpf1 crRNA, having a 5'-handle and a guide segment further comprising a seed region and a 3'-terminus. In some embodiments, the modified guide can be used with a Cpf1 of any one of *Acidaminococcus* sp. BV3L6 Cpf1 (AsCpf1); *Francisella tularensis* subsp. Novicida U112 Cpf1 (FnCpf1); *L. bacterium* MC2017 Cpf1 (Lb3Cpf1); *Butyrivibrio proteoclasticus* Cpf1 (BpCpf1); *Parcubacteria bacterium* GWC2011_GWC2_44_17 Cpf1 (PbCpf1); *Peregrinibacteria bacterium* GW2011_GWA_33_10 Cpf1 (PeCpf1); *Leptospira inadai* Cpf1 (LiCpf1); *Smithella* sp. SC_K08D17 Cpf1 (SsCpf1); *L. bacterium* MA2020 Cpf1 (Lb2Cpf1); *Porphyromonas crevioricanis* Cpf1 (PcCpf1); *Porphyromonas macacae* Cpf1 (PmCpf1); *Candidatus Methanoplasma termitum* Cpf1 (CMtCpf1); *Eubacterium eligens* Cpf1 (EeCpf1); *bovoculi* 237 Cpf1 (MbCpf1); *Prevotella disiens* Cpf1 (PdCpf1); or *L. bacterium* ND2006 Cpf1 (LbCpf1).

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromo-uridine, pseudouridine (Ψ), N1-methylpseudouridine (me1Ψ), 5-methoxyuridine (5moU), inosine, 7-methylguanosine, 2'-O-methyl 3'phosphorothioate (MS), S-constrained ethyl(cEt), phosphorothioate (PS), or 2'-O-methyl 3'thioPACE (MSP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In certain embodiments, one or more nucleotides in the seed region are chemically modified. In certain embodiments, one or more nucleotides in the 3'-terminus are chemically modified. In certain embodiments, none of the nucleotides in the 5'-handle is chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 to 10 nucleotides in the 3'-terminus are chemically modified. Such chemical modifications at the 3'-terminus of the Cpf1 CrRNA may improve Cpf1 activity (see Li, et al., Nature Biomedical Engineering, 2017, 1:0066). In a specific embodiment, 1, 2, 3, 4, 5, 6, 7, 8, 9 or 10 nucleotides in the 3'-terminus are replaced with 2'-fluoro analogues. In a specific embodiment, 1, 2, 3, 4, 5, 6, 7, 8, 9 or 10 nucleotides in the 3'-terminus are replaced with 2'-O-methyl (M) analogs.

In some embodiments, the loop of the 5'-handle of the guide is modified. In some embodiments, the loop of the 5'-handle of the guide is modified to have a deletion, an insertion, a split, or chemical modifications. In certain embodiments, the modified loop comprises 3, 4, or 5 nucleotides. In certain embodiments, the loop comprises the sequence of UCUU, UUUU, UAUU, or UGUU.

In some embodiments, the guide molecule forms a stem-loop with a separate non-covalently linked sequence, which can be DNA or RNA. In particular embodiments, the sequences forming the guide are first synthesized using the standard phosphoramidite synthetic protocol (Herdewijn, P., ed., Methods in Molecular Biology Col 288, Oligonucleotide Synthesis: Methods and Applications, Humana Press, New Jersey (2012)). In some embodiments, these sequences can be functionalized to contain an appropriate functional group for ligation using the standard protocol known in the art (Hermanson, G. T., Bioconjugate Techniques, Academic Press (2013)). Examples of functional groups include, but are not limited to, hydroxyl, amine, carboxylic acid, carboxylic acid halide, carboxylic acid active ester, aldehyde, carbonyl, chlorocarbonyl, imidazolylcarbonyl, hydrozide, semicarbazide, thio semicarbazide, thiol, maleimide, haloalkyl, sufonyl, ally, propargyl, diene, alkyne, and azide. Once this sequence is functionalized, a covalent chemical bond or linkage can be formed between this sequence and the direct repeat sequence. Examples of chemical bonds include, but are not limited to, those based on carbamates, ethers, esters, amides, imines, amidines, aminotriazines, hydrozone, disulfides, thioethers, thioesters, phosphorothioates, phosphorodithioates, sulfonamides, sulfonates, fulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, these stem-loop forming sequences can be chemically synthesized. In some embodiments, the chemical synthesis uses automated, solid-phase oligonucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

In certain embodiments, the guide molecule (capable of guiding Cpf1 to a target locus) comprises (1) a guide sequence capable of hybridizing to a target locus and (2) a tracr mate or direct repeat sequence whereby the direct repeat sequence is located upstream (i.e., 5') from the guide sequence. In a particular embodiment the seed sequence (i.e. the sequence essential critical for recognition and/or hybridization to the sequence at the target locus) of the Cpf1 guide sequence is approximately within the first 10 nucleotides of the guide sequence. In particular embodiments, the Cpf1 is FnCpf1 and the seed sequence is approximately within the first 5 nt on the 5' end of the guide sequence.

In a particular embodiment the guide molecule comprises a guide sequence linked to a direct repeat sequence, wherein the direct repeat sequence comprises one or more stem loops or optimized secondary structures. In particular embodiments, the direct repeat has a minimum length of 16 nts and a single stem loop. In further embodiments the direct repeat has a length longer than 16 nts, preferably more than 17 nts, and has more than one stem loops or optimized secondary structures. In particular embodiments the guide molecule comprises or consists of the guide sequence linked to all or part of the natural direct repeat sequence. A typical Type V Cpf1 guide molecule comprises (in 3' to 5' direction): a guide sequence a first complimentary stretch (the "repeat"), a loop (which is typically 4 or 5 nucleotides long), a second complimentary stretch (the "anti-repeat" being complimentary to the repeat), and a poly A (often poly U in RNA) tail (terminator). In certain embodiments, the direct repeat sequence retains its natural architecture and forms a single stem loop. In particular embodiments, certain aspects of the guide architecture can be modified, for example by addition, subtraction, or substitution of features, whereas certain other aspects of guide architecture are maintained. Preferred locations for engineered guide molecule modifications, including but not limited to insertions, deletions, and substitutions include guide termini and regions of the guide molecule that are exposed when complexed with the Cpf1 protein and/or target, for example the stemloop of the direct repeat sequence.

In particular embodiments, the stem comprises at least about 4 bp comprising complementary X and Y sequences, although stems of more, e.g., 5, 6, 7, 8, 9, 10, 11 or 12 or fewer, e.g., 3, 2, base pairs are also contemplated. Thus, for example X2-10 and Y2-10 (wherein X and Y represent any complementary set of nucleotides) may be contemplated. In one aspect, the stem made of the X and Y nucleotides, together with the loop will form a complete hairpin in the overall secondary structure; and, this may be advantageous and the amount of base pairs can be any amount that forms a complete hairpin. In one aspect, any complementary X:Y basepairing sequence (e.g., as to length) is tolerated, so long as the secondary structure of the entire guide molecule is preserved. In one aspect, the loop that connects the stem made of X:Y basepairs can be any sequence of the same length (e.g., 4 or 5 nucleotides) or longer that does not interrupt the overall secondary structure of the guide molecule. In one aspect, the stemloop can further comprise, e.g. an MS2 aptamer. In one aspect, the stem comprises about 5-7 bp comprising complementary X and Y sequences, although stems of more or fewer basepairs are also contemplated. In one aspect, non-Watson Crick basepairing is contemplated, where such pairing otherwise generally preserves the architecture of the stemloop at that position.

In particular embodiments the natural hairpin or stemloop structure of the guide molecule is extended or replaced by an extended stemloop. It has been demonstrated that extension of the stem can enhance the assembly of the guide molecule with the CRISPR-Cas protein (Chen et al. Cell. (2013); 155(7): 1479-1491). In particular embodiments the stem of the stemloop is extended by at least 1, 2, 3, 4, 5 or more complementary basepairs (i.e. corresponding to the addition of 2, 4, 6, 8, 10 or more nucleotides in the guide molecule). In particular embodiments these are located at the end of the stem, adjacent to the loop of the stemloop.

In particular embodiments, the susceptibility of the guide molecule to RNAses or to decreased expression can be reduced by slight modifications of the sequence of the guide molecule which do not affect its function. For instance, in particular embodiments, premature termination of transcription, such as premature transcription of U6 Pol-III, can be removed by modifying a putative Pol-III terminator (4 consecutive U's) in the guide molecules sequence. Where such sequence modification is required in the stemloop of the guide molecule, it is preferably ensured by a basepair flip.

In a particular embodiment the direct repeat may be modified to comprise one or more protein-binding RNA aptamers. In a particular embodiment, one or more aptamers may be included such as part of optimized secondary structure. Such aptamers may be capable of binding a bacteriophage coat protein as detailed further herein.

In some embodiments, the guide molecule forms a duplex with a target DNA strand comprising at least one target cytosine residue to be edited. Upon hybridization of the guide RNA molecule to the target DNA strand, the cytidine deaminase binds to the single DNA strand in the duplex made accessible by the mismatch in the guide sequence and catalyzes deamination of one or more target cytosine residues comprised within the stretch of mismatching nucleotides.

A guide sequence, and hence a nucleic acid-targeting guide RNA may be selected to target any target nucleic acid sequence. The target sequence may be DNA. The target sequence may be genomic DNA. The target sequence may be mitochondrial DNA.

In certain embodiments, the target sequence should be associated with a PAM (protospacer adjacent motif) or PFS (protospacer flanking sequence or site); that is, a short sequence recognized by the CRISPR complex. Depending on the nature of the CRISPR-Cas protein, the target sequence should be selected such that its complementary sequence in the DNA duplex (also referred to herein as the non-target sequence) is upstream or downstream of the PAM. In the embodiments of the present invention where the CRISPR-Cas protein is a Cpf1 protein, the complementary sequence of the target sequence is downstream or 3' of the PAM. The precise sequence and length requirements for the PAM differ depending on the Cpf1 protein used, but PAMs are typically 2-5 base pair sequences adjacent the protospacer (that is, the target sequence). Examples of the natural PAM sequences for different Cpf1 orthologues are provided herein below and the skilled person will be able to identify further PAM sequences for use with a given Cpf1 protein.

Further, engineering of the PAM Interacting (PI) domain may allow programing of PAM specificity, improve target site recognition fidelity, and increase the versatility of the CRISPR-Cas protein, for example as described for Cas9 in Kleinstiver BP et al. Engineered CRISPR-Cas9 nucleases with altered PAM specificities. Nature. 2015 Jul. 23; 523 (7561):481-5. doi: 10.1038/nature14592. As further detailed herein, the skilled person will understand that Cpf1 proteins may be modified analogously.

In particular embodiments, the guide sequence is selected in order to ensure optimal efficiency of the deaminase on the cytosine to be deaminated. The position of the cytosine in the target strand relative to the cleavage site of the Cpf1 nickase may be taken into account. In particular embodiments it is of interest to ensure that the nickase will act in the vicinity of the cytosine to be deaminated, on the non-target strand. For instance, in particular embodiments, the Cpf1 nickase cuts the non-targeting strand 17 nucleotides downstream of the PAM (e.g. AsCpf1, LbCpf1) or 18 nucleotides downstream of the PAM (e.g. FnCpf1), and it can be of interest to design the guide that the cytosine which is to correspond to the cytosine to be deaminated is located in the guide sequence within 10 bp upstream or downstream of the nickase cleavage site in the sequence of the corresponding non-target strand.

In particular embodiment, the guide is an escorted guide. By "escorted" is meant that the Cpf1 CRISPR-Cas system or complex or guide is delivered to a selected time or place within a cell, so that activity of the Cpf1 CRISPR-Cas system or complex or guide is spatially or temporally controlled. For example, the activity and destination of the Cpf1 CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time.

The escorted Cpf1 CRISPR-Cas systems or complexes have a guide molecule with a functional structure designed to improve guide molecule structure, architecture, stability, genetic expression, or any combination thereof. Such a structure can include an aptamer.

Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke B J, Stephens A W. "Escort aptamers: a delivery service for diagnosis and therapy." J Clin Invest 2000, 106:923-928.). Aptamers may also be constructed that function as molecular switches, responding to a que by changing properties, such as RNA aptamers that bind fluorophores to mimic the activity of green flourescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

Accordingly, in particular embodiments, the guide molecule is modified, e.g., by one or more aptamer(s) designed to improve guide molecule delivery, including delivery across the cellular membrane, to intracellular compartments, or into the nucleus. Such a structure can include, either in addition to the one or more aptamer(s) or without such one or more aptamer(s), moiety(ies) so as to render the guide molecule deliverable, inducible or responsive to a selected effector. The invention accordingly comprehends an guide molecule that responds to normal or pathological physiological conditions, including without limitation pH, hypoxia, $O_2$ concentration, temperature, protein concentration, enzymatic concentration, lipid structure, light exposure, mechanical disruption (e.g. ultrasound waves), magnetic fields, electric fields, or electromagnetic radiation.

Light responsiveness of an inducible system may be achieved via the activation and binding of cryptochrome-2 and CIB1. Blue light stimulation induces an activating conformational change in cryptochrome-2, resulting in recruitment of its binding partner CIB1. This binding is fast and reversible, achieving saturation in <15 sec following pulsed stimulation and returning to baseline<15 min after the end of stimulation. These rapid binding kinetics result in a system temporally bound only by the speed of transcription/translation and transcript/protein degradation, rather than uptake and clearance of inducing agents. Crytochrome-2 activation is also highly sensitive, allowing for the use of low light intensity stimulation and mitigating the risks of phototoxicity. Further, in a context such as the intact mammalian brain, variable light intensity may be used to control the size of a stimulated region, allowing for greater precision than vector delivery alone may offer.

The invention contemplates energy sources such as electromagnetic radiation, sound energy or thermal energy to induce the guide. Advantageously, the electromagnetic radiation is a component of visible light. In a preferred embodiment, the light is a blue light with a wavelength of about 450 to about 495 nm. In an especially preferred embodiment, the wavelength is about 488 nm. In another preferred embodiment, the light stimulation is via pulses. The light power may range from about 0-9 $mW/cm^2$. In a preferred embodiment, a stimulation paradigm of as low as 0.25 sec every 15 sec should result in maximal activation.

The chemical or energy sensitive guide may undergo a conformational change upon induction by the binding of a chemical source or by the energy allowing it act as a guide and have the Cpf1 CRISPR-Cas system or complex function. The invention can involve applying the chemical source or energy so as to have the guide function and the Cpf1 CRISPR-Cas system or complex function; and optionally further determining that the expression of the genomic locus is altered.

There are several different designs of this chemical inducible system: 1. ABI-PYL based system inducible by Abscisic Acid (ABA) (see, e.g., stke.sciencemag.org/cgi/content/abstract/sigtrans;4/164/rs2), 2. FKBP-FRB based system inducible by rapamycin (or related chemicals based on rapamycin) (see, e.g., www.nature.com/nmeth/journal/v2/n6/full/nmeth763.html), 3. GID1-GAI based system inducible by Gibberellin (GA) (see, e.g., www.nature.com/nchembio/journal/v8/n5/full/nchembio.922.html).

A chemical inducible system can be an estrogen receptor (ER) based system inducible by 4-hydroxytamoxifen (4OHT) (see, e.g., www.pnas.org/content/104/3/1027.abstract). A mutated ligand-binding domain of the estrogen receptor called ERT2 translocates into the nucleus of cells upon binding of 4-hydroxytamoxifen. In further embodiments of the invention any naturally occurring or engineered derivative of any nuclear receptor, thyroid hormone receptor, retinoic acid receptor, estrogen receptor, estrogen-related receptor, glucocorticoid receptor, progesterone receptor, androgen receptor may be used in inducible systems analogous to the ER based inducible system.

Another inducible system is based on the design using Transient receptor potential (TRP) ion channel based system inducible by energy, heat or radio-wave (see, e.g., www-.sciencemag.org/content/336/6081/604). These TRP family proteins respond to different stimuli, including light and heat. When this protein is activated by light or heat, the ion channel will open and allow the entering of ions such as calcium into the plasma membrane. This influx of ions will bind to intracellular ion interacting partners linked to a polypeptide including the guide and the other components of the Cpf1 CRISPR-Cas complex or system, and the binding will induce the change of sub-cellular localization of the polypeptide, leading to the entire polypeptide entering the nucleus of cells. Once inside the nucleus, the guide protein and the other components of the Cpf1 CRISPR-Cas complex will be active and modulating target gene expression in cells.

While light activation may be an advantageous embodiment, sometimes it may be disadvantageous especially for in vivo applications in which the light may not penetrate the skin or other organs. In this instance, other methods of energy activation are contemplated, in particular, electric field energy and/or ultrasound which have a similar effect.

Electric field energy is preferably administered substantially as described in the art, using one or more electric pulses of from about 1 Volt/cm to about 10 kVolts/cm under in vivo conditions. Instead of or in addition to the pulses, the electric field may be delivered in a continuous manner. The electric pulse may be applied for between 1 $\mu$s and 500 milliseconds, preferably between 1 $\mu$s and 100 milliseconds. The electric field may be applied continuously or in a pulsed manner for 5 about minutes.

As used herein, 'electric field energy' is the electrical energy to which a cell is exposed. Preferably the electric field has a strength of from about 1 Volt/cm to about 10 kVolts/cm or more under in vivo conditions (see WO97/49450).

As used herein, the term "electric field" includes one or more pulses at variable capacitance and voltage and including exponential and/or square wave and/or modulated wave and/or modulated square wave forms. References to electric fields and electricity should be taken to include reference the presence of an electric potential difference in the environment of a cell. Such an environment may be set up by way of static electricity, alternating current (AC), direct current (DC), etc, as known in the art. The electric field may be uniform, non-uniform or otherwise, and may vary in strength and/or direction in a time dependent manner.

Single or multiple applications of electric field, as well as single or multiple applications of ultrasound are also possible, in any order and in any combination. The ultrasound and/or the electric field may be delivered as single or multiple continuous applications, or as pulses (pulsatile delivery).

Electroporation has been used in both in vitro and in vivo procedures to introduce foreign material into living cells. With in vitro applications, a sample of live cells is first mixed with the agent of interest and placed between electrodes such as parallel plates. Then, the electrodes apply an electrical field to the cell/implant mixture. Examples of systems that perform in vitro electroporation include the Electro Cell Manipulator ECM600 product, and the Electro Square Porator T820, both made by the BTX Division of Genetronics, Inc (see U.S. Pat. No. 5,869,326).

The known electroporation techniques (both in vitro and in vivo) function by applying a brief high voltage pulse to electrodes positioned around the treatment region. The electric field generated between the electrodes causes the cell membranes to temporarily become porous, whereupon molecules of the agent of interest enter the cells. In known electroporation applications, this electric field comprises a single square wave pulse on the order of 1000 V/cm, of about 100 .mu.s duration. Such a pulse may be generated, for example, in known applications of the Electro Square Porator T820.

Preferably, the electric field has a strength of from about 1 V/cm to about 10 kV/cm under in vitro conditions. Thus, the electric field may have a strength of 1 V/cm, 2 V/cm, 3 V/cm, 4 V/cm, 5 V/cm, 6 V/cm, 7 V/cm, 8 V/cm, 9 V/cm, 10 V/cm, 20 V/cm, 50 V/cm, 100 V/cm, 200 V/cm, 300 V/cm, 400 V/cm, 500 V/cm, 600 V/cm, 700 V/cm, 800 V/cm, 900 V/cm, 1 kV/cm, 2 kV/cm, 5 kV/cm, 10 kV/cm, 20 kV/cm, 50 kV/cm or more. More preferably from about 0.5 kV/cm to about 4.0 kV/cm under in vitro conditions. Preferably the electric field has a strength of from about 1 V/cm to about 10 kV/cm under in vivo conditions. However, the electric field strengths may be lowered where the number of pulses delivered to the target site are increased. Thus, pulsatile delivery of electric fields at lower field strengths is envisaged.

Preferably the application of the electric field is in the form of multiple pulses such as double pulses of the same strength and capacitance or sequential pulses of varying strength and/or capacitance. As used herein, the term "pulse" includes one or more electric pulses at variable capacitance and voltage and including exponential and/or square wave and/or modulated wave/square wave forms.

Preferably the electric pulse is delivered as a waveform selected from an exponential wave form, a square wave form, a modulated wave form and a modulated square wave form.

A preferred embodiment employs direct current at low voltage. Thus, Applicants disclose the use of an electric field which is applied to the cell, tissue or tissue mass at a field strength of between 1V/cm and 20V/cm, for a period of 100 milliseconds or more, preferably 15 minutes or more.

Ultrasound is advantageously administered at a power level of from about 0.05 W/cm$^2$ to about 100 W/cm$^2$. Diagnostic or therapeutic ultrasound may be used, or combinations thereof.

As used herein, the term "ultrasound" refers to a form of energy which consists of mechanical vibrations the frequencies of which are so high they are above the range of human hearing. Lower frequency limit of the ultrasonic spectrum may generally be taken as about 20 kHz. Most diagnostic applications of ultrasound employ frequencies in the range 1 and 15 MHz' (From Ultrasonics in Clinical Diagnosis, P. N. T. Wells, ed., 2nd. Edition, Publ. Churchill Livingstone [Edinburgh, London & NY, 1977]).

Ultrasound has been used in both diagnostic and therapeutic applications. When used as a diagnostic tool ("diagnostic ultrasound"), ultrasound is typically used in an energy density range of up to about 100 mW/cm$^2$ (FDA recommendation), although energy densities of up to 750 mW/cm$^2$ have been used. In physiotherapy, ultrasound is typically used as an energy source in a range up to about 3 to 4 W/cm$^2$ (WHO recommendation). In other therapeutic applications, higher intensities of ultrasound may be employed, for example, HIFU at 100 W/cm up to 1 kW/cm$^2$ (or even higher) for short periods of time. The term "ultrasound" as used in this specification is intended to encompass diagnostic, therapeutic and focused ultrasound.

Focused ultrasound (FUS) allows thermal energy to be delivered without an invasive probe (see Morocz et al 1998 Journal of Magnetic Resonance Imaging Vol. 8, No. 1, pp. 136-142. Another form of focused ultrasound is high intensity focused ultrasound (HIFU) which is reviewed by Moussatov et al in Ultrasonics (1998) Vol. 36, No. 8, pp. 893-900 and TranHuuHue et al in Acustica (1997) Vol. 83, No. 6, pp. 1103-1106.

Preferably, a combination of diagnostic ultrasound and a therapeutic ultrasound is employed. This combination is not intended to be limiting, however, and the skilled reader will appreciate that any variety of combinations of ultrasound may be used. Additionally, the energy density, frequency of ultrasound, and period of exposure may be varied.

Preferably the exposure to an ultrasound energy source is at a power density of from about 0.05 to about 100 $Wcm^{-2}$. Even more preferably, the exposure to an ultrasound energy source is at a power density of from about 1 to about 15 $Wcm^{-2}$.

Preferably the exposure to an ultrasound energy source is at a frequency of from about 0.015 to about 10.0 MHz. More preferably the exposure to an ultrasound energy source is at a frequency of from about 0.02 to about 5.0 MHz or about 6.0 MHz. Most preferably, the ultrasound is applied at a frequency of 3 MHz.

Preferably the exposure is for periods of from about 10 milliseconds to about 60 minutes. Preferably the exposure is for periods of from about 1 second to about 5 minutes. More preferably, the ultrasound is applied for about 2 minutes. Depending on the particular target cell to be disrupted, however, the exposure may be for a longer duration, for example, for 15 minutes.

Advantageously, the target tissue is exposed to an ultrasound energy source at an acoustic power density of from about 0.05 $Wcm^{-2}$ to about 10 $Wcm^{-2}$ with a frequency ranging from about 0.015 to about 10 MHz (see WO 98/52609). However, alternatives are also possible, for example, exposure to an ultrasound energy source at an acoustic power density of above 100 $Wcm^{-2}$, but for reduced periods of time, for example, 1000 $Wcm^{-2}$ for periods in the millisecond range or less.

Preferably the application of the ultrasound is in the form of multiple pulses; thus, both continuous wave and pulsed wave (pulsatile delivery of ultrasound) may be employed in any combination. For example, continuous wave ultrasound may be applied, followed by pulsed wave ultrasound, or vice versa. This may be repeated any number of times, in any order and combination. The pulsed wave ultrasound may be applied against a background of continuous wave ultrasound, and any number of pulses may be used in any number of groups.

Preferably, the ultrasound may comprise pulsed wave ultrasound. In a highly preferred embodiment, the ultrasound is applied at a power density of 0.7 Wcm-2 or 1.25 Wcm-2 as a continuous wave. Higher power densities may be employed if pulsed wave ultrasound is used.

Use of ultrasound is advantageous as, like light, it may be focused accurately on a target. Moreover, ultrasound is advantageous as it may be focused more deeply into tissues unlike light. It is therefore better suited to whole-tissue penetration (such as but not limited to a lobe of the liver) or whole organ (such as but not limited to the entire liver or an entire muscle, such as the heart) therapy. Another important advantage is that ultrasound is a non-invasive stimulus which is used in a wide variety of diagnostic and therapeutic applications. By way of example, ultrasound is well known in medical imaging techniques and, additionally, in orthopedic therapy. Furthermore, instruments suitable for the application of ultrasound to a subject vertebrate are widely available and their use is well known in the art.

In particular embodiments, the guide molecule is modified by a secondary structure to increase the specificity of the CRISPR-Cas system and the secondary structure can protect against exonuclease activity and allow for 5' additions to the guide sequence also referred to herein as a protected guide molecule.

In one aspect, the invention provides for hybridizing a "protector RNA" to a sequence of the guide molecule, wherein the "protector RNA" is an RNA strand complementary to the 3' end of the guide molecule to thereby generate a partially double-stranded guide RNA. In an embodiment of the invention, protecting mismatched bases (i.e. the bases of the guide molecule which do not form part of the guide sequence) with a perfectly complementary protector sequence decreases the likelihood of target DNA binding to the mismatched basepairs at the 3' end. In particular embodiments of the invention, additional sequences comprising an extended length may also be present within the guide molecule such that the guide comprises a protector sequence within the guide molecule. This "protector sequence" ensures that the guide molecule comprises a "protected sequence" in addition to an "exposed sequence" (comprising the part of the guide sequence hybridizing to the target sequence). In particular embodiments, the guide molecule is modified by the presence of the protector guide to comprise a secondary structure such as a hairpin. Advantageously there are three or four to thirty or more, e.g., about 10 or more, contiguous base pairs having complementarity to the protected sequence, the guide sequence or both. It is advantageous that the protected portion does not impede thermodynamics of the CRISPR-Cas system interacting with its target. By providing such an extension including a partially double-stranded guide moleucle, the guide molecule is considered protected and results in improved specific binding of the CRISPR-Cas complex, while maintaining specific activity.

In particular embodiments, use is made of a truncated guide (tru-guide), i.e. a guide molecule which comprises a guide sequence which is truncated in length with respect to the canonical guide sequence length. As described by Nowak et al. (Nucleic Acids Res (2016) 44 (20): 9555-9564), such guides may allow catalytically active CRISPR-Cas enzyme to bind its target without cleaving the target DNA. In particular embodiments, a truncated guide is used which allows the binding of the target but retains only nickase activity of the CRISPR-Cas enzyme.

Crispr-Cas Enzyme

In its unmodified form, a CRISPR-Cas protein is a catalytically active protein. This implies that upon formation of a nucleic acid-targeting complex (comprising a guide RNA hybridized to a target sequence) one or both DNA strands in or near (e.g., within 1, 2, 3, 4, 5, 6, 7, 8, 9, 10, 20, 50, or more base pairs from) the target sequence is modified (e.g. cleaved). As used herein the term "sequence(s) associated with a target locus of interest" refers to sequences near the vicinity of the target sequence (e.g. within 1, 2, 3, 4, 5, 6, 7, 8, 9, 10, 20, 50, or more base pairs from the target sequence, wherein the target sequence is comprised within a target locus of interest). The unmodified catalytically active Cpf1 protein generates a staggered cut, whereby the cut sites are typically within the target sequence. More particularly, the staggered cut is typically 13-23 nucleotides distal to the PAM. In particular embodiments, the cut on the non-target strand is 17 nucleotides downstream of the PAM (i.e.

between nucleotide 17 and 18 downstream of the PAM), while the cut on the target strand (i.e. strand hybridizing with the guide sequence) occurs a further 4 nucleotides further from the sequence complementary to the PAM (this is 21 nucleotides upstream of the complement of the PAM on the 3' strand or between nucleotide 21 and 22 upstream of the complement of the PAM).

In the methods according to the present invention, the CRISPR-Cas protein is preferably mutated with respect to a corresponding wild-type enzyme such that the mutated CRISPR-Cas protein lacks the ability to cleave one or both DNA strands of a target locus containing a target sequence. In particular embodiments, one or more catalytic domains of the Cpf1 protein are mutated to produce a mutated Cas protein which cleaves only one DNA strand of a target sequence.

In particular embodiments, the CRISPR-Cas protein may be mutated with respect to a corresponding wild-type enzyme such that the mutated CRISPR-Cas protein lacks substantially all DNA cleavage activity. In some embodiments, a CRISPR-Cas protein may be considered to substantially lack all DNA and/or RNA cleavage activity when the cleavage activity of the mutated enzyme is about no more than 25%, 10%, 5%, 1%, 0.1%, 0.01%, or less of the nucleic acid cleavage activity of the non-mutated form of the enzyme; an example can be when the nucleic acid cleavage activity of the mutated form is nil or negligible as compared with the non-mutated form.

In certain embodiments of the methods provided herein the CRISPR-Cas protein is a mutated CRISPR-Cas protein which cleaves only one DNA strand, i.e. a nickase. More particularly, in the context of the present invention, the nickase ensures cleavage within the non-target sequence, i.e. the sequence which is on the opposite DNA strand of the target sequence and which is 3' of the PAM sequence. By means of further guidance, and without limitation, an arginine-to-alanine substitution (R1226A) in the Nuc domain of Cpf1 from *Acidaminococcus* sp. converts Cpf1 from a nuclease that cleaves both strands to a nickase (cleaves a single strand). It will be understood by the skilled person that where the enzyme is not AsCpf1, a mutation may be made at a residue in a corresponding position. In particular embodiments, the Cpf1 is FnCpf1 and the mutation is at the arginine at position R1218. In particular embodiments, the Cpf1 is LbCpf1 and the mutation is at the arginine at position R1138. In particular embodiments, the Cpf1 is MbCpf1 and the mutation is at the arginine at position R1293.

In certain embodiments of the methods provided herein the CRISPR-Cas protein has reduced or no catalytic activity. Where the CRISPR-Cas protein is a Cpf1 protein, the mutations may include but are not limited to one or more mutations in the catalytic RuvC-like domain, such as D908A or E993A with reference to the positions in AsCpf1.

In some embodiments, a CRISPR-Cas protein is considered to substantially lack all DNA cleavage activity when the DNA cleavage activity of the mutated enzyme is about no more than 25%, 10%, 5%, 1%, 0.1%, 0.01%, or less of the DNA cleavage activity of the non-mutated form of the enzyme; an example can be when the DNA cleavage activity of the mutated form is nil or negligible as compared with the non-mutated form. In these embodiments, the CRISPR-Cas protein is used as a generic DNA binding protein. The mutations may be artificially introduced mutations or gain- or loss-of-function mutations.

In addition to the mutations described above, the CRISPR-Cas protein may be additionally modified. As used herein, the term "modified" with regard to a CRISPR-Cas protein generally refers to a CRISPR-Cas protein having one or more modifications or mutations (including point mutations, truncations, insertions, deletions, chimeras, fusion proteins, etc.) compared to the wild type Cas protein from which it is derived. By derived is meant that the derived enzyme is largely based, in the sense of having a high degree of sequence homology with, a wildtype enzyme, but that it has been mutated (modified) in some way as known in the art or as described herein.

The additional modifications of the CRISPR-Cas protein may or may not cause an altered functionality. By means of example, and in particular with reference to CRISPR-Cas protein, modifications which do not result in an altered functionality include for instance codon optimization for expression into a particular host, or providing the nuclease with a particular marker (e.g. for visualization). Modifications with may result in altered functionality may also include mutations, including point mutations, insertions, deletions, truncations (including split nucleases), etc. Fusion proteins may without limitation include for instance fusions with heterologous domains or functional domains (e.g. localization signals, catalytic domains, etc.). In certain embodiments, various different modifications may be combined (e.g. a mutated nuclease which is catalytically inactive and which further is fused to a functional domain, such as for instance to induce DNA methylation or another nucleic acid modification, such as including without limitation a break (e.g. by a different nuclease (domain)), a mutation, a deletion, an insertion, a replacement, a ligation, a digestion, a break or a recombination). As used herein, "altered functionality" includes without limitation an altered specificity (e.g. altered target recognition, increased (e.g. "enhanced" Cas proteins) or decreased specificity, or altered PAM recognition), altered activity (e.g. increased or decreased catalytic activity, including catalytically inactive nucleases or nickases), and/or altered stability (e.g. fusions with destabilization domains). Suitable heterologous domains include without limitation a nuclease, a ligase, a repair protein, a methyltransferase, (viral) integrase, a recombinase, a transposase, an argonaute, a cytidine deaminase, a retron, a group II intron, a phosphatase, a phosphorylase, a sulfurylase, a kinase, a polymerase, an exonuclease, etc. Examples of all these modifications are known in the art. It will be understood that a "modified" nuclease as referred to herein, and in particular a "modified" Cas or "modified" CRISPR-Cas system or complex preferably still has the capacity to interact with or bind to the polynucleic acid (e.g. in complex with the guide molecule). Such modified Cas protein can be combined with the deaminase protein or active domain thereof as described herein.

In certain embodiments, CRISPR-Cas protein may comprise one or more modifications resulting in enhanced activity and/or specificity, such as including mutating residues that stabilize the targeted or non-targeted strand (e.g. eCas9; "Rationally engineered Cas9 nucleases with improved specificity", Slaymaker et al. (2016), Science, 351(6268): 84-88, incorporated herewith in its entirety by reference). In certain embodiments, the altered or modified activity of the engineered CRISPR protein comprises increased targeting efficiency or decreased off-target binding. In certain embodiments, the altered activity of the engineered CRISPR protein comprises modified cleavage activity. In certain embodiments, the altered activity comprises increased cleavage activity as to the target polynucleotide loci. In certain embodiments, the altered activity comprises decreased cleavage activity as to the target polynucleotide loci. In certain embodiments, the altered activity comprises decreased cleavage activity as to off-target polynucleotide loci. In certain embodiments, the altered or modified activity of the modified nuclease comprises altered helicase kinetics. In certain embodiments, the modified nuclease comprises a modification that alters association of the protein with the nucleic acid molecule comprising RNA (in the case of a Cas protein), or a strand of the target polynucleotide loci, or a strand of off-target polynucleotide loci. In an aspect of the invention, the engineered CRISPR protein comprises a modification that alters formation of the CRISPR complex. In certain embodiments, the altered activity comprises increased cleavage activity as to off-target polynucleotide loci. Accordingly, in certain embodiments, there is increased specificity for target polynucleotide loci as compared to off-target polynucleotide loci. In other embodiments, there is reduced specificity for target polynucleotide loci as compared to off-target polynucleotide loci. In certain embodiments, the mutations result in decreased off-target effects (e.g. cleavage or binding properties, activity, or kinetics), such as in case for Cas proteins for instance resulting in a lower tolerance for mismatches between target and guide RNA. Other mutations may lead to increased off-target effects (e.g. cleavage or binding properties, activity, or kinetics). Other mutations may lead to increased or decreased on-target effects (e.g. cleavage or binding properties, activity, or kinetics). In certain embodiments, the mutations result in altered (e.g. increased or decreased) helicase activity, association or formation of the functional nuclease complex (e.g. CRISPR-Cas complex). In certain embodiments, as described above, the mutations result in an altered PAM recognition, i.e. a different PAM may be (in addition or in the alternative) be recognized, compared to the unmodified Cas protein. Particularly preferred mutations include positively charged residues and/or (evolutionary) conserved residues, such as conserved positively charged residues, in order to enhance specificity. In certain embodiments, such residues may be mutated to uncharged residues, such as alanine.

Base Excision Repair Inhibitor

In some embodiments, the CD-functionalized CRISPR system further comprises a base excision repair (BER) inhibitor. Without wishing to be bound by any particular theory, cellular DNA-repair response to the presence of a U:G pairing in DNA may be responsible for a decrease in nucleobase editing efficiency in cells. Uracil DNA glycosylase catalyzes removal of uracil from DNA in cells, which may initiate base excision repair, such that the U:G pair is reversed to C:G. In some embodiments, the BER inhibitor is an uracyl glycosylase inhibitor or an active domain thereof.

In some embodiments, the BER inhibitor is an inhibitor of uracil DNA glycosylase (UDG). In some embodiments, the BER inhibitor is an inhibitor of human UDG. In some embodiments, the BER inhibitor is a polypeptide inhibitor. In some embodiments, the BER inhibitor is a protein that binds single-stranded DNA. For example, the BER inhibitor may be a Erwinia tasmaniensis single-stranded binding protein. In some embodiments, the BER inhibitor is a protein that binds uracil. In some embodiments, the BER inhibitor is a protein that binds uracil in DNA. In some embodiments, the BER inhibitor is a catalytically inactive UDG or binding domain thereof. In some embodiments, the BER inhibitor is a catalytically inactive UDG or binding domain thereof that does not excise uracil from the DNA. Other proteins that are capable of inhibiting (e.g., sterically blocking) UDG are within the scope of this disclosure. Additionally, any proteins that block or inhibit base-excision repair as also within the scope of this disclosure.

Without wishing to be bound by any particular theory, base excision repair may be inhibited by molecules that bind the edited strand, block the edited base, inhibit uracil DNA glycosylase, inhibit base excision repair, protect the edited base, and/or promote fixing of the non-targeted strand. Accordingly, the use of the BER inhibitor described herein can increase the editing efficiency of a cytidine deaminase that is capable of catalyzing a C to U change.

In particular embodiments, the uracil glycosylase inhibitor (UGI) is the uracil DNA glycosylase inhibitor of *Bacillus subtilis* bacteriophage PBS1 or an active fragment thereof, such as an 83 residue protein of *Bacillus subtilis* bacteriophage PBS1.

Suitable UGI protein and nucleotide sequences are provided herein and additional suitable UGI sequences are known to those in the art, and include, for example, those published in Wang et al., Uracil-DNA glycosylase inhibitor gene of bacteriophage PBS2 encodes a binding protein specific for uracil-DNA glycosylase. J. Biol. Chem. 264: 1 163-1 171(1989); Lundquist et al., Site-directed mutagenesis and characterization of uracil-DNA glycosylase inhibitor protein. Role of specific carboxylic amino acids in complex formation with *Escherichia coli* uracil-DNA glycosylase. J. Biol. Chem. 272:21408-21419(1997); Ravishankar et al., X-ray analysis of a complex of *Escherichia coli* uracil DNA glycosylase (EcUDG) with a proteinaceous inhibitor. The structure elucidation of a prokaryotic UDG. Nucleic Acids Res. 26:4880-4887(1998); and Putnam et al., Protein mimicry of DNA from crystal structures of the uracil-DNA glycosylase inhibitor protein and its complex with *Escherichia coli* uracil-DNA glycosylase. J. Mol. Biol. 287:331-346(1999), the entire contents of each are incorporated herein by reference.

In some embodiments, the UGI comprises the following amino acid sequence:

```
>sp|P14739|UNGI_BPPB2 Uracil-DNA glycosylase
inhibitor
                                    (SEQ ID NO: 35)
MTNLSDIIEKETGKQLVIQESILMLPEEVEEVIGNKPESDILVHTAYD

ESTDENVMLLTSDAPEYKPWALVIQDSNGENKIKML
```

In some embodiments, the UGI domain comprises a wild-type UGI or a UGI as set forth in SEQ ID NO: 35. In some embodiments, the UGI proteins provided herein include fragments of UGI and proteins homologous to a UGI or a UGI fragment. For example, in some embodiments, a UGI domain comprises a fragment of the amino acid sequence set forth in SEQ ID NO: 35. In some embodiments, a UGI fragment comprises an amino acid sequence that comprises at least 60%, at least 65%, at least 70%, at least 75%, at least 80%, at least 85%, at least 90%, at least 95%, at least 96%, at least 97%, at least 98%, at least 99%, or at least 99.5% of the amino acid sequence as set forth in SEQ ID NO: 35. In some embodiments, a UGI comprises an amino acid sequence homologous to the amino acid sequence set forth in SEQ ID NO: 35 or an amino acid sequence homologous to a fragment of the amino acid sequence set forth in SEQ ID NO: 35. In some embodiments, proteins comprising UGI or fragments of UGI or homologs of UGI or UGI fragments are referred to as "UGI variants." A UGI variant shares homology to UGI, or a fragment thereof. For example a UGI variant is at least 70% identical, at least 75% identical, at least 80% identical, at least 85% identical, at least 90% identical, at least 95% identical, at least 96% identical, at least 97% identical, at least 98% identical, at least 99% identical, at least 99.5% identical, or at least 99.9% identical to a wild type UGI or a UGI as set forth in SEQ ID NO: 35. In some embodiments, the UGI variant comprises a fragment of UGI, such that the fragment is at least 70% identical, at least 80% identical, at least 90% identical, at least 95% identical, at least 96% identical, at least 97% identical, at least 98% identical, at least 99% identical, at least 99.5% identical, or at least 99.9% to the corresponding fragment of wild-type UGI or a UGI as set forth in SEQ ID NO: 35.

It should be appreciated that additional proteins may be uracil glycosylase inhibitors. For example, other proteins that are capable of inhibiting (e.g., sterically blocking) a uracil-DNA glycosylase base-excision repair enzyme are within the scope of this disclosure. Additionally, any proteins that block or inhibit base-excision repair as also within the scope of this disclosure. In some embodiments, a protein that binds DNA is used. In another embodiment, a substitute for UGI is used. In some embodiments, a uracil glycosylase inhibitor is a protein that binds single-stranded DNA. For example, a uracil glycosylase inhibitor may be a *Erwinia tasmaniensis* single-stranded binding protein. In some embodiments, the single-stranded binding protein comprises the amino acid sequence (SEQ ID NO: 78). In some embodiments, a uracil glycosylase inhibitor is a protein that binds uracil. In some embodiments, a uracil glycosylase inhibitor is a protein that binds uracil in DNA. In some embodiments, a uracil glycosylase inhibitor is a catalytically inactive uracil DNA-glycosylase protein. In some embodiments, a uracil glycosylase inhibitor is a catalytically inactive uracil DNA-glycosylase protein that does not excise uracil from the DNA. For example, a uracil glycosylase inhibitor is a UdgX. In some embodiments, the UdgX comprises the amino acid sequence (SEQ ID NO: 79). As another example, a uracil glycosylase inhibitor is a catalytically inactive UDG. In some embodiments, a catalytically inactive UDG comprises the amino acid sequence (SEQ ID NO: 80). It should be appreciated that other uracil glycosylase inhibitors would be apparent to the skilled artisan and are within the scope of this disclosure. In some embodiments, a uracil glycosylase inhibitor is a protein that is homologous to any one of SEQ ID NOs: 78-80. In some embodiments, a uracil glycosylase inhibitor is a protein that is at least 50% identical, at least 55% identical at least 60% identical, at least 65% identical, at least 70% identical, at least 75% identical, at least 80% identical at least 85% identical, at least 90% identical, at least 95% identical, at least 96% identical, at least 98% identical, at least 99% identical, or at least 99.5% identical to any one of SEQ ID NOs: 78-80.

*Erwinia tasmaniensis* SSB (thermostable single-stranded DNA binding protein):

(SEQ ID NO: 78)
MASRGVNKVILVGNLGQDPEVRYMPNGGAVANITLATSESWRDKQTGE

TKEKTEWHRVVLFGKLAEVAGEYLRKGSQVYIEGALQTRKWTDQAGVE

KYTTEVVVNVGGTMQMLGGRSQGGGASAGGQNGGSNNGWGQPQQPQGG

NQFSGGAQQQARPQQQPQQNNAPANNEPPIDFDDDIP

UdgX (binds to Uracil in DNA but does not excise):

(SEQ ID NO: 79)
MAGAQDFVPHTADLAELAAAAGECRGCGLYRDATQAVFGAGGRSARIM

MIGEQPGDKEDLAGLPFVGPAGRLLDRALEAADIDRDALYVTNAVKHF

KFTRAAGGKRRIHKTPSRTEVVACRPWLIAEMTSVEPDVVVLLGATAA

KALLGNDFRVTQHRGEVLHVDDVPGDPALVATVHPSSLLRGPKEERES

AFAGLVDDLRVAADVRP

UDG (catalytically inactive human UDG, binds to Uracil in DNA but does not excise):

(SEQ ID NO: 80)
MIGQKTLYSFFSPSPARKRHAPSPEPAVQGTGVAGVPEESGDAAAIPAK

KAPAGQEEPGTPPSSPLSAEQLDRIQRNKAAALLRLAARNVPVGFGESW

KKHLSGEFGKPYFIKLMGFVAEERKHYTVYPPPHQVFTWTQMCDIKDVK

VVILGQEPYHGPNQAHGLCFSVQRPVPPPPSLENIYKELSTDIEDFVHP

GHGDLSGWAKQGVLLLNAVLTVRAHQANSHKERGWEQFTDAVVSWLNQN

SNGLVFLLWGSYAQKKGSAIDRKRHHVLQTAHPSPLSVYRGFFGCRHFS

KTNELLQKSGKKPIDWKEL

Accordingly, in the first design of the CD-functionalized CRISPR system discussed above, the CRISPR-Cas protein or the cytidine deaminase can be fused to or linked to a BER inhibitor (e.g., an inhibitor of uracyl DNA glycosylase). In some embodiments, the BER inhibitor can be comprised in one of the following structures (nCpf1=Cpf1 nickase; dCpf1=dead Cpf1): [CD]-[optional linker]-[nCpf1/dCpf1]-[optional linker]-[BER inhibitor]; [CD]-[optional linker]-[BER inhibitor]-[optional linker]-[nCpf1/dCpf1]; [BER inhibitor]-[optional linker]-[CD]-[optional linker]-[nCpf1/dCpf1]; [BER inhibitor]-[optional linker]-[nCpf1/dCpf1]-[optional linker]-[CD]; [nCpf1/dCpf1]-[optional linker]-[CD]-[optional linker]-[BER inhibitor]; [nCpf1/dCpf1]-[optional linker]-[BER inhibitor]-[optional linker]-[CD].

Similarly, in the second design of the CD-functionalized CRISPR system discussed above, the CRISPR-Cas protein, the cytidine deaminase, or the adaptor protein can be fused to or linked to a BER inhibitor (e.g., an inhibitor of uracil DNA glycosylase). In some embodiments, the BER inhibitor can be comprised in one of the following structures (nCpf1=Cpf1 nickase; dCpf1=dead Cpf1): [nCpf1/dCpf1]-[optional linker]-[BER inhibitor]; [BER inhibitor]-[optional linker]-[nCpf1/dCpf1]; [CD]-[optional linker]-[Adaptor]-[optional linker]-[BER inhibitor]; [CD]-[optional linker]-[BER inhibitor]-[optional linker]-[Adaptor]; [BER inhibitor]-[optional linker]-[CD]-[optional linker]-[Adaptor]; [BER inhibitor]-[optional linker]-[Adaptor]-[optional linker]-[CD]; [Adaptor]-[optional linker]-[CD]-[optional linker]-[BER inhibitor]; [Adaptor]-[optional linker]-[BER inhibitor]-[optional linker]-[CD].

In the third design of the CD-functionalized CRISPR system discussed above, the BER inhibitor can be inserted into an internal loop or unstructured region of a CRISPR-Cas protein.

Targeting to the Nucleus

In some embodiments, the methods of the present invention relate to modifying an Cytosine in a target locus of interest, whereby the target locus is within a cell. In order to improve targeting of the CRISPR-Cas protein and/or the cytidine deaminase protein or catalytic domain thereof used in the methods of the present invention to the nucleus, it may be advantageous to provide one or both of these components with one or more nuclear localization sequences (NLSs).

In preferred embodiments, the NLSs used in the context of the present invention are heterologous to the proteins. Non-limiting examples of NLSs include an NLS sequence derived from: the NLS of the SV40 virus large T-antigen, having the amino acid sequence PKKKRKV (SEQ ID NO: 37) or PKKKRKVEAS (SEQ ID NO: 38); the NLS from nucleoplasmin (e.g., the nucleoplasmin bipartite NLS with the sequence KRPAATKKAGQAKKKK (SEQ ID NO: 39)); the c-myc NLS having the amino acid sequence PAAKRVKLD (SEQ ID NO: 40) or RQRRNELKRSP (SEQ ID NO: 41); the hRNPA1 M9 NLS having the sequence NQSSNFGPMKGGNFGGRSSGPYGGGGQYFAK-PRNQGGY (SEQ ID NO: 42); the sequence RMRIZFKNKGKDTAELRRRRVEVSVELRKAKKD-EQILKRRNV (SEQ ID NO: 43) of the IBB domain from importin-alpha; the sequences VSRKRPRP (SEQ ID NO: 44) and PPKKARED (SEQ ID NO: 45) of the myoma T protein; the sequence PQPKKKPL (SEQ ID NO: 46) of human p53; the sequence SALIKKKKKMAP (SEQ ID NO: 47) of mouse c-abl IV; the sequences DRLRR (SEQ ID NO: 48) and PKQKKRK (SEQ ID NO: 49) of the influenza virus NS1; the sequence RKLKKKIKKL (SEQ ID NO: 50) of the Hepatitis virus delta antigen; the sequence REKKKFLKRR (SEQ ID NO: 51) of the mouse Mxl protein; the sequence KRKGDEVDGVDEVAKKKSKK (SEQ ID NO: 52) of the human poly(ADP-ribose) polymerase; and the sequence RKCLQAGMNLEARKTKK (SEQ ID NO: 53) of the steroid hormone receptors (human) glucocorticoid. In general, the one or more NLSs are of sufficient strength to drive accumulation of the DNA-targeting Cas protein in a detectable amount in the nucleus of a eukaryotic cell. In general, strength of nuclear localization activity may derive from the number of NLSs in the CRISPR-Cas protein, the particular NLS(s) used, or a combination of these factors. Detection of accumulation in the nucleus may be performed by any suitable technique. For example, a detectable marker may be fused to the nucleic acid-targeting protein, such that location within a cell may be visualized, such as in combination with a means for detecting the location of the nucleus (e.g., a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of nucleic acid-targeting complex formation (e.g., assay for deaminase activity) at the target sequence, or assay for altered gene expression activity affected by DNA-targeting complex formation and/or DNA-targeting), as compared to a control not exposed to the CRISPR-Cas protein and deaminase protein, or exposed to a CRISPR-Cas and/or deaminase protein lacking the one or more NLSs.

The CRISPR-Cas and/or cytidine deaminase proteins may be provided with 1 or more, such as with, 2, 3, 4, 5, 6, 7, 8, 9, 10, or more heterologous NLSs. In some embodiments, the proteins comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g., zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies.

In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. In preferred embodiments of the CRISPR-Cas proteins, an NLS attached to the C-terminal of the protein.

In certain embodiments of the methods provided herein, the CRISPR-Cas protein and the deaminase protein are delivered to the cell or expressed within the cell as separate proteins. In these embodiments, each of the CRISPR-Cas and deaminase protein can be provided with one or more NLSs as described herein. In certain embodiments, the CRISPR-Cas and deaminase proteins are delivered to the cell or expressed with the cell as a fusion protein. In these embodiments one or both of the CRISPR-Cas and deaminase protein is provided with one or more NLSs. Where the cytidine deaminase is fused to an adaptor protein (such as MS2) as described above, the one or more NLS can be provided on the adaptor protein, provided that this does not interfere with aptamer binding. In particular embodiments, the one or more NLS sequences may also function as linker sequences between the cytidine deaminase and the CRISPR-Cas protein.

In certain embodiments, guides of the invention comprise specific binding sites (e.g. aptamers) for adapter proteins, which may be linked to or fused to a cytidine deaminase or catalytic domain thereof. When such a guides forms a CRISPR complex (i.e. CRISPR-Cas protein binding to guide and target) the adapter proteins bind and, the cytidine deaminase or catalytic domain thereof associated with the adapter protein is positioned in a spatial orientation which is advantageous for the attributed function to be effective.

The skilled person will understand that modifications to the guide which allow for binding of the adapter+cytidine deaminase, but not proper positioning of the adapter+cytidine deaminase (e.g. due to steric hindrance within the three dimensional structure of the CRISPR complex) are modifications which are not intended. The one or more modified guide may be modified at the tetra loop, the stem loop 1, stem loop 2, or stem loop 3, as described herein, preferably at either the tetra loop or stem loop 2, and most preferably at both the tetra loop and stem loop 2.

Use of Orthogonal Catalytically Inactive CRISPR-Cas Proteins

In particular embodiments, the Cpf1 nickase is used in combination with an orthogonal catalytically inactive CRISPR-Cas protein to increase efficiency of said Cpf1 nickase (as described in Chen et al. 2017, Nature Communications 8:14958; doi:10.1038/ncomms14958). More particularly, the orthogonal catalytically inactive CRISPR-Cas protein is characterized by a different PAM recognition site than the Cpf1 nickase used in the CD-functionalized CRISPR system and the corresponding guide sequence is selected to bind to a target sequence proximal to that of the Cpf1 nickase of the CD-functionalized CRISPR system. The orthogonal catalytically inactive CRISPR-Cas protein as used in the context of the present invention does not form part of the CD-functionalized CRISPR system but merely functions to increase the efficiency of said Cpf1 nickase and is used in combination with a standard guide molecule as described in the art for said CRISPR-Cas protein. In particular embodiments, said orthogonal catalytically inactive CRISPR-Cas protein is a dead CRISPR-Cas protein, i.e. comprising one or more mutations which abolishes the nuclease activity of said CRISPR-Cas protein. In particular embodiments, the catalytically inactive orthogonal CRISPR-Cas protein is provided with two or more guide molecules which are capable of hybridizing to target sequences which are proximal to the target sequence of the Cpf1 nickase. In particular embodiments, at least two guide molecules are used to target said catalytically inactive CRISPR-Cas protein, of which at least one guide molecule is capable of hybridizing to a target sequence 5" of the target sequence of the Cpf1 nickase and at least one guide molecule is capable of hybridizing to a target sequence 3' of the target sequence of the Cpf1 nickase of the CD-functionalized CRISPR system, whereby said one or more target sequences may be on the same or the opposite DNA strand as the target sequence of the Cpf1 nickase. In particular embodiments, the guide sequences for the one or more guide molecules of the orthogonal catalytically inactive CRISPR-Cas protein are selected such that the target sequences are proximal to that of the guide molecule for the targeting of the CD-functionalized CRISPR, i.e. for the targeting of the Cpf1 nickase. In particular embodiments, the one or more target sequences of the orthogonal catalytically inactive CRISPR-Cas enzyme are each separated from the target sequence of the Cpf1 nickase by more than 5 but less than 450 basepairs. Optimal distances between the target sequences of the guides for use with the orthogonal catalytically inactive CRISPR-Cas protein and the target sequence of the CD-functionalized CRISPR system can be determined by the skilled person. In particular embodiments, the orthogonal CRISPR-Cas protein is a Class II, type II CRISPR protein. In particular embodiments, the orthogonal CRISPR-Cas protein is a Class II, type V CRISPR protein. In particular embodiments, the catalytically inactive orthogonal CRISPR-Cas protein. In particular embodiments, the catalytically inactive orthogonal CRISPR-Cas protein has been modified to alter its PAM specificity as described elsewhere herein. In particular embodiments, the Cpf1 protein nickase is a nickase which, by itself has limited activity in human cells, but which, in combination with an inactive orthogonal CRISPR-Cas protein and one or more corresponding proximal guides ensures the required nickase activity.

CRISPR Development and Use

The present invention may be further illustrated and extended based on aspects of CRISPR-Cas development and use as set forth in the following articles and particularly as relates to delivery of a CRISPR protein complex and uses of an RNA guided endonuclease in cells and organisms:

Multiplex genome engineering using CRISPR-Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121): 819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR-Cas-Mediated Genome Engineering. Wang H., Yang H., Shivalila C S., Dawlaty M M., Cheng A W., Zhang F., Jaenisch R. Cell May 9; 153(4):910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463):472-6. doi: 10.1038/Nature12466. Epub 2013 Aug. 23 (2013);

Double Nicking by RNA-Guided CRISPR Cas9 for Enhanced Genome Editing Specificity. Ran, FA., Hsu, PD., Lin, CY., Gootenberg, JS., Konermann, S., Trevino, AE., Scott, DA., Inoue, A., Matoba, S., Zhang, Y., & Zhang, F. Cell August 28. pii: S0092-8674(13) 01015-5 (2013-A);

DNA targeting specificity of RNA-guided Cas9 nucleases. Hsu, P., Scott, D., Weinstein, J., Ran, FA., Konermann, S., Agarwala, V., Li, Y., Fine, E., Wu, X., Shalem, O., Cradick, TJ., Marraffini, LA., Bao, G., & Zhang, F. Nat Biotechnol doi:10.1038/nbt.2647 (2013);

Genome engineering using the CRISPR-Cas9 system. Ran, FA., Hsu, PD., Wright, J., Agarwala, V., Scott, DA., Zhang, F. Nature Protocols November; 8(11): 2281-308 (2013-B);

Genome-Scale CRISPR-Cas9 Knockout Screening in Human Cells. Shalem, O., Sanjana, NE., Hartenian, E., Shi, X., Scott, DA., Mikkelson, T., Heckl, D., Ebert, BL., Root, DE., Doench, JG., Zhang, F. Science December 12. (2013);

Crystal structure of cas9 in complex with guide RNA and target DNA. Nishimasu, H., Ran, FA., Hsu, PD., Konermann, S., Shehata, SI., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure™, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR-Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh 00, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520 (7546):186-91(2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR-Cas9 cleavage of viral DNA efficiently suppresses hepatitis B virus," Scientific Reports 5:10833 doi: 10.1038/srep10833 (Jun. 2, 2015).

Nishimasu et al., Crystal Structure of *Staphylococcus aureus* Cas9," Cell 162, 1113-1126 (Aug. 27, 2015)

BCL11A enhancer dissection by Cas9-mediated in situ saturating mutagenesis, Canver et al., Nature 527 (7577):192-7 (Nov. 12, 2015) doi: 10.1038/nature15521. Epub 2015 Sep. 16.

Cpf1 Is a Single RNA-Guided Endonuclease of a Class 2 CRISPR-Cas System, Zetsche et al., Cell 163, 759-71 (Sep. 25, 2015).

Discovery and Functional Characterization of Diverse Class 2 CRISPR-Cas Systems, Shmakov et al., Molecular Cell, 60(3), 385-397 doi: 10.1016/j.molcel.2015.10.008 Epub Oct. 22, 2015.

Rationally engineered Cas9 nucleases with improved specificity, Slaymaker et al., Science 2016 Jan. 1 351 (6268): 84-88 doi: 10.1126/science.aad5227. Epub 2015 Dec. 1.

Gao et al, "Engineered Cpf1 Enzymes with Altered PAM Specificities," bioRxiv 091611; doi: dx.doi.org/10.1101/091611 (Dec. 4, 2016).

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence-specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR-Cas system for the one-step generation of mice carrying mutations in multiple genes which were traditionally generated in multiple steps by sequential recombination in embryonic stem cells and/or time-consuming intercrossing of mice with a single mutation. The CRISPR-Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR-Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and guide RNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR-Cas9 knockout and nucleotide preference at the cleavage site. The authors also found that the sequence preference for CRISPRi/a is substantially different from that for CRISPR-Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Canver et al. (2015) demonstrated a CRISPR-Cas9-based functional investigation of non-coding genomic elements. The authors we developed pooled CRISPR-Cas9 guide RNA libraries to perform in situ saturating mutagenesis of the human and mouse BCL11A enhancers which revealed critical features of the enhancers.

Zetsche et al. (2015) reported characterization of Cpf1, a class 2 CRISPR nuclease from *Francisella novicida* U112 having features distinct from Cas9. Cpf1 is a single RNA-guided endonuclease lacking tracrRNA, utilizes a T-rich protospacer-adjacent motif, and cleaves DNA via a staggered DNA double-stranded break.

Shmakov et al. (2015) reported three distinct Class 2 CRISPR-Cas systems. Two system CRISPR enzymes (C2c1 and C2c3) contain RuvC-like endonuclease domains distantly related to Cpf1. Unlike Cpf1, C2c1 depends on both crRNA and tracrRNA for DNA cleavage. The third enzyme (C2c2) contains two predicted HEPN RNase domains and is tracrRNA independent.

Slaymaker et al (2016) reported the use of structure-guided protein engineering to improve the specificity of *Streptococcus pyogenes* Cas9 (SpCas9). The authors developed "enhanced specificity" SpCas9 (eSpCas9) variants which maintained robust on-target cleavage with reduced off-target effects.

The methods and tools provided herein are exemplified for Cpf1, a type II nuclease that does not make use of tracrRNA. Orthologs of Cpf1 have been identified in different bacterial species as described herein. Further type II nucleases with similar properties can be identified using methods described in the art (Shmakov et al. 2015, 60:385-397; Abudayeh et al. 2016, Science, 5; 353(6299)). In particular embodiments, such methods for identifying novel CRISPR effector proteins may comprise the steps of selecting sequences from the database encoding a seed which identifies the presence of a CRISPR-Cas locus, identifying loci located within 10 kb of the seed comprising Open Reading Frames (ORFs) in the selected sequences, selecting therefrom loci comprising ORFs of which only a single ORF encodes a novel CRISPR effector having greater than 700 amino acids and no more than 90% homology to a known CRISPR effector. In particular embodiments, the seed is a protein that is common to the CRISPR-Cas system, such as Cas1. In further embodiments, the CRISPR array is used as a seed to identify new effector proteins.

The effectiveness of the present invention has been demonstrated. Preassembled recombinant CRISPR-Cpf1 complexes comprising Cpf1 and crRNA may be transfected, for example by electroporation, resulting in high mutation rates and absence of detectable off-target mutations. Hur, J. K. et al, Targeted mutagenesis in mice by electroporation of Cpf1 ribonucleoproteins, Nat Biotechnol. 2016 Jun. 6. doi: 10.1038/nbt.3596. Genome-wide analyses shows that Cpf1 is highly specific. By one measure, in vitro cleavage sites determined for Cpf1 in human HEK293T cells were significantly fewer that for SpCas9. Kim, D. et al., Genome-wide analysis reveals specificities of Cpf1 endonucleases in human cells, Nat Biotechnol. 2016 Jun. 6. doi: 10.1038/nbt.3609. An efficient multiplexed system employing Cpf1 has been demonstrated in *Drosophila* employing gRNAs processed from an array containing inventing tRNAs. Port, F. et al, Expansion of the CRISPR toolbox in an animal with tRNA-flanked Cas9 and Cpf1 gRNAs. doi: dx.doi.org/10.1101/046417.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

With respect to general information on CRISPR/Cas Systems, components thereof, and delivery of such components, including methods, materials, delivery vehicles, vectors, particles, and making and using thereof, including as to amounts and formulations, as well as CRISPR-Cas-expressing eukaryotic cells, CRISPR-Cas expressing eukaryotes, such as a mouse, reference is made to: U.S. Pat. Nos. 8,999,641, 8,993,233, 8,697,359, 8,771,945, 8,795,965, 8,865,406, 8,871,445, 8,889,356, 8,889,418, 8,895,308, 8,906,616, 8,932,814, and 8,945,839; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); Ser. No. 14/054,414 European Patent Applications EP 2 771 468 (EP13818570.7), EP 2 764 103 (EP13824232.6), and EP 2 784 162 (EP14170383.5); and PCT Patent Publications WO2014/093661 (PCT/US2013/074743), WO2014/093694 (PCT/US2013/074790), WO2014/093595 (PCT/US2013/074611), WO2014/093718 (PCT/US2013/074825), WO2014/093709 (PCT/US2013/074812), WO2014/093622 (PCT/US2013/074667), WO2014/093635 (PCT/US2013/

074691), WO2014/093655 (PCT/US2013/074736), WO2014/093712 (PCT/US2013/074819), WO2014/093701 (PCT/US2013/074800), WO2014/018423 (PCT/US2013/051418), WO2014/204723 (PCT/US2014/041790), WO2014/204724 (PCT/US2014/041800), WO2014/204725 (PCT/US2014/041803), WO2014/204726 (PCT/US2014/041804), WO2014/204727 (PCT/US2014/041806), WO2014/204728 (PCT/US2014/041808), WO2014/204729 (PCT/US2014/041809), WO2015/089351 (PCT/US2014/069897), WO2015/089354 (PCT/US2014/069902), WO2015/089364 (PCT/US2014/069925), WO2015/089427 (PCT/US2014/070068), WO2015/089462 (PCT/US2014/070127), WO2015/089419 (PCT/US2014/070057), WO2015/089465 (PCT/US2014/070135), WO2015/089486 (PCT/US2014/070175), WO2015/058052 (PCT/US2014/061077), WO2015/070083 (PCT/US2014/064663), WO2015/089354 (PCT/US2014/069902), WO2015/089351 (PCT/US2014/069897), WO2015/089364 (PCT/US2014/069925), WO2015/089427 (PCT/US2014/070068), WO2015/089473 (PCT/US2014/070152), WO2015/089486 (PCT/US2014/070175), WO2016/049258 (PCT/US2015/051830), WO2016/094867 (PCT/US2015/065385), WO2016/094872 (PCT/US2015/065393), WO2016/094874 (PCT/US2015/065396), WO2016/106244 (PCT/US2015/067177).

Mention is also made of U.S. application 62/180,709, 17 Jun. 2015, PROTECTED GUIDE RNAS (PGRNAS); U.S. application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. applications 62/091,462, 12 Dec. 2014, 62/096,324, 23 Dec. 2014, 62/180,681, 17 Jun. 2015, and 62/237,496, 5 Oct. 2015, DEAD GUIDES FOR CRISPR TRANSCRIPTION FACTORS; U.S. application 62/091,456, 12 Dec. 2014 and 62/180,692, 17 Jun. 2015, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, 62/181,641, 18 Jun. 2015, and 62/181,667, 18 Jun. 2015, RNA-TARGETING SYSTEM; U.S. application 62/096,656, 24 Dec. 2014 and 62/181,151, 17 Jun. 2015, CRISPR HAVING OR ASSOCIATED WITH DESTABILIZATION DOMAINS; U.S. application 62/096,697, 24 Dec. 2014, CRISPR HAVING OR ASSOCIATED WITH AAV; U.S. application 62/098,158, 30 Dec. 2014, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 61/939,154, 12 Feb. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. applications 62/054,675, 24 Sep. 2014 and 62/181,002, 17 Jun. 2015, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014 and 62/181,690, 18 Jun. 2015, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014 and 62/181,687, 18 Jun. 2015, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Mention is made of U.S. applications 62/181,659, 18 Jun. 2015 and 62/207,318, 19 Aug. 2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Mention is made of U.S. applications 62/181,663, 18 Jun. 2015 and 62/245,264, 22 Oct. 2015, NOVEL CRISPR ENZYMES AND SYSTEMS, U.S. applications 62/181,675, 18 Jun. 2015, 62/285,349, 22 Oct. 2015, 62/296,522, 17 Feb. 2016, and 62/320,231, 8 Apr. 2016, NOVEL CRISPR ENZYMES AND SYSTEMS, U.S. application 62/232,067, 24 Sep. 2015, U.S. application Ser. No. 14/975,085, 18 Dec. 2015, European application No. 16150428.7, U.S. application 62/205,733, 16 Aug. 2015, U.S. application 62/201,542, 5 Aug. 2015, U.S. application 62/193,507, 16 Jul. 2015, and U.S. application 62/181,739, 18 Jun. 2015, each entitled NOVEL CRISPR ENZYMES AND SYSTEMS and of U.S. application 62/245,270, 22 Oct. 2015, NOVEL CRISPR ENZYMES AND SYSTEMS. Mention is also made of U.S. application 61/939,256, 12 Feb. 2014, and WO 2015/089473 (PCT/US2014/070152), 12 Dec. 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of PCT/US2015/045504, 15 Aug. 2015, U.S. application 62/180,699, 17 Jun. 2015, and U.S. application 62/038,358, 17 Aug. 2014, each entitled GENOME EDITING USING CAS9 NICKASES.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Type-V CRISPR-Cas Protein

The application describes methods using Type-V CRISPR-Cas proteins. This is exemplified herein with Cpf1, whereby a number of orthologs or homologs have been identified. It will be apparent to the skilled person that further orthologs or homologs can be identified and that any of the functionalities described herein may be engineered into other orthologs, including chimeric enzymes comprising fragments from multiple orthologs.

Computational methods of identifying novel CRISPR-Cas loci are described in EP3009511 or US2016208243 and may comprise the following steps: detecting all contigs encoding the Cas1 protein; identifying all predicted protein coding genes within 20 kB of the cas1 gene; comparing the identified genes with Cas protein-specific profiles and predicting CRISPR arrays; selecting unclassified candidate CRISPR-Cas loci containing proteins larger than 500 amino acids (>500 aa); analyzing selected candidates using methods such as PSI-BLAST and TPred to screen for known protein domains, thereby identifying novel Class 2 CRISPR-Cas loci (see also Schmakov et al. 2015, Mol Cell. 60(3): 385-97). In addition to the above mentioned steps, additional analysis of the candidates may be conducted by searching metagenomics databases for additional homologs. Additionally or alternatively, to expand the search to non-autonomous CRISPR-Cas systems, the same procedure can be performed with the CRISPR array used as the seed.

In one aspect the detecting all contigs encoding the Cas1 protein is performed by GenemarkS which a gene prediction program as further described in "GeneMarkS: a self-training method for prediction of gene starts in microbial genomes. Implications for finding sequence motifs in regulatory regions." John Besemer, Alexandre Lomsadze and Mark Borodovsky, Nucleic Acids Research (2001) 29, pp 2607-2618, herein incorporated by reference.

In one aspect the identifying all predicted protein coding genes is carried out by comparing the identified genes with Cas protein-specific profiles and annotating them according to NCBI Conserved Domain Database (CDD) which is a protein annotation resource that consists of a collection of well-annotated multiple sequence alignment models for ancient domains and full-length proteins. These are available as position-specific score matrices (PSSMs) for fast identification of conserved domains in protein sequences via RPS-BLAST. CDD content includes NCBI-curated domains, which use 3D-structure information to explicitly define domain boundaries and provide insights into sequence/structure/function relationships, as well as domain models imported from a number of external source databases (Pfam, SMART, COG, PRK, TIGRFAM). In a further aspect, CRISPR arrays were predicted using a PILER-CR program which is a public domain software for finding CRISPR repeats as described in "PILER-CR: fast and accurate identification of CRISPR repeats", Edgar, R. C., BMC Bioinformatics, January 20; 8:18(2007), herein incorporated by reference.

In a further aspect, the case by case analysis is performed using PSI-BLAST (Position-Specific Iterative Basic Local Alignment Search Tool). PSI-BLAST derives a position-specific scoring matrix (PSSM) or profile from the multiple sequence alignment of sequences detected above a given score threshold using protein-protein BLAST. This PSSM is used to further search the database for new matches, and is updated for subsequent iterations with these newly detected sequences. Thus, PSI-BLAST provides a means of detecting distant relationships between proteins.

In another aspect, the case by case analysis is performed using HHpred, a method for sequence database searching and structure prediction that is as easy to use as BLAST or PSI-BLAST and that is at the same time much more sensitive in finding remote homologs. In fact, HHpred's sensitivity is competitive with the most powerful servers for structure prediction currently available. HHpred is the first server that is based on the pairwise comparison of profile hidden Markov models (HMMs). Whereas most conventional sequence search methods search sequence databases such as UniProt or the NR, HHpred searches alignment databases, like Pfam or SMART. This greatly simplifies the list of hits to a number of sequence families instead of a clutter of single sequences. All major publicly available profile and alignment databases are available through HHpred. HHpred accepts a single query sequence or a multiple alignment as input. Within only a few minutes it returns the search results in an easy-to-read format similar to that of PSI-BLAST. Search options include local or global alignment and scoring secondary structure similarity. HHpred can produce pairwise query-template sequence alignments, merged query-template multiple alignments (e.g. for transitive searches), as well as 3D structural models calculated by the MODELLER software from HHpred alignments.

Orthologs of Cpf1

The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of Homologous proteins may but need not be structurally related, or are only partially structurally related. An "orthologue" of a protein as used herein is a protein of a different species which performs the same or a similar function as the protein it is an orthologue of Orthologous proteins may but need not be structurally related, or are only partially structurally related. Homologs and orthologs may be identified by homology modelling (see, e.g., Greer, Science vol. 228 (1985) 1055, and Blundell et al. Eur J Biochem vol 172 (1988), 513) or "structural BLAST" (Dey F, Cliff Zhang Q, Petrey D, Honig B. Toward a "structural BLAST": using structural relationships to infer function. Protein Sci. 2013 April; 22(4):359-66. doi: 10.1002/pro.2225.). See also Shmakov et al. (2015) for application in the field of CRISPR-Cas loci. Homologous proteins may but need not be structurally related, or are only partially structurally related.

The Cpf1 gene is found in several diverse bacterial genomes, typically in the same locus with cas1, cas2, and cas4 genes and a CRISPR cassette (for example, FNFX1_1431-FNFX1_1428 of *Francisella* cf. *novicida* Fx1). Thus, the layout of this putative novel CRISPR-Cas system appears to be similar to that of type II-B. Furthermore, similar to Cas9, the Cpf1 protein contains a readily identifiable C-terminal region that is homologous to the transposon ORF-B and includes an active RuvC-like nuclease, an arginine-rich region, and a Zn finger (absent in Cas9). However, unlike Cas9, Cpf1 is also present in several genomes without a CRISPR-Cas context and its relatively high similarity with ORF-B suggests that it might be a transposon component. It was suggested that if this was a genuine CRISPR-Cas system and Cpf1 is a functional analog of Cas9 it would be a novel CRISPR-Cas type, namely type V (See Annotation and Classification of CRISPR-Cas Systems. Makarova K S, Koonin E V. Methods Mol Biol. 2015; 1311:47-75). However, as described herein, Cpf1 is denoted to be in subtype V-A to distinguish it from C2clp which does not have an identical domain structure and is hence denoted to be in subtype V-B.

The present invention encompasses the use of a Cpf1 effector protein, derived from a Cpf1 locus denoted as subtype V-A. Herein such effector proteins are also referred to as "Cpf1p", e.g., a Cpf1 protein (and such effector protein or Cpf1 protein or protein derived from a Cpf1 locus is also called "CRISPR-Cas protein").

In particular embodiments, the effector protein is a Cpf1 effector protein from an organism from a genus comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacterium, Carnobacterium, Rhodobacter, Listeria, Paludibacter, Clostridium, Lachnospiraceae, Clostridiaridium, Leptotrichia, Francisella, Legionella, Alicyclobacillus, Methanomethylophilus, Porphyromonas, Prevotella, Bacteroidetes, Helcococcus, Leptospira, Desulfovibrio, Desulfonatronum, Opitutaceae, Tuberibacillus, Bacillus, Brevibacillus, Methylobacterium, Butyrivibrio, Peregrinibacterium, Parcubacterium, Moraxella, Thiomicrospira* or *Acidaminococcus*. In particular embodiments, the Cpf1 effector protein is selected from an organism from a genus selected from *Eubacterium, Lachnospiraceae, Leptotrichia, Francisella, Methanomethylophilus, Porphyromonas, Prevotella, Leptospira, Butyrivibrio, Peregrinibacterium, Parcubacterium, Moraxella, Thiomicrospira* or *Acidaminococcus*.

In further particular embodiments, the Cpf1 effector protein is from an organism selected from *S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. difficile, C. tetani, C. sordellii; F. tularensis* 1, *P. albensis, L. bacterium, B. proteoclasticus, P. bacterium, P. crevioricanis, P. disiens* and *P. macacae*.

The effector protein may comprise a chimeric effector protein comprising a first fragment from a first effector protein (e.g., a Cpf1) ortholog and a second fragment from a second effector (e.g., a Cpf1) protein ortholog, and wherein the first and second effector protein orthologs are different. At least one of the first and second effector protein (e.g., a Cpf1) orthologs may comprise an effector protein (e.g., a Cpf1) from an organism comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacterium, Carnobacterium, Rhodobacter, Listeria, Paludibacter, Clostridium, Lachnospiraceae, Clostridiaridium, Leptotrichia, Francisella, Legionella, Alicyclobacillus, Methanomethylophilus, Porphyromonas, Prevotella, Bacteroidetes, Helcococcus, Leptospira, Desulfovibrio, Desulfonatronum, Opitutaceae, Tuberibacillus, Bacillus, Brevibacillus, Methylobacterium, Butyrivibrio, Peregrinibacterium, Parcubacterium, Moraxella, Thiomicrospira* or *Acidaminococcus*; e.g., a chimeric effector protein comprising a first fragment and a second fragment wherein each of the first and second fragments is selected from a Cpf1 of an organism comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacterium, Carnobacterium, Rhodobacter, Listeria, Paludibacter, Clostridium, Lachnospiraceae, Clostridiaridium, Leptotrichia, Francisella, Legionella, Alicyclobacillus, Methanomethylophilus, Porphyromonas, Prevotella, Bacteroidetes, Helcococcus, Leptospira, Desulfovibrio, Desulfonatronum, Opitutaceae, Tuberibacillus, Bacillus, Brevibacillus, Methylobacterium, Butyrivibrio, Peregrinibacterium, Parcubacterium, Moraxella, Thiomicrospira* or *Acidaminococcus* wherein the first and second fragments are not from the same bacteria; for instance a chimeric effector protein comprising a first fragment and a second fragment wherein each of the first and second fragments is selected from a Cpf1 of *S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. difficile, C. tetani, C. sordellii; Francisella tularensis* 1, *Prevotella albensis, Lachnospiraceae bacterium* MC2017 1, *Butyrivibrio proteoclasticus, Peregrinibacteria bacterium* GW2011_GWA2_33_10, *Parcubacteria bacterium* GW2011_GWC2_44_17, *Smithella* sp. SCADC, *Acidaminococcus* sp. BV3L6, *Lachnospiraceae bacterium* MA2020, *Candidatus Methanoplasma termitum, Eubacterium eligens, Moraxella bovoculi* 237, *Leptospira inadai, Lachnospiraceae bacterium* ND2006, *Porphyromonas crevioricanis* 3, *Prevotella disiens* and *Porphyromonas macacae*, wherein the first and second fragments are not from the same bacteria.

In a more preferred embodiment, the Cpf1p is derived from a bacterial species selected from *Francisella tularensis* 1, *Prevotella albensis, Lachnospiraceae bacterium* MC2017 1, *Butyrivibrio proteoclasticus, Peregrinibacteria bacterium* GW2011_GWA2_33_10, *Parcubacteria bacterium* GW2011_GWC2_44_17, *Smithella* sp. SCADC, *Acidaminococcus* sp. BV3L6, *Lachnospiraceae bacterium* MA2020, *Candidatus Methanoplasma termitum, Eubacterium eligens, Moraxella bovoculi* 237, *Moraxella bovoculi* AAX08_00205, *Moraxella bovoculi* AAX11_00205, *Butyrivibrio* sp. NC3005, *Thiomicrospira* sp. XS5, *Leptospira inadai, Lachnospiraceae bacterium* ND2006, *Porphyromonas crevioricanis* 3, *Prevotella disiens* and *Porphyromonas macacae*. In certain embodiments, the Cpf1p is derived from a bacterial species selected from *Acidaminococcus* sp. BV3L6, *Lachnospiraceae bacterium* M42020. In certain embodiments, the effector protein is derived from a subspecies of *Francisella tularensis* 1, including but not limited to *Francisella tularensis* subsp. *Novicida*. In certain preferred embodiments, the Cpf1p is derived from a bacterial species selected from *Acidaminococcus* sp. BV3L6, *Lachnospiraceae bacterium* ND2006, *Lachnospiraceae bacterium* MA2020, *Moraxella bovoculi* AAX08_00205, Moraxella bovoculi AAX11_00205, Butyrivibrio sp. NC3005, or Thiomicrospira sp. XS5.

In particular embodiments, the homologue or orthologue of Cpf1 as referred to herein has a sequence homology or identity of at least 80%, more preferably at least 85%, even more preferably at least 90%, such as for instance at least 95% with Cpf1. In further embodiments, the homologue or orthologue of Cpf1 as referred to herein has a sequence identity of at least 80%, more preferably at least 85%, even more preferably at least 90%, such as for instance at least 95% with the wild type Cpf1. Where the Cpf1 has one or more mutations (mutated), the homologue or orthologue of said Cpf1 as referred to herein has a sequence identity of at least 80%, more preferably at least 85%, even more preferably at least 90%, such as for instance at least 95% with the mutated Cpf1.

In an embodiment, the Cpf1 protein may be an ortholog of an organism of a genus which includes, but is not limited to Acidaminococcus sp, Lachnospiraceae bacterium or Moraxella bovoculi; in particular embodiments, the type V Cas protein may be an ortholog of an organism of a species which includes, but is not limited to Acidaminococcus sp. BV3L6; Lachnospiraceae bacterium ND2006 (LbCpf1) or Moraxella bovoculi 237.In particular embodiments, the homologue or orthologue of Cpf1 as referred to herein has a sequence homology or identity of at least 80%, more preferably at least 85%, even more preferably at least 90%, such as for instance at least 95% with one or more of the Cpf1 sequences disclosed herein. In further embodiments, the homologue or orthologue of Cpf as referred to herein has a sequence identity of at least 80%, more preferably at least 85%, even more preferably at least 90%, such as for instance at least 95% with the wild type FnCpf1, AsCpf1 or LbCpf1.

In particular embodiments, the Cpf1 protein of the invention has a sequence homology or identity of at least 60%, more particularly at least 70, such as at least 80%, more preferably at least 85%, even more preferably at least 90%, such as for instance at least 95% with FnCpf1, AsCpf1 or LbCpf1. In further embodiments, the Cpf1 protein as referred to herein has a sequence identity of at least 60%, such as at least 70%, more particularly at least 80%, more preferably at least 85%, even more preferably at least 90%, such as for instance at least 95% with the wild type AsCpf1 or LbCpf1. In particular embodiments, the Cpf1 protein of the present invention has less than 60% sequence identity with FnCpf1. The skilled person will understand that this includes truncated forms of the Cpf1 protein whereby the sequence identity is determined over the length of the truncated form. In particular embodiments, the Cpf1 enzyme is not FnCpf1.

In some embodiments, the CRISPR effector protein is a Cpf1 protein derived from an organism from the genus of Eubacterium. In some embodiments, the CRISPR effector protein is a Cpf1 protein derived from an organism from the bacterial species of Eubacterium rectale. In some embodiments, the amino acid sequence of the Cpf1 effector protein corresponds to NCBI Reference Sequence WP_055225123.1, NCBI Reference Sequence WP_055237260.1, NCBI Reference Sequence WP_055272206.1, or GenBank ID OLA16049.1. In some embodiments, the Cpf1 effector protein has a sequence homology or sequence identity of at least 60%, more particularly at least 70%, such as at least 80%, more preferably at least 85%, even more preferably at least 90%, such as for instance at least 95%, with NCBI Reference Sequence WP_055225123.1, NCBI Reference Sequence WP_055237260.1, NCBI Reference Sequence WP_055272206.1, or GenBank ID OLA16049.1. The skilled person will understand that this includes truncated forms of the Cpf1 protein whereby the sequence identity is determined over the length of the truncated form. In some embodiments, the Cpf1 effector recognizes the PAM sequence of TTTN or CTTN.

In some embodiments, the CRISPR effector protein is a Cpf1 protein derived from an organism from the genus of Eubacterium. In some embodiments, the CRISPR effector protein is a Cpf1 protein derived from an organism from the bacterial species of Eubacterium rectale. In some embodiments, the amino acid sequence of the Cpf1 effector protein corresponds to NCBI Reference Sequence WP_055225123.1, NCBI Reference Sequence WP_055237260.1, NCBI Reference Sequence WP_055272206.1, or GenBank ID OLA16049.1. In some embodiments, the Cpf1 effector protein has a sequence homology or sequence identity of at least 60%, more particularly at least 70, such as at least 80%, more preferably at least 85%, even more preferably at least 90%, such as for instance at least 95%, with NCBI Reference Sequence WP_055225123.1, NCBI Reference Sequence WP_055237260.1, NCBI Reference Sequence WP_055272206.1, or GenBank ID OLA16049.1. The skilled person will understand that this includes truncated forms of the Cpf1 protein whereby the sequence identity is determined over the length of the truncated form. In some embodiments, the Cpf1 effector recognizes the PAM sequence of TTTN or CTTN.

Codon Optimized Cpf1 Sequences

Where the effector protein is to be administered as a nucleic acid, the application envisages the use of codon-optimized Cpf1 sequences. An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667) as an example of a codon optimized sequence (from knowledge in the art and this disclosure, codon optimizing coding nucleic acid molecule(s), especially as to effector protein (e.g., Cpf1) is within the ambit of the skilled artisan). Whilst this is preferred, it will be appreciated that other examples are possible and codon optimization for a host species other than human, or for codon optimization for specific organs is known. In some embodiments, an enzyme coding sequence encoding a DNA/RNA-targeting Cas protein is codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g., 1, 2, 3, 4, 5, 10, 15, 20, 25, 50, or more, or all codons) in a sequence encoding a DNA/RNA-targeting Cas protein corresponds to the most frequently used codon for a particular amino acid. As to codon usage in yeast, reference is made to the online Yeast Genome database available at www.yeastgenome.org/community/codon_usage.shtml, or Codon selection in yeast, Bennetzen and Hall, J Biol Chem. 1982 Mar. 25; 257(6):3026-31. As to codon usage in plants including algae, reference is made to Codon usage in higher plants, green algae, and cyanobacteria, Campbell and Gowri, Plant Physiol. 1990 January; 92(1): 1-11.; as well as Codon usage in plant genes, Murray et al, Nucleic Acids Res. 1989 Jan. 25; 17(2):477-98; or Selection on the codon bias of chloroplast and cyanelle genes in different plant and algal lineages, Morton B R, J Mol Evol. 1998 April; 46(4):449-59.

In certain example embodiments, Cpf1 amino acids are followed by nuclear localization signals (NLS) (italics), a glycine-serine (GS) linker (underlined), and 3×HA tag (bold). In some embodiments, Cpf1 amino acid sequences correspond to sequences without the NLS, GS linker and 3× HA tag.

1- *Franscisella tularensis* subsp. novicida U112 (FnCpf1)

(SEQ ID NO: 54)

MSIYQEFVNKYSLSKTLRFELIPQGKTLENIKARGLILDDEKRAKDYKKA

KQIIDKYHQFFIEEILSSVCISEDLLQNYSDVYFKLKKSDDDNLQKDFKSAKDTIKKQ

ISEYIKDSEKFKNLFNQNLIDAKKGQESDLILWLKQSKDNGIELFKANSDITDIDEAL

EIIKSFKGWTTYFKGFHENRKNVYSSNDIPTSITYRIVDDNLPKFLENKAKYESLKDK

APEAINYEQIKKDLAEELTFDIDYKTSEVNQRVFSLDEVFEIANFNNYLNQSGITKFN

TIIGGKFVNGENTKRKGINEYINLYSQQINDKTLKKYKMSVLFKQILSDTESKSFVID

KLEDDSDVVTTMQSFYEQIAAFKTVEEKSIKETLSLLFDDLKAQKLDLSKIYFKNDK

SLTDLSQQVFDDYSVIGTAVLEYITQQIAPKNLDNPSKKEQELIAKKTEKAKYLSLE

TIKLALEEFNKHRDIDKQCRFEEILANFAAIPMIFDEIAQNKDNLAQISIKYQNQGKK

DLLQASAEDDVKAIKDLLDQTNNLLHKLKIFHISQSEDKANILDKDEHFYLVFEECY

FELANIVPLYNKIRNYITQKPYSDEKFKLNFENSTLANGWDKNKEPDNTAILFIKDD

KYYLGVMNKKNNKIFDDKAIKENKGEGYKKIVYKLLPGANKMLPKVFFSAKSIKF

YNPSEDILRIRNHSTHTKNGSPQKGYEKFEFNIEDCRKFIDFYKQSISKHPEWKDFGF

RFSDTQRYNSIDEFYREVENQGYKLTFENISESYIDSVVNQGKLYLFQIYNKDFSAY

SKGRPNLHTLYWKALFDERNLQDVVYKLNGEAELFYRKQSIPKKITHPAKEAIANK

NKDNPKKESVFEYDLIKDKRFTEDKFFFHCPITINFKSSGANKFNDEINLLLKEKAND

VHILSIDRGERHLAYYTLVDGKGNIIKQDTFNIIGNDRMKTNYHDKLAAIEKDRDSA

RKDWKKINNIKEMKEGYLSQVVHEIAKLVIEYNAIVVFEDLNFGFKRGRFKVEKQV

YQKLEKMLIEKLNYLVFKDNEFDKTGGVLRAYQLTAPFETFKKMGKQTGIIYYVPA

GFTSKICPVTGFVNQLYPKYESVSKSQEFFSKFDKICYNLDKGYFEFSFDYKNFGDK

AAKGKWTIASFGSRLINFRNSDKNHNWDTREVYPTKELEKLLKDYSIEYGHGECIK

AAICGESDKKFFAKLTSVLNTILQMRNSKTGTELDYLISPVADVNGNFFDSRQAPKN

MPQDADANGAYHIGLKGLMLLGRIKNNQEGKKLNLVIKNEEYFEFVQNRNN*KRPA*

*ATKKAGQAKKKKGS*<u>YPYDVPDYA</u>YPYDVPDYAYPYDVPDYA

3- *Lachnospiraceae bacterium* MC2017 (Lb3Cpf1)
(SEQ ID NO: 55)

MDYGNGQFERRAPLTKTITLRLKPIGETRETIREQKLLEQDAAFRKLVET

VTPIVDDCIRKIADNALCHFGTEYDFSCLGNAISKNDSKAIKKETEKVEKLLAKVLT

ENLPDGLRKVNDINSAAFIQDTLTSFVQDDADKRVLIQELKGKTVLMQRFLTTRITA

LTVWLPDRVFENFNIFIENAEKMRILLDSPLNEKIMKFDPDAEQYASLEFYGQCLSQ

KDIDSYNLIISGIYADDEVKNPGINEIVKEYNQQIRGDKDESPLPKLKKLHKQILMPV

EKAFFVRVLSNDSDARSILEKILKDTEMLPSKIIEAMKEADAGDIAVYGSRLHELSH

VIYGDHGKLSQIIYDKESKRISELMETLSPKERKESKKRLEGLEEHIRKSTYTFDELN

RYAEKNVMAAYIAAVEESCAEIMRKEKDLRTLLSKEDVKIRGNRHNTLIVKNYFN

AWTVFRNLIRILRRKSEAEIDSDFYDVLDDSVEVLSLTYKGENLCRSYITKKIGSDLK

PEIATYGSALRPNSRWWSPGEKFNVKFHTIVRRDGRLYYFILPKGAKPVELEDMDG

DIECLQMRKIPNPTIFLPKLVFKDPEAFFRDNPEADEFVFLSGMKAPVTITRETYEAY

RYKLYTVGKLRDGEVSEEEYKRALLQVLTAYKEFLENRMIYADLNFGFKDLEEYK

DSSEFIKQVETHNTFMCWAKVSSSQLDDLVKSGNGLLFEIWSERLESYYKYGNEKV

LRGYEGVLLSILKDENLVSMRTLLNSRPMLVYRPKESSKPMVVHRDGSRVVDRFD

KDGKYIPPEVHDELYRFFNNLLIKEKLGEKARKILDNKKVKVKVLESERVKWSKFY

DEQFAVTFSVKKNADCLDTTKDLNAEVMEQYSESNRLILIRNTTDILYYLVLDKNG

KVLKQRSLNIINDGARDVDWKERFRQVTKDRNEGYNEWDYSRTSNDLKEVYLNY

ALKEIAEAVIEYNAILIIEKMSNAFKDKYSFLDDVTFKGFETKLLAKLSDLHFRGIKD

GEPCSFTNPLQLCQNDSNKILQDGVIFMVPNSMTRSLDPDTGFIFAINDHNIRTKKA

KLNFLSKFDQLKVSSEGCLIMKYSGDSLPTHNTDNRVWNCCCNHPITNYDRETKKV

EFIEEPVEELSRVLEENGIETDTELNKLNERENVPGKVVDAIYSLVLNYLRGTVSGV

AGQRAVYYSPVTGKKYDISFIQAMNLNRKCDYYRIGSKERGEWTDFVAQLIN*KRPA*

*ATKKAGQAKKKKGS*<u>YPYDVPDYAYPYDVPDYAYPYDVPDYA</u>

4- *Butyrivibrio proteoclasticus* (BpCpf1)
(SEQ ID NO: 56)

MLLYENYTKRNQITKSLRLELRPQGKTLRNIKELNLLEQDKAIYALLERL

KPVIDEGIKDIARDTLKNCELSFEKLYEHFLSGDKKAYAKESERLKKEIVKTLIKNLP

EGIGKISEINSAKYLNGVLYDFIDKTHKDSEEKQNILSDILETKGYLALFSKFLTSRIT

TLEQSMPKRVIENFEIYAANIPKMQDALERGAVSFAIEYESICSVDYYNQILSQEDID

SYNRLISGIMDEDGAKEKGINQTISEKNIKIKSEHLEEKPFRILKQLHKQILEEREKAF

TIDHIDSDEEVVQVTKEAFEQTKEQWENIKKINGFYAKDPGDITLFIVVGPNQTHVL

SQLIYGEHDRIRLLLEEYEKNTLEVLPRRTKSEKARYDKFVNAVPKKVAKESHTFD

GLQKMTGDDRLFILYRDELARNYMRIKEAYGTFERDILKSRRGIKGNRDVQESLVS

FYDELTKFRSALRIINSGNDEKADPIFYNTFDGIFEKANRTYKAENLCRNYVTKSPA

DDARIMASCLGTPARLRTHWWNGEENFAINDVAMIRRGDEYYYFVLTPDVKPVDL

KTKDETDAQIFVQRKGAKSFLGLPKALFKCILEPYFESPEEIKNDKNCVIEEYVSKPL

TIDRRAYDIFKNGTFKKTNIGIDGLTEEKFKDDCRYLIDVYKEFIAVYTRYSCFNMS

GLKRADEYNDIGEFFSDVDTRLCTMEWIPVSFERINDMVDKKEGLLFLVRSMFLYN

RPRKPYERTFIQLFSDSNMEHTSMLLNSRAMIQYRAASLPRRVTHKKGSILVALRDS

NGEHIPMHIREAIYKMKNNFDISSEDFIMAKAYLAEHDVAIKKANEDIIRNRRYTED

KFFLSLSYTKNADISARTLDYINDKVEEDTQDSRMAVIVTRNLKDLTYVAVVDEKN

-continued

NVLEEKSLNEIDGVNYRELLKERTKIKYHDKTRLWQYDVSSKGLKEAYVELAVTQI

SKLATKYNAVVVVESMSSTFKDKFSFLDEQIFKAFEARLCARMSDLSFNTIKEGEA

GSISNPIQVSNNNGNSYQDGVIYFLNNAYTRTLCPDTGFVDVFDKTRLITMQSKRQF

FAKMKDIRIDDGEMLFTFNLEEYPTKRLLDRKEWTVKIAGDGSYFDKDKGEYVYV

NDIVREQIIPALLEDKAVFDGNMAEKFLDKTAISGKSVELIYKWFANALYGIITKKD

GEKIYRSPITGTEIDVSKNTTYNFGKKFMFKQEYRGDGDFLDAFLNYMQAQDIAV*K*

*RPAATKKAGQAKKKK*GSYPYDVPDYAYPYDVPDYAYPYDVPDYA

5- *Peregrinibacteria bacterium* GW2011_GWA_33_10 (PeCpf1)
(SEQ ID NO: 57)
MSNFFKNFTNLYELSKTLRFELKPVGDTLTNMKDHLEYDEKLQTFLKDQ

NIDDAYQALKPQFDEIHEEFITDSLESKKAKEIDFSEYLDLFQEKKELNDSEKKLRNK

IGETFNKAGEKWKKEKYPQYEWKKGSKIANGADILSCQDMLQFIKYKNPEDEKIK

NYIDDTLKGFFTYFGGFNQNRANYYETKKEASTAVATRIVHENLPKFCDNVIQFKHI

IKRKKDGTVEKTERKTEYLNAYQYLKNNNKITQIKDAETEKMIESTPIAEKIFDVYY

FSSCLSQKQIEEYNRIIGHYNLLINLYNQAKRSEGKHLSANEKKYKDLPKFKTLYKQ

IGCGKKKDLFYTIKCDTEEEANKSRNEGKESHSVEEIINKAQEAINKYFKSNNDCENT

NTVPDFINYILTKENYEGVYWSKAAMNTISDKYFANYHDLQDRLKEAKVFQKADK

KSEDDIKIPEAIELSGLFGVLDSLADWQTTLFKSSILSNEDKLKIITDSQTPSEALLKMI

FNDIEKNMESFLKETNDIITLKKYKGNKEGTEKIKQWFDYTLAINRMLKYFLVKEN

KIKGNSLDTNISEALKTLIYSDDAEWFKWYDALRNYLTQKPQDEAKENKLKLNFD

NPSLAGGWDVNKECSNFCVILKDKNEKKYLAIMKKGENTLFQKEWTEGRGKNLT

KKSNPLFEINNCEILSKMEYDFWADVSKMIPKCSTQLKAVVNHFKQSDNEFIFPIGY

KVTSGEKFREECKISKQDFELNNKVFNKNELSVTAMRYDLSSTQEKQYIKAFQKEY

WELLFKQEKRDTKLTNNEIFNEWINFCNKKYSELLSWERKYKDALTNWINFCKYFL

SKYPKTTLFNYSFKESENYNSLDEFYRDVDICSYKLNINTTINKSILDRLVEEGKLYL

FEIKNQDSNDGKSIGHKNNLHTIYWNAIFENFDNRPKLNGEAEIFYRKAISKDKLGI

VKGKKTKNGTEIIKNYRFSKEKFILHVPITLNFCSNNEYVNDIVNTKFYNFSNLHFLG

IDRGEKHLAYYSLVNKNGEIVDQGTLNLPFTDKDGNQRSIKKEKYFYNKQEDKWE

AKEVDCWNYNDLLDAMASNRDMARKNWQRIGTIKEAKNGYVSLVIRKIADLAVN

NERPAFIVLEDLNTGFKRSRQKIDKSVYQKFELALAKKLNFLVDKNAKRDEIGSPTK

ALQLTPPVNNYGDIENKKQAGIMLYTRANYTSQTDPATGWRKTIYLKAGPEETTY

KKDGKIKNKSVKDQIIETFTDIGFDGKDYYFEYDKGEFVDEKTGEIKPKKWRLYSG

ENGKSLDRFRGEREKDKYEWKIDKIDIVKILDDLFVNFDKNISLLKQLKEGVELTRN

NEHGTGESLRFAINLIQQIRNTGNNERDNDFILSPVRDENGKHFDSREYWDKETKGE

KISMPSSGDANGAFNIARKGIIMNAHILANSDSKDLSLFVSDEEWDLHLNNKTEWK

KQLNIFSSRKAMA*KRKKKRPAATKKAGQAKKKK*GSYPYDVPDYAYPYDVPDAYP

YDVPDYA

6- *Parcubacteria bacterium* GWC2011_GWC2_44_17 (PbCpf1)
(SEQ ID NO: 58)
MENIFDQFIGKYSLSKTLRFELKPVGKTEDFLKINKVFEKDQTIDDSYNQ

AKFYFDSLHQKFIDAALASDKTSELSFQNFADVLEKQNKIILDKKREMGALRKRDK

NAVGIDRLQKEINDAEDIIQKEKEKIYKDVRTLFDNEAESWKTYYQEREVDGKKITF

-continued

SKADLKQKGADFLTAAGILKVLKYEFPEEKEKEFQAKNQPSLFVEEKENPGQKRYI

FDSFDKFAGYLTKFQQTKKNLYAADGTSTAVATRIADNFIIFHQNTKVFRDKYKNN

HTDLGFDEENIFEIERYKNCLLQREIEHIKNENSYNKIIGRINKKIKEYRDQKAKDTK

LTKSDFPFFKNLDKQILGEVEKEKQLIEKTREKTEEDVLIERFKEFIENNEERFTAAK

KLMNAFCNGEFESEYEGIYLKNKAINTISRRWFVSDRDFELKLPQQKSKNKSEKNEP

KVKKFISIAEIKNAVEELDGDIFKAVFYDKKIIAQGGSKLEQFLVIWKYEFEYLFRDI

ERENGEKLLGYDSCLKIAKQLGIFPQEKEAREKATAVIKNYADAGLGIFQMMKYFS

LDDKDRKNTPGQLSTNFYAEYDGYYKDFEFIKYYNEFRNFITKKPFDEDKIKLNFEN

GALLKGWDENKEYDFMGVILKKEGRLYLGIMHKNHRKLFQSMGNAKGDNANRY

QKMIYKQIADASKDVPRLLLTSKKAMEKFKPSQEILRIKKEKTFKRESKNFSLRDLH

ALIEYYRNCIPQYSNWSFYDFQFQDTGKYQNIKEFTDDVQKYGYKISFRDIDDEYIN

QALNEGKMYLFEVVNKDIYNTKNGSKNLHTLYFEHILSAENLNDPVFKLSGMAEIF

QRQPSVNEREKITTQKNQCILDKGDRAYKYRRYTEKKIMFHMSLVLNTGKGEIKQV

QFNKIINQRISSSDNEMRVNVIGIDRGEKNLLYYSVVKQNGEIIEQASLNEINGVNYR

DKLIEREKERLKNRQSWKPVVKIKDLKKGYISHVIHKICQLIEKYSAIVVLEDLNMR

FKQIRGGIERSVYQQFEKALIDKLGYLVFKDNRDLRAPGGVLNGYQLSAPFVSFEK

MRKQTGILFYTQAEYTSKTDPITGFRKNVYISNSASLDKIKEAVKKFDAIGWDGKE

QSYFFKYNPYNLADEKYKNSTVSKEWAIFASAPRIRRQKGEDGYWKYDRVKVNEE

FEKLLKVWNFVNPKATDIKQEIIKKEKAGDLQGEKELDGRLRNFWHSFIYLFNLVL

ELRNSFSLQIKIKAGEVIAVDEGVDFIASPVKPFFTTPNPYIPSNLCWLAVENADANG

AYNIARKGVMILKKIREHAKKDPEFKKLPNLFISNAEWDEAARDWGKYAGTTALN

LDH*KRPAATKKAGQAKKKKGS*YPYDVPDYAYPYDVPDYAYPYDVPDYA

7- *Smithella* sp. SC_K08D17 (SsCpf1)

(SEQ ID NO: 59)

MQTLFENFTNQYPVSKTLRFELIPQGKTKDFIEQKGLLKKDEDRAEKYK

KVKNIIDEYBKDFIEKSLNGLKLDGLEKYKTLYLKQEKDDKDKKAFDKEKENLRK

QIANAFRNNEKFKTLFAKELIKNDLMSFACEEDKKNVKEFEAFTTYFTGFHQNRAN

MYVADEKRTAIASRLIHENLPKFIDNIKIFEKMKKEAPELLSPFNQTLKDMKDVIKG

TTLEEIFSLDYFNKTLTQSGIDIYNSVIGGRTPEEGKTKIKGLNEYINTDFNQKQTDK

KKRQPKFKQLYKQILSDRQSLSFIAEAFKNDTEILEAIEKFYVNELLHFSNEGKSTNV

LDAIKNAVSNLESFNLTKMYFRSGASLTDVSRKVFGEWSIINRALDNYYATTYPIKP

REKSEKYEERKEKWLKQDFNVSLIQTAIDEYDNETVKGKNSGKVIADYFAKFCDD

KETDLIQKVNEGYIAVKDLLNTPCPENEKLGSNKDQVKQIKAFMDSIMDIIVIHFVRP

LSLKDTDKEKDETFYSLFTPLYDHLTQTIALYNKVRNYLTQKPYSTEKIKLNFENST

LLGGWDLNKETDNTAIILRKDNLYYLGIMDKRHNRIFRNVPKADKKDFCYEKMVY

KLLPGANKMLPKVFFSQSRIQEFTPSAKLLENYANETHKKGDNFNLNHCHKLIDFF

KDSINKHEDWKNFDFRFSATSTYADLSGFYHEVEHQGYKISFQSVADSFIDDLVNE

GKLYLFQIYNKDFSPFSKGKPNLHTLYWKMLFDENNLKDVVYKLNGEAEVFYRKK

SIAEKNTTIHKANESIINKNPDNPKATSTFNYDIVKDKRYTIDKFQFHIPITMNFKAEG

IFNMNQRVNQFLKANPDINIIGIDRGERHLLYYALINQKGKILKQDTLNVIANEKQK

VDYHNLLDKKEGDRATARQEWGVIETIKELKEGYLSQVIHKLTDLMIENNAIIVME

DLNFGFKRGRQKVEKQVYQKFEKMLIDKLNYLVDKNKKANELGGLLNAFQLANK

-continued

FESFQKMGKQNGFIFYVPAWNTSKTDPATGFIDFLKPRYENLNQAKDFFEKFDSIRL

NSKADYFEFAFDFKNFTEKADGGRTKWTVCTTNEDRYAWNRALNNNRGSQEKYD

ITAELKSLFDGKVDYKSGKDLKQQIASQESADFFKALMKNLSITLSLRHNNGEKGD

NEQDYILSPVADSKGRFFDSRKADDDMPKNADANGAYHIALKGLWCLEQISKTDD

LKKVKLAISNKEWLEFVQTLKG*KRPAATKKAGQAKKKK*GSYPYDVPDYAYPYDVP
DYAYPYDVPDYA

8- *Acidaminococcus* sp. BV3L6 (AsCpf1)

(SEQ ID NO: 60)
MTQFEGFTNLYQVSKTLRFELIPQGKTLKHIQEQGFIEEDKARNDHYKEL

KPIIDRIYKTYADQCLQLVQLDWENLSAAIDSYRKEKTEETRNALIEEQATYRNAIH

DYFIGRTDNLTDAINKRHAEIYKGLFKAELFNGKVLKQLGTVTTTEHENALLRSFD

KFTTYFSGFYENRKNVFSAEDISTAIPHRIVQDNFPKFKENCHIFTRLITAVPSLREHF

ENVKKAIGIFVSTSIEEVFSFPFYNQLLTQTQIDLYNQLLGGISREAGTEKIKGLNEVL

NLAIQKNDETAHIIASLPHRFIPLFKQILSDRNTLSFILEEFKSDEEVIQSFCKYKTLLR

NENVLETAEALFNELNSIDLTHIFISHKKLETISSALCDHWDTLRNALYERRISELTG

KITKSAKEKVQRSLKHEDINLQEIISAAGKELSEAFKQKTSEILSHAHAALDQPLPTT

LKKQEEKEILKSQLDSLLGLYHLLDWFAVDESNEVDPEFSARLTGIKLEMEPSLSFY

NKARNYATKKPYSVEKFKLNFQMPTLASGWDVNKEKNNGAILFVKNGLYYLGIIVI

PKQKGRYKALSFEPTEKTSEGFDKMYYDYFPDAAKMIPKCSTQLKAVTAHFQTHT

TPILLSNNFIEPLEITKEIYDLNNPEKEPKKFQTAYAKKTGDQKGYREALCKWIDFTR

DFLSKYTKTTSIDLSSLRPSSQYKDLGEYYAELNPLLYHISFQRIAEKEIMDAVETGK

LYLFQIYNKDFAKGHEIGKPNLHTLYWTGLFSPENLAKTSIKLNGQAELFYRPKSRM

KRMAHRLGEKMLNKKLKDQKTPIPDTLYQELYDYVNHRLSHDLSDEARALLPNVI

TKEVSHEIIKDRRFTSDKFFFHVPITLNYQAANSPSKFNQRVNAYLKEHPETPIIGIDR

GERNLIYITVIDSTGKILEQRSLNTIQQFDYQKKLDNREKERVAARQAWSVVGTIKD

LKQGYLSQVIHEIVDLMIHYQAVVVLENLNFGFKSKRTGIAEKAVYQQFEKMLIDK

LNCLVLKDYPAEKVGGVLNPYQLTDQFTSFAKMGTQSGFLFYVPAPYTSKIDPLTG

FVDPFVWKTIKNHESRKHFLEGFDFLHYDVKTGDFILHFKMNRNLSFQRGLPGFMP

AWDIVFEKNETQFDAKGTPFIAGKRIVPVIENHRFTGRYRDLYPANELIALLEEKGIV

FRDGSNILPKLLENDDSHAIDTMVALIRSVLQMRNSNAATGEDYINSPVRDLNGVC

FDSRFQNPEWPMDADANGAYHIALKGQLLLNHLKESKDLKLQNGISNQDWLAYIQ

ELRN*KRPAATKKAGQAKKKK*GSYPYDVPDYAYPYDVPDYAYPYDVPDYA

9- *Lachnospiraceae bacterium* MA2020 (Lb2Cpf1)

(SEQ ID NO: 61)
MYYESLTKQYPVSKTIRNELIPIGKTLDNIRQNNILESDVKRKQNYEHVK

GILDEYHKQLINEALDNCTLPSLKIAAEIYLKNQKEVSDREDFNKTQDLLRKEVVEK

LKAHENFTKIGKKDILDLLEKLPSISEDDYNALESFRNFYTYFTSYNKVRENLYSDK

EKSSTVAYRLINENFPKFLDNVKSYRFVKTAGILADGLGEEEQDSLFIVETFNKTLT

QDGIDTYNSQVGKINSSINLYNQKNQKANGFRKIPKMKMLYKQILSDREESFIDEFQ

SDEVLIDNVESYGSVLIESLKSSKVSAFFDALRESKGKNVYVKNDLAKTAMSNIVFE

NWRTFDDLLNQEYDLANENKKKDDKYFEKRQKELKKNKSYSLEHLCNLSEDSCN

LIENYIHQISDDIENIIINNETFLRIVINEHDRSRKLAKNRKAVKAIKDFLDSIKVLERE

-continued

LKLINSSGQELEKDLIVYSAHEELLVELKQVDSLYNMTRNYLTKKPFSTEKVKLNF
NRSTLLNGWDRNKETDNLGVLLLKDGKYYLGIMNTSANKAFVNPPVAKTEKVFK
KVDYKLLPVPNQMLPKVFFAKSNIDFYNPSSEIYSNYKKGTHKKGNMFSLEDCHNL
IDFFKESISKHEDWSKFGFKFSDTASYNDISEFYREVEKQGYKLTYTDIDETYINDLIE
RNELYLFQIYNKDFSMYSKGKLNLHTLYFMMLFDQRNIDDVVYKLNGEAEVFYRP
ASISEDELIIHKAGEEIKNKNPNRARTKETSTFSYDIVKDKRYSKDKFTLHIPITMNFG
VDEVKRFNDAVNSAIRIDENVNVIGIDRGERNLLYVVVIDSKGNILEQISLNSIINKE
YDIETDYHALLDEREGGRDKARKDWNTVENIRDLKAGYLSQVVNVVAKLVLKYN
AIICLEDLNFGFKRGRQKVEKQVYQKFEKMLIDKLNYLVIDKSREQTSPKELGGAL
NALQLTSKFKSFKELGKQSGVIYYVPAYLTSKIDPTTGFANLFYMKCENVEKSKRFF
DGFDFIRFNALENVFEFGFDYRSFTQRACGINSKWTVCTNGERIIKYRNPDKNNMFD
EKVVVVTDEMKNLFEQYKIPYEDGRNVKDMIISNEEAEFYRRLYRLLQQTLQMRN
STSDGTRDYIISPVKNKREAYFNSELSDGSVPKDADANGAYNIARKGLWVLEQIRQ
KSEGEKINLAMTNAEWLEYAQTHLL*KRPAATKKAGQAKKKK*GSYPYDVPDYAYPY
DVPDYAYPYDVPDYA

10- *Candidatus Methanoplasma termitum* (CMtCpf1)
(SEQ ID NO: 62)
MNNYDEFTKLYPIQKTIRFELKPQGRTMEHLETFNFFEEDRDRAEKYKIL
KEAIDEYHKKFIDEHLTNMSLDWNSLKQISEKYYKSREEKDKKVFLSEQKRMRQEI
VSEFKKDDRFKDLFSKKLFSELLKEEIYKKGNHQEIDALKSFDKFSGYFIGLHENRK
NMYSDGDEITAISNRIVNENFPKFLDNLQKYQEARKKYPEWIIKAESALVAHNIKM
DEVFSLEYFNKVLNQEGIQRYNLALGGYVTKSGEKMMGLNDALNLAHQSEKSSKG
RIHMTPLFKQILSEKESFSYIPDVFTEDSQLLPSIGGFFAQIENDKDGNIFDRALELISS
YAEYDTERIYIRQADINRVSNVIFGEWGTLGGLMREYKADSINDINLERTCKKVDK
WLDSKEFALSDVLEAIKRTGNNDAFNEYISKMRTAREKIDAARKEMKFISEKISGDE
ESIHIIKTLLDSVQQFLHFFNLFKARQDIPLDGAFYAEFDEVHSKLFAIVPLYNKVRN
YLTKNNLNTKKIKLNFKNPTLANGWDQNKVYDYASLIFLRDGNYYLGIINPKRKK
NIKFEQGSGNGPFYRKMVYKQIPGPNKNLPRVFLTSTKGKKEYKPSKEIIEGYEADK
HIRGDKFDLDFCHKLIDFFKESIEKHKDWSKFNFYFSPTESYGDISEFYLDVEKQGY
RMHFENISAETIDEYVEKGDLFLFQIYNKDFVKAATGKKDMHTIYWNAAFSPENLQ
DVVVKLNGEAELFYRDKSDIKEIVHREGEILVNRTYNGRTPVPDKIHKKLTDYHNG
RTKDLGEAKEYLDKVRYFKAHYDITKDRRYLNDKIYFHVPLTLNFKANGKKNLNK
MVIEKFLSDEKAHIIGIDRGERNLLYYSIIDRSGKIIDQQSLNVIDGFDYREKLNQREI
EMKDARQSWNAIGKIKDLKEGYLSKAVHEITKMAIQYNAIVVMEELNYGFKRGRF
KVEKQIYQKFENMLIDKMNYLVFKDAPDESPGGVLNAYQLTNPLESFAKLGKQTGI
LFYVPAAYTSKIDPTTGFVNLFNTSSKTNAQERKEFLQKFESISYSAKDGGIFAFAFD
YRKFGTSKTDHKNVWTAYTNGERMRYIKEKKRNELFDPSKEIKEALTSSGIKYDGG
QNILPDILRSNNNGLIYTMYSSFIAAIQMRVYDGKEDYIISPIKNSKGEFFRTDPKRRE
LPIDADANGAYNIALRGELTMRAIAEKFDPDSEKMAKLELKHKDWFEFMQTRGD*K*
*RPAATKKAGQAKKKK*GSYPYDVPDYAYPYDVPDYAYPYDVPDYA

11- *Eubacterium eligens* (EeCpf1)

(SEQ ID NO: 63)

MNGNRSIVYREFVGVIPVAKTLRNELRPVGHTQEHIIQNGLIQEDELRQE
KSTELKNIMDDYYREYIDKSLSGVTDLDFTLLFELMNLVQSSPSKDNKKALEKEQS
KMREQICTHLQSDSNYKNIFNAKLLKEILPDFIKNYNQYDVKDKAGKLETLALFNG
FSTYFTDFFEKRKNVFTKEAVSTSIAYRIVHENSLIFLANMTSYKKISEKALDEIEVIE
KNNQDKMGDWELNQIFNPDFYNMVLIQSGIDFYNEICGVVNAHMNLYCQQTKNN
YNLFKMRKLHKQILAYTSTSFEVPKMFEDDMSVYNAVNAFIDETEKGNIIGKLKDI
VNKYDELDEKRIYISKDFYETLSCFMSGNWNLITGCVENFYDENIHAKGKSKEEKV
KKAVKEDKYKSINDVNDLVEKYIDEKERNEFKNSNAKQYIREISNIITDTETAHLEY
DDHISLIESEEKADEMKKRLDMYMNMYHWAKAFIVDEVLDRDEMFYSDIDDIYNI
LENIVPLYNRVRNYVTQKPYNSKKIKLNFQSPTLANGWSQSKEFDNNAIILIRDNKY
YLAIFNAKNKPDKKIIQGNSDKKNDNDYKKMVYNLLPGANKMLPKVFLSKKGIET
FKPSDYIISGYNAHKHIKTSENFDISFCRDLIDYFKNSIEKHAEWRKYEFKFSATDSY
SDISEFYREVEMQGYRIDWTYISEADINKLDEEGKIYLFQIYNKDFAENSTGKENLH
TMYFKNIFSEENLKDIIIKLNGQAELFYRRASVKNPVKHKKDSVLVNKTYKNQLDN
GDVVRIPIPDDIYNEIYKMYNGYIKESDLSEAAKEYLDKVEVRTAQKDIVKDYRYT
VDKYFIHTPITINYKVTARNNVNDMVVKYIAQNDDIHVIGIDRGERNLIYISVIDSHG
NIVKQKSYNILNNYDYKKKLVEKEKTREYARKNWKSIGNIKELKEGYISGVVHEIA
MLIVEYNAIIAMEDLNYGFKRGRFKVERQVYQKFESMLINKLNYFASKEKSVDEPG
GLLKGYQLTYVPDNIKNLGKQCGVIFYVPAAFTSKIDPSTGFISAFNFKSISTNASRK
QFFMQFDEIRYCAEKDMFSFGFDYNNFDTYNITMGKTQWTVYTNGERLQSEFNNA
RRTGKTKSINLTETIKLLLEDNEINYADGHDIRIDMEKMDEDKKSEFFAQLLSLYKL
TVQMRNSYTEAEEQENGISYDKIISPVINDEGEFFDSDNYKESDDKECKMPKDADA
NGAYCIALKGLYEVLKIKSEWTEDGFDRNCLKLPHAEWLDFIQNKRYE*KRPAATKK*
*AGQAKKKKGS*__YPYDVPDYAYPYDVPDYAYPYDVPDYA__

12- *Moraxella bovoculi* 237 (MbCpf1)

(SEQ ID NO: 64)

MLFQDFTHLYPLSKTVRFELKPIDRTLEHIHAKNFLSQDETMADMHQKV
KVILDDYHRDFIADMMGEVKLTKLAEFYDVYLKFRKNPKDDELQKQLKDLQAVL
RKEIVKPIGNGGKYKAGYDRLFGAKLFKDGKELGDLAKFVIAQEGESSPKLAHLAH
FEKFSTYFTGFHDNRKNMYSDEDKHTAIAYRLIHENLPRFIDNLQILTTIKQKHSALY
DQIINELTASGLDVSLASHLDGYHKLLTQEGITAYNTLLGGISGEAGSPKIQGINELIN
SHHNQHCHKSERIAKLRPLHKQILSDGMSVSFLPSKFADDSEMCQAVNEFYRHYAD
VFAKVQSLFDGFDDHQKDGIYVEHKNLNELSKQAFGDFALLGRVLDGYYVDVVN
PEFNERFAKAKTDNAKAKLTKEKDKFIKGVHSLASLEQAIEHYTARHDDESVQAG
KLGQYFKHGLAGVDNPIQKIHNNHSTIKGFLERERPAGERALPKIKSGKNPEMTQLR
QLKELLDNALNVAHFAKLLTTKTTLDNQDGNFYGEFGVLYDELAKIPTLYNKVRD
YLSQKPFSTEKYKLNFGNPTLLNGWDLNKEKDNFGVILQKDGCYYLALLDKAHKK
VFDNAPNTGKSIYQKMIYKYLEVRKQFPKVFFSKEAIAINYHPSKELVEIKDKGRQR
SDDERLKLYRFILECLKIHPKYDKKFEGAIGDIQLFKKDKKGREVPISEKDLFDKING
IFSSKPKLEMEDFFIGEFKRYNPSQDLVDQYNIYKKIDSNDRKKENFYNNHPKFKK
DLVRYYYESMCKHEEWEESFEFSKKLQDIGCYVDVNELFTEIETRRLNYKISFCNIN

-continued

ADYIDELVEQGQLYLFQIYNKDFSPKAHGKPNLHTLYFKALFSEDNLADPIYKLNG

EAQIFYRKASLDMNETTIHRAGEVLENKNPDNPKKRQFVYDIIKDKRYTQDKFMLH

VPITMNFGVQGMTIKEFNKKVNQSIQQYDEVNVIGIDRGERHLLYLTVINSKGEILE

QCSLNDITTASANGTQMTTPYHKILDKREIERLNARVGWGEIETIKELKSGYLSHVV

HQISQLMLKYNAIVVLEDLNFGFKRGRFKVEKQIYQNFENALIKKLNHLVLKDKAD

DEIGSYKNALQLTNNFTDLKSIGKQTGFLFYVPAWNTSKIDPETGFVDLLKPRYENI

AQSQAFFGKFDKICYNADKDYFEFHIDYAKFTDKAKNSRQIWTICSHGDKRYVYD

KTANQNKGAAKGINVNDELKSLFARHHINEKQPNLVMDICQNNDKEFHKSLMYLL

KTLLALRYSNASSDEDFILSPVANDEGVFFNSALADDTQPQNADANGAYHIALKGL

WLLNELKNSDDLNKVKLAIDNQTWLNFAQNR*KRPAATKKAGQAKKKK*GSYPYDVP

DYAYPYDVPDYAYPYDVPDYA

13- *Leptospira inadai* (LiCpf1)

(SEQ ID NO: 65)

MEDYSGFVNIYSIQKTLRFELKPVGKTLEHIEKKGFLKKDKIRAEDYKAV

KKIIDKYHRAYIEEVFDSVLHQKKKKDKTRFSTQFIKEIKEFSELYYKTEKNIPDKER

LEALSEKLRKMLVGAFKGEFSEEVAEKYKNLFSKELIRNEIEKFCETDEERKQVSNF

KSFTTYFTGFHSNRQNIYSDEKKSTAIGYRIIHQNLPKFLDNLKIIESIQRRFKDFPWS

DLKKNLKKIDKNIKLTEYFSIDGFVNVLNQKGIDAYNTILGGKSEESGEKIQGLNEYI

NLYRQKNNIDRKNLPNVKILFKQILGDRETKSFIPEAFPDDQSVLNSITEFAKYLKLD

KKKKSIIAELKKFLSSFNRYELDGIYLANDNSLASISTFLFDDWSFIKKSVSFKYDES

VGDPKKKIKSPLKYEKEKEKWLKQKYYTISFLNDAIESYSKSQDEKRVKIRLEAYFA

EFKSKDDAKKQFDLLERIEEAYAIVEPLLGAEYPRDRNLKADKKEVGKIKDFLDSIK

SLQFFLKPLLSAEIFDEKDLGFYNQLEGYYEEIDSIGHLYNKVRNYLTGKIYSKEKFK

LNFENSTLLKGWDENREVANLCVIFREDQKYYLGVMDKENNTILSDIPKVKPNELF

YEKMVYKLIPTPHMQLPRIIFSSDNLSIYNPSKSILKIREAKSFKEGKNFKLKDCHKFI

DFYKESISKNEDWSRFDFKFSKTSSYENISEFYREVERQGYNLDFKKVSKFYIDSLVE

DGKLYLFQIYNKDFSIFSKGKPNLHTIYFRSLFSKENLKDVCLKLNGEAEMFFRKKSI

NYDEKKKREGHHPELFEKLKYPILKDKRYSEDKFQFHLPISLNFKSKERLNFNLKVN

EFLKRNKDINIIGIDRGERNLLYLVMINQKGEILKQTLLDSMQSGKGRPEINYKEKL

QEKEIERDKARKSWGTVENIKELKEGYLSIVIHQISKLMVENNAIVVLEDLNIGFKR

GRQKVERQVYQKFEKMLIDKLNFLVFKENKPTEPGGVLKAYQLTDEFQSFEKLSK

QTGFLFYVPSWNTSKIDPRTGFIDFLHPAYENIEKAKQWINKFDSIRFNSKMDWFEF

TADTRKFSENLMLGKNRVWVICTTNVERYFTSKTANSSIQYNSIQITEKLKELFVDIP

FSNGQDLKPEILRKNDAVFFKSLLFYIKTTLSLRQNNGKKGEEEKDFILSPVVDSKG

RFFNSLEASDDEPKDADANGAYHIALKGLMNLLVLNETKEENLSRPKWKIKNKDW

LEFVWERNR*KRPAATKKAGQAKKKK*GSYPYDVPDYAYPYDVPDYAYPYDVPDYA

14- *Lachnospiraceae bacterium* ND2006 (LbCpf1)

(SEQ ID NO: 66)

MSKLEKFTNCYSLSKTLRFKAIPVGKTQENIDNKRLLVEDEKRAEDYKG

VKKLLDRYYLSFINDVLHSIKLKNLNNYISLFRKKTRTEKENKELENLEINLRKEIAK

AFKGNEGYKSLFKKDIIETILPEFLDDKDEIALVNSFNGFTTAFTGFFDNRENMFSEE

AKSTSIAFRCINENLTRYISNMDIFEKVDAIFDKHEVQEIKEKILNSDYDVEDFFEGEF

-continued

FNFVLTQEGIDVYNAIIGGFVTESGEKIKGLNEYINLYNQKTKQKLPKFKPLYKQVL

SDRESLSFYGEGYTSDEEVLEVFRNTLNKNSEIFSSIKKLEKLFKNFDEYSSAGIFVK

NGPAISTISKDIFGEWNVIRDKWNAEYDDIHLKKKAVVTEKYEDDRRKSFKKIGSFS

LEQLQEYADADLSVVEKLKEIIQKVDEIYKVYGSSEKLFDADFVLEKSLKKNDAV

VAIMKDLLDSVKSFENYIKAFFGEGKETNRDESFYGDFVLAYDILLKVDHIYDAIRN

YVTQKPYSKDKFKLYFQNPQFMGGWDKDKETDYRATILRYGSKYYLAIMDKKYA

KCLQKIDKDDVNGNYEKINYKLLPGPNKMLPKVFFSKKWMAYYNPSEDIQKIYKN

GTFKKGDMFNLNDCHKLIDFFKDSISRYPKWSNAYDFNFSETEKYKDIAGFYREVE

EQGYKVSFESASKKEVDKLVEEGKLYMFQIYNKDFSDKSHGTPNLHTMYFKLLFD

ENNHGQIRLSGGAELFMRRASLKKEELVVHPANSPIANKNPDNPKKTTTLSYDVYK

DKRFSEDQYELHIPIAINKCPKNIFKINTEVRVLLKHDDNPYVIGIDRGERNLLYIVV

VDGKGNIVEQYSLNEIINNFNGIRIKTDYHSLLDKKEKERFEARQNWTSIENIKELKA

GYISQVVHKICELVEKYDAVIALEDLNSGFKNSRVKVEKQVYQKFEKMLIDKLNY

MVDKKSNPCATGGALKGYQITNKFESFKSMSTQNGFIFYIPAWLTSKIDPSTGFVNL

LKTKYTSTABSKKFISSFDRIMYVPEEDLFEFALDYKNFSRTDADYIKKWKLYSYGN

RIRIFRNPKKNNVFDWEEVCLTSAYKELFNKYGINYQQGDIRALLCEQSDKAFYSSF

MALMSLMLQMRNSITGRTDVDFLISPVKNSDGIFYDSRNYEAQENAILPKNADANG

AYNIARKVLWAIGQFKKAEDEKLDKVKIAISNKEWLEYAQTSVKH*KRPAATKKAGQ*

*AKKKKGS*YPYDVPDYAYPYDVPDYAYPYDVPDYA

15- *Porphyromonas crevioricanis* (PcCpf1)

(SEQ ID NO: 67)

MDSLKDFTNLYPVSKTLRFELKPVGKTLENIEKAGILKEDEHRAESYRRV

KKIIDTYHKVFIDSSLENMAKMGIENEIKAMLQSFCELYKKDHRTEGEDKALDKIRA

VLRGLIVGAFTGVCGRRENTVQNEKYESLFKEKLIKEILPDFVLSTEAESLPFSVEEA

TRSLKEFDSFTSYFAGFYENRKNIYSTKPQSTAIAYRLIHENLPKFIDNILVFQKIKEPI

AKELEHIRADFSAGGYIKKDERLEDIFSLNYYIEIVLSQAGIEKYNALIGKIVTEGDGE

MKGLNEHINLYNQQRGREDRLPLFRPLYKQILSDREQLSYLPESFEKDEELLRALKE

FYDHIAEDILGRTQQLMTSISEYDLSRIYVRNDSQLTDISKKMLGDWNAIYMARER

AYDHEQAPKRITAKYERDRIKALKGEESISLANLNSCIAFLDNVRDCRVDTYLSTLG

QKEGPHGLSNLVENVFASYHEAEQLLSFPYPEENNLIQDKDNVVLIKNLLDNISDLQ

RFLKPLWGMGDEPDKDERFYGEYNYIRGALDQVIPLYNKVRNYLTRKPYSTRKVK

LNFGNSQLLSGWDRNKEKDNSCVILRKGQNFYLAIMNNRHKRSFENKMLPEYKEG

EPYFEKMDYKFLPDPNKMLPKVFLSKKGIEIYKPSPKLLEQYGHGTHKKGDTFSMD

DLHELIDFFKHSIEAHEDWKQFGFKFSDTATYENVSSFYREVEDQGYKLSFRKVSES

YVYSLIDQGKLYLFQIYNKDFSPCSKGTPNLHTLYWRMLFDERNLADVIYKLDGKA

EIFFREKSLKNDHPTHPAGKPIKKKSRQKKGEESLFEYDLVKDRRYTMDKFQFHVPI

TMNFKCSAGSKVNDMVNAHIREAKDMHVIGIDRGERNLLYICVIDSRGTILDQISLN

TINDIDYHDLLESRDKDRQQEHRNWQTIEGIKELKQGYLSQAVHRIAELMVAYKAV

VALEDLNMGFKRGRQKVESSVYQQFEKQLIDKLNYLVDKKKRPEDIGGLLRAYQF

TAPFKSFKEMGKQNGFLFYIPAWNTSNIDPTTGFVNLFHVQYENVDKAKSFFQKFD

SISYNPKKDWFEFAFDYKNFTKKAEGSRSMWILCTHGSRIKNFRNSQKNGQWDSEE

FALTEAFKSLFVRYEIDYTADLKTAIVDEKQKDFFVDLLKLFKLTVQMRNSWKEKD

LDYLISPVAGADGRFFDTREGNKSLPKDADANGAYNIALKGLWALRQIRQTSEGGK

LKLAISNKEWLQFVQERSYEKD*KRPAATKKAGQAKKKKGS*YPYDVPDYAYPYDVP

DYAYPYDVPDYA

16- *Prevotella disiens* (PdCpf1)

(SEQ ID NO: 68)

MENYQEFTNLFQLNKTLRFELKPIGKTCELLEEGKIFASGSFLEKDKVRA

DNVSYVKKEIDKKHKIFIEETLSSFSISNDLLKQYFDCYNELKAFKKDCKSDEEEVK

KTALRNKCTSIQRAMREAISQAFLKSPQKKLLAIKNLIENVFKADENVQHFSEFTSY

FSGFETNRENFYSDEEKSTSIAYRLVHDNLPIFIKNIYIFEKLKEQFDAKTLSEIFENY

KLYVAGSSLDEVFSLEYFNNTLTQKGIDNYNAVIGKIVKEDKQEIQGLNEHINLYNQ

KHKDRRLPFFISLKKQILSDREALSWLPDMFKNDSEVIKALKGFYIEDGFENNVLTP

LATLLSSLDKYNLNGIFIRNNEALSSLSQNVYRNFSIDEAIDANAELQTFNNYELIAN

ALRAKIKKETKQGRKSFEKYEEYIDKKVKAIDSLSIQEINELVENYVSEFNSNSGNM

PRKVEDYFSLMRKGDFGSNDLIENIKTKLSAAEKLLGTKYQETAKDIFKKDENSKLI

KELLDATKQFQHFIKPLLGTGEEADRDLVFYGDFLPLYEKFEELTLLYNKVRNRLT

QKPYSKDKIRLCFNKPKLMTGWVDSKTEKSDNGTQYGGYLFRKKNEIGEYDYFLG

ISSKAQLFRKNEAVIGDYERLDYYQPKANTIYGSAYEGENSYKEDKKRLNKVIIAYI

EQIKQTNIKKSIIESISKYPNISDDDKVTPSSLLEKIKKVSIDSYNGILSFKSFQSVNKE

VIDNLLKTISPLKNKAEFLDLINKDYQIFTEVQAVIDEICKQKTFIYFPISNVELEKEM

GDKDKPLCLFQISNKDLSFAKTFSANLRKKRGAENLHTMLFKALMEGNQDNLDLG

SGAIFYRAKSLDGNKPTHPANEAIKCRNVANKDKVSLFTYDIYKNRRYMENKFLFH

LSIVQNYKAANDSAQLNSSATEYIRKADDLHIIGIDRGERNLLYYSVIDMKGNIVEQ

DSLNIIRNNDLETDYHDLLDKREKERKANRQNWEAVEGIKDLKKGYLSQAVHQIA

QLMLKYNAIIALEDLGQMFVTRGQKIEKAVYQQFEKSLVDKLSYLVDKKRPYNEL

GGILKAYQLASSITKNNSDKQNGFLFYVPAWNTSKIDPVTGFTDLLRPKAMTIKEA

QDFFGAFDNISYNDKGYFEFETNYDKFKIRMKSAQTRWTICTFGNRIKRKKDKNY

WNYEEVELTEEFKKLFKDSNIDYENCNLKEEIQNKDNRKFFDDLIKLLQLTLQMRN

SDDKGNDYIISPVANAEGQFFDSRNGDKKLPLDADANGAYNIARKGLWNIRQIKQT

KNDKKLNLSISSTEWLDFVREKPYLK*KRPAATKKAGQAKKKKGS*YPYDVPDYAYPY

DVPDYAYPYDVPDYA

17- *Porphyromonas macacae* (PmCpf1)

(SEQ ID NO: 69)

MKTQHFFEDFTSLYSLSKTIRFELKPIGKTLENIKKNGLIRRDEQRLDDYE

KLKKVIDEYHEDFIANILSSFSFSEEILQSYIQNLSESEARAKIEKTMRDTLAKAFSED

ERYKSIFKKELVKKDIPVWCPAYKSLCKKFDNFTTSLVPFHENRKNLYTSNEITASIP

YRIVHVNLPKFIQNIEALCELQKKMGADLYLEMMENLRNVWPSFVKTPDDLCNLK

TYNHLMVQSSISEYNRFVGGYSTEDGTKHQGINEWINIYRQRNKEMRLPGLVFLHK

QILAKVDSSSFISDTLENDDQVFCVLRQFRKLFWNTVSSKEDDAASLKDLFCGLSGY

DPEAIYVSDAHLATISKNIFDRWNYISDAIRRKTEVLMPRKKESVERYAEKISKQIKK

RQSYSLAELDDLLAHYSEESLPAGFSLLSYFTSLGGQKYLVSDGEVILYEEGSNIWD

EVLIAFRDLQVILDKDFTEKKLGKDEEAVSVIKKALDSALRLRKFFDLLSGTGAEIR

RDSSFYALYTDRMDKLKGLLKMYDKVRNYLTKKPYSIEKFKLHFDNPSLLSGWDK

NKELNNLSVIFRQNGYYYLGIIVITPKGKNLFKTLPKLGAEEMFYEKMEYKQIAEPM

LMLPKVFFPKKTKPAFAPDQSVVDIYNKKTFKTGQKGFNKKDLYRLIDFYKEALTV

HEWKLFNFSFSPTEQYRNIGEFFDEVREQAYKVSMVNVPASYIDEAVENGKLYLFQ

IYNKDFSPYSKGIPNLHTLYWKALFSEQNQSRVYKLCGGGELFYRKASLHMQDTTV

HPKGISIHKKNLNKKGETSLFNYDLVKDKRFTEDKFFFHVPISINYKNKKITNVNQM

VRDYIAQNDDLQIIGIDRGERNLLYISRIDTRGNLLEQFSLNVIESDKGDLRTDYQKI

LGDREQERLRRRQEWKSIESIKDLKDGYMSQVVHKICNMVVEHKAIVVLENLNLSF

MKGRKKVEKSVYEKFERMLVDKLNYLVVDKKNLSNEPGGLYAAYQLTNPLFSFE

ELHRYPQSGILFFVDPWNTSLTDPSTGFVNLLGRINYTNVGDARKFFDRFNAIRYDG

KGNILFDLDLSRFDVRVETQRKLWTLTTFGSRIAKSKKSGKWMVERIENLSLCFLEL

FEQFNIGYRVEKDLKKAILSQDRKEFYVRLIYLFNLMMQIRNSDGEEDYILSPALNE

KNLQFDSRLIEAKDLPVDADANGAYNVARKGLMVVQRIKRGDHESIHRIGRAQWL

RYVQEGIVE*KRPAATKKAGQAKKKK*GSYPYDVPDYAYPYDVPDYAYPYDVPDYA

18- *Thiomicrospira* sp. XS5 (TsCpf1)

(SEQ ID NO: 70)

MTKTFDSEFFNLYSLQKTVRFELKPVGETASFVEDFKNEGLKRVVSEDE

RRAVDYQKVKEIIDDYHRDFIEESLNYFPEQVSKDALEQAFHLYQKLKAAKVEERE

KALKEWEALQKKLREKVVKCFSDSNKARFSRIDKKELIKEDLINWLVAQNREDDIP

TVETFNNFTTYFTGPHENRKNIYSKDDHATAISFRLIHENLPKFFDNVISFNKLKEGF

PELKFDKVKEDLEVDYDLKHAFEIEYFVNFVTQAGIDQYNYLLGGKTLEDGTKKQ

GMNEQINLFKQQQTRDKARQIPKLIPLFKQILSERTESQSFIPKQFESDQELFDSLQKL

HNNCQDKFTVLQQAILGLAEADLKKVFIKTSDLNALSNTIFGNYSVFSDALNLYKES

LKTKKAQEAFEKLPAHSIHDLIQYLEQFNSSLDAEKQQSTDTVLNYFIKTDELYSRFI

KSTSEAFTQVQPLFELEALSSKRRPPESEDEGAKGQEGFEQIKRIKAYLDTLMEAVH

FAKPLYLVKGRKMIEGLDKDQSFYEAFEMAYQELESLIIPIYNKARSYLSRKPFKAD

KFKINFDNNTLLSGWDANKETANASILFKKDGLYYLGIMPKGKTFLFDYFVSSEDS

EKLKQRRQKTAEEALAQDGESYFEKIRYKLLPGASKMLPKVFFSNKNIGFYNPSDDI

LRIRNTASHTKNGTPQKGHSKVEFNLNDCHKMIDFFKSSIQKHPEWGSFGFTFSDTS

DFEDMSAFYREVENQGYVISFDKIKETYIQSQVEQGNLYLFQIYNKDFSPYSKGKPN

LHTLYWKALFEEANLNNVVAKLNGEAEIFFRRHSIKASDKVVHPANQAIDNKNPHT

EKTQSTFEYDLVKDKRYTQDKFFFHVPISLNFKAQGVSKFNDKVNGFLKGNPDVNI

IGIDRGERHLLYFTVVNQKGEILVQESLNTLMSDKGHVNDYQQKLDKKEQERDAA

RKSWTTVENIKELKEGYLSHVVHKLAHLIIKYNAIVCLEDLNFGFKRGRFKVEKQV

YQKFEKALIDKLNYLVFKEKELGEVGHYLTAYQLTAPFESFKKLGKQSGILFYVPA

DYTSKIDPTTGFVNFLDLRYQSVEKAKQLLSDFNAIRFNSVQNYFEFEIDYKKLTPK

RKVGTQSKWVICTYGDVRYQNRRNQKGHWETEEVNVTEKLKALFASDSKTTTVID

YANDDNLIDVILEQDKASFFKELLWLLKLTMTLRHSKIKSEDDFILSPVKNEQGEFY

DSRKAGEVWPKDADANGAYHIALKGLWNLQQINQWEKGKTLNLAIKNQDWFSFI

QEKPYQE*KRPAATKKAGQAKKKK*GSYPYDVPDYAYPYDVPDYAYPYDVPDYA

19- *Moraxella bovoculi* AAX08_00205 (Mb2Cpf1)

(SEQ ID NO: 71)

MLFQDFTHLYPLSKTVRFELKPIGRTLEHIHAKNFLSQDETMADMYQKV

KVILDDYHRDFIADMMGEVKLTKLAEFYDVYLKFRKNPKDDGLQKQLKDLQAVL

-continued

RKESVKPIGSGGKYKTGYDRLFGAKLFKDGKELGDLAKFVIAQEGESSPKLAHLAH

FEKFSTYFTGFHDNRKNMYSDEDKHTAIAYRLIHENLPRFIDNLQILTTIKQKHSALY

DQIINELTASGLDVSLASHLDGYHKLLTQEGITAYNRIIGEVNGYTNKHNQICHKSE

RIAKLRPLHKQILSDGMGVSFLPSKFADDSEMCQAVNEFYRHYTDVFAKVQSLFDG

FDDHQKDGIYVEHKNLNELSKQAFGDFALLGRVLDGYYVDVVNPEFNERFAKAKT

DNAKAKLTKEKDKFIKGVHSLASLEQAIEHHTARHDDESVQAGKLGQYFKHGLAG

VDNPIQKIHNNHSTIKGFLERERPAGERALPKIKSGKNPEMTQLRQLKELLDNALNV

AHFAKLLTTKTTLDNQDGNFYGEFGVLYDELAKIPTLYNKVRDYLSQKPFSTEKYK

LNFGNPTLLNGWDLNKEKDNFGVILQKDGCYYLALLDKAHKKVFDNAPNTGKNV

YQKMVYKLLPGPNKMLPKVFFAKSNLDYYNPSAELLDKYAKGTHKKGDNFNLKD

CHALIDFFKAGINKHPEWQHFGFKFSPTSSYRDLSDFYREVEPQGYQVKFVDINAD

YIDELVEQGKLYLFQIYNKDFSPKAHGKPNLHTLYFKALFSEDNLADPIYKLNGEA

QIFYRKASLDMNETTIHRAGEVLENKNPDNPKKRQFVYDIIKDKRYTQDKFMLHVP

ITMNFGVQGMTIKEFNKKVNQSIQQYDEVNVIGIDRGERHLLYLTVINSKGEILEQR

SLNDITTASANGTQVTTPYHKILDKREIERLNARVGWGEIETIKELKSGYLSHVVHQI

NQLMLKYNAIVVLEDLNFGFKRGRFKVEKQIYQNFENALIKKLNHLVLKDKADDEI

GSYKNALQLTNNFTDLKSIGKQTGFLFYVPAWNTSKIDPETGFVDLLKPRYENIAQS

QAFFGKFDKICYNTDKGYFEFHIDYAKFTDKAKNSRQKWAICSHGDKRYVYDKTA

NQNKGAAKGINVNDELKSLFARYHINDKQPNLVMDICQNNDKEFHKSLMCLLKTL

LALRYSNASSDEDFILSPVANDEGVFFNSALADDTQPQNADANGAYHIALKGLWLL

NELKNSDDLNKVKLAIDNQTWLNFAQNR*KRPAATKKAGQAKKKK*GSYPYDVPDYA

YPYDVPDYAYPYDVPDYA

20- *Moraxella bovoculi* AAX11_00205 (Mb3Cpf1)

(SEQ ID NO: 72)

MLFQDFTHLYPLSKTVRFELKPIGKTLEHIHAKNFLNQDETMADMYQKV

KAILDDYHRDFIADMMGEVKLTKLAEFYDVYLKFRKNPKDDGLQKQLKDLQAVL

RKEIVKPIGNGGKYKAGYDRLFGAKLFKDGKELGDLAKFVIAQEGESSPKLAHLAH

FEKFSTYFTGFHDNRKNMYSDEDKHTAIAYRLIHENLPRFIDNLQILATIKQKHSAL

YDQIINELTASGLDVSLASHLDGYHKLLTQEGITAYNTLLGGISGEAGSRKIQGINEL

INSHHNQHCHKSERIAKLRPLHKQILSDGMGVSFLPSKFADDSEVCQAVNEFYRHY

ADVFAKVQSLFDGFDDYQKDGIYVEYKNLNELSKQAFGDFALLGRVLDGYYVDV

VNPEFNERFAKAKTDNAKAKLTKEKDKFIKGVHSLASLEQAIEHYTARHDDESVQ

AGKLGQYFKHGLAGVDNPIQKIHNNHSTIKGFLERERPAGERALPKIKSDKSPEIRQ

LKELLDNALNVAHFAKLLTTKTTLHNQDGNFYGEFGALYDELAKIATLYNKVRDY

LSQKPFSTEKYKLNFGNPTLLNGWDLNKEKDNFGVILQKDGCYYLALLDKAHKKV

FDNAPNTGKSVYQKMIYKLLPGPNKMLPKVFFAKSNLDYYNPSAELLDKYAQGTH

KKGDNFNLKDCHALIDFFKAGINKHPEWQHFGFKFSPTSSYQDLSDFYREVEPQGY

QVKFVDINADYINELVEQGQLYLFQIYNKDFSPKAHGKPNLHTLYFKALFSEDNLV

NPIYKLNGEAEIFYRKASLDMNETTIHRAGEVLENKNPDNPKKRQFVYDIIKDKRYT

QDKFMLHVPITMNFGVQGMTIKEFNKKVNQSIQQYDEVNVIGIDRGERHLLYLTVI

NSKGEILEQRSLNDITTASANGTQMTTPYHKILDKREIERLNARVGWGEIETIKELKS

-continued

GYLSHVVHQISQLMLKYNAIVVLEDLNFGFKRGRFKVEKQIYQNFENALIKKLNHL

VLKDKADDEIGSYKNALQLTNNFTDLKSIGKQTGFLFYVPAWNTSKIDPETGFVDL

LKPRYENIAQSQAFFGKFDKICYNADRGYFEFHIDYAKFNDKAKNSRQIWKICSHG

DKRYVYDKTANQNKGATIGVNVNDELKSLFTRYHINDKQPNLVMDICQNNDKEFH

KSLMYLLKTLLALRYSNASSDEDFILSPVANDEGVFFNSALADDTQPQNADANGAY

HIALKGLWLLNELKNSDDLNKVKLAIDNQTWLNFAQNR*KRPAATKKAGQAKKKK*G

SYPYDVPDYAYPYDVPDYAYPYDVPDYA

21- *Butyrivibrio* sp. NC3005 (BsCpf1)
(SEQ ID NO: 73)
MYYQNLTKKYPVSKTIRNELIPIGKTLENIRKNNILESDVKRKQDYEHVK

GIMDEYHKQLINEALDNYMLPSLNQAAEIYLKKHVDVEDREEFKKTQDLLRREVT

GRLKEHENYTKIGKKDILDLLEKLPSISEEDYNALESFRNFYTYFTSYNKVRENLYS

DEEKSSTVAYRLINENLPKFLDNIKSYAFVKAAGVLADCIEEEEQDALFMVETFNM

TLTQEGIDMYNYQIGKVNSAINLYNQKNHKVEEFKKIPKMKVLYKQILSDREEVFI

GEFKDDETLLSSIGAYGNVLMTYLKSEKINIFFDALRESEGKNVYVKNDLSKTTMS

NIVFGSWSAFDELLNQEYDLANENKKKDDKYFEKRQKELKKNKSYTLEQMSNLSK

EDISPIENYIERISEDIEKICIYNGEFEKIVVNEHDSSRKLSKNIKAVKVIKDYLDSIKEL

EHDIKLINGSGQELEKNLVVYVGQEEALEQLRPVDSLYNLTRNYLTKKPFSTEKVK

LNFNKSTLLNGWDKNKETDNLGILFFKDGKYYLGIMNTTANKAFVNPPAAKTENV

FKKVDYKLLPGSNKMLPKVFFAKSNIGYYNPSTELYSNYKKGTHKKGPSFSIDDCH

NLIDFFKESIKKHEDWSKFGFEFSDTADYRDISEFYREVEKQGYKLTFTDIDESYIND

LIEKNELYLFQIYNKDFSEYSKGKLNLHTLYFMMLFDQRNLDNVVYKLNGEAEVF

YRPASIAENELVIHKAGEGIKNKNPNRAKVKETSTFSYDIVKDKRYSKYKFTLHIPIT

MNFGVDEVRRFNDVINNALRTDDNVNVIGIDRGERNLLYVVVINSEGKILEQISLNS

IINKEYDIETNYHALLDEREDDRNKARKDWNTIENIKELKTGYLSQVVNVVAKLVL

KYNAIICLEDLNFGFKRGRQKVEKQVYQKFEKMLIEKLNYLVIDKSREQVSPEKMG

GALNALQLTSKFKSFAELGKQSGIIYYVPAYLTSKIDPTTGFVNLFYIKYENIEKAKQ

FFDGFDFIRFNKKDDMFEFSFDYKSFTQKACGIRSKWIVYTNGERIIKYPNPEKNNLF

DEKVINVTDEIKGLFKQYRIPYENGEDIKEIIISKAEADFYKRLFRLLHQTLQMRNST

SDGTRDYIISPVKNDRGEFFCSEFSEGTMPKDADANGAYNIARKGLWVLEQIRQKD

EGEKVNLSMTNAEWLKYAQLHLL*KRPAATKKAGQAKKKK*GSYPYDVPDYAYPYD

VPDYAYPYDVPDYA

Further Cpf1 orthologs include:

NCBI WP_055225123.1
(SEQ ID NO: 74)
MNNGTNNFQNFIGISSLQKTLRNALIPTETTQQFIVKNGIIKEDELRGENR

QILKDIMDDYYRGFISETLSSIDDIDWTSLFEKMEIQLKNGDNKDTLIKEQTEYRKAI

HKKFANDDRFKNMFSAKLISDILPEFVIHNNNYSASEKEEKTQVIKLFSRFATSFKD

YFKNRANCFSADDISSSSCHRIVNDNAEIFFSNALVYRRIVKSLSNDDINKISGDMKD

SLKEMSLEETYSYEKYGEFITQEGISFYNDICGKVNSFMNLYCQKNKENKNLYKLQ

KLHKQILCIADTSYEVPYKFESDEEVYQSVNGFLDNISSKHIVERLRKIGDNYNGYN

LDKIYIVSKFYESVSQKTYRDWETINTALEIHYNNILPGNGKSKADKVKKAVKNDL

-continued

QKSITEINELVSNYKLCSDDNIKAETYIHEISHILNNFEAQELKYNPEIHLVESELKAS
ELKNVLDVIMNAFHWCSVFMTEELVDKDNNFYAELEEIYDEIYPVISLYNLVRNYV
TQKPYSTKKIKLNFGIPTLADGWSKSKEYSNNAIILMRDNLYYLGIFNAKNKPDKKII
EGNTSENKGDYKKMIYNLLPGPNKMIPKVFLSSKTGVETYKPSAYILEGYKQNKHI
KSSKDFDITFCHDLIDYFKNCIAIHPEWKNFGFDFSDTSTYEDISGFYREVELQGYKI
DWTYISEKDIDLLQEKGQLYLFQIYNKDFSKKSTGNDNLHTMYLKNLFSEENLKDI
VLKLNGEAEIFFRKSSIKNPIIHKKGSILVNRTYEAEEKDQFGNQIVRKNIPENIYQEL
YKYFNDKSDKELSDEAAKLKNVVGHHEAATNIVKDYRYTYDKYFLHMPITINFKA
NKTGFINDRILQYIAKEKDLHVIGIDRGERNLIYVSVIDTCGNIVEQKSFNIVNGYDY
QIKLKQQEGARQIARKEWKEIGKIKEIKEGYLSLVIHEISKMVIKYNAIIAMEDLSYG
FKKGRFKVERQVYQKFETMLINKLNYLVFKDISITENGGLLKGYQLTYIPDKLKNV
GHQCGCIFYVPAAYTSKIDPTTGFVNIFKFKDLTVDAKREFIKKFDSIRYDSEKNLFC
FTFDYNNFITQNTVMSKSSWSVYTYGVRIKRRFVNGRFSNESDTIDITKDMEKTLE
MTDINWRDGHDLRQDIIDYEIVQHIFEIFRLTVQMRNSLSELEDRDYDRLISPVLNEN
NIFYDSAKAGDALPKDADANGAYCTALKGLYEIKQITENWKEDGKFSRDKLKISNK
DWFDFIQNKRYL

NCBI WP_055237260.1

(SEQ ID NO: 75)
MNNGTNNFQNFIGISSLQKTLRNALIPTETTQQFIVKNGIIKEDELRGENR
QILKDIMDDYYRGFISETLSSIDDIDWTSLFEKMEIQLKNGDNKDTLIKEQAEKRKAI
YKKFADDDRFKNMFSAKLISDILPEFVIHNNNYSASEKEEKTQVIKLFSRFATSFKD
YFKNRANCFSADDISSSSCHRIVNDNAEIFFSNALVYRRIVKNLSNDDINKISGDMK
DSLKEMSLDEIYSYEKYGEFITQEGISFYNDICGKVNSFMNLYCQKNKENKNLYKL
RKLHKQILCIADTSYEVPYKFESDEEVYQSVNGFLDNISSKHIVERLRKIGDNYNGY
NLDKIYIVSRFYESVSQKTYRDWETINTALEIHYNNILPGNGKSKADKVKKAVKND
LQKSITEINELVSNYKLCPDDNIKAETYIHEISHILNNFEAQELKYNPEIHLVESELKA
SELKNVLDVIMNAFHWCSVFMTEELVDKDNNFYAELEEIYDEIYPVISLYNLVRNY
VTQKPYSTKKIKLNFGIPTLADGWSKSKEYSNNAIILMRDNLYYLGIFNAKNKPDK
KIIEGNTSENKGDYKKMIYNLLPGPNKMIPKVFLSSKTGVETYKPSAYILEGYKQNK
HLKSSKDFDITFCRDLIDYFKNCIAIHPEWKNFGFDFSDTSTYEDISGFYREVELQGY
KIDWTYISEKDIDLLQEKGQLYLFQIYNKDFSKKSTGNDNLHTMYLKNLFSEENLK
DIVLKLNGEAEIFFRKSSIKNPIIHKKGSILVNRTYEAEEKDQFGNIQIVRKTIPENIYQ
ELYKYFNDKSDKELSDEAAKLKNVVGHHEAATNIVKDYRYTYDKYFLHMPITINF
KANKTSFINDRILQYIAKENDLHVIGIDRGERNLIYVSVIDTCGNIVEQKSFNIVNGY
DYQIKLKQQEGARQIARKEWKEIGKIKEIKEGYLSLVIHEISKMVIKYNAIIAMEDLS
YGFKKGRFKVERQVYQKFETMLINKLNYLVFKDISITENGGLLKGYQLTYIPEKLK
NVGHQCGCIFYVPAAYTSKIDPTTGFANIFKFKDLTVDAKREFIKKFDSIRYDSEKNL
FCFTFDYNNFITQNTVMSKSSWSVYTYGVRIKRRFVNGRFSNESDTIDITKDMEKTL
EMTDINWRDGHDLRQDIIDYEIVQHIFEIFKLTVQMRNSLSELEDRDYDRLISPVLNE
NNIFYDSAKAGDALPKDADANGAYCTALKGLYEIKQITENWKEDGKFSRDKLKISN
KDWFDFIQNKRYL

-continued

NCBI WP_055272206.1

(SEQ ID NO: 76)
MNNGTNNFQNFIGISSLQKTLRNALTPTETTQQFIVKNGIIKEDELRGENR

QILKDIMDDYYRGFISETLSSIDDIDWTSLFEKMEIQLKNGDNKDTLIKEQAEKRKAI

YKKFADDDRFKNMFSAKLISDILPEFVIHNNNYSASEKEEKTQVIKLFSRFATSFKD

YFKNRANCFSADDISSSSCHRIVNDNAEIFFSNALVYRRIVKNLSNDDINKISGDMK

DSLKKMSLEKIYSYEKYGEFITQEGISFYNDICGKVNSFMNLYCQKNKENKNLYKL

RKLHKQILCIADTSYEVPYKFESDEEVYQSVNGFLDNISSKHIVERLRKIGDNYNGY

NLDKIYIVSKFYESVSQKTYRDWETINTALEIHYNNILPGNGKSKADKVKKAVKND

LQKSITEINELVSNYKLCPDDNIKAETYIHEISHILNNFEAQELKYNPEIHLVESELKA

SELKNVLDVIMNAFHWCSVFMTEELVDKDNNFYAELEEIYDEIYPVISLYNLVRNY

VTQKPYSTKKIKLNFGIPTLADGWSKSKEYSNNAIILMRDNLYYLGIFNAKNKPEKK

IIEGNTSENKGDYKKMIYNLLPGPNKMIPKVFLSSKTGVETYKPSAYILEGYKQNKH

LKSSKDFDITFCRDLIDYFKNCIAIHPEWKNFGFDFSDTSTYEDISGFYREVELQGYKI

DWTYISEKDIDLLQEKGQLYLFQIYNKDFSKKSTGNDNLHTMYLKNLFSEENLKDV

VLKLNGEAEIFFRKSSIKNPIIHKKGSILVNRTYEAEEKDQFGNIQIVRKTIPENIYQEL

YKYFNDKSDKELSDEAAKLKNAVGHHEAATNIVKDYRYTYDKYFLHMPITINFKA

NKTSFINDRILQYIAKEKDLHVIGIDRGERNLIYVSVIDTCGNIVEQKSFNIVNGYDY

QIKLKQQEGARQIARKEWKEIGKIKEIKEGYLSLVIHEISKMVIKYNAIIAMEDLSYG

FKKGRFKVERQVYQKFETMLINKLNYLVFKDISITENGGLLKGYQLTYIPEKLKNV

GHQCGCIFYVPAAYTSKIDPTTGFVNIFKFKDLTVDAKREFIKKFDSIRYDSDKNLFC

FTFDYNNFITQNTVMSKSSWSVYTYGVRIKRRFVNGRFSNESDTIDITKDMETLE

MTDINWRDGHDLRQDIIDYEIVQHIFEIFKLTVQMRNSLSELEDRNYDRLISPVLNEN

NIFYDSAKAGDALPKDADANGAYCTALKGLYEIKQITENWKEDGKFSRDKLKISNK

DWFDFIQNKRYL

GenBank OLA16049.1

(SEQ ID NO: 77)
MNNGTNNFQNFIGISSLQKTLRNALIPTETTQQFIVKNGIIKEDELRGKNR

QILKDIMDDYYRGFISETLSSIDDIDWTSLFEKMEIQLKNGDNKDTLIKEQAEKRKAI

YKKFADDDRFKNMFSAKLISDILPEFVIHNNNYSASEKKEKTQVIKLFSRFATSFKD

YFKNRANCFSADDISSSSCHRIVNDNAEIFFSNALVYRRIVKNLSNDDINKISGDMK

DSLKEMSLEEIYSYEKYGEFITQEGISFYNDICGKVNSFMNLYCQKNKENKNLYKLR

KLHKQILCIADTSYEVPYKFESDEEVYQSVNGFLDNISSKHIVERLRKIGDNYNDYN

LDKIYIVSKFYESVSQKTYRDWETINTALEIHYNNILPGNGKSKADKVKKAVKNDL

QKSITEINELVSNYKLCSDDNIKAETYIHEISHILNNFEAHELKYNPEIHLVESELKAS

ELKNVLDIIMNAFHWCSVFMTEELVDKDNNFYAELEEIYDEIYPVISLYNLVRNYVT

QKPYSTKKIKLNFGIPTLADGWSKSKEYSNNAIILMRDNLYYLGIFNAKNKPDKKIIE

GNTSENKGDYKKMIYNLLPGPNKMIPKVFLSSKTGVETYKPSAYILEGYKQNKHLK

SSKDFDITFCHDLIDYFKNCIAIHPEWKNFGFDFSDTSAYEDISGFYREVELQGYKID

WTYISEKDIDLLQEKGQLYLFQIYNKDFSKKSTGNDNLHTMYLKNLFSEENLKDIV

LKLNGEAEIFFRKSSIKNPIIHKKGSILVNRTYEAEEKDQFGNIQIVRKTIPENIYQELY

KYFNDKSDKELSDEAAKLKNVVGHHEAATNIVKDYRYTYDKYFLHMPITINFKAN

KTSFINDRILQYIAKEKDLHVIGIDRGERNLIYVSVIDTCGNIVEQKSFNIVNGYDYQI

```
KLKQQEGARQIARKEWKEIGKIKEIKEGYLSLVIHEISKMVIKYNAIIAMEDLSYGFK

KGRFKVERQVYQKFETMLINKLNYLVFKDISITENGGLLKGYQLTYIPDKLKNVGH

QCGCIFYVPAAYTSKIDPTTGFVNIFKFKDLTVDAKREFIKKFDSIRYDSEKNLFCFT

FDYNNFITQNTVMSKSSWSVYTYGVRIKRRFVNGRFSNESDTIDITKDMEKTLEMT

DINWRDGHDLRQDIIDYEIVQHIFEIFKLTVQMRNSLSELEDRDYDRLISPVLNENNI

FYDSAKAGYALPKDADANGAYCIALKGLYEIKQITENWKEDGKFSRDKLKISNKD

WFDFIQNKRYL
```

Modified Cpf1 Enzymes

In particular embodiments, it is of interest to make use of an engineered Cpf1 protein as defined herein, such as Cpf1, wherein the protein complexes with a nucleic acid molecule comprising RNA to form a CRISPR complex, wherein when in the CRISPR complex, the nucleic acid molecule targets one or more target polynucleotide loci, the protein comprises at least one modification compared to unmodified Cpf1 protein, and wherein the CRISPR complex comprising the modified protein has altered activity as compared to the complex comprising the unmodified Cpf1 protein. It is to be understood that when referring herein to CRISPR "protein", the Cpf1 protein preferably is a modified CRISPR-Cas protein (e.g. having increased or decreased (or no) enzymatic activity, such as without limitation including Cpf1. The term "CRISPR protein" may be used interchangeably with "CRISPR-Cas protein", irrespective of whether the CRISPR protein has altered, such as increased or decreased (or no) enzymatic activity, compared to the wild type CRISPR protein.

Computational analysis of the primary structure of Cpf1 nucleases reveals three distinct regions. First a C-terminal RuvC like domain, which is the only functional characterized domain. Second a N-terminal alpha-helical region and thirst a mixed alpha and beta region, located between the RuvC like domain and the alpha-helical region.

Several small stretches of unstructured regions are predicted within the Cpf1 primary structure. Unstructured regions, which are exposed to the solvent and not conserved within different Cpf1 orthologs, are preferred sides for splits and insertions of small protein sequences. In addition, these sides can be used to generate chimeric proteins between Cpf1 orthologs.

Based on the above information, mutants can be generated which lead to inactivation of the enzyme or which modify the double strand nuclease to nickase activity. In alternative embodiments, this information is used to develop enzymes with reduced off-target effects (described elsewhere herein).

In certain of the above-described Cpf1 enzymes, the enzyme is modified by mutation of one or more residues (in the RuvC domain) including but not limited to positions R909, R912, R930, R947, K949, R951, R955, K965, K968, K1000, K1002, R1003, K1009, K1017, K1022, K1029, K1035, K1054, K1072, K1086, R1094, R1095, K1109, K1118, K1142, K1150, K1158, K1159, R1220, R1226, R1242, and/or R1252 with reference to amino acid position numbering of AsCpf1 (Acidaminococcus sp. BV3L6). In certain embodiments, the Cpf1 enzymes comprising said one or more mutations have modified, more preferably increased specificity for the target.

In certain of the above-described non-naturally-occurring CRISPR-Cas proteins, the enzyme is modified by mutation of one or more residues (in the RAD50) domain including but not limited positions K324, K335, K337, R331, K369, K370, R386, R392, R393, K400, K404, K406, K408, K414, K429, K436, K438, K459, K460, K464, R670, K675, R681, K686, K689, R699, K705, R725, K729, K739, K748, and/or K752 with reference to amino acid position numbering of AsCpf1 (Acidaminococcus sp. BV3L6). In certain embodiments, the Cpf1 enzymes comprising said one or more mutations have modified, more preferably increased specificity for the target.

In certain of the Cpf1 enzymes, the enzyme is modified by mutation of one or more residues including but not limited positions R912, T923, R947, K949, R951, R955, K965, K968, K1000, R1003, K1009, K1017, K1022, K1029, K1072, K1086, F1103, R1226, and/or R1252 with reference to amino acid position numbering of AsCpf1 (Acidaminococcus sp. BV3L6). In certain embodiments, the Cpf1 enzymes comprising said one or more mutations have modified, more preferably increased specificity for the target.

In certain embodiments, the Cpf1 enzyme is modified by mutation of one or more residues including but not limited positions R833, R836, K847, K879, K881, R883, R887, K897, K900, K932, R935, K940, K948, K953, K960, K984, K1003, K1017, R1033, R1138, R1165, and/or R1252 with reference to amino acid position numbering of LbCpf1 (Lachnospiraceae bacterium ND2006). In certain embodiments, the Cpf1 enzymes comprising said one or more mutations have modified, more preferably increased specificity for the target.

In certain embodiments, the Cpf1 enzyme is modified by mutation of one or more residues including but not limited positions K15, R18, K26, Q34, R43, K48, K51, R56, R84, K85, K87, N93, R103, N104, T118, K123, K134, R176, K177, R192, K200, K226, K273, K275, T291, R301, K307, K369, S404, V409, K414, K436, K438, K468, D482, K516, R518, K524, K530, K532, K548, K559, K570, R574, K592, D596, K603, K607, K613, C647, R681, K686, H720, K739, K748, K757, T766, K780, R790, P791, K796, K809, K815, T816, K860, R862, R863, K868, K897, R909, R912, T923, R947, K949, R951, R955, K965, K968, K1000, R1003, K1009, K1017, K1022, K1029, A1053, K1072, K1086, F1103, S1209, R1226, R1252, K1273, K1282, and/or K1288 with reference to amino acid position numbering of AsCpf1 (Acidaminococcus sp. BV3L6). In certain embodiments, the Cpf1 enzymes comprising said one or more mutations have modified, more preferably increased specificity for the target.

In certain embodiments, the enzyme is modified by mutation of one or more residues including but not limited positions K15, R18, K26, R34, R43, K48, K51, R56, K87, K88, D90, K96, K106, K107, K120, Q125, K143, R186, K187, R202, K210, K235, K296, K298, K314, K320, K326, K397, K444, K449, E454, A483, E491, K527, K541, K581, R583, K589, K595, K597, K613, K624, K635, K639, K656, K660, K667, K671, K677, K719, K725, K730, K763, K782, K791, R800, K809, K823, R833, K834, K839, K852, K858, K859, K869, K871, R872, K877, K905, R918, R921, K932, I960, K962, R964, R968, K978, K981, K1013, R1016, K1021, K1029, K1034, K1041, K1065, K1084, and/or K1098 with reference to amino acid position numbering of FnCpf1 (*Francisella novicida* U112). In certain embodiments, the Cpf1 enzymes comprising said one or more mutations have modified, more preferably increased specificity for the target.

In certain embodiments, the enzyme is modified by mutation of one or more residues including but not limited positions K15, R18, K26, K34, R43, K48, K51, R56, K83, K84, R86, K92, R102, K103, K116, K121, R158, E159, R174, R182, K206, K251, K253, K269, K271, K278, P342, K380, R385, K390, K415, K421, K457, K471, A506, R508, K514, K520, K522, K538, Y548, K560, K564, K580, K584, K591, K595, K601, K634, K640, R645, K679, K689, K707, T716, K725, R737, R747, R748, K753, K768, K774, K775, K785, K787, R788, Q793, K821, R833, R836, K847, K879, K881, R883, R887, K897, K900, K932, R935, K940, K948, K953, K960, K984, K1003, K1017, R1033, K1121, R1138, R1165, K1190, K1199, and/or K1208 with reference to amino acid position numbering of LbCpf1 (*Lachnospiraceae bacterium* ND2006). In certain embodiments, the Cpf1 enzymes comprising said one or more mutations have modified, more preferably increased specificity for the target.

In certain embodiments, the enzyme is modified by mutation of one or more residues including but not limited positions K14, R17, R25, K33, M42, Q47, K50, D55, K85, N86, K88, K94, R104, K105, K118, K123, K131, R174, K175, R190, R198, I221, K267, Q269, K285, K291, K297, K357, K403, K409, K414, K448, K460, K501, K515, K550, R552, K558, K564, K566, K582, K593, K604, K608, K623, K627, K633, K637, E643, K780, Y787, K792, K830, Q846, K858, K867, K876, K890, R900, K901, M906, K921, K927, K928, K937, K939, R940, K945, Q975, R987, R990, K1001, R1034, I1036, R1038, R1042, K1052, K1055, K1087, R1090, K1095, N1103, K1108, K1115, K1139, K1158, R1172, K1188, K1276, R1293, A1319, K1340, K1349, and/or K1356 with reference to amino acid position numbering of MbCpf1 (*Moraxella bovoculi* 237). In certain embodiments, the Cpf1 enzymes comprising said one or more mutations have modified, more preferably increased specificity for the target.

In certain of the above-described Cpf1 enzymes, the enzyme is modified by mutation of one or more residues including but not limited to positions D917, E1006, E1028, D1227, D1255A, N1257, according to FnCpf1 protein or any corresponding ortholog. In an aspect the invention provides a herein-discussed composition wherein the Cpf1 enzyme is an inactivated enzyme which comprises one or more mutations selected from the group consisting of D917A, E1006A, E1028A, D1227A, D1255A, N1257A, D917A, E1006A, E1028A, D1227A, D1255A and N1257A according to FnCpf1 protein or corresponding positions in a Cpf1 ortholog. In an aspect the invention provides a herein-discussed composition, wherein the CRISPR enzyme comprises D917, or E1006 and D917, or D917 and D1255, according to FnCpf1 protein or a corresponding position in a Cpf1 ortholog.

In one embodiment, the Cpf1 protein is modified with a mutation at S1228 (e.g., S1228A) with reference to amino acid position numbering of AsCpf1. See Yamano et al., *Cell* 165:949-962 (2016), which is incorporated herein by reference in its entirety.

In certain embodiments, the Cpf1 protein has been modified to recognize a non-natural PAM, such as recognizing a PAM having a sequence or comprising a sequence YCN, YCV, AYV, TYV, RYN, RCN, TGYV, NTTN, TTN, TRTN, TYTV, TYCT, TYCN, TRTN, NTTN, TACT, TYCC, TRTC, TATV, NTTV, TTV, TSTG, TVTS, TYYS, TCYS, TBYS, TCYS, TNYS, TYYS, TNTN, TSTG, TTCC, TCCC, TATC, TGTG, TCTG, TYCV, or TCTC. In particular embodiments, said mutated Cpf1 comprises one or more mutated amino acid residue at position 11, 12, 13, 14, 15, 16, 17, 34, 36, 39, 40, 43, 46, 47, 50, 54, 57, 58, 111, 126, 127, 128, 129, 130, 131, 132, 133, 134, 135, 136, 157, 158, 159, 160, 161, 162, 163, 164, 165, 166, 167, 168, 169, 170, 171, 172, 173, 174, 175, 176, 177, 178, 532, 533, 534, 535, 536, 537, 538, 539, 540, 541, 542, 543, 544, 545, 546, 547, 548, 549, 550, 551, 552, 553, 554, 555, 556, 565, 566, 567, 568, 569, 570, 571, 572, 573, 574, 575, 592, 593, 594, 595, 596, 597, 598, 599, 600, 601, 602, 603, 604, 605, 606, 607, 608, 609, 610, 611, 612, 613, 614, 615, 616, 617, 618, 619, 620, 626, 627, 628, 629, 630, 631, 632, 633, 634, 635, 636, 637, 638, 642, 643, 644, 645, 646, 647, 648, 649, 651, 652, 653, 654, 655, 656, 676, 679, 680, 682, 683, 684, 685, 686, 687, 688, 689, 690, 691, 692, 693, 707, 711, 714, 715, 716, 717, 718, 719, 720, 721, 722, 739, 765, 768, 769, 773, 777, 778, 779, 780, 781, 782, 783, 784, 785, 786, 871, 872, 873, 874, 875, 876, 877, 878, 879, 880, 881, 882, 883, 884, or 1048 of AsCpf1 or a position corresponding thereto in a Cpf1 ortholog; preferably, one or more mutated amino acid residue at position 130, 131, 132, 133, 134, 135, 136, 162, 163, 164, 165, 166, 167, 168, 169, 170, 171, 172, 173, 174, 175, 176, 177, 536, 537, 538, 539, 540, 541, 542, 543, 544, 545, 546, 547, 548, 549, 550, 551, 552, 570, 571, 572, 573, 595, 596, 597, 598, 599, 600, 601, 602, 603, 604, 605, 606, 607, 608, 609, 610, 611, 612, 613, 614, 615, 630, 631, 632, 646, 647, 648, 649, 650, 651, 652, 653, 683, 684, 685, 686, 687, 688, 689, or 690.

In certain embodiments, the Cpf1 protein is modified to have increased activity, i.e. wider PAM specificity. In particular embodiments, the Cpf1 protein is modified by mutation of one or more residues including but not limited positions 539, 542, 547, 548, 550, 551, 552, 167, 604, and/or 607 of AsCpf1, or the corresponding position of an AsCpf1 orthologue, homologue, or variant, preferably mutated amino acid residues at positions 542 or 542 and 607, wherein said mutations preferably are 542R and 607R, such as S542R and K607R; or preferably mutated amino acid residues at positions 542 and 548 (and optionally 552), wherein said mutations preferably are 542R and 548V (and optionally 552R), such as S542R and K548V (and optionally N552R); or at position 532, 538, 542, and/or 595 of LbCpf1, or the corresponding position of an AsCpf1 orthologue, homologue, or variant, preferably mutated amino acid residues at positions 532 or 532 and 595, wherein said mutations preferably are 532R and 595R, such as G532R and K595R; or preferably mutated amino acid residues at positions 532 and 538 (and optionally 542), wherein said mutations preferably are 532R and 538V (and optionally 542R), such as G532R and K538V (and optionally Y542R), most preferably wherein said mutations are S542R and K607R, S542R and K548V, or S542R, K548V and N552R of AsCpf1.

Deactivated/Inactivated Cpf1 Protein

Where the Cpf1 protein has nuclease activity, the Cpf1 protein may be modified to have diminished nuclease activity e.g., nuclease inactivation of at least 70%, at least 80%, at least 90%, at least 95%, at least 97%, or 100% as compared with the wild type enzyme; or to put in another way, a Cpf1 enzyme having advantageously about 0% of the nuclease activity of the non-mutated or wild type Cpf1 enzyme or CRISPR-Cas protein, or no more than about 3% or about 5% or about 10% of the nuclease activity of the non-mutated or wild type Cpf1 enzyme, e.g. of the non-mutated or wild type *Francisella novicida* U112 (FnCpf1), *Acidaminococcus* sp. BV3L6 (AsCpf1), *Lachnospiraceae bacterium* ND2006 (LbCpf1) or *Moraxella bovoculi* 237 (MbCpf1) Cpf1 enzyme or CRISPR-Cas protein. This is possible by introducing mutations into the nuclease domains of the Cpf1 and orthologs thereof.

In preferred embodiments of the present invention at least one Cpf1 protein is used which is a Cpf1 nickase. More particularly, a Cpf1 nickase is used which does not cleave the target strand but is capable of cleaving only the strand which is complementary to the target strand, i.e. the non-target DNA strand also referred to herein as the strand which is not complementary to the guide sequence. More particularly the Cpf1 nickase is a Cpf1 protein which comprises a mutation in the arginine at position 1226A in the Nuc domain of Cpf1 from *Acidaminococcus* sp., or a corresponding position in a Cpf1 ortholog. In further particular embodiments, the enzyme comprises an arginine-to-alanine substitution or an R1226A mutation. It will be understood by the skilled person that where the enzyme is not AsCpf1, a mutation may be made at a residue in a corresponding position. In particular embodiments, the Cpf1 is FnCpf1 and the mutation is at the arginine at position R1218. In particular embodiments, the Cpf1 is LbCpf1 and the mutation is at the arginine at position R1138. In particular embodiments, the Cpf1 is MbCpf1 and the mutation is at the arginine at position R1293.

In certain embodiments, use is made additionally or alternatively of a CRISPR-Cas protein which is engineered and can comprise one or more mutations that reduce or eliminate a nuclease activity. The amino acid positions in the FnCpf1p RuvC domain include but are not limited to D917A, E1006A, E1028A, D1227A, D1255A, N1257A, D917A, E1006A, E1028A, D1227A, D1255A and N1257A. Applicants have also identified a putative second nuclease domain which is most similar to PD-(D/E)XK nuclease superfamily and HincII endonuclease like. The point mutations to be generated in this putative nuclease domain to substantially reduce nuclease activity include but are not limited to N580A, N584A, T587A, W609A, D610A, K613A, E614A, D616A, K624A, D625A, K627A and Y629A. In a preferred embodiment, the mutation in the FnCpf1p RuvC domain is D917A or E1006A, wherein the D917A or E1006A mutation completely inactivates the DNA cleavage activity of the FnCpf1 effector protein. In another embodiment, the mutation in the FnCpf1p RuvC domain is D1255A, wherein the mutated FnCpf1 effector protein has significantly reduced nucleolytic activity.

More particularly, the inactivated Cpf1 enzymes include enzymes mutated in amino acid positions As908, As993, As1263 of AsCpf1 or corresponding positions in Cpf1 orthologs. Additionally, the inactivated Cpf1 enzymes include enzymes mutated in amino acid position Lb832, 925, 947 or 1180 of LbCpf1 or corresponding positions in Cpf1 orthologs. More particularly, the inactivated Cpf1 enzymes include enzymes comprising one or more of mutations AsD908A, AsE993A, AsD1263A of AsCpf1 or corresponding mutations in Cpf1 orthologs. Additionally, the inactivated Cpf1 enzymes include enzymes comprising one or more mutations LbD832A, E925A, D947A or D1180A of LbCpf1 or corresponding mutations in Cpf1 orthologs.

Mutations can also be made at neighboring residues, e.g., at amino acids near those indicated above that participate in the nuclease activity. In some embodiments, only the RuvC domain is inactivated, and in other embodiments, another putative nuclease domain is inactivated, wherein the effector protein complex functions as a nickase and cleaves only one DNA strand. In a preferred embodiment, the other putative nuclease domain is a HincII-like endonuclease domain.

The inactivated Cpf1 or Cpf1 nickase may have associated (e.g., via fusion protein) one or more functional domains, including for example, an cytidine deaminase or catalytic domain thereof. In some cases it is advantageous that additionally at least one heterologous NLS is provided. In some instances, it is advantageous to position the NLS at the N terminus. In general, the positioning of the one or more functional domain on the inactivated Cpf1 or Cpf1 nickase is one which allows for correct spatial orientation for the functional domain to affect the target with the attributed functional effect. For example, when the functional domain is an cytidine deaminase catalytic domain thereof, the cytidine deaminase catalytic domain is placed in a spatial orientation which allows it to contact and deaminate a target adenine. This may include positions other than the N-/C-terminus of Cpf1. In some embodiments, the cytidine deaminase protein or catalytic domain thereof is inserted into an internal loop of Cpf1.

Determination of PAM

Determination of PAM can be ensured as follows. This experiment closely parallels similar work in *E. coli* for the heterologous expression of StCas9 (Sapranauskas, R. et al. Nucleic Acids Res 39, 9275-9282 (2011)). Applicants introduce a plasmid containing both a PAM and a resistance gene into the heterologous *E. coli*, and then plate on the corresponding antibiotic. If there is DNA cleavage of the plasmid, Applicants observe no viable colonies.

In further detail, the assay is as follows for a DNA target. Two *E. coli* strains are used in this assay. One carries a plasmid that encodes the endogenous effector protein locus from the bacterial strain. The other strain carries an empty plasmid (e.g. pACYC184, control strain). All possible 7 or 8 bp PAM sequences are presented on an antibiotic resistance plasmid (pUC19 with ampicillin resistance gene). The PAM is located next to the sequence of proto-spacer 1 (the DNA target to the first spacer in the endogenous effector protein locus). Two PAM libraries were cloned. One has a 8 random bp 5' of the proto-spacer (e.g. total of 65536 different PAM sequences=complexity). The other library has 7 random bp 3' of the proto-spacer (e.g. total complexity is 16384 different PAMs). Both libraries were cloned to have in average 500 plasmids per possible PAM. Test strain and control strain were transformed with 5'PAM and 3'PAM library in separate transformations and transformed cells were plated separately on ampicillin plates. Recognition and subsequent cutting/interference with the plasmid renders a cell vulnerable to ampicillin and prevents growth. Approximately 12 h after transformation, all colonies formed by the test and control strains where harvested and plasmid DNA was isolated. Plasmid DNA was used as template for PCR amplification and subsequent deep sequencing. Representation of all PAMs in the untransformed libraries showed the expected representation of PAMs in transformed cells. Representation of all PAMs found in control strains showed the actual representation. Representation of all PAMs in test strain showed which PAMs are not recognized by the enzyme and comparison to the control strain allows extracting the sequence of the depleted PAM.

The following PAMs have been identified for certain wild-type Cpf1 orthologues: the *Acidaminococcus* sp. BV3L6 Cpf1 (AsCpf1), *Lachnospiraceae bacterium* ND2006 Cpf1 (LbCpf1) and *Prevotella albensis* (PaCpf1) can cleave target sites preceded by a TTTV PAM, where V is A/C or G, FnCpf1p, can cleave sites preceded by TTN, where N is A/C/G or T. The *Moraxella bovoculi* AAX08_00205, *Moraxella* bovoculi AAX11_00205, *Butyrivibrio* sp. NC3005, *Thiomicrospira* sp. XS5, or *Lachnospiraceae bacterium* MA2020 PAM is 5' TTN, where N is A/C/G or T. The natural PAM sequence is TTTV or BTTV, wherein B is T/C or G and V is A/C or G and the effector protein is *Moraxella lacunata* Cpf1.

Delivery

In some embodiments, the components of the CD-functionalized CRISPR-Cas system may be delivered in various form, such as combinations of DNA/RNA or RNA/RNA or protein RNA. For example, the Cpf1 protein may be delivered as a DNA-coding polynucleotide or an RNA-coding polynucleotide or as a protein. The guide may be delivered may be delivered as a DNA-coding polynucleotide or an RNA. All possible combinations are envisioned, including mixed forms of delivery.

In some aspects, the invention provides methods comprising delivering one or more polynucleotides, such as or one or more vectors as described herein, one or more transcripts thereof, and/or one or proteins transcribed therefrom, to a host cell.

Vectors

In general, the term "vector" refers to a nucleic acid molecule capable of transporting another nucleic acid to which it has been linked. It is a replicon, such as a plasmid, phage, or cosmid, into which another DNA segment may be inserted so as to bring about the replication of the inserted segment. Generally, a vector is capable of replication when associated with the proper control elements. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double-stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Vectors for and that result in expression in a eukaryotic cell can be referred to herein as "eukaryotic expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell). Advantageous vectors include lentiviruses and adeno-associated viruses, and types of such vectors can also be selected for targeting particular types of cells.

With regards to recombination and cloning methods, mention is made of U.S. patent application Ser. No. 10/815,730, published Sep. 2, 2004 as US 2004-0171156 A1, the contents of which are herein incorporated by reference in their entirety.

The term "regulatory element" is intended to include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). With regards to regulatory sequences, mention is made of U.S. patent application Ser. No. 10/491,026, the contents of which are incorporated by reference herein in their entirety. With regards to promoters, mention is made of PCT publication WO 2011/028929 and U.S. application Ser. No. 12/511,940, the contents of which are incorporated by reference herein in their entirety.

Advantageous vectors include lentiviruses and adeno-associated viruses, and types of such vectors can also be selected for targeting particular types of cells.

In particular embodiments, use is made of bicistronic vectors for the guide RNA and (optionally modified or mutated) the CRISPR-Cas protein fused to cytidine deaminase. Bicistronic expression vectors for guide RNA and (optionally modified or mutated) CRISPR-Cas protein fused to cytidine deaminase are preferred. In general and particularly in this embodiment, (optionally modified or mutated) CRISPR-Cas protein fused to cytidine deaminase is preferably driven by the CBh promoter. The RNA may preferably be driven by a Pol III promoter, such as a U6 promoter. Ideally the two are combined.

Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein. Examples of suitable inducible non-fusion *E. coli* expression vectors include pTrc (Amrann et al., (1988) Gene 69:301-315) and pET 1id (Studier et al., GENE EXPRESSION TECHNOLOGY: METHODS IN ENZYMOLOGY 185, Academic Press, San Diego, Calif. (1990) 60-89). In some embodiments, a vector is a yeast expression vector. Examples of vectors for expression in yeast *Saccharomyces cerevisiae* include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.). In some embodiments, a vector drives protein expression in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268-277), lymphoid-specific promoters (Calame and Eaton, 1988. *Adv. Immunol.* 43: 235-275), in particular promoters of T cell receptors (Winoto and Baltimore, 1989. *EMBO J.* 8: 729-733) and immunoglobulins (Baneiji, et al., 1983. *Cell* 33: 729-740; Queen and Baltimore, 1983. *Cell* 33: 741-748), neuron-specific promoters (e.g., the neurofilament promoter; Byrne and Ruddle, 1989. *Proc. Natl. Acad. Sci. USA* 86: 5473-5477), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. *Science* 249: 374-379) and the α-fetoprotein promoter (Campes and Tilghman, 1989. *Genes Dev.* 3: 537-546). With regards to these prokaryotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety. In some embodiments, a regulatory element is operably linked to one or more elements of a CRISPR system so as to drive expression of the one or more elements of the CRISPR system.

In some embodiments, one or more vectors driving expression of one or more elements of a nucleic acid-targeting system are introduced into a host cell such that expression of the elements of the nucleic acid-targeting system direct formation of a nucleic acid-targeting complex at one or more target sites. For example, a nucleic acid-targeting effector enzyme and a nucleic acid-targeting guide RNA could each be operably linked to separate regulatory elements on separate vectors. RNA(s) of the nucleic acid-targeting system can be delivered to a transgenic nucleic acid-targeting effector protein animal or mammal, e.g., an animal or mammal that constitutively or inducibly or conditionally expresses nucleic acid-targeting effector protein; or an animal or mammal that is otherwise expressing nucleic acid-targeting effector proteins or has cells containing nucleic acid-targeting effector proteins, such as by way of prior administration thereto of a vector or vectors that code for and express in vivo nucleic acid-targeting effector proteins. Alternatively, two or more of the elements expressed from the same or different regulatory elements, may be combined in a single vector, with one or more additional vectors providing any components of the nucleic acid-targeting system not included in the first vector. nucleic acid-targeting system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a nucleic acid-targeting effector protein and the nucleic acid-targeting guide RNA, embedded within one or more intron sequences (e.g., each in a different intron, two or more in at least one intron, or all in a single intron). In some embodiments, the nucleic acid-targeting effector protein and the nucleic acid-targeting guide RNA may be operably linked to and expressed from the same promoter. Delivery vehicles, vectors, particles, nanoparticles, formulations and components thereof for expression of one or more elements of a nucleic acid-targeting system are as used in the foregoing documents, such as WO 2014/093622 (PCT/US2013/074667). In some embodiments, a vector comprises one or more insertion sites, such as a restriction endonuclease recognition sequence (also referred to as a "cloning site"). In some embodiments, one or more insertion sites (e.g., about or more than about 1, 2, 3, 4, 5, 6, 7, 8, 9, 10, or more insertion sites) are located upstream and/or downstream of one or more sequence elements of one or more vectors. When multiple different guide sequences are used, a single expression construct may be used to target nucleic acid-targeting activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell. In some embodiments, a vector comprises a regulatory element operably linked to an enzyme-coding sequence encoding a nucleic acid-targeting effector protein. Nucleic acid-targeting effector protein or nucleic acid-targeting guide RNA or RNA(s) can be delivered separately; and advantageously at least one of these is delivered via a particle complex. nucleic acid-targeting effector protein mRNA can be delivered prior to the nucleic acid-targeting guide RNA to give time for nucleic acid-targeting effector protein to be expressed. Nucleic acid-targeting effector protein mRNA might be administered 1-12 hours (preferably around 2-6 hours) prior to the administration of nucleic acid-targeting guide RNA. Alternatively, nucleic acid-targeting effector protein mRNA and nucleic acid-targeting guide RNA can be administered together. Advantageously, a second booster dose of guide RNA can be administered 1-12 hours (preferably around 2-6 hours) after the initial administration of nucleic acid-targeting effector protein mRNA+ guide RNA. Additional administrations of nucleic acid-targeting effector protein mRNA and/or guide RNA might be useful to achieve the most efficient levels of genome modification.

Conventional viral and non-viral based gene transfer methods can be used to introduce nucleic acids in mammalian cells or target tissues. Such methods can be used to administer nucleic acids encoding components of a nucleic acid-targeting system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology, Doerfler and Bohm (eds) (1995); and Yu et al., Gene Therapy 1:13-26 (1994).

Methods of non-viral delivery of nucleic acids include lipofection, nucleofection, microinjection, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. Nos. 5,049,386, 4,946,787; and 4,897,355 and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration).

Plasmid delivery involves the cloning of a guide RNA into a CRISPR-Cas protein expressing plasmid and transfecting the DNA in cell culture. Plasmid backbones are available commercially and no specific equipment is required. They have the advantage of being modular, capable of carrying different sizes of CRISPR-Cas coding sequences (including those encoding larger sized proteins) as well as selection markers. Both an advantage of plasmids is that they can ensure transient, but sustained expression. However, delivery of plasmids is not straightforward such that in vivo efficiency is often low. The sustained expression can also be disadvantageous in that it can increase off-target editing. In addition excess build-up of the CRISPR-Cas protein can be toxic to the cells. Finally, plasmids always hold the risk of random integration of the dsDNA in the host genome, more particularly in view of the double-stranded breaks being generated (on and off-target).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787). This is discussed more in detail below.

The use of RNA or DNA viral based systems for the delivery of nucleic acids takes advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700).

In applications where transient expression is preferred, adenoviral based systems may be used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989).

The invention provides AAV that contains or consists essentially of an exogenous nucleic acid molecule encoding a CRISPR system, e.g., a plurality of cassettes comprising or consisting a first cassette comprising or consisting essentially of a promoter, a nucleic acid molecule encoding a CRISPR-associated (Cas) protein (putative nuclease or helicase proteins), e.g., Cpf1 and a terminator, and one or more, advantageously up to the packaging size limit of the vector, e.g., in total (including the first cassette) five, cassettes comprising or consisting essentially of a promoter, nucleic acid molecule encoding guide RNA (gRNA) and a terminator (e.g., each cassette schematically represented as Promoter-gRNA1-terminator, Promoter-gRNA2-terminator . . . Promoter-gRNA(N)-terminator, where N is a number that can be inserted that is at an upper limit of the packaging size limit of the vector), or two or more individual rAAVs, each containing one or more than one cassette of a CRISPR system, e.g., a first rAAV containing the first cassette comprising or consisting essentially of a promoter, a nucleic acid molecule encoding Cas, e.g., Cas (Cpf1) and a terminator, and a second rAAV containing one or more cassettes each comprising or consisting essentially of a promoter, nucleic acid molecule encoding guide RNA (gRNA) and a terminator (e.g., each cassette schematically represented as Promoter-gRNA1-terminator, Promoter-gRNA2-terminator . . . Promoter-gRNA(N)-terminator, where N is a number that can be inserted that is at an upper limit of the packaging size limit of the vector). Alternatively, because Cpf1 can process its own crRNA/gRNA, a single crRNA/gRNA array can be used for multiplex gene editing. Hence, instead of including multiple cassettes to deliver the gRNAs, the rAAV may contain a single cassette comprising or consisting essentially of a promoter, a plurality of crRNA/gRNA, and a terminator (e.g., schematically represented as Promoter-gRNA1-gRNA2 . . . gRNA(N)-terminator, where N is a number that can be inserted that is at an upper limit of the packaging size limit of the vector). See Zetsche et al Nature Biotechnology 35, 31-34 (2017), which is incorporated herein by reference in its entirety. As rAAV is a DNA virus, the nucleic acid molecules in the herein discussion concerning AAV or rAAV are advantageously DNA. The promoter is in some embodiments advantageously human Synapsin I promoter (hSyn). Additional methods for the delivery of nucleic acids to cells are known to those skilled in the art. See, for example, US20030087817, incorporated herein by reference.

In another embodiment, Cocal vesiculovirus envelope pseudotyped retroviral vector particles are contemplated (see, e.g., US Patent Publication No. 20120164118 assigned to the Fred Hutchinson Cancer Research Center). Cocal virus is in the Vesiculovirus genus, and is a causative agent of vesicular stomatitis in mammals. Cocal virus was originally isolated from mites in Trinidad (Jonkers et al., Am. J. Vet. Res. 25:236-242 (1964)), and infections have been identified in Trinidad, Brazil, and Argentina from insects, cattle, and horses. Many of the vesiculoviruses that infect mammals have been isolated from naturally infected arthropods, suggesting that they are vector-borne. Antibodies to vesiculoviruses are common among people living in rural areas where the viruses are endemic and laboratory-acquired; infections in humans usually result in influenza-like symptoms. The Cocal virus envelope glycoprotein shares 71.5% identity at the amino acid level with VSV-G Indiana, and phylogenetic comparison of the envelope gene of vesiculoviruses shows that Cocal virus is serologically distinct from, but most closely related to, VSV-G Indiana strains among the vesiculoviruses. Jonkers et al., Am. J. Vet. Res. 25:236-242 (1964) and Travassos da Rosa et al., Am. J. Tropical Med. & Hygiene 33:999-1006 (1984). The Cocal vesiculovirus envelope pseudotyped retroviral vector particles may include for example, lentiviral, alpharetroviral, betaretroviral, gammaretroviral, deltaretroviral, and epsilon-retroviral vector particles that may comprise retroviral Gag, Pol, and/or one or more accessory protein(s) and a Cocal vesiculovirus envelope protein. Within certain aspects of these embodiments, the Gag, Pol, and accessory proteins are lentiviral and/or gammaretroviral.

In some embodiments, a host cell is transiently or non-transiently transfected with one or more vectors described herein. In some embodiments, a cell is transfected as it naturally occurs in a subject optionally to be reintroduced therein. In some embodiments, a cell that is transfected is taken from a subject. In some embodiments, the cell is derived from cells taken from a subject, such as a cell line. A wide variety of cell lines for tissue culture are known in the art. Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKa, MiaPaCell, Panc1, PC-3, TF1, CTLL-2, C1R, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR293, BxPC3, C3H-10T1/2, C6/36, Cal-27, CHO, CHO-7, CHO-IR, CHO-K1, CHO-K2, CHO-T, CHO Dhfr -/-, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)).

In particular embodiments, transient expression and/or presence of one or more of the components of the CD-functionalized CRISPR system can be of interest, such as to reduce off-target effects. In some embodiments, a cell transfected with one or more vectors described herein is used to establish a new cell line comprising one or more vector-derived sequences. In some embodiments, a cell transiently transfected with the components of a CD-functionalized CRISPR system as described herein (such as by transient transfection of one or more vectors, or transfection with RNA), and modified through the activity of a CRISPR complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

In some embodiments it is envisaged to introduce the RNA and/or protein directly to the host cell. For instance, the CRISPR-Cas protein can be delivered as encoding mRNA together with an in vitro transcribed guide RNA. Such methods can reduce the time to ensure effect of the CRISPR-Cas protein and further prevents long-term expression of the CRISPR system components.

In some embodiments the RNA molecules of the invention are delivered in liposome or lipofectin formulations and the like and can be prepared by methods well known to those skilled in the art. Such methods are described, for example, in U.S. Pat. Nos. 5,593,972, 5,589,466, and 5,580,859, which are herein incorporated by reference. Delivery systems aimed specifically at the enhanced and improved delivery of siRNA into mammalian cells have been developed, (see, for example, Shen et al FEBS Let. 2003, 539: 111-114; Xia et al., Nat. Biotech. 2002, 20:1006-1010; Reich et al., Mol. Vision. 2003, 9: 210-216; Sorensen et al., J. Mol. Biol. 2003, 327: 761-766; Lewis et al., Nat. Gen. 2002, 32: 107-108 and Simeoni et al., NAR 2003, 31, 11: 2717-2724) and may be applied to the present invention. siRNA has recently been successfully used for inhibition of gene expression in primates (see for example, Tolentino et al., Retina 24(4):660 which may also be applied to the present invention).

Indeed, RNA delivery is a useful method of in vivo delivery. It is possible to deliver Cpf1, cytidine deaminase, and guide RNA into cells using liposomes or nanoparticles. Thus delivery of the CRISPR-Cas protein, such as a Cpf1, the delivery of the cytidine deaminase (which may be fused to the CRISPR-Cas protein or an adaptor protein), and/or delivery of the RNAs of the invention may be in RNA form and via microvesicles, liposomes or particle or particles. For example, Cpf1 mRNA, cytidine deaminase mRNA, and guide RNA can be packaged into liposomal particles for delivery in vivo. Liposomal transfection reagents such as lipofectamine from Life Technologies and other reagents on the market can effectively deliver RNA molecules into the liver.

Means of delivery of RNA also preferred include delivery of RNA via particles (Cho, S., Goldberg, M., Son, S., Xu, Q., Yang, F., Mei, Y., Bogatyrev, S., Langer, R. and Anderson, D., Lipid-like nanoparticles for small interfering RNA delivery to endothelial cells, Advanced Functional Materials, 19: 3112-3118, 2010) or exosomes (Schroeder, A., Levins, C., Cortez, C., Langer, R., and Anderson, D., Lipid-based nanotherapeutics for siRNA delivery, Journal of Internal Medicine, 267: 9-21, 2010, PMID: 20059641). Indeed, exosomes have been shown to be particularly useful in delivery siRNA, a system with some parallels to the CRISPR system. For instance, El-Andaloussi S, et al. ("Exosome-mediated delivery of siRNA in vitro and in vivo." Nat Protoc. 2012 December; 7(12):2112-26. doi: 10.1038/nprot.2012.131. Epub 2012 Nov. 15.) describe how exosomes are promising tools for drug delivery across different biological barriers and can be harnessed for delivery of siRNA in vitro and in vivo. Their approach is to generate targeted exosomes through transfection of an expression vector, comprising an exosomal protein fused with a peptide ligand. The exosomes are then purified and characterized from transfected cell supernatant, then RNA is loaded into the exosomes. Delivery or administration according to the invention can be performed with exosomes, in particular but not limited to the brain. Vitamin E (α-tocopherol) may be conjugated with CRISPR-Cas and delivered to the brain along with high density lipoprotein (HDL), for example in a similar manner as was done by Uno et al. (HUMAN GENE THERAPY 22:711-719 (June 2011)) for delivering short-interfering RNA (siRNA) to the brain. Mice were infused via Osmotic minipumps (model 1007D; Alzet, Cupertino, CA) filled with phosphate-buffered saline (PBS) or free Tocsi-BACE or Toc-siBACE/HDL and connected with Brain Infusion Kit 3 (Alzet). A brain-infusion cannula was placed about 0.5 mm posterior to the bregma at midline for infusion into the dorsal third ventricle. Uno et al. found that as little as 3 nmol of Toc-siRNA with HDL could induce a target reduction in comparable degree by the same ICV infusion method. A similar dosage of CRISPR-Cas conjugated to α-tocopherol and co-administered with HDL targeted to the brain may be contemplated for humans in the present invention, for example, about 3 nmol to about 3 μmol of CRISPR-Cas targeted to the brain may be contemplated. Zou et al. ((HUMAN GENE THERAPY 22:465-475 (April 2011)) describes a method of lentiviral-mediated delivery of short-hairpin RNAs targeting PKCγ for in vivo gene silencing in the spinal cord of rats. Zou et al. administered about 10 μl of a recombinant lentivirus having a titer of $1 \times 10^9$ transducing units (TU)/ml by an intrathecal catheter. A similar dosage of CRISPR-Cas expressed in a lentiviral vector targeted to the brain may be contemplated for humans in the present invention, for example, about 10-50 ml of CRISPR-Cas targeted to the brain in a lentivirus having a titer of $1 \times 10^9$ transducing units (TU)/ml may be contemplated.

Dosage of Vectors

In some embodiments, the vector, e.g., plasmid or viral vector is delivered to the tissue of interest by, for example, an intramuscular injection, while other times the delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector choice, the target cell, organism, or tissue, the general condition of the subject to be treated, the degree of transformation/modification sought, the administration route, the administration mode, the type of transformation/modification sought, etc.

Such a dosage may further contain, for example, a carrier (water, saline, ethanol, glycerol, lactose, sucrose, calcium phosphate, gelatin, dextran, agar, pectin, peanut oil, sesame oil, etc.), a diluent, a pharmaceutically-acceptable carrier (e.g., phosphate-buffered saline), a pharmaceutically-acceptable excipient, and/or other compounds known in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable exemplary ingredients include microcrystalline cellulose, carboxymethylcellulose sodium, polysorbate 80, phenyl-ethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof. A thorough discussion of pharmaceutically acceptable excipients is available in REMINGTON'S PHARMACEUTICAL SCIENCES (Mack Pub. Co., N.J. 1991) which is incorporated by reference herein.

In an embodiment herein the delivery is via an adenovirus, which may be at a single booster dose containing at least $1 \times 10^5$ particles (also referred to as particle units, pu) of adenoviral vector. In an embodiment herein, the dose preferably is at least about $1 \times 10^6$ particles (for example, about $1 \times 10^6$-$1 \times 10^{12}$ particles), more preferably at least about $1 \times 10^7$ particles, more preferably at least about $1 \times 10^8$ particles (e.g., about $1 \times 10^8$-$1 \times 10^{11}$ particles or about $1 \times 10^8$-$1 \times 10^{12}$ particles), and most preferably at least about $1 \times 10^0$ particles (e.g., about $1 \times 10^9$-$1 \times 10^{10}$ particles or about $1 \times 10^9$-$1 \times 10^{12}$ particles), or even at least about $1 \times 10^{10}$ particles (e.g., about $1 \times 10^{10}$-$1 \times 10^{12}$ particles) of the adenoviral vector. Alternatively, the dose comprises no more than about $1 \times 10^{14}$ particles, preferably no more than about $1 \times 10^{13}$ particles, even more preferably no more than about $1 \times 10^{12}$ particles, even more preferably no more than about $1 \times 10^{11}$ particles, and most preferably no more than about $1 \times 10^{10}$ particles (e.g., no more than about $1 \times 10^9$ articles). Thus, the dose may contain a single dose of adenoviral vector with, for example, about $1 \times 10^6$ particle units (pu), about $2 \times 10^6$ pu, about $4 \times 10^6$ pu, about $1 \times 10^7$ pu, about $2 \times 10^7$ pu, about $4 \times 10^7$ pu, about $1 \times 10^8$ pu, about $2 \times 10^8$ pu, about $4 \times 10^8$ pu, about $1 \times 10^9$ pu, about $2 \times 10^9$ pu, about $4 \times 10^9$ pu, about $1 \times 10^{10}$ pu, about $2 \times 10^{10}$ pu, about $4 \times 10^{10}$ pu, about $1 \times 10^{11}$ pu, about $2 \times 10^{11}$ pu, about $4 \times 10^{11}$ pu, about $1 \times 10^{12}$ pu, about $2 \times 10^{12}$ pu, or about $4 \times 10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In an embodiment herein, the delivery is via an AAV. A therapeutically effective dosage for in vivo delivery of the AAV to a human is believed to be in the range of from about 20 to about 50 ml of saline solution containing from about $1 \times 10^{10}$ to about $1 \times 10^{10}$ functional AAV/ml solution. The dosage may be adjusted to balance the therapeutic benefit against any side effects. In an embodiment herein, the AAV dose is generally in the range of concentrations of from about $1 \times 10^5$ to $1 \times 10^{50}$ genomes AAV, from about $1 \times 10^8$ to $1 \times 10^{20}$ genomes AAV, from about $1 \times 10^{10}$ to about $1 \times 10^{16}$ genomes, or about $1 \times 10^{11}$ to about $1 \times 10^{16}$ genomes AAV. A human dosage may be about $1 \times 10^{13}$ genomes AAV. Such concentrations may be delivered in from about 0.001 ml to about 100 ml, about 0.05 to about 50 ml, or about 10 to about 25 ml of a carrier solution. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

In an embodiment herein the delivery is via a plasmid. In such plasmid compositions, the dosage should be a sufficient amount of plasmid to elicit a response. For instance, suitable quantities of plasmid DNA in plasmid compositions can be from about 0.1 to about 2 mg, or from about 1 g to about 10 g per 70 kg individual. Plasmids of the invention will generally comprise (i) a promoter; (ii) a sequence encoding a CRISPR-Cas protein, operably linked to said promoter; (iii) a selectable marker; (iv) an origin of replication; and (v) a transcription terminator downstream of and operably linked to (ii). The plasmid can also encode the RNA components of a CRISPR complex, but one or more of these may instead be encoded on a different vector.

The doses herein are based on an average 70 kg individual. The frequency of administration is within the ambit of the medical or veterinary practitioner (e.g., physician, veterinarian), or scientist skilled in the art. It is also noted that mice used in experiments are typically about 20 g and from mice experiments one can scale up to a 70 kg individual.

The dosage used for the compositions provided herein include dosages for repeated administration or repeat dosing. In particular embodiments, the administration is repeated within a period of several weeks, months, or years. Suitable assays can be performed to obtain an optimal dosage regime. Repeated administration can allow the use of lower dosage, which can positively affect off-target modifications.

RNA Delivery

In particular embodiments, RNA based delivery is used. In these embodiments, mRNA of the CRISPR-Cas protein, mRNA of the cytidine deaminase (which may be fused to a CRISPR-Cas protein or an adaptor), are delivered together with in vitro transcribed guide RNA. Liang et al. describes efficient genome editing using RNA based delivery (Protein Cell. 2015 May; 6(5): 363-372). In some embodiments, the mRNA(s) encoding Cpf1 and/or cytidine deaminase can be chemically modified, which may lead to improved activity compared to plasmid-encoded Cpf1 and/or cytidine deaminase. For example, uridines in the mRNA(s) can be partially or fully substituted with pseudouridine ($\Psi$), $N^1$-methylpseudouridine (me$^1\Psi$), 5-methoxyuridine (5moU). See Li et al., Nature Biomedical Engineering 1, 0066 DOI:10.1038/s41551-017-0066 (2017), which is incorporated herein by reference in its entirety.

RNP

In particular embodiments, pre-complexed guide RNA, CRISPR-Cas protein, and cytidine deaminase (which may be fused to a CRISPR-Cas protein or an adaptor) are delivered as a ribonucleoprotein (RNP). RNPs have the advantage that they lead to rapid editing effects even more so than the RNA method because this process avoids the need for transcription. An important advantage is that both RNP delivery is transient, reducing off-target effects and toxicity issues. Efficient genome editing in different cell types has been observed by Kim et al. (2014, Genome Res. 24(6):1012-9), Paix et al. (2015, Genetics 204(1):47-54), Chu et al. (2016, BMC Biotechnol. 16:4), and Wang et al. (2013, Cell. 9; 153(4):910-8).

In particular embodiments, the ribonucleoprotein is delivered by way of a polypeptide-based shuttle agent as described in WO2016161516. WO2016161516 describes efficient transduction of polypeptide cargos using synthetic peptides comprising an endosome leakage domain (ELD) operably linked to a cell penetrating domain (CPD), to a histidine-rich domain and a CPD. Similarly these polypeptides can be used for the delivery of CRISPR-effector based RNPs in eukaryotic cells.

Particles

In some aspects or embodiments, a composition comprising a delivery particle formulation may be used. In some aspects or embodiments, the formulation comprises a CRISPR complex, the complex comprising a CRISPR protein and a guide which directs sequence-specific binding of the CRISPR complex to a target sequence. In some embodiments, the delivery particle comprises a lipid-based particle, optionally a lipid nanoparticle, or cationic lipid and optionally biodegradable polymer. In some embodiments, the cationic lipid comprises 1,2-dioleoyl-3-trimethylammonium-propane (DOTAP). In some embodiments, the hydrophilic polymer comprises ethylene glycol or polyethylene glycol. In some embodiments, the delivery particle further comprises a lipoprotein, preferably cholesterol. In some embodiments, the delivery particles are less than 500 nm in diameter, optionally less than 250 nm in diameter, optionally less than 100 nm in diameter, optionally about 35 nm to about 60 nm in diameter.

Several types of particle delivery systems and/or formulations are known to be useful in a diverse spectrum of biomedical applications. In general, a particle is defined as a small object that behaves as a whole unit with respect to its transport and properties. Particles are further classified according to diameter. Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm.

As used herein, a particle delivery system/formulation is defined as any biological delivery system/formulation which includes a particle in accordance with the present invention. A particle in accordance with the present invention is any entity having a greatest dimension (e.g. diameter) of less than 100 microns (µm). In some embodiments, inventive particles have a greatest dimension of less than 10 µm. In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm.

In terms of this invention, it is preferred to have one or more components of CRISPR complex, e.g., CRISPR-Cas protein or mRNA, or cytidine deaminase (which may be fused to a CRISPR-Cas protein or an adaptor) or mRNA, or guide RNA delivered using nanoparticles or lipid envelopes. Other delivery systems or vectors are may be used in conjunction with the nanoparticle aspects of the invention.

In general, a "nanoparticle" refers to any particle having a diameter of less than 1000 nm. In certain preferred embodiments, nanoparticles of the invention have a greatest dimension (e.g., diameter) of 500 nm or less. In other preferred embodiments, nanoparticles of the invention have a greatest dimension ranging between 25 nm and 200 nm. In other preferred embodiments, nanoparticles of the invention have a greatest dimension of 100 nm or less. In other preferred embodiments, nanoparticles of the invention have a greatest dimension ranging between 35 nm and 60 nm. It will be appreciated that reference made herein to particles or nanoparticles can be interchangeable, where appropriate.

It will be understood that the size of the particle will differ depending as to whether it is measured before or after loading. Accordingly, in particular embodiments, the term "nanoparticles" may apply only to the particles pre loading.

Nanoparticles encompassed in the present invention may be provided in different forms, e.g., as solid nanoparticles (e.g., metal such as silver, gold, iron, titanium), non-metal, lipid-based solids, polymers, suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present invention.

Semi-solid and soft nanoparticles have been manufactured, and are within the scope of the present invention. A prototype nanoparticle of semi-solid nature is the liposome. Various types of liposome nanoparticles are currently used clinically as delivery systems for anticancer drugs and vaccines. Nanoparticles with one half hydrophilic and the other half hydrophobic are termed Janus particles and are particularly effective for stabilizing emulsions. They can self-assemble at water/oil interfaces and act as solid surfactants.

Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF), ultraviolet-visible spectroscopy, dual polarization interferometry and nuclear magnetic resonance (NMR). Characterization (dimension measurements) may be made as to native particles (i.e., preloading) or after loading of the cargo (herein cargo refers to e.g., one or more components of CRISPR-Cas system e.g., CRISPR-Cas protein or mRNA, cytidine deaminase (which may be fused to a CRISPR-Cas protein or an adaptor) or mRNA, or guide RNA, or any combination thereof, and may include additional carriers and/or excipients) to provide particles of an optimal size for delivery for any in vitro, ex vivo and/or in vivo application of the present invention. In certain preferred embodiments, particle dimension (e.g., diameter) characterization is based on measurements using dynamic laser scattering (DLS). Mention is made of U.S. Pat. Nos. 8,709,843; 6,007,845; 5,855,913; 5,985,309; 5,543,158; and the publication by James E. Dahlman and Carmen Barnes et al. Nature Nanotechnology (2014) published online 11 May 2014, doi:10.1038/nnano.2014.84, concerning particles, methods of making and using them and measurements thereof.

Particles delivery systems within the scope of the present invention may be provided in any form, including but not limited to solid, semi-solid, emulsion, or colloidal particles. As such any of the delivery systems described herein, including but not limited to, e.g., lipid-based systems, liposomes, micelles, microvesicles, exosomes, or gene gun may be provided as particle delivery systems within the scope of the present invention.

CRISPR-Cas protein mRNA, cytidine deaminase (which may be fused to a CRISPR-Cas protein or an adaptor) or mRNA, and guide RNA may be delivered simultaneously using particles or lipid envelopes; for instance, CRISPR-Cas protein and RNA of the invention, e.g., as a complex, can be delivered via a particle as in Dahlman et al., WO2015089419 A2 and documents cited therein, such as 7C1 (see, e.g., James E. Dahlman and Carmen Barnes et al. Nature Nanotechnology (2014) published online 11 May 2014, doi:10.1038/nnano.2014.84), e.g., delivery particle comprising lipid or lipidoid and hydrophilic polymer, e.g., cationic lipid and hydrophilic polymer, for instance wherein the cationic lipid comprises 1,2-dioleoyl-3-trimethylammonium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the particle further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5), wherein particles are formed using an efficient, multistep process wherein first, effector protein and RNA are mixed together, e.g., at a 1:1 molar ratio, e.g., at room temperature, e.g., for 30 minutes, e.g., in sterile, nuclease free 1×PBS; and separately, DOTAP, DMPC, PEG, and cholesterol as applicable for the formulation are dissolved in alcohol, e.g., 100% ethanol; and, the two solutions are mixed together to form particles containing the complexes).

Nucleic acid-targeting effector proteins (e.g., a Type V protein such as Cpf1) mRNA and guide RNA may be delivered simultaneously using particles or lipid envelopes. Examples of suitable particles include but are not limited to those described in U.S. Pat. No. 9,301,923.

For example, Su X, Fricke J, Kavanagh D G, Irvine D J ("In vitro and in vivo mRNA delivery using lipid-enveloped pH-responsive polymer nanoparticles" Mol Pharm. 2011 Jun. 6; 8(3):774-87. doi: 10.1021/mp100390w. Epub 2011 Apr. 1) describes biodegradable core-shell structured nanoparticles with a poly(O-amino ester) (PBAE) core enveloped by a phospholipid bilayer shell. These were developed for in vivo mRNA delivery. The pH-responsive PBAE component was chosen to promote endosome disruption, while the lipid surface layer was selected to minimize toxicity of the polycation core. Such are, therefore, preferred for delivering RNA of the present invention.

In one embodiment, particles/nanoparticles based on self assembling bioadhesive polymers are contemplated, which may be applied to oral delivery of peptides, intravenous delivery of peptides and nasal delivery of peptides, all to the brain. Other embodiments, such as oral absorption and ocular delivery of hydrophobic drugs are also contemplated. The molecular envelope technology involves an engineered polymer envelope which is protected and delivered to the site of the disease (see, e.g., Mazza, M. et al. ACSNano, 2013. 7(2): 1016-1026; Siew, A., et al. Mol Pharm, 2012. 9(1):14-28; Lalatsa, A., et al. J Contr Rel, 2012. 161(2):523-36; Lalatsa, A., et al., Mol Pharm, 2012. 9(6):1665-80; Lalatsa, A., et al. Mol Pharm, 2012. 9(6):1764-74; Garrett, N. L., et al. J Biophotonics, 2012. 5(5-6):458-68; Garrett, N. L., et al. J Raman Spect, 2012. 43(5):681-688; Ahmad, S., et al. J Royal Soc Interface 2010. 7:S423-33; Uchegbu, I.F. Expert Opin Drug Deliv, 2006. 3(5):629-40; Qu, X., et al. Biomacromolecules, 2006. 7(12):3452-9 and Uchegbu, I. F., et al. Int J Pharm, 2001. 224:185-199). Doses of about 5 mg/kg are contemplated, with single or multiple doses, depending on the target tissue.

In one embodiment, particles/nanoparticles that can deliver RNA to a cancer cell to stop tumor growth developed by Dan Anderson's lab at MIT may be used/and or adapted to the CD-functionalized CRISPR-Cas system of the present invention. In particular, the Anderson lab developed fully automated, combinatorial systems for the synthesis, purification, characterization, and formulation of new biomaterials and nanoformulations. See, e.g., Alabi et al., Proc Natl Acad Sci USA. 2013 Aug. 6; 110(32):12881-6; Zhang et al., Adv Mater. 2013 Sep. 6; 25(33):4641-5; Jiang et al., Nano Lett. 2013 Mar. 13; 13(3):1059-64; Karagiannis et al., ACS Nano. 2012 Oct. 23; 6(10):8484-7; Whitehead et al., ACS Nano. 2012 Aug. 28; 6(8):6922-9 and Lee et al., Nat Nanotechnol. 2012 Jun. 3; 7(6):389-93.

US patent application 20110293703 relates to lipidoid compounds are also particularly useful in the administration of polynucleotides, which may be applied to deliver the CD-functionalized CRISPR-Cas system of the present invention. In one aspect, the aminoalcohol lipidoid compounds are combined with an agent to be delivered to a cell or a subject to form microparticles, nanoparticles, liposomes, or micelles. The agent to be delivered by the particles, liposomes, or micelles may be in the form of a gas, liquid, or solid, and the agent may be a polynucleotide, protein, peptide, or small molecule. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

US Patent Publication No. 20110293703 also provides methods of preparing the aminoalcohol lipidoid compounds. One or more equivalents of an amine are allowed to react with one or more equivalents of an epoxide-terminated compound under suitable conditions to form an aminoalcohol lipidoid compound of the present invention. In certain embodiments, all the amino groups of the amine are fully reacted with the epoxide-terminated compound to form tertiary amines. In other embodiments, all the amino groups of the amine are not fully reacted with the epoxide-terminated compound to form tertiary amines thereby resulting in primary or secondary amines in the aminoalcohol lipidoid compound. These primary or secondary amines are left as is or may be reacted with another electrophile such as a different epoxide-terminated compound. As will be appreciated by one skilled in the art, reacting an amine with less than excess of epoxide-terminated compound will result in a plurality of different aminoalcohol lipidoid compounds with various numbers of tails. Certain amines may be fully functionalized with two epoxide-derived compound tails while other molecules will not be completely functionalized with epoxide-derived compound tails. For example, a diamine or polyamine may include one, two, three, or four epoxide-derived compound tails off the various amino moieties of the molecule resulting in primary, secondary, and tertiary amines. In certain embodiments, all the amino groups are not fully functionalized. In certain embodiments, two of the same types of epoxide-terminated compounds are used. In other embodiments, two or more different epoxide-terminated compounds are used. The synthesis of the aminoalcohol lipidoid compounds is performed with or without solvent, and the synthesis may be performed at higher temperatures ranging from 30-100° C., preferably at approximately 50-90° C. The prepared aminoalcohol lipidoid compounds may be optionally purified. For example, the mixture of aminoalcohol lipidoid compounds may be purified to yield an aminoalcohol lipidoid compound with a particular number of epoxide-derived compound tails. Or the mixture may be purified to yield a particular stereo- or regioisomer. The aminoalcohol lipidoid compounds may also be alkylated using an alkyl halide (e.g., methyl iodide) or other alkylating agent, and/or they may be acylated.

US Patent Publication No. 20110293703 also provides libraries of aminoalcohol lipidoid compounds prepared by the inventive methods. These aminoalcohol lipidoid compounds may be prepared and/or screened using high-throughput techniques involving liquid handlers, robots, microtiter plates, computers, etc. In certain embodiments, the aminoalcohol lipidoid compounds are screened for their ability to transfect polynucleotides or other agents (e.g., proteins, peptides, small molecules) into the cell.

US Patent Publication No. 20130302401 relates to a class of poly(beta-amino alcohols) (PBAAs) has been prepared using combinatorial polymerization. The inventive PBAAs may be used in biotechnology and biomedical applications as coatings (such as coatings of films or multilayer films for medical devices or implants), additives, materials, excipients, non-biofouling agents, micropatterning agents, and cellular encapsulation agents. When used as surface coatings, these PBAAs elicited different levels of inflammation, both in vitro and in vivo, depending on their chemical structures. The large chemical diversity of this class of materials allowed us to identify polymer coatings that inhibit macrophage activation in vitro. Furthermore, these coatings reduce the recruitment of inflammatory cells, and reduce fibrosis, following the subcutaneous implantation of carboxylated polystyrene microparticles. These polymers may be used to form polyelectrolyte complex capsules for cell encapsulation. The invention may also have many other biological applications such as antimicrobial coatings, DNA or siRNA delivery, and stem cell tissue engineering. The teachings of US Patent Publication No. 20130302401 may be applied to the CD-functionalized CRISPR-Cas system of the present invention.

Preassembled recombinant CRISPR-Cas complexes comprising Cpf1, cytidine deaminase (which may be fused to Cpf1 or an adaptor protein), and guide RNA may be transfected, for example by electroporation, resulting in high mutation rates and absence of detectable off-target mutations. Hur, J. K. et al, Targeted mutagenesis in mice by electroporation of Cpf1 ribonucleoproteins, Nat Biotechnol. 2016 Jun. 6. doi: 10.1038/nbt.3596.

In terms of local delivery to the brain, this can be achieved in various ways. For instance, material can be delivered intrastriatally e.g. by injection. Injection can be performed stereotactically via a craniotomy.

In some embodiments, sugar-based particles may be used, for example GalNAc, as described herein and with reference to WO2014118272 (incorporated herein by reference) and Nair, J K et al., 2014, Journal of the American Chemical Society 136 (49), 16958-16961) and the teaching herein, especially in respect of delivery applies to all particles unless otherwise apparent. This may be considered to be a sugar-based particle and further details on other particle delivery systems and/or formulations are provided herein. GalNAc can therefore be considered to be a particle in the sense of the other particles described herein, such that general uses and other considerations, for instance delivery of said particles, apply to GalNAc particles as well. A solution-phase conjugation strategy may for example be used to attach triantennary GalNAc clusters (mol. wt. ~2000) activated as PFP (pentafluorophenyl) esters onto 5'-hexylamino modified oligonucleotides (5'-HA ASOs, mol. wt. ~8000 Da; Østergaard et al., Bioconjugate Chem., 2015, 26 (8), pp 1451-1455). Similarly, poly(acrylate) polymers have been described for in vivo nucleic acid delivery (see WO2013158141 incorporated herein by reference). In further alternative embodiments, pre-mixing CRISPR nanoparticles (or protein complexes) with naturally occurring serum proteins may be used in order to improve delivery (Akinc A et al, 2010, Molecular Therapy vol. 18 no. 7, 1357-1364).

Nanoclews

Further, the CD-functionalized CRISPR system may be delivered using nanoclews, for example as described in Sun W et al, *Cocoon-like self-degradable DNA nanoclew for anticancer drug delivery.*, J Am Chem Soc. 2014 Oct. 22; 136(42):14722-5. doi: 10.1021/ja5088024. Epub 2014 Oct. 13.; or in Sun W et al, *Self-Assembled DNA Nanoclews for the Efficient Delivery of CRISPR-Cas9 for Genome Editing.*, Angew Chem Int Ed Engl. 2015 Oct. 5; 54(41):12029-33. doi: 10.1002/anie.201506030. Epub 2015 Aug. 27.

LNP

In some embodiments, delivery is by encapsulation of the Cpf1 protein or mRNA form in a lipid particle such as an LNP. In some embodiments, therefore, lipid nanoparticles (LNPs) are contemplated. An antitransthyretin small interfering RNA has been encapsulated in lipid nanoparticles and delivered to humans (see, e.g., Coelho et al., N Engl J Med 2013; 369:819-29), and such a system may be adapted and applied to the CRISPR-Cas system of the present invention. Doses of about 0.01 to about 1 mg per kg of body weight administered intravenously are contemplated. Medications to reduce the risk of infusion-related reactions are contemplated, such as dexamethasone, acetaminophen, diphenhydramine or cetirizine, and ranitidine are contemplated. Multiple doses of about 0.3 mg per kilogram every 4 weeks for five doses are also contemplated.

LNPs have been shown to be highly effective in delivering siRNAs to the liver (see, e.g., Tabernero et al., Cancer Discovery, April 2013, Vol. 3, No. 4, pages 363-470) and are therefore contemplated for delivering RNA encoding CRISPR-Cas to the liver. A dosage of about four doses of 6 mg/kg of the LNP every two weeks may be contemplated. Tabernero et al. demonstrated that tumor regression was observed after the first 2 cycles of LNPs dosed at 0.7 mg/kg, and by the end of 6 cycles the patient had achieved a partial response with complete regression of the lymph node metastasis and substantial shrinkage of the liver tumors. A complete response was obtained after 40 doses in this patient, who has remained in remission and completed treatment after receiving doses over 26 months. Two patients with RCC and extrahepatic sites of disease including kidney, lung, and lymph nodes that were progressing following prior therapy with VEGF pathway inhibitors had stable disease at all sites for approximately 8 to 12 months, and a patient with PNET and liver metastases continued on the extension study for 18 months (36 doses) with stable disease.

However, the charge of the LNP must be taken into consideration. As cationic lipids combined with negatively charged lipids to induce nonbilayer structures that facilitate intracellular delivery. Because charged LNPs are rapidly cleared from circulation following intravenous injection, ionizable cationic lipids with pKa values below 7 were developed (see, e.g., Rosin et al, Molecular Therapy, vol. 19, no. 12, pages 1286-2200, December 2011). Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilinoleoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinKDMA), and 1,2-dilinoleyl-4-(2-dimethylaminoethyl)-[1,3]-dioxolane (DLinKC2-DMA). It has been shown that LNP siRNA systems containing these lipids exhibit remarkably different gene silencing properties in hepatocytes in vivo, with potencies varying according to the series DLinKC2-DMA>DLinKDMA>DLinDMA>>DLinDAP employing a Factor VII gene silencing model (see, e.g., Rosin et al, Molecular Therapy, vol. 19, no. 12, pages 1286-2200, December 2011). A dosage of 1 g/ml of LNP or CRISPR-Cas RNA in or associated with the LNP may be contemplated, especially for a formulation containing DLinKC2-DMA.

Preparation of LNPs and CRISPR-Cas encapsulation may be used/and or adapted from Rosin et al, Molecular Therapy, vol. 19, no. 12, pages 1286-2200, December 2011). The cationic lipids 1,2-dilinoleoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(ω-methoxy-poly(ethylene glycol)2000) carbamoyl]-1,2-dimyristyloxl-propyl-3-amine (PEG-C-DOMG) may be provided by Tekmira Pharmaceuticals (Vancouver, Canada) or synthesized. Cholesterol may be purchased from Sigma (St Louis, MO). The specific CRISPR-Cas RNA may be encapsulated in LNPs containing DLinDAP, DLinDMA, DLinK-DMA, and DLinKC2-DMA (cationic lipid:DSPC: CHOL: PEGS-DMG or PEG-C-DOMG at 40:10:40:10 molar ratios). When required, 0.2% SP-DiOC18 (Invitrogen, Burlington, Canada) may be incorporated to assess cellular uptake, intracellular delivery, and biodistribution. Encapsulation may be performed by dissolving lipid mixtures comprised of cationic lipid:DSPC:cholesterol:PEG-c-DOMG (40:10:40:10 molar ratio) in ethanol to a final lipid concentration of 10 mmol/l. This ethanol solution of lipid may be added drop-wise to 50 mmol/l citrate, pH 4.0 to form multilamellar vesicles to produce a final concentration of 30% ethanol vol/vol. Large unilamellar vesicles may be formed following extrusion of multilamellar vesicles through two stacked 80 nm Nuclepore polycarbonate filters using the Extruder (Northern Lipids, Vancouver, Canada). Encapsulation may be achieved by adding RNA dissolved at 2 mg/ml in 50 mmol/l citrate, pH 4.0 containing 30% ethanol vol/vol drop-wise to extruded preformed large unilamellar vesicles and incubation at 31° C. for 30 minutes with constant mixing to a final RNA/lipid weight ratio of 0.06/1 wt/wt. Removal of ethanol and neutralization of formulation buffer were performed by dialysis against phosphate-buffered saline (PBS), pH 7.4 for 16 hours using Spectra/Por 2 regenerated cellulose dialysis membranes. Nanoparticle size distribution may be determined by dynamic light scattering using a NICOMP 370 particle sizer, the vesicle/intensity modes, and Gaussian fitting (Nicomp Particle Sizing, Santa Barbara, CA). The particle size for all three LNP systems may be ~70 nm in diameter. RNA encapsulation efficiency may be determined by removal of free RNA using VivaPureD MiniH columns (Sartorius Stedim Biotech) from samples collected before and after dialysis. The encapsulated RNA may be extracted from the eluted nanoparticles and quantified at 260 nm. RNA to lipid ratio was determined by measurement of cholesterol content in vesicles using the Cholesterol E enzymatic assay from Wako Chemicals USA (Richmond, VA). In conjunction with the herein discussion of LNPs and PEG lipids, PEGylated liposomes or LNPs are likewise suitable for delivery of a CRISPR-Cas system or components thereof.

A lipid premix solution (20.4 mg/ml total lipid concentration) may be prepared in ethanol containing DLinKC2-DMA, DSPC, and cholesterol at 50:10:38.5 molar ratios. Sodium acetate may be added to the lipid premix at a molar ratio of 0.75:1 (sodium acetate:DLinKC2-DMA). The lipids may be subsequently hydrated by combining the mixture with 1.85 volumes of citrate buffer (10 mmol/l, pH 3.0) with vigorous stirring, resulting in spontaneous liposome formation in aqueous buffer containing 35% ethanol. The liposome solution may be incubated at 37° C. to allow for time-dependent increase in particle size. Aliquots may be removed at various times during incubation to investigate changes in liposome size by dynamic light scattering (Zetasizer Nano Z S, Malvern Instruments, Worcestershire, UK). Once the desired particle size is achieved, an aqueous PEG lipid solution (stock=10 mg/ml PEG-DMG in 35% (vol/vol) ethanol) may be added to the liposome mixture to yield a final PEG molar concentration of 3.5% of total lipid. Upon addition of PEG-lipids, the liposomes should their size, effectively quenching further growth. RNA may then be added to the empty liposomes at an RNA to total lipid ratio of approximately 1:10 (wt:wt), followed by incubation for 30 minutes at 37° C. to form loaded LNPs. The mixture may be subsequently dialyzed overnight in PBS and filtered with a 0.45-μm syringe filter.

Spherical Nucleic Acid (SNA™) constructs and other nanoparticles (particularly gold nanoparticles) are also contemplated as a means to delivery CRISPR-Cas system to intended targets. Significant data show that AuraSense Therapeutics' Spherical Nucleic Acid (SNA™) constructs, based upon nucleic acid-functionalized gold nanoparticles, are useful.

Literature that may be employed in conjunction with herein teachings include: Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19):7625-7630, Jensen et al., Sci. Transl. Med. 5, 209ra152 (2013) and Mirkin, et al., Small, 10:186-192.

Self-assembling nanoparticles with RNA may be constructed with polyethyleneimine (PEI) that is PEGylated with an Arg-Gly-Asp (RGD) peptide ligand attached at the distal end of the polyethylene glycol (PEG). This system has been used, for example, as a means to target tumor neovasculature expressing integrins and deliver siRNA inhibiting vascular endothelial growth factor receptor-2 (VEGF R2) expression and thereby achieve tumor angiogenesis (see, e.g., Schiffelers et al., Nucleic Acids Research, 2004, Vol. 32, No. 19). Nanoplexes may be prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. A dosage of about 100 to 200 mg of CRISPR-Cas is envisioned for delivery in the self-assembling nanoparticles of Schiffelers et al.

The nanoplexes of Bartlett et al. (PNAS, Sep. 25, 2007, vol. 104, no. 39) may also be applied to the present invention. The nanoplexes of Bartlett et al. are prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. The DOTA-siRNA of Bartlett et al. was synthesized as follows: 1,4,7,10-tetraazacyclododecane-1,4,7,10-tetraacetic acid mono(N-hydroxysuccinimide ester) (DOTA-NHSester) was ordered from Macrocyclics (Dallas, TX). The amine modified RNA sense strand with a 100-fold molar excess of DOTA-NHS-ester in carbonate buffer (pH 9) was added to a microcentrifuge tube. The contents were reacted by stirring for 4 h at room temperature. The DOTA-RNAsense conjugate was ethanol-precipitated, resuspended in water, and annealed to the unmodified antisense strand to yield DOTA-siRNA. All liquids were pretreated with Chelex-100 (Bio-Rad, Hercules, CA) to remove trace metal contaminants. Tf-targeted and nontargeted siRNA nanoparticles may be formed by using cyclodextrin-containing polycations. Typically, nanoparticles were formed in water at a charge ratio of 3 (+/−) and an siRNA concentration of 0.5 g/liter. One percent of the adamantane-PEG molecules on the surface of the targeted nanoparticles were modified with Tf (adamantane-PEG-Tf). The nanoparticles were suspended in a 5% (wt/vol) glucose carrier solution for injection.

Davis et al. (Nature, Vol 464, 15 Apr. 2010) conducts a RNA clinical trial that uses a targeted nanoparticle-delivery system (clinical trial registration number NCT00689065). Patients with solid cancers refractory to standard-of-care therapies are administered doses of targeted nanoparticles on days 1, 3, 8 and 10 of a 21-day cycle by a 30-min intravenous infusion. The nanoparticles consist of a synthetic delivery system containing: (1) a linear, cyclodextrin-based polymer (CDP), (2) a human transferrin protein (TF) targeting ligand displayed on the exterior of the nanoparticle to engage TF receptors (TFR) on the surface of the cancer cells, (3) a hydrophilic polymer (polyethylene glycol (PEG) used to promote nanoparticle stability in biological fluids), and (4) siRNA designed to reduce the expression of the RRM2 (sequence used in the clinic was previously denoted siR2B+5). The TFR has long been known to be upregulated in malignant cells, and RRM2 is an established anti-cancer target. These nanoparticles (clinical version denoted as CALAA-01) have been shown to be well tolerated in multi-dosing studies in non-human primates. Although a single patient with chronic myeloid leukaemia has been administered siRNA by liposomal delivery, Davis et al.'s clinical trial is the initial human trial to systemically deliver siRNA with a targeted delivery system and to treat patients with solid cancer. To ascertain whether the targeted delivery system can provide effective delivery of functional siRNA to human tumors, Davis et al. investigated biopsies from three patients from three different dosing cohorts; patients A, B and C, all of whom had metastatic melanoma and received CALAA-01 doses of 18, 24 and 30 mg m$^{-2}$ siRNA, respectively. Similar doses may also be contemplated for the CRISPR-Cas system of the present invention. The delivery of the invention may be achieved with nanoparticles containing a linear, cyclodextrin-based polymer (CDP), a human transferrin protein (TF) targeting ligand displayed on the exterior of the nanoparticle to engage TF receptors (TFR) on the surface of the cancer cells and/or a hydrophilic polymer (for example, polyethylene glycol (PEG) used to promote nanoparticle stability in biological fluids).

U.S. Pat. No. 8,709,843, incorporated herein by reference, provides a drug delivery system for targeted delivery of therapeutic agent-containing particles to tissues, cells, and intracellular compartments. The invention provides targeted particles comprising polymer conjugated to a surfactant, hydrophilic polymer or lipid. U.S. Pat. No. 6,007,845, incorporated herein by reference, provides particles which have a core of a multiblock copolymer formed by covalently linking a multifunctional compound with one or more hydrophobic polymers and one or more hydrophilic polymers, and contain a biologically active material. U.S. Pat. No. 5,855,913, incorporated herein by reference, provides a particulate composition having aerodynamically light particles having a tap density of less than 0.4 g/cm3 with a mean diameter of between 5 μm and 30 μm, incorporating a surfactant on the surface thereof for drug delivery to the pulmonary system. U.S. Pat. No. 5,985,309, incorporated herein by reference, provides particles incorporating a surfactant and/or a hydrophilic or hydrophobic complex of a positively or negatively charged therapeutic or diagnostic agent and a charged molecule of opposite charge for delivery to the pulmonary system. U.S. Pat. No. 5,543,158, incorporated herein by reference, provides biodegradable injectable particles having a biodegradable solid core containing a biologically active material and poly(alkylene glycol) moieties on the surface. WO2012135025 (also published as US20120251560), incorporated herein by reference, describes conjugated polyethyleneimine (PEI) polymers and conjugated aza-macrocycles (collectively referred to as "conjugated lipomer" or "lipomers"). In certain embodiments, it can envisioned that such conjugated lipomers can be used in the context of the CRISPR-Cas system to achieve in vitro, ex vivo and in vivo genomic perturbations to modify gene expression, including modulation of protein expression.

In one embodiment, the nanoparticle may be epoxide-modified lipid-polymer, advantageously 7C1 (see, e.g., James E. Dahlman and Carmen Barnes et al. Nature Nanotechnology (2014) published online 11 May 2014, doi: 10.1038/nnano.2014.84). C71 was synthesized by reacting C15 epoxide-terminated lipids with PEI600 at a 14:1 molar ratio, and was formulated with C14PEG2000 to produce nanoparticles (diameter between 35 and 60 nm) that were stable in PBS solution for at least 40 days.

An epoxide-modified lipid-polymer may be utilized to deliver the CRISPR-Cas system of the present invention to pulmonary, cardiovascular or renal cells, however, one of skill in the art may adapt the system to deliver to other target organs. Dosage ranging from about 0.05 to about 0.6 mg/kg are envisioned. Dosages over several days or weeks are also envisioned, with a total dosage of about 2 mg/kg.

In some embodiments, the LNP for delivering the RNA molecules is prepared by methods known in the art, such as those described in, for example, WO 2005/105152 (PCT/EP2005/004920), WO 2006/069782 (PCT/EP2005/014074), WO 2007/121947 (PCT/EP2007/003496), and WO 2015/082080 (PCT/EP2014/003274), which are herein incorporated by reference. LNPs aimed specifically at the enhanced and improved delivery of siRNA into mammalian cells are described in, for example, Aleku et al., Cancer Res., 68(23): 9788-98 (Dec. 1, 2008), Strumberg et al., Int. J. Clin. Pharmacol. Ther., 50(1): 76-8 (January 2012), Schultheis et al., J. Clin. Oncol., 32(36): 4141-48 (Dec. 20, 2014), and Fehring et al., Mol. Ther., 22(4): 811-20 (Apr. 22, 2014), which are herein incorporated by reference and may be applied to the present technology.

In some embodiments, the LNP includes any LNP disclosed in WO 2005/105152 (PCT/EP2005/004920), WO 2006/069782 (PCT/EP2005/014074), WO 2007/121947 (PCT/EP2007/003496), and WO 2015/082080 (PCT/EP2014/003274).

In some embodiments, the LNP includes at least one lipid having Formula I:

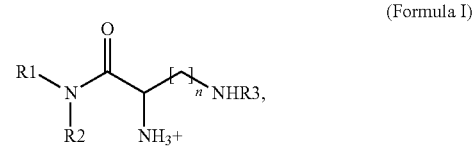

(Formula I)

wherein R1 and R2 are each and independently selected from the group comprising alkyl, n is any integer between 1 and 4, and R3 is an acyl selected from the group comprising lysyl, ornithyl, 2,4-diaminobutyryl, histidyl and an acyl moiety according to Formula II:

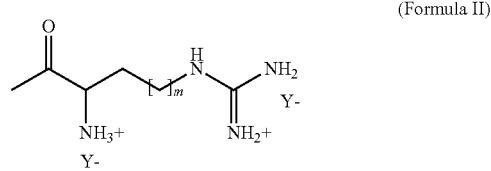

(Formula II)

wherein m is any integer from 1 to 3 and $Y^-$ is a pharmaceutically acceptable anion. In some embodiments, a lipid according to Formula I includes at least two asymmetric C atoms. In some embodiments, enantiomers of Formula I include, but are not limited to, R—R; S—S; R—S and S—R enantiomer.

In some embodiments, R1 is lauryl and R2 is myristyl. In another embodiment, R1 is palmityl and R2 is oleyl. In some embodiments, m is 1 or 2. In some embodiments, $Y^-$ is selected from halogenids, acetate or trifluoroacetate.

In some embodiments, the LNP comprises one or more lipids select from: β-arginyl-2,3-diamino propionic acid-N-palmityl-N-oleyl-amide trihydrochloride (Formula III):

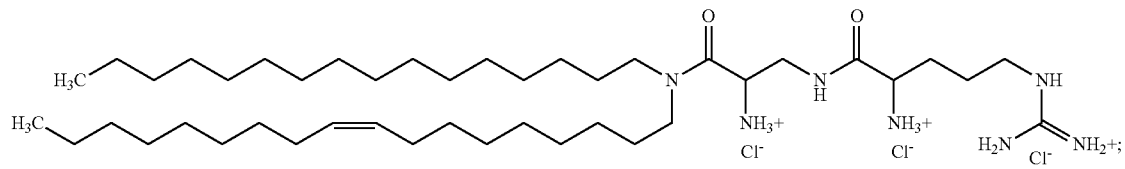

(Formula III)

β-arginyl-2,3-diamino propionic acid-N-lauryl-N-myristyl-amide trihydrochloride (Formula IV):

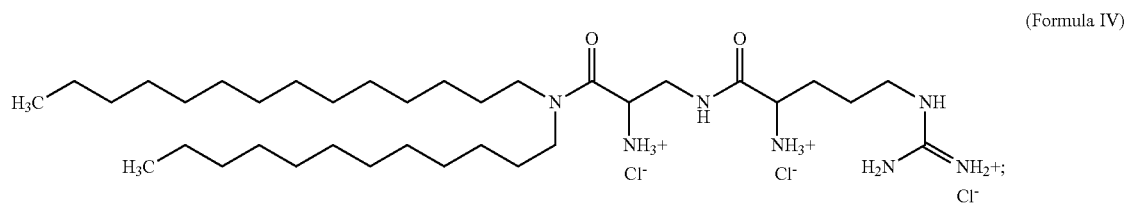

(Formula IV)

and ε-arginyl-lysine-N-lauryl-N-myristyl-amide trihydrochloride (Formula V):

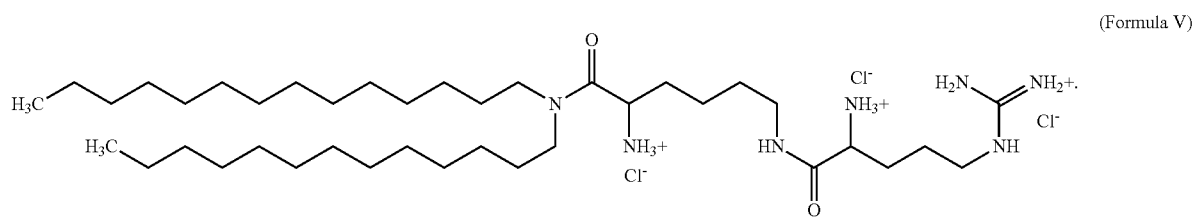

(Formula V)

In some embodiments, the LNP also includes a constituent. By way of example, but not by way of limitation, in some embodiments, the constituent is selected from peptides, proteins, oligonucleotides, polynucleotides, nucleic acids, or a combination thereof. In some embodiments, the constituent is an antibody, e.g., a monoclonal antibody. In some embodiments, the constituent is a nucleic acid selected from, e.g., ribozymes, aptamers, spiegelmers, DNA, RNA, PNA, LNA, or a combination thereof. In some embodiments, the nucleic acid is guide RNA and/or mRNA.

In some embodiments, the constituent of the LNP comprises an mRNA encoding a CRISPR-Cas protein. In some embodiments, the constituent of the LNP comprises an mRNA encoding a Type-II or Type-V CRISPR-Cas protein. In some embodiments, the constituent of the LNP comprises an mRNA encoding a cytidine deaminase (which may be fused to a CRISPR-Cas protein or an adaptor protein).

In some embodiments, the constituent of the LNP further comprises one or more guide RNA. In some embodiments, the LNP is configured to deliver the aforementioned mRNA and guide RNA to vascular endothelium. In some embodiments, the LNP is configured to deliver the aforementioned mRNA and guide RNA to pulmonary endothelium. In some embodiments, the LNP is configured to deliver the aforementioned mRNA and guide RNA to liver. In some embodiments, the LNP is configured to deliver the aforementioned mRNA and guide RNA to lung. In some embodiments, the LNP is configured to deliver the aforementioned mRNA and guide RNA to hearts. In some embodiments, the LNP is configured to deliver the aforementioned mRNA and guide RNA to spleen. In some embodiments, the LNP is configured to deliver the aforementioned mRNA and guide RNA to kidney. In some embodiments, the LNP is configured to deliver the aforementioned mRNA and guide RNA to pancreas. In some embodiments, the LNP is configured to deliver the aforementioned mRNA and guide RNA to brain. In some embodiments, the LNP is configured to deliver the aforementioned mRNA and guide RNA to macrophages.

In some embodiments, the LNP also includes at least one helper lipid. In some embodiments, the helper lipid is selected from phospholipids and steroids. In some embodiments, the phospholipids are di- and/or monoester of the phosphoric acid. In some embodiments, the phospholipids are phosphoglycerides and/or sphingolipids. In some embodiments, the steroids are naturally occurring and/or synthetic compounds based on the partially hydrogenated cyclopenta[a]phenanthrene. In some embodiments, the steroids contain 21 to 30 C atoms. In some embodiments, the steroid is cholesterol. In some embodiments, the helper lipid is selected from 1,2-diphytanoyl-sn-glycero-3-phosphoethanolamine (DPhyPE), ceramide, and 1,2-dioleoyl-sn-glycero-3-phosphoethanolamine (DOPE).

In some embodiments, the at least one helper lipid comprises a moiety selected from the group comprising a PEG moiety, a HEG moiety, a polyhydroxyethyl starch (polyHES) moiety and a polypropylene moiety. In some embodiments, the moiety has a molecule weight between about 500 to 10,000 Da or between about 2,000 to 5,000 Da. In some embodiments, the PEG moiety is selected from 1,2-distearoyl-sn-glycero-3 phosphoethanolamine, 1,2-dialkyl-snglycero-3-phosphoethanolamine, and Ceramide-PEG. In some embodiments, the PEG moiety has a molecular weight between about 500 to 10,000 Da or between about 2,000 to 5,000 Da. In some embodiments, the PEG moiety has a molecular weight of 2,000 Da.

In some embodiments, the helper lipid is between about 20 mol % to 80 mol % of the total lipid content of the composition. In some embodiments, the helper lipid component is between about 35 mol % to 65 mol % of the total lipid content of the LNP. In some embodiments, the LNP includes lipids at 50 mol % and the helper lipid at 50 mol % of the total lipid content of the LNP.

In some embodiments, the LNP includes any of β-3-arginyl-2,3-diaminopropionic acid-N-palmityl-N-oleyl-amide trihydrochloride, β-arginyl-2,3-diaminopropionic acid-N-lauryl-N-myristyl-amide trihydrochloride or ε-arginyl-lysine-N-lauryl-N-myristyl-amide trihydrochloride in combination with DPhyPE, wherein the content of DPhyPE is about 80 mol %, 65 mol %, 50 mol % and 35 mol % of the overall lipid content of the LNP. In some embodiments, the LNP includes β-arginyl-2,3-diamino propionic acid-N-pahnityl-N-oleyl-amide trihydrochloride (lipid) and 1,2-diphytanoyl-sn-glycero-3-phosphoethanolamine (helper lipid). In some embodiments, the LNP includes β-arginyl-2,3-diamino propionic acid-N-palmityl-N-oleyl-amide trihydrochloride (lipid), 1,2-diphytanoyl-sn-glycero-3-phosphoethanolamine (first helper lipid), and 1,2-distearoyl-sn-glycero-3-phosphoethanolamine-PEG2000 (second helper lipid).

In some embodiments, the second helper lipid is between about 0.05 mol % to 4.9 mol % or between about 1 mol % to 3 mol % of the total lipid content. In some embodiments, the LNP includes lipids at between about 45 mol % to 50 mol % of the total lipid content, a first helper lipid between about 45 mol % to 50 mol % of the total lipid content, under the proviso that there is a PEGylated second helper lipid between about 0.1 mol % to 5 mol %, between about 1 mol % to 4 mol %, or at about 2 mol % of the total lipid content, wherein the sum of the content of the lipids, the first helper lipid, and of the second helper lipid is 100 mol % of the total lipid content and wherein the sum of the first helper lipid and the second helper lipid is 50 mol % of the total lipid content. In some embodiments, the LNP comprises: (a) 50 mol % of β-arginyl-2,3-diamino propionic acid-N-palmityl-N-oleyl-amide trihydrochloride, 48 mol % of 1,2-diphytanoyl-sn-glycero-3-phosphoethanolamine; and 2 mol % 1,2-distearoyl-sn-glycero-3-phosphoethanolamine-PEG2000; or (b) 50 mol % of 0-arginyl-2,3-diamino propionic acid-N-palmityl-N-oleyl-amide trihydrochloride, 49 mol % 1,2-diphytanoyl-sn-glycero-3-phosphoethanolamine; and 1 mol % N(Carbonyl-methoxypolyethylenglycol-2000)-1,2-distearoyl-sn-glycero3-phosphoethanolamine, or a sodium salt thereof.

In some embodiments, the LNP contains a nucleic acid, wherein the charge ratio of nucleic acid backbone phosphates to cationic lipid nitrogen atoms is about 1: 1.5-7 or about 1:4.

In some embodiments, the LNP also includes a shielding compound, which is removable from the lipid composition under in vivo conditions. In some embodiments, the shielding compound is a biologically inert compound. In some embodiments, the shielding compound does not carry any charge on its surface or on the molecule as such. In some embodiments, the shielding compounds are polyethylene glycoles (PEGs), hydroxyethylglucose (HEG) based polymers, polyhydroxyethyl starch (polyHES) and polypropylene. In some embodiments, the PEG, HEG, polyHES, and a polypropylene weight between about 500 to 10,000 Da or between about 2000 to 5000 Da. In some embodiments, the shielding compound is PEG2000 or PEG5000.

In some embodiments, the LNP includes at least one lipid, a first helper lipid, and a shielding compound that is removable from the lipid composition under in vivo conditions. In some embodiments, the LNP also includes a second helper lipid. In some embodiments, the first helper lipid is ceramide. In some embodiments, the second helper lipid is ceramide. In some embodiments, the ceramide comprises at least one short carbon chain substituent of from 6 to 10 carbon atoms. In some embodiments, the ceramide comprises 8 carbon atoms. In some embodiments, the shielding compound is attached to a ceramide. In some embodiments, the shielding compound is attached to a ceramide. In some embodiments, the shielding compound is covalently attached to the ceramide. In some embodiments, the shielding compound is attached to a nucleic acid in the LNP. In some embodiments, the shielding compound is covalently attached to the nucleic acid. In some embodiments, the shielding compound is attached to the nucleic acid by a linker. In some embodiments, the linker is cleaved under physiological conditions. In some embodiments, the linker is selected from ssRNA, ssDNA, dsRNA, dsDNA, peptide, S—S-linkers and pH sensitive linkers. In some embodiments, the linker moiety is attached to the 3' end of the sense strand of the nucleic acid. In some embodiments, the shielding compound comprises a pH-sensitive linker or a pH-sensitive moiety. In some embodiments, the pH-sensitive linker or pH-sensitive moiety is an anionic linker or an anionic moiety. In some embodiments, the anionic linker or anionic moiety is less anionic or neutral in an acidic environment. In some embodiments, the pH-sensitive linker or the pH-sensitive moiety is selected from the oligo (glutamic acid), oligophenolate(s) and diethylene triamine penta acetic acid.

In any of the LNP embodiments in the previous paragraph, the LNP can have an osmolality between about 50 to 600 mosmole/kg, between about 250 to 350 mosmole/kg, or between about 280 to 320 mosmole/kg, and/or wherein the LNP formed by the lipid and/or one or two helper lipids and the shielding compound have a particle size between about 20 to 200 nm, between about 30 to 100 nm, or between about 40 to 80 nm.

In some embodiments, the shielding compound provides for a longer circulation time in vivo and allows for a better biodistribution of the nucleic acid containing LNP. In some embodiments, the shielding compound prevents immediate interaction of the LNP with serum compounds or compounds of other bodily fluids or cytoplasma membranes, e.g., cytoplasma membranes of the endothelial lining of the vasculature, into which the LNP is administered. Additionally or alternatively, in some embodiments, the shielding compounds also prevent elements of the immune system from immediately interacting with the LNP. Additionally or alternatively, in some embodiments, the shielding compound acts as an anti-opsonizing compound. Without wishing to be bound by any mechanism or theory, in some embodiments, the shielding compound forms a cover or coat that reduces the surface area of the LNP available for interaction with its environment. Additionally or alternatively, in some embodiments, the shielding compound shields the overall charge of the LNP.

In another embodiment, the LNP includes at least one cationic lipid having Formula VI:

(Formula VI)

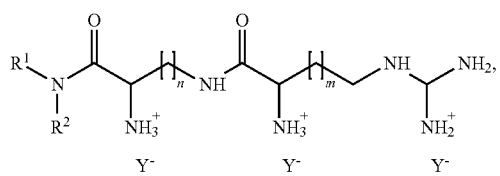

wherein n is 1, 2, 3, or 4, wherein m is 1, 2, or 3, wherein Y⁻ is anion, wherein each of R1 and R2 is individually and independently selected from the group consisting of linear C12-C18 alkyl and linear C12-C18 alkenyl, a sterol compound, wherein the sterol compound is selected from the group consisting of cholesterol and stigmasterol, and a PEGylated lipid, wherein the PEGylated lipid comprises a PEG moiety, wherein the PEGylated lipid is selected from the group consisting of:

a PEGylated phosphoethanolamine of Formula VII:

(Formula VII)

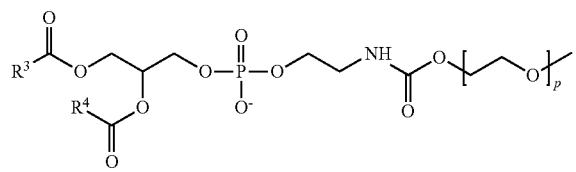

wherein R3 and R4 are individually and independently linear C13-C17 alkyl, and p is any integer between 15 to 130;

a PEGylated ceramide of Formula VIII:

wherein R5 is linear C7-C15 alkyl, and q is any number between 15 to 130; and a PEGylated diacylglycerol of Formula IX:

(Formula IX)

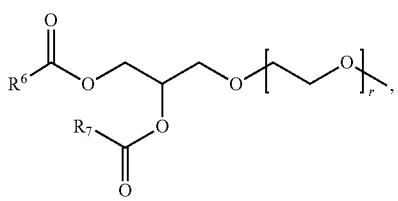

wherein each of R6 and R7 is individually and independently linear C11-C17 alkyl, and r is any integer from 15 to 130.

In some embodiments, $R^1$ and $R^2$ are different from each other. In some embodiments, $R^1$ is palmityl and $R^2$ is oleyl. In some embodiments, $R^1$ is lauryl and $R^2$ is myristyl. In some embodiments, $R^1$ and $R^2$ are the same. In some embodiments, each of $R^1$ and $R^2$ is individually and independently selected from the group consisting of C12 alkyl, C14 alkyl, C16 alkyl, C18 alkyl, C12 alkenyl, C14 alkenyl, C16 alkenyl and C18 alkenyl. In some embodiments, each of C12 alkenyl, C14 alkenyl, C16 alkenyl and C18 alkenyl comprises one or two double bonds. In some embodiments, C18 alkenyl is C18 alkenyl with one double bond between C9 and C10. In some embodiments, C18 alkenyl is cis-9-octadecyl.

In some embodiments, the cationic lipid is a compound of Formula X:

(Formula X)

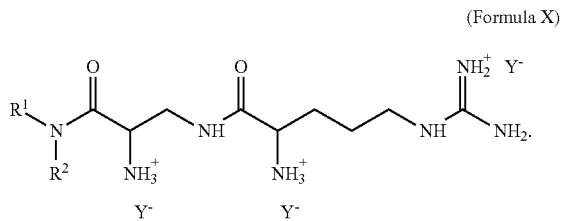

In some embodiments, Y⁻ is selected from halogenids, acetate and trifluoroacetate. In some embodiments, the cationic lipid is β-arginyl-2,3-diamino propionic acid-N-palmityl-N-oleyl-amide trihydrochloride of Formula III:

(Formula VIII)

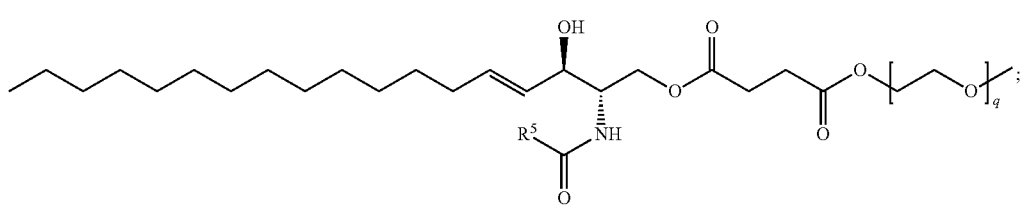

(Formula III)

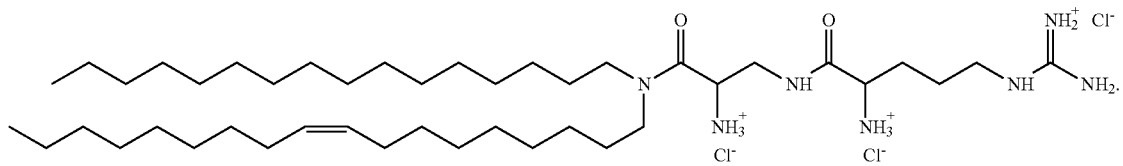

In some embodiments, the cationic lipid is β-arginyl-2,3-diamino propionic acid-N-lauryl-N-myristyl-amide trihydrochloride of Formula IV:

(Formula IV)

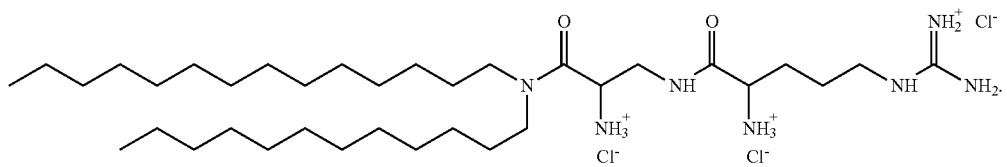

In some embodiments, the cationic lipid is s-arginyl-lysine-N-lauryl-N-myristyl-amide trihydrochloride of Formula V:

(Formula V)

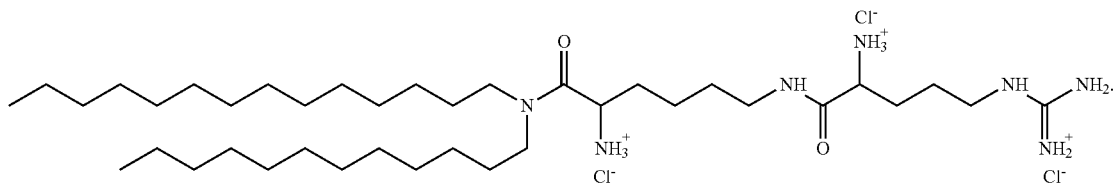

In some embodiments, the sterol compound is cholesterol. In some embodiments, the sterol compound is stigmasterin.

In some embodiments, the PEG moiety of the PEGylated lipid has a molecular weight from about 800 to 5,000 Da. In some embodiments, the molecular weight of the PEG moiety of the PEGylated lipid is about 800 Da. In some embodiments, the molecular weight of the PEG moiety of the PEGylated lipid is about 2,000 Da. In some embodiments, the molecular weight of the PEG moiety of the PEGylated lipid is about 5,000 Da. In some embodiments, the PEGylated lipid is a PEGylated phosphoethanolamine of Formula VII, wherein each of R3 and R4 is individually and independently linear C13-C17 alkyl, and p is any integer from 18, 19 or 20, or from 44, 45 or 46 or from 113, 114 or 115. In some embodiments, R3 and R4 are the same. In some embodiments, R3 and R4 are different. In some embodiments, each of R3 and R4 is individually and independently selected from the group consisting of C13 alkyl, C15 alkyl and C17 alkyl. In some embodiments, the PEGylated phosphoethanolamine of Formula VII is 1,2-distearoyl-sn-glycero-3-phosphoethanolamine-N-[methoxy(polyethylene glycol)-2000](ammonium salt):

(Formula XI)

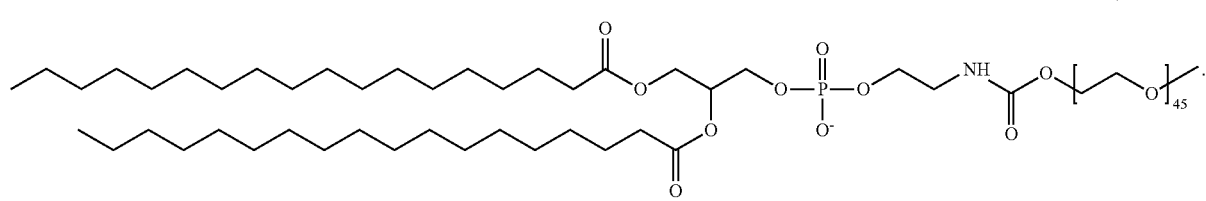

In some embodiments, the PEGylated phosphoethanolamine of Formula VII is 1,2-distearoyl-sn-glycero-3-phosphoethanolamine-N-[methoxy(polyethylene glycol)-5000](ammonium salt):

In some embodiments, the PEGylated lipid is a PEGylated diacylglycerol of Formula IX, wherein each of $R^6$ and $R^7$ is individually and independently linear C11-C17 alkyl, and r is any integer from 18, 19 or 20, or from 44, 45 or 46 or from (Formula XII)

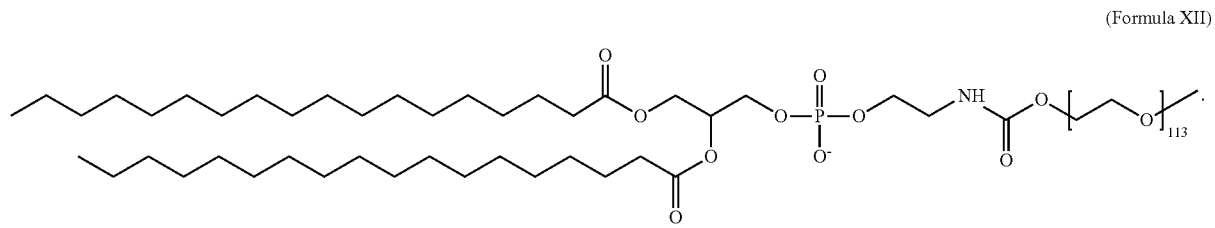

In some embodiments, the PEGylated lipid is a PEGylated ceramide of Formula VIII, wherein $R^5$ is linear C7-C15 alkyl, and q is any integer from 18, 19 or 20, or from 44, 45 or 46 or from 113, 114 or 115. In some embodiments, $R^5$ is linear C7 alkyl. In some embodiments, $R^5$ is linear C15 alkyl. In some embodiments, the PEGylated ceramide of Formula VIII is N-octanoyl-sphingosine-1-{succinyl[methoxy(polyethylene glycol)2000]}:

113, 114 or 115. In some embodiments, $R^6$ and $R^7$ are the same. In some embodiments, $R^6$ and $R^7$ are different. In some embodiments, each of $R^6$ and $R^7$ is individually and independently selected from the group consisting of linear C17 alkyl, linear C15 alkyl and linear C13 alkyl. In some embodiments, the PEGylated diacylglycerol of Formula IX 1,2-Distearoyl-sn-glycerol [methoxy(polyethylene glycol) 2000]:

(Formula XIII)

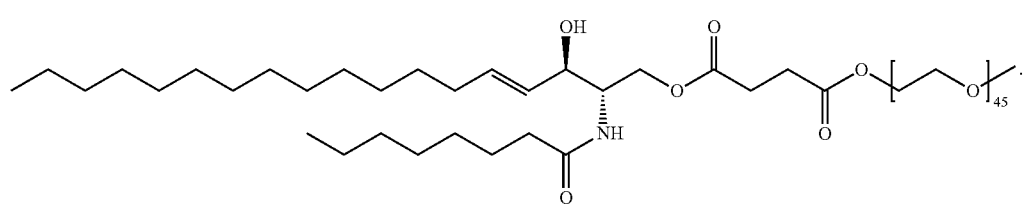

In some embodiments, the PEGylated ceramide of Formula VIII is N-palmitoyl-sphingosine-1-{succinyl[methoxy(polyethylene glycol)2000]}:

(Formula XIV)

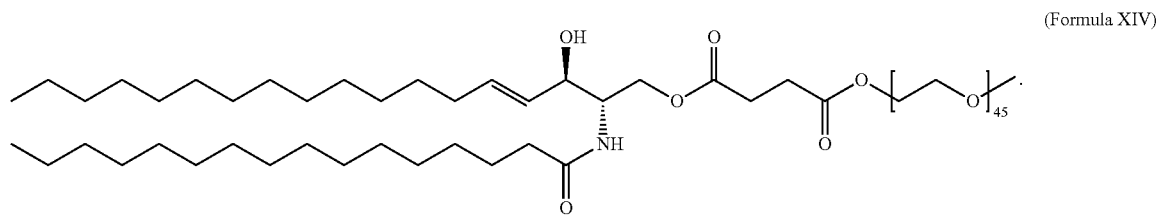

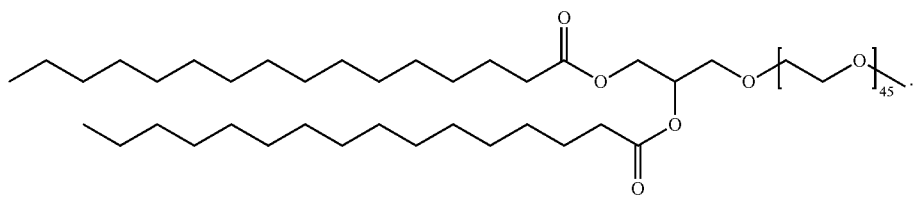

(Formula XV)

In some embodiments, the PEGylated diacylglycerol of Formula IX is 1,2-Dipalmitoyl-sn-glycerol [methoxy(polyethylene glycol)2000]:

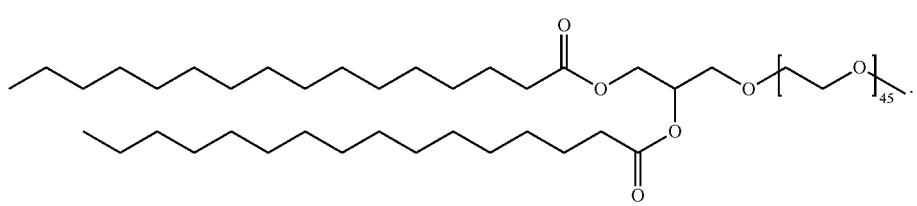

(Formula XVI)

In some embodiments, the PEGylated diacylglycerol of Formula IX is:

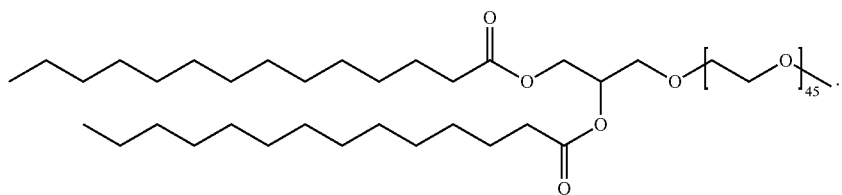

(Formula XVII)

In some embodiments, the LNP includes at least one cationic lipid selected from of Formulas III, IV, and V, at least one sterol compound selected from a cholesterol and stigmasterin, and wherein the PEGylated lipid is at least one selected from Formulas XI and XII. In some embodiments, the LNP includes at least one cationic lipid selected from Formulas III, IV, and V, at least one sterol compound selected from a cholesterol and stigmasterin, and wherein the PEGylated lipid is at least one selected from Formulas XIII and XIV. In some embodiments, the LNP includes at least one cationic lipid selected from Formulas III, IV, and V, at least one sterol compound selected from a cholesterol and stigmasterin, and wherein the PEGylated lipid is at least one selected from Formulas XV and XVI. In some embodiments, the LNP includes a cationic lipid of Formula III, a cholesterol as the sterol compound, and wherein the PEGylated lipid is Formula XI.

In any of the LNP embodiments in the previous paragraph, wherein the content of the cationic lipid composition is between about 65 mole % to 75 mole %, the content of the sterol compound is between about 24 mole % to 34 mole % and the content of the PEGylated lipid is between about 0.5 mole % to 1.5 mole %, wherein the sum of the content of the cationic lipid, of the sterol compound and of the PEGylated lipid for the lipid composition is 100 mole %. In some embodiments, the cationic lipid is about 70 mole %, the content of the sterol compound is about 29 mole % and the content of the PEGylated lipid is about 1 mole %. In some embodiments, the LNP is 70 mole % of Formula III, 29 mole % of cholesterol, and 1 mole % of Formula XI.

Exosomes

Exosomes are endogenous nano-vesicles that transport RNAs and proteins, and which can deliver RNA to the brain and other target organs. To reduce immunogenicity, Alvarez-Erviti et al. (2011, Nat Biotechnol 29: 341) used self-derived dendritic cells for exosome production. Targeting to the brain was achieved by engineering the dendritic cells to express Lamp2b, an exosomal membrane protein, fused to the neuron-specific RVG peptide. Purified exosomes were loaded with exogenous RNA by electroporation. Intravenously injected RVG-targeted exosomes delivered GAPDH siRNA specifically to neurons, microglia, oligodendrocytes in the brain, resulting in a specific gene knockdown. Pre-exposure to RVG exosomes did not attenuate knockdown, and non-specific uptake in other tissues was not observed. The therapeutic potential of exosome-mediated siRNA delivery was demonstrated by the strong mRNA (60%) and protein (62%) knockdown of BACE1, a therapeutic target in Alzheimer's disease.

To obtain a pool of immunologically inert exosomes, Alvarez-Erviti et al. harvested bone marrow from inbred C57BL/6 mice with a homogenous major histocompatibility complex (MHC) haplotype. As immature dendritic cells produce large quantities of exosomes devoid of T-cell activators such as MHC-II and CD86, Alvarez-Erviti et al. selected for dendritic cells with granulocyte/macrophagecolony stimulating factor (GM-CSF) for 7 d. Exosomes were purified from the culture supernatant the following day using well-established ultracentrifugation protocols. The exosomes produced were physically homogenous, with a size distribution peaking at 80 nm in diameter as determined by nanoparticle tracking analysis (NTA) and electron microscopy. Alvarez-Erviti et al. obtained 6-12 µg of exosomes (measured based on protein concentration) per $10^6$ cells.

Next, Alvarez-Erviti et al. investigated the possibility of loading modified exosomes with exogenous cargoes using electroporation protocols adapted for nanoscale applications. As electroporation for membrane particles at the nanometer scale is not well-characterized, nonspecific Cy5-labeled RNA was used for the empirical optimization of the electroporation protocol. The amount of encapsulated RNA was assayed after ultracentrifugation and lysis of exosomes. Electroporation at 400 V and 125 µF resulted in the greatest retention of RNA and was used for all subsequent experiments.

Alvarez-Erviti et al. administered 150 µg of each BACE1 siRNA encapsulated in 150 µg of RVG exosomes to normal C57BL/6 mice and compared the knockdown efficiency to four controls: untreated mice, mice injected with RVG exosomes only, mice injected with BACE1 siRNA complexed to an in vivo cationic liposome reagent and mice injected with BACE1 siRNA complexed to RVG-9R, the RVG peptide conjugated to 9 D-arginines that electrostatically binds to the siRNA. Cortical tissue samples were analyzed 3 d after administration and a significant protein knockdown (45%, P<0.05, versus 62%, P<0.01) in both siRNA-RVG-9R-treated and siRNARVG exosome-treated mice was observed, resulting from a significant decrease in BACE1 mRNA levels (66% [+ or –]15%, P<0.001 and 61% [+ or –]13% respectively, P<0.01). Moreover, Applicants demonstrated a significant decrease (55%, P<0.05) in the total [beta]-amyloid 1-42 levels, a main component of the amyloid plaques in Alzheimer's pathology, in the RVG-exosome-treated animals. The decrease observed was greater than the β-amyloid 1-40 decrease demonstrated in normal mice after intraventricular injection of BACE1 inhibitors. Alvarez-Erviti et al. carried out 5'-rapid amplification of cDNA ends (RACE) on BACE1 cleavage product, which provided evidence of RNAi-mediated knockdown by the siRNA.

Finally, Alvarez-Erviti et al. investigated whether RNA-RVG exosomes induced immune responses in vivo by assessing TL-6, IP-10, TNFα and IFN-α serum concentrations. Following exosome treatment, nonsignificant changes in all cytokines were registered similar to siRNA-transfection reagent treatment in contrast to siRNA-RVG-9R, which potently stimulated IL-6 secretion, confirming the immunologically inert profile of the exosome treatment. Given that exosomes encapsulate only 20% of siRNA, delivery with RVG-exosome appears to be more efficient than RVG-9R delivery as comparable mRNA knockdown and greater protein knockdown was achieved with fivefold less siRNA without the corresponding level of immune stimulation. This experiment demonstrated the therapeutic potential of RVG-exosome technology, which is potentially suited for long-term silencing of genes related to neurodegenerative diseases. The exosome delivery system of Alvarez-Erviti et al. may be applied to deliver the CD-functionalized CRISPR-Cas system of the present invention to therapeutic targets, especially neurodegenerative diseases. A dosage of about 100 to 1000 mg of CRISPR-Cas encapsulated in about 100 to 1000 mg of RVG exosomes may be contemplated for the present invention.

El-Andaloussi et al. (Nature Protocols 7, 2112-2126 (2012)) discloses how exosomes derived from cultured cells can be harnessed for delivery of RNA in vitro and in vivo. This protocol first describes the generation of targeted exosomes through transfection of an expression vector, comprising an exosomal protein fused with a peptide ligand. Next, El-Andaloussi et al. explain how to purify and characterize exosomes from transfected cell supernatant. Next, El-Andaloussi et al. detail crucial steps for loading RNA into exosomes. Finally, El-Andaloussi et al. outline how to use exosomes to efficiently deliver RNA in vitro and in vivo in mouse brain. Examples of anticipated results in which exosome-mediated RNA delivery is evaluated by functional assays and imaging are also provided. The entire protocol takes ~3 weeks. Delivery or administration according to the invention may be performed using exosomes produced from self-derived dendritic cells. From the herein teachings, this can be employed in the practice of the invention.

In another embodiment, the plasma exosomes of Wahlgren et al. (Nucleic Acids Research, 2012, Vol. 40, No. 17 e130) are contemplated. Exosomes are nano-sized vesicles (30-90 nm in size) produced by many cell types, including dendritic cells (DC), B cells, T cells, mast cells, epithelial cells and tumor cells. These vesicles are formed by inward budding of late endosomes and are then released to the extracellular environment upon fusion with the plasma membrane. Because exosomes naturally carry RNA between cells, this property may be useful in gene therapy, and from this disclosure can be employed in the practice of the instant invention.

Exosomes from plasma can be prepared by centrifugation of buffy coat at 900 g for 20 min to isolate the plasma followed by harvesting cell supernatants, centrifuging at 300 g for 10 min to eliminate cells and at 16 500 g for 30 min followed by filtration through a 0.22 mm filter. Exosomes are pelleted by ultracentrifugation at 120 OOOg for70 min. Chemical transfection of siRNA into exosomes is carried out according to the manufacturer's instructions in RNAi Human/Mouse Starter Kit (Quiagen, Hilden, Germany). siRNA is added to 100 ml PBS at a final concentration of 2 mmol/ml. After adding HiPerFect transfection reagent, the mixture is incubated for 10 min at RT. In order to remove the excess of micelles, the exosomes are re-isolated using aldehyde/sulfate latex beads. The chemical transfection of CRISPR-Cas into exosomes may be conducted similarly to siRNA. The exosomes may be co-cultured with monocytes and lymphocytes isolated from the peripheral blood of healthy donors. Therefore, it may be contemplated that exosomes containing CRISPR-Cas may be introduced to monocytes and lymphocytes of and autologously reintroduced into a human. Accordingly, delivery or administration according to the invention may be performed using plasma exosomes.

Liposomes

Delivery or administration according to the invention can be performed with liposomes. Liposomes are spherical vesicle structures composed of a uni- or multilamellar lipid bilayer surrounding internal aqueous compartments and a relatively impermeable outer lipophilic phospholipid bilayer. Liposomes have gained considerable attention as drug delivery carriers because they are biocompatible, non-toxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi:10.1155/2011/469679 for review).

Liposomes can be made from several different types of lipids; however, phospholipids are most commonly used to generate liposomes as drug carriers. Although liposome formation is spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review).

Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. Further, liposomes are prepared from hydrogenated egg phosphatidylcholine or egg phosphatidylcholine, cholesterol, and dicetyl phosphate, and their mean vesicle sizes were adjusted to about 50 and 100 nm. (see, e.g., Spuch and Navarro, Journal of Drug Delivery, vol. 2011, Article ID 469679, 12 pages, 2011. doi:10.1155/2011/469679 for review).

A liposome formulation may be mainly comprised of natural phospholipids and lipids such as 1,2-distearoyl-sn-glycero-3-phosphatidyl choline (DSPC), sphingomyelin, egg phosphatidylcholines and monosialoganglioside. Since this formulation is made up of phospholipids only, liposomal formulations have encountered many challenges, one of the ones being the instability in plasma. Several attempts to overcome these challenges have been made, specifically in the manipulation of the lipid membrane. One of these attempts focused on the manipulation of cholesterol. Addition of cholesterol to conventional formulations reduces rapid release of the encapsulated bioactive compound into the plasma or 1,2-dioleoyl-sn-glycero-3-phosphoethanolamine (DOPE) increases the stability (see, e.g., Spuch and Navarro, Journal of Drug Delivery, vol. 2011, Article ID 469679, 12 pages, 2011. doi:10.1155/2011/469679 for review).

In a particularly advantageous embodiment, Trojan Horse liposomes (also known as Molecular Trojan Horses) are desirable and protocols may be found at cshprotocols.cshlp.org/content/2010/4/pdb.prot5407.long. These particles allow delivery of a transgene to the entire brain after an intravascular injection. Without being bound by limitation, it is believed that neutral lipid particles with specific antibodies conjugated to surface allow crossing of the blood brain barrier via endocytosis. Trojan Horse Liposomes may be used to deliver the CRISPR family of nucleases to the brain via an intravascular injection, which would allow whole brain transgenic animals without the need for embryonic manipulation. About 1-5 g of DNA or RNA may be contemplated for in vivo administration in liposomes.

In another embodiment, the CD-functionalized CRISPR-Cas system or components thereof may be administered in liposomes, such as a stable nucleic-acid-lipid particle (SNALP) (see, e.g., Morrissey et al., Nature Biotechnology, Vol. 23, No. 8, August 2005). Daily intravenous injections of about 1, 3 or 5 mg/kg/day of a specific CRISPR-Cas targeted in a SNALP are contemplated. The daily treatment may be over about three days and then weekly for about five weeks. In another embodiment, a specific CRISPR-Cas encapsulated SNALP) administered by intravenous injection to at doses of about 1 or 2.5 mg/kg are also contemplated (see, e.g., Zimmerman et al., Nature Letters, Vol. 441, 4 May 2006). The SNALP formulation may contain the lipids 3-N-[(methoxypolyy(ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio (see, e.g., Zimmerman et al., Nature Letters, Vol. 441, 4 May 2006).

In another embodiment, stable nucleic-acid-lipid particles (SNALPs) have proven to be effective delivery molecules to highly vascularized HepG2-derived liver tumors but not in poorly vascularized HCT-116 derived liver tumors (see, e.g., Li, Gene Therapy (2012) 19, 775-780). The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulted SNALP liposomes are about 80-100 nm in size.

In yet another embodiment, a SNALP may comprise synthetic cholesterol (Sigma-Aldrich, St Louis, MO, USA), dipalmitoylphosphatidylcholine (Avanti Polar Lipids, Alabaster, AL, USA), 3-N-[(w-methoxy poly(ethylene glycol) 2000)carbamoyl]-1,2-dimyrestyloxypropylamine, and cationic 1,2-dilinoleyloxy-3-N,Ndimethylaminopropane (see, e.g., Geisbert et al., Lancet 2010; 375: 1896-905). A dosage of about 2 mg/kg total CRISPR-Cas per dose administered as, for example, a bolus intravenous infusion may be contemplated.

In yet another embodiment, a SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N;N-dimethyl)aminopropane (DLinDMA) (see, e.g., Judge, J. Clin. Invest. 119:661-673 (2009)). Formulations used for in vivo studies may comprise a final lipid/RNA mass ratio of about 9:1.

The safety profile of RNAi nanomedicines has been reviewed by Barros and Gollob of Alnylam Pharmaceuticals (see, e.g., Advanced Drug Delivery Reviews 64 (2012) 1730-1737). The stable nucleic acid lipid particle (SNALP) is comprised of four different lipids—an ionizable lipid (DLinDMA) that is cationic at low pH, a neutral helper lipid, cholesterol, and a diffusible polyethylene glycol (PEG)-lipid. The particle is approximately 80 nm in diameter and is charge-neutral at physiologic pH. During formulation, the ionizable lipid serves to condense lipid with the anionic RNA during particle formation. When positively charged under increasingly acidic endosomal conditions, the ionizable lipid also mediates the fusion of SNALP with the endosomal membrane enabling release of RNA into the cytoplasm. The PEG-lipid stabilizes the particle and reduces aggregation during formulation, and subsequently provides a neutral hydrophilic exterior that improves pharmacokinetic properties.

To date, two clinical programs have been initiated using SNALP formulations with RNA. Tekmira Pharmaceuticals recently completed a phase I single-dose study of SNALP-ApoB in adult volunteers with elevated LDL cholesterol. ApoB is predominantly expressed in the liver and jejunum and is essential for the assembly and secretion of VLDL and LDL. Seventeen subjects received a single dose of SNALP-ApoB (dose escalation across 7 dose levels). There was no evidence of liver toxicity (anticipated as the potential dose-limiting toxicity based on preclinical studies). One (of two) subjects at the highest dose experienced flu-like symptoms consistent with immune system stimulation, and the decision was made to conclude the trial.

Alnylam Pharmaceuticals has similarly advanced ALN-TTR01, which employs the SNALP technology described above and targets hepatocyte production of both mutant and wild-type TTR to treat TTR amyloidosis (ATTR). Three ATTR syndromes have been described: familial amyloidotic polyneuropathy (FAP) and familial amyloidotic cardiomyopathy (FAC) both caused by autosomal dominant mutations in TTR; and senile systemic amyloidosis (SSA) cause by wildtype TTR. A placebo-controlled, single dose-escalation phase I trial of ALN-TTR01 was recently completed in patients with ATTR. ALN-TTR01 was administered as a 15-minute IV infusion to 31 patients (23 with study drug and 8 with placebo) within a dose range of 0.01 to 1.0 mg/kg (based on siRNA). Treatment was well tolerated with no significant increases in liver function tests. Infusion-related reactions were noted in 3 of 23 patients at ≥0.4 mg/kg; all responded to slowing of the infusion rate and all continued on study. Minimal and transient elevations of serum cytokines IL-6, IP-10 and IL-Ira were noted in two patients at the highest dose of 1 mg/kg (as anticipated from preclinical and NHP studies). Lowering of serum TTR, the expected pharmacodynamics effect of ALN-TTR01, was observed at 1 mg/kg.

In yet another embodiment, a SNALP may be made by solubilizing a cationic lipid, DSPC, cholesterol and PEG-lipid e.g., in ethanol, e.g., at a molar ratio of 40:10:40:10, respectively (see, Semple et al., Nature Niotechnology, Volume 28 Number 2 Feb. 2010, pp. 172-177). The lipid mixture was added to an aqueous buffer (50 mM citrate, pH 4) with mixing to a final ethanol and lipid concentration of 30% (vol/vol) and 6.1 mg/ml, respectively, and allowed to equilibrate at 22° C. for 2 min before extrusion. The hydrated lipids were extruded through two stacked 80 nm pore-sized filters (Nuclepore) at 22° C. using a Lipex Extruder (Northern Lipids) until a vesicle diameter of 70-90 nm, as determined by dynamic light scattering analysis, was obtained. This generally required 1-3 passes. The siRNA (solubilized in a 50 mM citrate, pH 4 aqueous solution containing 30% ethanol) was added to the pre-equilibrated (35° C.) vesicles at a rate of ~5 ml/min with mixing. After a final target siRNA/lipid ratio of 0.06 (wt/wt) was reached, the mixture was incubated for a further 30 min at 35° C. to allow vesicle reorganization and encapsulation of the siRNA. The ethanol was then removed and the external buffer replaced with PBS (155 mM NaCl, 3 mM $Na_2HPO_4$, 1 mM $KH_2PO_4$, pH 7.5) by either dialysis or tangential flow diafiltration. siRNA were encapsulated in SNALP using a controlled step-wise dilution method process. The lipid constituents of KC2-SNALP were DLin-KC2-DMA (cationic lipid), dipalmitoylphosphatidylcholine (DPPC; Avanti Polar Lipids), synthetic cholesterol (Sigma) and PEG-C-DMA used at a molar ratio of 57.1:7.1:34.3:1.4. Upon formation of the loaded particles, SNALP were dialyzed against PBS and filter sterilized through a 0.2 m filter before use. Mean particle sizes were 75-85 nm and 90-95% of the siRNA was encapsulated within the lipid particles. The final siRNA/lipid ratio in formulations used for in vivo testing was ~0.15 (wt/wt). LNP-siRNA systems containing Factor VII siRNA were diluted to the appropriate concentrations in sterile PBS immediately before use and the formulations were administered intravenously through the lateral tail vein in a total volume of 10 ml/kg. This method and these delivery systems may be extrapolated to the CD-functionalized CRISPR-Cas system of the present invention.

Other Lipids

Other cationic lipids, such as amino lipid 2,2-dilinoleyl-4-dimethylaminoethyl-[1,3]-dioxolane (DLin-KC2-DMA) may be utilized to encapsulate CRISPR-Cas or components thereof or nucleic acid molecule(s) coding therefor e.g., similar to siRNA (see, e.g., Jayaraman, Angew. Chem. Int. Ed. 2012, 51, 8529-8533), and hence may be employed in the practice of the invention. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11±0.04 (n=56), the particles may be extruded up to three times through 80 nm membranes prior to adding the guide RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Michael S D Kormann et al. ("Expression of therapeutic proteins after delivery of chemically modified mRNA in mice: Nature Biotechnology, Volume:29, Pages: 154-157 (2011)) describes the use of lipid envelopes to deliver RNA. Use of lipid envelopes is also preferred in the present invention.

In another embodiment, lipids may be formulated with the CD-functionalized CRISPR-Cas system of the present invention or component(s) thereof or nucleic acid molecule(s) coding therefor to form lipid nanoparticles (LNPs). Lipids include, but are not limited to, DLin-KC2-DMA4, C12-200 and colipids distearoylphosphatidyl choline, cholesterol, and PEG-DMG may be formulated with CRISPR-Cas instead of siRNA (see, e.g., Novobrantseva, Molecular Therapy-Nucleic Acids (2012) 1, e4; doi:10.1038/mtna.2011.3) using a spontaneous vesicle formation procedure. The component molar ratio may be about 50/10/38.5/1.5 (DLin-KC2-DMA or C12-200/disteroylphosphatidyl choline/cholesterol/PEG-DMG). The final lipid:siRNA weight ratio may be ~12:1 and 9:1 in the case of DLin-KC2-DMA and C12-200 lipid nanoparticles (LNPs), respectively. The formulations may have mean particle diameters of ~80 nm with >90% entrapment efficiency. A 3 mg/kg dose may be contemplated.

Tekmira has a portfolio of approximately 95 patent families, in the U.S. and abroad, that are directed to various aspects of LNPs and LNP formulations (see, e.g., U.S. Pat. Nos. 7,982,027; 7,799,565; 8,058,069; 8,283,333; 7,901,708; 7,745,651; 7,803,397; 8,101,741; 8,188,263; 7,915,399; 8,236,943 and 7,838,658 and European Pat. Nos 1766035; 1519714; 1781593 and 1664316), all of which may be used and/or adapted to the present invention.

The CD-functionalized CRISPR-Cas system or components thereof or nucleic acid molecule(s) coding therefor may be delivered encapsulated in PLGA Microspheres such as that further described in US published applications 20130252281 and 20130245107 and 20130244279 (assigned to Moderna Therapeutics) which relate to aspects of formulation of compositions comprising modified nucleic acid molecules which may encode a protein, a protein precursor, or a partially or fully processed form of the protein or a protein precursor. The formulation may have a molar ratio 50:10:38.5:1.5-3.0 (cationic lipid:fusogenic lipid:cholesterol:PEG lipid). The PEG lipid may be selected from, but is not limited to PEG-c-DOMG, PEG-DMG. The fusogenic lipid may be DSPC. See also, Schrum et al., Delivery and Formulation of Engineered Nucleic Acids, US published application 20120251618.

Nanomerics' technology addresses bioavailability challenges for a broad range of therapeutics, including low molecular weight hydrophobic drugs, peptides, and nucleic acid based therapeutics (plasmid, siRNA, miRNA). Specific administration routes for which the technology has demonstrated clear advantages include the oral route, transport across the blood-brain-barrier, delivery to solid tumours, as well as to the eye. See, e.g., Mazza et al., 2013, ACS Nano. 2013 Feb. 26; 7(2):1016-26; Uchegbu and Siew, 2013, J Pharm Sci. 102(2):305-10 and Lalatsa et al., 2012, J Control Release. 2012 Jul. 20; 161(2):523-36.

US Patent Publication No. 20050019923 describes cationic dendrimers for delivering bioactive molecules, such as polynucleotide molecules, peptides and polypeptides and/or pharmaceutical agents, to a mammalian body. The dendrimers are suitable for targeting the delivery of the bioactive molecules to, for example, the liver, spleen, lung, kidney or heart (or even the brain). Dendrimers are synthetic 3-dimensional macromolecules that are prepared in a step-wise fashion from simple branched monomer units, the nature and functionality of which can be easily controlled and varied. Dendrimers are synthesised from the repeated addition of building blocks to a multifunctional core (divergent approach to synthesis), or towards a multifunctional core (convergent approach to synthesis) and each addition of a 3-dimensional shell of building blocks leads to the formation of a higher generation of the dendrimers. Polypropylenimine dendrimers start from a diaminobutane core to which is added twice the number of amino groups by a double Michael addition of acrylonitrile to the primary amines followed by the hydrogenation of the nitriles. This results in a doubling of the amino groups. Polypropylenimine dendrimers contain 100% protonable nitrogens and up to 64 terminal amino groups (generation 5, DAB 64). Protonable groups are usually amine groups which are able to accept protons at neutral pH. The use of dendrimers as gene delivery agents has largely focused on the use of the polyamidoamine. and phosphorous containing compounds with a mixture of amine/amide or $N-P(O_2)S$ as the conjugating units respectively with no work being reported on the use of the lower generation polypropylenimine dendrimers for gene delivery. Polypropylenimine dendrimers have also been studied as pH sensitive controlled release systems for drug delivery and for their encapsulation of guest molecules when chemically modified by peripheral amino acid groups. The cytotoxicity and interaction of polypropylenimine dendrimers with DNA as well as the transfection efficacy of DAB 64 has also been studied.

US Patent Publication No. 20050019923 is based upon the observation that, contrary to earlier reports, cationic dendrimers, such as polypropylenimine dendrimers, display suitable properties, such as specific targeting and low toxicity, for use in the targeted delivery of bioactive molecules, such as genetic material. In addition, derivatives of the cationic dendrimer also display suitable properties for the targeted delivery of bioactive molecules. See also, Bioactive Polymers, US published application 20080267903, which discloses "Various polymers, including cationic polyamine polymers and dendrimeric polymers, are shown to possess anti-proliferative activity, and may therefore be useful for treatment of disorders characterised by undesirable cellular proliferation such as neoplasms and tumours, inflammatory disorders (including autoimmune disorders), psoriasis and atherosclerosis. The polymers may be used alone as active agents, or as delivery vehicles for other therapeutic agents, such as drug molecules or nucleic acids for gene therapy. In such cases, the polymers' own intrinsic anti-tumour activity may complement the activity of the agent to be delivered." The disclosures of these patent publications may be employed in conjunction with herein teachings for delivery of CD-functionalized CRISPR-Cas system(s) or component (s) thereof or nucleic acid molecule(s) coding therefor.

Supercharged Proteins

Supercharged proteins are a class of engineered or naturally occurring proteins with unusually high positive or negative net theoretical charge and may be employed in delivery of CD-functionalized CRISPR-Cas system(s) or component(s) thereof or nucleic acid molecule(s) coding therefor. Both supernegatively and superpositively charged proteins exhibit a remarkable ability to withstand thermally or chemically induced aggregation. Superpositively charged proteins are also able to penetrate mammalian cells. Associating cargo with these proteins, such as plasmid DNA, RNA, or other proteins, can enable the functional delivery of these macromolecules into mammalian cells both in vitro and in vivo. The creation and characterization of supercharged proteins has been reported in 2007 (Lawrence et al., 2007, Journal of the American Chemical Society 129, 10110-10112).

The nonviral delivery of RNA and plasmid DNA into mammalian cells are valuable both for research and therapeutic applications (Akinc et al., 2010, Nat. Biotech. 26, 561-569). Purified+36 GFP protein (or other superpositively charged protein) is mixed with RNAs in the appropriate serum-free media and allowed to complex prior addition to cells. Inclusion of serum at this stage inhibits formation of the supercharged protein-RNA complexes and reduces the effectiveness of the treatment. The following protocol has been found to be effective for a variety of cell lines (McNaughton et al., 2009, Proc. Natl. Acad. Sci. USA 106, 6111-6116) (However, pilot experiments varying the dose of protein and RNA should be performed to optimize the procedure for specific cell lines): (1) One day before treatment, plate $1\times10^5$ cells per well in a 48-well plate. (2) On the day of treatment, dilute purified+36 GFP protein in serumfree media to a final concentration 200 nM. Add RNA to a final concentration of 50 nM. Vortex to mix and incubate at room temperature for 10 min. (3) During incubation, aspirate media from cells and wash once with PBS. (4) Following incubation of +36 GFP and RNA, add the protein-RNA complexes to cells. (5) Incubate cells with complexes at 37° C. for 4 h. (6) Following incubation, aspirate the media and wash three times with 20 U/mL heparin PBS. Incubate cells with serum-containing media for a further 48 h or longer depending upon the assay for activity. (7) Analyze cells by immunoblot, qPCR, phenotypic assay, or other appropriate method.

It has been further found +36 GFP to be an effective plasmid delivery reagent in a range of cells. As plasmid DNA is a larger cargo than siRNA, proportionately more +36 GFP protein is required to effectively complex plasmids. For effective plasmid delivery Applicants have developed a variant of +36 GFP bearing a C-terminal HA2 peptide tag, a known endosome-disrupting peptide derived from the influenza virus hemagglutinin protein. The following protocol has been effective in a variety of cells, but as above it is advised that plasmid DNA and supercharged protein doses be optimized for specific cell lines and delivery applications: (1) One day before treatment, plate $1\times10^5$ per well in a 48-well plate. (2) On the day of treatment, dilute purified b36 GFP protein in serumfree media to a final concentration 2 mM. Add 1 mg of plasmid DNA. Vortex to mix and incubate at room temperature for 10 min. (3) During incubation, aspirate media from cells and wash once with PBS.

(4) Following incubation of b36 GFP and plasmid DNA, gently add the protein-DNA complexes to cells. (5) Incubate cells with complexes at 37 C for 4 h. (6) Following incubation, aspirate the media and wash with PBS. Incubate cells in serum-containing media and incubate for a further 24-48 h. (7) Analyze plasmid delivery (e.g., by plasmid-driven gene expression) as appropriate.

See also, e.g., McNaughton et al., Proc. Natl. Acad. Sci. USA 106, 6111-6116 (2009); Cronican et al., ACS Chemical Biology 5, 747-752 (2010); Cronican et al., Chemistry & Biology 18, 833-838 (2011); Thompson et al., Methods in Enzymology 503, 293-319 (2012); Thompson, D. B., et al., Chemistry & Biology 19 (7), 831-843 (2012). The methods of the super charged proteins may be used and/or adapted for delivery of the CD-functionalized CRISPR-Cas system of the present invention. These systems in conjunction with herein teaching can be employed in the delivery of CD-functionalized CRISPR-Cas system(s) or component(s) thereof or nucleic acid molecule(s) coding therefor.

Cell Penetrating Peptides (CPPs)

In yet another embodiment, cell penetrating peptides (CPPs) are contemplated for the delivery of the CD-functionalized CRISPR-Cas system. CPPs are short peptides that facilitate cellular uptake of various molecular cargo (from nanosize particles to small chemical molecules and large fragments of DNA). The term "cargo" as used herein includes but is not limited to the group consisting of therapeutic agents, diagnostic probes, peptides, nucleic acids, antisense oligonucleotides, plasmids, proteins, particles, including nanoparticles, liposomes, chromophores, small molecules and radioactive materials. In aspects of the invention, the cargo may also comprise any component of the CD-functionalized CRISPR-Cas system or the entire CD-functionalized functional CRISPR-Cas system. Aspects of the present invention further provide methods for delivering a desired cargo into a subject comprising: (a) preparing a complex comprising the cell penetrating peptide of the present invention and a desired cargo, and (b) orally, intraarticularly, intraperitoneally, intrathecally, intraarterially, intranasally, intraparenchymally, subcutaneously, intramuscularly, intravenously, dermally, intrarectally, or topically administering the complex to a subject. The cargo is associated with the peptides either through chemical linkage via covalent bonds or through non-covalent interactions.

The function of the CPPs are to deliver the cargo into cells, a process that commonly occurs through endocytosis with the cargo delivered to the endosomes of living mammalian cells. Cell-penetrating peptides are of different sizes, amino acid sequences, and charges but all CPPs have one distinct characteristic, which is the ability to translocate the plasma membrane and facilitate the delivery of various molecular cargoes to the cytoplasm or an organelle. CPP translocation may be classified into three main entry mechanisms: direct penetration in the membrane, endocytosis-mediated entry, and translocation through the formation of a transitory structure. CPPs have found numerous applications in medicine as drug delivery agents in the treatment of different diseases including cancer and virus inhibitors, as well as contrast agents for cell labeling. Examples of the latter include acting as a carrier for GFP, MRI contrast agents, or quantum dots. CPPs hold great potential as in vitro and in vivo delivery vectors for use in research and medicine. CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake. One of the initial CPPs discovered was the trans-activating transcriptional activator (Tat) from Human Immunodeficiency Virus 1 (HIV-1) which was found to be efficiently taken up from the surrounding media by numerous cell types in culture. Since then, the number of known CPPs has expanded considerably and small molecule synthetic analogues with more effective protein transduction properties have been generated. CPPs include but are not limited to Penetratin, Tat (48-60), Transportan, and (R-AhX-R4) (Ahx=aminohexanoyl).

U.S. Pat. No. 8,372,951, provides a CPP derived from eosinophil cationic protein (ECP) which exhibits highly cell-penetrating efficiency and low toxicity. Aspects of delivering the CPP with its cargo into a vertebrate subject are also provided. Further aspects of CPPs and their delivery are described in U.S. Pat. Nos. 8,575,305; 8,614,194 and 8,044,019. CPPs can be used to deliver the CD-functionalized CRISPR-Cas system or components thereof. That CPPs can be employed to deliver the CD-functionalized CRISPR-Cas system or components thereof is also provided in the manuscript "Gene disruption by cell-penetrating peptide-mediated delivery of Cas9 protein and guide RNA", by Suresh Ramakrishna, Abu-Bonsrah Kwaku Dad, Jagadish Beloor, et al. Genome Res. 2014 Apr. 2, incorporated by reference in its entirety, wherein it is demonstrated that treatment with CPP-conjugated recombinant Cas9 protein and CPP-complexed guide RNAs lead to endogenous gene disruptions in human cell lines. In the paper the Cas9 protein was conjugated to CPP via a thioether bond, whereas the guide RNA was complexed with CPP, forming condensed, positively charged particles. It was shown that simultaneous and sequential treatment of human cells, including embryonic stem cells, dermal fibroblasts, HEK293T cells, HeLa cells, and embryonic carcinoma cells, with the modified Cas9 and guide RNA led to efficient gene disruptions with reduced off-target mutations relative to plasmid transfections.

Aerosol Delivery

Subjects treated for a lung disease may for example receive pharmaceutically effective amount of aerosolized AAV vector system per lung endobronchially delivered while spontaneously breathing. As such, aerosolized delivery is preferred for AAV delivery in general. An adenovirus or an AAV particle may be used for delivery. Suitable gene constructs, each operably linked to one or more regulatory sequences, may be cloned into the delivery vector.

Packaging and Promoters

The promoter used to drive CRISPR-Cas protein and cytidine deaminase coding nucleic acid molecule expression can include AAV ITR, which can serve as a promoter. This is advantageous for eliminating the need for an additional promoter element (which can take up space in the vector). The additional space freed up can be used to drive the expression of additional elements (gRNA, etc.). Also, ITR activity is relatively weaker, so can be used to reduce potential toxicity due to over expression of Cpf1.

For ubiquitous expression, promoters that can be used include: CMV, CAG, CBh, PGK, SV40, Ferritin heavy or light chains, etc. For brain or other CNS expression, SynapsinI can be used for all neurons, CaMKIIalpha can be used for excitatory neurons, GAD67 or GAD65 or VGAT can be used for GABAergic neurons. For liver expression, Albumin promoter can be used. For lung expression, SP-B can be used. For endothelial cells, ICAM can be used. For hematopoietic cells, IFNbeta or CD45 can be used. For Osteoblasts, the OG-2 can be used.

The promoter used to drive guide RNA can include Pol III promoters such as U6 or H1, as well as use of Pol II promoter and intronic cassettes to express guide RNA.

Adeno Associated Virus (AAV)

The CRISPR-Cas protein, cytidine deaminase, and one or more guide RNA can be delivered using adeno associated virus (AAV), lentivirus, adenovirus or other plasmid or viral vector types, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus. For plasmid delivery, the route of administration, formulation and dose can be as in U.S. Pat. No. 5,846,946 and as in clinical studies involving plasmids. Doses may be based on or extrapolated to an average 70 kg individual (e.g. a male adult human), and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The viral vectors can be injected into the tissue of interest. For cell-type specific genome modification, the expression of Cpf1 and cytidine deaminase can be driven by a cell-type specific promoter. For example, liver-specific expression might use the Albumin promoter and neuron-specific expression (e.g. for targeting CNS disorders) might use the Synapsin I promoter.

In terms of in vivo delivery, AAV is advantageous over other viral vectors for a couple of reasons: low toxicity (this may be due to the purification method not requiring ultra centrifugation of cell particles that can activate the immune response); and low probability of causing insertional mutagenesis because it doesn't integrate into the host genome.

AAV has a packaging limit of 4.5 or 4.75 Kb. This means that Cpf1 as well as a promoter and transcription terminator have to be all fit into the same viral vector. Constructs larger than 4.5 or 4.75 Kb will lead to significantly reduced virus production. SpCas9 is quite large, the gene itself is over 4.1 Kb, which makes it difficult for packing into AAV. Therefore embodiments of the invention include utilizing homologs of Cpf1 that are shorter.

As to AAV, the AAV can be AAV1, AAV2, AAV5 or any combination thereof. One can select the AAV of the AAV with regard to the cells to be targeted; e.g., one can select AAV serotypes 1, 2, 5 or a hybrid capsid AAV1, AAV2, AAV5 or any combination thereof for targeting brain or neuronal cells; and one can select AAV4 for targeting cardiac tissue. AAV8 is useful for delivery to the liver. The herein promoters and vectors are preferred individually. A tabulation of certain AAV serotypes as to these cells (see Grimm, D. et al, J. Virol. 82: 5887-5911 (2008)) is as follows:

| Cell Line | AAV-1 | AAV-2 | AAV-3 | AAV-4 | AAV-5 | AAV-6 | AAV-8 | AAV-9 |
|---|---|---|---|---|---|---|---|---|
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

Lentiviruses

Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types.

Lentiviruses may be prepared as follows. After cloning pCasES10 (which contains a lentiviral transfer plasmid backbone), HEK293FT at low passage (p=5) were seeded in a T-75 flask to 50% confluence the day before transfection in DMEM with 10% fetal bovine serum and without antibiotics. After 20 hours, media was changed to OptiMEM (serum-free) media and transfection was done 4 hours later. Cells were transfected with 10 μg of lentiviral transfer plasmid (pCasES10) and the following packaging plasmids: 5 μg of pMD2.G (VSV-g pseudotype), and 7.5 ug of psPAX2 (gag/pol/rev/tat). Transfection was done in 4 mL OptiMEM with a cationic lipid delivery agent (50 uL Lipofectamine 2000 and 100 ul Plus reagent). After 6 hours, the media was changed to antibiotic-free DMEM with 10% fetal bovine serum. These methods use serum during cell culture, but serum-free methods are preferred.

Lentivirus may be purified as follows. Viral supernatants were harvested after 48 hours. Supernatants were first cleared of debris and filtered through a 0.45 um low protein binding (PVDF) filter. They were then spun in a ultracentrifuge for 2 hours at 24,000 rpm. Viral pellets were resuspended in 50 ul of DMEM overnight at 4 C. They were then aliquoted and immediately frozen at −80° C.

In another embodiment, minimal non-primate lentiviral vectors based on the equine infectious anemia virus (EIAV) are also contemplated, especially for ocular gene therapy (see, e.g., Balagaan, J Gene Med 2006; 8: 275-285). In another embodiment, RetinoStat®, an equine infectious anemia virus-based lentiviral gene therapy vector that expresses angiostatic proteins endostatin and angiostatin that is delivered via a subretinal injection for the treatment of the web form of age-related macular degeneration is also contemplated (see, e.g., Binley et al., HUMAN GENE THERAPY 23:980-991 (September 2012)) and this vector may be modified for the CD-functionalized CRISPR-Cas system of the present invention.

In another embodiment, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) may be used/and or adapted to the CD-functionalized CRISPR-Cas system of the present invention. A minimum of 2.5×106 CD34+ cells per kilogram patient weight may be collected and prestimulated for 16 to 20 hours in X-VIVO 15 medium (Lonza) containing 2 µmol/L-glutamine, stem cell factor (100 ng/ml), Flt-3 ligand (Flt-3L) (100 ng/ml), and thrombopoietin (10 ng/ml) (CellGenix) at a density of 2×106 cells/ml. Prestimulated cells may be transduced with lentiviral at a multiplicity of infection of 5 for 16 to 24 hours in 75-cm2 tissue culture flasks coated with fibronectin (25 mg/cm2) (RetroNectin,Takara Bio Inc.).

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for the treatment of ocular diseases, see e.g., US Patent Publication Nos. 20060281180, 20090007284, US20110117189; US20090017543; US20070054961, US20100317109. Lentiviral vectors have also been disclosed for delivery to the brain, see, e.g., US Patent Publication Nos. US20110293571; US20110293571, US20040013648, US20070025970, US20090111106 and U.S. Pat. No. 7,259,015.

Application in Non-Animal Organisms

The CD-functionalized CRISPR system(s) (e.g., single or multiplexed) can be used in conjunction with recent advances in crop genomics. The systems described herein can be used to perform efficient and cost effective plant gene or genome interrogation or editing or manipulation—for instance, for rapid investigation and/or selection and/or interrogations and/or comparison and/or manipulations and/or transformation of plant genes or genomes; e.g., to create, identify, develop, optimize, or confer trait(s) or characteristic(s) to plant(s) or to transform a plant genome. There can accordingly be improved production of plants, new plants with new combinations of traits or characteristics or new plants with enhanced traits. The CD-functionalized CRISPR system can be used with regard to plants in Site-Directed Integration (SDI) or Gene Editing (GE) or any Near Reverse Breeding (NRB) or Reverse Breeding (RB) techniques. Aspects of utilizing the herein described Cpf1 effector protein system may be analogous to the use of the CRISPR-Cas (e.g. CRISPR-Cas9) system in plants, and mention is made of the University of Arizona website "CRISPR-PLANT" (www.genome.arizona.edu/crispr/) (supported by Penn State and AGI). Embodiments of the invention can be used in genome editing in plants or where RNAi or similar genome editing techniques have been used previously; see, e.g., Nekrasov, "Plant genome editing made easy: targeted mutagenesis in model and crop plants using the CRISPR-Cas system," Plant Methods 2013, 9:39 (doi:10.1186/1746-4811-9-39); Brooks, "Efficient gene editing in tomato in the first generation using the CRISPR-Cas9 system," Plant Physiology September 2014 pp 114.247577; Shan, "Targeted genome modification of crop plants using a CRISPR-Cas system," Nature Biotechnology 31, 686-688 (2013); Feng, "Efficient genome editing in plants using a CRISPR-Cas system," Cell Research (2013) 23:1229-1232. doi: 10.1038/cr.2013.114; published online 20 Aug. 2013; Xie, "RNA-guided genome editing in plants using a CRISPR-Cas system," Mol Plant. 2013 November; 6(6):1975-83. doi: 10.1093/mp/sst119. Epub 2013 Aug. 17; Xu, "Gene targeting using the *Agrobacterium tumefaciens*-mediated CRISPR-Cas system in rice," Rice 2014, 7:5 (2014), Zhou et al., "Exploiting SNPs for biallelic CRISPR mutations in the outcrossing woody perennial *Populus* reveals 4-coumarate: CoA ligase specificity and Redundancy," New Phytologist (2015) (Forum) 1-4 (available online only at www.newphytologist.com); Caliando et al, "Targeted DNA degradation using a CRISPR device stably carried in the host genome, NATURE COMMUNICATIONS 6:6989, DOI: 10.1038/ncomms7989, www.nature.com/naturecommunications DOI: 10.1038/ncomms7989; U.S. Pat. No. 6,603,061—*Agrobacterium*-Mediated Plant Transformation Method; U.S. Pat. No. 7,868,149—Plant Genome Sequences and Uses Thereof and US 2009/0100536—Transgenic Plants with Enhanced Agronomic Traits, all the contents and disclosure of each of which are herein incorporated by reference in their entirety. In the practice of the invention, the contents and disclosure of Morrell et al "Crop genomics: advances and applications," Nat Rev Genet. 2011 Dec. 29; 13(2):85-96; each of which is incorporated by reference herein including as to how herein embodiments may be used as to plants. Accordingly, reference herein to animal cells may also apply, mutatis mutandis, to plant cells unless otherwise apparent; and, the enzymes herein having reduced off-target effects and systems employing such enzymes can be used in plant applications, including those mentioned herein.

Application of CD-Functionalized CRISPR System to Plants and Yeast

In general, the term "plant" relates to any various photosynthetic, eukaryotic, unicellular or multicellular organism of the kingdom Plantae characteristically growing by cell division, containing chloroplasts, and having cell walls comprised of cellulose. The term plant encompasses monocotyledonous and dicotyledonous plants. Specifically, the plants are intended to comprise without limitation angiosperm and gymnosperm plants such as acacia, alfalfa, amaranth, apple, apricot, artichoke, ash tree, asparagus, avocado, banana, barley, beans, beet, birch, beech, blackberry, blueberry, broccoli, Brussel's sprouts, cabbage, canola, cantaloupe, carrot, cassava, cauliflower, cedar, a cereal, celery, chestnut, cherry, Chinese cabbage, citrus, clementine, clover, coffee, corn, cotton, cowpea, cucumber, cypress, eggplant, elm, endive, *eucalyptus*, fennel, figs, fir, geranium, grape, grapefruit, groundnuts, ground cherry, gum hemlock, hickory, kale, kiwifruit, kohlrabi, larch, lettuce, leek, lemon, lime, locust, pine, maidenhair, maize, mango, maple, melon, millet, mushroom, mustard, nuts, oak, oats, oil palm, okra, onion, orange, an ornamental plant or flower or tree, *papaya*, palm, parsley, parsnip, pea, peach, peanut, pear, peat, pepper, persimmon, pigeon pea, pine, pineapple, plantain, plum, pomegranate, potato, pumpkin, radicchio, radish, rapeseed, raspberry, rice, rye, sorghum, safflower, sallow, soybean, spinach, spruce, squash, strawberry, sugar beet, sugarcane, sunflower, sweet potato, sweet corn, tangerine, tea, tobacco, tomato, trees, triticale, turf grasses, turnips, vine, walnut, watercress, watermelon, wheat, yams, yew, and zucchini. The term plant also encompasses Algae, which are mainly photoautotrophs unified primarily by their lack of roots, leaves and other organs that characterize higher plants.

The methods for genome editing using the CD-functionalized CRISPR system as described herein can be used to confer desired traits on essentially any plant. A wide variety of plants and plant cell systems may be engineered for the desired physiological and agronomic characteristics described herein using the nucleic acid constructs of the present disclosure and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., *petunia*, rose, *chrysanthemum*), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the methods and systems can be used over a broad range of plants, such as for example with dicotyledonous plants belonging to the orders Magnoliales, Illiciales, Laurales, Piperales, Aristolochiaceae, Nymphaeales, Ranunculales, Papaveraceae, Sarraceniaceae, Trochodendrales, Hamamelidales, Eucommiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, San tales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales; the methods and CRISPR-Cas systems can be used with monocotyledonous plants such as those belonging to the orders Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Liliales, and Orchid ales, or with plants belonging to Gymnospermae, e.g those belonging to the orders Pinales, Ginkgoales, Cycadales, Araucariales, Cupressales and Gnetales.

The CD-functionalized CRISPR systems and methods of use described herein can be used over a broad range of plant species, included in the non-limitative list of dicot, monocot or gymnosperm genera hereunder: *Atropa, Alseodaphne, Anacardium, Arachis, Beilschmiedia, Brassica Carthamus, Cocculus, Croton, Cucumis, Citrus, Citrullus, Capsicum, Catharanthus, Cocos, Coffea, Cucurbita, Daucus, Duguetia, Eschscholzia, Ficus, Fragaria, Glaucium, Glycine, Gossypium, Helianthus, Hevea, Hyoscyamus, Lactuca, Landolphia, Linum, Litsea, Lycopersicon, Lupinus, Manihot, Majorana, Malus, Medicago, Nicotiana, Olea, Parthenium, Papaver, Persea, Phaseolus, Pistacia, Pisum, Pyrus, Prunus, Raphanus, Ricinus, Senecio, Sinomenium, Stephania, Sinapis, Solanum, Theobroma, Trifolium, Trigonella, Vicia, Vinca, Vilis,* and *Vigna*; and the genera *Allium, Andropogon, Eragrostis, Asparagus, Avena, Cynodon, Elaeis, Festuca, Festulolium, Hemerocallis, Hordeum, Lemna, Lolium, Musa, Oryza, Panicum, Pennisetum, Phleum, Poa, Secale, Sorghum, Triticum, Zea, Abies, Cunninghamia, Ephedra, Picea, Pinus,* and *Pseudotsuga.*

The CD-functionalized CRISPR systems and methods of use can also be used over a broad range of "algae" or "algae cells"; including for example algae selected from several eukaryotic phyla, including the Rhodophyta (red algae), Chlorophyta (green algae), Phaeophyta (brown algae), Bacillariophyta (diatoms), Eustigmatophyta and dinoflagellates as well as the prokaryotic phylum Cyanobacteria (blue-green algae). The term "algae" includes for example algae selected from: *Amphora, Anabaena, Ankistrodesmus, Botryococcus, Chaetoceros, Chlamydomonas, Chlorella, Chlorococcum, Cyclotella, Cylindrotheca, Dunaliella, Emiliania, Euglena, Haematococcus, Isochrysis, Monochrysis, Monoraphidium, Nannochloris, Nannochloropsis, Navicula, Nephrochloris, Nephroselmis, Nitzschia, Nodularia, Nostoc, Ochromonas, Oocystis, Oscillatoria, Pavlova, Phaeodactylum, Platymonas, Pleurochrysis, Porphyra, Pseudoanabaena, Pyramimonas, Stichococcus, Synechococcus, Synechocystis, Tetraselmis, Thalassiosira,* and *Trichodesmium.*

A part of a plant, i.e., a "plant tissue" may be treated according to the methods of the present invention to produce an improved plant. Plant tissue also encompasses plant cells. The term "plant cell" as used herein refers to individual units of a living plant, either in an intact whole plant or in an isolated form grown in in vitro tissue cultures, on media or agar, in suspension in a growth media or buffer or as a part of higher organized unites, such as, for example, plant tissue, a plant organ, or a whole plant.

A "protoplast" refers to a plant cell that has had its protective cell wall completely or partially removed using, for example, mechanical or enzymatic means resulting in an intact biochemical competent unit of living plant that can reform their cell wall, proliferate and regenerate grow into a whole plant under proper growing conditions.

The term "transformation" broadly refers to the process by which a plant host is genetically modified by the introduction of DNA by means of Agrobacteria or one of a variety of chemical or physical methods. As used herein, the term "plant host" refers to plants, including any cells, tissues, organs, or progeny of the plants. Many suitable plant tissues or plant cells can be transformed and include, but are not limited to, protoplasts, somatic embryos, pollen, leaves, seedlings, stems, calli, stolons, microtubers, and shoots. A plant tissue also refers to any clone of such a plant, seed, progeny, propagule whether generated sexually or asexually, and descendants of any of these, such as cuttings or seed.

The term "transformed" as used herein, refers to a cell, tissue, organ, or organism into which a foreign DNA molecule, such as a construct, has been introduced. The introduced DNA molecule may be integrated into the genomic DNA of the recipient cell, tissue, organ, or organism such that the introduced DNA molecule is transmitted to the subsequent progeny. In these embodiments, the "transformed" or "transgenic" cell or plant may also include progeny of the cell or plant and progeny produced from a breeding program employing such a transformed plant as a parent in a cross and exhibiting an altered phenotype resulting from the presence of the introduced DNA molecule. Preferably, the transgenic plant is fertile and capable of transmitting the introduced DNA to progeny through sexual reproduction.

The term "progeny", such as the progeny of a transgenic plant, is one that is born of, begotten by, or derived from a plant or the transgenic plant. The introduced DNA molecule may also be transiently introduced into the recipient cell such that the introduced DNA molecule is not inherited by subsequent progeny and thus not considered "transgenic". Accordingly, as used herein, a "non-transgenic" plant or plant cell is a plant which does not contain a foreign DNA stably integrated into its genome.

The term "plant promoter" as used herein is a promoter capable of initiating transcription in plant cells, whether or not its origin is a plant cell. Exemplary suitable plant promoters include, but are not limited to, those that are obtained from plants, plant viruses, and bacteria such as *Agrobacterium* or *Rhizobium* which comprise genes expressed in plant cells.

As used herein, a "fungal cell" refers to any type of eukaryotic cell within the kingdom of fungi. Phyla within the kingdom of fungi include Ascomycota, Basidiomycota, Blastocladiomycota, Chytridiomycota, Glomeromycota, Microsporidia, and Neocallimastigomycota. Fungal cells may include yeasts, molds, and filamentous fungi. In some embodiments, the fungal cell is a yeast cell.

As used herein, the term "yeast cell" refers to any fungal cell within the phyla Ascomycota and Basidiomycota. Yeast cells may include budding yeast cells, fission yeast cells, and mold cells. Without being limited to these organisms, many types of yeast used in laboratory and industrial settings are part of the phylum Ascomycota. In some embodiments, the yeast cell is an *S. cerevisiae, Kluyveromyces marxianus*, or *Issatchenkia orientalis* cell. Other yeast cells may include without limitation *Candida* spp. (e.g., *Candida albicans*), *Yarrowia* spp. (e.g., *Yarrowia lipolytica*), *Pichia* spp. (e.g., *Pichia pastoris*), *Kluyveromyces* spp. (e.g., *Kluyveromyces lactis* and *Kluyveromyces marxianus*), *Neurospora* spp. (e.g., *Neurospora crassa*), *Fusarium* spp. (e.g., *Fusarium oxysporum*), and *Issatchenkia* spp. (e.g., *Issatchenkia orientalis*, a.k.a. *Pichia kudriavzevii* and *Candida acidothermophilum*). In some embodiments, the fungal cell is a filamentous fungal cell. As used herein, the term "filamentous fungal cell" refers to any type of fungal cell that grows in filaments, i.e., hyphae or mycelia. Examples of filamentous fungal cells may include without limitation *Aspergillus* spp. (e.g., *Aspergillus niger*), *Trichoderma* spp. (e.g., *Trichoderma reesei*), *Rhizopus* spp. (e.g., *Rhizopus oryzae*), and *Mortierella* spp. (e.g., *Mortierella isabellina*).

In some embodiments, the fungal cell is an industrial strain. As used herein, "industrial strain" refers to any strain of fungal cell used in or isolated from an industrial process, e.g., production of a product on a commercial or industrial scale. Industrial strain may refer to a fungal species that is typically used in an industrial process, or it may refer to an isolate of a fungal species that may be also used for non-industrial purposes (e.g., laboratory research). Examples of industrial processes may include fermentation (e.g., in production of food or beverage products), distillation, biofuel production, production of a compound, and production of a polypeptide. Examples of industrial strains may include, without limitation, JAY270 and ATCC4124.

In some embodiments, the fungal cell is a polyploid cell. As used herein, a "polyploid" cell may refer to any cell whose genome is present in more than one copy. A polyploid cell may refer to a type of cell that is naturally found in a polyploid state, or it may refer to a cell that has been induced to exist in a polyploid state (e.g., through specific regulation, alteration, inactivation, activation, or modification of meiosis, cytokinesis, or DNA replication). A polyploid cell may refer to a cell whose entire genome is polyploid, or it may refer to a cell that is polyploid in a particular genomic locus of interest. Without wishing to be bound to theory, it is thought that the abundance of guide RNA may more often be a rate-limiting component in genome engineering of polyploid cells than in haploid cells, and thus the methods using the CD-functionalized CRISPR system described herein may take advantage of using a certain fungal cell type.

In some embodiments, the fungal cell is a diploid cell. As used herein, a "diploid" cell may refer to any cell whose genome is present in two copies. A diploid cell may refer to a type of cell that is naturally found in a diploid state, or it may refer to a cell that has been induced to exist in a diploid state (e.g., through specific regulation, alteration, inactivation, activation, or modification of meiosis, cytokinesis, or DNA replication). For example, the *S. cerevisiae* strain S228C may be maintained in a haploid or diploid state. A diploid cell may refer to a cell whose entire genome is diploid, or it may refer to a cell that is diploid in a particular genomic locus of interest. In some embodiments, the fungal cell is a haploid cell. As used herein, a "haploid" cell may refer to any cell whose genome is present in one copy. A haploid cell may refer to a type of cell that is naturally found in a haploid state, or it may refer to a cell that has been induced to exist in a haploid state (e.g., through specific regulation, alteration, inactivation, activation, or modification of meiosis, cytokinesis, or DNA replication). For example, the *S. cerevisiae* strain S228C may be maintained in a haploid or diploid state. A haploid cell may refer to a cell whose entire genome is haploid, or it may refer to a cell that is haploid in a particular genomic locus of interest.

As used herein, a "yeast expression vector" refers to a nucleic acid that contains one or more sequences encoding an RNA and/or polypeptide and may further contain any desired elements that control the expression of the nucleic acid(s), as well as any elements that enable the replication and maintenance of the expression vector inside the yeast cell. Many suitable yeast expression vectors and features thereof are known in the art; for example, various vectors and techniques are illustrated in Yeast Protocols, 2nd edition, Xiao, W., ed. (Humana Press, New York, 2007) and Buckholz, R. G. and Gleeson, M. A. (1991) Biotechnology (NY) 9(11): 1067-72. Yeast vectors may contain, without limitation, a centromeric (CEN) sequence, an autonomous replication sequence (ARS), a promoter, such as an RNA Polymerase III promoter, operably linked to a sequence or gene of interest, a terminator such as an RNA polymerase III terminator, an origin of replication, and a marker gene (e.g., auxotrophic, antibiotic, or other selectable markers). Examples of expression vectors for use in yeast may include plasmids, yeast artificial chromosomes, 2 plasmids, yeast integrative plasmids, yeast replicative plasmids, shuttle vectors, and episomal plasmids.

Stable Integration of CD-Functionalized CRISPR System Components in the Genome of Plants and Plant Cells In particular embodiments, it is envisaged that the polynucleotides encoding the components of the CD-functionalized CRISPR system are introduced for stable integration into the genome of a plant cell. In these embodiments, the design of the transformation vector or the expression system can be adjusted depending on for when, where and under what conditions the guide RNA and/or fusion protein of cytidine deaminase and Cpf1 are expressed.

In particular embodiments, it is envisaged to introduce the components of the CD-functionalized CRISPR system stably into the genomic DNA of a plant cell. Additionally or alternatively, it is envisaged to introduce the components of the CD-functionalized CRISPR system for stable integration into the DNA of a plant organelle such as, but not limited to a plastid, e mitochondrion or a chloroplast.

The expression system for stable integration into the genome of a plant cell may contain one or more of the following elements: a promoter element that can be used to express the RNA and/or fusion protein of cytidine deaminase and Cpf1 in a plant cell; a 5' untranslated region to enhance expression; an intron element to further enhance expression in certain cells, such as monocot cells; a multiple-cloning site to provide convenient restriction sites for inserting the guide RNA and/or the fusion protein of cytidine deaminase and Cpf1 encoding sequences and other desired elements; and a 3' untranslated region to provide for efficient termination of the expressed transcript.

The elements of the expression system may be on one or more expression constructs which are either circular such as a plasmid or transformation vector, or non-circular such as linear double-stranded DNA.

In a particular embodiment, a CD-functionalized CRISPR expression system comprises at least: a nucleotide sequence encoding a guide RNA (gRNA) that hybridizes with a target sequence in a plant, and wherein the guide RNA comprises a guide sequence and a direct repeat sequence, and a nucleotide sequence encoding a fusion protein of cytidine deaminase and Cpf1, wherein components (a) or (b) are located on the same or on different constructs, and whereby the different nucleotide sequences can be under control of the same or a different regulatory element operable in a plant cell.

DNA construct(s) containing the components of the CD-functionalized CRISPR system, and, where applicable, template sequence may be introduced into the genome of a plant, plant part, or plant cell by a variety of conventional techniques. The process generally comprises the steps of selecting a suitable host cell or host tissue, introducing the construct(s) into the host cell or host tissue, and regenerating plant cells or plants therefrom.

In particular embodiments, the DNA construct may be introduced into the plant cell using techniques such as but not limited to electroporation, microinjection, aerosol beam injection of plant cell protoplasts, or the DNA constructs can be introduced directly to plant tissue using biolistic methods, such as DNA particle bombardment (see also Fu et al., Transgenic Res. 2000 February; 9(1):11-9). The basis of particle bombardment is the acceleration of particles coated with gene/s of interest toward cells, resulting in the penetration of the protoplasm by the particles and typically stable integration into the genome. (see e.g. Klein et al, Nature (1987), Klein et ah, Bio/Technology (1992), Casas et ah, Proc. Natl. Acad. Sci. USA (1993).).

In particular embodiments, the DNA constructs containing components of the CD-functionalized CRISPR system may be introduced into the plant by *Agrobacterium*-mediated transformation. The DNA constructs may be combined with suitable T-DNA flanking regions and introduced into a conventional *Agrobacterium tumefaciens* host vector. The foreign DNA can be incorporated into the genome of plants by infecting the plants or by incubating plant protoplasts with *Agrobacterium* bacteria, containing one or more Ti (tumor-inducing) plasmids. (see e.g. Fraley et al., (1985), Rogers et al., (1987) and U.S. Pat. No. 5,563,055).

Plant Promoters

In order to ensure appropriate expression in a plant cell, the components of the CD-functionalized CRISPR system described herein are typically placed under control of a plant promoter, i.e. a promoter operable in plant cells. The use of different types of promoters is envisaged.

A constitutive plant promoter is a promoter that is able to express the open reading frame (ORF) that it controls in all or nearly all of the plant tissues during all or nearly all developmental stages of the plant (referred to as "constitutive expression"). One non-limiting example of a constitutive promoter is the cauliflower mosaic virus 35S promoter. "Regulated promoter" refers to promoters that direct gene expression not constitutively, but in a temporally- and/or spatially-regulated manner, and includes tissue-specific, tissue-preferred and inducible promoters. Different promoters may direct the expression of a gene in different tissues or cell types, or at different stages of development, or in response to different environmental conditions. In particular embodiments, one or more of the CD-functionalized CRISPR components are expressed under the control of a constitutive promoter, such as the cauliflower mosaic virus 35S promoter issue-preferred promoters can be utilized to target enhanced expression in certain cell types within a particular plant tissue, for instance vascular cells in leaves or roots or in specific cells of the seed. Examples of particular promoters for use in the CD-functionalized CRISPR system are found in Kawamata et al., (1997) Plant Cell Physiol 38:792-803; Yamamoto et al., (1997) Plant J 12:255-65; Hire et al, (1992) Plant Mol Biol 20:207-18, Kuster et al, (1995) Plant Mol Biol 29:759-72, and Capana et al., (1994) Plant Mol Biol 25:681-91.

Inducible promoters can be of interest to express one or more of the components of the CD-functionalized CRISPR system under limited circumstances to avoid non-specific activity of the deaminase. In particular embodiments, one or more elements of the CD-functionalized CRISPR system are expressed under control of an inducible promoter. Examples of promoters that are inducible and that allow for spatiotemporal control of gene editing or gene expression may use a form of energy. The form of energy may include but is not limited to sound energy, electromagnetic radiation, chemical energy and/or thermal energy. Examples of inducible systems include tetracycline inducible promoters (Tet-On or Tet-Off), small molecule two-hybrid transcription activations systems (FKBP, ABA, etc), or light inducible systems (Phytochrome, LOV domains, or cryptochrome)., such as a Light Inducible Transcriptional Effector (LITE) that direct changes in transcriptional activity in a sequence-specific manner. The components of a light inducible system may include a fusion protein of cytidine deaminase and Cpf1, a light-responsive cytochrome heterodimer (e.g. from *Arabidopsis thaliana*). Further examples of inducible DNA binding proteins and methods for their use are provided in U.S. 61/736,465 and U.S. 61/721,283, which is hereby incorporated by reference in its entirety.

In particular embodiments, transient or inducible expression can be achieved by using, for example, chemical-regulated promotors, i.e. whereby the application of an exogenous chemical induces gene expression. Modulating of gene expression can also be obtained by a chemical-repressible promoter, where application of the chemical represses gene expression. Chemical-inducible promoters include, but are not limited to, the maize ln2-2 promoter, activated by benzene sulfonamide herbicide safeners (De Veylder et al., (1997) Plant Cell Physiol 38:568-77), the maize GST promoter (GST-11-27, WO93/01294), activated by hydrophobic electrophilic compounds used as pre-emergent herbicides, and the tobacco PR-1 a promoter (Ono et al., (2004) Biosci Biotechnol Biochem 68:803-7) activated by salicylic acid. Promoters which are regulated by antibiotics, such as tetracycline-inducible and tetracycline-repressible promoters (Gatz et al., (1991) Mol Gen Genet 227: 229-37; U.S. Pat. Nos. 5,814,618 and 5,789,156) can also be used herein.

Translocation to and/or Expression in Specific Plant Organelles

The expression system may comprise elements for translocation to and/or expression in a specific plant organelle.

Chloroplast Targeting

In particular embodiments, it is envisaged that the CD-functionalized CRISPR system is used to specifically modify chloroplast genes or to ensure expression in the chloroplast. For this purpose use is made of chloroplast transformation methods or compartmentalization of the CD-functionalized CRISPR components to the chloroplast. For instance, the introduction of genetic modifications in the plastid genome can reduce biosafety issues such as gene flow through pollen.

Methods of chloroplast transformation are known in the art and include Particle bombardment, PEG treatment, and microinjection. Additionally, methods involving the translocation of transformation cassettes from the nuclear genome to the plastid can be used as described in WO2010061186.

Alternatively, it is envisaged to target one or more of the CD-functionalized CRISPR components to the plant chloroplast. This is achieved by incorporating in the expression construct a sequence encoding a chloroplast transit peptide (CTP) or plastid transit peptide, operably linked to the 5' region of the sequence encoding the fusion protein of cytidine deaminase and Cpf1. The CTP is removed in a processing step during translocation into the chloroplast. Chloroplast targeting of expressed proteins is well known to the skilled artisan (see for instance Protein Transport into Chloroplasts, 2010, Annual Review of Plant Biology, Vol. 61: 157-180). In such embodiments it is also desired to target the guide RNA to the plant chloroplast. Methods and constructs which can be used for translocating guide RNA into the chloroplast by means of a chloroplast localization sequence are described, for instance, in US 20040142476, incorporated herein by reference. Such variations of constructs can be incorporated into the expression systems of the invention to efficiently translocate the CD-functionalized CRISPR system components.

Introduction of Polynucleotides Encoding the CD-Functionalized CRISPR System in Algal Cells.

Transgenic algae (or other plants such as rape) may be particularly useful in the production of vegetable oils or biofuels such as alcohols (especially methanol and ethanol) or other products. These may be engineered to express or overexpress high levels of oil or alcohols for use in the oil or biofuel industries.

U.S. Pat. No. 8,945,839 describes a method for engineering Micro-Algae (*Chlamydomonas reinhardtii* cells) species) using Cas9. Using similar tools, the methods of the CD-functionalized CRISPR system described herein can be applied on *Chlamydomonas* species and other algae. In particular embodiments, a CRISPR-Cas protein (e.g., Cpf1), cytidine deaminase (which may be fused to the CRISPR-Cas protein or an aptamer-binding adaptor protein), and guide RNA are introduced in algae expressed using a vector that expresses the fusion protein of cytidine deaminase and Cpf1 under the control of a constitutive promoter such as Hsp70A-Rbc S2 or Beta2-tubulin. Guide RNA is optionally delivered using a vector containing T7 promoter. Alternatively, Cpf1 mRNA and in vitro transcribed guide RNA can be delivered to algal cells. Electroporation protocols are available to the skilled person such as the standard recommended protocol from the GeneArt *Chlamydomonas* Engineering kit.

Introduction of CD-Functionalized CRISPR System Components in Yeast Cells

In particular embodiments, the invention relates to the use of the CD-functionalized CRISPR system for genome editing of yeast cells. Methods for transforming yeast cells which can be used to introduce polynucleotides encoding the CD-functionalized CRISPR system components are described in Kawai et al., 2010, Bioeng Bugs. 2010 November-December; 1(6): 395-403). Non-limiting examples include transformation of yeast cells by lithium acetate treatment (which may further include carrier DNA and PEG treatment), bombardment or by electroporation.

Transient Expression of CD-Functionalized CRISPR System Components in Plants and Plant Cell In particular embodiments, it is envisaged that the guide RNA and/or CRISPR-Cas gene are transiently expressed in the plant cell. In these embodiments, the CD-functionalized CRISPR system can ensure modification of a target gene only when both the guide RNA, the CRISPR-Cas protein (e.g., Cpf1), and cytidine deaminase (which may be fused to the CRISPR-Cas protein or an aptamer-binding adaptor protein), are present in a cell, such that genomic modification can further be controlled. As the expression of the CRISPR-Cas protein is transient, plants regenerated from such plant cells typically contain no foreign DNA. In particular embodiments the CRISPR-Cas protein is stably expressed by the plant cell and the guide sequence is transiently expressed.

In particular embodiments, the CD-functionalized CRISPR system components can be introduced in the plant cells using a plant viral vector (Scholthof et al. 1996, Annu Rev Phytopathol. 1996; 34:299-323). In further particular embodiments, said viral vector is a vector from a DNA virus. For example, geminivirus (e.g., cabbage leaf curl virus, bean yellow dwarf virus, wheat dwarf virus, tomato leaf curl virus, maize streak virus, tobacco leaf curl virus, or tomato golden mosaic virus) or nanovirus (e.g., *Faba* bean necrotic yellow virus). In other particular embodiments, said viral vector is a vector from an RNA virus. For example, tobravirus (e.g., tobacco rattle virus, tobacco mosaic virus), potexvirus (e.g., potato virus X), or hordeivirus (e.g., barley stripe mosaic virus). The replicating genomes of plant viruses are non-integrative vectors.

In particular embodiments, the vector used for transient expression of CD-functionalized CRISPR system is for instance a pEAQ vector, which is tailored for *Agrobacterium*-mediated transient expression (Sainsbury F. et al., Plant Biotechnol J. 2009 September; 7(7):682-93) in the protoplast. Precise targeting of genomic locations was demonstrated using a modified Cabbage Leaf Curl virus (CaLCuV) vector to express guide RNAs in stable transgenic plants expressing a CRISPR enzyme (Scientific Reports 5, Article number: 14926 (2015), doi:10.1038/srep14926).

In particular embodiments, double-stranded DNA fragments encoding the guide RNA and/or the CRISPR-Cas gene can be transiently introduced into the plant cell. In such embodiments, the introduced double-stranded DNA fragments are provided in sufficient quantity to modify the cell but do not persist after a contemplated period of time has passed or after one or more cell divisions. Methods for direct DNA transfer in plants are known by the skilled artisan (see for instance Davey et al. Plant Mol Biol. 1989 September; 13(3):273-85.)

In other embodiments, an RNA polynucleotide encoding the CRISPR-Cas protein (e.g., Cpf1) and/or cytidine deaminase (which may be fused to the CRISPR-Cas protein or an aptamer-binding adaptor protein) is introduced into the plant cell, which is then translated and processed by the host cell generating the protein in sufficient quantity to modify the cell (in the presence of at least one guide RNA) but which does not persist after a contemplated period of time has passed or after one or more cell divisions. Methods for introducing mRNA to plant protoplasts for transient expression are known by the skilled artisan (see for instance in Gallie, Plant Cell Reports (1993), 13; 119-122).

Combinations of the different methods described above are also envisaged.

Delivery of CD-Functionalized CRISPR System Components to the Plant Cell

In particular embodiments, it is of interest to deliver one or more components of the CD-functionalized CRISPR system directly to the plant cell. This is of interest, inter alia, for the generation of non-transgenic plants (see below). In particular embodiments, one or more of the CD-functionalized CRISPR system components is prepared outside the plant or plant cell and delivered to the cell. For instance in particular embodiments, the CRISPR-Cas protein is prepared in vitro prior to introduction to the plant cell. The CRISPR-Cas protein can be prepared by various methods known by one of skill in the art and include recombinant production. After expression, the CRISPR-Cas protein is isolated, refolded if needed, purified and optionally treated to remove any purification tags, such as a His-tag. Once crude, partially purified, or more completely purified CRISPR-Cas protein is obtained, the protein may be introduced to the plant cell.

In particular embodiments, the CRISPR-Cas protein is mixed with guide RNA targeting the gene of interest to form a pre-assembled ribonucleoprotein.

The individual components or pre-assembled ribonucleoprotein can be introduced into the plant cell via electroporation, by bombardment with CRISPR-Cas-associated gene product coated particles, by chemical transfection or by some other means of transport across a cell membrane. For instance, transfection of a plant protoplast with a pre-assembled CRISPR ribonucleoprotein has been demonstrated to ensure targeted modification of the plant genome (as described by Woo et al. *Nature Biotechnology*, 2015; DOI: 10.1038/nbt.3389).

In particular embodiments, the CD-functionalized CRISPR system components are introduced into the plant cells using nanoparticles. The components, either as protein or nucleic acid or in a combination thereof, can be uploaded onto or packaged in nanoparticles and applied to the plants (such as for instance described in WO 2008042156 and US 20130185823). In particular, embodiments of the invention comprise nanoparticles uploaded with or packed with DNA molecule(s) encoding the CRISPR-Cas protein (e.g., Cpf1), DNA molecule(s) encoding cytidine deaminase (which may be fused to the CRISPR-Cas protein or an aptamer-binding adaptor protein), and DNA molecules encoding the guide RNA and/or isolated guide RNA as described in WO2015089419.

Further means of introducing one or more components of the CD-functionalized CRISPR system to the plant cell is by using cell penetrating peptides (CPP). Accordingly, in particular, embodiments the invention comprises compositions comprising a cell penetrating peptide linked to the CRISPR-Cas protein. In particular embodiments of the present invention, the CRISPR-Cas protein and/or guide RNA is coupled to one or more CPPs to effectively transport them inside plant protoplasts. Ramakrishna (Genome Res. 2014 June; 24(6):1020-7 for Cas9 in human cells). In other embodiments, the CRISPR-Cas gene and/or guide RNA are encoded by one or more circular or non-circular DNA molecule(s) which are coupled to one or more CPPs for plant protoplast delivery. The plant protoplasts are then regenerated to plant cells and further to plants. CPPs are generally described as short peptides of fewer than 35 amino acids either derived from proteins or from chimeric sequences which are capable of transporting biomolecules across cell membrane in a receptor independent manner. CPP can be cationic peptides, peptides having hydrophobic sequences, amphipathic peptides, peptides having proline-rich and antimicrobial sequence, and chimeric or bipartite peptides (Pooga and Langel 2005). CPPs are able to penetrate biological membranes and as such trigger the movement of various biomolecules across cell membranes into the cytoplasm and to improve their intracellular routing, and hence facilitate interaction of the biomolecule with the target. Examples of CPP include amongst others: Tat, a nuclear transcriptional activator protein required for viral replication by HIV type1, penetratin, Kaposi fibroblast growth factor (FGF) signal peptide sequence, integrin 33 signal peptide sequence; polyarginine peptide Args sequence, Guanine rich-molecular transporters, sweet arrow peptide, etc.

Use of the CD-Functionalized CRISPR System to Make Genetically Modified Non-Transgenic Plants In particular embodiments, the methods described herein are used to modify endogenous genes or to modify their expression without the permanent introduction into the genome of the plant of any foreign gene, including those encoding CRISPR components, so as to avoid the presence of foreign DNA in the genome of the plant. This can be of interest as the regulatory requirements for non-transgenic plants are less rigorous.

In particular embodiments, this is ensured by transient expression of the CD-functionalized CRISPR system components. In particular embodiments one or more of the components are expressed on one or more viral vectors which produce sufficient CRISPR-Cas protein, cytidine deaminase, and guide RNA to consistently steadily ensure modification of a gene of interest according to a method described herein.

In particular embodiments, transient expression of CD-functionalized CRISPR system constructs is ensured in plant protoplasts and thus not integrated into the genome. The limited window of expression can be sufficient to allow the CD-functionalized CRISPR system to ensure modification of a target gene as described herein.

In particular embodiments, the different components of the CD-functionalized CRISPR system are introduced in the plant cell, protoplast or plant tissue either separately or in mixture, with the aid of particulate delivering molecules such as nanoparticles or CPP molecules as described herein above.

The expression of the CD-functionalized CRISPR system components can induce targeted modification of the genome, by deaminase activity of the cytidine deaminase. The different strategies described herein above allow CRISPR-mediated targeted genome editing without requiring the introduction of the CD-functionalized CRISPR system components into the plant genome. Components which are transiently introduced into the plant cell are typically removed upon crossing.

Plant Cultures and Regeneration

In particular embodiments, plant cells which have a modified genome and that are produced or obtained by any of the methods described herein, can be cultured to regenerate a whole plant which possesses the transformed or modified genotype and thus the desired phenotype. Conventional regeneration techniques are well known to those skilled in the art. Particular examples of such regeneration techniques rely on manipulation of certain phytohormones in a tissue culture growth medium, and typically relying on a biocide and/or herbicide marker which has been introduced together with the desired nucleotide sequences. In further particular embodiments, plant regeneration is obtained from cultured protoplasts, plant callus, explants, organs, pollens, embryos or parts thereof (see e.g. Evans et al. (1983), Handbook of Plant Cell Culture, Klee et al (1987) Ann. Rev. of Plant Phys.).

In particular embodiments, transformed or improved plants as described herein can be self-pollinated to provide seed for homozygous improved plants of the invention (homozygous for the DNA modification) or crossed with non-transgenic plants or different improved plants to provide seed for heterozygous plants. Where a recombinant DNA was introduced into the plant cell, the resulting plant of such a crossing is a plant which is heterozygous for the recombinant DNA molecule. Both such homozygous and heterozygous plants obtained by crossing from the improved plants and comprising the genetic modification (which can be a recombinant DNA) are referred to herein as "progeny". Progeny plants are plants descended from the original transgenic plant and containing the genome modification or recombinant DNA molecule introduced by the methods provided herein. Alternatively, genetically modified plants can be obtained by one of the methods described supra using the CD-functionalized CRISPR system whereby no foreign DNA is incorporated into the genome. Progeny of such plants, obtained by further breeding may also contain the genetic modification. Breedings are performed by any breeding methods that are commonly used for different crops (e.g., Allard, Principles of Plant Breeding, John Wiley & Sons, NY, U. of CA, Davis, CA, 50-98 (1960).

Generation of Plants with Enhanced Agronomic Traits

The CD-functionalized CRISPR systems provided herein can be used to introduce targeted A-G and T-C mutations. By co-expression of multiple targeting RNAs directed to achieve multiple modifications in a single cell, multiplexed genome modification can be ensured. This technology can be used to high-precision engineering of plants with improved characteristics, including enhanced nutritional quality, increased resistance to diseases and resistance to biotic and abiotic stress, and increased production of commercially valuable plant products or heterologous compounds.

In particular embodiments, the CD-functionalized CRISPR system as described herein is used to introduce targeted A-G and T-C mutations. Such mutation can be a nonsense mutation (e.g., premature stop codon) or a missense mutation (e.g., encoding different amino acid residue). This is of interest where the A-G and T-C mutations in certain endogenous genes can confer or contribute to a desired trait.

The methods described herein generally result in the generation of "improved plants" in that they have one or more desirable traits compared to the wildtype plant. In particular embodiments, the plants, plant cells or plant parts obtained are transgenic plants, comprising an exogenous DNA sequence incorporated into the genome of all or part of the cells of the plant. In particular embodiments, non-transgenic genetically modified plants, plant parts or cells are obtained, in that no exogenous DNA sequence is incorporated into the genome of any of the plant cells of the plant. In such embodiments, the improved plants are non-transgenic. Where only the modification of an endogenous gene is ensured and no foreign genes are introduced or maintained in the plant genome, the resulting genetically modified crops contain no foreign genes and can thus basically be considered non-transgenic.

In particular embodiments, the polynucleotides are delivered into the cell by a DNA virus (e.g., a geminivirus) or an RNA virus (e.g., a tobravirus). In particular embodiments, the introducing steps include delivering to the plant cell a T-DNA containing one or more polynucleotide sequences encoding the CRISPR-Cas protein, the cytidine deaminase, and the guide RNA, where the delivering is via *Agrobacterium*. The polynucleotide sequence encoding the components of the CD-functionalized CRISPR system can be operably linked to a promoter, such as a constitutive promoter (e.g., a cauliflower mosaic virus 35S promoter), or a cell specific or inducible promoter. In particular embodiments, the polynucleotide is introduced by microprojectile bombardment. In particular embodiments, the method further includes screening the plant cell after the introducing steps to determine whether the expression of the gene of interest has been modified. In particular embodiments, the methods include the step of regenerating a plant from the plant cell. In further embodiments, the methods include cross breeding the plant to obtain a genetically desired plant lineage.

In particular embodiments of the methods described above, disease resistant crops are obtained by targeted mutation of disease susceptibility genes or genes encoding negative regulators (e.g. Mlo gene) of plant defense genes. In a particular embodiment, herbicide-tolerant crops are generated by targeted substitution of specific nucleotides in plant genes such as those encoding acetolactate synthase (ALS) and protoporphyrinogen oxidase (PPO). In particular embodiments drought and salt tolerant crops by targeted mutation of genes encoding negative regulators of abiotic stress tolerance, low amylose grains by targeted mutation of Waxy gene, rice or other grains with reduced rancidity by targeted mutation of major lipase genes in aleurone layer, etc. In particular embodiments. A more extensive list of endogenous genes encoding a traits of interest are listed below.

Use of CD-Functionalized CRISPR System to Modify Polyploid Plants

Many plants are polyploid, which means they carry duplicate copies of their genomes—sometimes as many as six, as in wheat. The methods according to the present invention, which make use of the CD-functionalized CRISPR system can be "multiplexed" to affect all copies of a gene, or to target dozens of genes at once. For instance, in particular embodiments, the methods of the present invention are used to simultaneously ensure a loss of function mutation in different genes responsible for suppressing defences against a disease. In particular embodiments, the methods of the present invention are used to simultaneously suppress the expression of the TaMLO-A1, TaMLO-B1 and TaMLO-D1 nucleic acid sequence in a wheat plant cell and regenerating a wheat plant therefrom, in order to ensure that the wheat plant is resistant to powdery mildew (see also WO2015109752).

Exemplary Genes Conferring Agronomic Traits

In particular embodiments, the invention encompasses methods which involve targeted A-G and T-C mutations in endogenous genes and their regulatory elements, such as listed below:

1. Genes that Confer Resistance to Pests or Diseases:

Plant disease resistance genes. A plant can be transformed with cloned resistance genes to engineer plants that are resistant to specific pathogen strains. See, e.g., Jones et al., Science 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. tomato encodes a protein kinase); Mindrinos et al., Cell 78:1089 (1994) (*Arabidopsis* may be RSP2 gene for resistance to *Pseudomonas syringae*). A plant gene that is upregulated or down regulated during pathogen infection can be engineered for pathogen resistance. See, e.g., Thomazella et al., bioRxiv 064824; doi: doi.org/10.1101/064824 Epub. Jul. 23, 2016 (tomato plants with deletions in the S1DMR6-1 which is normally upregulated during pathogen infection).

Genes conferring resistance to a pest, such as soybean cyst nematode. See e.g., PCT Application WO 96/30517; PCT Application WO 93/19181.

*Bacillus thuringiensis* proteins see, e.g., Geiser et al., Gene 48:109 (1986).

Lectins, see, for example, Van Damme et al., Plant Molec. Biol. 24:25 (1994.

Vitamin-binding protein, such as avidin, see PCT application US93/06487, teaching the use of avidin and avidin homologues as larvicides against insect pests.

Enzyme inhibitors such as protease or proteinase inhibitors or amylase inhibitors. See, e.g., Abe et al., J. Biol. Chem. 262:16793 (1987), Huub et al., Plant Molec. Biol. 21:985 (1993)), Sumitani et al., Biosci. Biotech. Biochem. 57:1243 (1993) and U.S. Pat. No. 5,494,813.

Insect-specific hormones or pheromones such as ecdysteroid or juvenile hormone, a variant thereof, a mimetic based thereon, or an antagonist or agonist thereof. See, for example Hammock et al., Nature 344:458 (1990).

Insect-specific peptides or neuropeptides which, upon expression, disrupts the physiology of the affected pest. For example Regan, J. Biol. Chem. 269:9 (1994) and Pratt et al., Biochem. Biophys. Res. Comm. 163:1243 (1989). See also U.S. Pat. No. 5,266,317.

Insect-specific venom produced in nature by a snake, a wasp, or any other organism. For example, see Pang et al., Gene 116: 165 (1992).

Enzymes responsible for a hyperaccumulation of a monoterpene, a sesquiterpene, a steroid, hydroxamic acid, a phenylpropanoid derivative or another nonprotein molecule with insecticidal activity.

Enzymes involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO93/02197, Kramer et al., Insect Biochem. Molec. Biol. 23:691 (1993) and Kawalleck et al., Plant Molec. Biol. 21:673 (1993).

Molecules that stimulates signal transduction. For example, see Botella et al., Plant Molec. Biol. 24:757 (1994), and Griess et al., Plant Physiol. 104:1467 (1994).

Viral-invasive proteins or a complex toxin derived therefrom. See Beachy et al., Ann. rev. Phytopathol. 28:451 (1990).

Developmental-arrestive proteins produced in nature by a pathogen or a parasite. See Lamb et al., Bio/Technology 10:1436 (1992) and Toubart et al., Plant J. 2:367 (1992).

A developmental-arrestive protein produced in nature by a plant. For example, Logemann et al., Bio/Technology 10:305 (1992).

In plants, pathogens are often host-specific. For example, some *Fusarium* species will causes tomato wilt but attacks only tomato, and other *Fusarium* species attack only wheat. Plants have existing and induced defenses to resist most pathogens. Mutations and recombination events across plant generations lead to genetic variability that gives rise to susceptibility, especially as pathogens reproduce with more frequency than plants. In plants there can be non-host resistance, e.g., the host and pathogen are incompatible or there can be partial resistance against all races of a pathogen, typically controlled by many genes and/or also complete resistance to some races of a pathogen but not to other races. Such resistance is typically controlled by a few genes. Using methods and components of the CD-functionalized CRISPR system, a new tool now exists to induce specific mutations in anticipation hereon. Accordingly, one can analyze the genome of sources of resistance genes, and in plants having desired characteristics or traits, use the method and components of the CD-functionalized CRISPR system to induce the rise of resistance genes. The present systems can do so with more precision than previous mutagenic agents and hence accelerate and improve plant breeding programs.

2. Genes Involved in Plant Diseases, Such as Those Listed in WO 2013046247:

Rice diseases: *Magnaporthe grisea, Cochliobolus miyabeanus, Rhizoctonia solani, Gibberella fujikuroi*; Wheat diseases: *Erysiphe graminis, Fusarium graminearum, F. avenaceum, F. culmorum, Microdochium nivale, Puccinia striiformis, P. graminis, P. recondita, Micronectriella nivale, Typhula* sp., *Ustilago tritici, Tilletia caries, Pseudocercosporella herpotrichoides, Mycosphaerella graminicola, Stagonospora nodorum, Pyrenophora tritici-repentis*; Barley diseases: *Erysiphe graminis, Fusarium graminearum, F. avenaceum, F. culmorum, Microdochium nivale, Puccinia striiformis, P. graminis, P. hordei, Ustilago nuda, Rhynchosporium secalis, Pyrenophora teres, Cochliobolus sativus, Pyrenophora graminea, Rhizoctonia solani*; Maize diseases: *Ustilago maydis, Cochliobolus heterostrophus, Gloeocercospora sorghi, Puccinia polysora, Cercospora zeae-maydis, Rhizoctonia solani*;

Citrus diseases: *Diaporthe citri, Elsinoe fawcettii, Penicillium digitatum, P. italicum, Phytophthora parasitica, Phytophthora citrophthora*; Apple diseases: *Monilinia mali, Valsa ceratosperma, Podosphaera leucotricha, Alternaria alternata* apple pathotype, *Venturia inaequalis, Colletotrichum acutatum, Phytophthora cactorum*;

Pear diseases: *Venturia nashicola, V. pirina, Alternaria alternata* Japanese pear pathotype, *Gymnosporangium haraeanum, Phytophthora cactorum*;

Peach diseases: *Monilinia fructicola, Cladosporium carpophilum, Phomopsis* sp.;

Grape diseases: *Elsinoe ampelina, Glomerella cingulata, Uncinula necator, Phakopsora ampelopsidis, Guignardia bidwellii, Plasmopara viticola*;

Persimmon diseases: *Gloeosporium kaki, Cercospora kaki, Mycosphaerella nawae*;

Gourd diseases: *Colletotrichum* lagenarium, Sphaerotheca *fuliginea, Mycosphaerella melonis, Fusarium oxysporum, Pseudoperonospora cubensis, Phytophthora* sp., *Pythium* sp.;

Tomato diseases: *Alternaria solani, Cladosporium fulvum, Phytophthora infestans; Pseudomonas syringae* pv. Tomato; *Phytophthora capsici; Xanthomonas;*

Eggplant diseases: *Phomopsis vexans, Erysiphe cichoracearum*; Brassicaceous vegetable diseases: *Alternaria japonica, Cercosporella brassicae, Plasmodiophora brassicae, Peronospora parasitica;*

Welsh onion diseases: *Puccinia allii, Peronospora destructor;*

Soybean diseases: *Cercospora kikuchii, Elsinoe glycines, Diaporthe phaseolorum* var. *sojae, Septoria glycines, Cercospora sojina, Phakopsora pachyrhizi, Phytophthora sojae, Rhizoctonia solani, Corynespora cassiicola, Sclerotinia sclerotiorum;*

Kidney bean diseases: *Colletotrichum lindemuthianum;*

Peanut diseases: *Cercospora personata, Cercospora arachidicola, Sclerotium rolfsii;*

Pea diseases pea: *Erysiphe pisi;*

Potato diseases: *Alternaria solani, Phytophthora infestans, Phytophthora erythroseptica, Spongospora* subterranean, f. sp. Subterranean;

Strawberry diseases: *Sphaerotheca humuli, Glomerella cingulata;*

Tea diseases: *Exobasidium reticulatum, Elsinoe leucospila, Pestalotiopsis* sp., *Colletotrichum* theae-*sinensis;*

Tobacco diseases: *Alternaria longipes, Erysiphe cichoracearum, Colletotrichum tabacum, Peronospora tabacina, Phytophthora nicotianae;*

Rapeseed diseases: *Sclerotinia sclerotiorum, Rhizoctonia solani;*

Cotton diseases: *Rhizoctonia solani;*

Beet diseases: *Cercospora beticola, Thanatephorus cucumeris, Aphanomyces cochlioides;*

Rose diseases: *Diplocarpon rosae, Sphaerotheca pannosa, Peronospora sparsa;*

Diseases of *chrysanthemum* and asteraceae: *Bremia lactucae, Septoria chrysanthemi*-indici, *Puccinia horiana;*

Diseases of various plants: *Pythium aphanidermatum, Pythium debaryanum, Pythium graminicola, Pythium irregulare, Pythium ultimum, Botrytis cinerea, Sclerotinia sclerotiorum;*

Radish diseases: *Alternaria brassicicola;*

Zoysia diseases: *Sclerotinia homoeocarpa, Rhizoctonia solani;*

Banana diseases: *Mycosphaerella fijiensis, Mycosphaerella musicola;*

Sunflower diseases: Plasmopara *halstedii;*

Seed diseases or diseases in the initial stage of growth of various plants caused by *Aspergillus* spp., *Penicillium* spp., *Fusarium* spp., *Gibberella* spp., *Trichoderma* spp., *Thielaviopsis* spp., *Rhizopus* spp., *Mucor* spp., *Corticium* spp., *Rhoma* spp., *Rhizoctonia* spp., *Diplodia* spp., or the like;

Virus diseases of various plants mediated by *Polymyxa* spp., *Olpidium* spp., or the like.

3. Examples of Genes that Confer Resistance to Herbicides:

Resistance to herbicides that inhibit the growing point or meristem, such as an imidazolinone or a sulfonylurea, for example, by Lee et al., EMBO J. 7:1241 (1988), and Miki et al., Theor. Appl. Genet. 80:449 (1990), respectively.

Glyphosate tolerance (resistance conferred by, e.g., mutant 5-enolpyruvylshikimate-3-phosphate synthase (EPSPs) genes, aroA genes and glyphosate acetyl transferase (GAT) genes, respectively), or resistance to other phosphono compounds such as by glufosinate (phosphinothricin acetyl transferase (PAT) genes from *Streptomyces* species, including *Streptomyces hygroscopicus* and *Streptomyces viridochromogenes*), and to pyridinoxy or phenoxy propionic acids and cyclohexanones by ACCase inhibitor-encoding genes. See, for example, U.S. Pat. Nos. 4,940,835 and 6,248,876, 4,769,061, EP No. 0 333 033 and U.S. Pat. No. 4,975,374. See also EP No. 0242246, DeGreef et al., Bio/Technology 7:61 (1989), Marshall et al., Theor. Appl. Genet. 83:435 (1992), WO 2005012515 to Castle et. al. and WO 2005107437.

Resistance to herbicides that inhibit photosynthesis, such as a triazine (psbA and gs+ genes) or a benzonitrile (nitrilase gene), and glutathione S-transferase in Przibila et al., Plant Cell 3:169 (1991), U.S. Pat. No. 4,810,648, and Hayes et al., Biochem. J. 285: 173 (1992).

Genes encoding Enzymes detoxifying the herbicide or a mutant glutamine synthase enzyme that is resistant to inhibition, e.g. n U.S. patent application Ser. No. 11/760,602. Or a detoxifying enzyme is an enzyme encoding a phosphinothricin acetyltransferase (such as the bar or pat protein from *Streptomyces* species). Phosphinothricin acetyltransferases are for example described in U.S. Pat. Nos. 5,561,236; 5,648,477; 5,646,024; 5,273,894; 5,637,489; 5,276,268; 5,739,082; 5,908,810 and 7,112,665.

Hydroxyphenylpyruvatedioxygenases (HPPD) inhibitors, naturally occurring HPPD resistant enzymes, or genes encoding a mutated or chimeric HPPD enzyme as described in WO 96/38567, WO 99/24585, and WO 99/24586, WO 2009/144079, WO 2002/046387, or U.S. Pat. No. 6,768,044.

4. Examples of Genes Involved in Abiotic Stress Tolerance:

Transgene capable of reducing the expression and/or the activity of poly(ADP-ribose) polymerase (PARP) gene in the plant cells or plants as described in WO 00/04173 or, WO/2006/045633.

Transgenes capable of reducing the expression and/or the activity of the PARG encoding genes of the plants or plants cells, as described e.g. in WO 2004/090140.

Transgenes coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphoribosyltransferase as described e.g. in EP 04077624.7, WO 2006/133827, PCT/EP07/002,433, EP 1999263, or WO 2007/107326.

Enzymes involved in carbohydrate biosynthesis include those described in e.g. EP 0571427, WO 95/04826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO 99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, EP 06090134.5, EP 06090228.5, EP 06090227.7, EP 07090007.1, EP 07090009.7, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. Nos. 5,824,790, 6,013,861, WO 94/04693, WO 94/09144, WO 94/11520, WO 95/35026 or WO 97/20936 or enzymes involved in the production of polyfructose, especially of the inulin and levan-type, as disclosed in EP 0663956, WO 96/01904, WO 96/21023, WO 98/39460, and WO 99/24593, the production of alpha-1,4-glucans as disclosed in WO 95/31553, US 2002031826, U.S. Pat. Nos. 6,284,479, 5,712,107, WO 97/47806, WO 97/47807, WO 97/47808 and WO 00/14249, the production of alpha-1,6 branched alpha-1,4-glucans, as disclosed in WO 00/73422, the production of alternan, as disclosed in e.g. WO 00/47727, WO 00/73422, EP 06077301.7, U.S. Pat. No. 5,908,975 and EP 0728213, the production of hyaluronan, as for example disclosed in WO 2006/032538, WO 2007/039314, WO 2007/039315, WO 2007/039316, JP 2006304779, and WO 2005/012529.

Genes that improve drought resistance. For example, WO 2013122472 discloses that the absence or reduced level of functional Ubiquitin Protein Ligase protein (UPL), more specifically, UPL3, leads to a decreased need for water or improved resistance to drought of said plant. Other examples of transgenic plants with increased drought tolerance are disclosed in, for example, US 2009/0144850, US 2007/0266453, and WO 2002/083911. US2009/0144850 describes a plant displaying a drought tolerance phenotype due to altered expression of a DR02 nucleic acid. US 2007/0266453 describes a plant displaying a drought tolerance phenotype due to altered expression of a DR03 nucleic acid and WO 2002/083911 describes a plant having an increased tolerance to drought stress due to a reduced activity of an ABC transporter which is expressed in guard cells. Another example is the work by Kasuga and co-authors (1999), who describe that overexpression of cDNA encoding DREB1 A in transgenic plants activated the expression of many stress tolerance genes under normal growing conditions and resulted in improved tolerance to drought, salt loading, and freezing. However, the expression of DREB1A also resulted in severe growth retardation under normal growing conditions (Kasuga (1999) Nat Biotechnol 17(3) 287-291).

In further particular embodiments, crop plants can be improved by influencing specific plant traits. For example, by developing pesticide-resistant plants, improving disease resistance in plants, improving plant insect and nematode resistance, improving plant resistance against parasitic weeds, improving plant drought tolerance, improving plant nutritional value, improving plant stress tolerance, avoiding self-pollination, plant forage digestibility biomass, grain yield etc. A few specific non-limiting examples are provided hereinbelow.

In addition to targeted mutation of single genes, CD-functionalized CRISPR system can be designed to allow targeted mutation of multiple genes, deletion of chromosomal fragment, site-specific integration of transgene, site-directed mutagenesis in vivo, and precise gene replacement or allele swapping in plants. Therefore, the methods described herein have broad applications in gene discovery and validation, mutational and cisgenic breeding, and hybrid breeding. These applications facilitate the production of a new generation of genetically modified crops with various improved agronomic traits such as herbicide resistance, disease resistance, abiotic stress tolerance, high yield, and superior quality.

Use of CD-Functionalized CRISPR System to Create Male Sterile Plants

Hybrid plants typically have advantageous agronomic traits compared to inbred plants. However, for self-pollinating plants, the generation of hybrids can be challenging. In different plant types, genes have been identified which are important for plant fertility, more particularly male fertility. For instance, in maize, at least two genes have been identified which are important in fertility (Amitabh Mohanty International Conference on New Plant Breeding Molecular Technologies Technology Development And Regulation, Oct. 9-10, 2014, Jaipur, India; Svitashev et al. Plant Physiol. 2015 October; 169(2):931-45; Djukanovic et al. Plant J. 2013 December; 76(5):888-99). The methods and systems provided herein can be used to target genes required for male fertility so as to generate male sterile plants which can easily be crossed to generate hybrids. In particular embodiments, the CD-functionalized CRISPR system provided herein is used for targeted mutagenesis of the cytochrome P450-like gene (MS26) or the meganuclease gene (MS45) thereby conferring male sterility to the maize plant. Maize plants which are as such genetically altered can be used in hybrid breeding programs.

Increasing the Fertility Stage in Plants

In particular embodiments, the methods and systems provided herein are used to prolong the fertility stage of a plant such as of a rice plant. For instance, a rice fertility stage gene such as Ehd3 can be targeted in order to generate a mutation in the gene and plantlets can be selected for a prolonged regeneration plant fertility stage (as described in CN 104004782).

Use of CD-Functionalized CRISPR System to Generate Genetic Variation in a Crop of Interest The availability of wild germplasm and genetic variations in crop plants is the key to crop improvement programs, but the available diversity in germplasms from crop plants is limited. The present invention envisages methods for generating a diversity of genetic variations in a germplasm of interest. In this application of the CD-functionalized CRISPR system a library of guide RNAs targeting different locations in the plant genome is provided and is introduced into plant cells together with the CRISPR-Cas protein and cytidine deaminase. In this way a collection of genome-scale point mutations and gene knock-outs can be generated. In particular embodiments, the methods comprise generating a plant part or plant from the cells so obtained and screening the cells for a trait of interest. The target genes can include both coding and non-coding regions. In particular embodiments, the trait is stress tolerance and the method is a method for the generation of stress-tolerant crop varieties.

Use of CD-Functionalized CRISPR to Affect Fruit-Ripening

Ripening is a normal phase in the maturation process of fruits and vegetables. Only a few days after it starts it renders a fruit or vegetable inedible. This process brings significant losses to both farmers and consumers. In particular embodiments, the methods of the present invention are used to reduce ethylene production. This is ensured by ensuring one or more of the following: a. Suppression of ACC synthase gene expression. ACC (1-aminocyclopropane-1-carboxylic acid) synthase is the enzyme responsible for the conversion of S-adenosylmethionine (SAM) to ACC; the second to the last step in ethylene biosynthesis. Enzyme expression is hindered when an antisense ("mirror-image") or truncated copy of the synthase gene is inserted into the plant's genome; b. Insertion of the ACC deaminase gene. The gene coding for the enzyme is obtained from *Pseudomonas chlororaphis*, a common nonpathogenic soil *bacterium*. It converts ACC to a different compound thereby reducing the amount of ACC available for ethylene production; c. Insertion of the SAM hydrolase gene. This approach is similar to ACC deaminase wherein ethylene production is hindered when the amount of its precursor metabolite is reduced; in this case SAM is converted to homoserine. The gene coding for the enzyme is obtained from *E. coli* T3 bacteriophage and d. Suppression of ACC oxidase gene expression. ACC oxidase is the enzyme which catalyzes the oxidation of ACC to ethylene, the last step in the ethylene biosynthetic pathway. Using the methods described herein, down regulation of the ACC oxidase gene results in the suppression of ethylene production, thereby delaying fruit ripening. In particular embodiments, additionally or alternatively to the modifications described above, the methods described herein are used to modify ethylene receptors, so as to interfere with ethylene signals obtained by the fruit. In particular embodiments, expression of the ETR1 gene, encoding an ethylene binding protein is modified, more particularly suppressed. In particular embodiments, additionally or alternatively to the modifications described above, the methods described herein are used to modify expression of the gene encoding Polygalacturonase (PG), which is the enzyme responsible for the breakdown of pectin, the substance that maintains the integrity of plant cell walls. Pectin breakdown occurs at the start of the ripening process resulting in the softening of the fruit. Accordingly, in particular embodiments, the methods described herein are used to introduce a mutation in the PG gene or to suppress activation of the PG gene in order to reduce the amount of PG enzyme produced thereby delaying pectin degradation.

Thus in particular embodiments, the methods comprise the use of the CD-functionalized CRISPR system to ensure one or more modifications of the genome of a plant cell such as described above, and regenerating a plant therefrom. In particular embodiments, the plant is a tomato plant.

Increasing Storage Life of Plants

In particular embodiments, the methods of the present invention are used to modify genes involved in the production of compounds which affect storage life of the plant or plant part. More particularly, the modification is in a gene that prevents the accumulation of reducing sugars in potato tubers. Upon high-temperature processing, these reducing sugars react with free amino acids, resulting in brown, bitter-tasting products and elevated levels of acrylamide, which is a potential carcinogen. In particular embodiments, the methods provided herein are used to reduce or inhibit expression of the vacuolar invertase gene (VInv), which encodes a protein that breaks down sucrose to glucose and fructose (Clasen et al. DOI: 10.1111/pbi.12370).

The Use of the CD-Functionalized CRISPR System to Ensure a Value Added Trait

In particular embodiments the CD-functionalized CRISPR system is used to produce nutritionally improved agricultural crops. In particular embodiments, the methods provided herein are adapted to generate "functional foods", i.e. a modified food or food ingredient that may provide a health benefit beyond the traditional nutrients it contains and/or "nutraceutical", i.e. substances that may be considered a food or part of a food and provides health benefits, including the prevention and treatment of disease. In particular embodiments, the nutraceutical is useful in the prevention and/or treatment of one or more of cancer, diabetes, cardiovascular disease, and hypertension.

Examples of nutritionally improved crops include (Newell-McGloughlin, Plant Physiology, July 2008, Vol. 147, pp. 939-953):

Modified protein quality, content and/or amino acid composition, such as have been described for Bahiagrass (Luciani et al. 2005, Florida Genetics Conference Poster), Canola (Roesler et al., 1997, Plant Physiol 113 75-81), Maize (Cromwell et al, 1967, 1969 J Anim Sci 26 1325-1331, O'Quin et al. 2000 J Anim Sci 78 2144-2149, Yang et al. 2002, Transgenic Res 11 11-20, Young et al. 2004, Plant J 38 910-922), Potato (Yu J and Ao, 1997 Acta Bot Sin 39 329-334; Chakraborty et al. 2000, Proc Natl Acad Sci USA 97 3724-3729; Li et al. 2001) Chin Sci Bull 46 482-484, Rice (Katsube et al. 1999, Plant Physiol 120 1063-1074), Soybean (Dinkins et al. 2001, Rapp 2002, In Vitro Cell Dev Biol Plant 37 742-747), Sweet Potato (Egnin and Prakash 1997, In Vitro Cell Dev Biol 33 52A).

Essential amino acid content, such as has been described for Canola (Falco et al. 1995, Bio/Technology 13 577-582), Lupin (White et al. 2001, J Sci Food Agric 81 147-154), Maize (Lai and Messing, 2002, Agbios 2008 GM crop database (Mar. 11, 2008)), Potato (Zeh et al. 2001, Plant Physiol 127 792-802), Sorghum (Zhao et al. 2003, Kluwer Academic Publishers, Dordrecht, The Netherlands, pp 413-416), Soybean (Falco et al. 1995 Bio/Technology 13 577-582; Galili et al. 2002 Crit Rev Plant Sci 21 167-204).

Oils and Fatty acids such as for Canola (Dehesh et al. (1996) Plant J 9 167-172 [PubMed]; Del Vecchio (1996) INFORM International News on Fats, Oils and Related Materials 7 230-243; Roesler et al. (1997) Plant Physiol 113 75-81 [PMC free article][PubMed]; Froman and Ursin (2002, 2003) Abstracts of Papers of the American Chemical Society 223 U35; James et al. (2003) Am J Clin Nutr 77 1140-1145 [PubMed]; Agbios (2008, above); coton (Chapman et al. (2001). J Am Oil Chem Soc 78 941-947; Liu et al. (2002) J Am Coll Nutr 21 205S-211S [PubMed]; O'Neill (2007) Australian Life Scientist. www.biotechnews.com.au/index.php/id;866694817;fp;4;fpid;2 (Jun. 17, 2008), Linseed (Abbadi et al., 2004, Plant Cell 16: 2734-2748), Maize (Young et al., 2004, Plant J 38 910-922), oil palm (Jalani et al. 1997, J Am Oil Chem Soc 74 1451-1455; Parveez, 2003, AgBiotechNet 113 1-8), Rice (Anai et al., 2003, Plant Cell Rep 21 988-992), Soybean (Reddy and Thomas, 1996, Nat Biotechnol 14 639-642; Kinney and Kwolton, 1998, Blackie Academic and Professional, London, pp 193-213), Sunflower (Arcadia, Biosciences 2008)

Carbohydrates, such as Fructans described for Chicory (Smeekens (1997) Trends Plant Sci 2 286-287, Sprenger et al. (1997) FEBS Lett 400 355-358, Sevenier et al. (1998) Nat Biotechnol 16 843-846), Maize (Caimi et al. (1996) Plant Physiol 110 355-363), Potato (Hellwege et al., 1997 Plant J 12 1057-1065), Sugar Beet (Smeekens et al. 1997, above), Inulin, such as described for Potato (Hellewege et al. 2000, Proc Natl Acad Sci USA 97 8699-8704), Starch, such as described for Rice (Schwall et al. (2000) Nat Biotechnol 18 551-554, Chiang et al. (2005) Mol Breed 15 125-143).

Vitamins and carotenoids, such as described for Canola (Shintani and DellaPenna (1998) Science 282 2098-2100), Maize (Rocheford et al. (2002). J Am Coll Nutr 21 191S-198S, Cahoon et al. (2003) Nat Biotechnol 21 1082-1087, Chen et al. (2003) Proc Natl Acad Sci USA 100 3525-3530), Mustardseed (Shewmaker et al. (1999) Plant J 20 401-412, Potato (Ducreux et al., 2005, J Exp Bot 56 81-89), Rice (Ye et al. (2000) Science 287 303-305, Strawberry (Agius et al. (2003), Nat Biotechnol 21 177-181), Tomato (Rosati et al. (2000) Plant J 24 413-419, Fraser et al. (2001) J Sci Food Agric 81 822-827, Mehta et al. (2002) Nat Biotechnol 20 613-618, Diaz de la Garza et al. (2004) Proc Natl Acad Sci USA 101 13720-13725, Enfissi et al. (2005) Plant Biotechnol J 3 17-27, DellaPenna (2007) Proc Natl Acad Sci USA 104 3675-3676.

Functional secondary metabolites, such as described for Apple (stilbenes, Szankowski et al. (2003) Plant Cell Rep 22: 141-149), Alfalfa (resveratrol, Hipskind and Paiva (2000) Mol Plant Microbe Interact 13 551-562), Kiwi (resveratrol, Kobayashi et al. (2000) Plant Cell Rep 19 904-910), Maize and Soybean (flavonoids, Yu et al. (2000) Plant Physiol 124 781-794), Potato (anthocyanin and alkaloid glycoside, Lukaszewicz et al. (2004) J Agric Food Chem 52 1526-1533), Rice (flavonoids & resveratrol, Stark-Lorenzen et al. (1997) Plant Cell Rep 16 668-673, Shin et al. (2006) Plant Biotechnol J 4 303-315), Tomato (+resveratrol, chlorogenic acid, flavonoids, stilbene; Rosati et al. (2000) above, Muir et al. (2001) Nature 19 470-474, Niggeweg et al. (2004) Nat Biotechnol 22 746-754, Giovinazzo et al. (2005) Plant Biotechnol J 3 57-69), wheat (caffeic and ferulic acids, resveratrol; United Press International (2002)); and Mineral availabilities such as described for Alfalfa (phytase, Austin-Phillips et al. (1999) www.molecularfarming.com/nonmedical.html), Lettuce (iron, Goto et al. (2000) Theor Appl Genet 100 658-664), Rice (iron, Lucca et al. (2002) J Am Coll Nutr 21 184S-190S), Maize, Soybean and wheate (phytase, Drakakaki et al. (2005) Plant Mol Biol 59 869-880, Denbow et al. (1998) Poult Sci 77 878-881, Brinch-Pedersen et al. (2000) Mol Breed 6 195-206).

In particular embodiments, the value-added trait is related to the envisaged health benefits of the compounds present in the plant. For instance, in particular embodiments, the value-added crop is obtained by applying the methods of the invention to ensure the modification of or induce/increase the synthesis of one or more of the following compounds:

Carotenoids, such as α-Carotene present in carrots which neutralizes free radicals that may cause damage to cells or β-Carotene present in various fruits and vegetables which neutralizes free radicals Lutein present in green vegetables which contributes to maintenance of healthy vision Lycopene present in tomato and tomato products, which is believed to reduce the risk of prostate cancer Zeaxanthin, present in citrus and maize, which contributes to maintenance of healthy vision Dietary fiber such as insoluble fiber present in wheat bran which may reduce the risk of breast and/or colon cancer and β-Glucan present in oat, soluble fiber present in *Psyllium* and whole cereal grains which may reduce the risk of cardiovascular disease (CVD)

Fatty acids, such as ω-3 fatty acids which may reduce the risk of CVD and improve mental and visual functions, Conjugated linoleic acid, which may improve body composition, may decrease risk of certain cancers and GLA which may reduce inflammation risk of cancer and CVD, may improve body composition Flavonoids such as Hydroxycinnamates, present in wheat which have Antioxidant-like activities, may reduce risk of degenerative diseases, flavonols, catechins and tannins present in fruits and vegetables which neutralize free radicals and may reduce risk of cancer Glucosinolates, indoles, isothiocyanates, such as Sulforaphane, present in Cruciferous vegetables (broccoli, kale), horseradish, which neutralize free radicals, may reduce risk of cancer Phenolics, such as stilbenes present in grape which May reduce risk of degenerative diseases, heart disease, and cancer, may have longevity effect and caffeic acid and ferulic acid present in vegetables and citrus which have Antioxidant-like activities, may reduce risk of degenerative diseases, heart disease, and eye disease, and epicatechin present in cacao which has Antioxidant-like activities, may reduce risk of degenerative diseases and heart disease Plant stanols/sterols present in maize, soy, wheat and wooden oils which May reduce risk of coronary heart disease by lowering blood cholesterol levels Fructans, insulins, fructo-oligosaccharides present in Jerusalem artichoke, shallot, onion powder which may improve gastrointestinal health Saponins present in soybean, which may lower LDL cholesterol Soybean protein present in soybean which may reduce risk of heart disease Phytoestrogens such as isoflavones present in soybean which May reduce menopause symptoms, such as hot flashes, may reduce osteoporosis and CVD and lignans present in flax, rye and vegetables, which May protect against heart disease and some cancers, may lower LDL cholesterol, total cholesterol.

Sulfides and thiols such as diallyl sulphide present in onion, garlic, olive, leek and scallion and Allyl methyl trisulfide, dithiolthiones present in cruciferous vegetables which may lower LDL cholesterol, helps to maintain healthy immune system Tannins, such as proanthocyanidins, present in cranberry, cocoa, which may improve urinary tract health, may reduce risk of CVD and high blood pressure.

In addition, the methods of the present invention also envisage modifying protein/starch functionality, shelf life, taste/aesthetics, fiber quality, and allergen, antinutrient, and toxin reduction traits.

Accordingly, the invention encompasses methods for producing plants with nutritional added value, said methods comprising introducing into a plant cell a gene encoding an enzyme involved in the production of a component of added nutritional value using the CD-functionalized CRISPR system as described herein and regenerating a plant from said plant cell, said plant characterized in an increase expression of said component of added nutritional value. In particular embodiments, the CD-functionalized CRISPR system is used to modify the endogenous synthesis of these compounds indirectly, e.g. by modifying one or more transcription factors that controls the metabolism of this compound. Methods for introducing a gene of interest into a plant cell and/or modifying an endogenous gene using the CD-functionalized CRISPR system are described herein above.

Some specific examples of modifications in plants that have been modified to confer value-added traits are: plants with modified fatty acid metabolism, for example, by transforming a plant with an antisense gene of stearyl-ACP desaturase to increase stearic acid content of the plant. See Knultzon et al., Proc. Natl. Acad. Sci. U.S.A. 89:2624 (1992). Another example involves decreasing phytate content, for example by cloning and then reintroducing DNA associated with the single allele which may be responsible for maize mutants characterized by low levels of phytic acid. See Raboy et al, Maydica 35:383 (1990).

Similarly, expression of the maize (*Zea mays*) Tfs C1 and R, which regulate the production of flavonoids in maize aleurone layers under the control of a strong promoter, resulted in a high accumulation rate of anthocyanins in *Arabidopsis* (*Arabidopsis thaliana*), presumably by activating the entire pathway (Bruce et al., 2000, Plant Cell 12:65-80). DellaPenna (Welsch et al., 2007 Annu Rev Plant Biol 57: 711-738) found that Tf RAP2.2 and its interacting partner SINAT2 increased carotenogenesis in *Arabidopsis* leaves. Expressing the Tf Dof1 induced the up-regulation of genes encoding enzymes for carbon skeleton production, a marked increase of amino acid content, and a reduction of the Glc level in transgenic *Arabidopsis* (Yanagisawa, 2004 Plant Cell Physiol 45: 386-391), and the DOF Tf AtDofl.1 (OBP2) up-regulated all steps in the glucosinolate biosynthetic pathway in *Arabidopsis* (Skirycz et al., 2006 Plant J 47: 10-24).

Reducing Allergen in Plants

In particular embodiments the methods provided herein are used to generate plants with a reduced level of allergens, making them safer for the consumer. In particular embodiments, the methods comprise modifying expression of one or more genes responsible for the production of plant allergens. For instance, in particular embodiments, the methods comprise down-regulating expression of a Lol p5 gene in a plant cell, such as a ryegrass plant cell and regenerating a plant therefrom so as to reduce allergenicity of the pollen of said plant (Bhalla et al. 1999, Proc. Natl. Acad. Sci. USA Vol. 96: 11676-11680).

Peanut allergies and allergies to legumes generally are a real and serious health concern. The CD-functionalized CRISPR system of the present invention can be used to identify and then mutate genes encoding allergenic proteins of such legumes. Without limitation as to such genes and proteins, Nicolaou et al. identifies allergenic proteins in peanuts, soybeans, lentils, peas, lupin, green beans, and mung beans. See, Nicolaou et al., Current Opinion in Allergy and Clinical Immunology 2011; 11(3):222).

Screening Methods for Endogenous Genes of Interest

The methods provided herein further allow the identification of genes of value encoding enzymes involved in the production of a component of added nutritional value or generally genes affecting agronomic traits of interest, across species, phyla, and plant kingdom. By selectively targeting e.g. genes encoding enzymes of metabolic pathways in plants using the CD-functionalized CRISPR system as described herein, the genes responsible for certain nutritional aspects of a plant can be identified. Similarly, by selectively targeting genes which may affect a desirable agronomic trait, the relevant genes can be identified. Accordingly, the present invention encompasses screening methods for genes encoding enzymes involved in the production of compounds with a particular nutritional value and/or agronomic traits.

Further Applications of the CD-Functionalized CRISPR System in Plants and Yeasts Use of CD-Functionalized CRISPR System in Biofuel Production The term "biofuel" as used herein is an alternative fuel made from plant and plant-derived resources. Renewable biofuels can be extracted from organic matter whose energy has been obtained through a process of carbon fixation or are made through the use or conversion of biomass. This biomass can be used directly for biofuels or can be converted to convenient energy containing substances by thermal conversion, chemical conversion, and biochemical conversion. This biomass conversion can result in fuel in solid, liquid, or gas form. There are two types of biofuels: bioethanol and biodiesel. Bioethanol is mainly produced by the sugar fermentation process of cellulose (starch), which is mostly derived from maize and sugar cane. Biodiesel on the other hand is mainly produced from oil crops such as rapeseed, palm, and soybean. Biofuels are used mainly for transportation.

Enhancing Plant Properties for Biofuel Production

In particular embodiments, the methods using the CD-functionalized CRISPR system as described herein are used to alter the properties of the cell wall in order to facilitate access by key hydrolysing agents for a more efficient release of sugars for fermentation. In particular embodiments, the biosynthesis of cellulose and/or lignin are modified. Cellulose is the major component of the cell wall. The biosynthesis of cellulose and lignin are co-regulated. By reducing the proportion of lignin in a plant the proportion of cellulose can be increased. In particular embodiments, the methods described herein are used to downregulate lignin biosynthesis in the plant so as to increase fermentable carbohydrates. More particularly, the methods described herein are used to downregulate at least a first lignin biosynthesis gene selected from the group consisting of 4-coumarate 3-hydroxylase (C3H), phenylalanine ammonia-lyase (PAL), cinnamate 4-hydroxylase (C4H), hydroxycinnamoyl transferase (HCT), caffeic acid O-methyltransferase (COMT), caffeoyl CoA 3-O-methyltransferase (CCoAOMT), ferulate 5-hydroxylase (F5H), cinnamyl alcohol dehydrogenase (CAD), cinnamoyl CoA-reductase (CCR), 4-coumarate-CoA ligase (4CL), monolignol-lignin-specific glycosyltransferase, and aldehyde dehydrogenase (ALDH) as disclosed in WO 2008064289 A2.

In particular embodiments, the methods described herein are used to produce plant mass that produces lower levels of acetic acid during fermentation (see also WO 2010096488). More particularly, the methods disclosed herein are used to generate mutations in homologs to CaslL to reduce polysaccharide acetylation.

Modifying Yeast for Biofuel Production

In particular embodiments, the CD-functionalized CRISPR system provided herein is used for bioethanol production by recombinant micro-organisms. For instance, the CD-functionalized CRISPR system can be used to engineer micro-organisms, such as yeast, to generate biofuel or biopolymers from fermentable sugars and optionally to be able to degrade plant-derived lignocellulose derived from agricultural waste as a source of fermentable sugars. In some embodiments, the CD-functionalized CRISPR system is used to modify endogenous metabolic pathways which compete with the biofuel production pathway.

Accordingly, in more particular embodiments, the methods described herein are used to modify a micro-organism as follows: to modify at least one nucleic acid encoding for an enzyme in a metabolic pathway in said host cell, wherein said pathway produces a metabolite other than acetaldehyde from pyruvate or ethanol from acetaldehyde, and wherein said modification results in a reduced production of said metabolite, or to introduce at least one nucleic acid encoding for an inhibitor of said enzyme.

Modifying Algae and Plants for Production of Vegetable Oils or Biofuels

Transgenic algae or other plants such as rape may be particularly useful in the production of vegetable oils or biofuels such as alcohols (especially methanol and ethanol), for instance. These may be engineered to express or overexpress high levels of oil or alcohols for use in the oil or biofuel industries.

According to particular embodiments of the invention, the CD-functionalized CRISPR system is used to generate lipid-rich diatoms which are useful in biofuel production.

In particular embodiments it is envisaged to specifically modify genes that are involved in the modification of the quantity of lipids and/or the quality of the lipids produced by the algal cell. Examples of genes encoding enzymes involved in the pathways of fatty acid synthesis can encode proteins having for instance acetyl-CoA carboxylase, fatty acid synthase, 3-ketoacyl_acyl-carrier protein synthase III, glycerol-3-phospate dehydrogenase (G3PDH), Enoyl-acyl carrier protein reductase (Enoyl-ACP-reductase), glycerol-3-phosphate acyltransferase, lysophosphatidic acyl transferase or diacylglycerol acyltransferase, phospholipid:diacylglycerol acyltransferase, phosphatidate phosphatase, fatty acid thioesterase such as palmitoyl protein thioesterase, or malic enzyme activities. In further embodiments it is envisaged to generate diatoms that have increased lipid accumulation. This can be achieved by targeting genes that decrease lipid catabolisation. Of particular interest for use in the methods of the present invention are genes involved in the activation of both triacylglycerol and free fatty acids, as well as genes directly involved in β-oxidation of fatty acids, such as acyl-CoA synthetase, 3-ketoacyl-CoA thiolase, acyl-CoA oxidase activity and phosphoglucomutase. The CD-functionalized CRISPR system and methods described herein can be used to specifically activate such genes in diatoms as to increase their lipid content.

Organisms such as microalgae are widely used for synthetic biology. Stovicek et al. (Metab. Eng. Comm., 2015; 2:13 describes genome editing of industrial yeast, for example, *Saccharomyces cerevisae*, to efficiently produce robust strains for industrial production. Stovicek used a CRISPR-Cas9 system codon-optimized for yeast to simultaneously disrupt both alleles of an endogenous gene and knock in a heterologous gene. Cas9 and guide RNA were expressed from genomic or episomal 2-based vector locations. The authors also showed that gene disruption efficiency could be improved by optimization of the levels of Cas9 and guide RNA expression. Hlavovi et al. (Biotechnol. Adv. 2015) discusses development of species or strains of microalgae using techniques such as CRISPR to target nuclear and chloroplast genes for insertional mutagenesis and screening.

U.S. Pat. No. 8,945,839 describes a method for engineering Micro-Algae (*Chlamydomonas reinhardtii* cells) species) using Cas9. Using similar tools, the methods of the CD-functionalized CRISPR system described herein can be applied on *Chlamydomonas* species and other algae. In particular embodiments, a CRISPR-Cas protein (e.g., Cpf1), cytidine deaminase (which may be fused to the CRISPR-Cas protein or an aptamer-binding adaptor protein), and guide RNA are introduced in algae expressed using a vector that expresses the CRISPR-Cas protein and optionally the cytidine deaminase under the control of a constitutive promoter such as Hsp70A-Rbc S2 or Beta2-tubulin. Guide RNA will be delivered using a vector containing T7 promoter. Alternatively, mRNA and in vitro transcribed guide RNA can be delivered to algal cells. Electroporation protocol follows standard recommended protocol from the GeneArt *Chlamydomonas* Engineering kit.

The Use of CD-Functionalized CRISPR System in the Generation of Micro-Organisms Capable of Fatty Acid Production In particular embodiments, the methods of the invention are used for the generation of genetically engineered micro-organisms capable of the production of fatty esters, such as fatty acid methyl esters ("FAME") and fatty acid ethyl esters ("FAEE").

Typically, host cells can be engineered to produce fatty esters from a carbon source, such as an alcohol, present in the medium, by expression or overexpression of a gene encoding a thioesterase, a gene encoding an acyl-CoA synthase, and a gene encoding an ester synthase. Accordingly, the methods provided herein are used to modify a micro-organisms so as to overexpress or introduce a thioesterase gene, a gene encoding an acyl-CoA synthase, and a gene encoding an ester synthase. In particular embodiments, the thioesterase gene is selected from tesA, 'tesA, tesB, fatB, fatB2, fatB3, fatA1, or fatA. In particular embodiments, the gene encoding an acyl-CoA synthase is selected from fadDJadK, BH3103, pfl-4354, EAV15023, fadD1, fadD2, RPC_4074, fadDD35, fadDD22, faa39, or an identified gene encoding an enzyme having the same properties. In particular embodiments, the gene encoding an ester synthase is a gene encoding a synthase/acyl-CoA:diacylglycerol acyltransferase from *Simmondsia chinensis*, *Acinetobacter* sp. ADP, *Alcanivorax borkumensis*, *Pseudomonas aeruginosa*, *Fundibacter jadensis*, *Arabidopsis thaliana*, or *Alcaligenes eutrophus*, or a variant thereof. Additionally or alternatively, the methods provided herein are used to decrease expression in said micro-organism of at least one of a gene encoding an acyl-CoA dehydrogenase, a gene encoding an outer membrane protein receptor, and a gene encoding a transcriptional regulator of fatty acid biosynthesis. In particular embodiments one or more of these genes is inactivated, such as by introduction of a mutation. In particular embodiments, the gene encoding an acyl-CoA dehydrogenase is fadE. In particular embodiments, the gene encoding a transcriptional regulator of fatty acid biosynthesis encodes a DNA transcription repressor, for example, fabR.

Additionally or alternatively, said micro-organism is modified to reduce expression of at least one of a gene encoding a pyruvate formate lyase, a gene encoding a lactate dehydrogenase, or both. In particular embodiments, the gene encoding a pyruvate formate lyase is pflB. In particular embodiments, the gene encoding a lactate dehydrogenase is ldhA. In particular embodiments one or more of these genes is inactivated, such as by introduction of a mutation therein.

In particular embodiments, the micro-organism is selected from the genus *Escherichia*, *Bacillus*, *Lactobacillus*, *Rhodococcus*, *Synechococcus*, *Synechocystis*, *Pseudomonas*, *Aspergillus*, *Trichoderma*, *Neurospora*, *Fusarium*, *Humicola*, *Rhizomucor*, *Kluyveromyces*, *Pichia*, *Mucor*, *Myceliophthora*, *Penicillium*, *Phanerochaete*, *Pleurotus*, *Trametes*, *Chrysosporium*, *Saccharomyces*, *Stenotrophomonas*, *Schizosaccharomyces*, *Yarrowia*, or *Streptomyces*.

The Use of CD-Functionalized CRISPR System in the Generation of Micro-Organisms Capable of Organic Acid Production The methods provided herein are further used to engineer micro-organisms capable of organic acid production, more particularly from pentose or hexose sugars. In particular embodiments, the methods comprise introducing into a micro-organism an exogenous LDH gene. In particular embodiments, the organic acid production in said micro-organisms is additionally or alternatively increased by inactivating endogenous genes encoding proteins involved in an endogenous metabolic pathway which produces a metabolite other than the organic acid of interest and/or wherein the endogenous metabolic pathway consumes the organic acid. In particular embodiments, the modification ensures that the production of the metabolite other than the organic acid of interest is reduced. According to particular embodiments, the methods are used to introduce at least one engineered gene deletion and/or inactivation of an endogenous pathway in which the organic acid is consumed or a gene encoding a product involved in an endogenous pathway which produces a metabolite other than the organic acid of interest. In particular embodiments, the at least one engineered gene deletion or inactivation is in one or more gene encoding an enzyme selected from the group consisting of pyruvate decarboxylase (pdc), fumarate reductase, alcohol dehydrogenase (adh), acetaldehyde dehydrogenase, phosphoenolpyruvate carboxylase (ppc), D-lactate dehydrogenase (d-ldh), L-lactate dehydrogenase (l-ldh), lactate 2-monooxygenase. In further embodiments the at least one engineered gene deletion and/or inactivation is in an endogenous gene encoding pyruvate decarboxylase (pdc).

In further embodiments, the micro-organism is engineered to produce lactic acid and the at least one engineered gene deletion and/or inactivation is in an endogenous gene encoding lactate dehydrogenase. Additionally or alternatively, the micro-organism comprises at least one engineered gene deletion or inactivation of an endogenous gene encoding a cytochrome-dependent lactate dehydrogenase, such as a cytochrome B2-dependent L-lactate dehydrogenase.

The Use of CD-Functionalized CRISPR System in the Generation of Improved Xylose or Cellobiose Utilizing Yeasts Strains In particular embodiments, the CD-functionalized CRISPR system may be applied to select for improved xylose or cellobiose utilizing yeast strains. Error-prone PCR can be used to amplify one (or more) genes involved in the xylose utilization or cellobiose utilization pathways. Examples of genes involved in xylose utilization pathways and cellobiose utilization pathways may include, without limitation, those described in Ha, S. J., et al. (2011) Proc.

Natl. Acad. Sci. USA 108(2):504-9 and Galazka, J. M., et al. (2010) Science 330(6000):84-6. Resulting libraries of double-stranded DNA molecules, each comprising a random mutation in such a selected gene could be co-transformed with the components of the CD-functionalized CRISPR system into a yeast strain (for instance S288C) and strains can be selected with enhanced xylose or cellobiose utilization capacity, as described in WO2015138855.

The Use of CD-Functionalized CRISPR System in the Generation of Improved Yeasts Strains for Use in Isoprenoid Biosynthesis Tadas Jakočiūnas et al. described the successful application of a multiplex CRISPR-Cas9 system for genome engineering of up to 5 different genomic loci in one transformation step in baker's yeast *Saccharomyces cerevisiae* (Metabolic Engineering Volume 28, March 2015, Pages 213-222) resulting in strains with high mevalonate production, a key intermediate for the industrially important isoprenoid biosynthesis pathway. In particular embodiments, the CD-functionalized CRISPR system may be applied in a multiplex genome engineering method as described herein for identifying additional high producing yeast strains for use in isoprenoid synthesis.

Improved Plants and Yeast Cells

The present invention also provides plants and yeast cells obtainable and obtained by the methods provided herein. The improved plants obtained by the methods described herein may be useful in food or feed production through expression of genes which, for instance ensure tolerance to plant pests, herbicides, drought, low or high temperatures, excessive water, etc.

The improved plants obtained by the methods described herein, especially crops and algae may be useful in food or feed production through expression of, for instance, higher protein, carbohydrate, nutrient or vitamin levels than would normally be seen in the wildtype. In this regard, improved plants, especially pulses and tubers are preferred.

Improved algae or other plants such as rape may be particularly useful in the production of vegetable oils or biofuels such as alcohols (especially methanol and ethanol), for instance. These may be engineered to express or overexpress high levels of oil or alcohols for use in the oil or biofuel industries.

The invention also provides for improved parts of a plant. Plant parts include, but are not limited to, leaves, stems, roots, tubers, seeds, endosperm, ovule, and pollen. Plant parts as envisaged herein may be viable, nonviable, regeneratable, and/or non-regeneratable.

It is also encompassed herein to provide plant cells and plants generated according to the methods of the invention. Gametes, seeds, embryos, either zygotic or somatic, progeny or hybrids of plants comprising the genetic modification, which are produced by traditional breeding methods, are also included within the scope of the present invention. Such plants may contain a heterologous or foreign DNA sequence inserted at or instead of a target sequence. Alternatively, such plants may contain only an alteration (mutation, deletion, insertion, substitution) in one or more nucleotides. As such, such plants will only be different from their progenitor plants by the presence of the particular modification.

Thus, the invention provides a plant, animal or cell, produced by the present methods, or a progeny thereof. The progeny may be a clone of the produced plant or animal, or may result from sexual reproduction by crossing with other individuals of the same species to introgress further desirable traits into their offspring. The cell may be in vivo or ex vivo in the cases of multicellular organisms, particularly animals or plants.

The methods for genome editing using the CD-functionalized CRISPR system as described herein can be used to confer desired traits on essentially any plant, algae, fungus, yeast, etc. A wide variety of plants, algae, fungus, yeast, etc and plant algae, fungus, yeast cell or tissue systems may be engineered for the desired physiological and agronomic characteristics described herein using the nucleic acid constructs of the present disclosure and the various transformation methods mentioned above.

In particular embodiments, the methods described herein are used to modify endogenous genes or to modify their expression without the permanent introduction into the genome of the plant, algae, fungus, yeast, etc of any foreign gene, including those encoding CRISPR components, so as to avoid the presence of foreign DNA in the genome of the plant. This can be of interest as the regulatory requirements for non-transgenic plants are less rigorous.

The methods described herein generally result in the generation of "improved plants, algae, fungi, yeast, etc" in that they have one or more desirable traits compared to the wildtype plant. In particular embodiments, non-transgenic genetically modified plants, algae, fungi, yeast, etc., parts or cells are obtained, in that no exogenous DNA sequence is incorporated into the genome of any of the cells of the plant. In such embodiments, the improved plants, algae, fungi, yeast, etc. are non-transgenic. Where only the modification of an endogenous gene is ensured and no foreign genes are introduced or maintained in the plant, algae, fungi, yeast, etc. genome, the resulting genetically modified crops contain no foreign genes and can thus basically be considered non-transgenic. The different applications of the CD-functionalized CRISPR system for plant, algae, fungi, yeast, etc. genome editing include, but are not limited to: editing of endogenous genes to confer an agricultural trait of interest. Examplary genes conferring agronomic traits include, but are not limited to genes that confer resistance to pests or diseases; genes involved in plant diseases, such as those listed in WO 2013046247; genes that confer resistance to herbicides, fungicides, or the like; genes involved in (abiotic) stress tolerance. Other aspects of the use of the CRISPR-Cas system include, but are not limited to: create (male) sterile plants; increasing the fertility stage in plants/algae etc; generate genetic variation in a crop of interest; affect fruit-ripening; increasing storage life of plants/algae etc; reducing allergen in plants/algae etc; ensure a value added trait (e.g. nutritional improvement); screening methods for endogenous genes of interest; biofuel, fatty acid, organic acid, etc production.

CD-Functionalized CRISPR System can be Used in Non-Human Organisms

In an aspect, the invention provides a non-human eukaryotic organism; preferably a multicellular eukaryotic organism, comprising a eukaryotic host cell according to any of the described embodiments. In other aspects, the invention provides a eukaryotic organism; preferably a multicellular eukaryotic organism, comprising a eukaryotic host cell according to any of the described embodiments. The organism in some embodiments of these aspects may be an animal; for example a mammal. Also, the organism may be an arthropod such as an insect. The present invention may also be extended to other agricultural applications such as, for example, farm and production animals. For example, pigs have many features that make them attractive as biomedical models, especially in regenerative medicine. In particular, pigs with severe combined immunodeficiency (SCID) may provide useful models for regenerative medicine, xenotransplantation (discussed also elsewhere herein), and tumor development and will aid in developing therapies for human SCID patients. Lee et al., (Proc Natl Acad Sci USA. 2014 May 20; 111(20):7260-5) utilized a reporter-guided transcription activator-like effector nuclease (TALEN) system to generated targeted modifications of recombination activating gene (RAG) 2 in somatic cells at high efficiency, including some that affected both alleles. The CD-functionalized CRISPR system may be applied to a similar system.

The methods of Lee et al., (Proc Natl Acad Sci USA. 2014 May 20; 111(20):7260-5) may be applied to the present invention analogously as follows. Mutated pigs are produced by targeted modification of RAG2 in fetal fibroblast cells followed by SCNT and embryo transfer. Constructs coding for CRISPR-Cas and a reporter are electroporated into fetal-derived fibroblast cells. After 48 h, transfected cells expressing the green fluorescent protein are sorted into individual wells of a 96-well plate at an estimated dilution of a single cell per well. Targeted modification of RAG2 are screened by amplifying a genomic DNA fragment flanking any CRISPR-Cas cutting sites followed by sequencing the PCR products. After screening and ensuring lack of off-site mutations, cells carrying targeted modification of RAG2 are used for SCNT. The polar body, along with a portion of the adjacent cytoplasm of oocyte, presumably containing the metaphase II plate, are removed, and a donor cell are placed in the perivitelline. The reconstructed embryos are then electrically porated to fuse the donor cell with the oocyte and then chemically activated. The activated embryos are incubated in Porcine Zygote Medium 3 (PZM3) with 0.5 µM Scriptaid (S7817; Sigma-Aldrich) for 14-16 h. Embryos are then washed to remove the Scriptaid and cultured in PZM3 until they were transferred into the oviducts of surrogate pigs.

The present invention is also applicable to modifying SNPs of other animals, such as cows. Tan et al. (Proc Natl Acad Sci USA. 2013 Oct. 8; 110(41): 16526-16531) expanded the livestock gene editing toolbox to include transcription activator-like (TAL) effector nuclease (TALEN)- and clustered regularly interspaced short palindromic repeats (CRISPR)/Cas9-stimulated homology-directed repair (HDR) using plasmid, rAAV, and oligonucleotide templates. Gene specific guide RNA sequences were cloned into the Church lab guide RNA vector (Addgene ID: 41824) according to their methods (Mali P, et al. (2013) RNA-Guided Human Genome Engineering via Cas9. Science 339(6121):823-826). The Cas9 nuclease was provided either by co-transfection of the hCas9 plasmid (Addgene ID: 41815) or mRNA synthesized from RCIScript-hCas9. This RCIScript-hCas9 was constructed by sub-cloning the XbaI-AgeI fragment from the hCas9 plasmid (encompassing the hCas9 cDNA) into the RCIScript plasmid.

Heo et al. (Stem Cells Dev. 2015 Feb. 1; 24(3):393-402. doi: 10.1089/scd.2014.0278. Epub 2014 Nov. 3) reported highly efficient gene targeting in the bovine genome using bovine pluripotent cells and clustered regularly interspaced short palindromic repeat (CRISPR)/Cas9 nuclease. First, Heo et al. generate induced pluripotent stem cells (iPSCs) from bovine somatic fibroblasts by the ectopic expression of yamanaka factors and GSK3β and MEK inhibitor (2i) treatment. Heo et al. observed that these bovine iPSCs are highly similar to naïve pluripotent stem cells with regard to gene expression and developmental potential in teratomas. Moreover, CRISPR-Cas9 nuclease, which was specific for the bovine NANOG locus, showed highly efficient editing of the bovine genome in bovine iPSCs and embryos.

Igenity® provides a profile analysis of animals, such as cows, to perform and transmit traits of economic traits of economic importance, such as carcass composition, carcass quality, maternal and reproductive traits and average daily gain. The analysis of a comprehensive Igenity® profile begins with the discovery of DNA markers (most often single nucleotide polymorphisms or SNPs). All the markers behind the Igenity® profile were discovered by independent scientists at research institutions, including universities, research organizations, and government entities such as USDA. Markers are then analyzed at Igenity® in validation populations. Igenity® uses multiple resource populations that represent various production environments and biological types, often working with industry partners from the seedstock, cow-calf, feedlot and/or packing segments of the beef industry to collect phenotypes that are not commonly available. Cattle genome databases are widely available, see, e.g., the NAGRP Cattle Genome Coordination Program (www.animalgenome.org/cattle/maps/db.html). Thus, the present invention maybe applied to target bovine SNPs. One of skill in the art may utilize the above protocols for targeting SNPs and apply them to bovine SNPs as described, for example, by Tan et al. or Heo et al.

Qingjian Zou et al. (Journal of Molecular Cell Biology Advance Access published Oct. 12, 2015) demonstrated increased muscle mass in dogs by targeting the first exon of the dog Myostatin (MSTN) gene (a negative regulator of skeletal muscle mass). First, the efficiency of the sgRNA was validated, using cotransfection of the sgRNA targeting MSTN with a Cas9 vector into canine embryonic fibroblasts (CEFs). Thereafter, MSTN KO dogs were generated by micro-injecting embryos with normal morphology with a mixture of Cas9 mRNA and MSTN sgRNA and auto-transplantation of the zygotes into the oviduct of the same female dog. The knock-out puppies displayed an obvious muscular phenotype on thighs compared with its wild-type littermate sister. This can also be performed using the CD-functionalized CRISPR systems provided herein.

Livestock—Pigs

Viral targets in livestock may include, in some embodiments, porcine CD163, for example on porcine macrophages. CD163 is associated with infection (thought to be through viral cell entry) by PRRSv (Porcine Reproductive and Respiratory Syndrome virus, an arterivirus). Infection by PRRSv, especially of porcine alveolar macrophages (found in the lung), results in a previously incurable porcine syndrome ("Mystery swine disease" or "blue ear disease") that causes suffering, including reproductive failure, weight loss and high mortality rates in domestic pigs. Opportunistic infections, such as enzootic pneumonia, meningitis and ear oedema, are often seen due to immune deficiency through loss of macrophage activity. It also has significant economic and environmental repercussions due to increased antibiotic use and financial loss (an estimated $660 m per year).

As reported by Kristin M Whitworth and Dr Randall Prather et al. (Nature Biotech 3434 published online 7 Dec. 2015) at the University of Missouri and in collaboration with Genus Plc, CD163 was targeted using CRISPR-Cas9 and the offspring of edited pigs were resistant when exposed to PRRSv. One founder male and one founder female, both of whom had mutations in exon 7 of CD163, were bred to produce offspring. The founder male possessed an 11-bp deletion in exon 7 on one allele, which results in a frameshift mutation and missense translation at amino acid 45 in domain 5 and a subsequent premature stop codon at amino acid 64. The other allele had a 2-bp addition in exon 7 and a 377-bp deletion in the preceding intron, which were predicted to result in the expression of the first 49 amino acids of domain 5, followed by a premature stop code at amino acid 85. The sow had a 7 bp addition in one allele that when translated was predicted to express the first 48 amino acids of domain 5, followed by a premature stop codon at amino acid 70. The sow's other allele was unamplifiable. Selected offspring were predicted to be a null animal (CD163−/−), i.e. a CD163 knock out.

Accordingly, in some embodiments, porcine alveolar macrophages may be targeted by the CRISPR protein. In some embodiments, porcine CD163 may be targeted by the CRISPR protein. In some embodiments, porcine CD163 may be knocked out through induction of a DSB or through insertions or deletions, for example targeting deletion or modification of exon 7, including one or more of those described above, or in other regions of the gene, for example deletion or modification of exon 5.

An edited pig and its progeny are also envisaged, for example a CD163 knock out pig. This may be for livestock, breeding or modelling purposes (i.e. a porcine model). Semen comprising the gene knock out is also provided.

CD163 is a member of the scavenger receptor cysteine-rich (SRCR) superfamily. Based on in vitro studies SRCR domain 5 of the protein is the domain responsible for unpackaging and release of the viral genome. As such, other members of the SRCR superfamily may also be targeted in order to assess resistance to other viruses. PRRSV is also a member of the mammalian arterivirus group, which also includes murine lactate dehydrogenase-elevating virus, simian hemorrhagic fever virus and equine arteritis virus. The arteriviruses share important pathogenesis properties, including macrophage tropism and the capacity to cause both severe disease and persistent infection. Accordingly, arteriviruses, and in particular murine lactate dehydrogenase-elevating virus, simian hemorrhagic fever virus and equine arteritis virus, may be targeted, for example through porcine CD163 or homologues thereof in other species, and murine, simian and equine models and knockout also provided.

Indeed, this approach may be extended to viruses or bacteria that cause other livestock diseases that may be transmitted to humans, such as Swine Influenza Virus (SIV) strains which include influenza C and the subtypes of influenza A known as H1N1, H1N2, H2N1, H3N1, H3N2, and H2N3, as well as pneumonia, meningitis and oedema mentioned above.

In some embodiments, the CD-functionalized CRISPR system described herein can be used to genetically modify a pig genome to inactivate one or more porcine endogenous retrovirus (PERVs) loci to facilitate clinical application of porcine-to-human xenotransplantation. See Yang et al., Science 350(6264):1101-1104 (2015), which is incorporated herein by reference in its entirety. In some embodiments, the CD-functionalized CRISPR system described herein can be used to produce a genetically modified pig that does not comprise any active porcine endogenous retrovirus (PERVs) locus.

Therapeutic Targeting with CD-Functionalized CRISPR System

As will be apparent, it is envisaged that CD-functionalized CRISPR system can be used to target any polynucleotide sequence of interest. The invention provides a non-naturally occurring or engineered composition, or one or more polynucleotides encoding components of said composition, or vector or delivery systems comprising one or more polynucleotides encoding components of said composition for use in a modifying a target cell in vivo, ex vivo or in vitro and, may be conducted in a manner alters the cell such that once modified the progeny or cell line of the CRISPR modified cell retains the altered phenotype. The modified cells and progeny may be part of a multi-cellular organism such as a plant or animal with ex vivo or in vivo application of CRISPR system to desired cell types. The CRISPR invention may be a therapeutic method of treatment. The therapeutic method of treatment may comprise gene or genome editing, or gene therapy.

Adoptive Cell Therapies

The present invention also contemplates use of the CD-functionalized CRISPR system described herein to modify cells for adoptive therapies. Aspects of the invention accordingly involve the adoptive transfer of immune system cells, such as T cells, specific for selected antigens, such as tumor associated antigens (see Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; and, Restifo et al., 2015, Adoptive immunotherapy for cancer: harnessing the T cell response. Nat. Rev. Immunol. 12(4): 269-281; and Jenson and Riddell, 2014, Design and implementation of adoptive therapy with chimeric antigen receptor-modified T cells. Immunol Rev. 257(1): 127-144). Various strategies may for example be employed to genetically modify T cells by altering the specificity of the T cell receptor (TCR) for example by introducing new TCR a and R chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088,379).

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004,811; 6,284,240; 6,392,013; 6,410,014; 6,753,162; 8,211,422; and, PCT Publication WO9215322). Alternative CAR constructs may be characterized as belonging to successive generations. First-generation CARs typically consist of a single-chain variable fragment of an antibody specific for an antigen, for example comprising a VL linked to a VH of a specific antibody, linked by a flexible linker, for example by a CD8α hinge domain and a CD8α transmembrane domain, to the transmembrane and intracellular signaling domains of either CD3ζ or FcRγ (scFv-CD3ζ or scFv-FcRγ; see U.S. Pat. Nos. 7,741,465; 5,912,172; 5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD3ζ; see U.S. Pat. Nos. 8,911,993; 8,916,381; 8,975,071; 9,101,584; 9,102,760; 9,102,761). Third-generation CARs include a combination of costimulatory endodomains, such a CD3ζ-chain, CD97, GDI1a-CD18, CD2, ICOS, CD27, CD154, CDS, OX40, 4-1BB, or CD28 signaling domains (for example scFv-CD28-4-1BB-CD3ζ or scFv-CD28-OX40-CD3ζ; see U.S. Pat. Nos. 8,906,682; 8,399,645; 5,686,281; PCT Publication No. WO2014134165; PCT Publication No. WO2012079000). Alternatively, costimulation may be orchestrated by expressing CARs in antigen-specific T cells, chosen so as to be activated and expanded following engagement of their native αβTCR, for example by antigen on professional antigen-presenting cells, with attendant costimulation. In addition, additional engineered receptors may be provided on the immunoresponsive cells, for example to improve targeting of a T-cell attack and/or minimize side effects.

Alternative techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3(and either CD28 or CD137. Viral vectors may for example include vectors based on HIV, SV40, EBV, HSV or BPV.

Cells that are targeted for transformation may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with γ-irradiated activating and propagating cells (AaPC), which co-express the cancer antigen and co-stimulatory molecules. The engineered CAR T-cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-γ). CAR T cells of this kind may for example be used in animal models, for example to threat tumor xenografts.

Approaches such as the foregoing may be adapted to provide methods of treating and/or increasing survival of a subject having a disease, such as a neoplasia, for example by administering an effective amount of an immunoresponsive cell comprising an antigen recognizing receptor that binds a selected antigen, wherein the binding activates the immunoreponsive cell, thereby treating or preventing the disease (such as a neoplasia, a pathogen infection, an autoimmune disorder, or an allogeneic transplant reaction). Dosing in CAR T cell therapies may for example involve administration of from 106 to 109 cells/kg, with or without a course of lymphodepletion, for example with cyclophosphamide.

In one embodiment, the treatment can be administrated into patients undergoing an immunosuppressive treatment. The cells or population of cells, may be made resistant to at least one immunosuppressive agent due to the inactivation of a gene encoding a receptor for such immunosuppressive agent. Not being bound by a theory, the immunosuppressive treatment should help the selection and expansion of the immunoresponsive or T cells according to the invention within the patient.

The administration of the cells or population of cells according to the present invention may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. Dosing in CAR T cell therapies may for example involve administration of from $10^6$ to $10^9$ cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tumor.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

In a further refinement of adoptive therapies, genome editing with a CD-functionalized CRISPR-Cas system as described herein may be used to tailor immunoresponsive cells to alternative implementations, for example providing edited CAR T cells (see Poirot et al., 2015, Multiplex genome edited T-cell manufacturing platform for "off-the-shelf" adoptive T-cell immunotherapies, Cancer Res 75 (18): 3853). For example, immunoresponsive cells may be edited to delete expression of some or all of the class of HLA type II and/or type I molecules, or to knockout selected genes that may inhibit the desired immune response, such as the PD1 gene.

Cells may be edited using a CD-functionalized CRISPR system as described herein. CD-functionalized CRISPR systems may be delivered to an immune cell by any method described herein. In preferred embodiments, cells are edited ex vivo and transferred to a subject in need thereof. Immunoresponsive cells, CAR-T cells or any cells used for adoptive cell transfer may be edited. Editing may be performed to eliminate potential alloreactive T-cell receptors (TCR), disrupt the target of a chemotherapeutic agent, block an immune checkpoint, activate a T cell, and/or increase the differentiation and/or proliferation of functionally exhausted or dysfunctional CD8+ T-cells (see PCT Patent Publications: WO2013176915, WO2014059173, WO2014172606, WO2014184744, and WO2014191128). Editing may result in inactivation of a gene.

T cell receptors (TCR) are cell surface receptors that participate in the activation of T cells in response to the presentation of antigen. The TCR is generally made from two chains, a and p, which assemble to form a heterodimer and associates with the CD3-transducing subunits to form the T cell receptor complex present on the cell surface. Each a and p chain of the TCR consists of an immunoglobulin-like N-terminal variable (V) and constant (C) region, a hydrophobic transmembrane domain, and a short cytoplasmic region. As for immunoglobulin molecules, the variable region of the α and β chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of graft versus host disease (GVHD). The inactivation of TCRa or TCRP can result in the elimination of the TCR from the surface of T cells preventing recognition of alloantigen and thus GVHD. However, TCR disruption generally results in the elimination of the CD3 signaling component and alters the means of further T cell expansion.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1; 112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic T cells. Therefore, to effectively use an adoptive immunotherapy approach in these conditions, the introduced cells would need to be resistant to the immunosuppressive treatment. Thus, in a particular embodiment, the present invention further comprises a step of modifying T cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor α-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to T cells for immunotherapy by inactivating the target of the immunosuppressive agent in T cells. As non-limiting examples, targets for an immunosuppressive agent can be a receptor for an immunosuppressive agent such as: CD52, glucocorticoid receptor (GR), a FKBP family gene member and a cyclophilin family gene member.

Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCD1). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDL1 or KIR. In further additional embodiments, the immune checkpoint targeted is a member of the TNFR superfamily such as CD40, OX40, CD137, GITR, CD27 or TIM-3.

Additional immune checkpoints include Src homology 2 domain-containing protein tyrosine phosphatase 1 (SHP-1) (Watson H A, et al., SHP-1: the next checkpoint target for cancer immunotherapy?Biochem Soc Trans. 2016 Apr. 15; 44(2):356-62). SHP-1 is a widely expressed inhibitory protein tyrosine phosphatase (PTP). In T-cells, it is a negative regulator of antigen-dependent activation and proliferation. It is a cytosolic protein, and therefore not amenable to antibody-mediated therapies, but its role in activation and proliferation makes it an attractive target for genetic manipulation in adoptive transfer strategies, such as chimeric antigen receptor (CAR) T cells. Immune checkpoints may also include T cell immunoreceptor with Ig and ITIM domains (TIGIT/Vstm3/WUCAM/VSIG9) and VISTA (Le Mercier I, et al., (2015) Beyond CTLA-4 and PD-1, the generation Z of negative checkpoint regulators. Front. Immunol. 6:418).

WO2014172606 relates to the use of MT1 and/or MT1 inhibitors to increase proliferation and/or activity of exhausted CD8+ T-cells and to decrease CD8+ T-cell exhaustion (e.g., decrease functionally exhausted or unresponsive CD8+ immune cells). In certain embodiments, metallothioneins are targeted by gene editing in adoptively transferred T cells.

In certain embodiments, targets of gene editing may be at least one targeted locus involved in the expression of an immune checkpoint protein. Such targets may include, but are not limited to CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, VISTA, GUCY1A2, GUCY1A3, GUCY1B2, GUCY1B3, MT1, MT2, CD40, OX40, CD137, GITR, CD27, SHP-1 or TIM-3. In preferred embodiments, the gene locus involved in the expression of PD-1 or CTLA-4 genes is targeted. In other preferred embodiments, combinations of genes are targeted, such as but not limited to PD-1 and TIGIT.

In other embodiments, at least two genes are edited. Pairs of genes may include, but are not limited to PD1 and TCRα, PD1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ.

Whether prior to or after genetic modification of the T cells, the T cells can be activated and expanded generally using methods as described, for example, in U.S. Pat. Nos. 6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. T cells can be expanded in vitro or in vivo.

The practice of the present invention employs techniques known in the field of immunology, biochemistry, chemistry, molecular biology, microbiology, cell biology, genomics and recombinant DNA, which are within the skill of the art. See MOLECULAR CLONING: A LABORATORY MANUAL, 2nd edition (1989) (Sambrook, Fritsch and Maniatis); MOLECULAR CLONING: A LABORATORY MANUAL, 4th edition (2012) (Green and Sambrook); CURRENT PROTOCOLS IN MOLECULAR BIOLOGY (1987) (F. M. Ausubel, et al. eds.); the series METHODS IN ENZYMOLOGY (Academic Press, Inc.); PCR 2: A PRACTICAL APPROACH (1995) (M. J. MacPherson, B. D. Hames and G. R. Taylor eds.); ANTIBODIES, A LABORATORY MANUAL (1988) (Harlow and Lane, eds.); ANTIBODIES A LABORATORY MANUAL, 2nd edition (2013) (E. A. Greenfield ed.); and ANIMAL CELL CULTURE (1987) (R. I. Freshney, ed.).

Correction of Disease-Associated Mutations and Pathogenic SNPs

In one aspect, the invention described herein provides methods for modifying an cytidine residue at a target locus with the aim of remedying and/or preventing a diseased condition that is or is likely to be caused by a T-to-C or A-to-G point mutation or a pathogenic single nucleotide polymorphism (SNP).

Pathogenic T-to-C or A-to-G mutations/SNPs associated with various diseases are reported in the ClinVar database, including but not limited to genetic diseases, cancer, metabolic diseases, or lysosomal storage diseases. Accordingly, an aspect of the invention relates to a method for correcting one or more pathogenic T-to-C or A-to-G mutations/SNPs associated with any of these diseases, as discussed below.

In some embodiments, the methods, systems, and compositions described herein are used to correct one or more pathogenic T-to-C or A-to-G mutations/SNPs reported in the ClinVar database. In some embodiments, the methods, systems, and compositions described herein are used to correct one or more pathogenic T-to-C or A-to-G mutations/SNPs associated with any of the diseases or disorders disclosed in WO2017/070632, titled "Nucleobase Editor and Uses Thereof," which is incorporated herein by reference in its entirety. Exemplary diseases or disorders that may be treated include, without limitation, 3-Methylglutaconic aciduria type 2, 46, XY gonadal dysgenesis, 4-Alpha-hydroxyphenylpyruvate hydroxylase deficiency, 6-pyruvoyl-tetrahydropterin synthase deficiency, achromatopsia, Acid-labile subunit deficiency, Acrodysostosis, acroerythrokeratoderma, ACTH resistance, ACTH-independent macronodular adrenal hyperplasia, Activated PBK-delta syndrome, Acute intermittent *porphyria*, Acute myeloid leukemia, Adams-Oliver syndrome 1/5/6, Adenylosuccinate lyase deficiency, Adrenoleukodystrophy, Adult neuronal ceroid lipofuscinosis, Adult onset ataxia with oculomotor apraxia, Advanced sleep phase syndrome, Age-related macular degeneration, Alagille syndrome, Alexander disease, Allan-Herndon-Dudley syndrome, Alport syndrome, X-linked recessive, Alternating hemiplegia of childhood, Alveolar capillary dysplasia with misalignment of pulmonary veins, Amelogenesis imperfecta, Amyloidogenic transthyretin amyloidosis, Amyotrophic lateral sclerosis, Anemia (nonspherocytic hemolytic, due to G6PD deficiency), Anemia (sideroblastic, pyridoxine-refractory, autosomal recessive), Anonychia, Antithrombin III deficiency, Aortic aneurysm, Aplastic anemia, Apolipoprotein C2 deficiency, Apparent mineralocorticoid excess, Aromatase deficiency, Arrhythmogenic right ventricular cardiomyopathy, Familial hypertrophic cardiomyopathy, Hypertrophic cardiomyopathy, Arthrogryposis multiplex congenital, Aspartylglycosaminuria, Asphyxiating thoracic dystrophy, Ataxia with vitamin E deficiency, Ataxia (spastic), Atrial fibrillation, Atrial septal defect, atypical hemolytic-uremic syndrome, autosomal dominant CD11C+/CD1C+ dendritic cell deficiency, Autosomal dominant progressive external ophthalmoplegia with mitochondrial DNA deletions, Baraitser-Winter syndrome, Bartter syndrome, Basa ganglia calcification, Beckwith-Wiedemann syndrome, Benign familial neonatal seizures, Benign scapuloperoneal muscular dystrophy, Bernard Soulier syndrome, Beta thalassemia *intermedia*, Beta-D-mannosidosis, Bietti crystalline corneoretinal dystrophy, Bile acid malabsorption, Biotinidase deficiency, Borjeson-Forssman-Lehmann syndrome, Boucher Neuhauser syndrome, Bowen-Conradi syndrome, Brachydactyly, Brown-Vialetto-Van laere syndrome, Brugada syndrome, Cardiac arrhythmia, Cardiofaciocutaneous syndrome, Cardiomyopathy, Carnevale syndrome, Carnitine palmitoyltransferase II deficiency, Carpenter syndrome, Cataract, Catecholaminergic polymorphic ventricular tachycardia, Central core disease, Centromeric instability of chromosomes 1,9 and 16 and immunodeficiency, Cerebral autosomal dominant arteriopathy, Cerebro-oculo-facio-skeletal syndrome, Ceroid lipofuscinosis, Charcot-Marie-Tooth disease, Cholestanol storage disease, Chondrocalcinosis, Chondrodysplasia, Chronic progressive multiple sclerosis, Coenzyme Q10 deficiency, Cohen syndrome, Combined deficiency of factor V and factor VIII, Combined immunodeficiency, Combined oxidative phosphorylation deficiency, Combined partial 1 7-alpha-hydroxylase/17,20-lyase deficiency, Complement factor d deficiency, Complete combined 17-alpha-hydroxylase/17,20-lyase deficiency, Cone-rod dystrophy, Congenital contractural arachnodactyly, Congenital disorder of glycosylation, Congenital lipomatous overgrowth, Neoplasm of ovary, PIK3CA Related Overgrowth Spectrum, Congenital long QT syndrome, Congenital muscular dystrophy, Congenital muscular hypertrophy-cerebral syndrome, Congenital myasthenic syndrome, Congenital myopathy with fiber type disproportion, Eichsfeld type congenital muscular dystrophy, Congenital stationary night blindness, Corneal dystrophy, Cornelia de Lange syndrome, Craniometaphyseal dysplasia, Crigler Najjar syndrome, Crouzon syndrome, Cutis *laxa* with osteodystrophy, Cyanosis, Cystic fibrosis, Cystinosis, Cytochrome-c oxidase deficiency, Mitochondrial complex I deficiency, D-2-hydroxyglutaric aciduria, Danon disease, Deafness with labyrinthine aplasia microtia and microdontia (LAMM), Deafness, Deficiency of acetyl-CoA acetyltransferase, Deficiency of ferroxidase, Deficiency of UDPglucose-hexose-1-phosphate uridylyltransferase, Dejerine-Sottas disease, Desbuquois syndrome, DFNA, Diabetes mellitus type 2, Diabetes-deafness syndrome, Diamond-Blackfan anemia, Diastrophic dysplasia, Dihydropteridine reductase deficiency, Dihydropyrimidinase deficiency, Dilated cardiomyopathy, Disseminated atypical mycobacterial infection, Distal arthrogryposis, Distal hereditary motor neuronopathy, Donnai Barrow syndrome, Duchenne muscular dystrophy, Becker muscular dystrophy, Dyschromatosis universalis hereditaria, Dyskeratosis congenital, Dystonia, Early infantile epileptic encephalopathy, Ehlers-Danlos syndrome, Eichsfeld type congenital muscular dystrophy, Emery-Dreifuss muscular dystrophy, Enamel-renal syndrome, Epidermolysis bullosa dystrophica inversa, Epidermolysis bullosa herpetiformis, Epilepsy, Episodic ataxia, Erythrokeratodermia *variabilis*, Erythropoietic protoporphyria, Exercise intolerance, Exudative vitreoretinopathy, Fabry disease, Factor V deficiency, Factor VII deficiency, Factor xiii deficiency, Familial adenomatous polyposis, breast cancer, ovarian cancer, cold urticaria!, chronic infantile neurological, cutaneous and articular syndrome, hemiplegic migraine, hypercholesterolemia, hypertrophic cardiomyopathy, hypoalphalipoproteinemia, hypokalemia-hypomagnesemia, juvenile gout, hyperlipoproteinemia, visceral amyloidosis, hypophosphatemic vitamin D refractory rickets, FG syndrome, Fibrosis of extraocular muscles, Finnish congenital nephrotic syndrome, focal epilepsy, Focal segmental glomerulosclerosis, Frontonasal dysplasia, Frontotemporal dementia, Fructose-biphosphatase deficiency, Gamstorp-Wohlfart syndrome, Ganglioside sialidase deficiency, GATA-I-related thrombocytopenia, Gaucher disease, Giant axonal neuropathy, Glanzmann thrombasthenia, Glomerulocystic kidney disease, Glomerulopathy, Glucocorticoid resistance, Glucose-6-phosphate transport defect, Glutaric aciduria, Glycogen storage disease, Gorlin syndrome, Holoprosencephaly, *GRACILE* syndrome, Haemorrhagic telangiectasia, Hemochromatosis, Hemoglobin H disease, Hemolytic anemia, Hemophagocytic lymphohistiocytosis, Carcinoma of colon, Myhre syndrome, leukoencephalopathy, Hereditary factor IX deficiency disease, Hereditary factor VIII deficiency disease, Hereditary factor XI deficiency disease, Hereditary fructosuria, Hereditary Nonpolyposis Colorectal Neoplasm, Hereditary pancreatitis, Hereditary pyropoikilocytosis, Elliptocytosis, Heterotaxy, Heterotopia, Histiocytic medullary reticulosis, Histiocytosis-lymphadenopathy plus syndrome, HNSHA due to aldolase A deficiency, Holocarboxylase synthetase deficiency, Homocysteinemia, Rowel-Evans syndrome, Hydatidiform mole, Hypercalciuric hypercalcemia, Hyperimmunoglobulin D, Mevalonic aciduria, Hyperinsulinemic hypoglycemia, Hyperkalemic Periodic Paralysis, Paramyotonia congenita of von Eulenburg, Hyperlipoproteinemia, Hypermanganesemia, Hypermethioninemia, Hyperphosphatasemia, Hypertension, hypomagnesemia, Hypobetalipoproteinemia, Hypocalcemia, Hypogonadotropic hypogonadism, Hypogonadotropic hypogonadism, Hypohidrotic ectodermal dysplasia, Hyper-IgM immunodeficiency, Hypohidrotic X-linked ectodermal dysplasia, Hypomagnesemia, Hypoparathyroidism, Idiopathic fibrosing alveolitis, Immunodeficiency, Immunoglobulin A deficiency, Infantile hypophosphatasia, Infantile Parkinsonism-dystonia, Insulin-dependent diabetes mellitus, Intermediate maple syrup urine disease, Ischiopatellar dysplasia, Islet cell hyperplasia, Isolated growth hormone deficiency, Isolated lutropin deficiency, Isovaleric acidemia, Joubert syndrome, Juvenile polyposis syndrome, Juvenile retinoschisis, Kallmann syndrome, Kartagener syndrome, Kugelberg-Welander disease, Lattice corneal dystrophy, Leber congenital amaurosis, Leber optic atrophy, Left ventricular noncompaction, Leigh disease, Mitochondrial complex I deficiency, Leprechaunism syndrome, Arthrogryposis, Anterior horn cell disease, Leukocyte adhesion deficiency, Leukodystrophy, Leukoencephalopathy, Ovarioleukodystrophy, L-ferritin deficiency, Li-Fraumeni syndrome, Limb-girdle muscular dystrophy-dystroglycanopathy, Loeys-Dietz syndrome, Long QT syndrome, Macrocephaly/autism syndrome, Macular corneal dystrophy, Macular dystrophy, Malignant hyperthermia susceptibility, Malignant tumor of prostate, Maple syrup urine disease, Marden Walker like syndrome, Marfan syndrome, Marie Unna hereditary hypotrichosis, Mast cell disease, Meconium ileus, Medium-chain acyl-coenzyme A dehydrogenase deficiency, Melnick-Fraser syndrome, Mental retardation, Merosin deficient congenital muscular dystrophy, Mesothelioma, Metachromatic leukodystrophy, Metaphyseal chondrodysplasia, Methemoglobinemia, methylmalonic aciduria, homocystinuria, Microcephaly, chorioretinopathy, lymphedema, Microphthalmia, Mild non-PKU hyperphenylalaninemia, Mitchell-Riley syndrome, mitochondrial 3-hydroxy-3-methylglutaryl-CoA synthase deficiency, Mitochondrial complex I deficiency, Mitochondrial complex III deficiency, Mitochondrial myopathy, Mucolipidosis III, Mucopolysaccharidosis, Multiple sulfatase deficiency, Myasthenic syndrome, *Mycobacterium tuberculosis*, Myeloperoxidase deficiency, Myhre syndrome, Myoclonic epilepsy, Myofibrillar myopathy, Myoglobinuria, Myopathy, Myopia, Myotonia congenital, Navajo neurohepatopathy, Nemaline myopathy, Neoplasm of stomach, Nephrogenic diabetes insipidus, Nephronophthisis, Nephrotic syndrome, Neurofibromatosis, Neutral lipid storage disease, Niemann-Pick disease, Non-ketotic hyperglycinemia, Noonan syndrome, Noonan syndrome-like disorder, Norum disease, Macular degeneration, N-terminal acetyltransferase deficiency, Oculocutaneous albinism, Oculodentodigital dysplasia, Ohdo syndrome, Optic nerve aplasia, Ornithine carbamoyltransferase deficiency, Orofaciodigital syndrome, Osteogenesis imperfecta, Osteopetrosis, Ovarian dysgenesis, Pachyonychia, Palmoplantar keratoderma, nonepidermolytic, Papillon-Lefevre syndrome, Haim-Munk syndrome, Periodontitis, Peeling skin syndrome, Pendred syndrome, Peroxisomal fatty acyl-coa reductase I disorder, Peroxisome biogenesis disorder, Pfeiffer syndrome, Phenylketonuria, Phenylketonuria, Hyperphenylalaninemia, non-PKU, Pituitary hormone deficiency, *Pityriasis rubra* pilaris, Polyarteritis nodosa, Polycystic kidney disease, Polycystic lipomembranous osteodysplasia, Polymicrogyria, Pontocerebellar hypoplasia, Porokeratosis, Posterior column ataxia, Primary erythromelalgia, hyperoxaluria, Progressive familial intrahepatic cholestasis, Progressive pseudorheumatoid dysplasia, Propionic acidemia, Pseudohermaphroditism, Pseudohypoaldosteronism, Pseudoxanthoma elasticum-like disorder, Purine-nucleoside phosphorylase deficiency, Pyridoxal 5-phosphate-dependent epilepsy, Renal dysplasia, retinal pigmentary dystrophy, cerebellar ataxia, skeletal dysplasia, Reticular dysgenesis, Retinitis pigmentosa, Usher syndrome, Retinoblastoma, Retinopathy, RRM2B-related mitochondrial disease, Rubinstein-Taybi syndrome, Schnyder crystalline corneal dystrophy, Sebaceous tumor, Severe congenital neutropenia, Severe myoclonic epilepsy in infancy, Severe X-linked myotubular myopathy, onychodysplasia, facial dysmorphism, hypotrichosis, Short-rib thoracic dysplasia, Sialic acid storage disease, Sialidosis, Sideroblastic anemia, Small fiber neuropathy, Smith-Magenis syndrome, Sorsby fundus dystrophy, Spastic ataxia, Spastic paraplegia, Spermatogenic failure, Spherocytosis, Sphingomyelin/cholesterol lipidosis, Spinocerebellar ataxia, Split-hand/foot malformation, Spondyloepimetaphyseal dysplasia, Platyspondylic lethal skeletal dysplasia, Squamous cell carcinoma of the head and neck, Stargardt disease, Sucrase-isomaltase deficiency, Sudden infant death syndrome, Supravalvular aortic stenosis, Surfactant metabolism dysfunction, Tangier disease, Tatton-Brown-rahman syndrome, Thoracic aortic aneurysms and aortic dissections, Thrombophilia, Thyroid hormone resistance, TNF receptor-associated periodic fever syndrome (TRAPS), Tooth agenesis, Torsades de pointes, Transposition of great arteries, Treacher Collins syndrome, Tuberous sclerosis syndrome, Tyrosinase-negative oculocutaneous albinism, Tyrosinase-positive oculocutaneous albinism, Tyrosinemia, UDPglucose-4-epimerase deficiency, Ullrich congenital muscular dystrophy, Bethlem myopathy Usher syndrome, UV-sensitive syndrome, Van der Woude syndrome, popliteal pterygium syndrome, Very long chain acyl-CoA dehydrogenase deficiency, Vesicoureteral reflux, Vitreoretinochoroidopathy, Von Hippel-Lindau syndrome, von Willebrand disease, Waardenburg syndrome, Warsaw breakage syndrome, WFSI-Related Disorders, Wilson disease, Xeroderma pigmentosum, X-linked agammaglobulinemia, X-linked hereditary motor and sensory neuropathy, X-linked severe combined immunodeficiency, and Zellweger syndrome.

In certain embodiments, the methods, systems, and compositions described herein are used to correct one or more pathogenic T-to-C or A-to-G mutations/SNPs as provided in the Table below.

complex to bind a first DNA strand at said target locus of interest, wherein said guide sequence is capable of hybridizing with a target sequence comprising said Cytosine within said first DNA strand to form a heteroduplex, wherein said guide sequence comprises a non-pairing Adenine or Uracil at a position corresponding to said Cytosine resulting in a C-A or C-U mismatch in said heteroduplex formed; wherein said Cpf1 nickase protein nicks a second DNA strand at said target locus of interest displaced by formation of said heteroduplex; and wherein said cytidine deaminase protein or catalytic domain thereof deaminates said Cytosine in said heteroduplex.

Embodiment 2. The method of Embodiment 1, wherein said cytidine deaminase protein or catalytic domain thereof is fused to N- or C-terminus of said Cpf1 nickase protein.

Embodiment 3. The method of Embodiment 2, wherein said cytidine deaminase protein or catalytic domain thereof is fused to said Cpf1 nickase protein by a linker.

| Candidate | Gene | Disease |
| --- | --- | --- |
| NM_007262.4(PARK7):c.497T>C (p.Leu166Pro) | PARK7 | Parkinson disease 7 |
| NM_174936.3(PCSK9):c.646T>C (p.Phe216Leu) | PCSK9 | Hypercholesterolemia, autosomal dominant, 3 |
| NM_000642.2(AGL):c.3083+2T>C | AGL | Glycogen storage disease type III |
| NM_213653.3(HFE2):c.842T>C (p.Ile281Thr) | HFE2 | Hemochromatosis type 2A |
| NM_170707.3(LMNA):c.799T>C (p.Tyr267His) | LMNA | Primary dilated cardiomyopathy\|not provided |
| NM_000488.3(SERPINC1):c.1141T>C (p.Ser381Pro) | SERPINC1 | Antithrombin III deficiency |
| NM_000465.3(BARD1):c.1159T>C (p.Phe387Leu) | BARD1 | Familial cancer of breast\|not specified\|Hereditary cancer-predisposing syndrome |
| NM_000030.2(AGXT):c.613T>C (p.Ser205Pro) | AGXT | Primary hyperoxaluria, type I\|not provided |
| NM_001302946.1(TRNT1):c.668T>C (p.Ile223Thr) | TRNT1 | Sideroblastic anemia with B-cell immunodeficiency, periodic fevers, and developmental delay |
| NM_138694.3(PKHD1):c.8068T>C (p.Trp2690Arg) | PKHD1 | Autosomal recessive polycystic kidney disease |
| NM_000162.3(GCK):c.1169T>C (p.Ile390Thr) | GCK | Maturity-onset diabetes of the young, type 2 |
| NM_017890.4(VPS13B):c.7504+2T>C | VPS13B | Cohen syndrome |
| NM_000155.3(GALT):c.512T>C (p.Phe171Ser) | GALT | Deficiency of UDPglucose-hexose-1-phosphate uridylyltransferase |
| NM_000277.1(PAH):c.691T>C (p.Ser231Pro) | PAH | Phenylketonuria\|not provided |
| NM_000138.4(FBN1):c.4531T>C (p.Cys1511Arg) | FBN1 | Marfan syndrome |
| NM_000527.4(LDLR):c.1745T>C (p.Leu582Pro) | LDLR | Familial hypercholesterolemia |

Additional Embodiments

Embodiment 1. A method of modifying a Cytosine in a target locus of interest, comprising delivering to said locus: (a) a Cpf1 nickase protein; (b) a guide molecule which comprises a guide sequence linked to a direct repeat; and (c) a cytidine deaminase protein or catalytic domain thereof; wherein said cytidine deaminase protein or catalytic domain thereof is covalently or non-covalently linked to said Cpf1 nickase protein or said guide molecule or is adapted to link thereto after delivery; wherein guide molecule forms a complex with said Cpf1 nickase protein and directs said Embodiment 4. The method of Embodiment 3, wherein said linker is (GGGGS)$_{3-11}$ (SEQ ID NOS: 1-9), GSG$_5$ (SEQ ID NO: 10) or (SEQ ID NO: 11)
LEPGEKPYKCPECGKSFSQSGALTRHQRTHTR.

Embodiment 5. The method of Embodiment 1, wherein said cytidine deaminase protein or catalytic domain thereof is linked to an adaptor protein, and said guide molecule or said Cpf1 nickase protein comprises an aptamer sequence capable of binding to said adaptor protein.

Embodiment 6. The method of Embodiment 5, wherein said adaptor sequence is selected from MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1.

Embodiment 7. The method of Embodiment 1, wherein said cytidine deaminase protein or catalytic domain thereof is inserted into an internal loop of said Cpf1 nickase protein.

Embodiment 8. The method of any of Embodiments 1-7, wherein said Cpf1 nickase protein comprises a mutation in the Nuc domain.

Embodiment 9. The method of Embodiment 8, wherein said Cpf1 nickase protein comprises a mutation corresponding to R1226A in AsCpf1.

Embodiment 10. The method of any of Embodiments 1-7, wherein said Cpf1 nickase protein has at least part of the Nuc domain removed.

Embodiment 11. The method of any of Embodiments 1-10, wherein said guide molecule binds to said Cpf1 nickase protein and is capable of forming said heteroduplex of about 24 nt with said target sequence.

Embodiment 12. The method of any of Embodiments 1-10, wherein said guide molecule binds to said Cpf1 nickase protein and is capable of forming said heteroduplex of more than 24 nt with said target sequence.

Embodiment 13. The method of any of Embodiments 1-12, wherein said guide sequence comprises at least one further non-pairing nucleotide with said target sequence, adjacent to said non-pairing Adenine or Uracil.

Embodiment 14. The method of Embodiment 13, wherein said guide sequence comprises a stretch of three to five consecutive non-pairing nucleotides with said target sequence.

Embodiment 15. The method of any of the preceding Embodiments, wherein said cytidine deaminase protein or catalytic domain thereof is a human, rat or lamprey cytidine deaminase protein or catalytic domain thereof.

Embodiment 16. The method of Embodiment 15, wherein said cytidine deaminase protein or catalytic domain thereof is an apolipoprotein B mRNA-editing complex (APOBEC) family deaminase, an activation-induced deaminase (AID), or a cytidine deaminase 1 (CDA1).

Embodiment 17. The method of Embodiment 16, wherein said cytidine deaminase protein or catalytic domain thereof is an APOBEC1 deaminase comprising one or more mutations corresponding to W90A, W90Y, R118A, H121R, H122R, R126A, R126E, or R132E in rat APOBEC1, or an APOBEC3G deaminase comprising one or more mutations corresponding to W285A, W285Y, R313A, D316R, D317R, R320A, R320E, or R326E in human APOBEC3G.

Embodiment 18. The method of any of the preceding Embodiments, wherein said Cpf1 nickase protein and optionally said cytidine deaminase protein or catalytic domain thereof comprise one or more heterologous nuclear localization signal(s) (NLS(s)).

Embodiment 19. The method of any of the preceding Embodiments, wherein said cytidine deaminase protein or catalytic domain thereof is delivered together with a uracil glycosylase inhibitor (UGI), where said UGI is covalently linked to said cytidine deaminase protein or catalytic domain thereof and/or said Cpf1 nickase protein.

Embodiment 20. The method of any of the preceding Embodiments, wherein said method comprises, determining said target sequence of interest and selecting a cytidine deaminase protein or catalytic domain thereof which most efficiently deaminates said Cytosine present in said target sequence.

Embodiment 21. The method of any of the preceding Embodiments, wherein said Cpf1 nickase protein is obtained from a Cpf1 nuclease derived from a bacterial species selected from the group consisting of *Francisella tularensis, Prevotella albensis, Lachnospiraceae bacterium, Butyrivibrio proteoclasticus, Peregrinibacteria bacterium, Parcubacteria bacterium, Smithella* sp., *Acidaminococcus* sp., *Lachnospiraceae bacterium, Candidatus Methanoplasma termitum, Eubacterium eligens, Moraxella bovoculi, Leptospira inadai, Porphyromonas crevioricanis, Prevotella disiens* and *Porphyromonas macacae, Succinivibrio dextrinosolvens, Prevotella disiens, Flavobacterium branchiophilum, Helcococcus kunzii, Eubacterium* sp., *Microgenomates (Roizmanbacteria) bacterium, Flavobacterium* sp., *Prevotella brevis, Moraxella caprae, Bacteroidetes oral, Porphyromonas cansulci, Synergistes jonesii, Prevotella bryantii, Anaerovibrio* sp., *Butyrivibrio fibrisolvens, Candidatus Methanomethylophilus, Butyrivibrio* sp., *Oribacterium* sp., *Pseudobutyrivibrio ruminis and Proteocatella sphenisci.*

Embodiment 22. The method of Embodiment 21, wherein said Cpf1 nickase protein is a FnCpf1 nickase and recognizes a PAM sequence of TTN, wherein N is A/C/G or T, or said Cpf1 nickase protein is a PaCpf1p, LbCpf1 or AsCpf1 nickase and recognizes a PAM sequence of TTTV, wherein V is A/C or G.

Embodiment 23. The method of Embodiment 21, wherein said Cpf1 nickase protein has been modified to and recognizes an altered PAM sequence.

Embodiment 24. The method of any of the preceding Embodiments, wherein said target locus of interest is within a cell.

Embodiment 25. The method of Embodiment 24, wherein said cell is a eukaryotic cell.

Embodiment 26. The method of Embodiment 24, wherein said cell is a non-human animal cell.

Embodiment 27. The method of Embodiment 24, wherein said cell is a human cell.

Embodiment 28. The method of Embodiment 24, wherein said cell is a plant cell.

Embodiment 29. The method of any of the preceding Embodiments, wherein said target locus of interest is within an animal.

Embodiment 30. The method of any of the preceding Embodiments, wherein said target locus of interest is within a plant.

Embodiment 31. The method of any of the preceding Embodiments, wherein said target locus of interest is comprised in a DNA molecule in vitro.

Embodiment 32. The method of any of the preceding Embodiments, wherein said components (a), (b) and (c) are delivered to the cell as a ribonucleoprotein complex.

Embodiment 33. The method of any of the preceding Embodiments, wherein said components (a), (b) and (c) are delivered to the cell as one or more polynucleotide molecules.

Embodiment 34. The method of Embodiment 33, wherein said one or more polynucleotide molecules comprise one or more mRNA molecules encoding components (a) and/or (c).

Embodiment 35. The method of Embodiment 33, wherein said one or more polynucleotide molecules are comprised within one or more vectors.

Embodiment 36. The method of Embodiment 35, wherein said one or more polynucleotide molecules comprise one or more regulatory elements operably configured to express said Cpf1 nickase protein, said guide molecule, and said cytidine deaminase protein or catalytic domain thereof, optionally wherein said one or more regulatory elements comprise inducible promoters.

Embodiment 37. The method of any of Embodiments 32-36, wherein said one or more polynucleotide molecules or said ribonucleoprotein complex are delivered via particles, vesicles, or one or more viral vectors.

Embodiment 38. The method of Embodiment 37, wherein said particles comprise a lipid, a sugar, a metal or a protein.

Embodiment 39. The method of Embodiment 38, wherein said particles comprise lipid nanoparticles.

Embodiment 40. The method of Embodiment 37, wherein said vesicles comprise exosomes or liposomes.

Embodiment 41. The method of Embodiment 37, wherein said one or more viral vectors comprise one or more of adenovirus, one or more lentivirus or one or more adeno-associated virus.

Embodiment 42. The method of any of the preceding Embodiments, which is a method of modifying a cell, a cell line or an organism by manipulation of one or more target sequences at genomic loci of interest.

Embodiment 43. The method of Embodiment 42, wherein deamination of said Cytosine at said target locus of interest remedies a disease caused by a T→C or A→G point mutation or pathogenic SNP.

Embodiment 44. The method of Embodiment 42, wherein deamination of said Cytosine at said target locus of interest inactivates a target gene at said target locus.

Embodiment 45. A modified cell obtained from the method of any of the preceding Embodiments, or progeny thereof, wherein said cell comprises a Uracil or a Thymine in replace of said Cytosine in said target locus of interest compared to a corresponding cell not subjected to said method.

Embodiment 46. The modified cell or progeny thereof of Embodiment 45, wherein said cell is a eukaryotic cell.

Embodiment 47. The modified cell or progeny thereof of Embodiment 45, wherein said cell is an animal cell.

Embodiment 48. The modified cell or progeny thereof of Embodiment 45, wherein said cell is a human cell.

Embodiment 49. The modified cell or progeny thereof of Embodiment 45, wherein said cell is a therapeutic T cell.

Embodiment 50. The modified cell or progeny thereof of Embodiment 45, wherein said cell is an antibody-producing B cell.

Embodiment 51. The modified cell or progeny thereof of Embodiment 45, wherein said cell is a plant cell.

Embodiment 52. A non-human animal comprising said modified cell of Embodiment 47.

Embodiment 53. A plant comprising said modified cell of Embodiment 51.

Embodiment 54. A method for cell therapy, comprising administering to a patient in need thereof said modified cell of any of Embodiments 45-50, wherein presence of said modified cell remedies a disease in said patient.

Embodiment 55. An engineered, non-naturally occurring system suitable for modifying a Cytosine in a target locus of interest, comprising: a guide molecule which comprises a guide sequence, or a nucleotide sequence encoding said guide molecule; a Cpf1 nickase protein, or a nucleotide sequence encoding said Cpf1 nickase protein; a cytidine deaminase protein or catalytic domain thereof, or a nucleotide sequence encoding said cytidine deaminase protein or catalytic domain thereof, wherein said cytidine deaminase protein or catalytic domain thereof is covalently or non-covalently linked to said Cpf1 nickase protein or said guide molecule or is adapted to link thereto after delivery; wherein said guide sequence is capable of hybridizing with a target sequence comprising a Cytosine on a first DNA strand at said target locus to form a heteroduplex, wherein said guide sequence comprises a non-pairing Adenine or Uracil at a position corresponding to said Cytosine resulting in a C-A or C-U mismatch in said heteroduplex formed; and wherein said Cpf1 nickase protein is capable of nicking a second DNA strand at said target locus.

Embodiment 56. An engineered, non-naturally occurring vector system suitable for modifying an Cytosine in a target locus of interest, comprising said nucleotide sequences of a), b) and c) of Embodiment 55.

Embodiment 57. The engineered, non-naturally occurring vector system of Embodiment 56, comprising one or more vectors comprising: a first regulatory element operably linked to a nucleotide sequence encoding said guide molecule which comprises a guide sequence, a second regulatory element operably linked to a nucleotide sequence encoding said Cpf1 nickase protein; and a nucleotide sequence encoding said cytidine deaminase protein or catalytic domain thereof which is under control of said first or second regulatory element or operably linked to a third regulatory element; wherein, if said nucleotide sequence encoding a cytidine deaminase protein or catalytic domain thereof is operably linked to a third regulatory element, said cytidine protein or catalytic domain thereof is adapted to link to said guide molecule or said Cpf1 nickase protein after expression; wherein components (a), (b) and (c) are located on the same or different vectors of said system.

Embodiment 58. An in vitro or ex vivo host cell or progeny thereof or cell line or progeny thereof comprising a system of any of Embodiments 55-57.

Embodiment 59. The host cell or progeny thereof or cell line or progeny thereof of Embodiment 58, wherein said cell is a eukaryotic cell.

Embodiment 60. The host cell or progeny thereof or cell line or progeny thereof of Embodiment 58, wherein said cell is an animal cell.

Embodiment 61. The host cell or progeny thereof or cell line or progeny thereof of Embodiment 58, wherein said cell is a human cell.

Embodiment 62. The host cell or progeny thereof or cell line or progeny thereof of Embodiment 58, wherein said cell is a plant cell.

WORKING EXAMPLES

Example 1

Cytosine deaminases (CDs) typically deaminates cytosines at specific sites in single stranded DNA. Previous efforts have attempted to fuse CD to Cas9 to achieve RNA-guided cytosine deamination on genomic DNA, with the CD editing a non-targeted DNA strand displaced by the binding of a Cas9-guide RNA complex to a targeted DNA strand.

The fact that CD can be directed to effect cytosine deamination on single stranded DNA of interest presents a unique opportunity to develop an RNA guided CD by taking advantage of the bubble formed between the guide RNA and its complementary DNA target in the presence of mismatching nucleotides. By using Cpf1 nickase to recruit a CD, the CD enzyme will then act on the cytosine in the accessible single stranded DNA in the mismatching bubble, whereas the Cpf1 nickase will nick the non-targeted DNA strand displaced by the binding of a Cpf1-guide RNA complex to the targeted DNA strand, which would facilitate subsequent conversion of the corresponding guanine on the non-targeted DNA.

In one embodiment, nickase Cpf1 can be used to nick the strand of DNA that is not complementary to the guide RNA. For AsCpf1 the mutation would be R1226A.

Designs for the Recruitment of CD to a Specific Locus:

1. NLS-tagged nickase Cpf1 is fused to CD on either the N- or C-terminal end. A variety of linkers are used including flexible linkers such as GSG$_5$ or less flexible linkers such as LEPGEKPYKCPECGKSFSQSGALTRHQRTHTR.

2. The guide RNA scaffold is modified with aptamers such as MS2 binding sites (e.g. Konermann et al., Nature 2015). NLS-tagged CD-MS2 binding protein fusions is co-introduced into target cells along with (NLS-tagged nickase Cpf1) and corresponding guide RNA.

3. CD is inserted into an internal loop of NLS-tagged nickase Cpf1.

Designs for the RNA Guide:

1. Normal length of RNA guide (24 nt for AsCpf1) is designed to target the genomic locus of interest.

2. RNA guide with longer than canonical length is used to form heteroduplexes outside of the protein-guide RNA-target DNA complex.

For each of these RNA guide designs, the base on the RNA that is opposite of the cytosine on the DNA strand would be specified as an A or U as opposed to G. The guide can be designed to comprise a stretch of two or more consecutive mismatches or non-pairing nucleotides, including up to about 6 consecutive mismatches or non-pairing nucleotides, preferably 3-5 consecutive mismatches or non-pairing nucleotides, and more preferably 3-4 consecutive mismatches or non-pairing nucleotides. The guide can be designed to comprise one or two mismatches or non-pairing nucleotides on each side of and adjacent to the aforementioned A or U opposite to the targeted C.

Choice and Designs of CDs:

A number of CDs are used, and each will have varying levels of activity. These CDs include:

```
Rat APOBEC1 (rAPOBEC1):
                                    (SEQ ID NO: 29)
MSSETGPVAVDPTLRRRIEPHEFEVFFDPRELRKETCLLYEINWGGRHSIW

RHTSQNTNKHVEVNFIEKFTTERYFCPNTRCSITWFLSWSPCGECSRAITE

FLSRYPHVTLFIYIARLYHHADPRNRQGLRDLISSGVTIQIMTEQESGYCW

RNFVNYSPSNEAHWPRYPHLWVRLYVLELYCIILGLPPCLNILRRKQPQLT

FFTIALQSCHYQRLPPHILWATGLK

Human APOBEC1 (hAPOBEC1)
                                    (SEQ ID NO: 30)
MTSEKGPSTGDPTLRRRIEPWEFDVFYDPRELRKEACLLYEIKWGMSRKIW

RSSGKNTTNHVEVNFIKKFTSERDFHPSMSCSITWFLSWSPCWECSQAIRE

FLSRHPGVTLVIYVARLFWHMDQQNRQGLRDLVNSGVTIQIMRASEYYHCW

RNFVNYPPGDEAHWPQYPPLWMMLYALELHCIILSLPPCLKISRRWQNHLT

FFRLHLQNCHYQTIPPHILLATGLIHPSVAWR

Human APOBEC3G (hAPOBEC3G):
                                    (SEQ ID NO: 31)
MELKYHPEMRFFHWFSKWRKLHRDQEYEVTWYISWSPCTKCTRDMATFLAE

DPKVTLTIFVARLYYFWDPDYQEALRSLCQKRDGPRATMKIMNYDEFQHCW

SKFVYSQRELFEPWNNLPKYYILLHIMLGEILRHSMDPPTFTFNFNNEPWV

RGRHETYLCYEVERMHNDTWVLLNQRRGFLCNQAPHKHGFLEGRHAELCFL

DVIPFWKLDLDQDYRVTCFTSWSPCFSCAQEMAKFISKNKHVSLCIFTARI

YDDQGRCQEGLRTLAEAGAKISIMTYSEFKHCWDTFVDHQGCPFQPWDGLD

EHSQDLSGRLRAILQNQEN

Petromyzon marinus (Lamprey) CDA1 (pmCDA1):
                                    (SEQ ID NO: 32)
MTDAEYVRIHEKLDIYTFKKQFFNNKKSVSHRCYVLFELKRRGERRACFWG

YAVNKPQSGTERGIHAEIFSIRKVEEYLRDNPGQFTINWYSSWSPCADCAE

KILEWYNQELRGNGHTLKIWACKLYYEKNARNQIGLWNLRDNGVGLNVMVS

EHYQCCRKIFIQSSHNQLNENRWLEKTLKRAEKRRSELSIMIQVKILHTTK

SPAV

Human AID (hAID):
                                    (SEQ ID NO: 33)
MDSLLMNRRKFLYQFKNVRWAKGRRETYLCYVVKRRDSATSFSLDFGYLRN

KNGCHVELLFLRYISDWDLDPGRCYRVTWFTSWSPCYDCARHVADFLRGNP

YLSLRIFTARLYFCEDRKAEPEGLRRLHRAGVQIAIMTFKDYFYCWNTFVE

NHERTFKAWEGLHENSVRLSRQLRRILLPLYEVDDLRDAFRTLGLLD

Human AID-DC (hAID-DC, truncated version of hAID):
                                    (SEQ ID NO: 34)
MDSLLMNRRKFLYQFKNVRWAKGRRETYLCYVVKRRDSATSFSLDFGYLRN

KNGCHVELLFLRYISDWDLDPGRCYRVTWFTSWSPCYDCARHVADFLRGNP

NLSLRIFTARLYFCEDRKAEPEGLRRLHRAGVQIAIMTFKDYFYCWNTFVE

NHERTFKAWEGLHENSVRLSRQLRRILL
```

Mutations can also be used to increase the specificity of base editing. For example, rAPOBEC1 mutants having one or more mutations of W90Y, R126E, and R132E can be used to increase the specificity of base editing.

In addition, a uracil glycosylase inhibitor (UGI) can be linked to the Cpf1 and/or the CD to inhibit uracil-DNA glycosylase base-excision repair enzyme and increase the efficiency of base editing. For example, rAPOBEC1 mutants having one or more mutations of W90Y, R126E, and R132E can be used to increase the specificity of deamination.

Uracil Glycosylase Inhibitor (UGI):

```
                                    (SEQ ID NO: 35)
TNLSDIIEKETGKQLVIQESILMLPEEVEEVIGNKPESDILVHTAYDESTD

ENVMLLTSDAPEYKPWALVIQDSNGENKIKML
```

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "cgreater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. An engineered, non-naturally occurring system capable of modifying a Cytosine in a target locus of interest, comprising:
   a) a guide molecule which comprises a guide sequence, or a nucleotide sequence encoding said guide molecule;
   b) a Cpf1 nickase protein, or a nucleotide sequence encoding said Cpf1 nickase protein, comprising a mutation in a Nuc domain; and
   c) a cytidine deaminase protein or catalytic domain thereof, or a nucleotide sequence encoding said cytidine deaminase protein or catalytic domain thereof;
   wherein the mutation in the Nuc domain comprises R1226A of the amino acid sequence of SEQ DI NO: 60 or a mutation of an arginine in a corresponding position of an amino acid sequence having at least 80% sequence identity to the amino acid sequence of SEQ ID NO: 60;
   wherein said cytidine deaminase protein or catalytic domain thereof is covalently or non-covalently linked to said Cpf1 nickase protein or said guide molecule or is adapted to link thereto after delivery to said target locus of locus; and
   wherein said guide sequence is capable of hybridizing with a target sequence comprising a Cytosine on a first DNA strand at said target locus to form a heteroduplex, wherein said guide sequence comprises a non-pairing Adenine or Uracil at a position corresponding to said Cytosine resulting in a C-A or C-U mismatch in said heteroduplex formed.

2. An engineered, non-naturally occurring vector system capable of modifying a Cytosine in a target locus of interest, comprising nucleotide sequences of said engineered, non-naturally occurring system of claim 1.

3. The engineered, non-naturally occurring vector system of claim 2, comprising one or more vectors comprising:
   a) a first regulatory element operably linked to a nucleotide sequence encoding said guide molecule which comprises a guide sequence;
   b) a second regulatory element operably linked to a nucleotide sequence encoding said Cpf1 nickase protein; and
   c) a nucleotide sequence encoding said cytidine deaminase protein or catalytic domain thereof which is under control of said first or second regulatory element or operably linked to a third regulatory element;
   wherein, if said nucleotide sequence encoding a cytidine deaminase protein or catalytic domain thereof is operably linked to a third regulatory element, said cytidine protein or catalytic domain thereof is adapted to link to said guide molecule or said Cpf1 nickase protein after expression; and
   wherein components (a), (b) and (c) are located on same or different vectors of said engineered, non-naturally occurring vector system.

4. An in vitro or ex vivo host cell or progeny thereof or cell line or progeny thereof comprising the system of claim 1, wherein optionally said cell is a eukaryotic cell.

5. The system of claim 1, wherein the mutation of an arginine in a corresponding position is in an amino acid sequence having at least 95% sequence identity to the amino acid sequence of SEQ ID NO:60.

6. A method of modifying a Cytosine in a target locus of interest, comprising delivering to said target locus of interest:
the engineered, non-naturally occurring system of claim 1;
wherein said guide molecule forms a complex with said Cpf1 nickase protein and directs said complex to bind a first DNA strand at said target locus of interest, wherein said guide sequence is capable of hybridizing with a target sequence comprising said Cytosine within said first DNA strand to form a heteroduplex, wherein said guide sequence comprises a non-pairing Adenine or Uracil at a position corresponding to said Cytosine resulting in a C-A or C-U mismatch in said heteroduplex formed;
wherein said Cpf1 nickase protein nicks a second DNA strand at said target locus of interest displaced by formation of said heteroduplex; and
wherein said cytidine deaminase protein or catalytic domain thereof deaminates said Cytosine in said heteroduplex.

7. The method of claim 6, wherein said cytidine deaminase protein or catalytic domain thereof:
is fused to the N- or C-terminus of said Cpf1 nickase protein;
is linked to an adaptor protein, and said guide molecule or said Cpf1 nickase protein comprises an aptamer sequence capable of binding to said adaptor protein;
is inserted into an internal loop of said Cpf1 nickase protein; or
is delivered together with an uracil glycosylase inhibitor (UGI), wherein said UGI is covalently linked to said cytidine deaminase protein or catalytic domain thereof and/or said Cpf1 nickase protein.

8. The method of claim 7, wherein said cytidine deaminase protein or catalytic domain thereof is fused to said Cpf1 nickase protein by a linker.

9. The method of claim 8, wherein said linker comprises an amino acid sequence of SEQ ID NOS: 1-11.

10. The method of claim 7, wherein said adaptor sequence is selected from the group consisting of MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1.

11. The method of claim 6, wherein said guide molecule binds to said Cpf1 nickase protein and:
is capable of forming said heteroduplex of about 24 nucleotides with said target sequence; or
is capable of forming said heteroduplex of more than 24 nucleotides with said target sequence.

12. The method of claim 6, wherein said guide sequence comprises at least one further non-pairing nucleotide with said target sequence, adjacent to said non-pairing Adenine or Uracil.

13. The method of claim 12, wherein said guide sequence comprises a stretch of three to five consecutive non-pairing nucleotides or six to eight consecutive non-pairing nucleotides with said target sequence.

14. The method of claim 6, wherein said cytidine deaminase protein or catalytic domain thereof is a human, rat or lamprey cytidine deaminase protein or catalytic domain thereof.

15. The method of claim 14, wherein said cytidine deaminase protein or catalytic domain thereof is an apolipoprotein B mRNA-editing complex (APOBEC) family deaminase, an activation-induced deaminase (AID), or a cytidine deaminase 1 (CDA1).

16. The method of claim 6, wherein said Cpf1 nickase protein and optionally said cytidine deaminase protein or catalytic domain thereof comprise one or more heterologous nuclear localization signal(s) (NLS(s)).

17. The method of claim 6, further comprising, determining said target locus of interest and selecting a cytidine deaminase protein or catalytic domain thereof which most efficiently deaminates said Cytosine present in said target locus of interest.

18. The method of claim 6, wherein said target locus of interest is within a cell, within an animal, within a plant, or comprised in a DNA molecule in vitro and wherein said cell is a prokaryotic cell, eukaryotic cell, a non-human animal cell, a human cell, or a plant cell.

19. The method of claim 6, wherein said engineered, non-naturally occurring system are delivered to a cell as a ribonucleoprotein complex, or as one or more polynucleotide molecules.

20. The method of claim 19, wherein said one or more polynucleotide molecules or said ribonucleoprotein complex are delivered via particles, vesicles, or one or more viral vectors.

21. The method of claim 20, wherein said particles comprise a lipid, a sugar, a metal, a protein, or lipid nanoparticles.

22. The method of claim 20, wherein said vesicles comprise exosomes or liposomes.

23. The method of claim 20, wherein said one or more viral vectors comprise one or more of adenovirus, one or more lentivirus or one or more adeno-associated virus.

24. The method of claim 6, wherein deamination of said Cytosine at said target locus of interest is associated with a disease caused by a T→C or A→G point mutation or pathogenic SNP.

25. The method of claim 6, wherein deamination of said Cytosine at said target locus of interest inactivates a target gene at said target locus of interest.

* * * * *